US007411054B2

(12) United States Patent
Meyers et al.

(10) Patent No.: US 7,411,054 B2
(45) Date of Patent: Aug. 12, 2008

(54) 25869, 25934, 26335, 50365, 21117, 38692, 46508, 16816, 16839, 49937, 49931 AND 49933 MOLECULES AND USES THEREFOR

(75) Inventors: Rachel E. Meyers, Newton, MA (US); Mark J. Williamson, Saugus, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/445,606

(22) Filed: Jun. 2, 2006

(65) Prior Publication Data

US 2007/0059730 A1 Mar. 15, 2007

Related U.S. Application Data

(63) Continuation of application No. 10/377,072, filed on Feb. 27, 2003, now abandoned, which is a continuation-in-part of application No. 09/935,291, filed on Aug. 21, 2001, now abandoned, and application No. 10/377,072, which is a continuation-in-part of application No. 09/908,664, filed on Jul. 17, 2001, now abandoned, and application No. 10/377,072, which is a continuation-in-part of application No. 09/895,860, filed on Jun. 29, 2001, now abandoned, and application No. 10/377,072, which is a continuation-in-part of application No. 09/888,911, filed on Jun. 25, 2001, now abandoned, and application No. 10/377,072, which is a continuation-in-part of application No. 09/861,801, filed on May 21, 2001, now abandoned, and application No. 10/377,072, which is a continuation-in-part of application No. 09/843,297, filed on Apr. 25, 2001, now Pat. No. 6,569,667, and application No. 10/377,072, which is a continuation-in-part of application No. 09/816,494, filed on Mar. 23, 2001, now Pat. No. 6,664,089, and application No. 10/377,072, which is a continuation-in-part of application No. 09/723,806, filed on Nov. 28, 2000, now Pat. No. 6,686,185.

(60) Provisional application No. 60/250,932, filed on Nov. 30, 2000, provisional application No. 60/226,504, filed on Aug. 21, 2000, provisional application No. 60/218,675, filed on Jul. 17, 2000, provisional application No. 60/215,370, filed on Jun. 29, 2000, provisional application No. 60/213,688, filed on Jun. 23, 2000, provisional application No. 60/205,508, filed on May 19, 2000, provisional application No. 60/199,801, filed on Apr. 26, 2000, provisional application No. 60/191,858, filed on Mar. 24, 2000, provisional application No. 60/187,455, filed on Mar. 7, 2000.

(51) Int. Cl.
*C12N 15/54* (2006.01)
*C12N 9/12* (2006.01)
*C12N 15/74* (2006.01)
*C12N 15/79* (2006.01)

(52) U.S. Cl. ............... 536/23.2; 435/194; 435/69.1; 435/252.3; 435/320.1

(58) Field of Classification Search ............ None
See application file for complete search history.

(56) References Cited

U.S. PATENT DOCUMENTS

| 5,854,067 | A * | 12/1998 | Newgard et al. | 435/366 |
| 5,891,717 | A * | 4/1999 | Newgard et al. | 435/325 |
| 6,673,549 | B1 * | 1/2004 | Furness et al. | 435/6 |
| 6,727,066 | B2 * | 4/2004 | Kaser | 435/6 |
| 7,070,947 | B2 * | 7/2006 | Meyers et al. | 435/18 |
| 7,193,069 | B2 * | 3/2007 | Isogai et al. | 536/23.1 |
| 2003/0211093 | A1 * | 11/2003 | Yue et al. | 424/94.5 |

FOREIGN PATENT DOCUMENTS

WO    WO 97/26357    *    7/1997

OTHER PUBLICATIONS

Altschul et al., J. Mol. Biol., 1990, 215:403-410.
Altschul et al., *Nucleic Acids Res.*, 1997, 25(17):3389-3402.
International Human Genome Sequencing Consortium, *Initial sequencing and analysis of the human genome*, Nature 1, vol. 409, Feb. 15, 2001.
Karlin et al., *Proc. Natl. Acad. Sci. USA*, 1990, 87(6):2264-2268.
Karlin et al., *Proc. Natl. Acad. Sci. USA*, 1993, 90(12):5873-5877.
Myers et al., *CABIOS*, 1988, 4:11-17.
The Human Genome The Sequence of the Human Genome, Science, vol. 291, Feb. 16, 2001.
Sonnhammer et al., *Proteins*, 1997, 28(3):405-420.
Weintraub et al., *Trends in Genetics*, Jan. 1985.
GenBank Accession No. AK026414; Suzuki, Submitted Aug. 29, 2000.
Deeb et al., "Human Hexokinase II: Sequence and Homology to other Hexokinases", *Biochem. and Biophys. Res. Comm.*, 197:68-74 (1993).
EMBL Accession No. AI949849, Mar. 14, 2000.
EMBL Accession No. BE159085, Dias Neto et al., Jul. 2, 2000.
EMBL Accession No. AW475040, Mar. 2, 2000.
Katabi et al., "Hexokinase Type II: A Novel Tumor-Specific Promoter for Gene-Targeted Therapy Differentially Expressed and Regularted in Human Cancer Celles", *Human Gene Therapy*, 10:155-164 (1999).
Mathupala et al., "Arrest of proliferation of highly glycolytic tumors upon Type II hexokinase down regulation via an antisense RNA approach", Proceedings of the American Association for Cancer Research, 40:22 (1999).

* cited by examiner

*Primary Examiner*—Nashaat T. Nashed
*Assistant Examiner*—William W. Moore

(57) ABSTRACT

The invention provides isolated nucleic acids molecules, designated 25869, 25934, 26335, 50365, 21117, 38692, 46508, 16816, 16839, 49937, 49931 and 49933 nucleic acid molecules. The invention also provides antisense nucleic acid molecules, recombinant expression vectors containing 25869, 25934, 26335, 50365, 21117, 38692, 46508, 16816, 16839, 49937, 49931 or 49933 nucleic acid molecules, host cells into which the expression vectors have been introduced, and nonhuman transgenic animals in which a 25869, 25934, 26335, 50365, 21117, 38692, 46508, 16816, 16839, 49937, 49931 or 49933 gene has been introduced or disrupted. The invention still further provides isolated 25869, 25934, 26335, 50365, 21117, 38692, 46508, 16816, 16839, 49937, 49931 or 49933 proteins, fusion proteins, antigenic peptides and anti-25869, 25934, 26335, 50365, 21117, 38692, 46508, 16816, 16839, 49937, 49931 or 49933 antibodies. Diagnostic and therapeutic methods utilizing compositions of the invention are also provided.

14 Claims, No Drawings

25869, 25934, 26335, 50365, 21117, 38692, 46508, 16816, 16839, 49937, 49931 AND 49933 MOLECULES AND USES THEREFOR

RELATED APPLICATIONS

The present application is a continuation of U.S. patent application Ser. No. 10/377,072, filed Feb. 27, 2003 now abandoned, which is a continuation-in-part of U.S. patent application Ser. No. 09/895,860, filed Jun. 29, 2001 (now abandoned), which claims the benefit of U.S. Provisional Application Ser. No. 60/215,370, filed Jun. 29, 2000 (now abandoned). U.S. patent application Ser. No. 10/377,072 is also a continuation-in-part of U.S. patent application Ser. No. 09/723,806, filed Nov. 28, 2000 (now U.S. Pat. No. 6,686, 185), which claims the benefit of U.S. Provisional Application Ser. No. 60/187,455, filed Mar. 7, 2000 (now abandoned). U.S. patent application Ser. No. 10/377,072 is also a continuation-in-part of U.S. patent application Ser. No. 09/843,297, filed Apr. 25, 2001 (now U.S. Pat. No. 6,569, 667), which claims the benefit of U.S. Provisional Application Ser. No. 60/199,801, filed Apr. 26, 2000 (now abandoned). U.S. patent application Ser. No. 10/377,072 is also a continuation-in-part of U.S. patent application Ser. No. 09/861,801, filed May 21, 2001 (now abandoned), which claims the benefit of U.S. Provisional Application Ser. No. 60/205,508, filed May 19, 2000 (now abandoned). U.S. patent application Ser. No. 10/377,072 is also a continuation-in-part of U.S. patent application Ser. No. 09/816,494, filed Mar. 23, 2001 (now U.S. Pat. No. 6,664,089), which claims the benefit of U.S. Provisional Application Ser. No. 60/191, 858, filed Mar. 24, 2000 (now abandoned). U.S. patent application Ser. No. 10/377,072 is also a continuation-in-part of U.S. patent application Ser. No. 09/888,911, filed Jun. 25, 2001 (now abandoned), which claims the benefit of U.S. Provisional Application Ser. No. 60/213,688, filed Jun. 23, 2000 (now abandoned). U.S. patent application Ser. No. 10/377,072 is also a continuation-in-part of U.S. patent application Ser. No. 09/908,664, filed Jul. 17, 2001 (now abandoned), which claims the benefit of U.S. Provisional Application Ser. No. 60/218,675, filed Jul. 17, 2000 (now abandoned). U.S. patent application Ser. No. 10/377,072 is also a continuation-in-part of U.S. patent application Ser. No. 09/935,291, filed Aug. 21, 2001 (now abandoned), which claims the benefit of U.S. Provisional Application Ser. No. 60/250,932, filed Nov. 30, 2000 (now abandoned) and of U.S. Provisional Application Ser. No. 60/226,504, filed Aug. 21, 2000 (now abandoned). The entire contents of each of the above-referenced patent applications are incorporated herein by this reference.

BACKGROUND OF THE INVENTION

The enormous variety of biochemical reactions that comprise life are nearly all mediated by a series of biological catalysts known as enzymes. Enzymes are proteins which possess specific properties that enable them to catalyze a series of reactions, allowing metabolic pathways to degrade and to reconstruct products needed to maintain organisms. By the binding of substrates through geometrically and physically complementary reactions, enzymes are stereospecific in binding substrates as well as in catalyzing reactions. The stringency for this stereospecificity varies as some enzymes are more specific to the identity of their substrates, while others are capable of binding multiple substrates and can catalyze numerous types of reactions.

Examples of enzymes include, for example, carboxylases, fatty acid desaturases, serine/threonine dehydratases, hexokinases, peptidyl tRNA hydrolases, dual specificity phosphatases, phospholipases and transporters. Such enzymes have the ability to, for example: (1) hydrolyze an ester linkage and/or liberate the free acid form of a substrate, e.g., hydrolysis of a triglyceride and/or liberation of free fatty acid(s) and glycerol; (2) catalyze the formation of a double bond, preferably, at positions up to 9 carbons from the carboxyl end of a molecule, e.g., a fatty acid, such as a polyunsaturated fatty acid; (3) catalyze the phosphorylation of a sugar, e.g., an aldohexoses and a ketohexoses (e.g., glucose, mannose, fructose, sorbitol and glucosamine); (4) catalyze sugar metabolism; (5) transfer a phosphate from a phosphate donor (e.g., ATP) to a sugar, e.g., an aldohexoses and a ketohexoses (e.g., glucose, mannose, fructose, sorbitol and glucosamine) to form a phosphorylated sugar, e.g., glucose-6-phosphate; (6) catalyze the removal of a phosphate group attached to a tyrosine residue in a protein target, e.g., a growth factor receptor; (7) catalyze the removal of a phosphate group attached to a serine or threonine residue in a protein e.g., a growth factor receptor; (8) hydrolyze covalent bond between peptide and tRNA within peptidyl-tRNAs; (9) catalyze the hydrolysis of phosphatidyl-inositol-4,5-bisphosphate (PIP2) producing diacylglycerol and inositol 1,4,5-trisphosphate; (10) transport of a substrate or target molecule (e.g., a $Ca^{2+}$ ion) from one side of a biological membrane to the other; and (11) be phosphorylated or dephosphorylated. Accordingly, there exits a need to identify additional human enzymes, for example, for use as disease markers and as targets for identifying various therapeutic modulators.

SUMMARY OF THE INVENTION

The present invention is based, at least in part, on the discovery of novel nucleic acid molecules and proteins encoded by such nucleic acid molecules, referred to herein as "25869, 25934, 26335, 50365, 21117, 38692, 46508, 16816, 16839, 49937, 49931 or 49933". The 25869, 25934, 26335, 50365, 21117, 38692, 46508, 16816, 16839, 49937, 49931 or 49933 nucleic acid and protein molecules of the present invention are useful as modulating agents in regulating a variety of cellular processes, e.g., including but not limited to cell proliferation, differentiation, growth and division. In particular, these nucleic acid molecules will be advantageous in the regulation of any cellular function, uncontrolled proliferation and differentiation, such as in cases of cancer. Accordingly, in one aspect, this invention provides isolated nucleic acid molecules encoding 25869, 25934, 26335, 50365, 21117, 38692, 46508, 16816, 16839, 49937, 49931 or 49933 proteins or biologically active portions thereof, as well as nucleic acid fragments suitable as primers or hybridization probes for the detection of 25869, 25934, 26335, 50365, 21117, 38692, 46508, 16816, 16839, 49937, 49931 or 49933-encoding nucleic acids.

The nucleotide sequence of the cDNA encoding 25869, 25934, 26335, 50365, 21117, 38692, 46508, 16816, 16839, 49937, 49931 or 49933, and the amino acid sequence of 25869, 25934, 26335, 50365, 21117, 38692, 46508, 16816, 16839, 49937, 49931 or 49933 polypeptides are depicted in Table 1.

TABLE 1

Sequences of the invention

| Gene Name | cDNA SEQ ID NO: | Protein SEQ ID NO: | Coding Region SEQ ID NO: | ATCC Accession Number |
|---|---|---|---|---|
| 25869 | 1 | 2 | 3 | |
| 25934 | 7 | 8 | 9 | |
| 26335 | 16 | 17 | 18 | |
| 50365 | 20 | 21 | 22 | |
| 21117 | 25 | 26 | 27 | |
| 38692 | 28 | 29 | 30 | |
| 46508 | 35 | 36 | 37 | |
| 16816 | 39 | 40 | 41 | |
| 16839 | 42 | 43 | 44 | |
| 49937 | 63 | 64 | 65 | |
| 49931 | 67 | 68 | 69 | |
| 49933 | 70 | 71 | 72 | |

Accordingly, in one aspect, the invention features a nucleic acid molecule which encodes a 25869, 25934, 26335, 50365, 21117, 38692, 46508, 16816, 16839, 49937, 49931 or 49933 protein or polypeptide, e.g., a biologically active portion of the 25869, 25934, 26335, 50365, 21117, 38692, 46508, 16816, 16839, 49937, 49931 or 49933 protein. In a preferred embodiment, the isolated nucleic acid molecule encodes a polypeptide having the amino acid sequence of SEQ ID NO:2, 8, 17, 21, 26, 29, 36, 40, 43, 64, 68 or 71. In other embodiments, the invention provides isolated 25869, 25934, 26335, 50365, 21117, 38692, 46508, 16816, 16839, 49937, 49931 or 49933 nucleic acid molecules having the nucleotide sequence shown in SEQ ID NO:1, 3, 7, 9, 16, 18, 20, 22, 25, 27, 28, 30, 35, 37, 39, 41, 42, 44, 63, 65, 67, 69, or 70 or 72. In still other embodiments, the invention provides nucleic acid molecules that are substantially identical (e.g., naturally occurring allelic variants) to the nucleotide sequence shown in SEQ ID NO: 1, 3, 7, 9, 16, 18, 20, 22, 25, 27, 28, 30, 35, 37, 39, 41, 42, 44, 63, 65, 67, 69, 70 or 72. In other embodiments, the invention provides a nucleic acid molecule which hybridizes under a stringent hybridization condition as described herein to a nucleic acid molecule comprising the nucleotide sequence of SEQ ID NO:1, 3, 7, 9, 16, 18, 20, 22, 25, 27, 28, 30, 35, 37, 39, 41, 42, 44, 63, 65, 67, 69, 70 or 72 wherein the nucleic acid encodes a full length 25869, 25934, 26335, 50365, 21117, 38692, 46508, 16816, 16839, 49937, 49931 or 49933 protein or an active fragment thereof.

In a related aspect, the invention further provides nucleic acid constructs which include a 25869, 25934, 26335, 50365, 21117, 38692, 46508, 16816, 16839, 49937, 49931 or 49933 nucleic acid molecule described herein. In certain embodiments, the nucleic acid molecules of the invention are operatively linked to native or heterologous regulatory sequences. Also included are vectors and host cells containing the 25869, 25934, 26335, 50365, 21117, 38692, 46508, 16816, 16839, 49937, 49931 or 49933 nucleic acid molecules of the invention e.g., vectors and host cells suitable for producing polypeptides.

In another related aspect, the invention provides nucleic acid fragments suitable as primers or hybridization probes for the detection of 25869, 25934, 26335, 50365, 21117, 38692, 46508, 16816, 16839, 49937, 49931 or 49933-encoding nucleic acids.

In still another related aspect, isolated nucleic acid molecules that are antisense to a 25869, 25934, 26335, 50365, 21117, 38692, 46508, 16816, 16839, 49937, 49931 or 49933 encoding nucleic acid molecule are provided.

In another aspect, the invention features 25869, 25934, 26335, 50365, 21117, 38692, 46508, 16816, 16839, 49937, 49931 or 49933 polypeptides, and biologically active or antigenic fragments thereof that are useful, e.g., as reagents or targets in assays applicable to treatment and diagnosis of 25869, 25934, 26335, 50365, 21117, 38692, 46508, 16816, 16839, 49937, 49931 or 49933-associated disorders. In another embodiment, the invention provides 25869, 25934, 26335, 50365, 21117, 38692, 46508, 16816, 16839, 49937, 49931 or 49933 polypeptides having a 25869, 25934, 26335, 50365, 21117, 38692, 46508, 16816, 16839, 49937, 49931 or 49933 activity.

In other embodiments, the invention provides 25869, 25934, 26335, 50365, 21117, 38692, 46508, 16816, 16839, 49937, 49931 or 49933 polypeptides, e.g., a 25869, 25934, 26335, 50365, 21117, 38692, 46508, 16816, 16839, 49937, 49931 or 49933 polypeptide having the amino acid sequence shown in SEQ ID NO:2, 8, 17, 21, 26, 29, 36, 40, 43, 64, 68 or 71, an amino acid sequence that is substantially identical to the amino acid sequence shown in SEQ ID NO:2, 8, 17, 21, 26, 29, 36, 40, 43, 64, 68 or 71, or an amino acid sequence encoded by a nucleic acid molecule having a nucleotide sequence which hybridizes under a stringent hybridization condition as described herein to a nucleic acid molecule comprising the nucleotide sequence of SEQ ID NO:1, 3, 7, 9, 16, 18, 20, 22, 25, 27, 28, 30, 35, 37, 39, 41, 42, 44, 63, 65, 67, 69, 70 or 72, wherein the nucleic acid encodes a full length 25869, 25934, 26335, 50365, 21117, 38692, 46508, 16816, 16839, 49937, 49931 or 49933 protein or an active fragment thereof.

In a related aspect, the invention further provides nucleic acid constructs which include a 25869, 25934, 26335, 50365, 21117, 38692, 46508, 16816, 168397, 49937, 49931 or 49933 nucleic acid molecule described herein.

In a related aspect, the invention provides 25869, 25934, 26335, 50365, 21117, 38692, 46508, 16816, 16839, 49937, 49931 or 49933 polypeptides or fragments operatively linked to non-25869, 25934, 26335, 50365, 21117, 38692, 46508, 16816, 16839, 49937, 49931 or 49933 polypeptides to form fusion proteins.

In another aspect, the invention features antibodies and antigen-binding fragments thereof, that react with, or more preferably specifically or selectively bind 25869, 25934, 26335, 50365, 21117, 38692, 46508, 16816, 16839, 49937, 49931 or 49933 polypeptides.

In another aspect, the invention provides methods of screening for compounds that modulate the expression or activity of the 25869, 25934, 26335, 50365, 21117, 38692, 46508, 16816, 16839, 49937, 49931 or 49933 polypeptides or nucleic acids.

In still another aspect, the invention provides a process for modulating 25869, 25934, 26335, 50365, 21117, 38692, 46508, 16816, 16839, 49937, 49931 or 49933 polypeptide or nucleic acid expression or activity, e.g., using the compounds identified in the screens described herein. In certain embodiments, the methods involve treatment of conditions related to aberrant activity or expression of the 25869, 25934, 26335, 50365, 21117, 38692, 46508, 16816, 16839, 49937, 49931 or 49933 polypeptides or nucleic acids, such as conditions or disorders involving aberrant or deficient 25869, 25934, 26335, 50365, 21117, 38692, 46508, 16816, 16839, 49937, 49931 or 49933 expression. Examples of such disorders include, but are not limited to cellular proliferative and/or differentiative disorders, angiogenic disorders, brain disorders, neurological disorders, blood vessel disorders, breast disorders, colon disorders, kidney disorders, lung disorders, ovarian disorders, prostate disorders, hematopoeitic disorders, pancreatic disorders, skeletal muscle disorders, skin disorders, hormonal disorders, immune e.g., inflammatory, disorders, cardiovascular disorders, lipid homeostasis disorders, endothelial cell disorders, liver disorders, disorders of the small intestine, pain disorders, viral diseases, metabolic disorders, bone metabolism disorders or platelet disorders.

The invention also provides assays for determining the activity of or the presence or absence of 25869, 25934, 26335, 50365, 21117, 38692, 46508, 16816, 16839, 49937, 49931 or 49933 polypeptides or nucleic acid molecules in a biological sample, including for disease diagnosis.

In a further aspect, the invention provides assays for determining the presence or absence of a genetic alteration in a 25869, 25934, 26335, 50365, 21117, 38692, 46508, 16816, 16839, 49937, 49931 or 49933 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 25869, 25934, 26335, 50365, 21117, 38692, 46508, 16816, 16839, 49937, 49931 or 49933 molecule. In one embodiment, the capture probe is a nucleic acid, e.g., a probe complementary to a 25869, 25934, 26335, 50365, 21117, 38692, 46508, 16816, 16839, 49937, 49931 or 49933 nucleic acid sequence. In another embodiment, the capture probe is a polypeptide, e.g., an antibody specific for 25869, 25934, 26335, 50365, 21117, 38692, 46508, 16816, 16839, 49937, 49931 or 49933 polypeptides. Also featured is a method of analyzing a sample by contacting the sample to the aforementioned array and detecting binding of the sample to the array.

Other features and advantages of the invention will be apparent from the following detailed description, and from the claims.

DETAILED DESCRIPTION OF THE INVENTION

Human 25869 (COE-1)

The present invention is based, at least in part, on the discovery of novel carboxylesterase family members, referred to herein as "25869", "Carboxylesterase" or "COE-1" nucleic acid and protein molecules. These novel molecules are capable of hydrolyzing ester-, thioester-, and amide-containing compounds (e.g., triglycerides) to their respective free acids, are upregulated in marmoset monkeys treated with cholestyramine, a cholesterol and/or lipid lowering drug, and play a role in or function in a variety of cellular processes, including lipid homeostasis, hydrolysis of endogenous and/or exogenous compounds; detoxification and/or activation of drugs, pro-drugs, toxins, and/or carcinogens; intra- or intercellular signaling; gene expression; and/or cellular growth and/or differentiation.

Carboxylesterases comprise a family of enzymes which catalyze the hydrolysis of a variety of ester-, thioester-, and amide-containing chemicals, as well as drugs (including pro-drugs) to their respective free acids. Carboxylesterases catalyze the hydrolysis of endogenous compounds such as short- and long-chain acyl-glycerols, long-chain acylcarnitine, and long-chain acyl-CoA esters (Satoh, T. and Hosokawa, M. (1998) *Annu. Rev. Pharmacol. Toxicol.* 38:257-88). The general enzymatic reaction that carboxylesterases catalyze is:

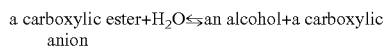

The hydrolytic activity of carboxylesterases is dependent on the presence of a "catalytic triad" of amino acid residues that are non-contiguous in the primary sequence but adjacent in the tertiary structure (Ollis, D. L. et al. (1992) *Protein Eng.* 5:197-211; Cygler, M. et al. (1993) *Protein Sci.* 2:366-382). In carboxylesterases, the catalytic triad residues are Ser/His/Glu (Satoh and Hosokawa (1998) supra; Oakeshott, J. G. et al. (1999) *Bioessays* 21:1031-1042).

The first step of the hydrolysis reaction catalyzed by carboxylesterases liberates the alcohol moiety of the substrate and forms a covalent linkage between the remaining acid moiety of the substrate and the serine residue of the catalytic triad. The second step cleaves this linkage and liberates the acid moiety of the substrate, largely through the action of the histidine residue of the catalytic triad (Oakeshott et al. (1999) supra).

While many well-studied carboxylesterases have catalytic triads, several members of the carboxyl/cholinesterase multigene family have been reported to lack a functional catalytic triad (Hortsch, M. et al. (1990) *Development* 110: 1327-1340; Auld, V. J. (1995) *Cell* 81:757-767; Ichtchenko, K. et al. (1995) *Cell* 81:435-443; Oakeshott, J. G. et al. (1995) *Trends. Ecol. Evol.* 10: 103-110) and, thus, to lack carboxylesterase activity. However, some of these enzymes have ligand-binding functions involved in signal transduction.

Carboxylesterases are responsible for the hydrolysis of many exogenous compounds, resulting in both the inactivation of drugs and the activation of pro-drugs (Satoh, T. (1987) *Reviews in Biochem. Toxicol.* 8:155-81; Heymann, E. (1980) *Enzymatic Basis of Detoxification* 2:291-323; Heymann, E. (1982) *Metabolic Basis of Detoxification* 1:229-45; Leinweber, F.-J. (1987) *Drug. Metab. Rev.* 18:379-439). Human liver and plasma carboxylesterase converts lovastatin to its active form (Tang, B. K. and Kalow, W. (1995) *Eur. J. Clin. Pharmacol.* 47:449-5 1) and converts an inactive prodrug form of prostaglandin F2α to its active metabolite (Cheng-Bennett, A. et al. (1994) *Br. J. Ophthalmol.* 78:560-67). A significant number of drugs and endogenous compounds are substrates of carboxylesterases, including dipivefrin hydrochloride (Nakamura, M. et al. (1993) *Ophthalmic Res.* 25:46-51), carbonates (McCracken, N. W. et al. (1993) *Biochem. Pharmacol.* 45:31-36; Huang, T. L. et al. (1993) *Pharmacol. Res.* 10:639-48), cocaine (Dean, R. A. (1995) *J. Pharmacol. Exp. Ther.* (1995) 275:965-71; Brzezinski, M. R. et al. (1994) *Biochem. Pharmacol.* 48:1747-55), salicylates (White, K. N. et al. (1994) *Biochem. Soc. Trans.* 22:220S), capsaicin (Park, Y. H. and Lee, S. S. (1994) *Biochem. Mol. Biol. Int.* 34:351-60), palmitoyl-coenzyme A (Hosokawa, M. et al. (1987) *Mol. Pharmacol.* 31:579-84; Hosokawa, M. et al. (1990) *Arch. Biochem. Biophys.* 277:219-27; Tsujita, T. and Okuda, H. (1993) *J. Lipid. Res.* 34:1773-81; Mentlein, R. et al. (1984) *Arch. Biochem. Biophys.* 234:612-21), haloperidol (Nambu, K. et al. (1987) *Biochem. Pharmacol.* 36:1715-22), imidapril (Yamada, Y. et al. (1992) *Arzneimittel Forsch.* 42:507-12), pyrrolizidine alkaloids (Dueker, S. R. et al. (1992) *Toxicol. Appl. Pharmacol.* 117:116-21; Dueker, S. R. et al. (1995) *Arch. Toxicol.* 69:725-28; Dueker, S. R. et al. (1992) *Drug. Metab. Dispos.* 20:275-80), and steroids (Lund-Pero, M. et al. (1994) *Clin. Chim. Acta.* 224:9-20).

The novel COE-1 molecules of the instant invention are members of the lipase subfamily of carboxylesterases and show significant homology to mouse and rat lipases. Analysis of the activity of a recently characterized hepatic microsomal lipase, ES-10, showed that increased expression of ES-10 in hepatic cell lines resulted in an increase in the rate of depletion of intracellular triacylglycerol stores, indicating that ES-10 is capable of hydrolysis of stored triacylglycerol. In addition, hepatocytes expressing ES-10 exhibited increased levels of apo-B 100 in the VLDL fraction (Lehner, R. and Vance, D. E. (1999) *Biochem. J.* 343:1-10; Robbi, M. et al. (1990) *Biochem. J.* 269:451-458).

Because the COE-1 molecules of the instant invention show significant homology to ES-10, COE-1 may function as an intracellular lipase, the activity of which may contribute to the mobilization of intracellular triacylglycerol stores, which can be used for lipoprotein assembly. Accordingly, modulation of COE-1 activity may result in the modulation of serum lipoprotein and/or triglyceride levels. For example, inhibition of COE-1 activity may have positive effects on serum lipoprotein and triglyceride profiles. In view of the foregoing activities, the COE-1 molecules of the present invention provide novel diagnostic targets and therapeutic agents to control carboxylesterase-associated disorders.

As used herein, a "carboxylesterase-associated disorder" includes a disorder, disease or condition which is caused or characterized by a misregulation (e.g., downregulation or upregulation) of carboxylesterase activity. Carboxylesterase-associated disorders can detrimentally affect cellular functions such as lipid homeostasis; cellular proliferation, growth, differentiation, or migration; inter- or intra-cellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, or mutagens).

In a preferred embodiment, a carboxylesterase-associated disorder is a "lipid homeostasis disorder". Other examples of carboxylesterase-associated disorders include cardiovascular disorders, neurological (CNS) disorders, cellular proliferation, growth, differentiation, or migration disorders, hormonal disorders, immune disorders and disorders affecting tissues in which COE-1 protein is expressed, e.g., the kidney, colon, liver, brain, small intestine, and skeletal muscle, as assessed by TaqMan analysis.

Members of the COE-1 family of proteins, for example, include at least one "carboxylesterase domain" in the protein or corresponding nucleic acid molecule. As used herein, the term "carboxylesterase domain" includes a protein domain having at least about 440-600 amino acid residues and a bit score of at least 440 when compared against a carboxylesterase Hidden Markov Model (HMM), e.g., PFAM Accession Number PF00135. Preferably, a carboxylesterase domain includes a protein having an amino acid sequence of about 460-580, 480-560, 500-540, or more preferably about 519 amino acid residues, and a bit score of at least 470, 480, 490, 500, or more preferably, 516.6. To identify the presence of a carboxylesterase domain in a COE-1 protein, and make the determination that a protein of interest has a particular profile, the amino acid sequence of the protein is searched against a database of known protein domains (e.g., the HMM database). The carboxylesterase domain (HMM) has been assigned the PFAM Accession number PF00135 (see the PFAM website, available online through Washington University in St. Louis). A search was performed against the HMM database resulting in the identification of a carboxylesterase domain in the amino acid sequence of human COE-1 at about residues 5-523 of SEQ ID NO:2.

A description of the Pfam database can be found in Sonhammer et al. (1997) *Proteins* 28:405-420, and a detailed description of HMMs can be found, for example, in Gribskov et al. (1990) *Methods Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

In another embodiment, a COE-1 family member of the present invention is identified based on the presence of a "catalytic triad" in the protein or corresponding nucleic acid molecule. As used herein, the term "catalytic triad" includes a group of three amino acid residues which are non-contiguous in the primary sequence but which are adjacent in the tertiary structure of a protein and which actively participate in an enzymatic reaction catalyzed by a carboxylesterase. In the carboxylesterases of the present invention, the catalytic triad residues are typically serine, histidine, and glutamic acid (Satoh and Hosokawa (1998) supra; Oakeshott et al. (1999) supra). The amino acid residues of the catalytic triad may also be referred to herein as the "catalytic residues" (e.g., the "catalytic serine" or "catalytic histidine") or the "active site residues" (e.g., the "active site serine" or "active site histidine"). In a preferred embodiment, the serine residue of a catalytic triad of the COE-1 molecules of the present invention is contained within a catalytic serine motif, as defined herein. In a further preferred embodiment, the serine residue of a catalytic triad of the COE-1 molecules of the present invention is contained within a carboxylesterases type-B serine active site. An alignment of the COE-1 amino acid sequence (SEQ ID NO:2), using the GAP program in the GCG software package (Blosum 62 matrix) and a gap weight of 12 and a length weight of 4, with a mouse liver carboxylesterase precursor (GenBank Accession No. Q63880; SEQ ID NO:4), identified two of the catalytic triad residues as serine$^{205}$ and histidine$^{426}$ of human COE-1.

In another embodiment, a COE-1 family member of the present invention is identified based on the presence of a "catalytic serine motif" in the protein or corresponding nucleic acid molecule. As used herein, a "catalytic serine motif" includes a group of five amino acid residues having the consensus sequence G-X-S-X-G (SEQ ID NO:6), wherein X indicates any amino acid residue. Catalytic serine motifs are found in all known lipases (Lehner, R. and Vance, D. E. (1999) *Biochem. J.* 343:1-10). In a preferred embodiment, a catalytic serine motif includes a catalytic serine, as defined herein. In a further preferred embodiment, a catalytic serine motif is contained within a carboxylesterases type-B serine active site. An alignment of the COE-1 amino acid sequence (SEQ ID NO:2), using the GAP program in the GCG software package (Blosum 62 matrix) and a gap weight of 12 and a length weight of 4, with a mouse liver carboxylesterase precursor (GenBank Accession No. Q63880; SEQ ID NO:4), identified a catalytic serine motif at about residues 203-207 of human COE-1 (SEQ ID NO:2).

In another embodiment, a COE-1 protein of the present invention is identified based on the presence of a "carboxylesterases type-B serine active site" in the protein or corresponding nucleic acid molecule. A carboxylesterases type-B serine active site functions as part of the catalytic active site of a carboxylesterase. The carboxylesterases type-B serine active site has been assigned ProSite Accession Number PS00122. To identify the presence of a carboxylesterases type-B serine active site in a COE-1 protein, and to make the determination that a protein of interest has a particular profile, the amino acid sequence of the protein may be searched against a database of known protein domains (e.g., the ProSite database) using the default parameters (available online through the Swiss Institute of Bioinformatics (SIB)). In a preferred embodiment, a carboxylesterases type-B serine active site comprises a catalytic serine motif, which further comprises a catalytic serine. A search was performed against the ProSite database resulting in the identification of a carboxylesterases type-B serine active site in the amino acid sequence of human COE-1 (SEQ ID NO:2) at about residues 192-207.

In another embodiment, a COE-1 family member of the present invention is identified based on the presence of an "ER retention signal" in the protein or corresponding nucleic acid molecule. As used herein, an "ER retention signal" includes a group of four amino acid residues located at the C-terminus of a polypeptide sequence which targets a protein to the lumen of the endoplasmic reticulum. Based on homology to other proteins known to have ER retention signals, an ER retention signal was identified in the amino acid sequence of human COE-1 (SEQ ID NO:2) at about residues 544-547.

Isolated proteins of the present invention, preferably COE-1 proteins, have an amino acid sequence sufficiently homologous to the amino acid sequence of SEQ ID NO:2, or are encoded by a nucleotide sequence sufficiently homologous to SEQ ID NO:1 or 3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 88%, 89%, 90%, 95%, 96%, 97%, 98%, 99%, 99.1%, 99.2%, 99.3%, 99.4%, 99.5%, 99.6%, 99.7%, 99.8%, 99.9% or more homology or identity across the amino acid sequences of the domains and contain at least one and preferably two structural domains or motifs, are defined herein as sufficiently homologous. Furthermore, amino acid or nucleotide sequences which share at least 50%, 55%, 60%, 65%, 70%, 75%, 80%, 85%, 85%, 88%, 89%, 90%, 95%, 96%, 97%, 98%, 99%, 99.1%, 99.2%, 99.3%, 99.4%, 99.5%, 99.6%, 99.7%, 99.8%, 99.9% or more homology or identity and share a common functional activity are defined herein as sufficiently homologous.

In a preferred embodiment, a COE-1 protein includes at least one or more of the following domains, motifs, and/or amino acid residues: a carboxylesterase domain, a catalytic triad, a catalytic serine, a catalytic histidine, a catalytic serine motif, a carboxylesterases type-B serine active site, and/or an ER retention signal, and has an amino acid sequence at least about 50%, 55%, 60%, 65%, 70%, 75%, 80%, 85%, 85%, 88%, 89%, 90%, 95%, 96%, 97%, 98%, 99%, 99.1%, 99.2%, 99.3%, 99.4%, 99.5%, 99.6%, 99.7%, 99.8%, 99.9% or more homologous or identical to the amino acid sequence of SEQ ID NO:2. In yet another preferred embodiment, a COE-1 protein includes at least one or more of the following domains, motifs, and/or amino acid residues: a carboxylesterase domain, a catalytic triad, a catalytic serine, a catalytic histidine, a catalytic serine motif, a carboxylesterases type-B serine active site, and/or an ER retention signal, and is encoded by a nucleic acid molecule having a nucleotide sequence which hybridizes under stringent hybridization conditions to a complement of a nucleic acid molecule comprising the nucleotide sequence of SEQ ID NO: 1 or 3. In another preferred embodiment, a COE-1 protein includes at least one or more of the following domains, motifs, and/or amino acid residues: a carboxylesterase domain, a catalytic triad, a catalytic serine, a catalytic histidine, a catalytic serine motif, a carboxylesterases type-B serine active site, and/or an ER retention signal, and has a COE-1 activity.

As used interchangeably herein, a "COE-1 activity", "biological activity of COE-1" or "functional activity of COE-1", includes an activity exerted or mediated by a COE-1 protein, polypeptide or nucleic acid molecule on a COE-1 responsive cell or on a COE-1 substrate, as determined in vivo or in vitro, according to standard techniques. In one embodiment, a COE-1 activity is a direct activity, such as an association with a COE-1 target molecule. As used herein, a "target molecule" or "binding partner" is a molecule with which a COE-1 protein binds or interacts in nature, such that COE-1-mediated function is achieved. A COE-1 target molecule can be a non-COE-1 molecule or a COE-1 protein or polypeptide of the present invention. In an exemplary embodiment, a COE-1 target molecule is a COE-1 substrate or ligand, e.g., a triglyceride. A COE-1 activity can also be an indirect activity, such as a cellular signaling activity mediated by interaction of the COE-1 protein with a COE-1 substrate or ligand.

In a preferred embodiment, a COE-1 activity is at least one of the following activities: (i) interaction with a COE-1 substrate or target molecule (e.g., a triglyceride); (ii) conversion of a COE-1 substrate or target molecule to a product (e.g., hydrolysis of an ester linkage and/or liberation of the free acid form of the substrate, e.g., hydrolysis of a triglyceride and/or liberation of free fatty acid(s) and glycerol); (iii) modulation of lipolysis; (iv) modulation of lipid uptake by a cell (e.g., a liver cell); (v) modulation of lipid synthesis and/or secretion; (vi) modulation of intracellular lipid release and/or turnover; (vii) modulation of intracellular lipid and/or triglyceride mass; (viii) modulation of secreted lipid and/or triglyceride mass; (ix) modulation of serum lipid, lipoprotein, and/or triglyceride levels; (x) modulation of lipid homeostasis; (xi) direct or indirect modulation of lipoprotein assembly; (xii) interaction with and/or hydrolysis of a second non-COE-1 protein; (xiii) activation/deactivation of a COE-1 substrate or target molecule (e.g., activation/deactivation of a carcinogen); (xiv) metabolism and/or detoxification of a drug; (xv) modulation of cellular signaling and/or gene transcription (e.g., either directly or indirectly); and/or (xvi) modulation of cellular proliferation and/or differentiation.

Isolation of the Human 25869 or COE-1 cDNA

The invention is based, at least in part, on the discovery of genes encoding novel members of the carboxylesterase family. The entire sequence of human clone Fbh25869 was determined and found to contain an open reading frame termed human "25869" or "COE-1."

The nucleotide sequence encoding the human COE-1 is set forth as SEQ ID NO: 1. The human COE-1 gene, which is approximately 2087 nucleotides in length, encodes a protein having a molecular weight of approximately 60.2 kD and which is approximately 547 amino acid residues in length as set forth as SEQ ID NO:2. The coding region (open reading frame) of SEQ ID NO: 1 is set forth as SEQ ID NO:3. Clone Fbh25869, comprises the coding region of human COE-1.

Analysis of the Human 25869 or COE-1 Molecules

The amino acid sequence of human COE-1 was analyzed using the program PSORT (available online) to predict the localization of the proteins within the cell. This program assesses the presence of different targeting and localization of amino acid sequences within the query sequence. The results of the analyses show that human COE-1 may be localized to the cytoplasm, to the nucleus, or to the mitochondria.

Searches of the amino acid sequence of human COE-1 were performed against the HMM database. These searches resulted in the identification of a "carboxylesterase domain" at about residues 5-523 of SEQ ID NO:2 (score=516.6).

Searches of the amino acid sequence of human COE-1 were further performed against the Prosite database. These searches resulted in the identification in the amino acid sequence of human COE-1 of a potential N-glycosylation site and a number of potential protein kinase C phosphorylation sites, casein kinase II phosphorylation sites, and N-myristoylation sites. These searches further resulted in the identification of a carboxylesterases type-B serine active site at about residues 192-207 of SEQ ID NO:2.

A "catalytic triad" was also identified in the human COE-1. An alignment of human COE-1 (SEQ ID NO:2) with a mouse liver carboxylesterase precursor (GenBank Accession No. Q63880; SEQ ID NO:4), identified two of the catalytic triad amino acids, namely $Ser^{205}$ and $His^{426}$ within SEQ ID NO:2.

A "catalytic serine motif" was also identified in the human COE-1. An alignment of human COE-1 (SEQ ID NO:2), using the GAP program in the GCG software package (Blosum 62 matrix) and a gap weight of 12 and a length weight of 4, with a mouse liver carboxylesterase precursor (GenBank Accession No. Q63880; SEQ ID NO:4), identified a catalytic serine motif at about residues 203-207 of human COE-1 (SEQ ID NO:2).

An "ER retention signal" was also identified in the human COE-1. Based on homology to other proteins known to have ER retention signals, an ER retention signal was identified in the amino acid sequence of human COE-1 (SEQ ID NO:2) at about residues 544-547.

Global alignments (using the GAP program in the GCG software package (Blosum 62 matrix) and a gap weight of 12 and a length weight of 4) of the human COE-1 amino acid sequence (SEQ ID NO:2) revealed that human COE-1 has a 67.3% identity with the amino acid sequence of a mouse liver carboxylesterase precursor (SEQ ID NO:4; GenBank Accession No. Q63880) and a 46% identity with the amino acid sequence of rat liver carboxylesterase 10 precursor (also referred to as ES-10; SEQ ID NO:5; GenBank Accession No. P16303).

Tissue Distribution of COE-1 mRNA

This example describes the tissue distribution of human COE-1 mRNA, as may be determined using in situ hybridization analysis. For in situ analysis, various tissues, e.g., tissues obtained from brain, are first frozen on dry ice. Ten-micrometer-thick sections of the tissues are postfixed with 4% formaldehyde in DEPC-treated 1×phosphate-buffered saline at room temperature for 10 minutes before being rinsed twice in DEPC 1×phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15 M NaCl plus 0.015 M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled ($5 \times 10^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 nM Tris-HCl (pH 7.6), 500 mM NaCl, and 1 mM EDTA), for 10 minutes, in TNE with 10 μg of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Analysis of Human COE-1 Expression Using the TaqMan Procedure

TAQMAN™ analysis on a panel of: (1) normal artery; (2) normal vein; (3) aortic smooth muscle cells—early; (4) coronary smooth muscle cells; (5) human umbilical vein endothelial cells (HUVECs)—static; (6) human umbilical vein endothelial cells (HUVECs)—shear; (7) normal heart; (8) heart—congestive heart failure (CHF); (9) kidney; (10) skeletal muscle; (11) normal adipose tissue; (12) pancreas; (13) primary osteoblasts; (14) differentiated osteoclasts; (15) normal skin; (16) normal spinal cord; (17) normal brain cortex; (18) brain—hypothalamus; (19) nerve; (20) dorsal root ganglion (DRG); (21) glial cells (astrocytes); (22) glioblastoma; (23) normal breast; (24) breast tumor; (25) normal ovary; (26) ovary tumor; (27) normal prostate; (28) prostate tumor; (29) epithelial cells (prostate); (30) normal colon; (31) colon tumor; (32) normal lung; (33) lung tumor; (34) lung—chronic obstructive pulmonary disease (COPD); (35) colon—inflammatory bowel disease (IBD); (36) normal liver; (37) liver—fibrosis; (38) dermal cells—fibroblasts; (39) normal spleen; (40) normal tonsil; (41) lymph node; (42) small intestine; (43) skin—decubitus; (44) synovium; (45) bone marrow mononuclear cells (BM-MNC); and (46) activated peripheral blood mononuclear cells (PBMCs), revealed that human 25869 or COE-1 was highly expressed in the kidney, colon, liver, brain, small intestine, and skeletal muscle. Expression of human COE-1 was also upregulated in marmoset monkeys treated with cholestyramine, a drug which lowers cholesterol and/or lipids in the blood.

Analysis of Human 25869 or COE-1 Activity

The activity, e.g., the lipase activity, of COE-1 molecules of the present invention may be determined by the use of any of the following assays. All of the following assays are performed as described in Lehner, R. and Vance, D. E. (1999) *Biochem. J.* 343: 1-10, the contents of which are incorporated herein by reference.

Materials

Oleic acid, essentially fatty acid-free bovine serum albumin (BSA), p-nitrophenyl fatty acyl esters and Protein A-Sepharose CL 4B are purchased from Sigma (St. Louis, Mo., U.S.A.). [9,10-3H]Triolein (28 mCi/mmol) is from Dupont NEN (Boston, Mass., U.S.A.). [1,3-$^3$H]glycerol (2.6 Ci/mmol), [U-$^{14}$C]glycerol (149 mCi/mmol), [9,10-$^3$H]oleic acid (10 Ci/mmol), L-[4,5-$^3$H]leucine (57 Ci/mmol) and ECL Western blotting reagents are obtained from Amersham Canada (Oakville, Ontario, Canada). Dulbecco's modified Eagle's medium (DMEM), sodium pyruvate, penicillin/streptomycin, fetal bovine and horse sera and Geneticin (G-418 sulfate) are from Gibco BRL (Life Technologies Inc., Grand Island, N.Y., U.S.A.). Triascin C is purchased from Biomol Research Laboratories, Inc. (Plymouth Meeting, Pa., U.S.A.). All other chemicals and solvents are of reagent or better quality and are obtained from any number of suppliers known to those of skill in the art. Sheep anti-[human apolipoprotein (apo)B] IgG is from Boehringer-Mannheim.

Cell Culture

Primary hepatocytes are isolated from male Sprague-Dawley rats (body weight 125-150 g), fed ad libitum, by collagenase perfusion of the liver. The cells are cultured in DMEM containing 15% (v/v) fetal bovine serum, as described in Yao, Z. and Vance, D. E. (1988) *J. Biol. Chem.* 263:449-509. HepG2 cells, obtained from A.T.C.C., are cultured in minimal Eagle's medium containing 0.1 mM nonessential amino acids, 1 mM sodium pyruvate, penicillin (10 units/ml), streptomycin (100 µg/ml) and 10% fetal bovine serum. McArdle RH7777 cells obtained from A.T.C.C., are cultured in DMEM containing pyruvate, antibiotics, 10% fetal bovine serum, and 10% (v/v) horse serum. All cultures are maintained in 100 mm dishes (Corning) at 37° C. in humidified air (89-91% saturation) containing 5% $CO_2$.

Generation of Stable Cell Lines Expressing COE-1 cDNA

Cells, e.g., McArdle RH7777 cells, are transfected with 10 µg of pBK-CMV plasmid vector (Stratagene) with or without COE-1 cDNA insert using a calcium precipitation procedure, as described in Chen, C. and Okayama, H. (1987) *Mol. Cell. Biol.* 7:2745-2752. Cells stably expressing either the empty vector or the vector containing the COE-1 cDNA are selected for resistance to the antibiotic G-418 (0.08% w/v). Transfected McArdle RH7777 cells are grown in DMEM supplemented with 10% horse serum and 10% fetal bovine serum, penicillin/streptomycin (40 units/ml) and 0.02% (w/v) G-418. Cells are maintained at 37° C. in humidified air containing 5% $CO_2$.

Preparation of Microsomal Membranes

Cells, e.g., McArdle RH7777 cells, from ten 100 mm diameter culture dishes (approximately 50 mg of protein) are harvested into 5 ml of 10 mM Tris/HCl, pH 7.4, containing 250 mM sucrose and 5 mM EDTA. Cells are homogenized with a Polytron, and the microsomal membranes are isolated by ultracentrifugation from a post-mitochondrial supernatant, as described in Lehner, R. and Kuksis, A. (1993) *J. Biol. Chem.* 268:8781-8786.

Lipase Assay

Lipolytic activities in microsomal membranes (50 µg of protein) isolated from 'mock' transfected (empty vector) and COE-1 cDNA transfected cells (e.g., McArdle RH7777 cells) are assessed using either radiolabeled triolein or a chromogenic substrate (p-nitrophenyl laurate) as described in Lehner, R. and Verger, R. (1997) *Biochemistry* 36:1861-1868.

Immunoblot Analysis

Cells, e.g., McArdle RH7777 cells (non-transfected, 'mock' transfected, and COE-1 cDNA transfected) are harvested in phosphate-buffered saline (PBS) and disrupted by brief sonication. Cell homogenates (35 µg of protein) are electrophoresed on an SDS/12% (w/v) polyacrylamide gel, transferred to a nitrocellulose membrane, and the expression of COE-1 is analyzed by blotting with anti-COE-1 antibodies using standard methods.

Lipid Uptake by Transfected Cells

Cells, e.g., McArdle RH7777 cells (at approximately 80% confluency in 60 mm diameter culture dishes) are incubated with 2 ml of serum-free DMEM containing 0.5% BSA and 100 µCi [$^3$H]oleic acid for 1 hour. The medium is aspirated, the cells are washed with DMEM/0.5% BSA, and subsequently the cells are incubated with 5 ml of DMEM/0.5% BAS for 2 hours. The medium is removed, diluted with DMEM/0.5% BSA and 5 ml aliquots are added to the cells, e.g., McArdle RH7777 cells, stably transfected with either pBK-CMV vector or with pBK-CMV containing COE-1 cDNA. Aliquots of medium (1 ml) are taken after 2, 4, and 6 hours of incubation. At the end of the incubation period, the cells are washed with ice-cold PBS, harvested in the same buffer, and dispersed by brief sonication. Cellular and medium lipids are extracted as described in Folch, J. et al. ((1957) *J. Biol. Chem.* 226:449-509) in the presence of nonlabeled lipid carriers. The lipids are applied to TLC plates and developed to one-third the height with chloroform/methanol/acetic acid/water (25:15:4:2, by volume) to separate glycerophospholipids, followed by development in heptane/isopropyl ether/acetic acid (60:40:4, by volume) to separate neutral lipids. Lipids are made visible by exposure to iodine; bands corresponding to various lipid classes are scraped, and the associated radioactivity is determined by scintillation counting.

Effect of Triascin C on Glycerolipid Synthesis and Secretion

Cells, e.g., McArdle RH7777 cells, stably transfected with pBK-CMV or pBK-CMV containing COE-1 cDNA are grown to approximately 70% confluency in 60 mm diameter dishes and incubated for 24 hours with serum-free DMEM containing 0.1 mM oleic acid complexed with BSA (0.13% final concentration). The medium is aspirated and the cells are incubated for 1 hour with DMEM containing 0.1 mM oleic acid/BSA and various concentrations of triascin C in DMSO. The final concentration of DMSO is 0.4%. After a 1 hour incubation±triascin C, 10 µCi/dish of [$^3$H]glycerol is added. Cells and medium are collected after 2 hours, lipids are extracted, and the radioactivity associated with phosphatidylcholine and triacylglycerol is analyzed as described above.

Intracellular Lipid Turnover in Transfected Cells

Cells, e.g., McArdle RH7777 cells, stably transfected with pBK-CMV or pBK-CMV containing COE-1 cDNA (grown to approximately 70% confluency) are incubated with serum-free DMEM containing 0.1 mM oleic acid complexed with BSA (0.13% final concentration) and 20 µCi [$^3$H]glycerol for 15 hours. After 13 hours, triascin C (20 µM final concentration) is added. After an additional 2 hours of labeling, medium is removed, cells are washed and incubated for 6 hours±triascin C (chase). Cells are harvested, lipids are extracted and separated by TLC, and the amount of radioactivity in phosphatidylcholine and triacylglycerol is determined.

Utilization of Intracellular Triacylglycerol Stores for Lipoprotein Assembly and Secretion Contribution of [$^{14}$C]glycerol-labeled Intracellular Triacylglycerol Pools in the Presence of Exogenous Oleate: Pulse-chase Protocol Cells are incubated for 2 hours with 0.375 mM oleic acid/0.5% BSA to increase the triacylglycerol stores. Cells are then washed and incubated for 1 hour with DMEM followed by 2 hours with 0.375 mM oleic acid/0.5% BSA and 0.25 µCi [$^{14}$C]glycerol. Radioactivity in cellular and medium phosphatidylcholine and triacylglycerol is analyzed following lipid extraction and TLC as described above.

Secretion of [$^3$H]glycerol-Prelabeled Intracellular Triacylglycerol Pools in the Absence of Oleate Cells are incubated for 16 hours with serum-free DMEM containing 0.375 mM oleic acid/0.5% BSA and 0.25 µCi [$^{14}$C]glycerol, washed and incubated with DMEM in the absence of extracellular oleate for up to 8 hours. Radioactivity in cellular medium lipids is analyzed.

Lipid Secretion from Transfected Cells

Cells, e.g., McArdle RH7777 cells, at 60-70% confluency are washed with DMEM and incubated in the absence of serum for 2 hours. One set of dishes is incubated for 4 hours with serum-free DMEM containing 0.5% BSA and 10 µCi [$^3$H]glycerol. The other set of dishes is incubated for 4 hours with serum-free DMEM containing 0.375 mM oleic acid/ 0.5% BSA and 10 µCi [$^3$H]glycerol. At the end of a 4 hour pulse, a set of oleate-treated cells is washed with DMEM and incubated for various times with serum-free DMEM containing 0.5% BSA (chase). Medium and cells are collected, and lipids are extracted in the presence of non-labeled lipid carriers. Lipids are separated by TLC and made visible by exposure to iodine, and the radioactivity associated with phosphatidylcholine and triacylglycerol is determined.

Triacylglycerol and Phosphatidylcholine Mass Secretion from Transfected Cells

The experimental design for determination of the mass of triacylglycerol and phosphatidylcholine secreted is identical to that described above, except that cells are grown in 100 mm diameter dishes, and medium from three dishes is combined. Lipids are extracted by TLC, and the mass of phosphatidylcholine is determined as described in Chalvardjian, A. and Rudnicki, E. (1970) *Anal. Biochem.* 36:225-226. The mass of triacylglycerol is determined according to the methods of Snyder, F. and Stephens, N. ((1959) *Biochim. Biophys. Acta* 34:244-245) using trioleoylglycerol as an authentic standard.

Determination of Intracellular and Secreted Triacylglycerol Mass

Cells (e.g., freshly prepared primary rat hepatocytes seeded at (5-6)×10$^6$ cells/60 mm diameter dish; McArdle RH7777 cells at 80% confluency; or HepG2 cells) are incubated for 12 hours in their respective growth media supplemented with 0.375 mM oleate/0.5% BSA. Cells are then washed with DMEM and incubated for 2 hours with DMEM containing 0.375 mM oleate/0.5% BSA. The media are then collected and triacylglycerol mass is analyzed (triacylglycerol secretion at 2 hours of supplementation with oleate). Cells are washed and incubated for 2 hours with DMEM in the absence of oleate. Medium is removed, the cells washed, and fresh DMEM replenished. The procedure is repeated every 2 hours. Media and cell lipids are extracted and triacylglycerol mass determined as described above.

ApoB Secretion

Cells stably transfected with either pBK-CMV or pBK-CMV containing COE-1 cDNA grown to approximately 70% confluency in 60 mm diameter dishes are incubated for 16 hours with serum-free DMEM. Cells are then incubated for 2 hours with DMEM containing 0.375 mM oleic acid/0.5% BSA, washed for 1 hour with leucine-free medium±oleic acid/BSA and incubated for 2 hours with 2 ml of either leucine-free DMEM containing 0.5% BSA and 250 µCi of [$^3$H]leucine, or leucine-free DMEM containing 0.375 mM oleic acid/0.5% BSA and 250 µCi [$^3$H]leucine. Medium is removed and briefly centrifuged to remove cellular debris. A 0.1 ml aliquot of 10×immunoprecipitation buffer (1.5 M NaCl, 0.5 M Tris/HCl, pH 7.4, 50 mM EDTA, 5% (v/v) Triton X-100, 1% (w/v) SDS; Wu, X. et al. (1996) *J. Lipid Res.* 37:1198-1206) is added to the culture medium (0.9 ml containing 1 mM final concentration of benzamidine). Anti (human apoB) IgG (10 µl) is then added. The mixture is incubated for 12 hours at 4° C., then 50 µl of Protein A-Sepharose is added, and the mixture is incubated for 3 more hours. The beads are pelleted by brief centrifugation, washed three times with an excess of immunoprecipitation buffer, then 0.1 µg of rat VLDL protein is added, followed by electrophoresis sample buffer (125 mM Tris/HCl, pH 6.8, 4% SDS, 20% (v/v) glycerol, 10% (v/v) β-mercaptoethanol, 0.02% Bromophenol Blue; Wu et al. (1996) supra). Samples are boiled and electrophoresed through 5% (w/v) polyacrylamide gels containing 0.1% SDS. Gels are silver stained (Rabilloud, T. et al. (1988) *Electrophoresis* 9:288-291), and bands corresponding to apoB48 and apoB100 are excised, dissolved at 60° C. in 0.2 ml of 60% (v/v) perchloric acid followed by 0.4 ml of 30% (v/v) hydrogen peroxide (Mahin, D. T. and Lofberg, R. T. (1966) *Anal. Biochem.* 16:500-509), and the radioactivity associated with apoB48 and apoB100 is determined using Hionic-Fluor scintillation cocktail (Packard Instrument Co., Meriden, Conn., U.S.A.).

For detection of apoB in VLDL, density centrifugation is performed according to Chung et al. ((1980) *J. Lipid Res.* 21:284-291). To 1.2 ml of medium (containing 1 mM benzamidine) are added 100 µl of freshly prepared rat plasma and 0.7 grams KBr (4 M final concentration of KBr, density 1.3 g/ml). The mixture is placed into 5.5 ml Quick-Seal centrifuge tubes (Beckman), carefully overlayed with 0.9% NaCl, and centrifuged for 45 minutes at 41,600 g (65,000 revolutions/minute; VTi 65.2 rotor). Fractions of 0.5 ml are collected from the bottom of the tubes, and the densities are determined. Top fractions containing VLDL have a density of <1.013 g/ml. Fractions are adjusted to 0.9 ml with water, and apoB is immunoprecipitated and analyzed as described above.

Other Methods 7.5 mM oleic acid/10% (w/v) BSA stock solution is prepared by dissolving fatty acid-free BSA in DMEM. The solution is heated to 56° C., added to 0.106 grams oleic acid, stirred until the solution clarifies, and sterilized by filtration.

Protein concentration is determined using the Bio-Rad Protein Assay kit using BSA as a protein standard.

Human 25934

The human 25934 sequence (SEQ ID NO:7), which is approximately 1512 nucleotides long including untranslated regions, contains a predicted methionine-initiated coding sequence of about 990 nucleotides (nucleotides 342-1334 of SEQ ID NO:7; SEQ ID NO:9). The coding sequence encodes a 330 amino acid protein (SEQ ID NO:8).

Human 25934 contains the following regions or other structural features: a desaturase domain located at about amino acid residues 51 to 295 of SEQ ID NO:8; two transmembrane regions at about amino acids 50-93 and 194-235 of SEQ ID NO:8; three cytoplasmic domains at about amino acids 1-49, 94-193, and 236-330 of SEQ ID NO:8; one predicted N-glycosylation site (PS00001) at about amino acids 233 to 236 of SEQ ID NO:8; one predicted cAmp and cGMP dependent protein kinase phosphorylation site (PS00004) at about amino acids 311 to 314 of SEQ ID NO:8; four predicted Protein Kinase C phosphorylation sites (PS00005) at about amino acids 98 to 100, 101 to 103, 255 to 257 and 308 to 310 of SEQ ID NO:8; two predicted Casein Kinase II phosphorylation sites (PS00006) located at about amino acids 138 to 141 and 283-286 of SEQ ID NO:8; four predicted N-myristoylation sites (PS00008) from about amino acids 23 to 28, 40 to 45, 59 to 64, and 88 to 93 of SEQ ID NO:8; one predicted amidation site (PS00009) from about amino acid 170 to 173 of SEQ ID NO:8; and one predicted fatty acid desaturase family 1 signature (PS00476) from about amino acid 268 to 282 of SEQ ID NO:8.

For general information regarding PFAM identifiers, PS prefix and PF prefix domain identification numbers, refer to Sonnhammer et al. (1997) *Protein* 28:405-420.

A plasmid containing the nucleotide sequence encoding human 25934 was deposited with American Type Culture Collection (ATCC), 10801 University Boulevard, Manassas, Va. 20110-2209, on _____ and assigned Accession Number _____. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The 25934 protein contains a significant number of structural characteristics in common with members of the desaturase family.

Based on sequence homology, 25934 polypeptide is predicted to be a member of the desaturase family of enzymes, specifically the stearoyl-Co desaturase family (SCD family, EC 1.14.99.5).

Fatty acid desaturases are critical regulatory enzymes of unsaturated fatty acid biosynthesis and catalyze the conversion of a single bond between two carbon atoms (C—C) to a double bond (C=C) in a fatty acyl chain. The resultant double bond is often referred to as an unsaturated bond. Eukaryotic fatty acid desaturases, typically, are iron containing enzymes that catalyze the NAD-(P)H and $O_2$-dependent introduction of double bonds into methylene-interrupted fatty acid chains. Examination of the deduced amino acid sequence from mammals, fungi, insects, higher plants and cyanobacteria has revealed three regions of conserved primary sequence containing HX(3 or 4)H, HX(2 or 3), and HX(2 or 3)HH. This motif is also present in the bacterial membrane enzymes alkaline hydroxylase (omega-hydroxylase) and xylene monooxygenase.

There are three types of eukaryotic fatty acid desaturases, acyl-CoA, acyl-ACP, and acyl-lipid desaturases (Ntambi et al., Biochem. and Biophys. Res. Com. 266:1-4, 1999). In plants and cyanobacteria, acyl-lipid desaturases catalyzing most desaturation reactions and introduce unsaturated bonds into fatty acids that are in a lipid-bound form. Acyl-ACP desaturases are present in the plastids of plant cells and insert a double bond into fatty acids that are bound to acyl carrier protein (ACP). In animals, yeast and fungal cells, Acyl-CoA introduce unsaturated bonds into fatty acids that are bound to coenzyme A (CoA). A gene cloned from this family is stearoyl-CoA desaturase and this gene has been identified in many organisms including mice, rats, humans, yeast, ovines, and hamsters.

Fatty acid desaturases can introduce an unsaturated bond at a specific position in a fatty acyl chain, for example, at the −6, −9, or −12 position. Desaturases are typically integral membrane proteins induced in the endoplasmic reticulum by dietary manipulations and then rapidly degraded (Ozols, J. (1997) MBC Vol. 8 (11): 2281-2290). Unsaturated fatty acids can be formed from a variety of fatty acids including palmitate and stearate resulting in the formation of unsaturated fatty acids palmitoleate (16:1), and oleate (18:1).

In mammals, the rate limiting step in the biosynthesis of monounsaturated fatty acids is the insertion of an unsaturated bond by stearoyl-CoA desaturase (SCD) in the -9 position of the fatty acid. SCD preferentially catalyzes the synthesis of oleic acid. Oleate enriched low density lipoprotein (LDL) exhibits increased affinity for the vessel wall, and is therefore pro-atherogenic (Rudel, L. L. et al. (1997) J. Clin. Invest. 1:100(1):74-83). SCD involvement in generating atherogenic LDL variants and in regulating triglyceride synthesis is further supported by the finding that polyunsaturated fatty acids (PUFA), which protect against atherosclerosis, negatively regulate the expression of the SCD gene (Rudel, L L et al. (1995) Atheroscler. Thromb. Vasc. Biol. 15(12):2101-10; Ntambi, J M (1999) J. Lipid Res. 40(9): 1549-58). Moreover, a mouse deficient for SCD exhibits significant reduction in triglycerides (Miyazaki, M. et al. (2000) J. Biol. Chem, in press).

SCD enzymes are structurally and functionally homologous to one another, and can convert a single bond to a double bond in a fatty acyl chain. SCD enzymes utilize oxygen and electrons from cytochrome $b_5$ for catalysis. Similar to other enzymes such as ribonucleotide reductases and methane monooxygenases, stearoyl-CoA desaturases can have a conserved iron binding motif which includes eight histidines (Shanklin et al. (1997) *Proc. Natl. Acad. Sci. USA* 94:2981-2986), "H—X(3-4)-H—X(7-41)-H—X(2-3)-H—H—X(61-189)-H—X(2-3)-H—H (SEQ ID NO:11)." The eight histidine residues common to desaturase family members are typically divided among three regions of the protein: region Ia (H—X(3-4)-H); region Ib (the first H—X(2-3)-H—H sequence); and region II (the second H—X(2-3)-H—H sequence) (Shanklin et al. (1994) *Biochemistry* 33:12787-94).

SCDs typically contain two or three long hydrophobic domains termed "transmembrane regions," each of which is capable of spanning the membrane two times (Shanklin et al. (1994) *Biochemistry* 33:12787-94). Because a transmembrane region is capable of traversing the membrane twice, amino acid residues flanking a transmembrane region reside on the same side of the membrane (Stukey et al. (1990) *J. Biol. Chem.* 265:20144-49). Thus, when region I (regions Ia and Ib) and region II are divided by a transmembrane region in a desaturase family member, the regions will typically reside on the same side of the membrane, e.g., the cytoplasmic face of the endoplasmic reticulum membrane.

A 25934 polypeptides include a "desaturase domain" or regions homologous with a "desaturase domain". As used herein, the term "desaturase domain" includes an amino acid sequence of about 25 to 600 amino acid residues in length and having a bit score for the alignment of the sequence to the fatty acid desaturase domain (HMM) of at least 50. Preferably, a desaturase domain includes at least about 50-500 amino acids, more preferably about 100-400 amino acid residues, or about 200-250 amino acids and has a bit score for the alignment of the sequence to the desaturase domain (HMM) of at least 60, 80, 100, 150, 200, 250, 300, 450, 500 or greater.

In a preferred embodiment, 25934 polypeptide or protein has a "desaturase domain" or a region which includes at least about 50-500 amino acids, more preferably about 100-400 amino acid residues, or about 200-250 amino acid residues and has at least about 70% 80% 90% 95%, 99%, or 100% homology with a "desaturase domain," e.g., the desaturase domain of human 25934 (e.g., residues 51-295 of SEQ ID NQ:8). Preferably, the desaturase domain of a 25934 polypeptide includes at least one, two, three, four, five, six, seven and preferably eight conserved histidines. Preferably, the histidines form an eight-histidine motif, which binds two iron atoms in the catalytic center. For example, a 25934 polypeptide contains histidine residues at about amino acids 94, 99, 131, 134, 135, 272, 275, and 276 of SEQ ID NO:8.

To identify the presence of a "desaturase" domain in a 25934 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "desaturase" domain in the amino acid sequence of human 25934 at about residues 51-295 of SEQ ID NO:8 (the identified desaturase consensus domain is set forth in SEQ ID NO:10).

A 25934 family member includes a desaturase domain and optionally also a fatty acid desaturase family 1 signature, i.e., a motif that matches the ProSite motif PS00476, "G-E-X-[FY]—H—N—[FY]—H—H—X—F—P—X-D-Y (SEQ ID NO:12)," e.g., this motif is found at about residues 268 to 282 of SEQ ID NO:8.

In one embodiment, a 25934 protein includes at least one, preferably two, transmembrane regions. As used herein, the term "transmembrane region" includes an amino acid sequence of about 20 amino acid residues in length that spans a phospholipid membrane, e.g., an endoplasmic reticulum membrane, twice. More preferably, a transmembrane region includes about at least 22, 24, 25, 30, 35, 40, 45, 50, 55, 60, 65, or 70 amino acid residues and spans a phospholipid membrane twice. Transmembrane regions are rich in hydrophobic residues, and typically have an a-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane regions are described in, for example, pfam.wustl.edu/cgi-bin/getdesc?name=7tm-1, and Zagotta W. N. et al, (1996) *Annual Rev. Neuronsci.* 19: 235-63, the contents of which are incorporated herein by reference.

In a preferred embodiment, a 25934 polypeptide or protein has at least one transmembrane region or a region which includes at least 20, 22, 24, 25, 30, 35, 40, 45, 50, 55, 60, 65, or 70 amino acid residues and has at least about 60%, 70% 80% 90% 95%, 99%, or 100% homology with a "transmembrane region," e.g., at least one transmembrane region of human 25934 (e.g., amino acid residues 50-93 or 194-235 of SEQ ID NO:8).

In one embodiment, a 25934 protein includes at least one cytoplasmic domain. When located at the N-terminal domain the cytoplasmic domain is referred to herein as an "N-terminal cytoplasmic domain". As used herein, an "N-terminal cytoplasmic domain" includes an amino acid sequence having about 1-200, preferably about 10-100, preferably about 20-90, more preferably about 30-80, more preferably about 35-70, more preferably about 40-60, or even more preferably about 45-55 amino acid residues in length and is located in the cytoplasm of a cell. The C-terminal amino acid residue of a "N-terminal cytoplasmic domain" is adjacent to an N-terminal amino acid residue of a transmembrane region in a 25934 protein. For example, an N-terminal cytoplasmic domain is located at about amino acid residues 1-49 of SEQ ID NO:8.

In a preferred embodiment, a 25934 polypeptide or protein has at least one N-terminal cytoplasmic domain or a region which includes at least about 5, preferably about 40-60, or even more preferably about 45-55 amino acid residues and has at least about 60%, 70% 80% 90% 95%, 99%, or 100% homology with an "N-terminal cytoplasmic domain," e.g., at least one N-terminal cytoplasmic domain of human 25934 (e.g., residues 1-49 of SEQ ID NO:8).

In another embodiment, a 25934 protein includes a "cytoplasmic loop" in the sequence of the protein. As used herein, a "cytoplasmic loop" includes an amino acid sequence having a length of at least about 10, preferably about 20-250, preferably about 30-150, more preferably about 80-120 amino acid residues and is located within the cytoplasm of a cell. Accordingly, the N-terminal amino acid residue of a "cytoplasmic loop" is adjacent to a C-terminal amino acid residue of a transmembrane region and the C-terminal residue of a "cytoplasmic loop" is adjacent to a N-terminal amino acid residue of a transmembrane region in a 25934 protein. For example, a cytoplasmic loop is found at about amino acid residues 94-193 of SEQ ID NO:8.

In a preferred embodiment, a 25934 polypeptide or protein has a cytoplasmic loop or a region which includes at least about 10, preferably about 20-250, preferably about 30-150, more preferably about 80-120 amino acid residues and has at least about 60%, 70% 80% 90% 95%, 99%, or 100% homology with an "cytoplasmic loop," e.g., the cytoplasmic loop of human 25934 (e.g., residues 94-193 of SEQ ID NO:8).

In another embodiment, a 25934 protein includes a "C-terminal cytoplasmic domain", also referred to herein as a C-terminal cytoplasmic tail, in the sequence of the protein. As used herein, a "C-terminal cytoplasmic domain" includes an amino acid sequence having a length of at least about 30, preferably about 50-150, preferably about 60-200, more preferably about 80-110 amino acid residues and is located within the cytoplasm of a cell. Accordingly, the N-terminal amino acid residue of a "C-terminal cytoplasmic domain" is adjacent to a C-terminal amino acid residue of a transmembrane region in a 25934 protein. For example, a C-terminal cytoplasmic domain is found at about amino acid residues 236-330 of SEQ ID NO:8.

In a preferred embodiment, a 25934 polypeptide or protein has a C-terminal cytoplasmic domain or a region which includes at least about 30, preferably about 50-150, preferably about 60-200, more preferably about 80-110 amino acid residues and has at least about 60%, 70% 80% 90% 95%, 99%, or 100% homology with an "C-terminal cytoplasmic domain," e.g., the C-terminal cytoplasmic domain of human 25934 (e.g., residues 236-330 of SEQ ID NO:8).

25934 polypeptides of the invention include 25934 fragments which include: all or part of a hydrophobic sequence e.g., all or part of the sequence from about residue 71 to about residue 91 of SEQ ID NO:8; all or part of a hydrophilic fragment; or other fragments that include a cysteine or a glycosylation site.

A multiple sequence alignment of the 25934 amino acid sequence with the human (SEQ ID NO:13), rat (SEQ ID NO:14), and chicken (SEQ ID NO:15) delta-9 desaturase proteins revealed 63.6%, 58.4%, and 58.4% identity between the 25934 amino acid sequence and the chicken, human and rat amino acid sequences, respectively.

As the 25934 polypeptides of the invention may modulate 25934-mediated activities, they may be useful as of for developing novel diagnostic and therapeutic agents for 25934-mediated or related disorders, as described below.

As used herein, a "25934 activity", "biological activity of 25934" or "functional activity of 25934", refers to an activity exerted by a 25934 protein, polypeptide or nucleic acid molecule on e.g., a 25934-responsive cell or on a 25934 substrate, e.g., a protein substrate, as determined in vivo or in vitro. In one embodiment, a 25934 activity is a direct activity, such as an association with a 25934 target molecule. A "target molecule" or "binding partner" is a molecule with which a 25934 protein binds or interacts in nature. In an exemplary embodiment, the binding partner is a fatty acid, e.g., myristic, palmitic or stearic acid. The 25934 proteins of the present invention can have one or more of the following activities: (1) catalyzing the formation of a double bond, preferably, at positions up to 9 carbons from the carboxyl end of a molecule, e.g., a fatty acid, such as a polyunsaturated fatty acid; (2) modulating the synthesis of monounsaturated fatty acids, e.g., modulating the synthesis of a fatty acid synthesized in an animal, e.g., oleic acid, palmitoyl- and stearoyl-CoA; (3) modulating the desaturation of a fatty acid, e.g., a polyunsaturated fatty acids; (4) modulating cellular lipid composition, e.g., modulating the ratio of saturated and unsaturated fatty acids; (5) modulating the energy state of adipocytes; (6) modulating membrane fluidity; (7) modulating lipid storage; (8) modulating proliferation and/or differentiation; (9) modulating lipoprotein (e.g., LDL) composition and/or concentration; (10) regulating triglyceride synthesis; (11) altering the HDL/LDL ration; or (12) modulating fatty acid metabolism.

Based on the above-described sequence similarities, the 25934 molecules of the present invention are predicted to have similar biological activities as other desaturase family members, and in particular, stearoyl CoA desaturases (SCD). For example, the 25934 polypeptide or a domain therein, e.g., desaturase domain, may function to catalyze the conversion of a single bond between two carbon atoms (C—C) to a double bond (C═C) in a fatty acid chain. This modification is expected to occur at the n9 position of the fatty acid. Desaturases are predicted to contribute to an unfavorable LDL content state, e.g., by increasing LDL-oleate, which is atherogenic (Rudel, L L. et al. (1997) J. Clin Invest. 1:100(1):74-83) as well as by playing a role in triglyceride metabolism and/or biosynthesis. As shown by TAQMAN™ analysis, Niacin treatment in the marmoset model results in significant repression of 25934 in the liver. Niacin has been shown to alter the composition of LDL and HDL to a favorable state, to cause a significant reduction in triglycerides, and to increase HDL concentration (Goldberg, A. (2000) Am. J. Cardiol. 85(9): 1100-5. Moreover, a mouse deficient for SCD exhibits significant reduction in triglycerides (Miyazaki, M. et al. (2000) J. Biol. Chem. 275(39):30132-8). Accordingly, the 25934 molecules can act-as novel diagnostic targets and therapeutic agents for controlling disorders associated with abnormal or aberrant desaturase activity and/or triglyceride levels. In particular, it is predicted that targeting the inhibition of 25934 nucleic acids and polypeptides will results in the favorable modification, and possible reduction, of LDL content and/or reduction of triglycerides. Thus, the 25934 molecules can act as novel targets for treating and/or diagnosing fatty acid metabolic disorders (e.g., desaturation of fatty acids) such as obesity and/or diabetes and more generally, cardiovascular disorders.

The term "cardiovascular disorders" or "disease" includes heart disorders, as well as disorders of the blood vessels of the circulation system caused by, e.g., abnormally high concentrations of lipids in the blood vessels.

In some embodiments, the therapeutic and prophylactic uses of the compositions of the invention, further include the administration of cholesterol lowering agents as a combination drug therapies. The term "combination therapy" as used herein refers to the administration to a subject (concurrently or sequentially) of two or more cholesterol lowering agents. Current combination therapy therapies using combinations of niacin and statins are being used with positive results to treat hyperlipidemia (Guyton, J R. (1999) Curr Cardiol Rep. 1(3): 244-250; Otto, C. et al. (1999) Internist (Berl) 40(12):1338-45). Other useful drug combinations include those derived by addition of fish oil, bile acid binding resins, or stanol esters, as well as nonstatin combinations susn as niacin-resin or fibrate-niacin (Guyton, J R. (1999) supra). For examples of dosages and administration schedules of the cholesterol lowering agents, the teachings of Guyton, J R. (1999) supra, Otto, C. et al. (1999) supra, Guyton, J R et al. (1998) Am J Cardiol 82(12A):82U-86U; Guyton, J R et al. (1998) Am J Cardiol. 82(6):737-43; Vega, G L et al. (1998) Am J. Cardiol. 81(4A): 36B-42B; Schectman, G. (1996) Ann Intern Med. 125(12): 990-1000; Nakamura, H. et al. (1993) Nippon Rinsho 51(8): 2101-7; Goldberg, A. et al. (2000) Am J Cardiol 85(9):1100-5; Morgan, J M et al. (1996) J Cardiovasc. Pharmac. Ther. 1(3):195-202; Stein, E A et al. (1996) J Cardiovasc Pharmacol Ther 1(2): 107-116; and Goldberg, A C (1998) Am J Cardiol 82(12A):35U-41U, are expressly incorporated by reference.

The 25934 molecules can also be used to treat, diagnose or prevent lipid disorders. Examples of lipid disorders include those disorders which affect fatty acid metabolism. Fatty acids are synthesized from acetyl-CoA, which is derived from carbohydrate, protein and other non-lipid sources, and the pathway produces saturated fatty acids, predominantly palmitic acid (10:0). In mammals, the fatty acids may be elongated and desaturated. Desaturation is catalyzed by desaturases which function by inserting one or more double bonds at positions up to 9 carbons from the carboxyl end of a fatty acid molecule.

The degree of fatty acid desaturation in cell membrane lipids determines membrane fluidity. The activity of the desaturase enzyme is critical for maintaining the ratio of saturated and unsaturated fatty acids in cell membranes. Alterations in this ratio can, e.g., alter the physical properties of membranes. Moreover, alterations in the ratio of fatty acids have been implicated in a range of diseases including diabetes, obesity, hypertension, cancer, developmental disorders, immune disorders and neurological and the above-described heart diseases. For example, tumor tissue and virus-transformed cells have a higher content of unsaturated fatty acids, especially oleic acid. Such shifts increase the metabolic rates of many lipid-dependent enzymes and are associated with a higher capacity for cell division.

As assessed by TAQMAN™ analysis, the 25934 mRNA is found in the brain, ovary, kidney and liver, therefore the molecules of the invention can be used to develop novel agents or compounds to treat, prevent and/or diagnose disorders involving aberrant activities of those cells. For example, the molecules of the invention can be used to treat, present and/or diagnose neurological disorders, brain disorders, ovarian disorders, kidney disorders and liver disorders, as described below.

Identification and Characterization of Human 25934 cDNA

The human 25934 sequence (SEQ ID NO:7), which is approximately 1512 nucleotides long including untranslated regions, contains a predicted methionine-initiated coding sequence of about 990 nucleotides (nucleotides 342 to 1334 of SEQ ID NO:7; SEQ ID NO:9). The coding sequence encodes a 330 amino acid protein (SEQ ID NO:8).

Tissue Distribution of 25934 mRNA

Endogenous human 25934 gene expression was determined using the Perkin-Elmer/ABI 7700 Sequence Detection System which employs TAQMAN™ technology. To determine the level of 25934 in various human tissues a primer/probe set was designed using Primer Express (Perkin-Elmer) software and primary cDNA sequence information. Total RNA was prepared from a series of human tissues using an RNEASY™ kit from Qiagen. First strand cDNA was prepared from 1 µg total RNA using an olign-dT primer and SUPERSCRIPT II™ reverse transcriptase (Gibco/BRL). cDNA obtained from approximately 50 ng total RNA was used per TAQMAN™ reaction.

25934 mRNA levels were analyzed in a variety of samples isolated from the human fetal heart, spinal cord, brain (cortex, hypothalamus, glial cells), ovary, kidney, liver, endothelial cells and smooth muscle cells (SMC). The highest relative 25934 mRNA expression, i.e., greater than 200 relative units, was observed in spinal cord, brain and ovary. High level mRNA expression, i.e., greater than 100 relative units was observed in the kidney, endothelial cells and human umbilical vein endothelial cells (HUVEC). Expression in liver (a target organ for 25934) was positive but lower relative to other tissues The relative 25934 mRNA expression levels were determined using an expanded TAQMAN™ panel of human liver tissues and then this panel was used to compare the expression of 25934 mRNA and stearoyl CoA desaturase (SCD) mRNA. Expression of 25934 mRNA in human liver is equivalent to the relative expression of the known SCD gene.

Further TAQMAN™ analyses also demonstrate an inhibition of 25934 mRNA expression in the marmoset animal model. Niacin treatment in the marmoset model results in significant repression of 25934 in the liver.

Tissue Distribution of 50365 mRNA by TAQMAN™ Analysis

Human 26335 (DHY)

The present invention is based, at least in part, on the discovery of novel molecules, referred to herein as "26335", "dehydratase" or "DHY" nucleic acid and protein molecules, which are novel members of a family of enzymes possessing dehydratase activity. These novel molecules are capable of deaminating serine or threonine to pyruvate or 2-oxobutyrate, respectively, by catalyzing a two-step reaction of dehydration of the amino acid, followed by hydrolysis of the resulting imine. These novel molecules may thus play a role in or function in a variety of cellular processes, e.g., cellular proliferation, growth, differentiation, migration, and inter- or intra-cellular communication.

The biosynthesis and metabolism of amino acids is of critical importance in many metabolic and catabolic pathways in cells, and is fundamental to the production of cellular proteins. A wide array of enzymes facilitate the synthesis, interconversion, and degradation of amino acids, including transaminases, oxidases, reductases, dehydrogenases, and kinases, among many others. One such family of enzymes, the serine and threonine dehydratases, catalyze the irreversible deamination of serine or threonine to pyruvate or 2-oxobutyrate, respectively.

The reaction mechanism for these enzymes has been characterized (Snell and Di Mari (1970) The Enzymes (Boyer, P. D., ed.), Academic Press: $3^{rd}$ ed. Vol. 2: 335-370; and Ogawa et al. (1989) *Biochim. Biophys. Acta* 996: 139-141). First, a Schiff base is formed between a pyridoxal-5' phosphate cofactor and a specific lysine residue which is strictly conserved within the serine and threonine dehydratase family. A new Schiff base is subsequently formed between the cofactor and the hydroxyamino acid by transimination, catalyzing the removal of the α-proton through stabilization of the resulting carbanion by the planar π-system of the prosthetic group. The hydroxyl group is eliminated, and the resultant enamine is freed by a second transimination. A tautomerization step results in the formation of a ketimine, which hydrolyses to the 2-oxoacid and ammonia (Gabowski et al. (1993) *Trends in Biological Sciences* 18: 297-300). A subclass of the serine dehydratases found in anaerobic bacteria substitutes an iron-sulfur cofactor for pyridoxal-5'-phosphate, and exhibits an altered reaction mechanism with similarities to the mechanism of aconitase (Hofmeister et al. (1993) *Eur J Biochem* 215(2):341-9). Threonine dehydratases, in general, are able to deaminate either threonine or serine, while the serine dehydratases have been found to be specific for the deamination of serine (Grabowski et al. (1992) *Eur. J. Biochem.* 199:89-94; and Alfoldi et al. (1968) *J. Bacteriol.* 96:1512-1518).

Members of the serine and threonine dehydratase family are found in nearly all organisms, from bacteria to yeast to mammals. Alignments of the amino acid sequences of family members from disparate organisms have revealed two conserved regions, termed C1 and C2. The conserved C1 domain is located approximately 50 amino acid residues from the N-terminus of the enzyme, and includes the consensus sequence (G)S(F)K(I)RG (Datta et al. (1987) *Proc. Natl. Acad. Sci. USA* 84: 393-397). This region of the protein has been shown to bind the cofactor, pyridoxal-5'-phosphate, at the conserved lysine residue (Schlitz and Schmitt (1981) *FEBS Lett.* 134:57-62). Conserved region C2 is located in the central region of the amino acid sequences of these enzymes, and is predicted to have a beta sheet-coil-beta sheet structure (Datta et al., supra). C2 is rich in glycine, and is thought to be involved in the catalytic activity of the enzymes (Marceau et al. (1988) *J. Biol. Chem.* 263: 16926-16933).

As used herein, the term "dehydratase" includes a molecule which is involved in the metabolism and catabolism of biochemical molecules necessary for energy metabolism, for intra- or intercellular signaling, and for metabolism or catabolism of metabolically important biomolecules. Typically, dehydratases are involved in the deamination of amino acids, e.g., serine or theronine. Examples of dehydratases include serine and threonine dehydratases. Thus, the DHY molecules of the present invention provide novel diagnostic targets and therapeutic agents to control dehydratase-associated disorders.

As used herein, a "dehydratase-associated disorder" includes a disorder, disease or condition which is caused or characterized by a misregulation (e.g., downregulation or upregulation) of dehydratase activity. Misregulation of dehydratase activity can result in the overproduction or lack of production of one or more amino acids or biologically important metabolic precursor molecules (e.g., pyruvate or 2-oxobutyrate), and, by extension, aberrant metabolite, energy molecules, and/or protein production in the cell as a whole. Proteins produced by the cell not only include those involved in normal cellular functioning (e.g., enzymes, receptors, chaperoning, and transcription factors), but also important signaling molecules (e.g., growth factors, cytokines, and neuropeptides). Dehydratase-associated disorders, therefore, can detrimentally affect cellular functions such as cellular proliferation, growth, differentiation, or migration, inter- or intracellular communication; and tissue function, such as cardiac function or musculoskeletal function. Examples of dehydratase-associated disorders include cellular proliferation, growth, differentiation, or migration disorders, CNS disorders, cardiovascular disorders and disorders affecting tissues in which DHY protein is expressed.

As used herein, a "dehydratase-mediated activity" includes an activity which involves the deamination of one or more amino acids, e.g., threonine or serine. Dehydratase-mediated activities include the production of biochemical molecules necessary for energy metabolism, for intra- or intercellular signaling (e.g., the production of growth factors), and for metabolism or catabolism of metabolically important biomolecules (e.g., isoleucine and protein production).

The family of DHY proteins comprises at least one "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19: 235-263, the contents of which are incorporated herein by reference. Amino acid residues 67-83, 167-187, 270-288, and 295-311 of the native DHY protein are predicted to comprise transmembrane domains. Accordingly, DHY proteins having at least 50-60% homology, preferably about 60-70%, more preferably about 70-80%, or about 80-90% homology with a transmembrane domain of human DHY are within the scope of the invention.

In another embodiment, a DHY molecule of the present invention is identified based on the presence of a "serine/threonine dehydratase pyridoxal-phosphate attachment site" in the protein or corresponding nucleic acid molecule. As used herein, the term "serine/threonine dehydratase pyridoxal-phosphate attachment site" includes a protein domain having an amino acid sequence of about 10-20 amino acid residues. Preferably, a serine/threonine dehydratase pyridoxal-phosphate attachment site has about 14 residues and the following consensus sequence: [DESH]-x(4,5)-[STVG]-x-[AS]-[FYI]-K-[DLIFSA]-[RVMF]-[GA[-[LIVMGA] (SEQ ID NO:19) (Datta et al. (1987) *Proc. Natl. Acad. Sci. USA* 84:393-397; and Ogawa et al. (1989) *Biochim. Biophys. Acta* 996:139-141). To identify the presence of a serine/threonine dehydratase pyridoxal-phosphate attachment site in a DHY protein, and make the determination that a protein of interest has a particular profile, the amino acid sequence of the protein may be searched against a database of known protein domains (e.g., the ProSite database). The serine/threonine dehydratase pyridoxal-phosphate attachment site has been assigned ProSite accession number PS00165. A search was performed against the ProSite database resulting in the identification of a serine/threonine dehydratase pyridoxal-phosphate attachment site in the amino acid sequence of human DHY (SEQ ID NO:17) at about residues 39-52 of SEQ ID NO:17.

In another embodiment, a DHY molecule of the present invention is identified based on the presence of a "serine/threonine dehydratase domain" in the protein or corresponding nucleic acid molecule. As used herein, the term "serine/threonine dehydratase domain" includes a protein domain having an amino acid sequence of about 200-400 amino acid residues and a bit score of about 50, 60, 70, 80, 90, 100, 110, 120, 130, 140, 150, 160, 170, 180, 190, 200, 210, or 220 or more. Preferably, a serine/threonine dehydratase domain includes at least about 250-350, or more preferably about 301 amino acid residues, and a bit score of at least 229. To identify the presence of a serine/threonine dehydratase domain in a DHY protein, and make the determination that a protein of interest has a particular profile, the amino acid sequence of the protein may be searched against a database of known protein domains (e.g., the HMM database). A search was performed against the HMM database resulting in the identification of a serine/threonine dehydratase domain in the amino acid sequence of human DHY (SEQ ID NO:17) at about residues 11-311 of SEQ ID NO:17.

In another embodiment, a DHY molecule of the present invention is identified based on the presence of a "pyridoxal phosphate-dependent lyase synthase domain" in the protein or corresponding nucleic acid molecule. As used herein, the term "pyridoxal phosphate-dependent lyase synthase domain" includes a protein domain having an amino acid sequence of about 200-300 amino acid residues and having a bit score for the alignment of the sequence to the pyridoxal phosphate-dependent lyase synthase domain of at least 10, 20, 30, 40, 50, 60, 70, 80 or higher. Preferably, a pyridoxal phosphate-dependent lyase synthase domain includes at least about 240-275, or more preferably about 265 amino acid residues, and has a bit score for the alignment of the sequence to the pyridoxal phosphate-dependent lyase synthase domain of at least 88. The pyridoxal phosphate-dependent lyase synthase domain has been assigned ProDom entry 206. To identify the presence of a pyridoxal phosphate-dependent lyase synthase domain in a DHY protein, and to make the determination that a protein of interest has a particular profile, the amino acid sequence of the protein may be searched against a database of known protein domains (e.g., the ProDom database) using the default parameters. A search was performed against the ProDom database resulting in the identification of a pyridoxal phosphate-dependent lyase synthase domain in the amino acid sequence of human DHY (SEQ ID NO:17) at about residues 18-282 of SEQ ID NO:17.

In a preferred embodiment, the DHY molecules of the invention include at least one or more of the following domains: a transmembrane domain, a serine/threonine dehydratase pyridoxal-phosphate attachment site, a serine/threonine dehydratase domain, and/or a pyridoxal phosphate-dependent lyase synthase domain.

Isolated proteins of the present invention, preferably DHY proteins, have an amino acid sequence sufficiently identical to the amino acid sequence of SEQ ID NO:17, or are encoded by a nucleotide sequence sufficiently identical to SEQ ID NO:16 or 18. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical.

As used interchangeably herein, an "DHY activity", "biological activity of DHY" or "functional activity of DHY", refers to an activity exerted by a DHY protein, polypeptide or nucleic acid molecule on a DHY responsive cell or tissue, or on a DHY protein substrate, as determined in vivo, or in vitro, according to standard techniques. In one embodiment, a DHY activity is a direct activity, such as an association with a DHY-target molecule. As used herein, a "target molecule" or "binding partner" is a molecule with which a DHY protein binds or interacts in nature, such that DHY-mediated function is achieved. A DHY target molecule can be a non-DHY molecule or a DHY protein or polypeptide of the present invention (e.g., pyridoxal-5'-phosphate). In an exemplary embodiment, a DHY target molecule is a DHY ligand (e.g., serine or threonine). Alternatively, a DHY activity is an indirect activity, such as a cellular signaling activity mediated by interaction of the DHY protein with a DHY ligand. The biological activities of DHY are described herein. For example, the DHY proteins of the present invention can have one or more of the following activities: 1) modulate metabolism and catabolism of biochemical molecules necessary for energy production or storage (e.g., amino acids, such as serine or threonine); 2) modulate intra- or intercellular signaling; 3) modulate metabolism or catabolism of metabolically important biomolecules; 4) modulate cellular growth and differentiation; 5) modulate cellular proliferation; and 6) modulate production of growth factors and cytokines.

Accordingly, another embodiment of the invention features isolated DHY proteins and polypeptides having a DHY activity. Other preferred proteins are DHY proteins having one or more of the following domains: a transmembrane domain, a serine/threonine dehydratase pyridoxal-phosphate attachment site, a serine/threonine dehydratase domain, and/or a pyridoxal phosphate-dependent lyase synthase domain and, preferably, a DHY activity.

Additional preferred proteins have one or more of the following domains: a transmembrane domain, a serine/threonine dehydratase pyridoxal-phosphate attachment site, a serine/threonine dehydratase domain, and/or a pyridoxal phosphate-dependent lyase synthase domain, and are, preferably, encoded by a nucleic acid molecule having a nucleotide sequence which hybridizes under stringent hybridization conditions to a nucleic acid molecule comprising the nucleotide sequence of SEQ ID NO:16 or 18.

Isolation of the 26335 or DHY cDNA

The invention is based, at least in part, on the discovery of a human gene encoding a novel protein, referred to herein as DHY. The entire sequence of human clone Fbh26335 was determined and found to contain an open reading frame termed human "26335" or "DHY", set forth in SEQ ID NO:16 and SEQ ID NO:18. The human DHY gene, which is approximately 1327 nucleotides in length, encodes a protein having a molecular weight of approximately 36.2 kD, which is approximately 329 amino acid residues in length and which is set forth in SEQ ID NO:17. The coding region (open reading frame) of SEQ ID NO:16, is set forth as SEQ ID NO:18.

Analysis of the Human DHY Molecule

The amino acid sequence of human DHY was analyzed using the program PSORT to predict the localization of the protein within the cell. This program assesses the presence of different targeting and localization amino acid sequences within the query sequence. The results of the analysis show that human DHY (SEQ ID NO:17) may be localized to the cytoplasm, to the mitochondrion, to golgi, to the endoplasmic reticulum, extracellular to the cell or to the cell wall, to vacuoles, to the nucleus, or to secretory vesicles.

A search of the amino acid sequence of DHY was performed against the MEMSAT database. This search resulted in the identification of four transmembrane domains in the amino acid sequence of human 26335 or DHY (SEQ ID NO:17) at about residues 67-83, 167-187, 270-288, and 295-311.

A search of the amino acid sequence of DHY was also performed against the ProSite database. This search resulted in the identification of a "serine/threonine dehydratase pyridoxal-phosphate attachment site" in the amino acid sequence of DHY (SEQ ID NO:17) at about residues 39-52.

A search of the amino acid sequence of DHY was also performed against the HMM database. This search resulted in the identification of a "serine/threonine dehydratase domain" in the amino acid sequence of DHY (SEQ ID NO:17) at about residues 11-311 (score=229.5).

A search of the amino acid sequence of DHY was also performed against the ProDom database. This search resulted in the identification of a "pyridoxal phosphate-dependent lyase synthase domain" in the amino acid sequence of human DHY (SEQ ID NO:17) at about residues 18-282 (score=88).

Tissue Distribution of Human 26335 or DHY mRNA using TaqMan™ Analysis

Highest expression of DHY mRNA was detected in HMVECL, U937/A10P10, bronchial epithelium, astrocytes, primary osteoblasts, keratinocytes, bronchial epithelium mix (BEA8-2B), congestive heart failure (CHF) heart tissue, the pituitary gland, fetal kidney tissue, fetal liver tissue, mesangial, T24Ctl, T24 (treated), adrenal gland tissue, Burkitt's Lymphoma tissue, mammary epithelium, WT LNCap+ casodex, A549 IL-1, SCC25 CDDP-tongue squamous cell carcinoma tissue, testes, K563 (red blood cell line), A459 control (random-primed), liver tissue, prostate tissue, normal colon tissue, HMC-1 (mast cell line), normal megakarocytes, colon to liver metastasis (CHT128), colon to liver metastasis (CHT133), normal breast tissue, PTH osteo, lung squamous cell carcinoma tissue PIT299, and d8 dendritic cells.

Lesser expression was also detected in HUVECL, HL60/S, prostate epithelium, coronary smooth muscle cells, fetal lung tissue, fetal thymus tissue, congestive heart failure (CHF) heart tissue, prostate smooth muscle tissue, thyroid tissue, LPS 24 hour osteoblasts, uterine smooth muscle tissue (treated), bronchial smooth muscle tissue, umbilical smooth muscle tissue (treated), A2780 WT, fetal liver tissue, fetal skin, fetal adrenal gland tissue, midterm placental tissue, lung carcinoma tissue, embryonic keritinocytes, testes, skin, adipose, placental tissue (random-primed), kidney tissue (random-primed), HPK (random primed), salivary gland, heart tissue, the thymus, stomach tissue, spleen tissue, small intestine tissue, normal breast epithelia, normal ovarian epithelia, colon carcinoma tissue, ovarian ascites, serum starved embryonic lung tissue, lung squamous cell carcinoma tissue, brain subcortical white matter, normal prostate tissue (ziplox), HUVEC L (umbilical endothelium).

No expression was detected in U937/A10p50, CaCo, Hela cells, HL60/Adr, fetal brain tissue, melanocytes, cerebellum, aortic endothelial cells, prostate fibroblast tissue, mammary gland tissue, natural killer cells, LPS 1 hr. osteoblasts, LPS 6 hr. osteoblasts, WT LNCap+ testosterone, A2780ADR, fetal spleen tissue, the esophagus, p65 con +/+, p65 IL-1 +/+, pulmonary artery smooth muscle tissue, erythroleukemia cells, SCC25 WT-tongue squamous cell carcinoma tissue, fetal hypothalamus, T cells (CD3 treated), T cells (CD3 IL-4/IL-10 treated), T cells (CD3 IFNg/TFNa treated), trachea tissue, ME180 IL-1 cervical carcinoma tissue, ME 180 control, MCP-1 mast cell line, HPKII, lung tissue (random primed), heart tissue (random primed), fetal brain tissue (random primed), testes (random primed), RAJI (Burkitt's lymphoma B cell), ST 486 (lymphoma B cell), HL60 (acute promyelocytic leukemia), umbilical cord smooth muscle tissue (treated, random primed), uterine smooth muscle (treated, random primed), mammary gland tissue (random primed), small intestine tissue (random primed), fetal liver tissue (random primed), skeletal liver tissue (random primed), stomach tissue (random primed), spleen tissue (random primed), liver tissue (random primed), brain tissue (random primed), uterine tissue, uterine tissue (random primed), thymus tissue (random primed), 9 week fetus, lung tissue, skeletal muscle, retinal pigmentosa epithelial tissue, retinal tissue, bone marrow, Th-1 induced T cell, Th-2 induced T cell, colon carcinoma tissue (NDR 109), colon carcinoma tissue (NDR82), fetal dorsal spinal cord tissue, lung adenocarcinoma tissue (PIT245), megakaryocytes, BMCD34+, IBD colon tissue, cervical cancer tissue, spinal cord, dorsal root ganglia, and ovarian epithelium tumor tissue.

Human 50365

The human 50365 sequence (SEQ ID NO:20, as recited below), which is approximately 3669 nucleotides long including untranslated regions, contains a predicted methionine-initiated coding sequence of about 2754 nucleotides, including the termination codon. The coding sequence encodes a 917 amino acid protein (SEQ ID NO:21, as recited below).

Human 50365 contains the following regions or other structural features: two hexokinase domains located at about amino acids 16 to 463 and 464 to 910 of SEQ ID NO:21, the latter of which includes a predicted hexokinase signature domain (PFAM Accession Number PS00378) from about amino acid residue 597 to about amino acid residue 622 of SEQ ID NO:21; two N-glycosylation sites (PS00001) from about amino acid 208 to about 211, and from about amino acid 655 to about 658, of SEQ ID NO:21; one glycosaminoglycan attachment site (PS00002) from about amino acid 896 to about 899 of SEQ ID NO:21; one cAMP- and cGMP-dependent protein kinase site (PS00004) from about amino acid 500 to 503 of SEQ ID NO:21; twelve protein kinase C phosphorylation sites (PS00005) from about amino acid 172 to 174, 379 to 381, 449 to 451, 508 to 510, 523 to 525, 547 to 549, 551 to 553, 772 to 774, 791 to 793, 826 to 828, 877 to 879, and 896 to 898, of SEQ ID NO:21; thirteen casein kinase II sites (PS00006) from about amino acid 35 to 38, 114 to 117, 161 to 164, 243 to 246, 275 to 278, 364 to 367, 569 to 572, 625 to 628, 722 to 725, 726 to 729, 787 to 790, 810 to 813, and 877 to 880, of SEQ ID NO:21; two tyrosine kinase phosphorylation sites (PS00007) from about amino acid 20 to 27, and 490 to 497, of SEQ ID NO:21; twenty-five N-myristylation sites (PS00008) from about amino acid 74 to 79, 151 to 156, 166 to 171, 179 to 184, 212 to 217, 227 to 232, 233 to 238, 299 to 304, 317 to 322, 348 to 353, 360 to 365, 411 to 416, 448 to 453, 518 to 523, 589 to 594, 613 to 618, 659 to 664, 674 to 679, 680 to 685, 746 to 751, 779 to 784, 807 to 812, 834 to 839, 858 to 863, and 895 to 900, of SEQ ID NO:21; and two amidation sites (PS00009) from amino acid 100 to 103, and amino acid 547 to 550 of SEQ ID NO:21.

Human 50365 is predicted to be a soluble, cytoplasmic polypeptide.

For general information regarding PFAM identifiers, PS prefix and PF prefix domain identification numbers, refer to Sonnhammer et al. (1997) *Protein* 28:405-420.

The 50365 protein contains a significant number of structural characteristics in common with members of the hexokinase family. Hexokinases are a family of sugar phosphorylating enzymes which carry out the phosphorylation of hexoses, for example, glucose, mannose, fructose, sorbitol and glucosamine, at the 6'-position. The phosphoryl donor can be MgATP, ITP, or dATP. Both α- and β-D-hexoses can be phosphorylated, although with different kinetic constants.

Four major isoenzymes are found in vertebrates: types I, II, III, and IV. The liver hexokinase isoenzyme (type IV) is also misleadingly known as glucokinase, and is expressed only in the liver and pancreatic β-cells. This isoenzyme has an important role in modulating insulin secretion. Structurally, the enzymes typically include a small N-terminal hydrophobic region, followed by two similar hexokinase domains of about 450 residues each. The second such region has catalytic activity, while the first has a regulatory role.

Hexokinases are present in nearly all cells. These enzymes have been identified as important for normal glycolytic activity. Irregularities in their function can lead to disorders such as diabetes and hemolytic anemia arising from hexokinase deficiency.

A 50365 polypeptide can include a "hexokinase domain" or regions homologous with a "hexokinase domain". Type I, II, and III mammalian hexokinase polypeptides typically include two hexokinase domains. Each domain can form a structural unit that includes features of an α/β sandwich. Each domain can include amino acids with regulatory and/or catalytic functions, e.g., including a pocket for ATP and hexose substrates.

As used herein, the term "hexokinase domain" includes an amino acid sequence of about 300 to about 600 amino acid residues in length and having a bit score for the alignment of the sequence to the hexokinase domain (HMM) of at least 300. Preferably, a hexokinase domain includes at least about 350 to about 500 amino acids, more preferably about 400 to about 490 amino acid residues and has a bit score for the alignment of the sequence to the hexokinase domain (HMM) of at least 500, 600, 700, 800 or greater. The hexokinase domain (HMM) has been assigned the PFAM Accession PF00349.

In a preferred embodiment 50365 polypeptide or protein has a "hexokinase domain" or a region which includes at least about 500 to about 1200, more preferably about 550 to about 1100 or about 600 to about 1000 amino acid residues and has at least about 60%, 70% 80% 90% 95%, 99%, or 100% homology with a "hexokinase domain," e.g., the hexokinase domain of human 50365 (e.g., residues 597 to 622 of SEQ ID NO:21).

Preferably, the hexokinase domain includes a "hexokinase signature domain". This term refers to a protein domain having an amino acid sequence of at least about 15 to about 30 more preferably about 20 to about 30 or about 24 to about 28 amino acid residues which includes the following amino acid sequence: "L-G-F-T-F—S—F—P—C-x-Q-x-S—I-x-x-G-x-L-I-x-W-T-K-G-F" (SEQ ID NO:24). Preferably, a 50365 polypeptide or protein has a "hexokinase signature domain" or a region which includes and has at least about 60%, 70% 80% 90% 95%, 99%, or 100% homology with a "hexokinase signature domain," e.g., the hexokinase signature domain of human 50365 (e.g., residues 597 to 622 of SEQ ID NO:21).

To identify the presence of a "hexokinase" domain in a 50365 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of two "hexokinase domains" in the amino acid sequence of human 50365 at about residues 16 to 463 and 464 to 910 of SEQ ID NO:21, the identified hexokinase domain consensus sequence is set forth in SEQ ID NO:23.

A 50365 family member can include at least one hexokinase domain. Furthermore, a 50365 family member can include at least one, preferably two N-glycosylation sites (PS00001); at least one glycosaminoglycan attachment site (PS00002); at least one cAMP- and cGMP-dependent protein kinase site (PS00004); at least one, two, three, four, five, six, seven, eight, nine, ten, eleven, or preferably twelve protein kinase C phosphorylation sites (PS00005); at least one, two, three, four, five, six, seven, eight, nine, ten, eleven, twelve, or preferably thirteen predicted casein kinase II phosphorylation sites (PS00006); at least one, or preferably two tyrosine kinase phosphorylation sites (PS00007); at least one, two, three, four, five, six, seven, eight, nine, ten, eleven, twelve, thirteen, fourteen, fifteen, sixteen, seventeen, eighteen, twenty, twenty-three, or preferably twenty-five predicted N-myristylation sites (PS00008); and at least one, preferably two amidation sites (PS00009).

50365 polypeptides of the invention include fragments which include: all or part of a hydrophobic sequence, e.g., the sequence of from about amino acid residue 365 to about amino acid residue 380, or from about amino acid residue 645 to about amino acid residue 655, of SEQ ID NO:21; all or part of a hydrophilic sequence, e.g., the sequence of from about amino acid residue 98 to about amino acid residue 120, or from about amino acid residue 715 to about amino acid residue 745 of SEQ ID NO:21.

As the 50365 polypeptides of the invention may modulate 50365-mediated activities, they may be useful as of for developing novel diagnostic and therapeutic agents for 50365-mediated or related disorders, as described below.

As used herein, a "50365 activity", "biological activity of 50365" or "functional activity of 50365", refers to an activity exerted by a 50365 protein, polypeptide or nucleic acid molecule on e.g., a 50365-responsive cell or on a 50365 substrate, e.g., a protein substrate, as determined in vivo or in vitro. In one embodiment, a 50365 activity is a direct activity, such as an association with a 50365 target molecule. A "target molecule" or "binding partner" is a molecule with which a 50365 protein binds or interacts in nature. In an exemplary embodiment, is a 50365 substrate, e.g., an aldohexose or ketohexose (e.g., glucose, mannose, fructose, sorbitol and glucosamine), or a phosphate-containing molecule, e.g., ITP, dATP, or MgATP as phosphoryl donor.

A 50365 activity can also be an indirect activity, e.g., a cellular signaling activity mediated by interaction of the 50365 protein with a 50365 substrate. For example, the 50365 proteins of the present invention can have one or more of the following activities: (1) it can catalyze the phosphorylation of a sugar, e.g., an aldohexoses and a ketohexoses (e.g., glucose, mannose, fructose, sorbitol and glucosamine); (2) it can catalyze sugar metabolism; (3) it can transfer a phosphate from a phosphate donor (e.g., ATP) to a sugar, e.g., an aldohexoses and a ketohexoses (e.g., glucose, mannose, fructose, sorbitol and glucosamine) to form a phosphorylated sugar, e.g., glucose-6-phosphate; (4) it can modulate glycolytic activities in a cell or tissue, e.g., a tissue in which a 50365 protein is expressed, e.g., muscle tissue and colon; or (5) it can modulate sugar metabolism; and/or (6) it can modulate cellular proliferation and/or differentiation.

Based on its structural features, the 50365 molecules of the present invention can have similar biological activities as hexokinase family members.

Expression of 50365 mRNA is modulated in a number of cancerous tissue samples. For example, 50365 mRNA is elevated in a number of colon tumors and colonic liver metastases (see, e.g., section entitled "Tissue Distribution of 50365 mRNA by TaqMan Analysis" below). Thus, the 50365 molecules can act as novel diagnostic targets and therapeutic agents for controlling disorders of neoplasia, e.g., cancer, a cell differentiative disorder, or a cell proliferative disorder as well as colon and lung disorders. 50365 molecules can also act as indicators and an agent for metabolic disorders, e.g., disorders of sugar metabolism and glycolysis.

Identification and Characterization of Human 50365 cDNA

The human 50365 nucleic acid sequence is recited as follows:

(SEQ ID NO:20)
CCACGCGTCCGGCCTGGACTGGAAGCGTGCAACACTCCAGAGTCGTAGGA

GTGAACACTGCACAGGAATCTCTGCCCATCTCAGGAGAAACCAAACTTGG

GGAAAATGTTTGCGGTCCACTTGATGGCATTTTACTTCAGCAAGCTGAAG

GAGGACCAGATCAAGAAGGTGGACAGGTTCCTGTATCACATGCGGCTCTC

CGATGACACCCTTTTGGACATCATGAGGCGGTTCCGGGCTGAGATGGAGA

AGGGCCTGGCAAAGGACACCAACCCCACGGCTGCAGTGAAGATGTTGCCC

ACCTTCGTCAGGGCCATTCCCGATGGTTCCGAAAATGGGGAGTTCCTTTC

CCTGGATCTCGGAGGGTCCAAGTTCCGAGTGCTGAAGGTGCAAGTCGCTG

AAGAGGGGAAGCGACACGTGCAGATGGAGAGTCAGTTCTACCCAACGCCC

AATGAAATCATCCGCGGGAACGGCATAGAGCTGTTTGAATATGTAGCTGA

CTGTCTGGCAGATTTCATGAAGACCAAAGATTTAAAGCATAAGAAATTGC

CCCTTGGCCTAACTTTTTCTTTCCCCTGTCGACAGACTAAACTGGAAGAG

GGTGTCCTACTTTCGTGGACAAAAAAGTTTAAGGCACGAGGAGTTCAGGA

CACGGATGTGGTGAGCCGTCTGACCAAAGCCATGAGAAGACACAAGGACA

TGGACGTGGACATCCTGGCCCTGGTCAATGACACCGTGGGGACCATGATG

ACCTGTGCCTATGACGACCCCTACTGCGAAGTTGGTGTCATCATCGGAAC

TGGCACCAATGCGTGTTACATGGAGGACATGAGCAACATTGACCTGGTGG

AGGGCGACGAGGGCAGGATGTGCATCAACACAGAGTGGGGGCCTTCGGG

GACGACGGGCCCTGGAGGACATTCGCACTGAGTTCGACAGGGAGCTGGA

CCTCGGCTCTCTCAACCCAGGAAAGCAACTGTTCGAGAAGATGATCAGTG

GCCTGTACCTGGGGGAGCTTGTCAGGCTTATCTTGCTGAAGATGGCCAAG

```
GCTGGCCTCCTGTTTGGTGGTGAGAAATCTTCTGCTCTCCACACTAAGGG
CAAGATCGAAACACGGCACGTGGCTGCCATGGAGAAGTATAAAGAAGGCC
TTGCTAATACAAGAGAGATCCTGGTGGACCTGGGTCTGGAACCGTCTGAG
GCTGACTGCATTGCCGTCCAGCATGTCTGTACCATCGTCTCCTTCCGCTC
GGCCAATCTCTGTGCAGCAGCTCTGGCGGCCATCCTGACACGCCTCCGGG
AGAACAAGAAGGTGGAACGGCTCCGGACCACAGTGGGCATGGACGGCACC
CTCTACAAGATACACCCTCAGTACCCAAAACGCCTGCACAAGGTGGTGAG
GAAACTGGTCCCAAGCTGTGATGTCCGCTTCCTCCTGTCAGAGAGTGGCA
GCACCAAGGGGCCGCCATGGTGACCGCGGTGGCCTCCCGCGTGCAGGCC
CAGCGGAAGCAGATCGACAGGGTGCTGGCTTTGTTCCAGCTGACCCGAGA
GCAGCTCGTGGACGTGCAGGCCAAGATGCGGGCTGAGCTGGAGTATGGGC
TGAAGAAGAAGAGCCACGGGCTGGCCACGGTCAGGATGCTGCCCACCTAC
GTCTGCGGGCTGCCGGACGGCACAGAGAAGGAAGTTTCTCGCCCTGGA
TCTTGGGGGAACCAACTTCCGGGTCCTCCTGGTGAAGATCAGAAGTGGAC
GGAGGTCAGTGCGAATGTACAACAAGATCTTCGCCATCCCCCTGGAGATC
ATGCAGGGCACTGGTGAGGAGCTCTTTGATCACATTGTGCAGTGCATCGC
CGACTTCCTGGACTACATGGGCCTCAAGGGAGCCTCCCTACCTTTGGGCT
TCACATTCTCATTTCCCTGCAGGCAGATGAGCATTGACAAGGGAACACTC
ATAGGGTGGACCAAAGGTTTCAAGGCCACTGACTGTGAAGGGGAGGACGT
GGTGGACATGCTCAGGGAAGCCATCAAGAGGAGAAACGAGTTTGACCTGG
ACATTGTTGCAGTCGTGAATGATACAGTGGGGACCATGATGACCTGTGGC
TATGAAGATCCTAATTGTGAGATTGGCCTGATTGCAGGAACAGGCAGCAA
CATGTGCTACATGGAGGACATGAGGAACATCGAGATGGTGGAGGGGGTG
AAGGGAAGATGTGCATCAATACAGAGTGGGGAGGATTTGGAGACAATGGC
TGCATAGATGACATCCGGACCCGATACGACACGGAGGTGGATGAGGGGTC
CTTGAATCCTGGCAAGCAGAGATACGAGAAAATGACCAGTGGGATGTACT
TGGGGGAGATTGTGCGGCAGATCCTGATCGACCTGACCAAGCAGGGTCTC
CTCTTCCGAGGGCAGATTTCAGAGCGTCTCCGGACCAGGGGCATCTTCGA
AACCAAGTTCCTGTCCCAGATCGAAAGCGATCGGCTGGCCCTTCTCCAGG
TCAGGAGGATTCTGCAGCAGCTGGGCCTGGACAGCACGTGTGAGGACAGC
ATCGTGGTGAAGGAGGTGTGCGGAGCCGTGTCCCGGCGGGCGGCCCAGCT
CTGCGGTGCTGGCCTGGCCGCTATAGTGGAAAAAAGGAGAGAAGACCAGG
GGCTAGAGCACCTGAGGATCACTGTGGGTGTGGACGGCACCCTGTACAAG
CTGCACCCTCACTTTTCTAGAATATTGCAGGAAACTGTGAAGGAACTAGC
CCCTCGATGTGATGTGACATTCATGCTGTCAGAAGATGGCAGTGGAAAAG
GGGCAGCACTGATCACTGCTGTGGCCAAGAGGTTACAGCAGGCACAGAAG
GAGAACTAGGAACCCCTGGGATTGACCTGATGCATCTTGGATACTGAAC
AGCTTTTCCTCTGGCAGATCAGTTGGTCAGAGACCAATGGGCACCCTCCT
GGCTGACCTCACCTTCTGGATGGCCGAAAGAGAACCCCAGGTTCTCGGGT
ACTCTTAGTATCTTGTACTGGATTTGCAGTGACATTACATGACATCTCTA
TTTGGTATATTTGGGCCAAAATGGGCCAACTTATGAAATCAAAGTGTCTG
TCCTGAGAGATCCCCTTTCAACACATTGTTCAGGTGAGGCTTGAGCTGTC
AATTCTCTATGGCTTTCAGTCTTGTGGCTGCGGGACTTGGAAATATATAG
AATCTGCCCATGTGGCTGGCAGGCTGTTTCCCCATTGGGATGCTTAAGCC
ATCTCTTATAGGGGATTGGACCCTGTACTTGTGGATGAACATTGGAGAGC
AAGAGGAACTCACGTTATGAACTAGGGGGATCTCATCTAACTTGTCCTTA
ACTTGCCATGTTGACTTCAAACCTGTTAAGAGAACAAAGACTTTGAAGTA
TCCAGCCCCAGGGTGCAGAGAGGTTGATTGCCAGGGAGCACTGCAGGAAT
CATTGCATGCTTAAAGCGAGTTATGTCAGCACCCTGTAGGATTTTGTTCC
TTATTAAGTGTGTGCCATGTGGTGGGGTGCTGTCTGGGGCATCTGTTTTT
CATTTTGCCTGTGGTTTGTGTTGCAGSTGTTGATAGTTGTTTTAAGGATT
GTTAGGTATAGGAAATCCAGTAAATTAATAAAAAAATTTTGATTTTCCAA
TAAAAAAAAAAAAAAAAAA.
```

The human 50365 sequence (SEQ ID NO:20) is approximately 3669 nucleotides long. The nucleic acid sequence includes an initiation codon (ATG) and a termination codon (TAA) which are underscored and bolded above. The region between and inclusive of the initiation codon and the termination codon is a methionine-initiated coding sequence of about 2754 nucleotides (SEQ ID NO:22), including the termination codon. The coding sequence encodes a 917 amino acid protein (SEQ ID NO:21), which is recited as follows:

```
                                            (SEQ ID NO:21)
MFAVHLMAFYFSKLKEDQIKKVDRFLYHMRLSDDTLLDIMRRFRAEMEKG

LAKDTNPTAAVKMLPTFVRAIPDGSENGEFLSLDLGGSKFRVLKVQVAEE

GKRHVQMESQFYPTPNEIIRGNGIELFEYVADCLADFMKTKDLKHKKLPL

GLTFSFPCRQTKLEEGVLLSWTKKFKARGVQDTDVVSRLTKAMRRHKDMD

VDILALVNDTVGTMMTCAYDDPYCEVGVIIGTGTNACYMEDMSNIDLVEG

DEGRMCINTEWGAFGDDGALEDIRTEFDRELDLGSLNPGKQLFEKMISGL

YLGELVRLILLKMAKAGLLFGGEKSSALHTKGKIETRHVAAMEKYKEGLA

NTREILVDLGLEPSEADCIAVQHVCTIVSFRSANLCAAALAAILTRLREN

KKVERLRTTVGMDGTLYKIHPQYPKRLHKVVRKLVPSCDVRFLLSESGST

KGAAMVTAVASRVQAQRKQIDRVLALFQLTREQLVDVQAKMRAELEYGLK

KKSHGLATVRMLPTYVCGLPDGTEKGKFLALDLGGTNFRVLLVKIRSGRR

SVRMYNKIFAIPLEIMQGTGEELFDHIVQCIADFLDYMGLKGASLPLGFT

FSFPCRQMSIDKGTLIGWTKGFKATDCEGEDVVDMLREAIKRRNEFDLDI

VAVVNDTVGTMMTCGYEDPNCEIGLIAGTGSNMCYMEDMRNIEMVEGGEG

KMCINTEWGGFGDNGCIDDIRTRYDTEVDEGSLNPGKQRYEKMTSGMYLG

EIVRQILIDLTKQGLLFRGQISERLRTRGIFETKFLSQIESDRLALLQVR

RILQQLGLDSTCEDSIVVKEVCGAVSRRAAQLCGAGLAAIVEKRREDQGL

EHLRITVGVDGTLYKLHPHFSRILQETVKELAPRCDVTFMLSEDGSGKGA

ALITAVAKRLQQAQKEN.
```

Tissue Distribution of 50365 mRNA by TaqMan Analysis

Endogenous human 50365 gene expression was determined using the Perkin-Elmer/ABI 7700 Sequence Detection System which employs TAQMAN™ technology.

To determine the level of 50365 in various human tissues a primer/probe set was designed. Total RNA was prepared from a series of human tissues using an RNEAST™ kit from Qiagen. First strand cDNA was prepared from 1 pg total RNA using an oligo-dT primer and SUPERSCRIPT II™ reverse transcriptase (Gibco/BRL). cDNA obtained from approximately 50 ng total RNA was used per TAQMAN™ reaction. Tissues tested include the human tissues and several cell lines shown in Tables 2 and 3 below. 50365 mRNA was detected in colon and liver tissue, and upregulated in colonic liver metastases (Table 2). In addition, 50365 mRNA was also detectable in adenomas and adenocarcinomas. 50365 expression was also found to a lesser extent in some lung tumor and ovary tumor tissues (Table 3).

TABLE 2

| Tissue Type | Expression |
| --- | --- |
| CHT 410 Colon Normal | 0.32 |
| CHT 425 Colon Normal | 0.41 |
| CHT 371 Colon Normal | 1.06 |
| PIT 281 Colon Normal | 0.00 |
| NDR 211 Colon Normal | 0.22 |
| CHT 122 Adenomas | 0.21 |
| CHT 887 Adenomas | 1.65 |
| CHT 414 Colonic Adenocarcinoma-B | 0.47 |
| CHT 841 Colonic Adenocarcinoma-B | 0.05 |
| CHT 890 Colonic Adenocarcinoma-B | 0.58 |
| CHT 910 Colonic Adenocarcinoma-B | 3.85 |
| CHT 377 Colonic Adenocarcinoma-B | 0.00 |
| CHT 520 Colonic Adenocarcinoma-C | 0.80 |
| CHT 596 Colonic Adenocarcinoma-C | 0.77 |
| CHT 907 Colonic Adenocarcinoma-C | 2.41 |
| CHT 372 Colonic Adenocarcinoma-C | 2.09 |
| NDR 210 Colonic Adenocarcinoma-C | 0.95 |
| CHT 1365 Colonic Adenocarcinoma-C | 2.54 |
| CLN 740 Liver Normal | 0.00 |
| CLN 741 Liver Normal | 0.00 |
| NDR 165 Liver Normal | 0.00 |
| NDR 150 Liver Normal | 0.14 |
| PIT 236 Liver Normal | 0.00 |
| CHT 1878 Liver Normal | 0.00 |
| CHT 119 Colon Liver Metastasis | 7.52 |
| CHT 131 Colon Liver Metastasis | 0.77 |
| CHT 218 Colon Liver Metastasis | 5.45 |
| CHT 739 Colon Liver Metastasis | 10.53 |
| CHT 755 Colon Liver Metastasis | 3.64 |
| CHT 215 Colon Abdominal Metastasis | 0.24 |
| PIT 337 Colon Normal | 0.29 |
| CHT 807 Colonic Adenocarcinoma-B | 61.64 |
| CHT 382 Colonic Adenocarcinoma-B | 57.11 |
| CHT 077 Colon Liver Metastasis | 180.49 |

The mRNA expression data for 50365 mRNA tabulated in Table 2 indicate that 50365 expression is upregulated in some adenomas and adenocarcinomas, and in most colonic liver metastases (see "Relative Expression" values). Relative expression in Table 2 is relative to expression of β2-macroglobulin.

TABLE 3

| Tissue Type | Expression |
| --- | --- |
| PIT 400 Breast Normal | 0.00 |
| PIT 372 Breast Normal | 0.00 |
| CHT 559 Breast Normal | 0.00 |

TABLE 3-continued

| Tissue Type | Expression |
| --- | --- |
| MDA 236-Breast Tumor: PD-IDC(ILC?) | 0.00 |
| MDA 304 Breast Tumor: MD-IDC | 0.00 |
| CHT 2002 Breast Tumor: IDC | 0.00 |
| CHT 562 Breast Tumor: IDC | 0.00 |
| NDR 138 Breast Tumor ILC (LG) | 0.00 |
| CHT 1841 Lymph node (Breast Metastasis) | 0.00 |
| PIT 58 Lung (Breast Metastasis) | 0.00 |
| CHT 620 Ovary Normal | 0.00 |
| PIT 208 Ovary Normal | 0.00 |
| CLN 012 Ovary Tumor | 0.00 |
| CLN 07 Ovary Tumor | 0.05 |
| CLN 17 Ovary Tumor | 1.38 |
| MDA 25 Ovary Tumor | 0.00 |
| MDA 216 Ovary Tumor | 0.00 |
| PIT 298 Lung Normal | 0.00 |
| MDA 185 Lung Normal | 0.00 |
| CLN 930 Lung Normal | 0.00 |
| MPI 215 Lung Tumor—SmC | 0.00 |
| MDA 259 Lung Tumor-PDNSCCL | 0.00 |
| CHT 832 Lung Tumor-PDNSCCL | 0.97 |
| MDA 262 Lung Tumor—Small Cell Carcinoma | 0.00 |
| CHT 793 Lung Tumor-Adenocarcinoma | 0.03 |
| CHT 331 Lung Tumor-Adenocarcinoma | 0.00 |
| CHT 405 Colon Normal | 0.16 |
| CHT 523 Colon Normal | 0.65 |
| CHT 371 Colon Normal | 2.38 |
| CHT 382 Colon Tumor: MD | 0.88 |
| CHT 528 Colon Tumor: MD | 7.84 |
| CLN 609 Colon Tumor | 2.21 |
| NDR 210 Colon Tumor: MD-PD | 0.84 |
| CHT 340 Colon-Liver Metastasis | 3.23 |
| NDR 100 Colon-Liver Metastasis | 1.11 |
| PIT 260 Liver Normal (female) | 1.17 |
| CHT 1653 Cervix Squamous CC | 0.00 |
| CHT 569 Cervix Squamous CC | 0.00 |
| A24 HMVEC-Arr | 0.00 |
| C48 HMVEC-Prol | 0.00 |
| Pooled Hemangiomas | 0.00 |
| HCT116N22 Normal Oxygenation | 0.97 |
| HCT116H22 Hypoxic | 0.00 |

50365 mRNA was analyzed by TaqMan in a number of cell lines derived from normal and tumor cells (Table 3). Relative expression in Table 3 is relative to expression of β2-macroglobulin. Elevated 50365 mRNA expression levels were detected in some colon cell lines, e.g., normal colon, colon tumor; colonic liver metastases; some lung cell lines, e.g., lung tumor-PDNSCCL (poorly differentiated non-small cell carcinoma of the lung), lung tumor-adenocarcinoma; and an ovary tumor cell line. 50365 mRNA was also detected under normal oxygenation conditions.

Human 21117

The human 21117 sequence (SEQ ID NO:25), which is approximately 3544 nucleotides long including untranslated regions, contains a predicted methionine-initiated coding sequence of about 1998 nucleotides (nucleotides 589 to 2586 of SEQ ID NO:25; SEQ ID NO:27). The coding sequence encodes a 665 amino acid protein (SEQ ID NO:26).

Human 21117 contains the following regions or other structural features: a dual specificity phosphatase catalytic domain (PF00782) located from about amino acid residue 158 to 297 of SEQ ID NO:26; a rhodanese-like domain (PF00581) located from about amino acid residue 11 to 131 of SEQ ID NO:26; and one tyrosine specific protein phosphatase active site (PS00383) at amino acids 242 to 254 of SEQ ID NO:26.

The 21117 protein additionally includes: six predicted N-glycosylation sites (PS00001) at amino acids 38 to 41, 49 to 52, 190 to 193, 212 to 215, 300 to 303, and 640 to 643 of SEQ ID NO:26; two predicted cAMP and cGMP-dependent protein kinase phosphorylation sites (PS00004) at amino acids 277 to 280 and 624 to 627 of SEQ ID NO:26; twelve predicted Protein Kinase C sites (PS00005) at about amino acids 12 to 14, 23 to 25, 72 to 74, 82 to 84, 393 to 395, 439 to 441, 473 to 475, 481 to 483, 486 to 488, 596 to 598, 604 to 606, and 609 to 611 of SEQ ID NO:26; thirteen casein kinase II phosphorylation sites (PS00006) at amino acids 21 to 24, 91 to 94, 214 to 217, 266 to 269, 369 to 372, 421 to 424, 434 to 437, 458 to 461, 508 to 511, 589 to 592, 612 to 615, 617 to 620, and 642 to 645 of SEQ ID NO:26; and seven predicted N-myristoylation sites (PS00008) from about amino acid 134 to 139, 247 to 252, 329 to 334, 382 to 387, 520 to 525, 574 to 579, and 650 to 655 of SEQ ID NO:26.

21117 polypeptides of the invention include 21117 fragments that include: all or part of a hydrophobic sequence e.g., all or part of the sequence from about residue 91 to about residue 106 of SEQ ID NO:26; and/or all or part of a hydrophilic sequence e.g., all or part of the sequence from about residue 592 to about residue 633 of SEQ ID NO:26. Other fragments include a cysteine residue or a glycosylation site.

Human 38692

The human 38692 sequence (SEQ ID NO:28), which is approximately 1114 nucleotides long including untranslated regions, contains a predicted methionine-initiated coding sequence of about 672 nucleotides (nucleotides 89 to 760 of SEQ ID NO:28; SEQ ID NO:30). The coding sequence encodes a 223 amino acid protein (SEQ ID NO:29).

Human 38692 contains the following regions or other structural features: a dual specificity phosphatase catalytic domain (PF00782) located from about amino acid residue 28 to 173 of SEQ ID NO:29; one predicted Protein Kinase C phosphorylation site (PS00005) at about amino acids 201 to 203 of SEQ ID NO:29; one predicted casein kinase II phosphorylation site (PS0006) at amino acids 205 to 208 of SEQ ID NO:29; two predicted N-myristoylation sites (PS00008) from about amino acid 123 to 128 and 197 to 202 of SEQ ID NO:29; and two tyrosine kinase phosphorylation sites (PS00007) at amino acids 15 to 23 and 142 to 149 of SEQ ID NO:29.

38692 polypeptides of the invention include 38692 fragments that include: all or part of a hydrophobic sequence, e.g., all or part of the sequence from about residue 31 to about residue 41 of SEQ ID NO:29; and/or all or part of a hydrophilic fragment e.g., all or part of the sequence from about residue 200 to about residue 212 of SEQ ID NO:29. Other fragments include cysteine residues.

21117 and 38692 Dual Specificity Phosphatase Proteins

The intracellular phosphorylation of proteins is critical for a plethora of regulatory and signalling pathways in eukaryotic cells. Phosphorylation events can govern a wide range of cellular processes, including cell proliferation, differentiation, transcription, and morphology. An essential component of these signalling pathways is the ability of the cell to desensitize, recycle, and counteract phosphorylation signals. The cell primarily utilizes enzymes, termed phosphatases, which remove the phosphate on tyrosine, serine, and threonine side chains. The protein phosphatases are divided into three groups according to catalytic function: (1) protein phosphatases that dephosphorylate serine and threonine residues; (2) protein phosphatases which dephosphorylate tyrosine residues; and (3) dual specificity protein phosphatases which dephosphorylate serine, threonine and tyrosine residues.

Serine/threonine protein phosphatases are associated with the regulation of cholesterol biosynthesis, glycogen metabolism, muscle contractility, calcium ion channels, protein synthesis, regulation of the G2 to M transition of the cell cycle, regulation of glycolysis (6-phosphofructo-2-kinase and pyruvate kinase), glycogenolysis (phosphorylase kinase subunit), gluconeogenesis (fructose-2,6-bisphosphatase and pyruvate kinase), amino-acid degradation (phenylalanine hydroxylase), lipid metabolism (acetyl-CoA carboxylase), catecholamine synthesis (tyrosine hydroxylase) and protein synthesis (elongation factor 2).

Protein tyrosine phosphatases (PTPs) are a family of intracellular and integral membrane phosphatases that dephosphorylate tyrosine residues in proteins. PTPs have been identified in mammals, *Drosophila* and *Schiz. pombe* and are implicated in the control of normal and neoplastic growth and proliferation. They have also been found encoded by plasmids in bacteria of the genus *Yersinia*, where they are implicated in pathogenicity.

Dual specificity phosphatases hydrolyze phosphotyrosine, phosphothreonine, and phosphoserine residues (for a review, see, e.g., Fauman and Saper (1996) *Trends in Biochem.* 21:412). This class of proteins is exemplified by the VH1 or vaccinia virus late H1 gene protein, whose catalytic activity is required for vaccinia virus replication. A human homolog of VH1, VHR, has also been identified. VH1-like dual specificity phosphatase can also include the phosphatases PAC-1 and CL100/MKP-1, hVH-2/MKP-2, hVH-3, MKP-3, MKP-X, MKP-4, hVH-5, and M3/6 proteins. The PAC-1 and CL100 proteins hydrolyze phosphothreonine and phosphotyrosine residues on phosphorylated MAP (mitogen activated protein) kinases. In order to modulate signalling events, the activity and expression of dual specificity phosphatases can be finely regulated. For example, the PAC-1 and CL100 phosphatase can be induced by growth factors (Keyse, S (1995) *Biochim. Biophys. Acta* 1265:152-160).

The 21117 and 38692 proteins contain a significant number of structural characteristics in common with members of the dual specificity phosphatase family.

Dual specificity phosphatase proteins are characterized by a common fold. Examples of members of the dual specificity phosphatase family include MAP kinase phosphatase-1 (MKP-1), which dephosphorylates MAP kinase on both threonine and tyrosine residues and a human, vaccinia H1-related phosphatase (VHR), which also removes the phosphate from phosphothreonine and phosphotyrosine residues. Dual specificity phosphatases are exemplified by the VH1 or vaccinia virus late H1 gene protein, which hydrolyzes both phosphotyrosine, phosphothreonine, and phosphoserine. VH1 catalytic activity is required for viral replication. A human homolog of VH1, VHR, has been identified. The three dimensional structure of this family is based on models from x-ray crystallographic data of protein tyrosine phosphatases, and human VHR. The VHR structure includes a core domain consisting of a five-stranded mixed β-sheet and six α-helices. This structure closely superimposes on the structure of phosphotyrosine protein phosphatases. However, dual specificity phosphatases lack the KNRY motif, and the N-terminal structures of tyrosine protein phosphatases which endow these enzymes with a deep active site specific for aryl phosphates. Thus, dual specificity phosphatases have a shallower active site relative to tyrosine protein phosphatases and can accommodate phosphoserine and phosphothreonine substrates. Even so dual specificity phosphatases can have a greater than 50-fold faster rate of phosphatase activity for phosphotyrosine substrates than phosphothreonine or phosphoserine substrates.

Similar to the broader class of phosphatases, dual specificity phosphatases have a highly conserved active site including three catalytic residues, a cysteine, an arginine, and an aspartic acid. The active site cysteine and arginine are found in the "C—$X_5$—R" motif of the tyrosine phosphatase signature (Prosite PS00383). This motif forms a binding pocket for three of the phosphate oxyanions. The cysteine acts as a nucleophile to accept the $PO_3$ group. The reaction transiently generates a phospho-cysteine intermediate before the phosphate is transferred to water. The active site arginine stabilizes the transition-state by hydrogen bonding to phosphate oxygens. In addition the histidine preceding the active site cysteine and the serine or threonine following the active site arginine are responsible for lowering the $pK_a$ of the cysteine to stabilize a negative charge on the cysteine. The active site aspartic acid accelerates the reaction by donating a protein to generate an uncharged hydroxyl (for a review, see Fauman and Saper (1996) Trends in Biochem. 21:412). A C—$X_5$—R motif is found in the 21117 protein at about amino acids 242 to 254 of SEQ ID NO:26.

The 21117 and 38692 proteins of the present invention show significant homology to members of the dual specificity phosphatase family. Dual specificity phosphatases are known to play critical roles in growth factor signaling. For example, vaccinia H1-related (VHR)-like phosphatases are known to dephosphorylate growth factor receptors and thereby eliminate their signaling. MAP-kinase phosphatases terminate MAP-kinase activity, thus leading to inhibition of growth factor-mediated mitogenic signaling. Thus, dual specificity phosphatases play a key role in inhibiting proliferation and stimulating the differentiation of cells. As the 21117 and 38692 proteins show homology to dual specificity phosphatases, these proteins are likely to be involved in modulating (e.g., inhibiting) the proliferation and (e.g., stimulating) the differentiation of the cells in which they are expressed, e.g., hematopoietic cells such as eythroid cells, myeloid cells, monocytes, or megakaryocytes. Accordingly, the 21117 and 38692 molecules of the invention may be useful for developing novel diagnostic and therapeutic agents for 21117 and 38692-mediated or related disorders, as described below.

A 21117 or 38692 polypeptide of the invention can include a "dual specificity phosphatase catalytic domain" or regions homologous with a "dual specificity phosphatase catalytic domain". As used herein, the term "dual specificity phosphatase catalytic domain" refers to an amino acid sequence having about 50 to 250, preferably about 100 to 200, more preferably about 120 to 160 amino acid residues and having a bit score for the alignment of the sequence to the dual specificity phosphatase domain (HMM) of at least 50, preferably 100, more preferably 120, 200, or more. The dual specificity phosphatase catalytic domain (HMM) has been assigned the PFAM Accession Number PF00782.

A dual specificity phosphatase domain preferably includes the conserved active site residues cysteine and arginine in a C—$X_5$—R motif found at about amino acids 242 to 254 of SEQ ID NO:26 (the 21117 protein). Preferably, a dual specificity phosphatase domain includes a conserved general amino acid, e.g., aspartic acid. For example, a 21117 protein has an aspartic acid located at about residue 213 of SEQ ID NO:26 and a 38692 protein has an aspartic acid located at about residue 89 of SEQ ID NO:29. Typically, dual specificity phosphatases are able to dephosphorylate tyrosine residues and serine/threonine residues.

In a preferred embodiment, a 21117 or 38692 polypeptide or protein has a "dual specificity phosphatase catalytic domain" or a region that includes at least about 50 to 250, preferably about 100 to 200, more preferably about 120 to 160, and even more preferably about 130 to 150 amino acid residues and has at least about 70% 80% 90% 95%, 99%, or 100% homology with a "dual specificity phosphatase catalytic domain," e.g., the dual specificity phosphatase catalytic domain of human 21117 (e.g., residues 158 to 297 of SEQ ID NO:26) or 38692 (e.g., residues 28 to 173 of SEQ ID NO:29).

To identify the presence of a "dual specificity phosphatase catalytic domain" in a 21117 or 38692 protein sequence and to make the determination that a polypeptide or protein of interest has a particular profile, the amino acid sequence of the protein can be searched against a database of HMMs (e.g., the Pfam database, release 2.1) using default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314, the contents of which are incorporated herein by reference. A search was performed against the HMM database resulting in the identification of a "dual specificity phosphatase catalytic domain" e.g., the dual specificity phosphatase catalytic domain of human 21117 (amino acids 158 to 297 of SEQ ID NO:26) or human 38692 (amino acids 28 to 173 of SEQ ID NO:29). The identified dual specificity phosphatase catalytic domain consensus sequences of human 21117 and of human 38692 are set forth in SEQ ID NO:31 and 32, respectively.

Human 21117 also contains a "rhodanese-like" domain (PF00581) from about amino acid 11 to 131 of SEQ ID NO:26. The rhodanese-like domain is occasionally found in a single copy in phosphatases, such as Cdc25 phosphatase, a dual-specificity phosphatase. Rhodanese is about 300 amino acids in length and has a conserved domain at the N-terminus and at the C-terminus. A cysteine residue is part of the active site of the enzyme. In a preferred embodiment, a 21117 polypeptide or protein has a "rhodanese-like domain" or a region that includes at least about 80 to 300 amino acids, preferably about 100 to 150 amino acid residues, and has at least about 70% 80% 90% 95%, 99%, or 100% homology with a "rhodanese-like domain," e.g., the rhodanese-like domain of human 21117 (e.g., residues 11 to 131 of SEQ ID NO:26). A search was performed against the HMM database resulting in the identification of two "rhodanese-like domains" in human 21117 (amino acids 11 to 131 and amino acids 12 to 134 of SEQ ID NO:26). The identified rhodanese-like domain consensus sequences of human 21117 are set forth in SEQ ID NO:33 and 34.

As used herein, a "21117 or 38692 activity", "biological activity of 21117 or 38692" or "functional activity of 21117 or 38692", refers to an activity exerted by a 21117 or 38692 protein, polypeptide or nucleic acid molecule on e.g., a 21117 or 38692-responsive cell or on a 21117 or 38692 substrate, e.g., a protein substrate, as determined in vivo or in vitro. In one embodiment, an 21117 or 38692 activity is a direct activity, such as an association with a 21117 or 38692 target molecule. A "target molecule" or "binding partner" is a molecule with which a 21117 or 38692 protein binds or interacts in nature. A 21117 or 38692 activity can also be an indirect activity, e.g., a cellular signaling activity mediated by interaction of the 21117 or 38692 protein with an 21117 or 38692 receptor.

Based on the above-described sequence similarities, the 21117 or 38692 molecules of the present invention are predicted to have similar biological activities as dual specificity phosphatase family members, probably of the VHR-type. Since VHR-phosphatases inhibit growth factor signaling by dephosphorylating, e.g., growth factor receptors, the 21117 or 38692 molecules of the invention are predicted to have one or more of the following activities: (1) catalyze the removal of a phosphate group attached to a tyrosine residue in a protein target, e.g., a growth factor receptor; (2) catalyze the removal of a phosphate group attached to a serine or threonine residue in a protein e.g., a growth factor receptor; (3) modulate growth factor activity; (4) modulate an intracellular signaling pathway, e.g., a MAP kinase or ERK kinase pathway; (5) modulate (e.g., stimulate) cell differentiation, e.g., differentiation of a 38692- or a 21117-expressing cell, e.g., a breast, colon, lung, or adipose cell, a bone cell, an endothelial cell, a liver cell, or a hematopoietic cell (e.g., a myeloid (neutrophil) cell, a monocyte, an erythroid cell, a bone marrow cell, a CD34-expressing cell, a megakaryocyte); (6) stimulate hematopoiesis; (7) modulate cell proliferation, e.g., proliferation of a 38692- or a 21117-expressing cell, e.g., a breast, colon, lung, or adipose cell, a bone cell, an endothelial cell, a liver cell, or a hematopoietic cell (e.g., a myeloid (neutrophil) cell, a monocyte, an erythroid cell, a bone marrow cell, a CD34-expressing cell, a megakaryocyte); (8) inactivate cell surface growth factor receptors, e.g., tyrosine kinase receptors; or (9) modulate apoptosis, of a cell, e.g., a cancer cell, e.g., a leukemic cell.

As assessed by TAQMAN™ analysis described herein, 38692 mRNA is expressed in hematopoietic cells, and in particular, in erythroid cell lineages, therefore the molecules of the invention can be used to develop novel agents or compounds to treat and/or diagnose disorders involving aberrant activities of those cells e.g., hematopoietic, and in particular, erythroid disorders, as described below. For example, 38692 polypeptide is expressed in megakaryocytes, fetal liver CD34+ cells, erythroid progenitor cells (e.g., bone marrow glycophorin A positive cells (BM GPA+)), and Bone Marrow Glycophorin A (BM GPA) low CD71+.

As used herein, a "CD34-positive cell" refers to a cell that expresses detectable levels of the CD34 antigen, preferably human CD34 antigen. The sequence for human CD34 is provided in SwissProt Accession Number P28906. The CD34 antigen is typically present on immature hematopoietic precursor cells and hematopoietic colony-forming cells in the bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)-positive B- and T-lymphoid precursors in normal bone also are CD34+. The CD34 antigen is typically present on early myeloid cells that express the CD33 antigen, but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early haematopoietic progenitor cells and decreases as the cells mature. The antigen is undetectably on fully differentiated haematopoietic cells. Approximately 60% of acute B-lymphoid leukemia's and acute myeloid leukemia express the CD34 antigen. The antigen is not expressed on chronic lymphoid leukemia (B or T lineage) or lymphomas.

As the 38692 polypeptides of the invention may modulate 38692-mediated activities, they may be useful as of for developing novel diagnostic and therapeutic agents for 38692-mediated or related disorders, e.g., hematopoietic related disorders, or erythroid-associated disorders. As assessed by TAQMAN™ analysis, 38692 is expressed at high levels in fetal liver, HepG2.2.15-A liver cells, and Hep3B hypoxia cells, therefore the molecules of the invention can be used to develop novel agents or compounds to treat and/or diagnose liver related disorders.

Further TAQMAN™ analyses have demonstrated that 21117 mRNA is expressed in normal breast, normal colon, normal adipose tissue, prostate tumor and lung chronic obstructive pulmonary disorder (COPD) tissue. Thus, diagnostic and therapeutic methods of using the 21117 molecules of the invention to treat/diagnose breast, colon, adipose, prostate, and lung disorders are also contemplated by the present invention.

Identification and Characterization of Human 38692 and 21117 cDNA

The human 21117 sequence (SEQ ID NO:25), which is approximately 3544 nucleotides long including untranslated regions, contains a predicted methionine-initiated coding sequence of about 1998 nucleotides (nucleotides 589 to 2586 of SEQ ID NO:25; SEQ ID NO:27). The coding sequence encodes a 666 amino acid protein (SEQ ID NO:26).

The human 38692 sequence (SEQ ID NO:28), which is approximately 1114 nucleotides long including untranslated regions, contains a predicted methionine-initiated coding sequence of about 672 nucleotides (nucleotides 89 to 760 of SEQ ID NO:28; SEQ ID NO:30). The coding sequence encodes a 224 amino acid protein (SEQ ID NO:29).

Tissue Distribution of 38692 or 21117 mRNA

Endogenous human 21117 and 38692 gene expression was determined using the Perkin-Elmer/ABI 7700 Sequence Detection System which employs TAQMAN™ technology.

To determine the level of 21117 mRNA in various human tissues a primer/probe set was designed using Primer Express (Perkin-Elmer) software and primary cDNA sequence information. Total RNA was prepared from a series of tissues using an RNEASY™ kit from Qiagen. First strand cDNA was prepared from 1 μg total RNA using an oligo-dT primer and SUPERSCRIPT II™ reverse transcriptase (Gibco/BRL). cDNA obtained from approximately 50 ng total RNA was used per TAQMAN™ reaction.

21117 mRNA levels were analyzed in a variety of tissue samples, both normal and diseased, including (1) Aorta/normal; (2) Fetal heart/normal; (3) Heart normal; (4) Heart/Coronary heart failure (CHF); (5) Vein/Normal; (6) SMC (Aortic), (7) Spinal cord/Normal; (8) Brain cortex/Normal; (9) Brain hypothalamus/Normal; (10) Glial cells (Astrocytes); (11) Brain/Glioblastoma; (12) Breast/Normal; (13) Breast tumor/IDC; (14) ovary/Normal; (15) ovary/Tumor; (16) Pancreas; (17) Prostate/Normal; (18) Prostate/Tumr; (19) Colon/normal; (20) Colon/tumor; (21) Colon/IBD (inflammatory bowel disease); (22) Kidney/normal; (23) Liver/normal; (24) Liver fibrosis; (25) Fetal Liver/normal; (26) Lung/normal; (27) Lung/tumor; (28) Lung/chronic obstructive pulmonary disease (COPD); (29) Spleen/normal; (30) Tonsil/normal; (31) Lymph node/normal; (32) Thymus/normal; (33) Epithelial Cells (prostate); (34) Endothelial Cells (aortic); (35) Skeletal Muscle/Normal; (36) Fibroblasts (Dermal); (37) Skin/normal; (38) Adipose/Normal; (39) Osteoblasts(primary); (40) Osteoblasts (undifferentiated); (41) Osteoblasts (differentiated); (42) Osteoclasts; (43) Aortic Smooth Muscle Cells (SMC) Early; (44) Aortic SMC Late; (45) Osteoclasts (undiff); (46) shear human umbilical vein endothelial cells (HUVEC). High relative levels of expression were detected in normal colon, normal breast, chronic obstructive pulmonary disease lung tissue, normal adipose tissue, and undifferentiated osteoblasts.

38692 expression was determined by TAQMAN™ assays on mRNA derived from various tissues and cell lines, including (1) Lung; (2) Kidney; (3) Spleen; (4) Fetal Liver; (5) Granulocytes; (6) NHDF resting; (7) NHDF/TGF-treated for 48 hr; (8) NHLF/CTN-treated for 48 hr; (9) NHLF/TGF-treated for 48 hr; (10) NC Heps; (11) Passage Stellates; (12) Liver Pool; (13) LF/CHT 339; (14) LF/NDR 191; (15) LF/NDR 079; (16) Lymph Nodes NDR 173; (17) Tonsils; (18) TH1 24 hr; (19) CD4; (20) CD14 Resting; (21) CD19; (22) CD3 Resting; (23) bone marrow mononuclear cells (BM MNC) LP26; (24) mPB CD34+; (25) adult bone marrow (ABM) CD34+; (26) Cord Blood CD34+; (27) Erythroid; (28) Megakaryocytes LP16; (29) Neutrophils d14; (30) NBM CD15+/CD14−/34+; (31) mBM CD15+/CD11b−; (32) BM/glycophorin A (GPA); (33) Hepatocyte (Hep)G2-A; (34) HepG2.2.15-A; (35) HBV-Liver MAI-1; (36) HL60; (37) leukemia cell line K562; (38) Molt 4; (39) liver cell line Hep3B Nor; (40)Hep3B Hypoxia, as well as various hematopoietic cell lines, including, (1) Lung; (2) Colon; (3) Heart; (4) Spleen; (5) Kidney; (6) Liver NDR 200; (7) Fetal Liver; (8) Skeletal Muscle; (9) m BM (bone marrow) mononuclear cells (MNC); (10) mBM MNC LP7; (11) mBM CD34+ LP92; (12) mobilized peripheral blood (mPB) CD34+ LF41; (13) mPB CD34+ LF48; (14) adult bone marrow (ABM) CD34+ LP91; (15) ABM CD34+ LP29; (16) Cord Blood CD34+ LF109; (17) Fetal Liver CD34+ LP93; (18) Fetal Liver CD34+ LP45, (19) Bone Marrow Glycophorin-A positive (BM GPA+) LP85; (20) BM GPA+ LP34-1; (21) BM GPA low CD71+ LF38; (22) BM GPA low CD71+ LP85-2; (23) mobilized peripheral blood (mPB) CD41+/CD14− LP94; (24) BM CD41+/C D14− LP78; (25) mBM CD15+ LP15; (26) mBM CD15+/CD11b− LP7-4; (27) mBM CD15+/CD11b+ LP15-2; (28) BM CD15+/CD11b− LF80-4; (29) BM CD15+/CD11b− LP23-2; (30) BM CD15+/CD34− LP27-2; (31) BM CD15+/CD34− LP41-1; (32) Erythrocyte (Ery) d6 LP25-1; (33) Ery d6 LP31-1; (34) Ery d10 LP24-4; (35) Ery d12 LF24-8; (36) Ery d12 LF24-9; (37) Ery d14 GPA+ LP31-4; (38) Ery d14 CD36+ LP31-7; (39) Megakaryocyte (Meg) 24 hr LF23-2; (40) Meg 44 hr LF6-2; (41) Meg d7 LP31-2; (42) Meg d12 LF26; (43) Meg d14 LP31-5; (44) Neutrophil d4 LF30; (45) Neutrophil d6 LF26; (46) Neutrophil d6 LP27; (47) Neutrophil d7 LP31-3; (48) Neutrophil d12 LP27; (49) Neutrophil d12 LP26B; (50) Neutrophil d14 LP31-6. In some samples, mRNA expression was detected at the indicated times in culture (e.g., 24 hrs., 48 hrs., days in culture).

Tissue Distribution of 46508 mRNA by TAQMAN™ Analysis

Human 46508

The human 46508 sequence (SEQ ID NO:35), which is approximately 1182 nucleotides long including untranslated regions, contains a predicted methionine-initiated coding sequence of about 684 nucleotides, including the termination codon. The coding sequence encodes a 227 amino acid protein (SEQ ID NO:36).

Human 46508 contains the following regions or other structural features: a peptidyl-tRNA hydrolase domain (PFAM Accession PF01195) located at about amino acid residues 44 to 221 of SEQ ID NO:36; two Protein Kinase C sites (PS00005) at about amino acids 13 to 15, and 150 to 152 of SEQ ID NO:36; two Casein Kinase II sites (PS00006) located at about amino acids 125 to 128, and 194 to 197 of SEQ ID NO:36; seven N-myristoylation sites (PS00008) located at about amino acids 4 to 9, 17 to 22, 23 to 28, 53 to 58, 74 to 79, 149 to 154, and 156 to 161 of SEQ ID NO:36; one amidation site (PS00009) located at about amino acid 40 to 43 of SEQ ID NO:36; and one glycosaminoglycan attachment site (PS00002) located at about amino acids 3 to 6 of SEQ ID NO:36.

For general information regarding PFAM identifiers, PS prefix and PF prefix domain identification numbers, refer to Sonnhammer et al; (1997) *Protein* 28:405-420.

The 46508 protein contains a significant number of structural characteristics in common with members of the peptidyl-tRNA hydrolase family.

Peptidyl-tRNA hydrolases are a family of important enzymes which hydrolyze ester linkages between the peptide moiety and the tRNA of peptidyl-tRNAs (Kössel, H (1969) *Biochim. Biophys. Acta* 204:191-202; Garcia-Villegas, M. R. (1991) *EMBO J.* 10:3549-3555). The esterase activity of peptidyl-tRNA hydrolases cleaves the covalent bond between the nascent peptide and the tRNA. Such cleavage results in the recycling of tRNA. The peptidyl-tRNA hydrolase from *E. coli* is well characterized, and homologous proteins are found in many eubacterial species. In *E. coli*, the gene encoding peptidyl-tRNA hydrolase is essential. Further, the required level of peptidyl-tRNA hydrolase activity for viability is escalated under conditions that increase premature translational termination such as exposure to antibiotics (Menninger and Coleman (1993) *Antimicrob. Agents Chemother.* 37:2027-2029.) and reduced when tRNAs particularly prone to dissociate from the ribosome are supplied in excess (Heurgue-Hamard et al. (1996) *EMBO J.* 15:2826-2833).

The x-ray crystal structure of *E. coli* peptidyl-tRNA hydrolase was determined at high resolution (Schmitt et al. (1997) *EMBO J.* 16:4760-4769). The monomeric protein contains single monomeric α/β globular domain of seven β-strands and six α-helices. The peptidyl-tRNA hydrolase enzyme structure has structural similarity to an aminopeptidase from *Aeromonas proteolytica* (GenPept:640150)(Chevrier, B. et al. (1994) *Structure* 2:283-291) and to a lesser extent to bovine purine nucleoside phosphorylase (GenPept:2624420) (Koellner, G. et al. (1997) *J. Mol. Biol.* 265:202-216.). Genetic data and structural analysis indicate that three residues, asparagine 10, histidine 20, and aspartic acid 93 in the *E. coli* enzyme are critical residues for catalysis. In addition, asparagine 68 and asparagine 114 of the *E. coli* enzyme are poised to make favorable electrostatic contacts with the peptide region of the peptidyl-tRNA substrate whereas arginine 133 of the *E. coli* sequence may contact the tRNA portion of the substrate. The amino acid identities of these positions are conserved in alignments of eubacterial peptidyl-tRNA transferases.

The 46508 polypeptide (SEQ ID NO:36) has the three conserved residues important for catalysis, namely: an asparagine at position 51, a histidine at position 59, and an aspartic acid at position 134 of SEQ ID NO:36. In addition, conserved asparagines and a conserved arginine, residues 68, 114, and 133 of the *E. coli* peptidyl-tRNA hydrolase, respectively, contribute to the specificity of substrate recognition. The 46508 polypeptide (SEQ ID NO:36) also has these three conserved residues, namely, an asparagine at position 109, an asparagine at position 155, and an arginine at position 173 of SEQ ID NO:36.

Cells which utilize the translation machinery more intensely than quiescent cells, e.g. rapidly growing cells, environmentally stressed cells, and virally infected cells, are likely to produce more peptidyl-tRNA substrates. Further, because of the increased translation activity, such cells also require larger tRNA pools than quiescent cells either in their cytoplasm or mitochondria, or both. Accordingly the activity of peptidyl-tRNA hydrolase enzymes may be required by such cells. Thus, inhibition of 46508 activity might be a successful route to treatment of a variety of disorders, including but not limited to, cell proliferation, cell differentiation, viral infection, and metabolism.

A 46508 polypeptide can include a "peptidyl-tRNA hydrolase domain" or regions homologous with a "peptidyl-tRNA hydrolase domain". A 46508 polypeptide can optionally further include at least one glycosaminoglycan attachment site; at least one, preferably two, protein kinase C phosphorylation sites; at least one, preferable two, casein kinase II phosphorylation sites; at least one, two, three, four, five, six, preferably seven, N-myristoylation sites; and at least one amidation site.

As used herein, the term "peptidyl-tRNA hydrolase domain" includes an amino acid sequence of about 160 to 240 amino acid residues in length and having a bit score for the alignment of the sequence to the peptidyl-tRNA hydrolase domain profile (Pfam HMM) of at least 80. Preferably, the peptidyl-tRNA hydrolase domain has an amino acid sequence of about 170 to about 200 amino acids, more preferable about 170 to 190 amino acids, or about 177 amino acids, and has a bit score for the alignment of the sequence to the peptidyl-tRNA hydrolase domain (HMM) of at least 100, preferably of at least 120, more preferably of at least 130 or greater. Preferably, the peptidyl-tRNA hydrolase domain further includes the following highly conserved residues :one, preferably two, more preferably three asparagine residues, a histidine residue, an aspartic acid, and an arginine corresponding respectively to asparagine 51, asparagine 109, asparagine 155, histidine 59, aspartic acid 134, and arginine 173 of SEQ ID NO:36. The peptidyl-tRNA hydrolase domain (HMM) has been assigned the PFAM Accession.

In a preferred embodiment 46508 polypeptide or protein has a "peptidyl-tRNA hydrolase domain" or a region which includes at least about 120 to about 200 amino acids, more preferably about 160 to 190, 170 to 180, or about 177 amino acid residues and has at least about 60%, 70% 80% 90% 95%, 99%, or 100% homology with a "peptidyl-tRNA hydrolase domain," e.g., the peptidyl-tRNA hydrolase domain of human 46508 (e.g., residues 44 to 221 of SEQ ID NO:36).

To identify the presence of a "peptidyl-tRNA hydrolase" domain in a 46508 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314, the contents of which are incorporated herein by reference. A search was performed against the HMM database resulting in the identification of a "peptidyl-tRNA hydrolase" domain in the amino acid sequence of human 46508 at about residues 44 to about 221 of SEQ ID NO:36. The identified peptidyl-tRNA hydrolase domain consensus sequence is set forth as SEQ ID NO:38.

A 46508 family member can include at least one peptidyl-tRNA hydrolase domain or regions homologous with a peptidyl-tRNA hydrolase domain. Furthermore, a 46508 family member can include at least one, preferably two, protein kinase C phosphorylation sites (PS00005); at least one, preferable two, casein kinase II phosphorylation sites (PS00006); at least one, two, three, four, five, six, preferably seven, N-myristoylation sites; and at least one amidation site.

46508 polypeptides of the invention include fragments which include: all or part of a hydrophobic sequence, e.g., the sequence from about amino acid 60 to 70, from about 86 to 102, and from about 189 to 195 of SEQ ID NO:36; all or part of a hydrophilic sequence, e.g., the sequence of from about amino acid 77 to 85, from about 217 to 224 of SEQ ID NO:36, a sequence which includes a Cys, or a glycosylation site, of SEQ ID NO:36.

As the 46508 polypeptides of the invention may modulate 46508-mediated activities, they may be useful as of for developing novel diagnostic and therapeutic agents for 46508-mediated or related disorders, as described below.

As used herein, a "46508 activity", "biological activity of 46508" or "functional activity of 46508", refers to an activity exerted by a 46508 protein, polypeptide or nucleic acid molecule. For example, a 46508 activity can be an activity exerted by 46508 in a physiological milieu on, e.g., a 46508-responsive cell or on a 46508 substrate, e.g., a protein substrate. A 46508 activity can be determined in vivo or in vitro. In one embodiment, a 46508 activity is a direct activity, such as an association with a 46508 target molecule. A "target molecule" or "binding partner" is a molecule with which a 46508 protein binds or interacts in nature. In an other embodiment, 46508 activity can also be an indirect activity, e.g. a cellular signaling activity mediated by interaction of the 46508 protein with a second protein or with a nucleic acid.

The features of the 46508 molecules of the present invention can provide similar biological activities as peptidyl-tRNA hydrolase family members. For example, the 46508 proteins of the present invention can have one or more of the following activities: (1) ability to bind tRNA; (2) ability to bind peptide fragments; (3) ability to bind peptidyl-tRNAs; (4) ability to hydrolyze covalent bond between peptide and tRNA within peptidyl-tRNAs; or (5) ability to modulate translational efficiency. The 46508 polypeptide may perform one or more of these properties in the milieu of the cell cytoplasm and/or of the cell mitochondria.

As shown below, increased 46508 mRNA expression is detected in a variety of malignant and non-malignant tissues, including cardiovascular tissues (e.g., endothelial cells, coronary smooth muscle cells), pancreas, neural tissues (e.g., brain, hypothalamus, DRG), skin, immune, e.g., erythroid cells, as well as a number of primary and metastatic tumors, e.g., ovarian, breast, prostate and lung tumors. Thus, the 46508 molecules can act as novel diagnostic targets and therapeutic agents for controlling disorders of involving aberrant activity of those cells, e.g., cell proliferative disorders (e.g., cancer), cardiovascular disorders, neurological disorders, pain disorders, pancreatic disorders, breast disorders, colon disorders, ovarian disorders, lung disorders, skin and immune, e.g., erythroid, disorders.

High transcriptional expression of 46508 was observed in tumor samples compared to normal organ control samples. For example, high expression was observed in 5/5 primary ovarian tumor samples, 4/4 primary colon tumor samples, 2/2 colon to liver metastases, and 3/6 primary lung tumor samples. Additionally, high expression was observed in proliferating HMVEC cells when compared to arrested HMVEC cells. Therefore, 46508 may mediate or be involved in cellular proliferative and/or differentiative disorders.

Moderate expression of 46508 was observed in normal heart tissue samples, and in both normal and tumor breast tissue samples, and thus 46508 may mediate disorders involving the heart, e.g. cardiovascular disorders; and it may mediate disorders of the breast, e.g, breast disorders. High to moderate expression of 46508 was also observed in normal pancreas tissue, in the skin and in the normal brain cortex and hypothalamus, therefore, 46508 may mediate disorders involving the pancreas, e.g. pancreatic disorders; it may mediate disorders involving the skin, e.g., skin disorders; and it may mediate disorders involving the brain cortex or hypothalamus, e.g. disorders of the brain.

46508 mRNA expression was also detected in the dorsal root ganglia (DRG). Therefore, 46508-associated disorders can detrimentally affect regulation and modulation of the pain response; and vasoconstriction, inflammatory response and pain therefrom. Examples of such disorders in which the 46508 molecules of the invention may be directly or indirectly involved include pain, pain syndromes, and inflammatory disorders, including inflammatory pain.

Normal and tumorous samples of ovarian tissue also showed expression of 46508 mRNA. Various data indicates that 46508 is highly expressed in several ovarian cell lines, including SKOV3/Var, A2780, MDA 2774 and ES-2. Thus 46508 may mediate diseases involving the ovary.

Moderate expression of 46508 mRNA was also noted in normal colon tissue, in normal and tumor prostate samples, in fibrotic liver tissue samples, in both normal and lung tumor samples and high expression was noted in colon tumor samples. Thus 46508 may mediate diseases involving the colon, e.g. colon disorders; it may mediate diseases involving the prostate, e.g. prostate disorders; it may mediate diseases involving the liver, e.g. liver disorders; and it may mediate diseases involving the lung, e.g. lung disorders;

Identification and Characterization of Human 46508 cDNA

The human 46508 sequence (SEQ ID NO:35), which is approximately 1180 nucleotides long, including untranslated regions, contains a predicted methionine-initiated coding sequence of about 684 nucleotides, including the termination codon (nucleotides indicated as "coding" of SEQ ID NO:35; SEQ ID NO:37). The coding sequence encodes a 227 amino acid protein (SEQ ID NO:36).

Tissue Distribution of 46508 mRNA by TaqMan Analysis

Endogenous human 46508 gene expression was determined using the Perkin-Elmer/ABI 7700 Sequence Detection System which employs TAQMAN™ technology.

To determine the level of 46508 in various human tissues a primer/probe set was designed. Total RNA was prepared from a series of human tissues using an RNEASY™ kit from Qiagen. First strand cDNA was prepared from 1 μg total RNA using an oligo-dT primer and SUPERSCRIPT II™ reverse transcriptase (Gibco/BRL). cDNA obtained from approximately 50 ng total RNA was used per TAQMAN™ reaction. Tissues tested include the human tissues and several cell lines shown in Tables 4, 5 and 6.

Table 4 below shows expression of 46508 mRNA in various normal and diseased tissues, detected using TAQMAN™ analysis. The highest transcriptional expression of 46508 was noted in HUVEC cell line, with moderate to high expression found in normal pancreas, brain, hypothalamus, skeletal muscle, DRG (dorsal root ganglion) and skin. Moderate expression also noted in normal and tumor pairs of breast, ovarian, prostate, colon and lung tissue along with fibrotic liver, normal heart and diseased heart (CHF, congestive heart failure) samples.

Table 4. Tissue Distribution of 46508 by TAQMAN™ Analysis

TABLE 4

| Tissue Distribution of 46508 mRNA by TaqMan Analysis | |
|---|---|
| Tissue Type | Expression |
| Artery normal | 8.6685 |
| Aorta diseased | 5.2992 |
| Vein normal | 1.7725 |
| Coronary SMC | 17.1577 |
| HUVEC | 49.0365 |
| Hemangioma | 5.0834 |
| Heart normal | 8.2009 |
| Heart CHF | 7.1393 |
| Kidney | 9.4204 |
| Skeletal Muscle | 16.6308 |
| Adipose normal | 3.9608 |
| Pancreas | 20.3335 |
| primary osteoblasts | 2.7431 |
| Osteoclasts (diff) | 0.8955 |
| Skin normal | 13.0031 |
| Spinal cord normal | 5.1365 |
| Brain Cortex normal | 24.2647 |
| Brain Hypothalamus normal | 25.2951 |
| Nerve | 7.8942 |
| DRG (Dorsal Root Ganglion) | 16.5159 |
| Breast normal | 6.5016 |
| Breast tumor | 11.4382 |
| Ovary normal | 10.0965 |
| Ovary Tumor | 6.7542 |
| Prostate Normal | 10.273 |
| Prostate Tumor | 11.0485 |
| Salivary glands | 2.1822 |
| Colon normal | 3.5327 |
| Colon Tumor | 14.9885 |
| Lung normal | 4.9273 |
| Lung tumor | 7.3655 |
| Lung COPD | 5.0658 |
| Colon IBD | 3.14 |
| Liver normal | 9.3229 |
| Liver fibrosis | 8.6385 |
| Spleen normal | 2.4129 |
| Tonsil normal | 2.83 |
| Lymph node normal | 5.3176 |
| Small intestine normal | 2.0573 |
| Macrophages | 1.3526 |
| Synovium | 2.3388 |
| BM-MNC | 0.2563 |
| Activated PBMC | 1.5538 |
| Neutrophils | 1.5755 |
| Megakaryocytes | 1.57 |
| Erythroid | 15.3566 |
| positive control | 21.1969 |

Table 5 below also shows expression of 46508 mRNA in various normal and diseased tissues, detected using TaqMan analysis. Table 5 shows the high transcriptional expression of 46508 in tumor samples compared to normal organ matched controls. High transcriptional expression was noted in 5/5 primary ovarian tumors, 4/4 primary colon tumors, 2/2 colon to liver metastases, 3/6 primary lung tumors and proliferating HMVEC cells when compared to arrested HMVEC cells.

TABLE 5

Expression of 46508 mRNA in Normal and Cancerous Tissues

| Tissue Type | Expression |
|---|---|
| PIT 400 Breast Normal | 28.36 |
| PIT 372 Breast Normal | 36.40 |
| CHT 1228 Breast Normal | 8.88 |
| MDA 304 Breast Tumor: MD-IDC | 8.34 |
| CHT 2002 Breast Tumor: IDC | 3.55 |
| MDA 236-Breast Tumor: PD-IDC | 3.21 |
| CHT 562 Breast Tumor: IDC | 13.51 |
| NDR 138 Breast Tumor ILC (LG) | 25.30 |
| CHT 1841 Lymph node (Breast met) | 7.19 |
| PIT 58 Lung (Breast met) | 12.22 |
| CHT 620 Ovary Normal | 14.83 |
| CHT 619 Ovary Normal | 7.09 |
| CLN 012 Ovary Tumor | 40.53 |
| CLN 07 Ovary Tumor | 28.26 |
| CLN 17 Ovary Tumor | 94.40 |
| MDA 25 Ovary Tumor | 80.21 |
| CLN 08 Ovary Tumor | 28.07 |
| PIT 298 Lung Normal | 2.14 |
| MDA 185 Lung Normal | 6.05 |
| CLN 930 Lung Normal | 12.13 |
| MPI 215 Lung Tumor - SmC | 9.69 |
| MDA 259 Lung Tumor - PDNSCCL | 13.94 |
| CHT 832 Lung Tumor - PDNSCCL | 8.64 |
| MDA 262 Lung Tumor - SCC | 68.87 |
| CHT 793 Lung Tumor - ACA | 20.83 |
| CHT 331 Lung Tumor - ACA | 8.14 |
| CHT 405 Colon Normal | 2.50 |
| CHT 1685 Colon Normal | 2.10 |
| CHT 371 Colon Normal | 0.95 |
| CHT 382 Colon Tumor: MD | 69.11 |
| CHT 528 Colon Tumor: MD | 54.79 |
| CLN 609 Colon Tumor | 15.25 |
| NDR 210 Colon Tumor: MD-PD | 121.16 |
| CHT 340 Colon-Liver Met | 15.25 |
| CHT 1637 Colon-Liver Met | 10.82 |
| PIT 260 Liver N (female) | 1.46 |
| CHT 1653 Cervix Squamous CC | 19.51 |
| CHT 569 Cervix Squamous CC | 1.31 |
| A24 HMVEC-Arrested | 11.56 |
| C48 HMVEC-Proliferating | 31.80 |
| Pooled Hemangiomas | 1.16 |
| HCT116N22 Normoxic | 76.42 |
| HCT116H22 Hypoxic | 68.39 |

Table 6 indicates that 46508 mRNA is highly expressed in several ovarian cell lines including SKOV3/Var, A2780, MDA2774 and ES-2. The table allows comparisons between two normal ovarian surface epithelium samples (MDA 127 Normal Ovary and MDA 224 Normal Ovary) and two ovarian ascites (MDA 124 Ovarian Ascites and MDA 126 Ovarian Ascites) samples. Expression of 46508 mRNA is upregulated in one of the ascites samples. The table also shows an experiment where the ovarian cancer cell line, HEY, was serum starved for 24 hours. Time points were taken at 0, 1, 3, 6, 9 and 12 hours after the addition of 10% serum (HEY 0 hr, HEY 1 hr, HEY 3 hr, HEY 6 hr, HEY 9 hr, and HEY 12 hr, respectively). Since cMyc protein is highly upregulated at 1 hour after addition of serum and phosphorylated at 6 hours, the experiment is a good model for identifying targets that are downstream of cMyc. These data indicate that 46508 mRNA may be regulated in a manner similar to cMyc since the expression increases from 1 to 9 hours after the addition of serum.

Also shown are data involving the ovarian cancer cell lines SKOV3 and SKOV3/Variant. These cell lines were grown in three different cellular environments: on plastic, in soft agar, and as a subcutaneous tumor in nude mice (all cells grown in 10% serum). The plastic sample was used as the "control" in each experiment. The SKOV3/Var cell line is a variant of the parental cell line SKOV3 which is resistant to cisplatin. These data indicate that 46508 mRNA is upregulated in environments that may be more similar to the tumor in vivo (the soft agar and subcutaneous tumor) compared to growth on plastic.

TABLE 6

Expression in Various Ovarian Cells

| Tissue Type | Expression |
|---|---|
| SKOV-3 No GF | 40.67 |
| SKOV-3 EGF '15 | 41.52 |
| SKOV-3 EGF '30 | 46.23 |
| SKOV-3 EGF '60 | 38.88 |
| SKOV-3 Hrg '15 | 36.02 |
| SKOV-3 Hrg '30 | 41.67 |
| SKOV-3 Hrg '60 | 48.87 |
| SKOV-3 Serum '30 | 54.98 |
| SKOV-3var No GF | 151.25 |
| SKOV-3var EGF '15 | 140.63 |
| SKOV-3var EGF '30 | 126.74 |
| SKOV-3var EGF '60 | 125.43 |
| SKOV-3var Hrg '15 | 141.61 |
| SKOV-3var Hrg '30 | 170.76 |
| SKOV-3var Hrg '60 | 140.15 |
| SKOV-3var Serum '30 | 190.78 |
| HEY Plastic | 50.94 |
| HEY Soft Agar | 22.96 |
| SKOV-3 | 35.65 |
| SKOV-3var | 122.00 |
| A2780 | 159.87 |
| A2780-ADR | 60.79 |
| OVCAR-3 | 54.98 |
| OVCAR-4 | 59.75 |
| MDA2774 | 123.28 |
| DOV13 | 36.52 |
| Caov-3 | 18.14 |
| ES-2 | 101.18 |
| HEY 0 hr | 55.17 |
| HEY 1 hr | 62.50 |
| HEY 3 hr | 74.84 |
| HEY 6 hr | 69.59 |
| HEY 9 hr | 77.75 |
| HEY 12 hr | 68.63 |
| SKOV-3 SubQ Tumor | 18.01 |
| SKOV-3 Variant Plastic | 152.30 |
| SKOV-3 Var SubQ Tumor | 9.39 |
| MDA 127 Normal Ovary | 11.44 |
| MDA 224 Normal Ovary | 17.10 |
| MDA 124 Ovarian Ascites | 18.84 |
| MDA 126 Ovarian Ascites | 41.67 |
| HEY | 63.81 |
| SKOV-3 Plastic | 72.80 |

Human 16816

The human 16816 sequence (SEQ ID NO:39), which is approximately 2629 nucleotides long including untranslated regions, contains a predicted methionine-initiated coding sequence of about 2289 nucleotides (nucleotides 257-2545 of SEQ ID NO:39; SEQ ID NO:41), including the terminal codon. The coding sequence encodes a 762 amino acid protein (SEQ ID NO:40).

This mature protein form is approximately 762 amino acid residues in length (from about amino acid 1 to amino acid 762 of SEQ ID NO:40). Human 16816 contains the following regions or other structural features: one predicted phosphatidylinositol-specific phospholipase C domain X (PFAM Accession Number PF00388) located at about amino acid residues 291-436 of SEQ ID NO:40; one predicted phosphatidylinositol-specific phospholipase C domain Y (PFAM Accession Number PF00387) located at about amino acid residues 492-609 of SEQ ID NO:40; two predicted EF hand domains (PFAM Accession Number PF00036) located at about amino acid residues 138-166 and 174-202 of SEQ ID NO:40; one predicted C2 domain (PFAM Accession Number PF00168) located at about amino acid residues 291-436 and 492-609 of SEQ ID NO:40, two cAMP- and cGMP-dependent protein kinase phosphorylation sites (PS00004) located at about amino acids 435-438 and 482-485 of SEQ ID NO:40; nine predicted protein kinase C phosphorylation sites (PS00005) located at about amino acids 31-33, 56-58, 68-70, 203-205, 257-259, 355-357, 504-506, 666-668 and 741-743 of SEQ ID NO:40; seventeen predicted casein kinase II phosphorylation sites (PS00006) located at about amino 11-14, 62-65, 80-83, 100-103, 108-111, 127-130, 155-158, 223-226, 318-321, 410-413, 422-425, 438-441, 463-466, 467-470, 522-525, 649-652 and 710-713 of SEQ ID NO:40; four predicted N-myristoylation sites (PS00008) located at about amino acids 188-193, 219-224, 414-419 and 684-689 of SEQ ID NO:40; two predicted amidation sites (PS00009) located at about amino acids 96-99 and 433-436 of SEQ ID NO:40; one RGD cell attachment sequence (PS00016) located at about amino acids 145-147 of SEQ ID NO:40; and/or two EF hand calcium-binding domains (PS00018) located at about amino acids 147-159 and 183-195 of SEQ ID NO:40.

In one embodiment, a 16816 family member can include at least one phosphatidylinositol-specific phospholipase C domain X (PFAM Accession Number PF00388); at least one phosphatidylinositol-specific phospholipase C domain Y (PFAM Accession Number PF00387); at least one preferably two EF hand domains (PFAM Accession Number PF00036 or PS00018); at least one predicted C2 domain (PFAM Accession Number PF00168). Furthermore, a 16816 family member can include at least one and preferably two cAMP- and cGMP-dependent protein kinase phosphorylation sites; at least one, two, three, four, five, six, seven, eight, and preferably nine protein kinase C phosphorylation sites (PS00005); at least one, two, three, four, five, six, seven, eight, nine, ten, eleven, twelve, thirteen, fourteen, fifteen, sixteen and preferably seventeen casein kinase II phosphorylation sites (PS00006); at least one, two, three, and preferably four N-myristolyation sites (PS00008); at least one and preferably two predicted amidation sites; or at least one RGD cell attachment sequence.

16816 polypeptides of the invention include fragments which include: all or part of a hydrophobic sequence, e.g., the sequence from about amino acid 485 to 500, from about 650 to 660, and from about 685 to 700 of SEQ ID NO:40; all or part of a hydrophilic sequence, e.g., the sequence from about amino acid 125 to 150, from about 465 to 480, and from about 665 to 680 of SEQ ID NO:40; a sequence which includes a Cys, or a glycosylation site.

Human 16839

The human 16839 sequence (SEQ ID NO:42), which is approximately 2171 nucleotides long including untranslated regions, contains a predicted methionine-initiated coding sequence of about 1827 nucleotides (nucleotides 232-2058 of SEQ ID NO:42; SEQ ID NO:44), including the terminal codon. The coding sequence encodes a 608 amino acid protein (SEQ ID NO:43).

This mature protein form is approximately 608 amino acid residues in length (from about amino acid 1 to amino acid 608 of SEQ ID NO:43). Human 16839 contains the following regions or other structural features: one EF hand domain (PFAM Accession Number PF00036) located at about amino acids 39 to 67 of SEQ ID NO:43; one phosphatidylinositol-specific phospholipase C domain X (PFAM Accession Number PF00388) located at about amino acids 156 to 300 of SEQ ID NO:43; one phosphatidylinositol-specific phospholipase C domain Y (PFAM Accession Number PF00387) located at about amino acids 348 to 465 of SEQ ID NO:43; one C2 domain (PFAM Accession Number PF00168) located at about amino acids 484 to 572 of SEQ ID NO:43; two N-glycosylation sites (PS00001) located at about amino acids 376-379 and 537-540 of SEQ ID NO:43; three cAMP- and cGMP-dependent protein kinase phosphorylation sites (PS00004) located at about amino acids 310-313, 337-340 and 385-388 of SEQ ID NO:43; ten predicted protein kinase C phosphorylation sites (PS00005) located at about amino acids 24-26, 68-70, 220-222, 303-305, 313-315, 340-342, 399-401, 485-487, 501-503 and 533-535 of SEQ ID NO:43; eight predicted casein kinase II phosphorylation sites (PS00006) located at about amino 56-59, 68-71, 79-82, 267-270, 303-306, 356-359, 378-381 and 411-414 of SEQ ID NO:43; and three predicted N-myristoylation sites (PS00008) located at about amino acids 16-21, 479-484 and 560-565 of SEQ ID NO:43.

In one embodiment, a 16839 family member can include at least one EF hand domain (PFAM Accession Number PF00036); at least one phosphatidylinositol-specific phospholipase C domain X (PFAM Accession Number PF00388); at least one phosphatidylinositol-specific phospholipase C domain Y (PFAM Accession Number PF00387); at least one C2 domain (PFAM Accession Number PF00168). Furthermore, a 16839 family member can include at least one N-glycosylation site (PS00001); at least one, two and preferably three cAMP- and cGMP-dependent protein kinase phosphorylation sites; at least one, two, three, four, five, six, seven, eight, nine and preferably ten protein kinase C phosphorylation sites (PS00005); at least one, two, three, four, five, six, seven, and preferably eight casein kinase II phosphorylation sites (PS00006); at least one, two, and preferably three N-myristolyation sites (PS00008).

16839 polypeptides of the invention include fragments which include: all or part of a hydrophobic sequence, e.g., the sequence from about amino acid 340 to 350, from about 480 to 490, and from about 540 to 560 of SEQ ID NO:43; all or part of a hydrophilic sequence, e.g., the sequence from about amino acid 300 to 325, from about 360 to 390, and from about 405 to 420 of SEQ ID NO:43; a sequence which includes a Cys, or a glycosylation site.

16816 and 16839 Phospholipase C Proteins

The 16816 and 16839 protein contain a significant number of structural characteristics in common with members of the phospholipase C family.

Phospholipase C (PLC) belongs to a family of enzymes, also known as disulfide isomerases, which play an important role in mediating signal transduction pathways. Many extracellular signaling molecules including hormones, growth factors, neurotransmitters, and immunoglobulins bind to their respective cell surface receptors and activate PLCs. Activated PLCs then catalyze the hydrolysis of phosphatidyl-inositol-4,5-bisphosphate (PIP2), a component of the plasma membrane, to produce diacylglycerol and inositol 1,4,5-trisphosphate (IP3).

In their respective biochemical pathways, IP3 and diacylglycerol serve as second messengers and trigger a series of intracellular responses. IP3 induces the release of calcium from internal cellular storage, and diacylglycerol activates protein kinase C (PKC). Both pathways are part of transmembrane signal transduction mechanisms, which regulate numerous cellular processes, including secretion, neural activity, metabolism, and proliferation.

PLC molecules have been found in a broad spectrum of organisms including bacteria, simple eukaryotes, plants and animals (Munnik et al., Biochim. Biophys. Acta. 1389:222-272, (1998)). Several distinct isoforms of PLC have been identified in animals and are categorized as PLC-beta, PLC-gamma, and PLC-delta. Subtypes are designated by adding Arabic numbers after the Greek letters, e.g., PLC-beta-1. PLCs have a molecular mass of 62-68 kDa, and their amino acid sequences show two regions of significant similarity.

The present invention is based, at least in part, on the discovery of novel molecules, referred to herein as "phospholipase C" or "16816" or "16839" nucleic acid and polypeptide molecules, which play a role in or function in modulating signal transduction pathways.

PLC molecules have been found in a broad spectrum of organisms including bacteria, simple eukaryotes, plants and animals. Members of a family can also have common functional characteristics. Members of the PLC family share one or more common domains such as a pleckstrin homology domain, an EF hand domain, a phosphatidylinositol-specific phospholipase domain X (PLC-X) domain, a phosphatidylinositol-specific phospholipase domain Y (PLC-Y) domain or a C2 domain. Members of this family can also have common functional characteristics, e.g., the ability to hydrolyze phosphatidylinositols.

A 16816 polypeptide can include a "pleckstrin homology (PH) domain" or regions homologous with a "PH domain". As used herein, the term "PH domain" refers to a protein domain having an amino acid sequence of about 10 to 200, preferably about 50 to 150, more preferably about 108 amino acid residues. By "PH domain" is meant a domain that can function as a recognition site for a phosphatidylinositol, e.g., a 3,4,5-trisphosphate (PIP3) or another kinase ligand product, and can function as a means to localize PLC to the cytoplasmic face of the plasma membrane.

As used herein, the term "PH domain" includes an amino acid sequence of about 108 amino acid residues in length and having a bit score for the alignment of the sequence to the PH domain (HMM) of at least 10. Preferably, a PH domain includes at least about 10-200 amino acids, more preferably about 50-150 amino acid residues, or about 75-110 amino acids and has a bit score for the alignment of the sequence to the PH domain (HMM) of at least 20, 30, or greater.

In a preferred embodiment a 16816 polypeptide or protein has a "PH domain" or a region which includes at least about 10-200 amino acids, more preferably about 50-150 amino acid residues, or about 107 amino acid residues and has at least about 60%, 70% 80% 90% 95%, 99%, or 100% homology with a "PH domain," e.g., the PH domain of human 16816 (e.g., residues 17-124 of SEQ ID NO:40). The identified PH domain consensus sequence is set forth as SEQ ID NO:45.

A 16816 or 16839 polypeptide can also include an "EF hand domain" or regions homologous with an "EF hand domain". As used herein, the term "EF hand domain" refers to a protein domain having an amino acid sequence of about 5 to 50, preferably about 5 to 40, more preferably about 28-29 amino acid residues. By "EF hand domain" is meant a type of calcium-binding domain that consists of a twelve residue loop flanked on both sides by a twelve residue alpha-helical domain. In an EF-hand loop the calcium ion is coordinated in a pentagonal bipyramidal configuration. The six residues involved in the binding are in positions 1, 3, 5, 7, 9 and 12; these residues are denoted by X, Y, Z, −Y, −X and −Z. The invariant Glu or Asp at position 12 provides two oxygens for liganding Ca (bidentate ligand). Preferably, the EF hand domain includes the following amino acid consensus sequence having Prosite signatures as PS00018, or sequences homologous thereto. D-x-[DNS]-{ILVFYW}-[DENSTG]-[DNQGHRK]-{GP}-[LIVMC]-[DENQSTAGC]-x(2)-[DE]-[LIVMFYW] (SEQ ID NO:62). In the above conserved motif, and other motifs described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (( )) indicate the number of residues represented by the accompanying amino acid. The EF hand domains are located in mostly hydrophilic regions of the molecule of human 16816 or 16839 polypeptide and which corresponds to about amino acids 138-166 and 172-202 of SEQ ID NO:40; or amino acids 39-67 of SEQ ID NO:43. The EF hand domain (HMM) has been assigned the PFAM Accession Number PF00036.

The "EF hand domain" includes an amino acid sequence of about 28 amino acid residues in length and can have a bit score for the alignment of the sequence to the EF hand (HMM) of at least 5. Preferably, an EF hand domain includes at least about 5-50 amino acids, or at least about 5-40, or about 28 amino acids and has a bit score for the alignment of the sequence to the EF hand (HMM) of at least 5, 10, 15, 20, or greater.

In a preferred embodiment, the 16816 or 16839 polypeptide or protein has an "EF hand domain" or a region which includes at least about 5-50, more preferably about 5-40 or 28-29 amino acid residues and has at least about 60%, 70% 80% 90% 95%, 99%, or 100% homology with an "EF hand domain," e.g., the EF hand domain of human 16816 or 16839 (e.g., residues 138-166 and 172-202 of SEQ ID NO:40; or amino acids 39-67 of SEQ ID NO:43). The identified EF hand domain consensus sequences within 16816 are set forth as SEQ ID NO:46 and 47, and the identified EF hand domain consensus sequence within 16839 is set forth as SEQ ID NO:56.

A 16816 or 16839 polypeptide can also include a "phosphatidylinositol-specific phospholipase C domain X (referred to herein as "PLC-X domain")" or regions homologous with a "PLC-X domain". As used herein, the term "PLC-X domain" refers to a protein domain having an amino acid sequence of about 8 to 200, preferably about 15 to 170, more preferably about 145 amino acid residues. By "PLC-X domain" is meant a subdomain that composes the catalytic site of the phospholipase, e.g., PLC-X subdomain can fold together with another subdomain, e.g., phosphatidylinositol-specific phospholipase C domain Y such that a functioning catalytic site that hydrolyzes a phosphatidylinositol is formed, e.g., phosphatidylinositol 4,5-bisphosphate, is formed.

The "PLC-X domain" includes an amino acid sequence of about 145 amino acid residues in length and can have a bit score for the alignment of the sequence to the phosphatidylinositol-specific phospholipase-C domain X (HMM) of at least 50. Preferably, a PLC-X domain includes at least about 15-170 amino acids, or at least about 20-150, or about 145 amino acids and has a bit score for the alignment of the sequence to the phosphatidylinositol-specific phospholipase-C domain X (HMM) of at least 60, 70, 80, 90, 100, 150, 200, 250, or greater.

In a preferred embodiment, the 16816 or 16839 polypeptide or protein has a "PLC-X" or a region which includes at least about 8-200, more preferably about 15-170 or 20-150 amino acid residues and has at least about 60%, 70% 80% 90% 95%, 99%, or 100% homology with a "PLC-X domain," e.g., the PLC-X domain of human 16816 or 16839 (e.g., residues 291-436 of SEQ ID NO:40; or residues 156-300 of SEQ ID NO:43). The identified PLC-X domain consensus sequence of 16816 is set forth in SEQ ID NO:48 and the identified PLC-X domain consensus sequence of 16839 is set forth in SEQ ID NO:57.

A 16816 or 16839 polypeptide can include a "phosphatidylinositol-specific phospholipase C domain Y (referred to herein as PLC-Y domain)" or regions homologous with a "PLC-Y domain". As used herein, the term "PLC-Y domain" refers to a protein domain having an amino acid sequence of about 8 to 200, preferably about 15 to 170, more preferably about 117 amino acid residues. By "PLC-Y domain" is meant a subdomain that composes the catalytic site of the phospholipase, e.g., the subdomain can fold together with another subdomain, e.g., PLC-X domain such that a functioning catalytic site that hydrolyzes a phosphatidylinositol, e.g., phosphatidylinositol 4,5-bisphosphate, is formed.

The "PLC-Y domain" includes an amino acid sequence of about 117 amino acid residues in length and can have a bit score for the alignment of the sequence to the PLC-Y domain (HMM) of at least 50. Preferably, a PLC-Y domain includes at least about 15-170 amino acids, or at least about 20-150, or about 117 amino acids and has a bit score for the alignment of the sequence to the PLC-Y domain (HMM) of at least 60, 70, 80, 90, 100, 110, 120, 140, 160, 180, or greater.

In a preferred embodiment 16816 or 16839 polypeptide or protein has a "PLC-Y domain" or a region which includes at least about 8-200, more preferably about 15-170 or 20-150 amino acid residues and has at least about 60%, 70% 80% 90% 95%, 99%, or 100% homology with a "PLC-Y domain" e.g., PLC-Y domain of human 16816 or 16839 (e.g., residues 492-609 of SEQ ID NO:40; or residues 348465 of SEQ ID NO:43). The identified PLC-Y domain consensus sequence of 16816 is set forth in SEQ ID NO:49 and the identified PLC-Y domain consensus sequence of 16839 is set forth in SEQ ID NO:58.

A 16816 or 16839 polypeptide can include a "calcium (Ca2+) binding domain (referred to as C2 domain")" or regions homologous with a "C2 domain". As used herein, the term "C2" refers to a protein domain having an amino acid sequence of about 8 to 200, preferably about 15 to 170, more preferably about 20 to 100, or still more preferably about 90 amino acid residues. By "C2 domain" is meant a domain that can mediate interaction with calcium or phospholipids.

The "C2 domain" includes an amino acid sequence of about 90 amino acid residues in length and can have a bit score for the alignment of the sequence to the C2 domain (HMM) of at least 50. Preferably, a C2 includes at least about 8-200, or at least about 15-170, or at least 20-100, or about 90 amino acids and has a bit score for the alignment of the sequence to the C2 domain (HMM) of at least 60, 70, 80, 85, or greater.

In a preferred embodiment, a 16816 or 16839 polypeptide or protein has a "C2" or a region which includes at least about 10-200, more preferably about 15-170 or 20-100 amino acid residues and has at least about 60%, 70% 80% 90% 95%, 99%, or 100% homology with a "C2," e.g., the C2 domain of human 16816 or 16839 (e.g., residues 629-719 of SEQ ID NO:40; or residues 484-572 of SEQ ID NO:43). The identified C2 domain consensus sequence of 16816 is set forth in SEQ ID NO:50 and the identified C2 domain consensus sequence of 16839 is set forth in SEQ ID NO:59.

To identify the presence of a "PH domain," "EF hand," "PLC-X domain," "PLC-Y domain," or a "C2 domain" in a 16816 or 16839 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

A search was performed against the HMM database resulting in the identification of a "PH domain" in the amino acid sequence of human 16816 at about residues 17-124 of SEQ ID NO:40. The identified PH domain consensus sequence of 16816 is set forth in SEQ ID NO:45. This search also resulted in the identification of "EF domain(s)" in the amino acid sequence of human 16816 or 16839 at about residues 138-166 and 172-202 of SEQ ID NO:40 or amino acids 39-67 of SEQ ID NO:43 respectively. The identified EF domain consensus sequences of 16816 are set forth in SEQ ID NO:46 and 47 and the identified EF domain consensus sequence of 16839 is set forth in SEQ ID NO:56. This search also resulted in the identification of a "C2 domain" in the amino acid sequence of human 16816 or 16839 at about residues 629-719 of SEQ ID NO:40 and residues 484-572 of SEQ ID NO:43, respectively. The identified C2 domain consensus sequence of 16816 is set forth in SEQ ID NO:50 and the identified C2 domain consensus sequence of 16839 is set forth in SEQ ID NO:59. This search also resulted in the identification of a "PLC-Y domain" in the amino acid sequence of human 16816 or 16839 at about residues 492-609 of SEQ ID NO:40 and residues 348-465 of SEQ ID NO:43. The identified PLC-Y domain consensus sequence of 16816 is set forth in SEQ ID NO:49 and the identified PLC-Y domain consensus sequence of 16839 is set forth in SEQ ID NO:58. This search additionally resulted in the identification of a "PLC-X domain" in the amino acid sequence of human 16816 or 16839 at about residues 291-436 of SEQ ID NO:40 and residues 156-300 of SEQ ID NO:43. The identified PLC-X domain consensus sequence of 16816 is set forth in SEQ ID NO:48 and the identified PLC-X domain consensus sequence of 16839 is set forth in SEQ ID NO:57.

To identify the presence of a "phospholipase C" domain in a 16816 or 16839 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263-267). The ProDom protein domain database consists of an automatic compilation of homologous domains. Current versions of ProDom are built using recursive PSI-BLAST searches (Altschul S F et al. (1997) Nucleic Acids Res. 25:3389-3402; Gouzy et al. (1999) Computers and Chemistry 23:333-340) of the SWISS-PROT 38 and TREMBL protein databases. The database automatically generates a consensus sequence for each domain. A BLAST search was performed against the HMM database resulting in the identification of a "phospholipase C" domain in the amino acid sequence of human 16816 or 16839.

The phospholipase C domain is homologous to ProDom family PD001214 ("phospholipase phosphodiesterase hydrolase phosphoinositide-specific 1-phosphatidylinositol-45-bisphosphate degradation transducer lipid beta" SEQ ID NO:51, ProDomain Release 2001.1). An alignment of the phospholipase C domain (amino acids 275 to 436 of SEQ ID NO:40) of human 16816 with a consensus amino acid sequence (SEQ ID NO:51) derived from a hidden Markov model shows that the consensus sequence for SEQ ID NO:51 is 54% identical over amino acids 275 to 436 of SEQ ID NO:40.

The phospholipase C domain is also homologous to ProDom family PD186804 ("phospholipase C delta calcium-binding PLC-III hydrolase phosphodiesterase lipid PLC-delta-11-phosphatidylinositol-45-bisphosphate" SEQ ID NO:52, ProDomain Release 2001.1. An alignment of the phospholipase C domain (amino acids 1 to 191 of SEQ ID NO:40) of human 16816 with a consensus amino acid sequence (SEQ ID NO:52) derived from a hidden Markov model shows that the consensus sequence for SEQ ID NO:52 is 44% identical over amino acids 1 to 191 of SEQ ID NO:40.

The phospholipase C domain is also homologous to ProDom family PD001202 ("phospholipase phosphodiesterase hydrolase phosphoinositide-specific 1-phosphatidylinositol-45-bisphosphate degradation lipid transducer beta" SEQ ID NOs:53 and 61, ProDomain Release 2001.1. An alignment of the phospholipase C domain (amino acids 491 to 608 of SEQ ID NO:40) of human 16816 with a consensus amino acid sequence (SEQ ID NO:53) derived from a hidden Markov model demonstrates that the consensus sequence for SEQ ID NO:53 is 57% identical over amino acids 491 to 608 of SEQ ID NO:40. An alignment of the phospholipase C domain (amino acids 350 to 473 of SEQ ID NO:43) of human 16839 with a consensus amino acid sequence (SEQ ID NO:61) derived from a hidden Markov model demonstrates that the consensus sequence for SEQ ID NO:61 is 47% identical over amino acids 350 to 473 of SEQ ID NO:43.

The phospholipase C domain is also homologous to ProDom family PD033204 ("C phospholipase delta-4 delta4 phospholipase" SEQ ID NO:54, ProDomain Release 2001.1. An alignment of the phospholipase C domain (amino acids 722 to 761 of SEQ ID NO:40) of human 16816 with a consensus amino acid sequence (SEQ ID NO:54) derived from a hidden Markov model demonstrates that the consensus sequence for SEQ ID NO:54 is 70% identical over amino acids 722 to 761 of SEQ ID NO:40.

The phospholipase C domain is also homologous to ProDom family PD270355 ("1-phosphatidylinositol-4 phosphodiesterase-like bisphosphate" SEQ ID NO:55, ProDomain Release 2001.1. An alignment of the phospholipase C domain (amino acids 562 to 621 of SEQ ID NO:40) of human 16816 with a consensus amino acid sequence (SEQ ID NO:55) derived from a hidden Markov model demonstrates that the consensus sequence for SEQ ID NO:55 is 46% identical over amino acids 562 to 621 of SEQ ID NO:40.

The phospholipase C domain is also homologous to ProDom family PD001214 ("phospholipase phosphodiesterase hydrolase phosphoinositide-specific 1-phosphatidylinositol-45-bisphosphate degradation transducer lipid beta" SEQ ID NO:60, ProDomain Release 2001.1. An alignment of the phospholipase C domain (amino acids 140 to 324 of SEQ ID NO:43) of human 16839 with a consensus amino acid sequence (SEQ ID NO:60) derived from a hidden Markov model shows that the consensus sequence for SEQ ID NO:60 is 48% identical over amino acids 140 to 324 of SEQ ID NO:43.

As the 16816 or 16839 polypeptide of the invention may modulate 16816 or 16839-mediated activity, they may be useful as of for developing novel diagnostic and therapeutic agents for 16816 or 16839-mediated or related disorders, as described below. As used herein, a "16816 or 16839 activity", "biological activity of 16816 or 16839" or "functional activity of 16816 or 16839", refers to an activity exerted by a 16816 or 16839 protein, polypeptide or nucleic acid molecule on e.g., a 16816 or 16839-responsive cell or on a 16816 or 16839 substrate, e.g., a protein substrate, as determined in vivo or in vitro. In one embodiment, a 16816 or 16839 activity is a direct activity, such as an association with a 16816 or 16839 target molecule. A "target molecule" or "binding partner" is a molecule with which a 16816 or 16839 protein binds or interacts with in nature. In an exemplary embodiment, it is a receptor, e.g., a tyrosine kinase receptor. In another embodiment, 16816 or 16839 can associate with a second messenger molecule such as a specialized adaptor molecule; with inositol phosphates and inositol lipids; membrane proteins; or with a guanine nucleotide binding-regulatory protein (G-protein). A 16816 or 16839 activity can also be an indirect activity, e.g., a cellular signaling activity mediated by interaction of the 16816 or 16839 protein with a receptor or another signaling molecule. For example, the 16816 or 16839 proteins of the present invention can have one or more of the following activities: (1) transduction of transmembrane signals; (2) lipid-metabolizing activity, e.g., 16816 or 16839 can catalyze the hydrolysis of phosphatidyl-inositol-4,5-bisphosphate (PIP2) producing diacylglycerol and inositol 1,4,5-trisphosphate; (3) the regulation of transmission of signals from cellular receptors such as hormones such as serotonin, growth factors such as platelet-derived growth factor (PDGF), fibroblast growth factor (FGF), and nerve growth factor (NGF), neurotransmitters and immunoglobulins; (4) modulation of cell proliferation; (5) modulation of cell differentiation; (6) modulation of cell migration; (7) modulation of fertilization; and (8) modulation of hypertension.

Based on the above-described sequence similarities, the 16816 or 16839 molecules of the present invention are predicted to have similar biological activities as members of the PLC family. Members of the PLC family play a very important role in transmembrane signal transduction. Extracellular signaling molecules including hormones, growth factors, neurotransmitters, and immunoglobulins bind to their respective cell surface receptors and activate phospholipase-C. PLC molecules have many functions including: glycogenolysis in liver cells, histamine secretion by mast cells, serotonin release by blood platelets, aggregation by blood platelets, insulin release by pancreatic islet cells, epinephrine secretion by adrenal chromaffin cells, and smooth muscle contraction. In general, biological systems that are activated by receptor tyrosine kinase cause the activation of phospholipase-C. The role of an activated PLC is to catalyze the hydrolysis of phosphatidyl-inositol-4,5-bisphosphate (PIP2), a minor component of the plasma membrane, to produce diacylglycerol and inositol 1,4,5-trisphosphate (IP3). Inositol trisphosphate releases calcium from intracellular stores and increases the influx of calcium from the extracellular fluid. The calcium ions directly regulate target enzymes and indirectly affect other enzymes by functioning as a second messenger and interacting with calcium-binding proteins, such as troponin C and calmodulin. For example, calcium ions regulate muscle contraction, glycogen breakdown and exocytosis. Diacylglycerol, a product of the hydrolysis by PLCs, acts as a second messenger by activating protein kinase C. Activated protein kinase C phosphorylates a great number of intracellular proteins at the serine and threonine residues and modulates different signaling pathways. For example, the phosphorylation of glycogen synthase by protein kinase C stops the synthesis of glycogen. Moreover, protein kinase C controls cell division and proliferation. Both pathways are part of transmembrane signal transduction mechanisms, which regulate cellular processes, which include secretion, neural activity, metabolism, differentiation and proliferation.

Both 16816 and 16839 proteins are homologous to the phospholipase C molecule, PLC1. Stimulation of 16816 or 16839 activity is desirable in situations in which 16816 or 16839 is abnormally downregulated and/or in which increased 16816 or 16839 activity is likely to have a beneficial effect. For example, research on chromosome 20q has associated this gene locus with tumor suppressor activity. Deletions and mutations of the 20q chromosome have been associated with myelodysplasia and myeloproliferative disorders. PLC1 is one of the genes present at this locus, and has been found to deleted in these cases. (Asimakopoulos et al. (1994) *Blood* 84(9):3086-94). As such, 16816 and 16839 may play a role in preventing or treating myeloid disorders.

Likewise, inhibition of 16816 or 16839 activity is desirable in situations in which 16816 or 16839 is abnormally upregulated and/or in which decreased 16816 or 16839 activity is likely to have a beneficial effect. It has been shown that PLC1 overexpression is associated with hepatocellular carcinoma. One antibody, k-PLC1, was shown to react with PLC1 (Wiedmann et al. (1987) *Hepatology* 7(3):543-50). As such, inhibitors such as 16816- or 16839-specific antibodies may be useful to reduce the quantity of PLC1 in such situations, and potentially decrease the severity and/or occurrence of hepatocellular carcinoma. Thus, the 16816 or 16839 molecules can act as novel diagnostic targets and therapeutic agents for controlling disorders caused by abnormal or aberrant PLC activity. Evidence indicates that a high percentage of primary human mammary carcinomas concomitantly show abnormally high levels of PLC-gamma-1 (Kassis et al., *Clin Cancer Res., August;* 5(8):2251-60, 1999). Likewise, studies on spontaneous hypertensive rats have suggested that one of the main causes for the hypertension is an abnormal activation of PLC-delta-1 resulting from point mutations in the X and Y regions of the PLC amino acid sequence (Sanada et al., *Hypertension* 33(4): 1036-42, 1999). Therefore, the 16816 or 16839 molecules can act as novel diagnostic targets and therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

As the 16816 or 16839 polypeptides of the invention may modulate 16816 or 16839-mediated activities, they may be useful for developing novel diagnostic and therapeutic agents for 16816 or 16839-mediated or related disorders, as described below.

Accordingly, 16816 or 16839 protein may mediate various disorders, including cellular proliferative and/or differentiative disorders, brain disorders, heart disorders, blood vessel disorders, and platelet disorders.

Identification and Characterization of Human 16816 or 16839 cDNAs

The human 16816 or 16839 sequence (SEQ ID NO:39 or SEQ ID NO:42), which is approximately 2629 or 2171 nucleotides long, respectively, including untranslated regions, contains a predicted methionine-initiated coding sequence of about 2289 or 1827 nucleotides, respectively (nucleotides 257-2545 of SEQ ID NO:39; SEQ ID NO:41; or nucleotides 232-2058 of SEQ ID NO:42; SEQ ID NO:44). The coding sequence encodes a 762 or 608 amino acid protein (SEQ ID NO:40 or SEQ ID NO:43), respectively.

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 16816 or 16839 expression was measured by TAQ-MAN™ quantitative PCR (Perkin Elmer Applied Biosystems) in cDNA prepared from a variety of normal and diseased (e.g., cancerous) human tissues or cell lines. Probes were designed by PrimerExpress software (PE Biosystems) based on the sequenced of the human 16816 or 16839 gene. Each human 16816 or 16839 gene probe was labeled using FAM (6-carboxyfluorescein), and the 132-microglobulin reference probe was labeled with a different fluorescent dye, VIC. The differential labeling of the target gene and internal reference gene thus enabled measurement in same well. Forward and reverse primers and the probes for both 132-microglobulin and target gene were added to the TAQMAN™ Universal PCR Master Mix (PE Applied Biosystems). Although the final concentration of primer and probe could vary, each was internally consistent within a given experiment. A typical experiment contained 200 nM of forward and reverse primers plus 100 nM probe for 13-2 microglobulin and 600 nM forward and reverse primers plus 200 nM probe for the target gene. TAQMAN™ matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 16816 or 16839 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 16816 or 16839 gene is normalized by subtracting the Ct value of the β-2 microglobulin gene to obtain a ΔCt value using the following formula: $\Delta Ct = Ct_{human\ 59914\ and\ 59921} - Ct_{\beta-2\ microglobulin}$. Expression is then calibrated against a cDNA sample showing a comparatively low level of expression of the human 16816 or 16839 gene. The ΔCt value for the calibrator sample is then subtracted from ΔCt for each tissue sample according to the following formula: $\Delta\Delta Ct = \Delta Ct_{sample} - \Delta Ct_{calibrator}$. Relative expression is then calculated using the arithmetic formula given by 2−ΔΔCt. Expression of the target human 16816 or 16839 gene in each of the tissues tested is then graphically represented as discussed in more detail below.

TAQMAN™ real-time quantitative RT-PCR is used to detect the presence of RNA transcript corresponding to human 16816 relative to a no template control in a panel of human tissues or cells. It is found that the highest expression of 16816 orthologs are expressed in skeletal muscle tissue as shown in Table 7.

TABLE 7

| Tissue Type | mean 16816 | mean βeta 2 | ∂Ct | expression |
|---|---|---|---|---|
| Aorta/normal | 38.87 | 23.105 | 15.765 | 0 |
| Fetal heart/normal | 33.43 | 20.82 | 12.61 | 0.159960132 |
| Heart normal | 34.62 | 18.985 | 15.635 | 0.019651514 |
| Heart/CHF | 35.64 | 20.47 | 15.17 | 0 |
| Vein/Normal | 33.81 | 19.15 | 14.66 | 0.038627826 |
| Spinal cord/Normal | 33.175 | 19.43 | 13.745 | 0.072835434 |
| Brain cortex/Normal | 30.42 | 21.2 | 9.22 | 1.676885618 |
| Brain hypothalamus/Normal | 30.415 | 20.155 | 10.26 | 0.815515546 |
| Glial cells (Astrocytes) | 33.495 | 21.58 | 11.915 | 0.258956968 |
| Brain/Glioblastoma | 29.77 | 18.41 | 11.36 | 0.380451455 |
| Breast/Normal | 34.145 | 19.195 | 14.95 | 0.031593778 |
| Breast tumor/IDC | 33.215 | 18.82 | 14.395 | 0.046416588 |
| OVARY/Normal | 35.47 | 21.23 | 14.24 | 0 |
| OVARY/Tumor | 37.815 | 19.785 | 18.03 | 0 |
| Pancreas | 35.73 | 18.125 | 17.605 | 0 |
| Prostate/Normal | 30.895 | 19.255 | 11.64 | 0.313336401 |
| Prostate/Tumor | 31.695 | 18.255 | 13.44 | 0.089982252 |
| Colon/normal | 31.035 | 17.45 | 13.585 | 0.081378093 |
| Colon/tumor | 36.88 | 18.84 | 18.04 | 0 |
| Colon/IBD | 35.185 | 18.445 | 16.74 | 0 |
| Kidney/normal | 30.255 | 21.005 | 9.25 | 1.642375811 |
| Liver/normal | 36.48 | 19.18 | 17.3 | 0 |
| Liver fibrosis | 35.16 | 20.015 | 15.145 | 0 |
| Fetal Liver/normal | 37.02 | 22.14 | 14.88 | 0 |
| Lung/normal | 33.93 | 18.02 | 15.91 | 0.016241 |
| Lung/tumor | 34.845 | 18.955 | 15.89 | 0.016467716 |
| Lung/COPD | 33.345 | 18.13 | 15.215 | 0.026292302 |
| Spleen/normal | 39.23 | 20.19 | 19.04 | 0 |
| Tonsil/normal | 35.72 | 17.955 | 17.765 | 0 |
| Lymph node/normal | 34.55 | 18.485 | 16.065 | 0.014586568 |
| Thymus/normal | 33.475 | 19.675 | 13.8 | 0.070110984 |
| Epithelial Cells (prostate) | 31.825 | 20.57 | 11.255 | 0.409173406 |
| Endothelial Cells (aortic) | 32.815 | 20.775 | 12.04 | 0.237464587 |
| Skeletal Muscle/Normal | 24.19 | 19.34 | 4.85 | 34.674046 |
| Fibroblasts (Dermal) | 31.89 | 18.915 | 12.975 | 0.124204064 |
| Skin/normal | 34.805 | 20.945 | 13.86 | 0.067254951 |
| Adipose/Normal | 32.94 | 18.88 | 14.06 | 0.058548835 |
| Osteoblasts (primary) | 32.595 | 20.175 | 12.42 | 0.182476715 |
| Osteoblasts (Undiff) | 31.05 | 19.025 | 12.025 | 0.239946435 |
| Osteoblasts(Diff) | 30.815 | 18.315 | 12.5 | 0.172633492 |
| Osteoclasts | 34.17 | 17.725 | 16.445 | 0.011208867 |
| Aortic SMC Early | 34.705 | 20.23 | 14.475 | 0.043912768 |
| Aortic SMC Late | 34.18 | 22.97 | 11.21 | 0.42213732 |
| shear HUVEC | 31.315 | 20.955 | 10.36 | 0.76090291 |
| static HUVEC | 31.465 | 20.875 | 10.59 | 0.64877237 |

TAQMAN™ real-time quantitative RT-PCR is used to detect the presence of RNA transcript corresponding to human 16839 relative to a no template control in a panel of human tissues or cells. It is found that 16839 orthologs are expressed in teste as shown in the Table 8 and DRG as shown in Table 9.

TABLE 8

| Tissue Type | 16839.20 | β2.803 | ∂Ct | Expression |
|---|---|---|---|---|
| Adrenal Gland | 40.00 | 19.21 | 20.80 | 0.00 |
| Brain | 40.00 | 21.01 | 18.99 | 0.00 |
| Heart | 40.00 | 18.97 | 21.04 | 0.00 |
| Kidney | 39.90 | 18.98 | 20.92 | 0.00 |
| Liver | 40.00 | 18.61 | 21.40 | 0.00 |
| Lung | 40.00 | 17.12 | 22.88 | 0.00 |
| Mammary Gland | 40.00 | 17.94 | 22.07 | 0.00 |
| Pancreas | 40.00 | 20.50 | 19.50 | 0.00 |
| Placenta | 40.00 | 17.83 | 22.18 | 0.00 |
| Prostate | 40.00 | 17.20 | 22.80 | 0.00 |
| Salivary Gland | 40.00 | 18.48 | 21.52 | 0.00 |
| Muscle | 40.00 | 20.56 | 19.45 | 0.00 |
| Sm. Intestine | 40.00 | 18.82 | 21.19 | 0.00 |
| Spleen | 40.00 | 16.64 | 23.36 | 0.00 |
| Stomach | 40.00 | 18.52 | 21.48 | 0.00 |
| Teste | 26.97 | 20.05 | 6.92 | 1.69 |
| Thymus | 40.00 | 17.66 | 22.35 | 0.00 |
| Trachea | 40.00 | 18.93 | 21.07 | 0.00 |
| Uterus | 40.00 | 18.80 | 21.20 | 0.00 |
| Spinal Cord | 40.00 | 18.94 | 21.07 | 0.00 |
| DRG | 40.00 | 19.50 | 20.51 | 0.00 |
| Skin | 39.10 | 18.44 | 20.66 | 0.00 |

TABLE 9

| Tissue Type | Mean | β 2 Mean | ∂∂ Ct | Expression |
|---|---|---|---|---|
| Artery normal | 40 | 19.38 | 20.62 | 0 |
| Vein normal | 39.38 | 18.47 | 20.91 | 0 |
| Aortic SMC EARLY | 38.88 | 19.23 | 19.64 | 0 |
| Coronary SMC | 39.92 | 20.55 | 19.38 | 0 |
| Static HUVEC | 39.06 | 18.66 | 20.4 | 0 |
| Heart normal | 40 | 17.21 | 22.79 | 0 |
| Heart CHF | 39.26 | 17.18 | 22.07 | 0 |
| Kidney | 34.14 | 17.21 | 16.93 | 0.008 |
| Skeletal Muscle | 40 | 20.26 | 19.74 | 0 |
| Adipose normal | 40 | 18.7 | 21.31 | 0 |
| Pancreas | 39.41 | 19.23 | 20.18 | 0 |
| primary osteoblasts | 37.65 | 17.54 | 20.11 | 0 |
| Osteoclasts (diff) | 35.13 | 15.82 | 19.31 | 0 |
| Skin normal | 39.13 | 19.16 | 19.98 | 0 |
| Spinal cord normal | 40 | 18.59 | 21.41 | 0 |
| Brain Cortex normal | 38.95 | 18.59 | 20.36 | 0 |
| Brain Hypothalamus normal | 40 | 19.43 | 20.57 | 0 |
| Nerve | 40 | 22.34 | 17.66 | 0 |
| DRG (Dorsal Root Ganglion) | 34.58 | 19.82 | 14.76 | 0.0362 |
| Glial Cells (Astrocytes) | 38.84 | 20.34 | 18.5 | 0 |
| Glioblastoma | 38.91 | 16.52 | 22.39 | 0 |
| Breast normal | 39.6 | 18.93 | 20.67 | 0 |
| Breast tumor | 39.98 | 17.11 | 22.88 | 0 |
| Ovary normal | 38.79 | 18.03 | 20.76 | 0 |
| Ovary Tumor | 40 | 18.23 | 21.77 | 0 |
| Prostate Normal | 38.15 | 18.3 | 19.85 | 0 |
| Prostate Tumor | 38.36 | 16.03 | 22.33 | 0 |
| Epithelial Cells (Prostate) | 39.45 | 19.29 | 20.16 | 0 |
| Colon normal | 39.44 | 16.6 | 22.84 | 0 |
| Colon Tumor | 38.73 | 16.22 | 22.51 | 0 |
| Lung normal | 38.99 | 16.12 | 22.87 | 0 |
| Lung tumor | 37.2 | 16.58 | 20.63 | 0 |
| Lung COPD | 38.73 | 16.72 | 22 | 0 |
| Colon IBD | 38.3 | 15.77 | 22.54 | 0 |
| Liver normal | 39.88 | 17.98 | 21.91 | 0 |
| Liver fibrosis | 37.62 | 19.28 | 18.34 | 0 |
| Dermal Cells-fibroblasts | 37.84 | 17.66 | 20.18 | 0 |
| Spleen normal | 37.22 | 18.06 | 19.16 | 0 |
| Tonsil normal | 37.55 | 15.44 | 22.11 | 0 |
| Lymph node | 39.7 | 17.23 | 22.47 | 0 |
| Resting PBMC | 40 | 18.8 | 21.2 | 0 |
| Skin-Decubitus | 36.45 | 18.82 | 17.64 | 0 |
| Synovium | 37.98 | 17.66 | 20.32 | 0 |
| BM-MNC (Bone marrow mononuclear cells) | 38.51 | 14.83 | 23.68 | 0 |
| Activated PBMC | 37.06 | 13.93 | 23.13 | 0 |
| Shear HUVEC | 38 | 17.99 | 20.01 | 0.0009 |

Expression of 16839 was also detected in a panel of tissues and liver cell lines as shown in Table 10.

TABLE 10

| Tissue Type | Mean | 18S Mean | ∂∂ Ct | Expression |
|---|---|---|---|---|
| PIT 278/Heart | 33.06 | 13.77 | 19.29 | 0.0016 |
| PIT 351/Kidney | 30.36 | 12.56 | 17.81 | 0.0044 |
| PIT 915/Skeletal Muscle | 38.28 | 11.87 | 26.41 | 0 |
| NDR 63/Liver | 33.23 | 11.69 | 21.54 | 0.0003 |
| NDR 242/Liver | 34.26 | 12.63 | 21.63 | 0.0003 |
| PIT 260/Liver | 33.58 | 11.77 | 21.81 | 0.0003 |
| CHT 756/Liver | 31.77 | 11.65 | 20.13 | 0.0009 |
| MPI 155/Liver | 34.91 | 14.68 | 20.23 | 0.0008 |
| MPI 146/Liver | 30.91 | 11.95 | 18.97 | 0.002 |
| CHT 902/Liver | 35.72 | 12.49 | 23.22 | 0 |
| PIT 45/Liver | 33.97 | 12.14 | 21.84 | 0.0003 |
| PIT 292/Liver | 35.46 | 13.65 | 21.82 | 0 |
| CLN 784/Liver | 32.56 | 11.76 | 20.8 | 0.0005 |
| NDR 752/Liver | 31.09 | 11.04 | 20.06 | 0.0009 |
| CHT 1679/Liver | 35.38 | 11.7 | 23.68 | 0 |
| CHT 1420/Liver | 33.06 | 11.15 | 21.91 | 0.0003 |
| CHT 339/Liver | 35.68 | 11.23 | 24.45 | 0 |
| CHT 1237/Liver | 33.41 | 11.02 | 22.4 | 0.0002 |

Expression of 16839 was also detected in a panel of breast tumor cell lines as shown in Table 11.

TABLE 11

| Tissue Type | Mean 16839.4 | β 2 Mean | ∂∂ Ct | Expression |
|---|---|---|---|---|
| MCF10MS | 35.1 | 18.84 | 16.25 | 0 |
| MCF10A | 33.88 | 18.81 | 15.07 | 0.03 |
| MCF10AT.cl1 | 34.2 | 18.88 | 15.32 | 0.02 |
| MCF10AT.cl3 | 35.19 | 18.22 | 16.98 | 0 |
| MCF10AT1 | 36.74 | 19.19 | 17.56 | 0 |
| MCF10AT3B | 36.23 | 18.93 | 17.3 | 0 |
| MCF10CA1a.cl1 | 36.94 | 16.34 | 20.59 | 0 |
| MCF10AT3B Agar | 37.76 | 25.07 | 12.68 | 0 |
| MCF10CA1a.cl1 Agar | 37.93 | 23.13 | 14.8 | 0 |
| MCF10A.m25 Plastic | 32.39 | 23.05 | 9.35 | 1.54 |
| MCF10CA Agar | 33.63 | 20.71 | 12.93 | 0.13 |
| MCF10CA Plastic | 35.98 | 20.56 | 15.43 | 0 |
| MCF3B Agar | 37.34 | 21 | 16.34 | 0 |
| MCF3B Plastic | 32.67 | 20.54 | 12.14 | 0.22 |
| MCF10A EGF 0 hr | 28.23 | 16.57 | 11.66 | 0.31 |
| MCF10A EGF 0.5 hr | 28.84 | 16.61 | 12.23 | 0.21 |
| MCF10A EGF 1 hr | 28.68 | 16.79 | 11.9 | 0.26 |
| MCF10A EGF 2 hr | 29.54 | 16.88 | 12.66 | 0.15 |
| MCF10A EGF 4 hr | 31.21 | 16.97 | 14.24 | 0.05 |
| MCF10A EGF 8 hr | 31.16 | 16.65 | 14.51 | 0.04 |
| MCF10A IGF1A 0 hr | 30.54 | 20.41 | 10.13 | 0.90 |
| MCF10A IGF1A 0.5 hr | 30.89 | 21.36 | 9.52 | 1.36 |
| MCF10A IGF1A 1 hr | 29.7 | 20.84 | 8.86 | 2.15 |
| MCF10A IGF1A 3 hr | 30.14 | 21.09 | 9.05 | 1.89 |
| MCF10A IGF1A 24 hr | 28.53 | 20.43 | 8.1 | 3.66 |
| MCF10AT3B.cl5 Plastic | 36.57 | 20.54 | 16.03 | 0 |
| MCF10AT3B.cl6 Plastic | 38.18 | 20.7 | 17.48 | 0 |
| MCF10AT3B.cl3 Plastic | 39.13 | 20.8 | 18.34 | 0 |
| MCF10AT3B.cl1 Plastic | 35.92 | 21.07 | 14.85 | 0 |
| MCF10AT3B.cl4 Plastic | 38.1 | 20.95 | 17.15 | 0 |
| MCF10AT3B.cl2 Plastic | 36.49 | 20.75 | 15.74 | 0 |
| MCF10AT3B.cl5 Agar | 39.22 | 22.68 | 16.54 | 0 |
| MCF10AT3B.cl6 Agar | 35.7 | 23.13 | 12.57 | 0 |
| MCF-7 | 37.46 | 22.25 | 15.22 | 0 |
| ZR-75 | 37.54 | 21.25 | 16.3 | 0 |
| T47D | 37.19 | 20.72 | 16.47 | 0 |
| MDA-231 | 33.55 | 19.7 | 13.85 | 0.07 |
| MDA-435 | 34.73 | 19.39 | 15.35 | 0.02 |
| SkBr3 | 37.16 | 19.86 | 17.3 | 0 |
| Hs578Bst | 36.52 | 18.93 | 17.59 | 0 |
| Hs578T | 31.36 | 19 | 12.35 | 0.19 |

Expression of 16839 was also detected in an oncology phase panel as shown in Table 12 and shows highest relative expression in lung tumor (CHT 832 lung T-PDNCSCCL) and upregulation of 16839 was found in 3/7 lung tumor tissue or cell samples.

TABLE 12

| Tissue Type | Mean 16839.4 | β 2 Mean | ∂∂ Ct | Expression |
|---|---|---|---|---|
| PIT 400 Breast N | 35.4 | 19.18 | 16.23 | 0 |
| PIT 372 Breast N | 35.38 | 19.66 | 15.72 | 0 |
| CHT 558 Breast N | 36.38 | 19.02 | 17.36 | 0 |

TABLE 12-continued

| Tissue Type | Mean 16839.4 | β 2 Mean | ∂∂ Ct | Expression |
|---|---|---|---|---|
| CLN 168 Breast T: IDC | 38.45 | 19.84 | 18.62 | 0 |
| MDA 304 Breast T: MD-IDC | 37.04 | 17.84 | 19.2 | 0 |
| NDR 58 Breast T: IDC | 38.83 | 17.84 | 20.99 | 0 |
| NDR 05 Breast T: IDC | 35.22 | 20.57 | 14.65 | 0 |
| CHT 562 Breast T: IDC | 34.08 | 18.71 | 15.37 | 0.02 |
| NDR 12 Breast T | 35.52 | 21.39 | 14.13 | 0 |
| PIT 208 Ovary N | 37.06 | 18.56 | 18.5 | 0 |
| CHT 620 Ovary N | 36.05 | 19.2 | 16.85 | 0 |
| CLN 03 Ovary T | 40 | 19.83 | 20.17 | 0 |
| CLN 17 Ovary T | 39.49 | 20 | 19.5 | 0 |
| MDA 25 Ovary T | 38.42 | 21.65 | 16.78 | 0 |
| MDA 216 Ovary T | 38.04 | 20.11 | 17.93 | 0 |
| CLN 012 Ovary T | 39.27 | 21.3 | 17.98 | 0 |
| MDA 185 Lung N | 40 | 19.43 | 20.57 | 0 |
| CLN 930 Lung N | 37.99 | 20.29 | 17.7 | 0 |
| MDA 183 Lung N | 39.65 | 18.11 | 21.54 | 0 |
| MPI 215 Lung T—SmC | 31.34 | 18.62 | 12.72 | 0.15 |
| MDA 259 Lung T-PDNSCCL | 37.42 | 19.93 | 17.49 | 0 |
| CHT 832 Lung T-PDNSCCL | 28.18 | 18.86 | 9.32 | 1.56 |
| MDA 253 Lung T-PDNSCC | 33.39 | 18.05 | 15.35 | 0.02 |
| MDA 262 Lung T-SCC | 38.79 | 22.28 | 16.51 | 0 |
| CHT 211 Lung T-AC | 39.1 | 19.29 | 19.82 | 0 |
| CHT 793 Lung T-ACA | 35.74 | 18.55 | 17.19 | 0 |
| CHT 396 Colon N | 39.82 | 17.7 | 22.13 | 0 |
| CHT 523 Colon N | 39.99 | 18.52 | 21.47 | 0 |
| CHT 452 Colon N | 40 | 17.5 | 22.5 | 0 |
| CHT 382 Colon T: MD | 38.42 | 17.97 | 20.45 | 0 |
| CHT 528 Colon T: MD | 34.85 | 17.54 | 17.32 | 0.01 |
| CLN 609 Colon T | 38.1 | 18.82 | 19.29 | 0 |
| CHT 372 Colon T: MD-PD | 37.83 | 19.24 | 18.59 | 0 |
| CHT 340 Colon-Liver Met | 37.93 | 19.99 | 17.94 | 0 |
| NDR 100 Colon-Liver Met | 36.52 | 18.26 | 18.27 | 0 |
| PIT 260 Liver N (female) | 35.31 | 16.93 | 18.37 | 0 |
| ONC 102 Hemangioma | 36.36 | 19.04 | 17.32 | 0 |
| A24 HMVEC-Arr | 35.31 | 18.75 | 16.55 | 0 |
| C48 HMVEC-Prol | 35.12 | 19.18 | 15.94 | 0 |

Human 49937, 49931 and 49933

The present invention is based, at least in part, on the discovery of novel calcium transporter family members, referred to interchangeably herein as "P-type ATPase", "E1-E2 ATPase", "human E1-E2 ATPase", or "HEAT" nucleic acid and protein molecules (e.g., HEAT-1 (49937), HEAT-2 (49931) and HEAT-3(49933)). These novel molecules are members of the E1-E2 ATPase superfamily and are highly expressed in human vessels, endothelial cells, and vascular smooth muscle cells, e.g., coronary vascular smooth muscle cells.

The E1-E2 ATPase family is a large superfamily of cation transport enzymes that contains at least 80 members found in diverse organisms such as bacteria, archaea, and eukaryotes (Palmgren, M. G. and Axelsen, K. B. (1998) *Biochim. Biophys. Acta.* 1365:37-45). These enzymes are involved in ATP hydrolysis-dependent transmembrane movement of a variety of inorganic cations (e.g., $H^+$, $Na^+$, $K^+$, $Ca^{2+}$, $Cu^{2+}$, $Cd^+$, and $Mg^{2+}$ ions) across a concentration gradient, whereby the enzyme converts the free energy of ATP hydrolysis into electrochemical ion gradients. E1-E2 ATPases are also known as "P-type" ATPases, referring to the existence of a covalent high-energy phosphoryl-enzyme intermediate in the chemical reaction pathway of these transporters. The superfamily contains four major groups: $Ca^{2+}$ transporting ATPases; $Na^+/K^+$- and gastric $H^+/K^+$ transporting ATPases; plasma membrane $H^+$ transporting ATPases of plants, fungi, and lower eukaryotes; and all bacterial P-type ATPases (Kuhlbrandt et al. (1998) *Curr. Opin. Struct. Biol.* 8:510-516).

The E1-E2 ATPases are involved in ATP hydrolysis-dependent transmembrane movement of inorganic cations (e.g., $Ca^{2+}$ ions) across a concentration gradient. E1-E2 ATPases are phosphorylated at a highly conserved DKTG sequence. Phosphorylation at this site is thought to control the enzyme's substrate affinity. Most E1-E2 ATPases contain ten alpha-helical transmembrane domains, although additional domains may be present. Members of the E1-E2 ATPase superfamily are able to generate electrochemical ion gradients which enable a variety of processes in the cell such as absorption, secretion, transmembrane signaling, nerve impulse transmission, excitation/contraction coupling, and growth and differentiation (Scarborough (1999) *Curr. Opin. Cell Biol.* 11:517-522).

As indicated in herein, the HEAT molecules of the present invention, e.g., HEAT-2, are up-regulated during shear, proliferation, and tube formation of endothelial cells and, thus, are believed to be involved in angiogenesis. Calcium ions are involved in the regulation of many cellular activities. In vascular smooth muscle cells, transient increases in intracellular calcium levels mediate contraction. Thus, maintenance of a low steady-state level of calcium is critical to maintaining proper cell function. Additionally, since the main determinant of the contraction-relaxation cycle of smooth muscle is calcium, calcium concentration is an important factor in the regulation of vascular tone. The normal concentration of calcium in the cell is in the submicromolar range, while the concentration in the extracellular compartment is in the millimolar range. In order to maintain intracellular calcium concentration in the submicromolar range, several mechanisms are operative in most cells. In smooth muscle cells, these regulatory mechanisms include calcium extrusion via $Ca^{2+}$-transporting E1-E2 ATPases at the plasma membrane and at the sarcoplasmic/endoplasmic reticulum.

Thus, as the HEAT molecules of the present invention are $Ca^{2+}$-transporting E1-E2 ATPases, and are highly expressed in vessels, endothelial cells, and vascular smooth muscle cells, these molecules are believed to be involved in vasotone regulation of vascular smooth muscle cells, e.g., coronary vascular smooth muscle cells. For example, activation of a HEAT molecule of the invention, e.g., HEAT-3, may result in decreased cytosolic calcium concentrations, thus reducing vascular tone. Inhibition of a HEAT molecule of the invention, e.g., HEAT-3, may result in decreased intracellular calcium store, which may subsequently lower the calcium release by vasopressor stimulation, thereby reducing vascular smooth muscle tone.

Accordingly, the HEAT molecules of the present invention provide novel diagnostic targets and therapeutic agents for cardivascular disorders. The HEAT molecules of the present invention further provide novel diagnostic targets and therapeutic agents for cellular proliferation, growth, or differentiation disorders. Additional disorders that may be treated using the molecules of the present invention include disorders affecting tissues in which HEAT protein is expressed (e.g., vessels, endothelial cells, and vascular smooth muscle cells).

The family of HEAT proteins of the present invention comprises at least one "transmembrane domain," preferably at least 2, 3, or 4 transmembrane domains, more preferably 5, 6, 7, 8, or 9 transmembrane domains, even more preferably 10 or 11 transmembrane domains, and most preferably, 12 transmembrane domains. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) *Annu. Rev. Neurosci.* 19:235-263, the contents of which are incorporated herein by reference. Amino acid residues 8-25, 47-65, 231-253, 256-276, 428-448, 464-484, 936-954, 963-987, 994-1015, 1049-1065, 1079-1102, and 1118-1134 of the human HEAT-1 protein (SEQ ID NO:64) are predicted to comprise transmembrane domains. Amino acid residues 29-50; 211-227, 234-253, 294-317, 410-434, 449-469, 941-960, 968-985, 1000-1020, 1076-1092, 1105-1129, 1144-1160 of the human HEAT-2 protein (SEQ ID NO:68) are predicted to comprise transmembrane domains. Amino acid residues 65-89, 99-116, 242-258, 265-281, 445-464, 493-509, 990-1007, 1015-1031, 1049-1073, 1103-1119, 1134-1151, 1171-1187 of the human HEAT-3 protein (SEQ ID NO:71) are also predicted to comprise transmembrane domains.

In another embodiment, members of the HEAT family of proteins include at least one "E1-E2 ATPase domain" in the protein or corresponding nucleic acid molecule. As used herein, the term "E1-E2 ATPase" domain includes a protein domain having at least about 70-110 amino acid residues and a bit score of at least 30 when compared against an E1-E2 ATPase Hidden Markov Model (HMM), e.g., PFAM Accession Number PF00122. Preferably, an E1-E2 ATPase domain includes a protein having an amino acid sequence of about 80-100, or more preferably about 87, 89, or 90 amino acid residues, and a bit score of at least 35, 40, 50, or more preferably, 37.0, 51.4, or 53.4. To identify the presence of an E1-E2 ATPase domain in a HEAT protein, and make the determination that a protein of interest has a particular profile, the amino acid sequence of the protein is searched against a database of known protein motifs and/or domains (e.g., the HMM database). The E1-E2 ATPase domain (HMM) has been assigned the PFAM Accession number PF00122 (see the PFAM website, available online through Washington University in Saint Louis). A search was performed against the HMM database resulting in the identification of an E1-E2 ATPase domain in the amino acid sequence of human HEAT-1 at about residues 299-387 of SEQ ID NO:64. A search was also performed against the HMM database resulting in the identification of an E1-E2 ATPase domain in the amino acid sequence of human HEAT-2 at about residues 278-365 of SEQ ID NO:68. A search was further performed against the HMM database resulting in the identification of an E1-E2 ATPase domain in the amino acid sequence of human HEAT-3 at about residues 302-392 of SEQ ID NO:71.

A description of the Pfam database can be found in Sonhammer et al. (1997) *Proteins* 28:405-420, and a detailed description of HMMs can be found, for example, in Gribskov et al. (1990) *Methods Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

Preferably an E1-E2 ATPase domain is at least about 70-110 amino acid residues and has an "E1-E2 ATPase activity", for example, the ability to interact with a HEAT substrate or target molecule (e.g., ATP or a cation such as $Ca^{2+}$); to transport a HEAT substrate or target molecule (e.g., a cation such as $Ca^{2+}$) from one side of a biological membrane to the other; to adopt an E1 conformation or an E2 conformation; to convert a HEAT substrate or target molecule to a product (e.g., to hydrolyze ATP); to interact with a second non-HEAT protein; to modulate intra- or inter-cellular signaling and/or gene transcription (e.g., either directly or indirectly); to modulate vascular smooth muscle tone; to modulate cellular growth and/or proliferation; and/or to modulate angiogenesis. Accordingly, identifying the presence of an "E1-E2 ATPase domain" can include isolating a fragment of a HEAT molecule (e.g., a HEAT polypeptide) and assaying for the ability of the fragment to exhibit one of the aforementioned E1-E2 ATPase domain activities.

In another embodiment, a HEAT molecule of the present invention may also be identified based on its ability to adopt an E1 conformation or an E2 conformation. As used herein, an "E1 conformation" of a HEAT protein includes a 3-dimensional conformation of a HEAT protein which does not exhibit HEAT activity (e.g., the ability to transport $Ca^{2+}$), as defined herein. An E1 conformation of a HEAT protein usually occurs when the HEAT protein is unphosphorylated. As used herein, an "E2 conformation" of a HEAT protein includes a 3-dimensional conformation of a HEAT protein which exhibits HEAT activity (e.g., the ability to transport c $Ca^{2+}$), as defined herein. An E2 conformation of a HEAT protein usually occurs when the HEAT protein is phosphorylated.

In another embodiment, a HEAT protein of the present invention is identified based on the presence of an "E1-E2 ATPases phosphorylation site" in the protein or corresponding nucleic acid molecule. An E1-E2 ATPases phosphorylation site functions in accepting a phosphate moiety and has the following consensus sequence: D-K-T-G-T-[LIVM]-[TI] (SEQ ID NO:73), wherein D is phosphorylated. The use of amino acids in brackets indicates that the amino acid at the indicated position may be any one of the amino acids within the brackets, e.g., [TI] indicates any of one of either T (threonine) or I (isoleucine). The E1-E2 ATPases phosphorylation site has been assigned ProSite Accession Number PS00154. To identify the presence of an E1-E2 ATPases phosphorylation site in a HEAT protein, and to make the determination that a protein of interest has a particular profile, the amino acid sequence of the protein may be searched against a database of known protein domains (e.g., the ProSite database) using the default parameters (available online through the Swiss Institute for Bioinformatics). A search was performed against the ProSite database resulting in the identification of an E1-E2 ATPases phosphorylation site in the amino acid sequence of human HEAT-1 (SEQ ID NO:64) at about residues 513-519. A similar search resulted in the identification of an E1-E2 phosphorylation site in the amino acid sequence of human HEAT-2 (SEQ ID NO:68) at about residues 498-504 and in the amino acid sequence of human HEAT-3 (SEQ ID NO:71) at about residues 533-539.

Preferably an E1-E2 ATPase phosphorylation site has a "phosphorylation site activity," for example, the ability to be phosphorylated; to be dephosphorylated; to regulate the E1-E2 conformational change of the HEAT protein in which it is contained; to regulate transport of $Ca^{2+}$ across a biological membrane by the HEAT protein in which it is contained; and/or to regulate the activity (as defined herein) of the HEAT protein in which it is contained. Accordingly, identifying the presence of an "E1-E2 ATPases phosphorylation site" can include isolating a fragment of a HEAT molecule (e.g., a HEAT polypeptide) and assaying for the ability of the fragment to exhibit one of the aforementioned phosphorylation site activities.

The family of HEAT proteins of the present invention also comprises at least one "large extramembrane domain" in the protein or corresponding nucleic acid molecule. As used herein, a "large extramembrane domain" includes a domain having greater than 20 amino acid residues that is found between transmembrane domains, preferably on the cytoplasmic side of the plasma membrane, and does not span or traverse the plasma membrane. A large extramembrane domain preferably includes at least one, two, three, four or more motifs or consensus sequences characteristic of P-type or E1-E2 ATPases, i.e., includes one, two, three, four, or more "P-type ATPase consensus sequences or motifs". As used herein, the phrase "P-type ATPase consensus sequences or motifs" includes any consensus sequence or motif known in the art to be characteristic of P-type ATPases, including, but not limited to, the P-type ATPase sequence 1 motif (as defined herein), the P-type ATPase sequence 2 motif (as defined herein), the P-type ATPase sequence 3 motif (as defined herein), and the E1-E2 ATPases phosphorylation site (as defined herein).

In one embodiment, the family of HEAT proteins of the present invention comprises at least one "N-terminal" large extramembrane domain in the protein or corresponding nucleic acid molecule. As used herein, an "N-terminal" large extramembrane domain is found in the N-terminal $\frac{1}{3}^{rd}$ of the protein, preferably between the fourth and fifth transmembrane domains of a HEAT protein, and includes about 50-270, 50-250, 60-230, 70-210, 80-190, 90-170, or preferably, 92, 151, or 163 amino acid residues. In a preferred embodiment, an N-terminal large extramembrane domain includes at least one P-type ATPase sequence 1 motif (as described herein). An N-terminal large extramembrane domain was identified in the amino acid sequence of human HEAT-1 at about residues 277-427 of SEQ ID NO:64. An N-terminal large extramembrane domain was also identified in the amino acid sequence of human HEAT-2 at about residues 318-409 of SEQ ID NO:68 and in the amino acid sequence of human HEAT-3 at about residues 282-444 of SEQ ID NO:71.

The family of HEAT proteins of the present invention also comprises at least one "C-terminal" large extramembrane domain in the protein or corresponding nucleic acid molecule. As used herein, a "C-terminal" large extramembrane domain is found in the C-terminal $\frac{2}{3}^{rds}$ of the protein, preferably between the sixth and seventh transmembrane domains of a HEAT protein and includes about 340-590, 360-570, 380-550, 400-530, 420-510, 440-490, or preferably, 451, 471, or 480 amino acid residues. In a preferred embodiment, a C-terminal large extramembrane domain includes at least one or more of the following motifs: a P-type ATPase sequence 2 motif (as described herein), a P-type ATPase sequence 3 motif (as defined herein), and/or an E1-E2 ATPases phosphorylation site (as defined herein). A C-terminal large extramembrane domain was identified in the amino acid sequence of human HEAT-1 at about residues 485-935 of SEQ ID NO:64, in the amino acid sequence of human HEAT-2 at about residues 470-940 of SEQ ID NO:68, and in the amino acid sequence of human HEAT-3 at about residues 510-989 of SEQ ID NO:71.

In another embodiment, a HEAT protein of the present invention includes at least one "P-type ATPase sequence 1 motif" in the protein or corresponding nucleic acid molecule. As used herein, a "P-type ATPase sequence 1 motif" is a conserved sequence motif diagnostic for P-type ATPases (Tang, X. et al. (1996) *Science* 272:1495-1497; Fagan, M. J. and Saier, M. H. (1994) *J. Mol. Evol.* 38:57). A P-type ATPase sequence 1 motif is involved in the coupling of ATP hydrolysis with transport (e.g., transport of $Ca^{2+}$). The consensus sequence for a P-type ATPase sequence 1 motif is [DNS]-[QENR]-[SA]-[LIVSAN]-[LIV]-[TSN]-G-E-[SN] (SEQ ID NO:75). The use of amino acids in brackets indicates that the amino acid at the indicated position may be any one of the amino acids within the brackets, e.g., [SA] indicates any of one of either S (serine) or A (alanine). In a preferred embodiment, a P-type ATPase sequence 1 motif is contained within an N-terminal large extramembrane domain. In another preferred embodiment, a P-type ATPase sequence 1 motif in the HEAT proteins of the present invention has at least 1, 2, 3, 4, 5, 6, 7, 8 or more amino acid resides which match the consensus sequence for a P-type ATPase sequence 1 motif. A P-type ATPase sequence 1 motif was identified in the amino acid sequence of human HEAT-1 at about residues 341-349 of SEQ ID NO:64, in the amino acid sequence of human HEAT-2 at about residues 318-326 of SEQ ID NO:68, and in the amino acid sequence of human HEAT-3 at about residues 348-356 of SEQ ID NO:71.

In another embodiment, a HEAT protein of the present invention includes at least one "P-type ATPase sequence 2 motif" in the protein or corresponding nucleic acid molecule. As used herein, a "P-type ATPase sequence 2 motif" is a conserved sequence motif diagnostic for P-type ATPases (Tang, X. et al. (1996) *Science* 272:1495-1497; Fagan, M. J. and Saier, M. H. (1994) *J. Mol. Evol.* 38:57). Preferably, a P-type ATPase sequence 2 motif overlaps with and/or includes an E1-E2 ATPases phosphorylation site (as defined herein). The consensus sequence for a P-type ATPase sequence 2 motif is [LIV]-[CAML]-[STFL]-D-K-T-G-T-[LI]-T (SEQ ID NO:76). The use of amino acids in brackets indicates that the amino acid at the indicated position may be any one of the amino acids within the brackets, e.g., [LI] indicates any of one of either L (leucine) or I (isoleucine). In a preferred embodiment, a P-type ATPase sequence 2 motif is contained within a C-terminal large extramembrane domain. In another preferred embodiment, a P-type ATPase sequence 2 motif in the HEAT proteins of the present invention has at least 1, 2, 3, 4, 5, 6, 7, 8, 9 or more amino acid resides which match the consensus sequence for a P-type ATPase sequence 2 motif. A P-type ATPase sequence 2 motif was identified in the amino acid sequence of human HEAT-1 at about residues 510-519 of SEQ ID NO:64, in the amino acid sequence of human HEAT-2 at about residues 495-504 of SEQ ID NO:68, and in the amino acid sequence of human HEAT-3 at about residues 530-539 of SEQ ID NO:71.

In yet another embodiment, a HEAT protein of the present invention includes at least one "P-type ATPase sequence 3 motif" in the protein or corresponding nucleic acid molecule. As used herein, a "P-type ATPase sequence 3 motif" is a conserved sequence motif diagnostic for P-type ATPases (Tang, X. et al. (1996) *Science* 272:1495-1497; Fagan, M. J. and Saier, M. H. (1994) *J. Mol. Evol.* 38:57). A P-type ATPase sequence 3 motif is involved in ATP binding. The consensus sequence for a P-type ATPase sequence 3 motif is [TIV]-G-D-G-X-N-D-[ASG]-P-[ASV]-L (SEQ ID NO:77). X indicates that the amino acid at the indicated position may be any amino acid (i.e., is not conserved). The use of amino acids in brackets indicates that the amino acid at the indicated position may be any one of the amino acids within the brackets, e.g., [TIV] indicates any of one of either T (threonine), I (isoleucine), or V (valine). In a preferred embodiment, a P-type ATPase sequence 3 motif is contained within a C-terminal large extramembrane domain. In another preferred embodiment, a P-type ATPase sequence 3 motif in the HEAT proteins of the present invention has at least 1, 2, 3, 4, 5, 6, 7, 8 or more amino acid resides (including the amino acid at the position indicated by "X") which match the consensus sequence for a P-type ATPase sequence 3 motif. A P-type ATPase sequence 3 motif was identified in the amino acid sequence of human HEAT-1 at about residues 876-886 of SEQ ID NO:64, in the amino acid sequence of human HEAT-2 at about residues 881-891 of SEQ ID NO:68, and in the amino acid sequence of human HEAT-3 at about residues 862-872 of SEQ ID NO:71.

Isolated HEAT proteins of the present invention have an amino acid sequence sufficiently homologous to the amino acid sequence of SEQ ID NO:64, 68, or 71, or are encoded by a nucleotide sequence sufficiently homologous to SEQ ID NO:63, 65, 67, 69, 70, or 72. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homology or identity across the amino acid sequences of the domains and contain at least one and preferably two structural domains or motifs, are defined herein as sufficiently homologous. Furthermore, amino acid or nucleotide sequences which share at least 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homology or identity and share a common functional activity are defined herein as sufficiently homologous.

In a preferred embodiment, a HEAT protein includes at least one or more of the following domains or motifs: a transmembrane domain, an E1-E2 ATPase domain, an E1-E2 ATPases phosphorylation site, an N-terminal large extramembrane domain, a C-terminal large extramembrane domain, a P-type ATPase sequence 1 motif, a P-type ATPase sequence 2 motif, and/or a P-type ATPase sequence 3 motif, and has an amino acid sequence at least about 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more homologous or identical to the amino acid sequence of SEQ ID NO:64, 68, or 71. In yet another preferred embodiment, a HEAT protein includes at least one or more of the following domains or motifs: a transmembrane domain, an E1-E2 ATPase domain, an E1-E2 ATPases phosphorylation site, an N-terminal large extramembrane domain, a C-terminal large extramembrane domain, a P-type ATPase sequence 1 motif, a P-type ATPase sequence 2 motif, and/or a P-type ATPase sequence 3 motif, and is encoded by a nucleic acid molecule having a nucleotide sequence which hybridizes under stringent hybridization conditions to a complement of a nucleic acid molecule comprising the nucleotide sequence of SEQ ID NO:63, 65, 67, 69, 70, or 72. In another preferred embodiment, a HEAT protein includes at least one or more of the following domains or motifs: a transmembrane domain, an E1-E2 ATPase domain, an E1-E2 ATPases phosphorylation site, an N-terminal large extramembrane domain, a C-terminal large extramembrane domain, a P-type ATPase sequence 1 motif, a P-type ATPase sequence 2 motif, and/or a P-type ATPase sequence 3 motif, and has a HEAT activity.

As used interchangeably herein, a "HEAT activity", "biological activity of HEAT" or "functional activity of HEAT", includes an activity exerted or mediated by a HEAT protein, polypeptide or nucleic acid molecule on a HEAT responsive cell or on a HEAT substrate, as determined in vivo or in vitro, according to standard techniques. In one embodiment, a HEAT activity is a direct activity, such as an association with a HEAT target molecule. As used herein, a "target molecule" or "binding partner" is a molecule with which a HEAT protein binds or interacts in nature, such that HEAT-mediated function is achieved. A HEAT target molecule can be a non-HEAT molecule or a HEAT protein or polypeptide of the present invention. In an exemplary embodiment, a HEAT target molecule is a HEAT substrate (e.g., a $Ca^{2+}$ ion; ATP; or a non-HEAT protein). A HEAT activity can also be an indirect activity, such as a cellular signaling activity mediated by interaction of the HEAT protein with a HEAT substrate (e.g., regulation of vascular smooth muscle tone, cellular growth and/or proliferation, and/or angiogenesis).

In a preferred embodiment, a HEAT activity is at least one of the following activities: (i) interaction with a HEAT substrate or target molecule (e.g., a $Ca^{2+}$ ion; ATP; or a non-HEAT protein); (ii) transport of a HEAT substrate or target molecule (e.g., a $Ca^{2+}$ ion) from one side of a biological membrane to the other; (iii) the ability to be phosphorylated or dephosphorylated; (iv) adoption of an E1 conformation or an E2 conformation; (v) conversion of a HEAT substrate or target molecule to a product (e.g., hydrolysis of ATP to ADP and free phosphate); (vi) interaction with a second non-HEAT protein; (vii) modulation of intra- or inter-cellular signaling and/or gene transcription (e.g., either directly or indirectly); (viii) modulation of vascular smooth muscle tone; (ix) modulation of cellular growth and/or proliferation; and/or (x) modulation of angiogenesis.

Isolation of the Human HEAT cDNAs

The invention is based, at least in part, on the discovery of genes encoding novel members of the E1-E2 ATPase family. The entire sequence of human clones Fbh49937, Fbh49931, and Fbh49933 were determined and found to contain open reading frames termed human "HEAT-1," human "HEAT-2," and human "HEAT-3," respectively.

The nucleotide sequence encoding the human HEAT-1 gene, which is approximately 4055 nucleotides in length, is set forth as SEQ ID NO:63. The protein encoded by this nucleic acid molecule has a molecular weight of approximately 129.8 kD, it comprises about 1180 amino acids and it has the amino acid sequence set forth as SEQ ID NO:64. The coding region (open reading frame) of SEQ ID NO:63 is set forth as SEQ ID NO:65.

The nucleotide sequence encoding the human HEAT-2 gene, which is approximately 7249 nucleotides in length, is set forth as SEQ ID NO:67. The protein encoded by this nucleic acid molecule has a molecular weight of approximately 138.2 kD, it comprises about 1256 amino acids and it has the amino acid sequence set forth as SEQ ID NO:68. The coding region (open reading frame) of SEQ ID NO:67 is set forth as SEQ ID NO:69.

The nucleotide sequence encoding the human HEAT-3 gene, which is approximately 3919 nucleotides in length, is set forth as SEQ ID NO:70. The protein encoded by this nucleic acid molecule has a molecular weight of approximately 132.5 kD, it comprises about 1204 amino acids and it has the amino acid sequence set forth as SEQ ID NO:71. The coding region (open reading frame) of SEQ ID NO:70 is set forth as SEQ ID NO:72.

Analysis of the Human HEAT Molecules

The amino acid sequences of human HEAT-1, HEAT-2, and HEAT-3 were analyzed using the program PSORT (available online; see Nakai, K. and Kanehisa, M. (1992) *Genomics*

14:897-911) to predict the localization of the proteins within the cell. This program assesses the presence of different targeting and localization of amino acid sequences within the query sequence. The results of the analyses show that human HEAT-1 may be localized to the endoplasmic reticulum, mitochondria, secretory vesicles, or vacuoles. The results of these analyses further show that human HEAT-2 may be localized to the endoplasmic reticulum or the mitochondria and that human HEAT-3 may be localized to endoplasmic reticulum, the mitochondria, or vacuoles.

Analyses of the amino acid sequence of human HEAT-1, HEAT-2, and HEAT-3 were performed using MEMSAT. These analyses resulted in the identification of twelve possible transmembrane domains in the amino acid sequence of human HEAT-2 at residues 29-50, 211-227, 234-253, 294-317, 410-434, 449-469, 941-960, 968-985, 1000-1020, 1076-1092, 1105-1129, and 1144-1160 of SEQ ID NO:68. These analyses further resulted in the identification of twelve possible transmembrane domains in the amino acid sequence of human HEAT-3 at residues 65-89, 99-116, 242-258, 265-281, 445-464, 493-509, 990-1007, 1015-1031, 1049-1073, 1049-1073, 1103-1119, 1134-1151, and 1171-1187 of SEQ ID NO:71. Further analysis of the amino acid sequence of SEQ ID NO:71 (e.g., a Clustal W (1.74) multiple sequence alignment, for example, of the human HEAT-3 amino acid sequence with a known *C. elegans* cation-transporting ATPase (YE56*elegans*; SEQ ID NO:74; GenBank Accession No. P90747)) clearly identifies the twelve transmembrane domains of the HEAT-3 gene. The analysis of human HEAT-1 predicted twelve possible transmembrane domains in the amino acid sequence of human HEAT-1 (SEQ ID NO:64) at about residues 8-25, 47-65, 256-276, 428-448, 464-484, 900-920, 936-954, 963-987, 994-1015, 1049-1065, 1079-1102, and 1118-1134. The potential transmembrane domain at about residues 900-920 has a notably low score of only 0.4 by MEMSAT analysis. Further analysis of the amino acid sequence of SEQ ID NO:64 (e.g., alignment with, for example, a known *C. elegans* E1-E2 ATPase cation transporter (SEQ ID NO:66)) resulted in the identification of a twelfth transmembrane domain at about amino acid residues 231-253 of SEQ ID NO:64. Accordingly, the human HEAT-1 protein of SEQ ID NO:64 is predicted to have at least twelve transmembrane domains, for example, at about residues 8-25, 47-65, 231-253, 256-276, 428-448, 464-484, 936-954, 963-987, 994-1015, 1049-1065, 1079-1102, and 1118-1134.

Searches of the amino acid sequences of human HEAT-1, HEAT-2, and HEAT-3 were also performed against the HMM database. These searches resulted in the identification of an "E1-E2 ATPase" domain in the amino acid sequence of HEAT-1 at about residues 299-387 (score=51.4) of SEQ ID NO:64. These searches also resulted in the identification of an "E1-E2 ATPase" domain in the amino acid sequence of human HEAT-2 at about residues 278-365 (score=53.4) of SEQ ID NO:68. These searches further resulted in the identification of an "E1-E2 ATPase" domain in the amino acid sequence of human HEAT-3 at about residues 302-392 (score=37.0) of SEQ ID NO:71.

Searches of the amino acid sequence of human HEAT-1 were performed against the Prosite database. These searches resulted in the identification of an "E1-E2 ATPases phosphorylation site" at about residues 513-519 of SEQ ID NO:64. These searches also resulted in the identification in the amino acid sequence of human HEAT-1 of a number of potential N-glycosylation sites, cAMP- and cGMP-dependent protein kinase phosphorylation sites, protein kinase C phosphorylation sites, casein kinase II phosphorylation sites, and N-myristoylation sites.

Searches of the amino acid sequence of human HEAT-2 were also performed against the Prosite database. These searches resulted in the identification of an "E1-E2 ATPases phosphorylation site" at about residues 498-504 of SEQ ID NO:68. These searches also resulted in the identification in the amino acid sequence of human HEAT-2 of a number of potential N-glycosylation sites, cAMP- and cGMP-dependent protein kinase phosphorylation sites, protein kinase C phosphorylation sites, casein kinase II phosphorylation sites, tyrosine phosphorylation sites, and N-myristoylation sites.

Searches of the amino acid sequence of human HEAT-3 were further performed against the Prosite database. These searches resulted in the identification of an "E1-E2 ATPases phosphorylation site" at about residues 533-539 of SEQ ID NO:71. These searches also resulted in the identification in the amino acid sequence of human HEAT-3 of a number of potential N-glycosylation sites, cAMP- and cGMP-dependent protein kinase phosphorylation sites, protein kinase C phosphorylation sites, casein kinase II phosphorylation sites, and N-myristoylation sites.

The amino acid sequence of human HEAT-2 was used as a database query using the BLASTP program. This search established that human HEAT-2 has the highest homology to a putative yeast $Ca^{2+}$-transporting ATPase (high score=798, probability=2.9e-87).

Table 13 depicts an alignment of a region important in calcium binding from HEAT-1, HEAT-2, HEAT-3 with similar sequences from a number of E1-E2 ATPases of various substrate specificities from a number of different organisms. This region includes the sixth transmembrane domain from each of HEAT-1, HEAT-2, and HEAT-3, as well as a number of amino acid residues adjacent to the sixth transmembrane domain. Amino acid residues determined to be important for calcium binding by mutagenesis of a SERCA calcium-transporting E1-E2 ATPase are indicated ("SERCA mutagenesis"). Amino acid residues in this region that are critical for calcium binding are indicated in bold. Substrate specificities are as follows: Type V (calcium), $Ca^{2+}$ (calcium), $Cu^{2+}$ (copper), $Na^+/K^+$ (sodium/potassium), and PL (phospholipid).

TABLE 13

| Gene Name | GenBank Acc No. | Sequence | SEQ ID NO: | Substrate Specificity |
|---|---|---|---|---|
| SERCA mutagenesis | | IPEGLPA | 78 | |
| Fbh49937FL (HEAT-1) | | DLVTVVVPPALPAAMTVCTLYAQSRLRR | 79 | |
| Fbh49931FL (HEAT-2) | | DIITITVPPALPAAMTAGIVYAQRRLKK | 80 | |

TABLE 13-continued

| Gene Name | GenBank Acc No. | Sequence | SEQ ID NO: | Substrate Specificity |
|---|---|---|---|---|
| Fbh49933FL (HEAT-3) | | LILTSVVPPELPIELSLAVNTSLIALAK | 81 | |
| ATC9_Yeast_yor291 | Q12697 | DIITIVVPPALPATLTIGTNFALSRLKEK | 82 | Type V |
| ATC6_Yeast_SPF1_ye1031w | P39986 | LIITSVVPPELPMELTMAVNSSLAALAK | 83 | Type V |
| ATCY_SCHPO_sp_0140220 | O14022 | VLTILVPPALPATLSVGIANSIARLSRA | 84 | Type V |
| Gp_7324471_CE | AAF59622 | DLVTIVVPPALPAVMGIGIFYAQRRLRQK | 85 | Type V |
| Sp_Q21286_YBF7_CAEEL | Q21286 | DIITIVVPPALPAAMSVGIINANSRLKKK | 86 | Type V |
| YH2M_CAEEL_sp_q27533 | Q27533 | DIITITVPPALPAAMSVGIINAQLRLKKK | 87 | Type V |
| YE56_CAEEL_CAB05683 | CAB05683 | LILTSVIPPELPIELSLAVNSSLMALQKL | 88 | Type V |
| ATP2A1_H_AAB53112 | AAB53112 | ALAVAAIPEGLPAVITTCLALGTRRMAKK | 89 | $Ca^{2+}$ |
| Rabbit SERCA1 | P04191 | ALAVAAIPEGLPAVITTCLALGTRRMAKK | 90 | $Ca^{2+}$ |
| ATCB_Chick_SERCA1 | P13585 | ALAVAAIPEGLPAVITTCLALGTRRMAKK | 91 | $Ca^{2+}$ |
| ATC2_FELCA_SERCA2 | Q00779 | ALAVAAIPEGLPAVITTCLALGTRRMAKK | 92 | $Ca^{2+}$ |
| SERCA *Procambarus clarkii* | AAB82291 | ALAVAAIPEGLPAVITTCLALGTRRMAKK | 93 | $Ca^{2+}$ |
| hSERCA2 | P16615 | ALAVAAIPEGLPAVITTCLALGTRRMAKK | 94 | $Ca^{2+}$ |
| hSERCA3 | Q93084 | ALAVAAIPEGLPAVITTCLALGTRRMARK | 95 | $Ca^{2+}$ |
| ATCB_DROME_P22700_158416 | P22700 | AVAVAAIPEGLPAVITTCLALGTRRMAKK | 96 | $Ca^{2+}$ |
| ATC1_Yeast_PMR1 | P13586 | SLAVAAIPEGLPIIVTVTLALGVLRMAKR | 97 | $Ca^{2+}$ |
| Y_PMC1 | P38929 | TVIVVAVPEGLPLAVTLALAFATTRMTKD | 98 | $Ca^{2+}$ |
| hPMCA1 | P20020 | TVLVVAVPEGLPLAVTISLAYSVKKMMKD | 99 | $Ca^{2+}$ |
| hPMCA2 | Q01814 | TVLVVAVPEGLPLAVTISLAYSVKKMMKD | 100 | $Ca^{2+}$ |
| Rat PMCA1 | | TVLVVAVPEGLPLAVTISLAYSVKKMMKD | 101 | $Ca^{2+}$ |
| PMCA3_H | Q16720 | TVLVVAVPEGLPLAVTISLAYSVKKMMKD | 102 | $Ca^{2+}$ |
| PMCA4_H | P23634 | TVLVVAVPEGLPLAVTISLAYSVKKMMKD | 103 | $Ca^{2+}$ |
| Pcalp_Yeast | P38360 | TVLIVSCPCVIGLAVPIVFVIASGVAAKR | 104 | $Cu^{2+}$ |
| AT7A_Human | Q04656 | TVLCIACPCSLGLATPTAVMVGTGVGAQN | 105 | $Cu^{2+}$ |
| AT7B_Human | P35670 | TVLCIACPCSLGLATPTAVMVGTGVAAQN | 106 | $Cu^{2+}$ |
| ATNA_DROME_P13607_732656 | P13607 | GIIVANVPEGLLATVTVCLTLTAKRMASK | 107 | $Cu^{2+}$ |
| ATNA_HYDAT | P35317 | GIIVANVPEGLLATVTVCLTLTAKKMAKK | 108 | $Na^+/K^+$ |
| ATN1_BUFMA | P30714 | GIIVANVPEGLLATVTVCLTLTAKRMARK | 109 | $Na^+/K^+$ |
| ATN1_Human | P05023 | GIIVANVPEGLLATVTVCLTLTAKRMARK | 110 | $Na^+/K^+$ |

TABLE 13-continued

| Gene Name | GenBank Acc No. | Sequence | SEQ ID NO: | Substrate Specificity |
|---|---|---|---|---|
| ATN2 Human | P50993 | GIIVANVPEGLLATVTVCLTLTAKRMARK | 111 | $Na^+/K^+$ |
| ATN3 Human | P13637 | GIIVANVPEGLLATVTVCLTVTAKRMARK | 112 | $Na^+/K^+$ |
| ATPP2_H_AAD34706 | AAD34706 | ILFNNLIPISLLVTLEVVKFTQAYFINWD | 113 | PL |
| DRS2_ATC4_yeast | P39524 | ILFSNLVPISLFVTVELIKYYQAFMIGSD | 114 | PL |

15

Tissue Expression Analysis of HEAT-1, HEAT-2, and HEAT-3 mRNA Using Transcriptional Profiling and Taqman Analysis This example describes the tissue distribution of human HEAT-2 mRNA, as determined using transcriptional profiling analysis and the TaqMan™ procedure. For transcriptional profiling analysis, an array of several thousand cDNA clones are spotted onto a nylon membrane and probed with a complex probe prepared by radiolabeling cDNA made from mRNA from, for example, normal tissue, and another, separate probe made from mRNA from another tissue, for example, diseased tissue. Expression levels of each gene in the first (e.g., normal) and the second (e.g., diseased) tissue are then compared. Transcriptional profiling thus allows assessment of the expression level of several thousand genes in an mRNA sample at the same time.

Endothelial Cell Paradigms

To induce tube formation, human microvascular endothelial cells isolated from the lung (HMVECs) were plated on Matrigel to induce capillary-like tube formation. At 5 hours, the cells were actively forming tubes, and RNA was harvested. Additional RNA samples were prepared from cells 25 hours after plating on Matrigel when tube formation was complete, and from actively proliferating and confluent HMVECs grown on plastic.

Cells were also treated with laminar shear stress (LSS) of 7 dyn/cm² for 24-30 hours, LSS plus one or six additional hours of 12 dyn/cm² ("1 h up" or "6 h up"), or LSS plus one or six additional hours of 2 dyn/cm² ("1 h down" or "6 h down").

HEAT-1

The expression levels of human HEAT-1 mRNA in various human and monkey cell types and tissues was first determined using the TAQMAN™ procedure. The tissues and cells tested correspond to (1) normal artery; (2) normal vein; (3) aortic smooth muscle cells (early); (4) coronary smooth muscle cells; (5) umbilical vein endothelial cells (static); (6) umbilical vein endothelial cells (shear); (7) normal heart; (8) heart (congestive heart failure); (9) kidney; (10) skeletal muscle; (11) normal adipose tissue; (12) pancreas; (13) primary osteoblasts; (14) differentiated osteoclasts; (15) normal skin; (16) normal spinal cord; (17) normal brain cortex; (18) normal brain hypothalamus; (19) nerve; (20) dorsal root ganglion; (21) glial cells (astrocytes); (22) glioblastoma; (23) normal breast; (24) breast tumor; (25) normal ovary; (26) ovarian tumor; (27) normal prostate; (28) prostate tumor; (29) epithelial cells (prostate); (30) normal colon; (31) colon tumor; (32) normal lung; (33) lung tumor; (34) lung (chronic obstructive pulmonary disease); (35) colon (inflammatory bowel disease); (36) normal liver; (37) liver fibrosis; (38) dermal cells (fibroblasts); (39) normal spleen; (40) normal tonsil; (41) lymph node; (42) small intestine; (43) skin (decubitus); (44) synovium; (45) bone marrow mononuclear cells; and (46) activated peripheral blood mononuclear cells. As assessed by this TAQMAN™ analysis, HEAT-1 is highly expressed in coronary artery vascular smooth muscle cells, prostate epithelial cells, pancreas, and brain (including cortex, hypothalamus, dorsal root ganglion cells, and glial cells/astrocytes).

The expression levels of human HEAT-1 mRNA in various human vascular rich organs was then determined using the TAQMAN™ procedur, the samples tested include (1) confluent microvascular endothelial cells; (2) aortic smooth muscle cells; (3) fetal heart; (4) normal heart atrium; (5) normal heart atrium; (6) normal heart ventricle; (7) normal heart ventricle; (8) normal heart ventricle; (9) normal heart ventricle; (10) normal heart ventricle; (11) diseased heart ventricle; (12) diseased heart ventricle; (13) disease heart ventricle; (14) normal kidney; (15) normal kidney; (16) normal kidney; (17) normal kidney; (18) normal kidney; (19) hypertensive kidney; (20) hypertensive kidney; (21) hypertensive kidney; (22) hypertensive kidney; (23) skeletal muscle; (24) skeletal muscle; (25) liver; (26) liver; (27) normal fetal adrenal gland; (28) Wilms tumor; (29) Wilms tumor; (30) normal spinal cord; and (31) diseased cartilage. As assessed by this TAQMAN™ panel, HEAT-1 is highly expressed in Wilms' tumor, normal spinal cord, and microvascular endothelial cells.

In another TAQMAN™ experiment, the expression levels of human HEAT-1 mRNA in various human and monkey vessels, namely (1) human aortic smooth muscle cells; (2) human microvascular endothelial cells; (3) human adipose tissue; (4) human normal carotid artery; (5) human normal carotid artery; (6) human normal muscular artery; (7) human diseased iliac artery; (8) human diseased tibial artery; (9) human diseased aorta; (10) human normal saphenous vein; (11) human normal saphenous vein; (12) human normal saphenous vein; (13) human normal saphenous vein; (14) human diseased saphenous vein; (15) human normal vein; (16) human normal vein; (17) human normal vein; (18) monkey normal coronary artery; (19) monkey normal coronary artery; (20) monkey normal coronary artery; (21) monkey normal coronary artery; (22) monkey normal vein; and (23) no transcriptase control, was determined. This TAQMAN™ panel demonstrated that HEAT-1 is highly expressed in vessels such as arteries and veins.

The expression levels of human HEAT-1 mRNA in various human coronary vascular cell types, namely (1) aortic smooth muscle cells; (2) aortic smooth muscle cells; (3) aortic smooth muscle cells; (4) coronary smooth muscle cells; (5) coronary smooth muscle cells; (6) coronary smooth muscle cells; (7) coronary smooth muscle cells; (8) macrophages; (9)

macrophages treated with IFNγ; (10) macrophages treated with CD40; (11) macrophages treated with LPS; (12) umbilical vein endothelial cells; (13) microvascular endothelial cells; (14) aortic endothelial cells; (15) aortic endothelial cells; (16) cortex renal epithelium; (17) renal proximal tubule epithelium; (18) mesangial cells; (19) skeletal muscle; (20) skeletal muscle; and (21) lung fibroblasts was also determined using the TAQMAN™ procedure. This TAQMAN™ panel demonstrated that HEAT-1 is highly expressed in coronary and vascular smooth muscle cells, as compared to other cell types.

The expression levels of human HEAT-1 mRNA in various human endothelial cell paradigms was determined using the TAQMAN™ procedure. These experiments demonstrated that human HEAT-1 is upregulated during shear stress of endothelial cells and that human HEAT-1 is upregulated during proliferation and tube formation of endothelial cells. These data strongly link human HEAT-1 to a role in angiogenesis.

HEAT-2

The expression levels of human HEAT-2 mRNA in various human and monkey cell types and tissues was first determined using transcriptional profiling. The samples tested include (1) human aortic smooth muscle cells; (2) human coronary artery smooth muscle cells; (3) human umbilical vein endothelial cells; (4) human microvascular endothelial cells (lung); (5) monkey aorta; (6) monkey vein; (7) monkey heart; and (8) monkey liver. As shown in these experiments, HEAT-2 is highly expressed in coronary artery vascular smooth muscle cells, as compared to other tissues such as aortic vascular smooth muscle cells, umbilical vein endothelial cells, microvascular endothelial cells, heart, liver, aorta, and vein. The expression levels of human HEAT-2 mRNA in various human cell types and tissues was then confirmed in a second experiment using the TAQMAN™ procedure using a panel consisting of the following tissues and samples: (1) normal aorta; (2) normal fetal heart; (3) normal heart; (4) heart (congestive heart failure); (5) normal vein; (6) aortic smooth muscle cells; (7) normal spinal cord; (8) brain (normal cortex); (9) brain (hypothalamus); (10) glial cells (astrocytes); (11) brain (glioblastoma); (12) normal breast; (13) breast tumor (infiltrating ductal carcinoma); (14) normal ovary; (15) ovarian tumor; (16) pancreas; (17) normal prostate; (18) prostate tumor; (19) normal colon; (20) colon tumor; (21) colon (inflammatory bowel disease); (22) normal kidney; (23) normal liver; (24) fibrotic liver; (25) normal fetal liver; (26) normal lung; (27) lung tumor; (28) lung (chronic obstructive pulmonary disease); (29) normal spleen; (30) normal tonsil; (31) normal lymph node; (32) normal thymus; (33) epithelial cells (from prostate); (34) aortic endothelial cells; (35) skeletal muscle; (36) dermal fibroblasts; (37) normal skin; (38) normal adipose tissue; (39) primary osteoblasts; (40) undifferentiated osteoblasts; (41) differentiated osteoblasts; (42) osteoclasts; (43) aortic smooth muscle cells (early); (44) aortic smooth muscle cells (late); (45) human umbilical vein endothelial cells (shear); and (46) human umbilical vein endothelial cells (static).

The expression levels of human BEAT-2 mRNA in various human vascular rich organs, namely (1) normal human heart; (2) normal human heart; (3) normal human heart; (4) normal human heart; (5) normal human heart; (6) normal human heart; (7) normal human heart; (8) normal human heart; (9) diseased human heart; (10) diseased human right ventricle; (11) diseased human left ventricle; (12) normal monkey heart; (13) normal monkey heart; (14) normal monkey heart; (15) normal human kidney; (16) normal human kidney; (17) normal human kidney; (18) normal human kidney; (19) normal human kidney; (20) human hypertensive kidney; (21) human hypertensive kidney; (22) human hypertensive kidney; (23) human hypertensive kidney; (24) human hypertensive kidney; (25) human liver; (26) human liver; (27) human liver; (28) human skeletal muscle; (29) human skeletal muscle; and (30) human skeletal muscle, was then determined using the TAQMAN™ procedure. These experiments demonstrated that HEAT-2 is highly expressed in the heart.

In another experiment, the expression levels of human HEAT-2 mRNA in various human and monkey vessels, namely (1) human adipose tissue; (2) human normal artery; (3) human normal artery; (4) human carotid artery; (5) human carotid artery; (6) human normal artery; (7) human diseased artery; (8) human diseased artery; (9) human diseased artery; (10) human normal vein; (11) human normal vein; (12) human vein; (13) human vein; (14) human normal vein; (15) human varicose vein; (16) confluent human microvascular endothelial cells; (17) human aortic smooth muscle cells; (18) monkey aorta; (19) monkey aorta; (20) monkey aorta; (21) monkey artery; (22) monkey artery; (23) monkey renal artery; (24) monkey renal artery; (25) monkey renal artery; (26) monkey renal artery; (27) monkey renal artery; (28) monkey coronary artery; (29) monkey coronary artery; (30) monkey coronary artery; (31) monkey coronary artery; (32) monkey coronary artery; (33) monkey coronary artery; and (34) monkey coronary artery, was determined using the TAQMAN™ procedure and in situ hybridization. These experiments demonstrated that HEAT-2 is highly expressed in vessels such as arteries and veins.

The expression levels of human HEAT-2 mRNA in various human coronary vascular cell types, namely (1) aortic smooth muscle cells; (2) aortic smooth muscle cells; (3) aortic smooth muscle cells; (4) aortic smooth muscle cells; (5) coronary smooth muscle cells; (6) coronary smooth muscle cells; (7) coronary smooth muscle cells; (8) coronary smooth muscle cells; (9) macrophages; (10) macrophages treated with IFNγ; (11) macrophages treated with CD40; (12) macrophages treated with LPS; (13) umbilical vein endothelial cells; (14) microvascular endothelial cells; (15) aortic endothelial cells; (16) coronary artery endothelial cells; (17) coronary artery endothelial cells; (18) cortex renal epithelium; (19) renal proximal tubule epithelium; (20) mesangial cells; (21) skeletal muscle; (22) skeletal muscle; and (23) lung fibroblasts, was also determined using the TAQMAN™ procedure. As determined by these experiments, HEAT-2 is highly expressed in coronary vascular smooth muscle cells, as compared to other cell types.

The expression levels of human HEAT-2 mRNA in various human endothelial cell paradigms was determined using the TAQMAN™ procedure. The samples tested include (1) umbilical vein endothelial cells (static); (2) umbilical vein endothelial cells (shear regulated); (3) umbilical vein endothelial cells (proliferating); (4) umbilical vein endothelial cells (confluent); (5) umbilical vein endothelial cells (without growth factor treatment); (6) umbilical vein endothelial cells (Interleukin-1 stimulated); (7) microvascular endothelial cells (proliferating); (8) microvascular endothelial cells (confluent); (9) microvascular endothelial cells (proliferating); (10) microvascular endothelial cells (confluent); (11) microvascular endothelial cells (proliferating); (12) microvascular endothelial cells (confluent); (13) microvascular endothelial cells (without growth factor treatment); (14) coronary microvascular endothelial cells (proliferating); (15) coronary microvascular endothelial cells (confluent); (16) microvascular endothelial cells (5% serum plus growth factors); (17) microvascular endothelial cells (5% serum without growth factors); (18) microvascular endothelial cells (hEGF treated); (19) microvascular endothelial cells (VEGF treated); (20) microvascular endothelial cells (bFGF treated); (21) microvascular endothelial cells (IGF treated); (22) 293 cells; (23) umbilical vein endothelial cells (static 25 h); (24) umbilical vein endothelial cells (laminar shear stress); (25) umbilical vein endothelial cells (laminar shear stress+1 h up); (26) umbilical vein endothelial cells (laminar shear stress+1 h down); (27) umbilical vein endothelial cells (static 30 h); (28) umbilical vein endothelial cells (laminar shear stress); (29) umbilical vein endothelial cells (laminar shear stress+6 h up); (30) umbilical vein endothelial cells (static 30 h); (31) umbilical vein endothelial cells (laminar shear stress); and (32) umbilical vein endothelial cells (laminar shear stress+6 h down). These experiments demonstrate that HEAT-2 is upregulated during shear and proliferation of endothelial cells. These data strongly link HEAT-2 to a role in angiogenesis.

Human HEAT-2 was also shown to be upregulated during tube formation of endothelial cells. The expression level of human HEAT-2 is 5-fold higher in the 5-hour Matrigel sample than in any other sample, indicating that expression is significantly induced during the process of capillary-like tube formation. There is also significantly higher expression in proliferating HMVECs than in confluent HMVECs grown on plastic. These results indicate a pro-angiogenic function for human HEAT-2.

Human HEAT-2 mRNA expression was also detected by in situ hybridization analysis in human endothelial cells and myocytes in the heart and in endothelial cells and inflammatory cells in ApoE knockout mouse diseased aortic roots.

HEAT-3

The expression levels of human HEAT-3 mRNA in various human and monkey cell types and tissues, namely (1) normal aorta; (2) normal fetal heart; (3) normal heart; (4) heart (congestive heart failure); (5) normal vein; (6) normal spinal cord; (7) normal brain cortex; (8) normal brain hypothalamus; (9) glial cells (astrocytes); (10) glioblastoma (brain); (11) normal breast; (12) breast tumor (infiltrating ductal carcinoma); (13) normal ovary; (14) ovarian tumor; (15) pancreas; (16) normal prostate; (17) prostate tumor; (18) normal colon; (19) colon tumor; (20) colon (inflammatory bowel disease); (21) normal kidney; (22) normal liver; (23) liver fibrosis; (24) normal fetal liver; (25) normal lung; (26) lung tumor; (27) lung (chronic obstructive pulmonary disease); (28) normal spleen; (29) normal tonsil; (30) normal lymph node; (31) normal thymus; (32) epithelial cells (prostate); (33) endothelial cells (aortic); (34) normal skeletal muscle; (35) fibroblasts (dermal); (36) normal skin; (37) normal adipose tissue; (38) primary osteoblasts; (39) undifferentiated osteoblasts; (40) differentiated osteoblasts; (41) osteoclasts; (42) aortic smooth muscle cells (early); (43) aortic smooth muscle cells (late); (44) umbilical vein endothelial cells (laminar shear stress); (45) umbilical vein endothelial cells (static); and (46) undifferentiated osteoclasts, was first determined using the TAQMAN™ procedure. These results demonstrate that HEAT-3 is highly expressed in coronary artery vascular smooth muscle cells, prostate epithelial cells, pancreas, and brain (including cortex, hypothalamus, and glial cells/astrocytes).

The expression levels of human HEAT-3 mRNA in various human vascular rich organs, namely (1) normal heart; (2) normal heart; (3) normal heart; (4) normal heart; (5) normal heart; (6) normal heart; (7) normal heart; (8) normal heart; (9) diseased heart; (10) diseased right ventricle; (11) normal fetal heart; (12) normal kidney; (13) normal kidney; (14) normal kidney; (15) normal kidney; (16) normal kidney; (17) hypertensive kidney; (18) hypertensive kidney; (19) hypertensive kidney; (20) hypertensive kidney; (21) hypertensive kidney; (22) skeletal muscle; (23) skeletal muscle; (24) skeletal muscle; (25) liver; (26) liver; (27) normal monkey heart; (28) normal monkey heart; (29) normal monkey heart; (30) normal monkey heart; (31) smooth muscle cells (SMC); (32) confluent human microvascular endothelial cells (HMVECs); (33) M human umbilical vein endothelial cells (HUVECs); (34) human umbilical vein endothelial cells (HUVECs) vehicle; (35) M human amniotic endothelial cells (HAECs); and (36) human amniotic endothelial cells (HAECs) vehicle, was then determined using the TAQMAN™ procedure. These experiments demonstrated that HEAT-3 is expressed in the heart, kidney, and skeletal muscle.

In another experiment, the expression levels of human HEAT-3 mRNA in various vessels, namely (1) aortic smooth muscle cells; (2) microvascular endothelial cells; (3) adipose tissue; (4) normal artery; (5) normal artery; (6) normal artery; (7) diseased artery; (8) diseased artery; (9) diseased aorta; (10) normal vein; (11) normal vein; (12) normal vein; (13) normal vein; (14) diseased vein; (15) normal vein; (16) normal vein; (17) normal vein; (18) LC smooth muscle cells; (19) LC smooth muscle cells; (20) aortic smooth muscle cells; (21) human microvascular endothelial cells; (22) normal human carotid artery; (23) normal human carotid artery; (24) normal human muscular artery; (25) human diseased iliac artery; (26) human diseased tibial artery; (27) human diseased aorta; (28) human normal saphenous vein; (29) human normal saphenous vein; (30) human normal saphenous vein; (31) human normal saphenous vein; (32) human diseased saphenous vein; (33) human normal vein; and (34) human normal saphenous vein, was determined using the TAQMAN™ procedure. These experiments demonstrated that HEAT-3 is highly expressed in vessels such as arteries and veins.

The expression levels of human HEAT-3 mRNA in various human coronary vascular cell types, namely (1) aortic smooth muscle cells; (2) aortic smooth muscle cells; (3) coronary smooth muscle cells; (4) coronary smooth muscle cells; (5) coronary smooth muscle cells; (6) coronary smooth muscle cells; (7) macrophages; (8) macrophages treated with IFNγ; (9) macrophages treated with CD40; (10) macrophages treated with LPS; (11) microvascular endothelial cells; (12) aortic endothelial cells; (13) coronary artery endothelial cells; (14) cortex renal epithelium; (15) renal proximal tubule epithelium; (16) mesangial cells; and (17) skeletal muscle, was also determined using the TAQMAN™ procedure. These experiments demonstrate that HEAT-3 is highly expressed in coronary and aortic vascular smooth muscle cells, as well as in renal proximal tubule epithelium, as compared to other cell types.

Tissue Distribution of HEAT mRNA Using In Situ Analysis

Using in situ hybridization analysis, HEAT-2 mRNA was found to be expressed in human endothelial cells and myocytes in the heart and in endothelial cells and inflammatory cells in ApoE knockout mice diseased aortic roots.

Assesment of Microvessel Contraction

The following describes the assessment of microvessel contraction using rat microvessels, as described in, for example, Bischoff, A. et al. (2000) Br. J. Pharmacol. 130: 1871-1877. Microvessels (e.g., mesenteric or renal microvessels such as interlobar arteries) are prepared from rats (e.g., adult Wistar rats) as described in Chen et al. (1996) *Naunyn-Schmiedeberg's Arch. Pharmacol.* 353:314-323 and Chen et al. (1997) *J. Auton. Pharmacol.* 17:137-146. Rats are killed by either decapitation or an overdose of thiobutabarbitone. The vessels are mounted on 40 µm diameter stainless steel wires in a myograph chamber for isometric recording of tension development. The vessels are then bathed in Krebs-Henseleit buffer of the following composition: 119 mM NaCl, 25 mM NaHCO$_3$, 4.7 mM KCl, 1.18 mM KH$_2$PO$_4$, 1.17 mM MgSO$_4$, 2.5 mM CaCl$_2$, 0.026 mM EDTA, and 5.5 mM D-glucose. The buffer temperature is maintained at 37° C., and the chamber is gassed with 5% CO2/95% O2 to maintain a pH of 7.4. Additionally, 5 µM cocaine and 1 µM (±)-propranolol may be added to block neuronal catecholoamine uptake and β-adrenoceptor activation by high noradrenaline concentration. Following equilibration, the vessels are challenged several times with 125 mM KCl and 10 µM noradrenaline. The vessels are then treated with 100 µM carbachol; vessels with a relaxation response of at least 50% indicate a functionally intact epithelium.

Assesment of Intracellular Free Calcium Concentrations in Cultured Rat Aortic Smooth Muscle Cells The following describes the assessment of intracellular free calcium concentrations in cultured rat aortic smooth muscle cells, as described in, for example, Bischoff, A. et al. (2000) *Br. J. Pharmacol.* 130:1871-1877. Vascular smooth muscle cells are prepared from rat thoracic aorta according to Rosskoph et al. (1995) *Cell Physiol. Biochem.* 5:276-285). Briefly, freshly prepared aortae are incubated for 30 minutes at room temperature with 125 U/ml collagenase I in Hank's balanced salt solution (HBSS) of the following composition: 118 mM NaCl, 5 mM KCl, 1 mM CaCl$_2$, 1 mM MgCl$_2$, 5 mM D-glucose, and 15 mM HEPES pH 7.4. Thereafter, remaining connective tissue and endothelium are removed, the aortae are cut into small pieces and incubated for 4-6 hours at 37° C. in DMEM/F12 medium with 100 U/ml penicillin, 100 µg/ml streptomycin, and 250 ng/ml amphotericin B. Treatment with collagenase (125 U/ml) and elastase (0.5 mg/ml) in HBSS without Ca$^{2+}$ and Mg$^{2+}$ follow for 2 hours at 37° C. The reaction is stopped by addition of DMEM/F12 medium containing 20% fetal calf serum and penicillin, streptomycin, and amphotericin B, and the cells are plated onto 60-mm cell culture plates. The cells are used between passage 3 and 6. The Ca$^{2+}$ concentration measurements are performed as described in Meyer zu Heringdorf et al. (1996) *Naunyn-Schmiedeberg's Arch. Pharmacol.* 354:397-403. Briefly, the cells are loaded with 1 µM fura2/AM for 1 hour at room temperature in HBSS, washed with HBSS, and used for fluorescence measurements within the next hour. Ca$^{2+}$ concentrations are measured in a continuously stirred cell suspension at room temperature in a Hitachi F2000 spectrofluorometer as described in Meyer zu Heringdorf et al. (1996) supra.

Calcium Transport Assay

The following describes the assessment of calcium transport by HEAT molecules in cultured COS-1 cells, as described in, for example, Maruyama, K. and MacLennan, D. H. (1988) *Proc. Natl. Acad. Sci. USA* 85:3314-3318.

Cell Culture and DNA Transfection

COS-1 or HEK-293 cells are maintained in Dulbecco's modified Eagle's medium (DMEM) with 0.1 mM α-MEM nonessential amino acids, 4 mM L-glutamine, 100 units of pennicillin per ml, 100 µg of streptomycin per ml, and 10% fetal calf serum under 5% CO$_2$/95% air at 37° C. Transfection of HEAT-containing DNA is carried out by the DEAE dextran-chloroquine shock method (Sompayrac, L. M. and Danna, K. J. (1981) *Proc. Natl. Acad. Sci. USA* 78:7575-7578; Gorman, C. (1985) in *DNA Cloning: A Practical Approach*, ed. Gover, D. M. (IRL, Washington, D.C.), Vol. 2, pp. 143-190) with 25 µg of cesium chloride gradient-purified DNA and 1.5 mg of DEAE dextran per 10 cm Petri dish. Cells are then incubated for 3 hours at 37° C. in 6 ml of DMEM containing 300 µg of chloroquine, washed, and cultured in DMEM for 48 or 72 hours. Control cells are treated in the same way with vector DNA or with no added DNA.

Isolation of Microsomal Fraction

For isolation of a microsomal fraction (Resh, M. D. and Erikson, R. L. (1985) *J. Cell Biol.* 100:409-417; Yamada, S. and Ikemoto, N. (1980) *J. Biol. Chem.* 255:3108-3119), cells from five 10 cm Petri dishes are washed twice with 5 ml of a solution of 0.137 M NaCl/2.7 mM KCl/8 mM Na$_2$HPO$_4$/1.5 mM KH$_2$PO$_4$ (PBS), harvested in a solution of 5 mM EDTA in PBS and washed with 5 ml of PBS. The cells are swollen at 0° C. for 10 minutes in 2 ml of a hypotonic solution of 10 mM Tris-HCl, pH 7.5/0.5 mM MgCl$_2$, and then phenylmethylsolfonyl fluoride and Trasylol are added to 0.1 mM and 100 units/ml, respectively. The cells are homogenized with 30 strokes in a glass Dounce homogenizer, and the homogenate is diluted with an equal volume of a solution of 0.5 M sucrose/6 mM 2-mercaptoenthanol, 40 µM CaCl$_2$/300 mM KCl/10 mM Tris-HCl, pH 7.5. The suspension is centrifuged at 10,000×g for 20 minutes to pellet nuclei and mitochondria. The supernatant is brought to a concentration of 0.6 M KCl by the addition of 0.9 ml of a 2.5 M solution. The suspension is centrifuged at 100,000×g for 60 minutes to sediment the microsomal fraction. The pellet is suspended in a solution containing 0.25 M sucrose, 0.15 M KCl, 3 mM 2-mercaptoethanol, 20 µM CaCl$_2$, 10 mM Tris-HCl (pH 7.5), and centrifuged again at 100,000×g for 60 minutes. The final pellet, containing approximately 100 µg of protein, is suspended in the same solution at a protein concentration of 1 mg/ml.

Ca$^{2+}$ Transport Assay

Ca$^{2+}$ transport activity is assayed in a reaction mixture containing 20 µM Mops-KOH (pH 6.8), 100 mM KCl, 5 mM CaCl$_2$, 5 mM ATP, 0.45 mM CaCl$_2$ (containing $^{45}$Ca at a specific activity of 10$^6$ cpm/mol), 0.5 mM EGTA, and 5 mM potassium oxalate. The uptake reaction is initiated by the addition of 10 µg of microsomal protein to 1 ml of reaction mixture at room temperature. At different time points, 0.15 ml samples are filtered through a 0.3 µm Millipore filter and washed with 10 ml of 0.15 M KCl. Radioactivity on the filter is measured by liquid scintillation counting. For the measurement of Ca$^{2+}$ ion dependency, free Ca$^{2+}$ concentration is calculated by the computer program of Fabiato and Fabiato ((1979) *J. Physiol.* (*London*) 75:463-505). For the measurement of ATP dependency, an ATP regenerating system consisting of 2.5 mM phosphoenolpyruvate and 50 µg of pyruvate kinase per ml is used.

Measurement of Phosphorylated HEAT Intermediate

Microsomal protein (5 µg) is added to 0.1 ml of a solution of 20 mM Mops, pH 6.8/100 mM KCl/5 mM MgCl$_2$/0.5 mM EGTA in the presence or absence of 0.5 mM CaCl$_2$. The reaction, at ice temperature, is started by the addition of 5 µM ATP (10$^6$ cpm/nmol) and stopped after 5 seconds by the addition of 0.6 ml of a mixture of 5% trichloroacetic acid and 5 mM potassium phosphate. Incorporation of $^{32}$P is determined either by collecting the protein on a filter for scintillation counting or by separating the protein in acidic NaDodSO$_4$/polyacrylamide gels for autoradiography Sarkadi, B. et al. (1986) *J. Biol. Chem.* 261:9552-9557).

Analysis of HEAT-3 Activity

The full-length HEAT-3 was inserted into the multiple cloning site in the pCDNA3 vector. The DNA for the clone was amplified and transfected into HEK-293 cells using calcium phosphate precipitation. After 72 hours, the cells were harvested, microsomal fractions isolated, and $^{45}$Ca-uptake measured as a function of calcium concentration using a filter assay.

Two different HEAT-3 fusion proteins were generated. One HEAT-3 fusion protein was created by inserting the 3× Flag epitope at the 3' end of the HEAT-3 gene. Another HEAT-3 fusion protein was created by inserting the green fluorescent protein (GFP) at the 3' end of the HEAT-3 gene. Fluorescence of this protein could be observed with the naked eye and by confocal microscopy. Measurement of expression using Western blotting with an anti-GFP antibody showed that HEAT-3 is well expressed in the microsomal fraction.

Confocal microscopy showed that the expression pattern of HEAT-3 is similar to SERCA1, indicating that HEAT-3 is targeted to and localized in the endoplasmic reticulum of HEK-293 cells.

$Ca^{2+}$ uptake experiments (as described above) were performed using both the Flag and GFP fusion proteins. An increase in $Ca^{2+}$ uptake of HEAT-3 was shown over GFP vector alone. Five independent experiments were performed to confirm the increase of calcium uptake with HEAT-3 as compared to vector alone. The Flag fusion protein showed an increase of calcium uptake as compared to Flag vector alone. In these experiments, the Vmax for HEAT-3 was lower (about 20×) than the Vmax for SERCA1 under the same conditions. The KCa for HEAT-3 was about 6.00 pCa units, as compared with about 6.38 pCa units for SERCA1. In the presence of ATP, there is 2-3 fold more calcium uptake compared to uptake in the absence of ATP, indicating that the calcium uptake by HEAT-3 is ATP dependent.

Definitions

The 25869, 25934, 26335, 50365, 21117, 38692, 46508, 16816, 16839, 49937, 49931 or 49933 protein, fragments thereof, and derivatives and other variants of the sequence in SEQ ID NO:2, 8, 17, 21, 26, 29, 36, 40, 43, 64, 68 or 71 thereof are collectively referred to as "polypeptides or proteins of the invention" or "25869, 25934, 26335, 50365, 21117, 38692, 46508, 16816, 16839, 49937, 49931 or 49933 polypeptides or proteins". Nucleic acid molecules encoding such polypeptides or proteins are collectively referred to as "nucleic acids of the invention" or "25869, 25934, 26335, 50365, 21117, 38692, 46508, 16816, 16839, 49937, 49931 or 49933 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, N.Y., 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 25869, 25934, 26335, 50365, 21117, 38692, 46508, 16816, 16839, 49937, 49931 or 49933 protein, preferably a mammalian 25869, 25934, 26335, 50365, 21117, 38692, 46508, 16816, 16839, 49937, 49931 or 49933 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 25869, 25934, 26335, 50365, 21117, 38692, 46508, 16816, 16839, 49937, 49931 or 49933 protein having less than about 30%, 20%, 10% and more preferably 5% (by dry weight), of non-25869, 25934, 26335, 50365, 21117, 38692, 46508, 16816, 16839, 49937, 49931 or 49933 protein (also referred to herein as a "contaminating protein"), or of chemical precursors or non-25869, 25934, 26335, 50365, 21117, 38692, 46508, 16816, 16839, 49937, 49931 or 49933 chemicals. When the 25869, 25934, 26335, 50365, 21117, 38692, 46508, 16816, 16839, 49937, 49931 or 49933 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 25869, 25934, 26335, 50365, 21117, 38692, 46508, 16816, 16839, 49937, 49931 or 49933 (e.g., the sequence of SEQ ID NO:1, 3, 7, 9, 16, 18, 20, 22, 25, 27, 28, 30, 35, 37, 39, 41, 42, 44, 63, 65, 67, 69, 70 or 72) without abolishing or more preferably, without substantially altering a biological activity, whereas an "essential" amino acid residue results in such a change. For example, amino acid residues that are conserved among the polypeptides of the present invention, e.g., those present in the conserved domains, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 25869, 25934, 26335, 50365, 21117, 38692, 46508, 16816, 16839, 49937, 49931 or 49933 protein is preferably replaced with another amino acid residue from the same side chain family. Alternatively, in another embodiment, mutations can be introduced randomly along all or part of a 25869, 25934, 26335, 50365, 21117, 38692, 46508, 16816, 16839, 49937, 49931 or 49933 coding sequence, such as by saturation mutagenesis, and the resultant mutants can be screened for 25869, 25934, 26335, 50365, 21117, 38692, 46508, 16816, 16839, 49937, 49931 or 49933 biological activity to identify mutants that retain activity. Following mutagenesis of SEQ ID NO:1, 3, 7, 9, 16, 18, 20, 22, 25, 27, 28, 30, 35, 37, 39, 41, 42, 44, 63, 65, 67, 69, 70 or 72, the encoded protein can be expressed recombinantly and the activity of the protein can be determined.

As used herein, a "biologically active portion" of a 25869, 25934, 26335, 50365, 21117, 38692, 46508, 16816, 16839, 49937, 49931 or 49933 protein includes a fragment of a 25869, 25934, 26335, 50365, 21117, 38692, 46508, 16816, 16839, 49937, 49931 or 49933 protein which participates in an interaction between a 25869, 25934, 26335, 50365, 21117, 38692, 46508, 16816, 16839, 49937, 49931 or 49933 molecule and a non-25869, 25934, 26335, 50365, 21117, 38692, 46508, 16816, 16839, 49937, 49931 or 49933 molecule. Biologically active portions of a 25869, 25934, 26335, 50365, 21117, 38692, 46508, 16816, 16839, 49937, 49931 or 49933 protein include peptides comprising amino acid sequences sufficiently homologous to or derived from the amino acid sequence of the 25869, 25934, 26335, 50365, 21117, 38692, 46508, 16816, 16839, 49937, 49931 or 49933 protein, e.g., the amino acid sequence shown in SEQ ID NO:2, 8, 17, 21, 26, 29, 36, 40, 43, 64, 68 or 71, which include fewer amino acids than the full length 25869, 25934, 26335, 50365, 21117, 38692, 46508, 16816, 16839, 49937, 49931 or 49933 protein, and exhibit at least one activity of a 25869, 25934, 26335, 50365, 21117, 38692, 46508, 16816, 16839, 49937, 49931 or 49933 protein. Typically, biologically active portions comprise a domain or motif with at least one activity of the 25869, 25934, 26335, 50365, 21117, 38692, 46508, 16816, 16839, 49937, 49931 or 49933 protein. A biologically active portion of a 25869, 25934, 26335, 50365, 21117, 38692, 46508, 16816, 16839, 49937, 49931 or 49933 protein can be a polypeptide which is, for example, 10, 25, 50, 100, 200 or more amino acids in length. Biologically active portions of a 25869, 25934, 26335, 50365, 21117, 38692, 46508, 16816, 16839, 49937, 49931 or 49933 protein can be used as targets for developing agents which modulate a 25869, 25934, 26335, 50365, 21117, 38692, 46508, 16816, 16839, 49937, 49931 or 49933 mediated activity.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to 25869, 25934, 26335, 50365, 21117, 38692, 46508, 16816, 16839, 49937, 49931 or 49933 nucleic acid molecules of the invention. BLAST protein searches can be performed with the XBLAST program, score=50, wordlength=3 to obtain amino acid sequences homologous to 25869, 25934, 26335, 50365, 21117, 38692, 46508, 16816, 16839, 49937, 49931 or 49933 protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used.

Particular 25869, 25934, 26335, 50365, 21117, 38692, 46508, 16816, 16839, 49937, 49931 or 49933 polypeptides of the present invention have an amino acid sequence substantially identical to the amino acid sequence of SEQ ID NO:2, 8, 17, 21, 26, 29, 36, 40, 43, 64, 68 or 71. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2, 8, 17, 21, 26, 29, 36, 40, 43, 64, 68 or 71 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequencese encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1, 3, 7, 9, 16, 18, 20, 22, 25, 27, 28, 30, 35, 37, 39, 41, 42, 44, 63, 65, 67, 69, 70 or 72 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

As used herein, cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders of the lung include, but are not limited to, tumors such as bronchogenic carcinoma, including paraneoplastic syndromes, bronchioloalveolar carcinoma, neuroendocrine tumors, such as bronchial carcinoid, miscellaneous tumors, metastatic tumors, and pleural tumors, including solitary fibrous tumors (pleural fibroma) and malignant mesothelioma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders involving the colon include, but are not limited to, tumors of the colon, such as non-neoplastic polyps, adenomas, familial syndromes, colorectal carcinogenesis, colorectal carcinoma, and carcinoid tumors.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Other disorders related to angiogenesis and which may, therefore, be treated using the molecules described herein, include diabetic retinopathy, neovascularization (e.g., intraocular neovascularization), psoriasis, endometriosis, Grave's disease, ischemic disease, chronic inflammatory diseases, macular degeneration, neovascular glaucoma, retinal fibroplasia, uveitis, eye diseases associated with choroidal neovascularization and iris neovascularization, hereditary hemorrhagic telangiectasia, fibrodysplasia ossificans progressiva, idiopathic pulmonary fibrosis, autosomal dominant polycystic kidney disease, synovitis, familial exudative vitreoretinopathy (FEVR), Alagille syndrome, Knobloch syndrome, disseminated lymphangiomatosis, toxic epidermal necrolysis, Von Hippel Lindau disease (VHL), microbial-related dysplastic and neoplastic angiomatous proliferative processes (e.g., verruga peruana (VP)), Proteus syndrome (PS), Castleman's disease, and Klippel-Trenaunay-Weber syndrome.

Proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As used herein, disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

As used herein, neurological disorders include disorders of the central nervous system (CNS) and the peripheral nervous system, e.g., cognitive and neurodegenerative disorders, Examples of neurological disorders include, but are not limited to, autonomic function disorders such as hypertension and sleep disorders, and neuropsychiatric disorders, such as depression, schizophrenia, schizoaffective disorder, Korsakoff's psychosis, alcoholism, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans) and other Lewy diffuse body diseases, progressive supranuclear palsy, corticobasal degenration, multiple system atrophy, including striatonigral degenration, Shy-Drager syndrome, and olivopontocerebellar atrophy, and Huntington's disease, senile dementia, Gilles de la Tourette's syndrome, epilepsy, and Jakob-Creutzfieldt disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutanebous syndromes (phakomatoses), including neurofibromotosis, including Type 1 neurofibromatosis (NF1) and TYPE 2 neurofibromatosis (NF2), tuberous sclerosis, and Von Hippel-Lindau disease. Further CNS-related disorders include, for example, those listed in the American Psychiatric Association's Diagnostic and Statistical manual of Mental Disorders (DSM), the most current version of which is incorporated herein by reference in its entirety.

As used herein, disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

As used herein, disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas, tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

As used herein, disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

As used herein, disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

As used herein, disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g., adenocarcinoma or carcinoma, of the prostate.

As used herein, the term "hematopoietic disorder" includes neoplastic and non-neoplastic hematopoietic or immune disorders. Examples of neoplastic immune disorders include, but are not limited to, erythroid leukemias, or leukemias of erythroid precursor cells, e.g., poorly differentiated acute leukemias such as erythroblastic leukemia and acute megakaryoblastic leukemia; acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97). In particular, AML can include the uncontrolled proliferation of CD34+ cells such as AML subtypes M1 and M2, myeloblastic leukemias with and without maturation, and AML subtype M6, erythroleukemia (Di Guglielmo's disease). Additional neoplastic disorders include a myelodysplastic syndrome or preleukemic disorder, e.g., oligoblastic leukemia, smoldering leukemia. Additional cancers of the erythroid lineage include erythroblastosis, and other relevant diseases of the bone marrow.

The term "leukemia" or "leukemic cancer" is intended to have its clinical meaning, namely, a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

Examples of non-neoplastic hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions,leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, the term "erythroid associated disorders" include disorders involving aberrant (increased or deficient) erythroblast proliferation, e.g., an erythroleukemia, and aberrant (increased or deficient) erythroblast differentiation, e.g., an anemia. Erythrocyte-associated disorders include anemias such as, for example, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in nonhematolic disorders, for example, as a result of chemotherapy, alcoholism, or liver disease; anemia of chronic disease, such as chronic renal failure; and endocrine deficiency diseases.

Agents that modulate polypeptide or nucleic acid activity or expression of the molecules of the invention can be used to treat anemias, in particular, anemias associated with cancer chemotherapy, chronic renal failure, malignancies, adult and juvenile rheumatoid arthritis, disorders of haemoglobin synthesis, prematurity, and zidovudine treatment of HIV infection. A subject receiving the treatment can be additionally treated with a second agent, e.g., erythropoietin, to futher ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz, Ann. Rev. Med. 29:51 (1978); Eschbach and Adamson, Kidney Intl. 28:1 (1985). Recombinant human erythropoietin (rHuEpo or epoetin alfa) is commercially available as EPOGEN.RTM. (epoetin alfa, recombinant human erythropoietin) (Amgen Inc., Thousand Oaks, Calif.) and as PROCRIT.RTM. (epoetin alfa, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

As used herein. disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

As used herein, skeletal muscle disorders include, but are not limited to, muscular dystrophy (e.g., Duchenne muscular dystrophy, Becker muscular dystrophy, Emery-Dreifuss muscular dystrophy, limb-girdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies (e.g., dermatomyositis and polymyositis), myotonia congenita, paramyotonia congenita, central core disease, nemaline myopathy, myotubular myopathy, and periodic paralysis), tumors such as rhabdomyosarcoma, and metabolic diseases of muscle (e.g., phosphorylase deficiency, acid maltase deficiency, phosphofructokinase deficiency, debrancher enzyme deficiency, mitochondrial myopathy, carnitine deficiency, carnitine palmityl transferase deficiency, phosphoglycerate kinase deficiency, phosphoglycerate mutase deficiency, lactate dehydrogenase deficiency, and myoadenylate deaminase deficiency).

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

As used herein, hormonal disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Examples of immune, e.g., inflammatory, (e.g. respiratory inflammatory) disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovascular disease or disorder also can include an endothelial cell disorder.

As used herein, the term "atherosclerosis" is intended to have its clinical meaning. This term refers to a cardiovascular condition occurring as a result of narrowing down of the arterial walls. The narrowing is due to the formation of plaques (raised patches) or streaks in the inner lining of the arteries. These plaques consist of foam cells of low-density lipoproteins, oxidized-LDL, decaying muscle cells, fibrous tissue, clumps of blood platelets, cholesterol, and sometimes calcium. They tend to form in regions of turbulent blood flow and are found most often in people with high concentrations of cholesterol in the bloodstream. The number and thickness of plaques increase with age, causing loss of the smooth lining of the blood vessels and encouraging the formation of thrombi (blood clots). Sometimes fragments of thrombi break off and form emboli, which travel through the bloodstream and block smaller vessels. The blood supply is restricted to the heart, eventually forming a blood clot leading to death. The major causes of atherosclerosis are hypercholesterolemia (and low HDL), hypoalphoproteinemia, and hyperlipidemia marked by high circulating cholesterol and high lipids like LDL-cholesterol and triglycerides in the blood. These lipids are deposited in the arterial walls, obstructing the blood flow and forming atherosclerotic plaques leading to death.

As used herein the term "hypercholesterolemia" is a condition with elevated levels of circulating total cholesterol, LDL-cholesterol and VLDL-cholesterol as per the guidelines of the Expert Panel Report of the National Cholesterol Educational Program (NCEP) of Detection, Evaluation of Treatment of high cholesterol in adults (see, Arch. Int. Med. (1988) 148, 36-39).

As used herein the term "hyperlipidemia" or "hyperlipemia" is a condition where the blood lipid parameters are elevated in the blood. This condition manifests an abnormally high concentration of fats. The lipid fractions in the circulating blood are, total cholesterol, low density lipoproteins, very low density lipoproteins and triglycerides.

As used herein the term "lipoprotein" such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

As used herein, the term "triglyceride" means a lipid or neutral fat consisting of glycerol combined with three fatty acid molecules.

As used herein the term "xanthomatosis" is a disease evidenced by a yellowish swelling or plaques in the skin resulting from deposits of fat. The presence of xanthomas are usually accompanied by raised blood cholesterol levels.

As used herein the term "apolipoprotein B" or "apoprotein B" or "Apo B" refers to the protein component of the LDL cholesterol transport proteins. Cholesterol synthesized de novo is transported from the liver and intestine to peripheral tissues in the form of lipoproteins. Most of the apolipoprotein B is secreted into the circulatory system as VLDL.

As used herein the term "apolipoprotein A" or "apoprotein A" or "Apo A" refers to the protein component of the HDL cholesterol transport proteins.

"Procedural vascular trauma" includes the effects of surgical/medical-mechanical interventions into mammalian vasculature, but does not include vascular trauma due to the organic vascular pathologies listed hereinabove, or to unintended traumas, such as due to an accident. Thus, procedural vascular traumas within the scope of the present treatment method include (1) organ grafting or transplantation, such as transplantation and grafting of heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, or indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PTFE hemodialysis shunt used for arteriovenous communications; and (6) placement of an intravascular stent, which may be metallic, plastic or a biodegradable polymer. See U.S. patent application Ser. No. 08/389,712, filed Feb. 15, 1995, which is incorporated by reference herein. For a general discussion of implantable devices and biomaterials from which they can be formed, see H. Kambic et al., "Biomaterials in Artificial Organs", Chem. Eng. News, 30 (Apr. 14, 1986), the disclosure of which is incorporated by reference herein.

As used herein, "cholesterol lowering agents" include agents which are useful for lowering serum cholesterol such as for example bile acid sequestering resins (e.g. colestipol hydrochloride or cholestyramine), fish oil, stanol esters, an ApoAII-lowering agent, a VLDL lowering agent, an ApoAI-stimulating agent, fibric acid derivatives (e.g. clofibrate, fenofibrate, or gemfibrozil), thiazolidenediones (e.g. troglitazone), or HMG-CoA reductase inhibitors (e.g. statins, such as fluvastatin sodium, lovastatin, pravastatin sodium, or simvastatin), as well as nicotinic acid niacin, or probucol.

"VLDL-lowering agent" includes an agent which decreases the hepatic synthesis of triglyceride-rich lipoproteins or increases the catabolism of triglyceride-rich lipoproteins, e.g., fibrates such as gemfibrozil, or the statins, increases the expression of the apoE-mediated clearance pathway, or improves insulin sensitivity in diabetics, e.g., the thiazolidene diones.

As used herein, a "lipid homeostasis disorder" includes a disorder, disease, or condition associated with, caused by, and/or linked to abnormal regulation (e.g., upregulation or downregulation) of lipid metabolism. Lipid homeostasis disorders may be caused by or associated with aberrant lipolysis, aberrant lipid uptake, aberrant lipid synthesis and/or secretion, aberrant intracellular lipid release and/or turnover, aberrant intracellular triglyceride release and/or turnover, aberrant intracellular lipid and/or triglyceride mass, and/or aberrant secreted lipid and/or triglyceride mass within or from a cell, e.g., a liver cell. Lipid homeostasis disorders include, but are not limited to, atherosclerosis, obesity, diabetes, insulin resistance, hyperlipidemia, hypolipidemia, dyslipidemia, hypercholesterolemia, hypocholesterolemia, triglyceride storage disease, cardiovascular disease, coronary artery disease, hypertension, stroke, overweight, anorexia, cachexia, hyperlipoproteinemia, hypolipoproteinemia, Niemann Pick disease, hypertriglyceridemia, hypotriglyceridemia, pancreatitis, diffuse idiopathic skeletal hyperostosis (DISH), atherogenic lipoprotein phenotype (ALP), epilepsy, liver disease, fatty liver, steatohepatitis, and polycystic ovarian syndrome.

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Examples of pain conditions include, but are not limited to, pain elicited during various forms of tissue injury, e.g., inflammation, infection, and ischemia; pain associated with musculoskeletal disorders, e.g., joint pain, or arthritis; tooth pain; headaches, e.g., migrane; pain associated with surgery; pain related to inflammation, e.g., irritable bowel syndrome; chest pain; or hyperalgesia, e.g., excessive sensitivity to pain (described in, for example, Fields (1987) Pain, N.Y.: McGraw-Hill). Other examples of pain disorders or pain syndromes include, but are not limited to, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, nonulcer dyspepsia, interstitial cystitis, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia (the inability to feel pain). Other examples of pain conditions include pain induced by parturition, or post partum pain.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Additionally, the molecules of the invention can play an important role in the etiology of certain viral diseases, including but not limited to Hepatitis B, Hepatitis C and Herpes Simplex Virus (HSV). Modulators of the activity of the molecules of the invention could be used to control viral diseases. The modulators can be used in the treatment and/or diagnosis of viral infected tissue or virus-associated tissue fibrosis, especially liver and liver fibrosis. Also, such modulators can be used in the treatment and/or diagnosis of virus-associated carcinoma, especially hepatocellular cancer.

Additionally, molecules of the invention can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields (1987) Pain, N.Y.:McGraw-Hill); pain-associated with musculoskeletal disorders, e.g., joint pain; tooth pain; headaches; pain associated with surgery; pain related to irritable bowel syndrome; or chest pain.

Aberrant expression and/or activity of the molecules of the invention can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by the molecules of the invention in bone cells, e.g. osteoclasts and osteoblasts, that can in turn result in bone formation and degeneration. For example, molecules of the invention can support different activities of bone resorbing osteoclasts such as the stimulation of differentiation of monocytes and mononuclear phagocytes into osteoclasts. Accordingly, molecules of the invention that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystophy, osteosclerosis, anti-convulsant treatment, osteopenia, fibrogenesis-imperfecta ossium, secondary hyperparathyroidism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

As used herein, platelet disorders include, but are not limited to, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Various aspects of the invention are described in further detail below.

Isolated Nucleic Acid Molecules

In one aspect, the invention provides, an isolated or purified, nucleic acid molecule that encodes a 25869, 25934, 26335, 50365, 21117, 38692, 46508, 16816, 16839, 49937, 49931 or 49933 polypeptide described herein, e.g., a full length 25869, 25934, 26335, 50365, 21117, 38692, 46508, 16816, 16839, 49937, 49931 or 49933 protein or a fragment thereof, e.g., a biologically active portion of 25869, 25934, 26335, 50365, 21117, 38692, 46508, 16816, 16839, 49937, 49931 or 49933 protein. Also included is a nucleic acid fragment suitable for use as a hybridization probe, which can be used, e.g., to identify a nucleic acid molecule encoding a polypeptide of the invention, 25869, 25934, 26335, 50365, 21117, 38692, 46508, 16816, 16839, 49937, 49931 or 49933 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, 3, 7, 9, 16, 18, 20, 22, 25, 27, 28, 30, 35, 37, 39, 41, 42, 44, 63, 65, 67, 69, 70 or 72, or a portion of any of this nucleotide sequence. In one embodiment, the nucleic acid molecule includes sequences encoding the human 25869, 25934, 26335, 50365, 21117, 38692, 46508, 16816, 16839, 49937, 49931 or 49933 protein (i.e., "the coding region" of SEQ ID NO:1, 7, 16, 20, 25, 28, 35, 39, 42, 63, 67 or 70, as shown in SEQ ID NO:3, 9, 18, 22, 27, 30, 37, 41, 44, 65, 69 or 72, respectively), as well as 5' untranslated sequences and 3' untranslated sequences. Alternatively, the nucleic acid molecule can include only the coding region of SEQ ID NO:1, 7, 16, 20, 25, 28, 35, 39,42, 63, 67 or 70 (e.g., SEQ ID NO:3, 9, 18, 22, 27, 30, 37, 41, 44, 65, 69 or 72) and, e.g., no flanking sequences which normally accompany the subject sequence. In another embodiment, the nucleic acid molecule encodes a sequence corresponding to a fragment of the protein corresponding to conserved domains identified within SEQ ID NO:2, 8, 17, 21, 26, 29, 36, 40, 43, 64, 68 or 71.

In another embodiment, an isolated nucleic acid molecule of the invention includes a nucleic acid molecule which is a complement of the nucleotide sequence shown in SEQ ID NO:1, 3, 7, 9, 16, 18, 20, 22, 25, 27, 28, 30, 35, 37, 39, 41, 42, 44, 63, 65, 67, 69, 70 or 72, or a portion of any of these nucleotide sequences. In other embodiments, the nucleic acid molecule of the invention is sufficiently complementary to the nucleotide sequence shown in SEQ ID NO:1, 3, 7, 9, 16, 18, 20, 22, 25, 27, 28, 30, 35, 37, 39, 41, 42, 44, 63, 65, 67, 69, 70 or 72 such that it can hybridize to the nucleotide sequence shown in SEQ ID NO:1, 3, 7, 9, 16, 18, 20, 22, 25, 27, 28, 30, 35, 37, 39,41, 42, 44, 63, 65, 67, 69, 70 or 72, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, 3, 7, 9, 16, 18, 20, 22, 25, 27, 28, 30, 35, 37, 39, 41, 42, 44, 63, 65, 67, 69, 70 or 72, or a portion, preferably of the same length, of any of these nucleotide sequences.

25869, 25934, 26335, 50365, 21117, 38692, 46508, 16816, 16839, 49937, 49931 or 49933 Nucleic Acid Fragments A nucleic acid molecule of the invention can include only a portion of the nucleic acid sequence of SEQ ID NO:1, 3, 7, 9, 16, 18, 20, 22, 25, 27, 28, 30, 35, 37, 39, 41, 42, 44, 63, 65, 67, 69, 70 or 72. For example, such a nucleic acid molecule can include a fragment which can be used as a probe or primer or a fragment encoding a portion of a 25869, 25934, 26335, 50365, 21117, 38692, 46508, 16816, 16839, 49937, 49931 or 49933 protein, e.g., an immunogenic or biologically active portion of a 25869, 25934, 26335, 50365, 21117, 38692, 46508, 16816, 16839, 49937, 49931 or 49933 protein. A fragment can comprise those nucleotides of SEQ ID NO:1, 3, 7, 9, 16, 18, 20, 22, 25, 27, 28, 30, 35, 37, 39, 41, 42, 44, 63, 65, 67, 69, 70 or 72, which encode a domain of human 25869, 25934, 26335, 50365, 21117, 38692, 46508, 16816, 16839, 49937, 49931 or 49933. The nucleotide sequence determined from the cloning of the 25869, 25934, 26335, 50365, 21117, 38692, 46508, 16816, 16839, 49937, 49931 or 49933 gene allows for the generation of probes and primers designed for use in identifying and/or cloning other 25869, 25934, 26335, 50365, 21117, 38692, 46508, 16816, 16839, 49937, 49931 or 49933 family members, or fragments thereof, as well as 25869, 25934, 26335, 50365, 21117, 38692, 46508, 16816, 16839, 49937, 49931 or 49933 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 25869, 25934, 26335, 50365, 21117, 38692, 46508, 16816, 16839, 49937, 49931 or 49933 nucleic acid fragment can include a sequence corresponding to a domain, as described herein.

25869, 25934, 26335, 50365, 21117, 38692, 46508, 16816, 16839, 49937, 49931 or 49933 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 3, 7, 9, 16, 18, 20, 22, 25, 27, 28, 30, 35, 37, 39, 41, 42, 44, 63, 65, 67, 69, 70 or 72, or of a naturally occurring allelic variant or mutant of SEQ ID NO:1, 3, 7, 9, 16, 18, 20, 22, 25, 27, 28, 30, 35, 37, 39, 41, 42, 44, 63, 65, 67, 69, 70 or 72.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or antisense strand of a nucleic acid which encodes a domain identified in the 25869, 25934, 26335, 50365, 21117, 38692, 46508, 16816, 16839, 49937, 49931 or 49933 sequences.

In another embodiment a set of primers is provided, e.g., primers suitable for use in a PCR, which can be used to amplify a selected region of a 25869, 25934, 26335, 50365, 21117, 38692, 46508, 16816, 16839, 49937, 49931 or 49933 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant.

A nucleic acid fragment can encode an epitope bearing region of a polypeptide described herein.

A nucleic acid fragment encoding a "biologically active portion of a 25869, 25934, 26335, 50365, 21117, 38692, 46508, 16816, 16839, 49937, 49931 or 49933 polypeptide" can be prepared by isolating a portion of the nucleotide sequence of SEQ ID NO:1, 3, 7, 9, 16, 18, 20, 22, 25, 27, 28, 30, 35, 37, 39, 41, 42, 44, 63, 65, 67, 69, 70 or 72, which encodes a polypeptide having a 25869, 25934, 26335, 50365, 21117, 38692, 46508, 16816, 16839, 49937, 49931 or 49933 biological activity (e.g., the biological activities of the 25869, 25934, 26335, 50365, 21117, 38692, 46508, 16816, 16839, 49937, 49931 or 49933 proteins are described herein), expressing the encoded portion of the 25869, 25934, 26335, 50365, 21117, 38692, 46508, 16816, 16839, 49937, 49931 or 49933 protein (e.g., by recombinant expression in vitro) and assessing the activity of the encoded portion of the 25869, 25934, 26335, 50365, 21117, 38692, 46508, 16816, 16839, 49937, 49931 or 49933 protein. A nucleic acid fragment encoding a biologically active portion of a 25869, 25934, 26335, 50365, 21117, 38692, 46508, 16816, 16839, 49937, 49931 or 49933 polypeptide, can comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3806, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7249 or more nucleotides in length and hybridizes under stringent hybridization conditions to a nucleic acid molecule of SEQ ID NO:1, 3, 7, 9, 16, 18, 20, 22, 25, 27, 28, 30, 35, 37, 39, 41, 42, 44, 63, 65, 67, 69, 70 or 72.

25869, 25934, 26335, 50365, 21117, 38692, 46508, 16816, 16839, 49937, 49931 or 49933 Nucleic Acid Variants The invention further encompasses nucleic acid molecules that differ from the nucleotide sequence shown in SEQ ID NO:1, 3, 7, 9, 16, 18, 20, 22, 25, 27, 28, 30, 35, 37, 39, 41, 42, 44, 63, 65, 67, 69, 70 or 72. Such differences can be due to degeneracy of the genetic code (and result in a nucleic acid which encodes the same 25869, 25934, 26335, 50365, 21117, 38692, 46508, 16816, 16839, 49937, 49931 or 49933 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 8, 17, 21, 26, 29, 36, 40, 43, 64, 68 or 71. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, 3, 7, 9, 16, 18, 20, 22, 25, 27, 28, 30, 35, 37, 39, 41, 42, 44, 63, 65, 67, 69, 70 or 72, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:2, 8, 17, 21, 26, 29, 36, 40, 43, 64, 68 or 71 or a fragment of this sequence. Such nucleic acid molecules can readily be identified as being able to hybridize under stringent conditions, to the nucleotide sequence shown in SEQ ID NO:2, 8, 17, 21, 26, 29, 36, 40, 43, 64, 68 or 71 or a fragment of the sequence. Nucleic acid molecules corresponding to orthologs, homologs, and allelic variants of the 25869, 25934, 26335, 50365, 21117, 38692, 46508, 16816, 16839, 49937, 49931 or 49933 cDNAs of the invention can further be isolated by mapping to the same chromosome or locus as the 25869, 25934, 26335, 50365, 21117, 38692, 46508, 16816, 16839, 49937, 49931 or 49933 gene.

Preferred variants include those that are correlated with activities specific to the molecules of the invention, i.e. carboxylase activity, fatty acid desaturase activity, serine/threonine dehydratase activity, hexokinase activity, peptidyl tRNA hydrolase activity, dual specificity phosphatase activity, phospholipase activity, transporter activity, or other.

Allelic variants of 25869, 25934, 26335, 50365, 21117, 38692, 46508, 16816, 16839, 49937, 49931 or 49933, e.g., human 25869, 25934, 26335, 50365, 21117, 38692, 46508, 16816, 16839, 49937, 49931 or 49933, include both functional and non-functional proteins. Functional allelic variants are naturally occurring amino acid sequence variants of the 25869, 25934, 26335, 50365, 21117, 38692, 46508, 16816, 16839, 49937, 49931 or 49933 protein within a population that maintain the ability to (1) hydrolyze an ester linkage and/or liberate the free acid form of a substrate, e.g., hydrolysis of a triglyceride and/or liberation of free fatty acid(s) and glycerol; (2) catalyze the formation of a double bond, preferably, at positions up to 9 carbons from the carboxyl end of a molecule, e.g., a fatty acid, such as a polyunsaturated fatty acid; (3) catalyze the phosphorylation of a sugar, e.g., an aldohexoses and a ketohexoses (e.g., glucose, mannose, fructose, sorbitol and glucosamine); (4) catalyze sugar metabolism; (5) transfer a phosphate from a phosphate donor (e.g., ATP) to a sugar, e.g., an aldohexoses and a ketohexoses (e.g., glucose, mannose, fructose, sorbitol and glucosamine) to form a phosphorylated sugar, e.g., glucose-6-phosphate; (6) catalyze the removal of a phosphate group attached to a tyrosine residue in a protein target, e.g., a growth factor receptor; (7) catalyze the removal of a phosphate group attached to a serine or threonine residue in a protein e.g., a growth factor receptor; (8) hydrolyze covalent bond between peptide and tRNA within peptidyl-tRNAs; (9) catalyze the hydrolysis of phosphatidyl-inositol-4,5-bisphosphate (PIP2) producing diacylglycerol and inositol 1,4,5-trisphosphate; (10) transport a substrate or target molecule (e.g., a $Ca^{2+}$ ion) from one side of a biological membrane to the other; or (11) be phosphorylated or dephosphorylated. Functional allelic variants will typically contain only conservative substitution of one or more amino acids of SEQ ID NO:2, 8, 17, 21, 26, 29, 36, 40, 43, 64, 68 or 71, or substitution, deletion or insertion of non-critical residues in non-critical regions of the protein. Non-functional allelic variants are naturally-occurring amino acid sequence variants of the 25869, 25934, 26335, 50365, 21117, 38692, 46508, 16816, 16839, 49937, 49931 or 49933, e.g., human 25869, 25934, 26335, 50365, 21117, 38692, 46508, 16816, 16839, 49937, 49931 or 49933, protein within a population that do not have the ability to (1) hydrolyze an ester linkage and/or liberate the free acid form of a substrate, e.g., hydrolysis of a triglyceride and/or liberation of free fatty acid(s) and glycerol; (2) catalyze the formation of a double bond, preferably, at positions up to 9 carbons from the carboxyl end of a molecule, e.g., a fatty acid, such as a polyunsaturated fatty acid; (3) catalyze the phosphorylation of a sugar, e.g., an aldohexoses and a ketohexoses (e.g., glucose, mannose, fructose, sorbitol and glucosamine); (4) catalyze sugar metabolism; (5) transfer a phosphate from a phosphate donor (e.g., ATP) to a sugar, e.g., an aldohexoses and a ketohexoses (e.g., glucose, mannose, fructose, sorbitol and glucosamine) to form a phosphorylated sugar, e.g., glucose-6-phosphate; (6) catalyze the removal of a phosphate group attached to a tyrosine residue in a protein target, e.g., a growth factor receptor; (7) catalyze the removal of a phosphate group attached to a serine or threonine residue in a protein e.g., a growth factor receptor; (8) hydrolyze covalent bond between peptide and tRNA within peptidyl-tRNAs; (9) catalyze the hydrolysis of phosphatidyl-inositol-4,5-bisphosphate (PIP2) producing diacylglycerol and inositol 1,4,5-trisphosphate; (10) transport a substrate or target molecule (e.g., a $Ca^{2+}$ ion) from one side of a biological membrane to the other; or (11) be phosphorylated or dephosphorylated. Non-functional allelic variants will typically contain a non-conservative substitution, a deletion, or insertion, or premature truncation of the amino acid sequence of SEQ ID NO:2, 8, 17, 21, 26, 29, 36, 40, 43, 64, 68 or 71, or a substitution, insertion, or deletion in critical residues or critical regions of the protein.

Moreover, nucleic acid molecules encoding other 25869, 25934, 26335, 50365, 21117, 38692, 46508, 16816, 16839, 49937, 49931 or 49933 family members and, thus, which have a nucleotide sequence which differs from the 25869, 25934, 26335, 50365, 21117, 38692, 46508, 16816, 16839, 49937, 49931 or 49933 sequences of SEQ ID NO:1, 3, 7, 9, 16, 18, 20, 22, 25, 27, 28, 30, 35, 37, 39, 41, 42, 44, 63, 65, 67, 69, 70 or 72 are intended to be within the scope of the invention.

Antisense Nucleic Acid Molecules, Ribozymes and Modified 25869, 25934, 26335, 50365, 21117, 38692, 46508, 16816, 16839, 49937 49931 or 49933 Nucleic Acid Molecules In another aspect, the invention features, an isolated nucleic acid molecule which is antisense to 25869, 25934, 26335, 50365, 21117, 38692, 46508, 16816, 16839, 49937, 49931 or 49933. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 25869, 25934, 26335, 50365, 21117, 38692, 46508, 16816, 16839, 49937, 49931 or 49933 coding strand, or to only a portion thereof (e.g., the coding region of human 25869, 25934, 26335, 50365, 21117, 38692, 46508, 16816, 16839, 49937, 49931 or 49933 corresponding to SEQ ID NO:3, 9, 18, 22, 27, 30, 37, 41, 44, 65, 69 or 72, respectively). In another embodiment, the antisense nucleic acid molecule is antisense to a "noncoding region" of the coding strand of a nucleotide sequence encoding 25869, 25934, 26335, 50365, 21117, 38692, 46508, 16816, 16839, 49937, 49931 or 49933 (e.g., the 5' and 3' untranslated regions).

An antisense nucleic acid can be designed such that it is complementary to the entire coding region of 25869, 25934, 26335, 50365, 21117, 38692, 46508, 16816, 16839, 49937, 49931 or 49933 mRNA, but more preferably is an oligonucleotide which is antisense to only a portion of the coding or noncoding region of 25869, 25934, 26335, 50365, 21117, 38692, 46508, 16816, 16839, 49937, 49931 or 49933 mRNA. For example, the antisense oligonucleotide can be complementary to the region surrounding the translation start site of 25869, 25934, 26335, 50365, 21117, 38692, 46508, 16816, 16839, 49937, 49931 or 49933 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 25869, 25934, 26335, 50365, 21117, 38692, 46508, 16816, 16839, 49937, 49931 or 49933 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res;* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. A ribozyme having specificity for a 25869, 25934, 26335, 50365, 21117, 38692, 46508, 16816, 16839, 49937, 49931 or 49933-encoding nucleic acid can include one or more sequences complementary to the nucleotide sequence of a 25869, 25934, 26335, 50365, 21117, 38692, 46508, 16816, 16839, 49937, 49931 or 49933 cDNA disclosed herein (i.e., SEQ ID NO: 1, 3, 7, 9, 16, 18, 20, 22, 25, 27, 28, 30, 35, 37, 39, 41, 42, 44, 63, 65, 67, 69, 70 or 72), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 25869, 25934, 26335, 50365, 21117, 38692, 46508, 16816, 16839, 49937, 49931 or 49933-encoding mRNA. See, e.g., Cech et al. U.S. Pat. No. 4,987,071; and Cech et al. U.S. Pat. No. 5,116,742. Alternatively, 25869, 25934, 26335, 50365, 21117, 38692, 46508, 16816, 16839, 49937, 49931 or 49933 mRNA can be used to select a catalytic RNA having a specific ribonuclease activity from a pool of RNA molecules. See, e.g., Bartel and Szostak (1993) *Science* 261:1411-1418.

25869, 25934, 26335, 50365, 21117, 38692, 46508, 16816, 16839, 49937, 49931 or 49933 gene expression can be inhibited by targeting nucleotide sequences complementary to the regulatory region of the 25869, 25934, 26335, 50365, 21117, 38692, 46508, 16816, 16839, 49937, 49931 or 49933 (e.g., the 25869, 25934, 26335, 50365, 21117, 38692, 46508, 16816, 16839, 49937, 49931 or 49933 promoter and/or enhancers) to form triple helical structures that prevent transcription of the 25869, 25934, 26335, 50365, 21117, 38692, 46508, 16816, 16839, 49937, 49931 or 49933 gene in target cells. See generally, Helene (1991) *Anticancer Drug Des.* 6:569-84; Helene (1992) *Ann. N.Y. Acad. Sci.* 660:27-36; and Maher (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 25869, 25934, 26335, 50365, 21117, 38692, 46508, 16816, 16839, 49937, 49931 or 49933 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4: 5-23).

As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci.* 93: 14670-675.

PNAs of 25869, 25934, 26335, 50365, 21117, 38692, 46508, 16816, 16839, 49937, 49931 or 49933 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 25869, 25934, 26335, 50365, 21117, 38692, 46508, 16816, 16839, 49937, 49931 or 49933 nucleic acid molecules can also be used in the analysis of single base pair mutations in a gene, (e.g., by PNA-directed PCR clamping); as 'artificial restriction enzymes' when used in combination with other enzymes, (e.g., Si nucleases (Hyrup et al. (1996) supra)); or as probes or primers for DNA sequencing or hybridization (Hyrup et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 25869, 25934, 26335, 50365, 21117, 38692, 46508, 16816, 16839, 49937, 49931 or 49933 nucleic acid of the invention, two complementary regions one having a fluorophore and one a quencher such that the molecular beacon is useful for quantitating the presence of the 25869, 25934, 26335, 50365, 21117, 38692, 46508, 16816, 16839, 49937, 49931 or 49933 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 25869, 25934, 26335, 50365, 21117, 38692, 46508, 16816, 16839, 49937, 49931 or 49933 Polypeptides In another aspect, the invention features, an isolated 25869, 25934, 26335, 50365, 21117, 38692, 46508, 16816, 16839, 49937, 49931 or 49933 protein, or fragment, e.g., a biologically active portion, for use as immunogens or antigens to raise or test (or more generally to bind) anti-25869, 25934, 26335, 50365, 21117, 38692, 46508, 16816, 16839, 49937, 49931 or 49933 antibodies. 25869, 25934, 26335, 50365, 21117, 38692, 46508, 16816, 16839, 49937, 49931 or 49933 protein can be isolated from cells or tissue sources using standard protein purification techniques. 25869, 25934, 26335, 50365, 21117, 38692, 46508, 16816, 16839, 49937, 49931 or 49933 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present in a native cell.

In a preferred embodiment, a 25934, 26335, 50365, 21117, 38692, 46508, 16816, 16839, 49937, 49931 or 49933 polypeptide has one or more of the following characteristics: it has the ability to (1) hydrolyze an ester linkage and/or liberate the free acid form of a substrate, e.g., hydrolysis of a triglyceride and/or liberation of free fatty acid(s) and glycerol; (2) catalyze the formation of a double bond, preferably, at positions up to 9 carbons from the carboxyl end of a molecule, e.g., a fatty acid, such as a polyunsaturated fatty acid; (3) catalyze the phosphorylation of a sugar, e.g., an aldohexoses and a ketohexoses (e.g., glucose, mannose, fructose, sorbitol and glucosamine); (4) catalyze sugar metabolism; (5) transfer a phosphate from a phosphate donor (e.g., ATP) to a sugar, e.g., an aldohexoses and a ketohexoses (e.g., glucose, mannose, fructose, sorbitol and glucosamine) to form a phosphorylated sugar, e.g., glucose-6-phosphate; (6) catalyze the removal of a phosphate group attached to a tyrosine residue in a protein target, e.g., a growth factor receptor; (7) catalyze the removal of a phosphate group attached to a serine or threonine residue in a protein e.g., a growth factor receptor; (8) hydrolyze covalent bond between peptide and tRNA within peptidyl-tRNAs; (9) catalyze the hydrolysis of phosphatidyl-inositol-4,5-bisphosphate (PIP2) producing diacylglycerol and inositol 1,4,5-trisphosphate; (10) transport a substrate or target molecule (e.g., a $Ca^{2+}$ ion) from one side of a biological membrane to the other; (11) be phosphorylated or dephosphorylated; (12) it has a molecular weight, e.g., a deduced molecular weight, preferably ignoring any contribution of post translational modifications, amino acid composition or other physical characteristic of a 25869, 25934, 26335, 50365, 21117, 38692, 46508, 16816, 16839, 49937, 49931 or 49933 polypeptide, e.g., a polypeptide of SEQ ID NO:2, 8, 17, 21, 26, 29, 36, 40, 43, 64, 68 or 71; (13) it has an overall sequence similarity of at least 60%, preferably at least 70%, more preferably at least 80, 90, or 95%, with a polypeptide of SEQ ID NO:2, 8, 17, 21, 26, 29, 36, 40, 43, 64, 68 or 71; (14) it is expressed in a multitude of human tissues and cell lines (refer to section for each molecule of the invention); and (15) it has specific domains which are preferably about 70%, 80%, 90% or 95% identical to the identified amino acid residues of SEQ ID NO:2, 8, 17, 21, 26, 29, 36, 40, 43, 64, 68 or 71 (refer to section for each molecule of the invention for domain names and locations within amino acid sequence).

In a preferred embodiment the 25869, 25934, 26335, 50365, 21117, 38692, 46508, 16816, 16839, 49937, 49931 or 49933 protein, or fragment thereof, differs from the corresponding sequence in SEQ ID NO:2, 8, 17, 21, 26, 29, 36, 40, 43, 64, 68 or 71. In one embodiment it differs by at least one but by less than 15, 10 or 5 amino acid residues. In another it differs from the corresponding sequence in SEQ ID NO:2, 8, 17, 21, 26, 29, 36, 40, 43, 64, 68 or 71 by at least one residue but less than 20%, 15%, 10% or 5% of the residues in it differ from the corresponding sequence in SEQ ID NO:2, 8, 17, 21, 26, 29, 36, 40, 43, 64, 68 or 71. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the identified or conserved domain(s) within SEQ ID NO:2, 8, 17, 21, 26, 29, 36, 40, 43, 64, 68 or 71. In another embodiment one or more differences are in the cidentified or conserved domain(s) within SEQ ID NO:2, 8, 17, 21, 26, 29, 36, 40, 43, 64, 68 or 71.

Other embodiments include a protein that contains one or more changes in amino acid sequence, e.g., a change in an amino acid residue which is not essential for activity. Such 25869, 25934, 26335, 50365, 21117, 38692, 46508, 16816, 16839, 49937, 49931 or 49933 proteins differ in amino acid sequence from SEQ ID NO:2, 8, 17, 21, 26, 29, 36, 40, 43, 64, 68 or 71, yet retain biological activity.

In one embodiment, the protein includes an amino acid sequence at least about 60%, 65%, 70%, 75%, 80%, 85%, 90%, 95%, 98% or more homologous to SEQ ID NO:2, 8, 17, 21, 26, 29, 36, 40, 43, 64, 68 or 71.

A 25869, 25934, 26335, 50365, 21117, 38692, 46508, 16816, 16839, 49937, 49931 or 49933 protein or fragment is provided which varies from the sequence of SEQ ID NO:2, 8, 17, 21, 26, 29, 36, 40, 43, 64, 68 or 71 in regions defined by amino acids that are not within identified or conserved domains or regions by at least one but by less than 15, 10 or 5 amino acid residues in the protein or fragment but which does not differ from SEQ ID NO:2, 8, 17, 21, 26, 29, 36, 40, 43, 64, 68 or 71 in regions defined by amino acids that are within identified or conserved domains or regions. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 25869, 25934, 26335, 50365, 21117, 38692, 46508, 16816, 16839, 49937, 49931 or 49933 protein includes an identified domain (refer to section for each molecule of the invention). Moreover, other biologically active portions, in which other regions of the protein are deleted, can be prepared by recombinant techniques and evaluated for one or more of the functional activities of a native 25869, 25934, 26335, 50365, 21117, 38692, 46508, 16816, 16839, 49937, 49931 or 49933 protein.

In a preferred embodiment, the 25869, 25934, 26335, 50365, 21117, 38692, 46508, 16816, 16839, 49937, 49931 or 49933 protein has an amino acid sequence shown in SEQ ID NO:2, 8, 17, 21, 26, 29, 36, 40, 43, 64, 68 or 71. In other embodiments, the 25869, 25934, 26335, 50365, 21117, 38692, 46508, 16816, 16839, 49937, 49931 or 49933 protein is sufficiently or substantially identical to SEQ ID NO:2, 8, 17, 21, 26, 29, 36, 40, 43, 64, 68 or 71. In yet another embodiment, the 25869, 25934, 26335, 50365, 21117, 38692, 46508, 16816, 16839, 49937, 49931 or 49933 protein is sufficiently or substantially identical to SEQ ID NO:2, 8, 17, 21, 26, 29, 36, 40, 43, 64, 68 or 71 and retains the functional activity of the protein of SEQ ID NO:2, 8, 17, 21, 26, 29, 36, 40, 43, 64, 68 or 71, as described in detail in the subsections above.

25869, 25934, 26335, 50365, 21117, 38692, 46508, 16816, 16839, 49937, 49931 or 49933 Chimeric or Fusion Proteins In another aspect, the invention provides 25869, 25934, 26335, 50365, 21117, 38692, 46508, 16816, 16839, 49937, 49931 or 49933 chimeric or fusion proteins. As used herein, a 25869, 25934, 26335, 50365, 21117, 38692, 46508, 16816, 16839, 49937, 49931 or 49933 "chimeric protein" or "fusion protein" includes a 25869, 25934, 26335, 50365, 21117, 38692, 46508, 16816, 16839, 49937, 49931 or 49933 polypeptide linked to a non-25869, 25934, 26335, 50365, 21117, 38692, 46508, 16816, 16839, 49937, 49931 or 49933 polypeptide. A "non-25869, 25934, 26335, 50365, 21117, 38692, 46508, 16816, 16839, 49937, 49931 or 49933 polypeptide" refers to a polypeptide having an amino acid sequence corresponding to a protein which is not substantially homologous to the 25869, 25934, 26335, 50365, 21117, 38692, 46508, 16816, 16839, 49937, 49931 or 49933 protein, e.g., a protein which is different from the 25869, 25934, 26335, 50365, 21117, 38692, 46508, 16816, 16839, 49937, 49931 or 49933 protein and which is derived from the same or a different organism. The 25869, 25934, 26335, 50365, 21117, 38692, 46508, 16816, 16839, 49937, 49931 or 49933 polypeptide of the fusion protein can correspond to all or a portion e.g., a fragment described herein of a 25869, 25934, 26335, 50365, 21117, 38692, 46508, 16816, 16839, 49937, 49931 or 49933 amino acid sequence. In a preferred embodiment, a 25869, 25934, 26335, 50365, 21117, 38692, 46508, 16816, 16839, 49937, 49931 or 49933 fusion protein includes at least one (or two) biologically active portion of a 25869, 25934, 26335, 50365, 21117, 38692, 46508, 16816, 16839, 49937, 49931 or 49933 protein. The non-25869, 25934, 26335, 50365, 21117, 38692, 46508, 16816, 16839, 49937, 49931 or 49933 polypeptide can be fused to the N-terminus or C-terminus of the 25869, 25934, 26335, 50365, 21117, 38692, 46508, 16816, 16839, 49937, 49931 or 49933 polypeptide.

The fusion protein can include a moiety which has a high affinity for a ligand. For example, the fusion protein can be a GST-25869, 25934, 26335, 50365, 21117, 38692, 46508, 16816, 16839, 49937, 49931 or 49933 fusion protein in which the 25869, 25934, 26335, 50365, 21117, 38692, 46508, 16816, 16839, 49937, 49931 or 49933 sequences are fused to the C-terminus of the GST sequences. Such fusion proteins can facilitate the purification of recombinant 25869, 25934, 26335, 50365, 21117, 38692, 46508, 16816, 16839, 49937, 49931 or 49933. Alternatively, the fusion protein can be a 25869, 25934, 26335, 50365, 21117, 38692, 46508, 16816, 16839, 49937, 49931 or 49933 protein containing a heterologous signal sequence at its N-terminus. In certain host cells (e.g., mammalian host cells), expression and/or secretion of 25869, 25934, 26335, 50365, 21117, 38692, 46508, 16816, 16839, 49937, 49931 or 49933 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 25869, 25934, 26335, 50365, 21117, 38692, 46508, 16816, 16839, 49937, 49931 or 49933 fusion proteins of the invention can be incorporated into pharmaceutical compositions and administered to a subject in vivo. The 25869, 25934, 26335, 50365, 21117, 38692, 46508, 16816, 16839, 49937, 49931 or 49933 fusion proteins can be used to affect the bioavailability of a 25869, 25934, 26335, 50365, 21117, 38692, 46508, 16816, 16839, 49937, 49931 or 49933 substrate. 25869, 25934, 26335, 50365, 21117, 38692, 46508, 16816, 16839, 49937, 49931 or 49933 fusion proteins can be useful therapeutically for the treatment of disorders caused by, for example, (i) aberrant modification or mutation of a gene encoding a 25869, 25934, 26335, 50365, 21117, 38692, 46508, 16816, 16839, 49937, 49931 or 49933 protein; (ii) mis-regulation of the 25869, 25934, 26335, 50365, 21117, 38692, 46508, 16816, 16839, 49937, 49931 or 49933 gene; and (iii) aberrant post-translational modification of a 25869, 25934, 26335, 50365, 21117, 38692, 46508, 16816, 16839, 49937, 49931or 49933 protein.

Moreover, the 25869, 25934, 26335, 50365, 21117, 38692, 46508, 16816, 16839, 49937, 49931 or 49933-fusion proteins of the invention can be used as immunogens to produce anti-25869, 25934, 26335, 50365, 21117, 38692, 46508, 16816, 16839, 49937, 49931 or 49933 antibodies in a subject, to purify 25869, 25934, 26335, 50365, 21117, 38692, 46508, 16816, 16839, 49937, 49931 or 49933 ligands and in screening assays to identify molecules which inhibit the interaction of 25869, 25934, 26335, 50365, 21117, 38692, 46508, 16816, 16839, 49937, 49931 or 49933 with a 25869, 25934, 26335, 50365, 21117, 38692, 46508, 16816, 16839, 49937, 49931 or 49933 substrate.

Expression vectors are commercially available that already encode a fusion moiety (e.g., a GST polypeptide). A 25869, 25934, 26335, 50365, 21117, 38692, 46508, 16816, 16839, 49937, 49931 or 49933-encoding nucleic acid can be cloned into such an expression vector such that the fusion moiety is linked in-frame to the 25869, 25934, 26335, 50365, 21117, 38692, 46508, 16816, 16839, 49937, 49931 or 49933 protein.

Variants of 25869, 25934, 26335, 50365, 21117, 38692, 46508, 16816, 16839, 49937, 49931 or 49933 Proteins In another aspect, the invention also features a variant of a 25869, 25934, 26335, 50365, 21117, 38692, 46508, 16816, 16839, 49937, 49931 or 49933 polypeptide, e.g., which functions as an agonist (mimetics) or as an antagonist. Variants of the 25869, 25934, 26335, 50365, 21117, 38692, 46508, 16816, 16839, 49937, 49931 or 49933 proteins can be generated by mutagenesis, e.g., discrete point mutation, the insertion or deletion of sequences or the truncation of a 25869, 25934, 26335, 50365, 21117, 38692, 46508, 16816, 16839, 49937, 49931 or 49933 protein. An agonist of the 25869, 25934, 26335, 50365, 21117, 38692, 46508, 16816, 16839, 49937, 49931 or 49933 proteins can retain substantially the same, or a subset, of the biological activities of the naturally occurring form of a 25869, 25934, 26335, 50365, 21117, 38692, 46508, 16816, 16839, 49937, 49931 or 49933 protein. An antagonist of a 25869, 25934, 26335, 50365, 21117, 38692, 46508, 16816, 16839, 49937, 49931 or 49933 protein can inhibit one or more of the activities of the naturally occurring form of the 25869, 25934, 26335, 50365, 21117, 38692, 46508, 16816, 16839, 49937, 49931 or 49933 protein by, for example, competitively modulating a 25869, 25934, 26335, 50365, 21117, 38692, 46508, 16816, 16839, 49937, 49931 or 49933-mediated activity of a 25869, 25934, 26335, 50365, 21117, 38692, 46508, 16816, 16839, 49937, 49931 or 49933 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 25869, 25934, 26335, 50365, 21117, 38692, 46508, 16816, 16839, 49937, 49931 or 49933 protein.

Variants of a 25869, 25934, 26335, 50365, 21117, 38692, 46508, 16816, 16839, 49937, 49931 or 49933 protein can be identified by screening combinatorial libraries of mutants, e.g., truncation mutants, of a 25869, 25934, 26335, 50365, 21117, 38692, 46508, 16816, 16839, 49937, 49931 or 49933 protein for agonist or antagonist activity.

Libraries of fragments e.g., N terminal, C terminal, or internal fragments, of a 25869, 25934, 26335, 50365, 21117, 38692, 46508, 16816, 16839, 49937, 49931 or 49933 protein coding sequence can be used to generate a variegated population of fragments for screening and subsequent selection of variants of a 25869, 25934, 26335, 50365, 21117, 38692, 46508, 16816, 16839, 49937, 49931 or 49933 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 25869, 25934, 26335, 50365, 21117, 38692, 46508, 16816, 16839, 49937, 49931 or 49933 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 25869, 25934, 26335, 50365, 21117, 38692, 46508, 16816, 16839, 49937, 49931 or 49933 library. For example, a library of expression vectors can be transfected into a cell line, e.g., a cell line, which ordinarily responds to 25869, 25934, 26335, 50365, 21117, 38692, 46508, 16816, 16839, 49937, 49931 or 49933 in a substrate-dependent manner. The transfected cells are then contacted with 25869, 25934, 26335, 50365, 21117, 38692, 46508, 16816, 16839, 49937, 49931 or 49933 and the effect of the expression of the mutant on signaling by the 25869, 25934, 26335, 50365, 21117, 38692, 46508, 16816, 16839, 49937, 49931 or 49933 substrate can be detected, e.g., by measuring either carboxylase activity, fatty acid desaturase activity, serine/threonine dehydratase activity, hexokinase activity, peptidyl tRNA hydrolase activity, dual specificity phosphatase activity, phospholipase activity, transporter activity, or other activity disclosed herein. Plasmid DNA can then be recovered from the cells which score for inhibition, or alternatively, potentiation of signaling by the 25869, 25934, 26335, 50365, 21117, 38692, 46508, 16816, 16839, 49937, 49931 or 49933 substrate, and the individual clones further characterized.

In another aspect, the invention features a method of making a 25869, 25934, 26335, 50365, 21117, 38692, 46508, 16816, 16839, 49937, 49931 or 49933 polypeptide, e.g., a peptide having a non-wild type activity, e.g., an antagonist, agonist, or super agonist of a naturally occurring 25869, 25934, 26335, 50365, 21117, 38692, 46508, 16816, 16839, 49937, 49931 or 49933 polypeptide, e.g., a naturally occurring 25869, 25934, 26335, 50365, 21117, 38692, 46508, 16816, 16839, 49937, 49931 or 49933 polypeptide. The method includes altering the sequence of a 25869, 25934, 26335, 50365, 21117, 38692, 46508, 16816, 16839, 49937, 49931 or 49933 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 25869, 25934, 26335, 50365, 21117, 38692, 46508, 16816, 16839, 49937, 49931 or 49933 polypeptide a biological activity of a naturally occurring 25869, 25934, 26335, 50365, 21117, 38692, 46508, 16816, 16839, 49937, 49931 or 49933 polypeptide. The method includes altering the sequence, e.g., by substitution or deletion of one or more residues, of a 25869, 25934, 26335, 50365, 21117, 38692, 46508, 16816, 16839, 49937, 49931 or 49933 polypeptide, e.g., altering the sequence of a non-conserved region, or a domain or residue described herein, and testing the altered polypeptide for the desired activity.

Anti-25869, 25934, 26335, 50365, 21117, 38692, 46508, 16816, 16839, 49937, 49931 or 49933 Antibodies In another aspect, the invention provides an anti-25869, 25934, 26335, 50365, 21117, 38692, 46508, 16816, 16839, 49937, 49931 or 49933 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 25869, 25934, 26335, 50365, 21117, 38692, 46508, 16816, 16839, 49937, 49931 or 49933 protein or, antigenic peptide fragment of 25869, 25934, 26335, 50365, 21117, 38692, 46508, 16816, 16839, 49937, 49931 or 49933 can be used as an immunogen or can be used to identify anti-25869, 25934, 26335, 50365, 21117, 38692, 46508, 16816, 16839, 49937, 49931 or 49933 antibodies made with other immunogens, e.g., cells, membrane preparations, and the like. The antigenic peptide of 25869, 25934, 26335, 50365, 21117, 38692, 46508, 16816, 16839, 49937, 49931 or 49933 should include at least 8 amino acid residues of the amino acid sequence shown in SEQ ID NO:2, 8, 17, 21, 26, 29, 36, 40, 43, 64, 68 or 71 and encompasses an epitope of 25869, 25934, 26335, 50365, 21117, 38692, 46508, 16816, 16839, 49937, 49931 or 49933. Preferably, the antigenic peptide includes at least 10 amino acid residues, more preferably at least 15 amino acid residues, even more preferably at least 20 amino acid residues, and most preferably at least 30 amino acid residues.

Fragments of 25869, 25934, 26335, 50365, 21117, 38692, 46508, 16816, 16839, 49937, 49931 or 49933 which include hydrophilic regions of SEQ ID NO:2, 8, 17, 21, 26, 29, 36, 40, 43, 64, 68 or 71 can be used to make, e.g., used as immunogens or used to characterize the specificity of an antibody, antibodies against hydrophilic regions of the 25869, 25934, 26335, 50365, 21117, 38692, 46508, 16816, 16839, 49937, 49931 or 49933 protein. Similarly, fragments of 25869, 25934, 26335, 50365, 21117, 38692, 46508, 16816, 16839, 49937, 49931 or 49933 which include hydrophobic regions of SEQ ID NO:2, 8, 17, 21, 26, 29, 36, 40, 43, 64, 68 or 71 can be used to make an antibody against a hydrophobic region of the 25869, 25934, 26335, 50365, 21117, 38692, 46508, 16816, 16839, 49937, 49931 or 49933 protein; fragments of 25869, 25934, 26335, 50365, 21117, 38692, 46508, 16816, 16839, 49937, 49931 or 49933 which include residues within extra cellular domain(s) of SEQ ID NO:2, 8, 17, 21, 26, 29, 36, 40, 43, 64, 68 or 71 can be used to make an antibody against an extracellular or non-cytoplasmic region of the 25869, 25934, 26335, 50365, 21117, 38692, 46508, 16816, 16839, 49937, 49931 or 49933 protein; fragments of 25869, 25934, 26335, 50365, 21117, 38692, 46508, 16816, 16839, 49937, 49931 or 49933 which include residues within intracellular regions of SEQ ID NO:2, 8, 17, 21, 26, 29, 36, 40, 43, 64, 68 or 71 can be used to make an antibody against an intracellular region of the 25869, 25934, 26335, 50365, 21117, 38692, 46508, 16816, 16839, 49937, 49931 or 49933 protein; a fragment of 25869, 25934, 26335, 50365, 21117, 38692, 46508, 16816, 16839, 49937, 49931 or 49933 which include residues within identified or conserved domains of SEQ ID NO:2, 8, 17, 21, 26, 29, 36, 40, 43, 64, 68 or 71 can be used to make an antibody against the identified or conserved domain of the 25869, 25934, 26335, 50365, 21117, 38692, 46508, 16816, 16839, 49937, 49931 or 49933 protein.

Antibodies reactive with, or specific or selective for, any of these regions, or other regions or domains described herein are provided.

Preferred epitopes encompassed by the antigenic peptide are regions of 25869, 25934, 26335, 50365, 21117, 38692, 46508, 16816, 16839, 49937, 49931 or 49933 located on the surface of the protein, e.g., hydrophilic regions, as well as regions with high antigenicity. For example, an Emini surface probability analysis of the human 25869, 25934, 26335, 50365, 21117, 38692, 46508, 16816, 16839, 49937, 49931 or 49933 protein sequence can be used to indicate the regions that have a particularly high probability of being localized to the surface of the 25869, 25934, 26335, 50365, 21117, 38692, 46508, 16816, 16839, 49937, 49931 or 49933 protein and are thus likely to constitute surface residues useful for targeting antibody production.

In a preferred embodiment the antibody can bind to the extracellular portion of the 25869, 25934, 26335, 50365, 21117, 38692, 46508, 16816, 16839, 49937, 49931 or 49933 protein, e.g., it can bind to a whole cell which expresses the 25869, 25934, 26335, 50365, 21117, 38692, 46508, 16816, 16839, 49937, 49931 or 49933 protein. In another embodiment, the antibody binds an intracellular portion of the 25869, 25934, 26335, 50365, 21117, 38692, 46508, 16816, 16839, 49937, 49931 or 49933 protein.

In a preferred embodiment the antibody binds an epitope on any domain or region on 25869, 25934, 26335, 50365, 21117, 38692, 46508, 16816, 16839, 49937, 49931 or 49933 proteins described herein.

Additionally, chimeric, humanized, and completely human antibodies are also within the scope of the invention. Chimeric, humanized, but most preferably, completely human antibodies ate desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559).

A humanized or complementarity determining region (CDR)-grafted antibody will have at least one or two, but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 25869, 25934, 26335, 50365, 21117, 38692, 46508, 16816, 16839, 49937, 49931 or 49933 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, (1987) *From Genes to Clones* (Verlagsgesellschaft, Weinheim, Germany). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison (1985) *Science* 229:1202-1207, by Oi et al. (1986) *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 25869, 25934, 26335, 50365, 21117, 38692, 46508, 16816, 16839, 49937, 49931 or 49933 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

The anti-25869, 25934, 26335, 50365, 21117, 38692, 46508, 16816, 16839, 49937, 49931 or 49933 antibody can be a single chain antibody. A single-chain antibody (scFV) can be engineered as described in, for example, Colcher et al. (1999) *Ann. N Y Acad. Sci.* 880:263-80; and Reiter (1996) *Clin. Cancer Res.* 2:245-52. The single chain antibody can be dimerized or multimerized to generate multivalent antibodies having specificities for different epitopes of the same target 25869, 25934, 26335, 50365, 21117, 38692, 46508, 16816, 16839, 49937, 49931 or 49933 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Radioactive ions include, but are not limited to iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-25869, 25934, 26335, 50365, 21117, 38692, 46508, 16816, 16839, 49937, 49931 or 49933 antibody (e.g., monoclonal antibody) can be used to isolate 25869, 25934, 26335, 50365, 21117, 38692, 46508, 16816, 16839, 49937, 49931 or 49933 by standard techniques, such as affinity chromatography or immunoprecipitation. Moreover, an anti-25869, 25934, 26335, 50365, 21117, 38692, 46508, 16816, 16839, 49937, 49931 or 49933 antibody can be used to detect 25869, 25934, 26335, 50365, 21117, 38692, 46508, 16816, 16839, 49937, 49931 or 49933 protein (e.g., in a cellular lysate or cell supernatant) in order to evaluate the abundance and pattern of expression of the protein. Anti-25869, 25934, 26335, 50365, 21117, 38692, 46508, 16816, 16839, 49937, 49931 or 49933 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In preferred embodiments, an antibody can be made by immunizing with a purified 25869, 25934, 26335, 50365, 21117, 38692, 46508, 16816, 16839, 49937, 49931 or 49933 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native 25869, 25934, 26335, 50365, 21117, 38692, 46508, 16816, 16839, 49937, 49931 or 49933 protein, only denatured or otherwise non-native 25869, 25934, 26335, 50365, 21117, 38692, 46508, 16816, 16839, 49937, 49931 or 49933 protein, or which bind both, are within the invention. Antibodies with linear or conformational epitopes are within the invention. Conformational epitopes sometimes can be identified by identifying antibodies which bind to native but not denatured 25869, 25934, 26335, 50365, 21117, 38692, 46508, 16816, 16839, 49937, 49931 or 49933 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 25869, 25934, 26335, 50365, 21117, 38692, 46508, 16816, 16839, 49937, 49931 or 49933 nucleic acid in a form suitable for expression of the nucleic acid in a host cell.

Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 25869, 25934, 26335, 50365, 21117, 38692, 46508, 16816, 16839, 49937, 49931 or 49933 proteins, mutant forms of 25869, 25934, 26335, 50365, 21117, 38692, 46508, 16816, 16839, 49937, 49931 or 49933 proteins, fusion proteins, and the like).

The recombinant expression vectors of the invention can be designed for expression of 25869, 25934, 26335, 50365, 21117, 38692, 46508, 16816, 16839, 49937, 49931 or 49933 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 25869, 25934, 26335, 50365, 21117, 38692, 46508, 16816, 16839, 49937, 49931 or 49933 activity assays, (e.g., direct assays or competitive assays described in detail below), or to generate antibodies specific or selective for 25869, 25934, 26335, 50365, 21117, 38692, 46508, 16816, 16839, 49937, 49931 or 49933 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman (1990) Gene Expression Technology: Methods in Enzymology 185, Academic Press, San Diego, Calif. 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

The 25869, 25934, 26335, 50365, 21117, 38692, 46508, 16816, 16839, 49937, 49931 or 49933 expression vector can be a yeast expression vector, a vector for expression in insect cells, e.g., a baculovirus expression vector or a vector suitable for expression in mammalian cells.

When, used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al., (1986) *Reviews—Trends in Genetics* 1:1.

Another aspect the invention provides a host cell which includes a nucleic acid molecule described herein, e.g., a 25869, 25934, 26335, 50365, 21117, 38692, 46508, 16816, 16839, 49937, 49931 or 49933 nucleic acid molecule within a recombinant expression vector or a 25869, 25934, 26335, 50365, 21117, 38692, 46508, 16816, 16839, 49937, 49931 or 49933 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 25869, 25934, 26335, 50365, 21117, 38692, 46508, 16816, 16839, 49937, 49931 or 49933 protein can be expressed in bacterial cells such as *E. coli*, insect cells, yeast or mammalian cells (such as Chinese hamster ovary (CHO) cells or CV-1 origin, SV-40 (COS) cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 25869, 25934, 26335, 50365, 21117, 38692, 46508, 16816, 16839, 49937, 49931 or 49933 protein. Accordingly, the invention further provides methods for producing a 25869, 25934, 26335, 50365, 21117, 38692, 46508, 16816, 16839, 49937, 49931 or 49933 protein using the host cells of the invention. In one embodiment, the method includes culturing the host cell of the invention (into which a recombinant expression vector encoding a 25869, 25934, 26335, 50365, 21117, 38692, 46508, 16816, 16839, 49937, 49931 or 49933 protein has been introduced) in a suitable medium such that a 25869, 25934, 26335, 50365, 21117, 38692, 46508, 16816, 16839, 49937, 49931 or 49933 protein is produced. In another embodiment, the method further includes isolating a 25869, 25934, 26335, 50365, 21117, 38692, 46508, 16816, 16839, 49937, 49931 or 49933 protein from the medium or the host cell.

In another aspect, the invention features, a cell or purified preparation of cells which include a 25869, 25934, 26335, 50365, 21117, 38692, 46508, 16816, 16839, 49937, 49931 or 49933 transgene, or which otherwise misexpress 25869, 25934, 26335, 50365, 21117, 38692, 46508, 16816, 16839, 49937, 49931 or 49933. The cell preparation can consist of human or non-human cells, e.g., rodent cells, e.g., mouse or rat cells, rabbit cells, or pig cells. In preferred embodiments, the cell or cells include a 25869, 25934, 26335, 50365, 21117, 38692, 46508, 16816, 16839, 49937, 49931 or 49933 transgene, e.g., a heterologous form of a 25869, 25934, 26335, 50365, 21117, 38692, 46508, 16816, 16839, 49937, 49931 or 49933, e.g., a gene derived from humans (in the case of a non-human cell). The 25869, 25934, 26335, 50365, 21117, 38692, 46508, 16816, 16839, 49937, 49931 or 49933 transgene can be misexpressed, e.g., overexpressed or underexpressed. In other preferred embodiments, the cell or cells include a gene which misexpresses an endogenous 25869, 25934, 26335, 50365, 21117, 38692, 46508, 16816, 16839, 49937, 49931 or 49933, e.g., a gene the expression of which is disrupted, e.g., a knockout. Such cells can serve as a model for studying disorders which are related to mutated or misexpressed 25869, 25934, 26335, 50365, 21117, 38692, 46508, 16816, 16839, 49937, 49931 or 49933 alleles or for use in drug screening.

In another aspect, the invention features, a human cell, e.g., a hematopoietic stem cell, transformed with nucleic acid which encodes a subject 25869, 25934, 26335, 50365, 21117, 38692, 46508, 16816, 16839, 49937, 49931 or 49933 polypeptide.

Also provided are cells, preferably human cells, e.g., human hematopoietic or fibroblast cells, in which an endogenous 25869, 25934, 26335, 50365, 21117, 38692, 46508, 16816, 16839, 49937, 49931 or 49933 is under the control of a regulatory sequence that does not normally control the expression of the endogenous 25869, 25934, 26335, 50365, 21117, 38692, 46508, 16816, 16839, 49937, 49931 or 49933 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 25869, 25934, 26335, 50365, 21117, 38692, 46508, 16816, 16839, 49937, 49931 or 49933 gene. For example, an endogenous 25869, 25934, 26335, 50365, 21117, 38692, 46508, 16816, 16839, 49937, 49931 or 49933 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 25869, 25934, 26335, 50365, 21117, 38692, 46508, 16816, 16839, 49937, 49931 or 49933 protein and for identifying and/or evaluating modulators of 25869, 25934, 26335, 50365, 21117, 38692, 46508, 16816, 16839, 49937, 49931 or 49933 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 25869, 25934, 26335, 50365, 21117, 38692, 46508, 16816, 16839, 49937, 49931 or 49933 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 25869, 25934, 26335, 50365, 21117, 38692, 46508, 16816, 16839, 49937, 49931 or 49933 protein to particular cells. A transgenic founder animal can be identified based upon the presence of a 25869, 25934, 26335, 50365, 21117, 38692, 46508, 16816, 16839, 49937, 49931 or 49933 transgene in its genome and/or expression of 25869, 25934, 26335, 50365, 21117, 38692, 46508, 16816, 16839, 49937, 49931 or 49933 mRNA in tissues or cells of the animals. A transgenic founder animal can then be used to breed additional animals carrying the transgene. Moreover, transgenic animals carrying a transgene encoding a 25869, 25934, 26335, 50365, 21117, 38692, 46508, 16816, 16839, 49937, 49931 or 49933 protein can further be bred to other transgenic animals carrying other transgenes.

25869, 25934, 26335, 50365, 21117, 38692, 46508, 16816, 16839, 49937, 49931 or 49933 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

For example, the following animal models may be used in the methods of the invention: the hypertensive transgenic mouse model that lacks fat and has lipoatrophic diabetes (Reitmann, M. L. et al. (1999) *Ann. N.Y. Acad. Sci.* 192:289-96; Moitra J. et al. (1998) *Genes Dev.* 12:3168-81); a VEGF transgenic animal model for atherosclerosis and angiogenesis (Sueishi, K. et al. (1997) *Ann. N.Y. Acad. Sci.* 811:311-324); guinea pigs, which are used as models for cholesterol and lipoprotein metabolism, as well as early atherosclerosis development (Fernandez, M. L. (2001) *J. Nutr.* 131(1):10-20); the macrophage scavenger receptor class A (SR-A) transgenic mouse, which shows reduced atherosclerosis (De Winther, M. P. et al. (2000) *Int. J. Tissue React.* 22(2-3):85-91); the St. Thomas' Hospital rabbit strain, an animal model with genetically elevated plasma levels of VLDL, IDL, and low-density lipoprotein (LDL) (Nordestgaard, B. G. et al. (1992) *Eur. J. Epidemiol.* 8 Suppl 1:92-8); the Watanabe heritable hyperlipidemic (WHHL) rabbit, the animal model for familial hypercholesterolemia (Buja, L. M. et al. (1990) *Eur. Heart J.* 11 Suppl E:41-52); atherosclerosis induced in Cynomolgus macaque monkeys by feeding cholesterol (Weingand, K. W. (1989) *Exp. Mol. Pathol.* 50(1):1-15); atherosclerosis induced by infection with Marek's disease herpesvirus in chickens (1999) *Am. Heart J.* 138(5 Pt 2):S465-8); genetically selected lines of Japanese quail, highly susceptible (SUS) and resistant (RES) to atherosclerosis (1987) *Atherosclerosis* 68(1-2):77-8); the atherosclerotic and hypertensive strain of male broad-breasted white turkeys (BBWT) (Pagnan, A. (1980) *Artery* 6(4):320-7); diet-induced, apoE deficiency-induced, or LDL receptor-deficiency induced atherosclerosis in mice (Smith, J. D. (1997) *J. Intern. Med.* 242(2): 99-109); the JCR:LA-corpulent rat, an experimental model for the obese-diabetic-dyslipidemic syndrome that mimics the human condition and exhibits spontaneous development of atherosclerosis and myocardial lesions (Brindley, D. N. (1995) *Metabolism* 44(2 Suppl 2):23-7); marmosets or other animals treated with cholestyramine or other cholesterol and/or lipid lowering drugs; and numerous other animal models of atherosclerosis (reviewed in Bocan, T. M. (1998) *Curr. Pharm. Des.* 4(1):37-52; Fekete, S. (1993) *Acta Vet. Hung.* 41(1-2):3-9).

Further examples of animals that can be used include the transgenic mouse described in U.S. Pat. No. 5,932,779 that contains a mutation in an endogenous melanocortin-4-receptor (MC4-R) gene; animals having mutations which lead to syndromes that include obesity symptoms (described in, for example, Friedman, J. M. et al. (1991) *Mamm. Genome* 1: 130-144; Friedman, J. M. and Liebel, R. L. (1992) *Cell* 69:217-220; Bray, G. A. (1992) *Prog. Brain Res.* 93:333-341; and Bray, G. A. (1989) *Amer. J. Clin. Nutr.* 5:891-902); the animals described in Stubdal, H. et al. (2000) *Mol. Cell Biol.* 20(3):878-82 (the mouse tubby phenotype characterized by maturity-onset obesity); the animals described in Abadie, J. M. et al. (2000) *Lipids* 35(6):613-20 (the obese Zucker rat (ZR), a genetic model of human youth-onset obesity and type 2 diabetes mellitus); the animals described in Shaughnessy, S. et al. (2000) *Diabetes* 49(6):904-11 (mice null for the adipocyte fatty acid binding protein); or the animals described in Loskutoff, D. J. et al. (2000) *Ann. N.Y. Acad. Sci.* 902:272-81 (the fat mouse). Other examples of animals that may be used include non-recombinant, non-genetic animal models of obesity such as, for example, rabbit, mouse, or rat models in which the animal has been exposed to long-term over-eating.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 25869, 25934, 26335, 50365, 21117, 38692, 46508, 16816, 16839, 49937, 49931 or 49933 protein (e.g., via a recombinant expression vector in a host cell in gene therapy applications), to detect a 25869, 25934, 26335, 50365, 21117, 38692, 46508, 16816, 16839, 49937, 49931 or 49933 mRNA (e.g., in a biological sample) or a genetic alteration in a 25869, 25934, 26335, 50365, 21117, 38692, 46508, 16816, 16839, 49937, 49931 or 49933 gene, and to modulate 25869, 25934, 26335, 50365, 21117, 38692, 46508, 16816, 16839, 49937, 49931 or 49933 activity, as described further below. The 25869, 25934, 26335, 50365, 21117, 38692, 46508, 16816, 16839, 49937, 49931 or 49933 proteins can be used to treat disorders characterized by insufficient, aberrant or excessive production of a 25869, 25934, 26335, 50365, 21117, 38692, 46508, 16816, 16839, 49937, 49931 or 49933 substrate or production of 25869, 25934, 26335, 50365, 21117, 38692, 46508, 16816, 16839, 49937, 49931 or 49933 inhibitors. In addition, the 25869, 25934, 26335, 50365, 21117, 38692, 46508, 16816, 16839, 49937, 49931 or 49933 proteins can be used to screen for naturally occurring 25869, 25934, 26335, 50365, 21117, 38692, 46508, 16816, 16839, 49937, 49931 or 49933 substrates, to screen for drugs or compounds which modulate 25869, 25934, 26335, 50365, 21117, 38692, 46508, 16816, 16839, 49937, 49931 or 49933 activity, as well as to treat disorders characterized by insufficient, aberrant or excessive production of 25869, 25934, 26335, 50365, 21117, 38692, 46508, 16816, 16839, 49937, 49931 or 49933 protein or production of 25869, 25934, 26335, 50365, 21117, 38692, 46508, 16816, 16839, 49937, 49931 or 49933 protein forms which have decreased, aberrant or unwanted activity compared to 25869, 25934, 26335, 50365, 21117, 38692, 46508, 16816, 16839, 49937, 49931 or 49933 wild type protein (e.g., aberrant or deficient carboxylase actvity, fatty acid desaturase activity, serine/threonine dehydratase activity, hexokinase activity, peptidyl tRNA hydrolase actvity, dual specificity phosphatase activity, phospholipase activity, transporter actvity, or other activity disclosed herein). Moreover, the anti-25869, 25934, 26335, 50365, 21117, 38692, 46508, 16816, 16839, 49937, 49931 or 49933 antibodies of the invention can be used to detect and isolate 25869, 25934, 26335, 50365, 21117, 38692, 46508, 16816, 16839, 49937, 49931 or 49933 proteins, regulate the bioavailability of 25869, 25934, 26335, 50365, 21117, 38692, 46508, 16816, 16839, 49937, 49931 or 49933 proteins, and modulate 25869, 25934, 26335, 50365, 21117, 38692, 46508, 16816, 16839, 49937, 49931 or 49933 activity.

A method of evaluating a compound for the ability to interact with, e.g., bind, a subject 25869, 25934, 26335, 50365, 21117, 38692, 46508, 16816, 16839, 49937, 49931 or 49933 polypeptide is provided. The method includes: contacting the compound with the subject 25869, 25934, 26335, 50365, 21117, 38692, 46508, 16816, 16839, 49937, 49931 or 49933 polypeptide; and evaluating ability of the compound to interact with, e.g., to bind or form a complex with the subject 25869, 25934, 26335, 50365, 21117, 38692, 46508, 16816, 16839, 49937, 49931 or 49933 polypeptide. This method can be performed in vitro, e.g., in a cell free system, or in vivo, e.g., in a two-hybrid interaction trap assay. This method can be used to identify naturally occurring molecules which interact with subject 25869, 25934, 26335, 50365, 21117, 38692, 46508, 16816, 16839, 49937, 49931 or 49933 polypeptide. It can also be used to find natural or synthetic inhibitors of subject 25869, 25934, 26335, 50365, 21117, 38692, 46508, 16816, 16839, 49937, 49931 or 49933 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 25869, 25934, 26335, 50365, 21117, 38692, 46508, 16816, 16839, 49937, 49931 or 49933 proteins, have a stimulatory or inhibitory effect on, for example, 25869, 25934, 26335, 50365, 21117, 38692, 46508, 16816, 16839, 49937, 49931 or 49933 expression or 25869, 25934, 26335, 50365, 21117, 38692, 46508, 16816, 16839, 49937, 49931 or 49933 activity, or have a stimulatory or inhibitory effect on, for example, the expression or activity of a 25869, 25934, 26335, 50365, 21117, 38692, 46508, 16816, 16839, 49937, 49931 or 49933 substrate. Compounds thus identified can be used to modulate the activity of target gene products (e.g., 25869, 25934, 26335, 50365, 21117, 38692, 46508, 16816, 16839, 49937, 49931 or 49933 genes) in a therapeutic protocol, to elaborate the biological function of the target gene product, or to identify compounds that disrupt normal target gene interactions.

In one embodiment, the invention provides assays for screening candidate or test compounds which are substrates of a 25869, 25934, 26335, 50365, 21117, 38692, 46508, 16816, 16839, 49937, 49931 or 49933 protein or polypeptide or a biologically active portion thereof. In another embodiment, the invention provides assays for screening candidate or test compounds which bind to or modulate the activity of a 25869, 25934, 26335, 50365, 21117, 38692, 46508, 16816, 16839, 49937, 49931 or 49933 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909-13; Erb et al. (1994) *Proc. Natl. Acad. Sci. USA* 91:11422-426; Zuckermann et al. (1994). *J. Med. Chem.* 37:2678-85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233-51.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390; Devlin (1990)

Science 249:404-406; Cwirla et al. (1990) Proc. Natl. Acad. Sci. 87:6378-6382; Felici (1991) J. Mol. Biol. 222:301-310; Ladner supra.).

In one embodiment, an assay is a cell-based assay in which a cell which expresses a 25869, 25934, 26335, 50365, 21117, 38692, 46508, 16816, 16839, 49937, 49931 or 49933 protein or biologically active portion thereof is contacted with a test compound, and the ability of the test compound to modulate 25869, 25934, 26335, 50365, 21117, 38692, 46508, 16816, 16839, 49937, 49931 or 49933 activity is determined. Determining the ability of the test compound to modulate 25869, 25934, 26335, 50365, 21117, 38692, 46508, 16816, 16839, 49937, 49931 or 49933 activity can be accomplished by monitoring, for example, carboxylase actvity, fatty acid desaturase activity, serine/threonine dehydratase activity, hexokinase activity, peptidyl tRNA hydrolase actvity, dual specificity phosphatase activity, phospholipase activity, transporter actvity, or other activity disclosed herein. The cell, for example, can be of mammalian origin, e.g., human.

The ability of the test compound to modulate 25869, 25934, 26335, 50365, 21117, 38692, 46508, 16816, 16839, 49937, 49931 or 49933 binding to a compound, e.g., a 25869, 25934, 26335, 50365, 21117, 38692, 46508, 16816, 16839, 49937, 49931 or 49933 substrate, or to bind to 25869, 25934, 26335, 50365, 21117, 38692, 46508, 16816, 16839, 49937, 49931 or 49933 can also be evaluated. This can be accomplished, for example, by coupling the compound, e.g., the substrate, with a radioisotope or enzymatic label such that binding of the compound, e.g., the substrate, to 25869, 25934, 26335, 50365, 21117, 38692, 46508, 16816, 16839, 49937, 49931 or 49933 can be determined by detecting the labeled compound, e.g., substrate, in a complex. Alternatively, 25869, 25934, 26335, 50365, 21117, 38692, 46508, 16816, 16839, 49937, 49931 or 49933 could be coupled with a radioisotope or enzymatic label to monitor the ability of a test compound to modulate 25869, 25934, 26335, 50365, 21117, 38692, 46508, 16816, 16839, 49937, 49931 or 49933 binding to a 25869, 25934, 26335, 50365, 21117, 38692, 46508, 16816, 16839, 49937, 49931 or 49933 substrate in a complex. For example, compounds (e.g., 25869, 25934, 26335, 50365, 21117, 38692, 46508, 16816, 16839, 49937, 49931 or 49933 substrates) can be labeled with $^{125}I$, $^{14}C$, $^{35}S$ or $^{3}H$., either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 25869, 25934, 26335, 50365, 21117, 38692, 46508, 16816, 16839, 49937, 49931 or 49933 substrate) to interact with 25869, 25934, 26335, 50365, 21117, 38692, 46508, 16816, 16839, 49937, 49931 or 49933 with or without the labeling of any of the interactants can be evaluated. For example, a microphysiometer can be used to detect the interaction of a compound with 25869, 25934, 26335, 50365, 21117, 38692, 46508, 16816, 16839, 49937, 49931 or 49933 without the labeling of either the compound or the 25869, 25934, 26335, 50365, 21117, 38692, 46508, 16816, 16839, 49937, 49931 or 49933. McConnell et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 25869, 25934, 26335, 50365, 21117, 38692, 46508, 16816, 16839, 49937, 49931 or 49933.

In yet another embodiment, a cell-free assay is provided in which a 25869, 25934, 26335, 50365, 21117, 38692, 46508, 16816, 16839, 49937, 49931 or 49933 protein or biologically active portion thereof is contacted with a test compound and the ability of the test compound to bind to the 25869, 25934, 26335, 50365, 21117, 38692, 46508, 16816, 16839, 49937, 49931 or 49933 protein or biologically active portion thereof is evaluated. Preferred biologically active portions of the 25869, 25934, 26335, 50365, 21117, 38692, 46508, 16816, 16839, 49937, 49931 or 49933 proteins to be used in assays of the present invention include fragments which participate in interactions with non-25869, 25934, 26335, 50365, 21117, 38692, 46508, 16816, 16839, 49937, 49931 or 49933 molecules, e.g., fragments with high surface probability scores.

Soluble and/or membrane-bound forms of isolated proteins (e.g., 25869, 25934, 26335, 50365, 21117, 38692, 46508, 16816, 16839, 49937, 49931 or 49933 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 25869, 25934, 26335, 50365, 21117, 38692, 46508, 16816, 16839, 49937, 49931 or 49933 protein to bind to a target molecule can be accomplished using real-time Biomolecular Interaction Analysis (BIA) (see, e.g., Sjolander and Urbanic-zky (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 25869, 25934, 26335, 50365, 21117, 38692, 46508, 16816, 16839, 49937, 49931 or 49933, an anti-25869, 25934, 26335, 50365, 21117, 38692, 46508, 16816, 16839, 49937, 49931 or 49933 antibody or its target molecule to facilitate separation of complexed from uncomplexed forms of one or both of the proteins, as well as to accommodate automation of the assay. Binding of a test compound to a 25869, 25934, 26335, 50365, 21117, 38692, 46508, 16816, 16839, 49937, 49931 or 49933 protein, or interaction of a 25869, 25934, 26335, 50365, 21117, 38692, 46508, 16816, 16839, 49937, 49931 or 49933 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/25869, 25934, 26335, 50365, 21117, 38692, 46508, 16816, 16839, 49937, 49931 or 49933 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 25869, 25934, 26335, 50365, 21117, 38692, 46508, 16816, 16839, 49937, 49931 or 49933 protein, and the mixture incubated under conditions conducive to complex formation (e.g., at physiological conditions for salt and pH).

Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 25869, 25934, 26335, 50365, 21117, 38692, 46508, 16816, 16839, 49937, 49931 or 49933 binding or activity determined using standard techniques.

Other techniques for immobilizing either a 25869, 25934, 26335, 50365, 21117, 38692, 46508, 16816, 16839, 49937, 49931 or 49933 protein or a target molecule on matrices include using conjugation of biotin and streptavidin. Biotinylated 25869, 25934, 26335, 50365, 21117, 38692, 46508, 16816, 16839, 49937, 49931 or 49933 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 25869, 25934, 26335, 50365, 21117, 38692, 46508, 16816, 16839, 49937, 49931 or 49933 protein or target molecules but which do not interfere with binding of the 25869, 25934, 26335, 50365, 21117, 38692, 46508, 16816, 16839, 49937, 49931 or 49933 protein to its target molecule. Such antibodies can be derivatized to the wells of the plate, and unbound target or 25869, 25934, 26335, 50365, 21117, 38692, 46508, 16816, 16839, 49937, 49931 or 49933 protein trapped in the wells by antibody conjugation. Methods for detecting such complexes, in addition to those described above for the GST-immobilized complexes, include immunodetection of complexes using antibodies reactive with the 25869, 25934, 26335, 50365, 21117, 38692, 46508, 16816, 16839, 49937, 49931 or 49933 protein or target molecule, as well as enzyme-linked assays which rely on detecting an enzymatic activity associated with the 25869, 25934, 26335, 50365, 21117, 38692, 46508, 16816, 16839, 49937, 49931 or 49933 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18:284-7); chromatography (gel filtration chromatography, ion-exchange chromatography); electrophoresis (see, e.g., Ausubel et al., eds. (1999) *Current Protocols in Molecular Biology*, J. Wiley, New York.); and immunoprecipitation (see, for example, Ausubel et al., eds. (1999) *Current Protocols in Molecular Biology*, J. Wiley, New York). Such resins and chromatographic techniques are known to one skilled in the art (see, e.g., Heegaard (1998) *J Mol Recognit* 11:141-8; Hage and Tweed (1997) *J Chromatogr B Biomed Sci Appl.* 699:499-525). Further, fluorescence energy transfer can also be conveniently utilized, as described herein, to detect binding without further purification of the complex from solution.

In a preferred embodiment, the assay includes contacting the 25869, 25934, 26335, 50365, 21117, 38692, 46508, 16816, 16839, 49937, 49931 or 49933 protein or biologically active portion thereof with a known compound which binds 25869, 25934, 26335, 50365, 21117, 38692, 46508, 16816, 16839, 49937, 49931 or 49933 to form an assay mixture, contacting the assay mixture with a test compound, and determining the ability of the test compound to interact with a 25869, 25934, 26335, 50365, 21117, 38692, 46508, 16816, 16839, 49937, 49931 or 49933 protein, wherein determining the ability of the test compound to interact with a 25869, 25934, 26335, 50365, 21117, 38692, 46508, 16816, 16839, 49937, 49931 or 49933 protein includes determining the ability of the test compound to preferentially bind to 25869, 25934, 26335, 50365, 21117, 38692, 46508, 16816, 16839, 49937, 49931 or 49933 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 25869, 25934, 26335, 50365, 21117, 38692, 46508, 16816, 16839, 49937, 49931 or 49933 genes herein identified. In an alternative embodiment, the invention provides methods for determining the ability of the test compound to modulate the activity of a 25869, 25934, 26335, 50365, 21117, 38692, 46508, 16816, 16839, 49937, 49931 or 49933 protein through modulation of the activity of a downstream effector of a 25869, 25934, 26335, 50365, 21117, 38692, 46508, 16816, 16839, 49937, 49931 or 49933 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner.

Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 25869, 25934, 26335, 50365, 21117, 38692, 46508, 16816, 16839, 49937, 49931 or 49933 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 25869, 25934, 26335, 50365, 21117, 38692, 46508, 16816, 16839, 49937, 49931 or 49933 ("25869, 25934, 26335, 50365, 21117, 38692, 46508, 16816, 16839, 49937, 49931 or 49933-binding proteins" or "25869, 25934, 26335, 50365, 21117, 38692, 46508, 16816, 16839, 49937, 49931 or 49933-bp") and are involved in 25869, 25934, 26335, 50365, 21117, 38692, 46508, 16816, 16839, 49937, 49931 or 49933 activity. Such 25869, 25934, 26335, 50365, 21117, 38692, 46508, 16816, 16839, 49937, 49931 or 49933-bps can be activators or inhibitors of signals by the 25869, 25934, 26335, 50365, 21117, 38692, 46508, 16816, 16839, 49937, 49931 or 49933 proteins or 25869, 25934, 26335, 50365, 21117, 38692, 46508, 16816, 16839, 49937, 49931 or 49933 targets as, for example, downstream elements of a 25869, 25934, 26335, 50365, 21117, 38692, 46508, 16816, 16839, 49937, 49931 or 49933-mediated signaling pathway.

The two-hybrid system is based on the modular nature of most transcription factors, which consist of separable DNA-binding and activation domains. Briefly, the assay utilizes two different DNA constructs. In one construct, the gene that codes for a 25869, 25934, 26335, 50365, 21117, 38692, 46508, 16816, 16839, 49937, 49931 or 49933 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 25869, 25934, 26335, 50365, 21117, 38692, 46508, 16816, 16839, 49937, 49931 or 49933 protein can be the fused to the activator domain.) If the "bait" and the "prey" proteins are able to interact, in vivo, forming a 25869, 25934, 26335, 50365, 21117, 38692, 46508, 16816, 16839, 49937, 49931 or 49933-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 25869, 25934, 26335, 50365, 21117, 38692, 46508, 16816, 16839, 49937, 49931 or 49933 protein.

In another embodiment, modulators of 25869, 25934, 26335, 50365, 21117, 38692, 46508, 16816, 16839, 49937, 49931 or 49933 expression are identified. For example, a cell or cell free mixture is contacted with a candidate compound and the expression of 25869, 25934, 26335, 50365, 21117, 38692, 46508, 16816, 16839, 49937, 49931 or 49933 mRNA or protein evaluated relative to the level of expression of 25869, 25934, 26335, 50365, 21117, 38692, 46508, 16816, 16839, 49937, 49931 or 49933 mRNA or protein in the absence of the candidate compound. When expression of 25869, 25934, 26335, 50365, 21117, 38692, 46508, 16816, 16839, 49937, 49931 or 49933 mRNA or protein is greater in the presence of the candidate compound than in its absence, the candidate compound is identified as a stimulator of 25869, 25934, 26335, 50365, 21117, 38692, 46508, 16816, 16839, 49937, 49931 or 49933 mRNA or protein expression. Alternatively, when expression of 25869, 25934, 26335, 50365, 21117, 38692, 46508, 16816, 16839, 49937, 49931 or 49933 mRNA or protein is less (statistically significantly less) in the presence of the candidate compound than in its absence, the candidate compound is identified as an inhibitor of 25869, 25934, 26335, 50365, 21117, 38692, 46508, 16816, 16839, 49937, 49931 or 49933 mRNA or protein expression. The level of 25869, 25934, 26335, 50365, 21117, 38692, 46508, 16816, 16839, 49937, 49931 or 49933 mRNA or protein expression can be determined by methods described herein for detecting 25869, 25934, 26335, 50365, 21117, 38692, 46508, 16816, 16839, 49937, 49931 or 49933 mRNA or protein.

In another aspect, the invention pertains to a combination of two or more of the assays described herein. For example, a modulating agent can be identified using a cell based or a cell free assay, and the ability of the agent to modulate the activity of a 25869, 25934, 26335, 50365, 21117, 38692, 46508, 16816, 16839, 49937, 49931 or 49933 protein can be confirmed in vivo, e.g., in an animal such as an animal model for aberrant or deficient carboxylase actvity, fatty acid desaturase activity, serine/threonine dehydratase activity, hexokinase activity, pepfidyl tRNA hydrolase actvity, dual specificity phosphatase activity, phospholipase activity, transporter actvity, or other activity disclosed herein.

This invention further pertains to novel agents identified by the above-described screening assays. Accordingly, it is within the scope of this invention to further use an agent identified as described herein (e.g., a 25869, 25934, 26335, 50365, 21117, 38692, 46508, 16816, 16839, 49937, 49931 or 49933 modulating agent, an antisense 25869, 25934, 26335, 50365, 21117, 38692, 46508, 16816, 16839, 49937, 49931 or 49933 nucleic acid molecule, a 25869, 25934, 26335, 50365, 21117, 38692, 46508, 16816, 16839, 49937, 49931 or 49933-specific antibody, or a 25869, 25934, 26335, 50365, 21117, 38692, 46508, 16816, 16839, 49937, 49931 or 49933-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 25869, 25934, 26335, 50365, 21117, 38692, 46508, 16816, 16839, 49937, 49931 or 49933 with a disease; (ii) identify an individual from a minute biological sample (tissue typing); and (iii) aid in forensic identification of a biological sample. These applications are described in the subsections below.

Chromosome Mapping

The 25869, 25934, 26335, 50365, 21117, 38692, 46508, 16816, 16839, 49937, 49931 or 49933 nucleotide sequences or portions thereof can be used to map the location of the 25869, 25934, 26335, 50365, 21117, 38692, 46508, 16816, 16839, 49937, 49931 or 49933 genes on a chromosome. This process is called chromosome mapping. Chromosome mapping is useful in correlating the 25869, 25934, 26335, 50365, 21117, 38692, 46508, 16816, 16839, 49937, 49931 or 49933 sequences with genes associated with disease.

Briefly, 25869, 25934, 26335, 50365, 21117, 38692, 46508, 16816, 16839, 49937, 49931 or 49933 genes can be mapped to chromosomes by preparing PCR primers (preferably 15-25 bp in length) from the 25869, 25934, 26335, 50365, 21117, 38692, 46508, 16816, 16839, 49937, 49931 or 49933 nucleotide sequences. These primers can then be used for PCR screening of somatic cell hybrids containing individual human chromosomes. Only those hybrids containing the human gene corresponding to the 25869, 25934, 26335, 50365, 21117, 38692, 46508, 16816, 16839, 49937, 49931 or 49933 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919-924).

Other mapping strategies e.g., in situ hybridization (described in Fan et al. (1990) *Proc. Natl. Acad. Sci. USA*, 87:6223-27), pre-screening with labeled flow-sorted chromosomes, and pre-selection by hybridization to chromosome specific cDNA libraries can be used to map 25869, 25934, 26335, 50365, 21117, 38692, 46508, 16816, 16839, 49937, 49931 or 49933 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature,* 325:783-787.

Moreover, differences in the DNA sequences between individuals affected and unaffected with a disease associated with the 25869, 25934, 26335, 50365, 21117, 38692, 46508, 16816, 16839, 49937, 49931 or 49933 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 25869, 25934, 26335, 50365, 21117, 38692, 46508, 16816, 16839, 49937, 49931 or 49933 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 25869, 25934, 26335, 50365, 21117, 38692, 46508, 16816, 16839, 49937, 49931 or 49933 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 7, 16, 20, 25, 28, 35, 39, 42, 63, 67 or 70 can provide positive individual identification with a panel of perhaps 10 to 1,000 primers which each yield a noncoding amplified sequence of 100 bases. If predicted coding sequences, such as those in SEQ ID NO:3, 9, 18, 22, 27, 30, 37, 41, 44, 65, 69 or 72 are used, a more appropriate number of primers for positive individual identification would be 500-2,000.

If a panel of reagents from 25869, 25934, 26335, 50365, 21117, 38692, 46508, 16816, 16839, 49937, 49931 or 49933 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 25869, 25934, 26335, 50365, 21117, 38692, 46508, 16816, 16839, 49937, 49931 or 49933 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 7, 16, 20, 25, 28, 35, 39, 42, 63, 67 or 70 (e.g., fragments derived from the noncoding regions of SEQ ID NO:1, 7, 16, 20, 25, 28, 35, 39, 42, 63, 67 or 70 having a length of at least 20 bases, preferably at least 30 bases) are particularly appropriate for this use.

The 25869, 25934, 26335, 50365, 21117, 38692, 46508, 16816, 16839, 49937, 49931 or 49933 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 25869, 25934, 26335, 50365, 21117, 38692, 46508, 16816, 16839, 49937, 49931 or 49933 probes can be used to identify tissue by species and/or by organ type.

In a similar fashion, these reagents, e.g., 25869, 25934, 26335, 50365, 21117, 38692, 46508, 16816, 16839, 49937, 49931 or 49933 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 25869, 25934, 26335, 50365, 21117, 38692, 46508, 16816, 16839, 49937, 49931 or 49933. Such disorders include, e.g., a disorder associated with the misexpression of 25869, 25934, 26335, 50365, 21117, 38692, 46508, 16816, 16839, 49937, 49931 or 49933 gene; cellular proliferative and/or differentiative disorders, angiogenic disorders, brain disorders, neurological disorders, blood vessel disorders, breast disorders, colon disorders, kidney disorders, lung disorders, ovarian disorders, prostate disorders, hematopoeitic disorders, pancreatic disorders, skeletal muscle disorders, skin disorders, hormonal disorders, immune e.g., inflammatory, disorders, cardiovascular disorders, lipid homeostasis disorders, endothelial cell disorders, liver disorders, disorders of the small intestine, pain disorders, viral diseases, metabolic disorders, bone metabolism disorders or platelet disorders.

The method includes one or more of the following: detecting, in a tissue of the subject, the presence or absence of a mutation which affects the expression of the 25869, 25934, 26335, 50365, 21117, 38692, 46508, 16816, 16839, 49937, 49931 or 49933 gene, or detecting the presence or absence of a mutation in a region which controls the expression of the gene, e.g., a mutation in the 5' control region; detecting, in a tissue of the subject, the presence or absence of a mutation which alters the structure of the 25869, 25934, 26335, 50365, 21117, 38692, 46508, 16816, 16839, 49937, 49931 or 49933 gene; detecting, in a tissue of the subject, the misexpression of the 25869, 25934, 26335, 50365, 21117, 38692, 46508, 16816, 16839, 49937, 49931 or 49933 gene, at the mRNA level, e.g., detecting a non-wild type level of an mRNA; or detecting, in a tissue of the subject, the misexpression of the gene, at the protein level, e.g., detecting a non-wild type level of a 25869, 25934, 26335, 50365, 21117, 38692, 46508, 16816, 16839, 49937, 49931 or 49933 polypeptide.

In preferred embodiments the method includes: ascertaining the existence of at least one of: a deletion of one or more nucleotides from the 25869, 25934, 26335, 50365, 21117, 38692, 46508, 16816, 16839, 49937, 49931 or 49933 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, 7, 16, 20, 25, 28, 35, 39, 42, 63, 67 or 70, or naturally occurring mutants thereof or 5' or 3' flanking sequences naturally associated with the 25869, 25934, 26335, 50365, 21117, 38692, 46508, 16816, 16839, 49937, 49931 or 49933 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 25869, 25934, 26335, 50365, 21117, 38692, 46508, 16816, 16839, 49937, 49931 or 49933 gene; the presence of a non-wild type splicing pattern of a messenger RNA transcript of the gene; or a non-wild type level of 25869, 25934, 26335, 50365, 21117, 38692, 46508, 16816, 16839, 49937, 49931 or 49933.

Methods of the invention can be used prenatally or to determine if a subject's offspring will be a risk for a disorder.

In preferred embodiments the method includes determining the structure of a 25869, 25934, 26335, 50365, 21117, 38692, 46508, 16816, 16839, 49937, 49931 or 49933 gene, an abnormal structure being indicative of risk for the disorder.

In preferred embodiments the method includes contacting a sample from the subject with an antibody to the 25869, 25934, 26335, 50365, 21117, 38692, 46508, 16816, 16839, 49937, 49931 or 49933 protein or a nucleic acid, which hybridizes specifically with the gene. These and other embodiments are discussed below.

Diagnostic and Prognostic Assays

The presence, level, or absence of 25869, 25934, 26335, 50365, 21117, 38692, 46508, 16816, 16839, 49937, 49931 or 49933 protein or nucleic acid in a biological sample can be evaluated by obtaining a biological sample from a test subject and contacting the biological sample with a compound or an agent capable of detecting 25869, 25934, 26335, 50365, 21117, 38692, 46508, 16816, 16839, 49937, 49931 or 49933 protein or nucleic acid (e.g., mRNA, genomic DNA) that encodes 25869, 25934, 26335, 50365, 21117, 38692, 46508, 16816, 16839, 49937, 49931 or 49933 protein such that the presence of 25869, 25934, 26335, 50365, 21117, 38692, 46508, 16816, 16839, 49937, 49931 or 49933 protein or nucleic acid is detected in the biological sample. The term "biological sample" includes tissues, cells and biological fluids isolated from a subject, as well as tissues, cells and fluids present within a subject. A preferred biological sample is serum. The level of expression of the 25869, 25934, 26335, 50365, 21117, 38692, 46508, 16816, 16839, 49937, 49931 or 49933 gene can be measured in a number of ways, including, but not limited to: measuring the mRNA encoded by the 25869, 25934, 26335, 50365, 21117, 38692, 46508, 16816, 16839, 49937, 49931 or 49933 genes; measuring the amount of protein encoded by the 25869, 25934, 26335, 50365, 21117, 38692, 46508, 16816, 16839, 49937, 49931 or 49933 genes; or measuring the activity of the protein encoded by the 25869, 25934, 26335, 50365, 21117, 38692, 46508, 16816, 16839, 49937, 49931 or 49933 genes.

The level of mRNA corresponding to the 25869, 25934, 26335, 50365, 21117, 38692, 46508, 16816, 16839, 49937, 49931 or 49933 gene in a cell can be determined both by in situ and by in vitro formats.

The isolated mRNA can be used in hybridization or amplification assays that include, but ate not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 25869, 25934, 26335, 50365, 21117, 38692, 46508, 16816, 16839, 49937, 49931 or 49933 nucleic acid, such as the nucleic acid of SEQ ID NO:1, 7, 16, 20, 25, 28, 35, 39, 42, 63, 67 or 70, or a portion thereof, such as an oligonucleotide of at least 7, 15, 30, 50, 100, 250 or 500 nucleotides in length and sufficient to specifically hybridize under stringent conditions to 25869, 25934, 26335, 50365, 21117, 38692, 46508, 16816, 16839, 49937, 49931 or 49933 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 25869, 25934, 26335, 50365, 21117, 38692, 46508, 16816, 16839, 49937, 49931 or 49933 genes.

The level of mRNA in a sample that is encoded by one of 25869, 25934, 26335, 50365, 21117, 38692, 46508, 16816, 16839, 49937, 49931 or 49933 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 25869, 25934, 26335, 50365, 21117, 38692, 46508, 16816, 16839, 49937, 49931 or 49933 gene being analyzed.

In another embodiment, the methods further contacting a control sample with a compound or agent capable of detecting 25869, 25934, 26335, 50365, 21117, 38692, 46508, 16816, 16839, 49937, 49931 or 49933 mRNA, or genomic DNA, and comparing the presence of 25869, 25934, 26335, 50365, 21117, 38692, 46508, 16816, 16839, 49937, 49931 or 49933 mRNA or genomic DNA in the control sample with the presence of 25869, 25934, 26335, 50365, 21117, 38692, 46508, 16816, 16839, 49937, 49931 or 49933 mRNA or genomic DNA in the test sample.

A variety of methods can be used to determine the level of protein encoded by 25869, 25934, 26335, 50365, 21117, 38692, 46508, 16816, 16839, 49937, 49931 or 49933. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 25869, 25934, 26335, 50365, 21117, 38692, 46508, 16816, 16839, 49937, 49931 or 49933 protein in a biological sample in vitro as well as in vivo. In vitro techniques for detection of 25869, 25934, 26335, 50365, 21117, 38692, 46508, 16816, 16839, 49937, 49931 or 49933 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 25869, 25934, 26335, 50365, 21117, 38692, 46508, 16816, 16839, 49937, 49931 or 49933 protein include introducing into a subject a labeled anti-25869, 25934, 26335, 50365, 21117, 38692, 46508, 16816, 16839, 49937, 49931 or 49933 antibody. For example, the antibody can be labeled with a radioactive marker whose presence and location in a subject can be detected by standard imaging techniques.

In another embodiment, the methods further include contacting the control sample with a compound or agent capable of detecting 25869, 25934, 26335, 50365, 21117, 38692, 46508, 16816, 16839, 49937, 49931 or 49933 protein, and comparing the presence of 25869, 25934, 26335, 50365, 21117, 38692, 46508, 16816, 16839, 49937, 49931 or 49933 protein in the control sample with the presence of 25869, 25934, 26335, 50365, 21117, 38692, 46508, 16816, 16839, 49937, 49931 or 49933 protein in the test sample.

The invention also includes kits for detecting the presence of 25869, 25934, 26335, 50365, 21117, 38692, 46508, 16816, 16839, 49937, 49931 or 49933 in a biological sample. For example, the kit can include a compound or agent capable of detecting 25869, 25934, 26335, 50365, 21117, 38692, 46508, 16816, 16839, 49937, 49931 or 49933 protein or mRNA in a biological sample; and a standard. The compound or agent can be packaged in a suitable container. The kit can further comprise instructions for using the kit to detect 25869, 25934, 26335, 50365, 21117, 38692, 46508, 16816, 16839, 49937, 49931 or 49933 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 25869, 25934, 26335, 50365, 21117, 38692, 46508, 16816, 16839, 49937, 49931 or 49933 expression or activity. As used herein, the term "unwanted" includes an unwanted phenomenon involved in a biological response such as pain or deregulated cell proliferation.

In one embodiment, a disease or disorder associated with aberrant or unwanted 25869, 25934, 26335, 50365, 21117, 38692, 46508, 16816, 16839, 49937, 49931 or 49933 expression or activity is identified. A test sample is obtained from a subject and 25869, 25934, 26335, 50365, 21117, 38692, 46508, 16816, 16839, 49937, 49931 or 49933 protein or nucleic acid (e.g., mRNA or genomic DNA) is evaluated, wherein the level, e.g., the presence or absence, of 25869, 25934, 26335, 50365, 21117, 38692, 46508, 16816, 16839, 49937, 49931 or 49933 protein or nucleic acid is diagnostic for a subject having or at risk of developing a disease or disorder associated with aberrant or unwanted 25869, 25934, 26335, 50365, 21117, 38692, 46508, 16816, 16839, 49937, 49931 or 49933 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 25869, 25934, 26335, 50365, 21117, 38692, 46508, 16816, 16839, 49937, 49931 or 49933 expression or activity. For example, such methods can be used to determine whether a subject can be effectively treated with an agent for a cellular proliferative and/or differentiative disorders, angiogenic disorders, brain disorders, neurological disorders, blood vessel disorders, breast disorders, colon disorders, kidney disorders, lung disorders, ovarian disorders, prostate disorders, hematopoeitic disorders, pancreatic disorders, skeletal muscle disorders, skin disorders, hormonal disorders, immune e.g., inflammatory, disorders, cardiovascular disorders, lipid homeostasis disorders, endothelial cell disorders, liver disorders, disorders of the small intestine, pain disorders, viral diseases, metabolic disorders, bone metabolism disorders or platelet disorders.

The methods of the invention can also be used to detect genetic alterations in a 25869, 25934, 26335, 50365, 21117, 38692, 46508, 16816, 16839, 49937, 49931 or 49933 gene, thereby determining if a subject with the altered gene is at risk for a disorder characterized by misregulation in 25869, 25934, 26335, 50365, 21117, 38692, 46508, 16816, 16839, 49937, 49931 or 49933 protein activity or nucleic acid expression, such as a cellular proliferative and/or differentiative disorders, angiogenic disorders, brain disorders, neurological disorders, blood vessel disorders, breast disorders, colon disorders, kidney disorders, lung disorders, ovarian disorders, prostate disorders, hematopoeitic disorders, pancreatic disorders, skeletal muscle disorders, skin disorders, hormonal disorders, immune e.g., inflammatory, disorders, cardiovascular disorders, lipid homeostasis disorders, endothelial cell disorders, liver disorders, disorders of the small intestine, pain disorders, viral diseases, metabolic disorders, bone metabolism disorders or platelet disorders. In preferred embodiments, the methods include detecting, in a sample from the subject, the presence or absence of a genetic alteration characterized by at least one of an alteration affecting the integrity of a gene encoding a 25869, 25934, 26335, 50365, 21117, 38692, 46508, 16816, 16839, 49937, 49931 or 49933-protein, or the mis-expression of the 25869, 25934, 26335, 50365, 21117, 38692, 46508, 16816, 16839, 49937, 49931 or 49933 gene. For example, such genetic alterations can be detected by ascertaining the existence of at least one of 1) a deletion of one or more nucleotides from a 25869, 25934, 26335, 50365, 21117, 38692, 46508, 16816, 16839, 49937, 49931 or 49933 gene; 2) an addition of one or more nucleotides to a 25869, 25934, 26335, 50365, 21117, 38692, 46508, 16816, 16839, 49937, 49931 or 49933 gene; 3) a substitution of one or more nucleotides of a 25869, 25934, 26335, 50365, 21117, 38692, 46508, 16816, 16839, 49937, 49931 or 49933 gene, 4) a chromosomal rearrangement of a 25869, 25934, 26335, 50365, 21117, 38692, 46508, 16816, 16839, 49937, 49931 or 49933 gene; 5) an alteration in the level of a messenger RNA transcript of a 25869, 25934, 26335, 50365, 21117, 38692, 46508, 16816, 16839, 49937, 49931 or 49933 gene, 6) aberrant modification of a 25869, 25934, 26335, 50365, 21117, 38692, 46508, 16816, 16839, 49937, 49931 or 49933 gene, such as of the methylation pattern of the genomic DNA, 7) the presence of a non-wild type splicing pattern of a messenger RNA transcript of a 25869, 25934, 26335, 50365, 21117, 38692, 46508, 16816, 16839, 49937, 49931 or 49933 gene, 8) a non-wild type level of a 25869, 25934, 26335, 50365, 21117, 38692, 46508, 16816, 16839, 49937, 49931 or 49933-protein, 9) allelic loss of a 25869, 25934, 26335, 50365, 21117, 38692, 46508, 16816, 16839, 49937, 49931 or 49933 gene, and 10) inappropriate post-translational modification of a 25869, 25934, 26335, 50365, 21117, 38692, 46508, 16816, 16839, 49937, 49931 or 49933-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 25869, 25934, 26335, 50365, 21117, 38692, 46508, 16816, 16839, 49937, 49931 or 49933-gene. This method can include the steps of collecting a sample of cells from a subject, isolating nucleic acid (e.g., genomic, mRNA or both) from the sample, contacting the nucleic acid sample with one or more primers which specifically hybridize to a 25869, 25934, 26335, 50365, 21117, 38692, 46508, 16816, 16839, 49937, 49931 or 49933 gene under conditions such that hybridization and amplification of the 25869, 25934, 26335, 50365, 21117, 38692, 46508, 16816, 16839, 49937, 49931 or 49933 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 25869, 25934, 26335, 50365, 21117, 38692, 46508, 16816, 16839, 49937, 49931 or 49933 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498, 531) can be used to score for the presence of specific mutations by development or loss of a ribozyme cleavage site.

In other embodiments, genetic mutations in 25869, 25934, 26335, 50365, 21117, 38692, 46508, 16816, 16839, 49937, 49931 or 49933 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Human Mutation* 7: 244-255; Kozal et al. (1996) *Nature Medicine* 2: 753-759). For example, genetic mutations in 25869, 25934, 26335, 50365, 21117, 38692, 46508, 16816, 16839, 49937, 49931 or 49933 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 25869, 25934, 26335, 50365, 21117, 38692, 46508, 16816, 16839, 49937, 49931 or 49933 gene and detect mutations by comparing the sequence of the sample 25869, 25934, 26335, 50365, 21117, 38692, 46508, 16816, 16839, 49937, 49931 or 49933 with the corresponding wild-type (control) sequence. Automated sequencing procedures can be utilized when performing the diagnostic assays (Naeve et al. (1995) *Biotechniques* 19:448-53), including sequencing by mass spectrometry.

Other methods for detecting mutations in the 25869, 25934, 26335, 50365, 21117, 38692, 46508, 16816, 16839, 49937, 49931 or 49933 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 25869, 25934, 26335, 50365, 21117, 38692, 46508, 16816, 16839, 49937, 49931 or 49933 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 25869, 25934, 26335, 50365, 21117, 38692, 46508, 16816, 16839, 49937, 49931 or 49933 genes. For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 25869, 25934, 26335, 50365, 21117, 38692, 46508, 16816, 16839, 49937, 49931 or 49933 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification can also be performed using Taq ligase for amplification (Barany (1991) *Proc. Natl. Acad. Sci USA* 88:189-93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 25869, 25934, 26335, 50365, 21117, 38692, 46508, 16816, 16839, 49937, 49931 or 49933 gene.

Use of 25869, 25934, 26335, 50365, 21117, 38692, 46508, 16816, 16839, 49937, 49931 or 49933 Molecules as Surrogate Markers The 25869, 25934, 26335, 50365, 21117, 38692, 46508, 16816, 16839, 49937, 49931 or 49933 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 25869, 25934, 26335, 50365, 21117, 38692, 46508, 16816, 16839, 49937, 49931 or 49933 molecules of the invention can be detected, and can be correlated with one or more biological states in vivo. For example, the 25869, 25934, 26335, 50365, 21117, 38692, 46508, 16816, 16839, 49937, 49931 or 49933 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 25869, 25934, 26335, 50365, 21117, 38692, 46508, 16816, 16839, 49937, 49931 or 49933 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 25869, 25934, 26335, 50365, 21117, 38692, 46508, 16816, 16839, 49937, 49931 or 49933 marker) transcription or expression, the amplified marker can be in a quantity which is more readily detectable than the drug itself. Also, the marker can be more easily detected due to the nature of the marker itself; for example, using the methods described herein, anti-25869, 25934, 26335, 50365, 21117, 38692, 46508, 16816, 16839, 49937, 49931 or 49933 antibodies can be employed in an immune-based detection system for a 25869, 25934, 26335, 50365, 21117, 38692, 46508, 16816, 16839, 49937, 49931 or 49933 protein marker, or 25869, 25934, 26335, 50365, 21117, 38692, 46508, 16816, 16839, 49937, 49931 or 49933-specific radiolabeled probes can be used to detect a 25869, 25934, 26335, 50365, 21117, 38692, 46508, 16816, 16839, 49937, 49931 or 49933 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

The 25869, 25934, 26335, 50365, 21117, 38692, 46508, 16816, 16839, 49937, 49931 or 49933 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 25869, 25934, 26335, 50365, 21117, 38692, 46508, 16816, 16839, 49937, 49931 or 49933 protein or RNA) for specific tumor markers in a subject, a drug or course of treatment can be selected that is optimized for the treatment of the specific tumor likely to be present in the subject. Similarly, the presence or absence of a specific sequence mutation in 25869, 25934, 26335, 50365, 21117, 38692, 46508, 16816, 16839, 49937, 49931 or 49933 DNA can correlate with a 25869, 25934, 26335, 50365, 21117, 38692, 46508, 16816, 16839, 49937, 49931 or 49933 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-25869, 25934, 26335, 50365, 21117, 38692, 46508, 16816, 16839, 49937, 49931 or 49933 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be fused to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody, unconjugated or conjugated as described herein, can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 25869, 25934, 26335, 50365, 21117, 38692, 46508, 16816, 16839, 49937, 49931 or 49933 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 25869, 25934, 26335, 50365, 21117, 38692, 46508, 16816, 16839, 49937, 49931 or 49933 molecules of the present invention or 25869, 25934, 26335, 50365, 21117, 38692, 46508, 16816, 16839, 49937, 49931 or 49933 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 25869, 25934, 26335, 50365, 21117, 38692, 46508, 16816, 16839, 49937, 49931 or 49933 expression or activity, by administering to the subject a 25869, 25934, 26335, 50365, 21117, 38692, 46508, 16816, 16839, 49937, 49931 or 49933 or an agent which modulates 25869, 25934, 26335, 50365, 21117, 38692, 46508, 16816, 16839, 49937, 49931 or 49933 expression or at least one 25869, 25934, 26335, 50365, 21117, 38692, 46508, 16816, 16839, 49937, 49931 or 49933 activity. Subjects at risk for a disease which is caused or contributed to by aberrant or unwanted 25869, 25934, 26335, 50365, 21117, 38692, 46508, 16816, 16839, 49937, 49931 or 49933 expression or activity can be identified by, for example, any or a combination of diagnostic or prognostic assays as described herein. Administration of a prophylactic agent can occur prior to the manifestation of symptoms characteristic of the 25869, 25934, 26335, 50365, 21117, 38692, 46508, 16816, 16839, 49937, 49931 or 49933 aberrance, such that a disease or disorder is prevented or, alternatively, delayed in its progression. Depending on the type of 25869, 25934, 26335, 50365, 21117, 38692, 46508, 16816, 16839, 49937, 49931 or 49933 aberrance, for example, a 25869, 25934, 26335, 50365, 21117, 38692, 46508, 16816, 16839, 49937, 49931 or 49933, 25869, 25934, 26335, 50365, 21117, 38692, 46508, 16816, 16839, 49937, 49931 or 49933 agonist or 25869, 25934, 26335, 50365, 21117, 38692, 46508, 16816, 16839, 49937, 49931 or 49933 antagonist agent can be used for treating the subject. The appropriate agent can be determined based on screening assays described herein.

It is possible that some 25869, 25934, 26335, 50365, 21117, 38692, 46508, 16816, 16839, 49937, 49931 or 49933 disorders can be caused, at least in part, by an abnormal level of gene product, or by the presence of a gene product exhibiting abnormal activity. As such, the reduction in the level and/or activity of such gene products would bring about the amelioration of disorder symptoms.

The 25869, 25934, 26335, 50365, 21117, 38692, 46508, 16816, 16839, 49937, 49931 or 49933 molecules can act as novel diagnostic targets and therapeutic agents for controlling one or more of a cellular proliferative and/or differentiative disorder, angiogenic disorder, brain disorder, neurological disorder, blood vessel disorder, breast disorder, colon disorder, kidney disorder, lung disorder, ovarian disorder, prostate disorder, hematopoeitic disorder, pancreatic disorder, skeletal muscle disorder, skin disorder, hormonal disorder, immune e.g., inflammatory, disorder, cardiovascular disorder, lipid homeostasis disorder, endothelial cell disorder, liver disorder, disorder of the small intestine, pain disorder, viral disease, metabolic disorder bone metabolism disorders or platelet disorders, all of which are described above.

As discussed, successful treatment of 25869, 25934, 26335, 50365, 21117, 38692, 46508, 16816, 16839, 49937, 49931 or 49933 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 25869, 25934, 26335, 50365, 21117, 38692, 46508, 16816, 16839, 49937, 49931 or 49933 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 25869, 25934, 26335, 50365, 21117, 38692, 46508, 16816, 16839, 49937, 49931 or 49933 expression is through the use of aptamer molecules specific for 25869, 25934, 26335, 50365, 21117, 38692, 46508, 16816, 16839, 49937, 49931 or 49933 protein. Aptamers are nucleic acid molecules having a tertiary structure which permits them to specifically or selectively bind to protein ligands (see, e.g., Osborne et al. (1997) Curr. Opin. Chem Biol. 1: 5-9; and Patel (1997) Curr Opin Chem Biol 1:32-46). Since nucleic acid molecules can in many cases be more conveniently introduced into target cells than therapeutic protein molecules can be, aptamers offer a method by which 25869, 25934, 26335, 50365, 21117, 38692, 46508, 16816, 16839, 49937, 49931 or 49933 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 25869, 25934, 26335, 50365, 21117, 38692, 46508, 16816, 16839, 49937, 49931 or 49933 disorders. For a description of antibodies, see the Antibody section above.

In circumstances wherein injection of an animal or a human subject with a 25869, 25934, 26335, 50365, 21117, 38692, 46508, 16816, 16839, 49937, 49931 or 49933 protein or epitope for stimulating antibody production is harmful to the subject, it is possible to generate an immune response against 25869, 25934, 26335, 50365, 21117, 38692, 46508, 16816, 16839, 49937, 49931 or 49933 through the use of anti-idiotypic antibodies (see, for example, Herlyn (1999) Ann Med 31:66-78; and Bhattacharya-Chatterjee and Foon (1998) Cancer Treat Res. 94:51-68). If an anti-idiotypic antibody is introduced into a mammal or human subject, it should stimulate the production of anti-anti-idiotypic antibodies, which should be specific to the 25869, 25934, 26335, 50365, 21117, 38692, 46508, 16816, 16839, 49937, 49931 or 49933 protein.

Vaccines directed to a disease characterized by 25869, 25934, 26335, 50365, 21117, 38692, 46508, 16816, 16839, 49937, 49931 or 49933 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 25869, 25934, 26335, 50365, 21117, 38692, 46508, 16816, 16839, 49937, 49931 or 49933 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 25869, 25934, 26335, 50365, 21117, 38692, 46508, 16816, 16839, 49937, 49931 or 49933 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89-94 and in Shea (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645-647. Through the use of isotope-labeling, the "free" concentration of compound which modulates the expression or activity of 25869, 25934, 26335, 50365, 21117, 38692, 46508, 16816, 16839, 49937, 49931 or 49933 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al (1995) *Analytical Chemistry* 67:2142-2144.

Another aspect of the invention pertains to methods of modulating 25869, 25934, 26335, 50365, 21117, 38692, 46508, 16816, 16839, 49937, 49931 or 49933 expression or activity for therapeutic purposes. Accordingly, in an exemplary embodiment, the modulatory method of the invention involves contacting a cell with a 25869, 25934, 26335, 50365, 21117, 38692, 46508, 16816, 16839, 49937, 49931 or 49933 or agent that modulates one or more of the activities of 25869, 25934, 26335, 50365, 21117, 38692, 46508, 16816, 16839, 49937, 49931 or 49933 protein activity associated with the cell. An agent that modulates 25869, 25934, 26335, 50365, 21117, 38692, 46508, 16816, 16839, 49937, 49931 or 49933 protein activity can be an agent as described herein, such as a nucleic acid or a protein, a naturally-occurring target molecule of a 25869, 25934, 26335, 50365, 21117, 38692, 46508, 16816, 16839, 49937, 49931 or 49933 protein (e.g., a 25869, 25934, 26335, 50365, 21117, 38692, 46508, 16816, 16839, 49937, 49931 or 49933 substrate or receptor), a 25869, 25934, 26335, 50365, 21117, 38692, 46508, 16816, 16839, 49937, 49931 or 49933 antibody, a 25869, 25934, 26335, 50365, 21117, 38692, 46508, 16816, 16839, 49937, 49931 or 49933 agonist or antagonist, a peptidomimetic of a 25869, 25934, 26335, 50365, 21117, 38692, 46508, 16816, 16839, 49937, 49931 or 49933 agonist or antagonist, or other small molecule.

In one embodiment, the agent stimulates one or 25869, 25934, 26335, 50365, 21117, 38692, 46508, 16816, 16839, 49937, 49931 or 49933 activities. Examples of such stimulatory agents include active 25869, 25934, 26335, 50365, 21117, 38692, 46508, 16816, 16839, 49937, 49931 or 49933 protein and a nucleic acid molecule encoding 25869, 25934, 26335, 50365, 21117, 38692, 46508, 16816, 16839, 49937, 49931 or 49933. In another embodiment, the agent inhibits one or more 25869, 25934, 26335, 50365, 21117, 38692, 46508, 16816, 16839, 49937, 49931 or 49933 activities. Examples of such inhibitory agents include antisense 25869, 25934, 26335, 50365, 21117, 38692, 46508, 16816, 16839, 49937, 49931 or 49933 nucleic acid molecules, anti-25869, 25934, 26335, 50365, 21117, 38692, 46508, 16816, 16839, 49937, 49931 or 49933 antibodies, and 25869, 25934, 26335, 50365, 21117, 38692, 46508, 16816, 16839, 49937, 49931 or 49933 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 25869, 25934, 26335, 50365, 21117, 38692, 46508, 16816, 16839, 49937, 49931 or 49933 protein or nucleic acid molecule. In one embodiment, the method involves administering an agent (e.g., an agent identified by a screening assay described herein), or combination of agents that modulates (e.g., up regulates or down regulates) 25869, 25934, 26335, 50365, 21117, 38692, 46508, 16816, 16839, 49937, 49931 or 49933 expression or activity. In another embodiment, the method involves administering a 25869, 25934, 26335, 50365, 21117, 38692, 46508, 16816, 16839, 49937, 49931 or 49933 protein or nucleic acid molecule as therapy to compensate for reduced, aberrant, or unwanted 25869, 25934, 26335, 50365, 21117, 38692, 46508, 16816, 16839, 49937, 49931 or 49933 expression or activity.

Stimulation of 25869, 25934, 26335, 50365, 21117, 38692, 46508, 16816, 16839, 49937, 49931 or 49933 activity is desirable in situations in which 25869, 25934, 26335, 50365, 21117, 38692, 46508, 16816, 16839, 49937, 49931 or 49933 is abnormally downregulated and/or in which increased 25869, 25934, 26335, 50365, 21117, 38692, 46508, 16816, 16839, 49937, 49931 or 49933 activity is likely to have a beneficial effect. For example, stimulation of 25869, 25934, 26335, 50365, 21117, 38692, 46508, 16816, 16839, 49937, 49931 or 49933 activity is desirable in situations in which a 25869, 25934, 26335, 50365, 21117, 38692, 46508, 16816, 16839, 49937, 49931 or 49933 is downregulated and/or in which increased 25869, 25934, 26335, 50365, 21117, 38692, 46508, 16816, 16839, 49937, 49931 or 49933 activity is likely to have a beneficial effect. Likewise, inhibition of 25869, 25934, 26335, 50365, 21117, 38692, 46508, 16816, 16839, 49937, 49931 or 49933 activity is desirable in situations in which 25869, 25934, 26335, 50365, 21117, 38692, 46508, 16816, 16839, 49937, 49931 or 49933 is abnormally upregulated and/or in which decreased 25869, 25934, 26335, 50365, 21117, 38692, 46508, 16816, 16839, 49937, 49931 or 49933 activity is likely to have a beneficial effect.

Pharmacogenomics

The 25869, 25934, 26335, 50365, 21117, 38692, 46508, 16816, 16839, 49937, 49931 or 49933 molecules of the present invention, as well as agents, or modulators which have a stimulatory or inhibitory effect on 25869, 25934, 26335, 50365, 21117, 38692, 46508, 16816, 16839, 49937, 49931 or 49933 activity (e.g., 25869, 25934, 26335, 50365, 21117, 38692, 46508, 16816, 16839, 49937, 49931 or 49933 gene expression) as identified by a screening assay described herein can be administered to individuals to treat (prophylactically or therapeutically) 25869, 25934, 26335, 50365, 21117, 38692, 46508, 16816, 16839, 49937, 49931 or 49933-associated disorders (e.g., aberrant or deficient carboxylase actvity, fatty acid desaturase activity, serine/threonine dehydratase activity, hexokinase activity, peptidyl tRNA hydrolase actvity, dual specificity phosphatase activity, phospholipase activity, transporter actvity, or other activity disclosed herein) associated with aberrant or unwanted 25869, 25934, 26335, 50365, 21117, 38692, 46508, 16816, 16839, 49937, 49931 or 49933 activity.

In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 25869, 25934, 26335, 50365, 21117, 38692, 46508, 16816, 16839, 49937, 49931 or 49933 molecule or 25869, 25934, 26335, 50365, 21117, 38692, 46508, 16816, 16839, 49937, 49931 or 49933 modulator as well as tailoring the dosage and/or therapeutic regimen of treatment with a 25869, 25934, 26335, 50365, 21117, 38692, 46508, 16816, 16839, 49937, 49931 or 49933 molecule or 25869, 25934, 26335, 50365, 21117, 38692, 46508, 16816, 16839, 49937, 49931 or 49933 modulator.

Pharmacogenomics deals with clinically significant hereditary variations in the response to drugs due to altered drug disposition and abnormal action in affected persons. See, for example, Eichelbaum et al. (1996) Clin. Exp. Pharmacol. Physiol. 23:983-985 and Linder et al. (1997) Clin. Chem. 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 25869, 25934, 26335, 50365, 21117, 38692, 46508, 16816, 16839, 49937, 49931 or 49933 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 25869, 25934, 26335, 50365, 21117, 38692, 46508, 16816, 16839, 49937, 49931 or 49933 molecule or 25869, 25934, 26335, 50365, 21117, 38692, 46508, 16816, 16839, 49937, 49931 or 49933 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 25869, 25934, 26335, 50365, 21117, 38692, 46508, 16816, 16839, 49937, 49931 or 49933 molecule or 25869, 25934, 26335, 50365, 21117, 38692, 46508, 16816, 16839, 49937, 49931 or 49933 modulator, such as a modulator identified by one of the exemplary screening assays described herein.

The present invention further provides methods for identifying new agents, or combinations, that are based on identifying agents that modulate the activity of one or more of the gene products encoded by one or more of the 25869, 25934, 26335, 50365, 21117, 38692, 46508, 16816, 16839, 49937, 49931 or 49933 genes of the present invention, wherein these products can be associated with resistance of the cells to a therapeutic agent. Specifically, the activity of the proteins encoded by the 25869, 25934, 26335, 50365, 21117, 38692, 46508, 16816, 16839, 49937, 49931 or 49933 genes of the present invention can be used as a basis for identifying agents for overcoming agent resistance. By blocking the activity of one or more of the resistance proteins, target cells, e.g., human cells, will become sensitive to treatment with an agent to which the unmodified target cells were resistant.

Monitoring the influence of agents (e.g., drugs) on the expression or activity of a 25869, 25934, 26335, 50365, 21117, 38692, 46508, 16816, 16839, 49937, 49931 or 49933 protein can be applied in clinical trials. For example, the effectiveness of an agent determined by a screening assay as described herein to increase 25869, 25934, 26335, 50365, 21117, 38692, 46508, 16816, 16839, 49937, 49931 or 49933 gene expression, protein levels, or upregulate 25869, 25934, 26335, 50365, 21117, 38692, 46508, 16816, 16839, 49937, 49931 or 49933 activity, can be monitored in clinical trials of subjects exhibiting decreased 25869, 25934, 26335, 50365, 21117, 38692, 46508, 16816, 16839, 49937, 49931 or 49933 gene expression, protein levels, or downregulated 25869, 25934, 26335, 50365, 21117, 38692, 46508, 16816, 16839, 49937, 49931 or 49933 activity. Alternatively, the effectiveness of an agent determined by a screening assay to decrease 25869, 25934, 26335, 50365, 21117, 38692, 46508, 16816, 16839, 49937, 49931 or 49933 gene expression, protein levels, or downregulate 25869, 25934, 26335, 50365, 21117, 38692, 46508, 16816, 16839, 49937, 49931 or 49933 activity, can be monitored in clinical trials of subjects exhibiting increased 25869, 25934, 26335, 50365, 21117, 38692, 46508, 16816, 16839, 49937, 49931 or 49933 gene expression, protein levels, or upregulated 25869, 25934, 26335, 50365, 21117, 38692, 46508, 16816, 16839, 49937, 49931 or 49933 activity. In such clinical trials, the expression or activity of a 25869, 25934, 26335, 50365, 21117, 38692, 46508, 16816, 16839, 49937, 49931 or 49933 gene, and preferably, other genes that have been implicated in, for example, a [FAMILYNAME]-associated or another 25869, 25934, 26335, 50365, 21117, 38692, 46508, 16816, 16839, 49937, 49931 or 49933-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 25869, 25934, 26335, 50365, 21117, 38692, 46508, 16816, 16839, 49937, 49931 or 49933 or from a cell or subject in which a 25869, 25934, 26335, 50365, 21117, 38692, 46508, 16816, 16839, 49937, 49931 or 49933 mediated response has been elicited; contacting the array with a 25869, 25934, 26335, 50365, 21117, 38692, 46508, 16816, 16839, 49937, 49931 or 49933 nucleic acid (preferably purified), a 25869, 25934, 26335, 50365, 21117, 38692, 46508, 16816, 16839, 49937, 49931 or 49933 polypeptide (preferably purified), or an anti-25869, 25934, 26335, 50365, 21117, 38692, 46508, 16816, 16839, 49937, 49931 or 49933 antibody, and thereby evaluating the plurality of capture probes. Binding, e.g., in the case of a nucleic acid, hybridization with a capture probe at an address of the plurality, is detected, e.g., by a signal generated from a label attached to the 25869, 25934, 26335, 50365, 21117, 38692, 46508, 16816, 16839, 49937, 49931 or 49933 nucleic acid, polypeptide, or antibody.

The capture probes can be a set of nucleic acids from a selected sample, e.g., a sample of nucleic acids derived from a control or non-stimulated tissue or cell.

The method can include contacting the 25869, 25934, 26335, 50365, 21117, 38692, 46508, 16816, 16839, 49937, 49931 or 49933 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 25869, 25934, 26335, 50365, 21117, 38692, 46508, 16816, 16839, 49937, 49931 or 49933. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 25869, 25934, 26335, 50365, 21117, 38692, 46508, 16816, 16839, 49937, 49931 or 49933, e.g., analyzing structure, function, or relatedness to other nucleic acid or amino acid sequences. The method includes: providing a 25869, 25934, 26335, 50365, 21117, 38692, 46508, 16816, 16839, 49937, 49931 or 49933 nucleic acid or amino acid sequence; comparing the 25869, 25934, 26335, 50365, 21117, 38692, 46508, 16816, 16839, 49937, 49931 or 49933 sequence with one or more preferably a plurality of sequences from a collection of sequences, e.g., a nucleic acid or protein sequence database; to thereby analyze 25869, 25934, 26335, 50365, 21117, 38692, 46508, 16816, 16839, 49937, 49931 or 49933.

The method can include evaluating the sequence identity between a 25869, 25934, 26335, 50365, 21117, 38692, 46508, 16816, 16839, 49937, 49931 or 49933 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 25869, 25934, 26335, 50365, 21117, 38692, 46508, 16816, 16839, 49937, 49931 or 49933. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 25869, 25934, 26335, 50365, 21117, 38692, 46508, 16816, 16839, 49937, 49931 or 49933 molecules are provided in a variety of mediums to facilitate use thereof. A sequence can be provided as a manufacture, other than an isolated nucleic acid or amino acid molecule, which contains a 25869, 25934, 26335, 50365, 21117, 38692, 46508, 16816, 16839, 49937, 49931 or 49933 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 25869, 25934, 26335, 50365, 21117, 38692, 46508, 16816, 16839, 49937, 49931 or 49933 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 25869, 25934, 26335, 50365, 21117, 38692, 46508, 16816, 16839, 49937, 49931 or 49933 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 25869, 25934, 26335, 50365, 21117, 38692, 46508, 16816, 16839, 49937, 49931 or 49933 sequence information.

A variety of data storage structures are available to a skilled artisan for creating a computer readable medium having recorded thereon a 25869, 25934, 26335, 50365, 21117, 38692, 46508, 16816, 16839, 49937, 49931 or 49933 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 25869, 25934, 26335, 50365, 21117, 38692, 46508, 16816, 16839, 49937, 49931 or 49933 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, wherein the method comprises the steps of determining 25869, 25934, 26335, 50365, 21117, 38692, 46508, 16816, 16839, 49937, 49931 or 49933 sequence information associated with the subject and based on the 25869, 25934, 26335, 50365, 21117, 38692, 46508, 16816, 16839, 49937, 49931 or 49933 sequence information, determining whether the subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder and/or recommending a particular treatment for the disease, disorder, or pre-disease condition.

The present invention further provides in an electronic system and/or in a network, a method for determining whether a subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a disease associated with 25869, 25934, 26335, 50365, 21117, 38692, 46508, 16816, 16839, 49937, 49931 or 49933, wherein the method comprises the steps of determining 25869, 25934, 26335, 50365, 21117, 38692, 46508, 16816, 16839, 49937, 49931 or 49933 sequence information associated with the subject, and based on the 25869, 25934, 26335, 50365, 21117, 38692, 46508, 16816, 16839, 49937, 49931 or 49933 sequence information, determining whether the subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a protein kinase, methyltransferase, acyl-CoA dehydrogenase, short chain dehydogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a protein kinase, methyltransferase, acyl-CoA dehydrogenase, short chain dehydrogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, said method comprising the steps of receiving 25869, 25934, 26335, 50365, 21117, 38692, 46508, 16816, 16839, 49937, 49931 or 49933 sequence information from the subject and/or information related thereto, receiving phenotypic information associated with the subject, acquiring information from the network corresponding to 25869, 25934, 26335, 50365, 21117, 38692, 46508, 16816, 16839, 49937, 49931 or 49933 and/or corresponding to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, and based on one or more of the phenotypic information, the 25869, 25934, 26335, 50365, 21117, 38692, 46508, 16816, 16839, 49937, 49931 or 49933 information (e.g., sequence information and/or information related thereto), and the acquired information, determining whether the subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder. The method may further comprise the step of recommending a particular treatment for the disease, disorder, or pre-disease condition.

The present invention also provides a business method for determining whether a subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, said method comprising the steps of receiving information related to 25869, 25934, 26335, 50365, 21117, 38692, 46508, 16816, 16839, 49937, 49931 or 49933 (e.g., sequence information and/or information related thereto), receiving phenotypic information associated with the subject, acquiring information from the network related to 25869, 25934, 26335, 50365, 21117, 38692, 46508, 16816, 16839, 49937, 49931 or 49933 and/or related to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, and based on one or more of the phenotypic information, the 25869, 25934, 26335, 50365, 21117, 38692, 46508, 16816, 16839, 49937, 49931 or 49933 information, and the acquired information, determining whether the subject has a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder or a pre-disposition to a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder. The method may further comprise the step of recommending a particular treatment for the disease, disorder, or pre-disease condition.

The invention also includes an array comprising a 25869, 25934, 26335, 50365, 21117, 38692, 46508, 16816, 16839, 49937, 49931 or 49933 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 25869, 25934, 26335, 50365, 21117, 38692, 46508, 16816, 16839, 49937, 49931 or 49933. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, progression of protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder, and processes, such a cellular transformation associated with the protein kinase, methyltransferase, acyl-CoA dehydrogenase, short chain dehyrdogenase, reductase, acyltransferase, phosphatase, transferase, ATP-ase or synthase-associated or another 25869, 25934, 26335, 50365, 21117, 38692, 46508, 16816, 16839, 49937, 49931 or 49933-associated disease or disorder.

The array is also useful for ascertaining the effect of the expression of a gene on the expression of other genes in the same cell or in different cells (e.g., acertaining the effect of 25869, 25934, 26335, 50365, 21117, 38692, 46508, 16816, 16839, 49937, 49931 or 49933 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 25869, 25934, 26335, 50365, 21117, 38692, 46508, 16816, 16839, 49937, 49931 or 49933) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 25869, 25934, 26335, 50365, 21117, 38692, 46508, 16816, 16839, 49937, 49931 or 49933 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 25869, 25934, 26335, 50365, 21117, 38692, 46508, 16816, 16839, 49937, 49931 or 49933 sequence, or record, in computer readable form; comparing a second sequence to the 25869, 25934, 26335, 50365, 21117, 38692, 46508, 16816, 16839, 49937, 49931 or 49933 sequence; thereby analyzing a sequence. Comparison can include comparing to sequences for sequence identity or determining if one sequence is included within the other, e.g., determining if the 25869, 25934, 26335, 50365, 21117, 38692, 46508, 16816, 16839, 49937, 49931 or 49933 sequence includes a sequence being compared. In a preferred embodiment the 25869, 25934, 26335, 50365, 21117, 38692, 46508, 16816, 16839, 49937, 49931 or 49933 or second sequence is stored on a first computer, e.g., at a first site and the comparison is performed, read, or recorded on a second computer, e.g., at a second site. E.g., the 25869, 25934, 26335, 50365, 21117, 38692, 46508, 16816, 16839, 49937, 49931 or 49933 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

EXEMPLIFICATION

Example 1

Tissue Distribution of 25869, 25934, 26335, 50365, 21117, 38692, 46508, 16816, 16839, 49937, 49931 or 49933 mRNA Northern blot hybridizations with various RNA samples can be performed under standard conditions and washed under stringent conditions, i.e., 0.2×SSC at 65° C. A DNA probe corresponding to all or a portion of the 25869, 25934, 26335, 50365, 21117, 38692, 46508, 16816, 16839, 49937, 49931 or 49933 cDNA (SEQ ID NO:1, 3, 7, 9, 16, 18, 20, 22, 25, 27, 28, 30, 35, 37, 39, 41, 42, 44, 63, 65, 67, 69, 70 or 72) or 25869, 25934, 26335, 50365, 21117, 38692, 46508, 16816, 16839, 49937, 49931 or 49933 cDNA can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 2

TaqMan™ Procedure

The Taqman™ procedure is a quantitative, real-time PCR-based approach to detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest and served as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe included an oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separated the reporter dye and the quencher dye, resulting in increased fluorescence of the reporter. Accumulation of PCR products was detected directly by monitoring the increase in fluorescence of the reporter dye. When the probe was intact, the proximity of the reporter dye to the quencher dye resulted in suppression of the reporter fluorescence. During PCR, if the target of interest was present, the probe specifically annealed between the forward and reverse primer sites. The 5'-3' nucleolytic activity of the AmpliTaq™ Gold DNA Polymerase cleaved the probe between the reporter and the quencher only if the probe hybridized to the target. The probe fragments were then displaced from the target, and polymerization of the strand continued. The 3' end of the probe was blocked to prevent extension of the probe during PCR. This process occurred in every cycle and did not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control GAPDH or β-actin gene confirming efficient removal of genomic DNA contamination.

Example 3

In Situ Hybridization Procedure

For in situ analysis, various tissues, e.g. tissues obtained from brain, are first frozen on dry ice. Ten-micrometer-thick sections of the tissues are postfixed with 4% formaldehyde in DEPC treated 1×phosphate-buffered saline at room temperature for 10 minutes before being rinsed twice in DEPC 1×phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 ug of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Example 4

Recombinant Expression of 25869, 25934, 26335, 50365, 21117, 38692, 46508, 16816, 16839, 49937, 49931 or 49933 in Bacterial Cells In this example, 25869, 25934, 26335, 50365, 21117, 38692, 46508, 16816, 16839, 49937, 49931 or 49933 is expressed as a recombinant glutathione-S-transferase (GST) fusion polypeptide in E. coli and the fusion polypeptide is isolated and characterized. Specifically, 25869, 25934, 26335, 50365, 21117, 38692, 46508, 16816, 16839, 49937, 49931 or 49933 is fused to GST and this fusion polypeptide is expressed in E. coli, e.g., strain PEB199. Expression of the GST-25869, -25934, -26335, -50365, -21117, -38692, -46508, -16816, -16839, -49937, -49931 or -49933 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 25869, 25934, 26335, 50365, 21117, 38692, 46508, 16816, 16839, 49937, 49931 or 49933 Protein in COS Cells To express the 25869, 25934, 26335, 50365, 21117, 38692, 46508, 16816, 16839, 49937, 49931 or 49933 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 25869, 25934, 26335, 50365, 21117, 38692, 46508, 16816, 16839, 49937, 49931 or 49933 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 25869, 25934, 26335, 50365, 21117, 38692, 46508, 16816, 16839, 49937, 49931 or 49933 DNA sequence is amplified by PCR using two primers. The 5' primer contains the restriction site of interest followed by approximately twenty nucleotides of the 25869, 25934, 26335, 50365, 21117, 38692, 46508, 16816, 16839, 49937, 49931 or 49933 coding sequence starting from the initiation codon; the 3' end sequence contains complementary sequences to the other restriction site of interest, a translation stop codon, the HA tag or FLAG tag and the last 20 nucleotides of the 25869, 25934, 26335, 50365, 21117, 38692, 46508, 16816, 16839, 49937, 49931 or 49933 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 25869, 25934, 26335, 50365, 21117, 38692, 46508, 16816, 16839, 49937, 49931 or 49933 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 25869-, 25934-, 26335-, 50365-, 21117-, 38692-, 46508-, 16816-, 16839-, 49937-, 49931- or 49933-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989. The expression of the 25869, 25934, 26335, 50365, 21117, 38692, 46508, 16816, 16839, 49937, 49931 or 49933 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 25869, 25934, 26335, 50365, 21117, 38692, 46508, 16816, 16839, 49937, 49931 or 49933 coding sequence is cloned directly into the polylinker of the pCDNA/Amp vector using the appropriate restriction sites. The resulting plasmid is transfected into COS cells in the manner described above, and the expression of the 25869, 25934, 26335, 50365, 21117, 38692, 46508, 16816, 16839, 49937, 49931 or 49933 polypeptide is detected by radiolabelling and immunoprecipitation using a 25869, 25934, 26335, 50365, 21117, 38692, 46508, 16816, 16839, 49937, 49931 or 49933 specific monoclonal antibody.

The contents of all references, patents and published patent applications cited throughout this application are incorporated herein by reference.

Equivalents

Those skilled in the art will recognize, or be able to ascertain using no more than routine experimentation, many equivalents to the specific embodiments of the invention described herein.

What is claimed is:

1. An isolated nucleic acid selected from the group consisting of:
   a) a nucleic acid comprising the nucleotide sequence of SEQ ID NO:20 or SEQ ID NO:22;
   b) a nucleic acid which encodes a polypeptide comprising the amino acid sequence of SEQ ID NO:21;
   c) a nucleic acid comprising a nucleotide sequence which is at least 95% identical to the nucleotide sequence of SEQ ID NO:20 or SEQ ID NO:22, wherein the nucleotide sequence encodes a polypeptide which has hexokinase activity; and
   d) a nucleic acid which encodes a polypeptide comprising an amino acid sequence which is at least 95% identical to the amino acid sequence of SEQ ID NO:21, wherein the polypeptide has hexokinase activity.

2. The nucleic acid of claim 1, wherein the nucleic acid encodes a polypeptide comprising an amino acid sequence which is at least 95% identical to the amino acid sequence of SEQ ID NO:21, wherein the polypeptide has hexokinase activity.

3. The nucleic acid of claim 1, wherein the nucleic acid comprises a nucleotide sequence which is at least 95% identical to the nucleotide sequence of SEQ ID NO:20 or SEQ ID NO;22, wherein the nucleotide sequence encodes a polypeptide which has hexokinase activity.

4. The nucleic acid of claim 1, wherein the nucleic acid comprises the nucleotide sequence of SEQ ID NO:20 or SEQ ID NO:22.

5. The nucleic acid of claim 1, wherein the nucleic acid encodes a polypeptide comprising the amino acid sequence of SEQ ID NO:21.

6. The nucleic acid of claim 1, wherein the nucleic acid consists of the nucleotide sequence of SEQ ID NO:20 or SEQ ID NO:22.

7. The nucleic acid of claim 1, wherein the nucleic acid consists of a nucleotide sequence which encodes the amino acid sequence of SEQ ID NO:21.

8. A vector comprising the nucleic acid of claim 1.

9. A vector comprising the nucleic acid of claim 2.

10. A vector comprising the nucleic acid of claim 3.

11. An isolated host cell comprising the nucleic acid of claim 1.

12. An isolated host cell comprising the nucleic acid of claim 2.

13. An isolated host cell comprising the nucleic acid of claim 3.

14. A method for producing a polypeptide selected from the group consisting of:
   a) a polypeptide comprising the amino acid sequence of SEQ ID NO:21;
   b) a polypeptide encoded by a nucleic acid comprising the nucleotide sequence of SEQ ID NO:20 or SEQ ID NO122;
   c) a polypeptide comprising an amino acid sequence which is at least 95% identical to the amino acid sequence of SEQ ID NO:21, wherein the polypeptide has hexokinase activity; and
   d) a polypeptide encoded by a nucleic acid comprising a nucleotide sequence which is at least 95% identical to the nucleotide sequence of SEQ ID NO:20 or SEQ ID NO:22, wherein the polypeptide has hexokinase activity;
   the method comprising culturing the host cell of claim 11 under conditions in which the polypeptide is expressed, whereby the polypeptide is produced.

* * * * *

UNITED STATES PATENT AND TRADEMARK OFFICE
CERTIFICATE OF CORRECTION

PATENT NO. : 7,411,054 B2 Page 1 of 1
APPLICATION NO. : 11/445606
DATED : August 12, 2008
INVENTOR(S) : Rachel E. Meyers and Mark J. Williamson It is certified that error appears in the above-identified patent and that said Letters Patent is hereby corrected as shown below:

Please make the following corrections to the claims:

CLAIMS:

In Claim 14, column 404, lines 27-28, change "SEQ ID NO122;" to --SEQ ID NO:22;--

Signed and Sealed this

Third Day of February, 2009

JOHN DOLL
*Acting Director of the United States Patent and Trademark Office*

SEQUENCE LISTING

<160> NUMBER OF SEQ ID NOS: 114

<210> SEQ ID NO 1
<211> LENGTH: 2087
<212> TYPE: DNA
<213> ORGANISM: Homo Sapiens
<220> FEATURE:
<221> NAME/KEY: CDS
<222> LOCATION: (222)...(1865)

<400> SEQUENCE: 1

```
accacgcgtc cgcagcttgg tcaacagagc tagaccctgt ctcaaacaca aaaaataaaa      60
acaaagaaat gggcaagtgg ctggccccaa ggcacaaggc cctagtggca ggcccggtct     120
ggcctggagt ggagtggtag tgactctcag gcaggcaggg aggaggaagt tgggcgtcaa     180
cctaagacca ggctcaccgg cttgctggga aggttaccaa g atg ctg tgt ggg ccc     236
                                              Met Leu Cys Gly Pro
                                                1               5 gaa gtt gct cag cct gaa gta gac acc acc ctg ggt cgt gtg cga ggc       284
Glu Val Ala Gln Pro Glu Val Asp Thr Thr Leu Gly Arg Val Arg Gly
               10                  15                  20 cgg cag gtg ggc gtg aag ggc aca gac cgc ctt gtg aat gtc ttt ctg       332
Arg Gln Val Gly Val Lys Gly Thr Asp Arg Leu Val Asn Val Phe Leu
           25                  30                  35 ggc att cca ttt gcc cag ccg cca ctg ggc cct gac cgg ttc tca gcc       380
Gly Ile Pro Phe Ala Gln Pro Pro Leu Gly Pro Asp Arg Phe Ser Ala
       40                  45                  50 cca cac cca gca cag ccc tgg gag ggt gtg cgg gat gcc agc act gcg       428
Pro His Pro Ala Gln Pro Trp Glu Gly Val Arg Asp Ala Ser Thr Ala
   55                  60                  65 ccc cca atg tgc cta caa gac gtg gag agc atg aac agc aga ttt         476
Pro Pro Met Cys Leu Gln Asp Val Glu Ser Met Asn Ser Ser Arg Phe
70                  75                  80                  85 gtc ctc aac gga aaa cag cag atc ttc tcc gtt tca gag gac tgc ctg       524
Val Leu Asn Gly Lys Gln Gln Ile Phe Ser Val Ser Glu Asp Cys Leu
```

-continued

|  |  |  |  | 90 |  |  |  | 95 |  |  |  | 100 |  |  |  |  |
|---|---|---|---|---|---|---|---|---|---|---|---|---|---|---|---|---|
| gtc | ctc | aac | gtc | tat | agc | cca | gct | gag | gtc | ccc | gca | ggg | tcc | ggt | agg | 572 |
| Val | Leu | Asn | Val | Tyr | Ser | Pro | Ala | Glu | Val | Pro | Ala | Gly | Ser | Gly | Arg |  |
|  |  |  |  | 105 |  |  |  | 110 |  |  |  | 115 |  |  |  |  |
| ccg | gtc | atg | gta | tgg | gtc | cat | gga | ggc | gct | ctg | ata | act | ggc | gct | gcc | 620 |
| Pro | Val | Met | Val | Trp | Val | His | Gly | Gly | Ala | Leu | Ile | Thr | Gly | Ala | Ala |  |
|  |  |  | 120 |  |  |  |  | 125 |  |  |  | 130 |  |  |  |  |
| acc | tcc | tac | gat | gga | tca | gct | ctg | gct | gcc | tat | ggg | gat | gtg | gtc | gtg | 668 |
| Thr | Ser | Tyr | Asp | Gly | Ser | Ala | Leu | Ala | Ala | Tyr | Gly | Asp | Val | Val | Val |  |
|  | 135 |  |  |  |  | 140 |  |  |  |  | 145 |  |  |  |  |  |
| gtt | aca | gtc | cag | tac | cgc | ctt | ggg | gtc | ctt | ggc | ttc | ttc | agc | act | gga | 716 |
| Val | Thr | Val | Gln | Tyr | Arg | Leu | Gly | Val | Leu | Gly | Phe | Phe | Ser | Thr | Gly |  |
| 150 |  |  |  |  | 155 |  |  |  |  | 160 |  |  |  |  | 165 |  |
| gat | gag | cat | gca | cct | ggc | aac | cag | ggc | ttc | cta | gat | gtg | gta | gct | gct | 764 |
| Asp | Glu | His | Ala | Pro | Gly | Asn | Gln | Gly | Phe | Leu | Asp | Val | Val | Ala | Ala |  |
|  |  |  |  | 170 |  |  |  | 175 |  |  |  | 180 |  |  |  |  |
| ttg | cgc | tgg | gtg | caa | gaa | aac | atc | gcc | ccc | ttc | ggg | ggt | gac | ctc | aac | 812 |
| Leu | Arg | Trp | Val | Gln | Glu | Asn | Ile | Ala | Pro | Phe | Gly | Gly | Asp | Leu | Asn |  |
|  |  |  | 185 |  |  |  |  | 190 |  |  |  | 195 |  |  |  |  |
| tgt | gtc | act | gtc | ttt | ggt | gga | tct | gcc | ggt | ggg | agc | atc | atc | tct | ggc | 860 |
| Cys | Val | Thr | Val | Phe | Gly | Gly | Ser | Ala | Gly | Gly | Ser | Ile | Ile | Ser | Gly |  |
|  |  | 200 |  |  |  |  | 205 |  |  |  |  | 210 |  |  |  |  |
| ctg | gtc | ctg | tcc | cca | gtg | gct | gca | ggg | ctg | ttc | cac | aga | gcc | atc | aca | 908 |
| Leu | Val | Leu | Ser | Pro | Val | Ala | Ala | Gly | Leu | Phe | His | Arg | Ala | Ile | Thr |  |
|  | 215 |  |  |  |  | 220 |  |  |  |  | 225 |  |  |  |  |  |
| cag | agt | ggg | gtc | atc | acc | acc | cca | ggg | atc | atc | gac | tct | cac | cct | tgg | 956 |
| Gln | Ser | Gly | Val | Ile | Thr | Thr | Pro | Gly | Ile | Ile | Asp | Ser | His | Pro | Trp |  |
| 230 |  |  |  |  | 235 |  |  |  |  | 240 |  |  |  |  | 245 |  |
| ccc | cta | gct | cag | aaa | atc | gca | aac | acc | ttg | gcc | tgc | agc | tcc | agc | tcc | 1004 |
| Pro | Leu | Ala | Gln | Lys | Ile | Ala | Asn | Thr | Leu | Ala | Cys | Ser | Ser | Ser | Ser |  |
|  |  |  |  | 250 |  |  |  | 255 |  |  |  | 260 |  |  |  |  |
| ccg | gct | gag | atg | gtg | cag | tgc | ctt | cag | cag | aaa | gaa | gga | gaa | gag | ctg | 1052 |
| Pro | Ala | Glu | Met | Val | Gln | Cys | Leu | Gln | Gln | Lys | Glu | Gly | Glu | Glu | Leu |  |
|  |  |  | 265 |  |  |  |  | 270 |  |  |  | 275 |  |  |  |  |
| gtc | ctt | agc | aag | aag | ctg | aaa | aat | act | atc | tat | cct | ctc | acc | gtt | gat | 1100 |
| Val | Leu | Ser | Lys | Lys | Leu | Lys | Asn | Thr | Ile | Tyr | Pro | Leu | Thr | Val | Asp |  |
|  |  | 280 |  |  |  |  | 285 |  |  |  |  | 290 |  |  |  |  |
| ggc | act | gtc | ttc | ccc | aaa | agc | ccc | aag | gaa | ctc | ctg | aag | gag | aag | ccc | 1148 |
| Gly | Thr | Val | Phe | Pro | Lys | Ser | Pro | Lys | Glu | Leu | Leu | Lys | Glu | Lys | Pro |  |
| 295 |  |  |  |  | 300 |  |  |  |  | 305 |  |  |  |  |  |  |
| ttc | cac | tct | gtg | ccc | ttc | ctc | atg | ggt | gtc | aac | aac | cat | gag | ttc | agc | 1196 |
| Phe | His | Ser | Val | Pro | Phe | Leu | Met | Gly | Val | Asn | Asn | His | Glu | Phe | Ser |  |
| 310 |  |  |  |  | 315 |  |  |  |  | 320 |  |  |  |  | 325 |  |
| tgg | ctc | atc | ccc | agg | ggc | tgg | ggt | ctc | ctg | gat | aca | atg | gag | cag | atg | 1244 |
| Trp | Leu | Ile | Pro | Arg | Gly | Trp | Gly | Leu | Leu | Asp | Thr | Met | Glu | Gln | Met |  |
|  |  |  |  | 330 |  |  |  | 335 |  |  |  | 340 |  |  |  |  |
| agc | cgg | gag | gac | atg | ctg | gcc | atc | tca | aca | ccc | gtc | ttg | acc | agt | ctg | 1292 |
| Ser | Arg | Glu | Asp | Met | Leu | Ala | Ile | Ser | Thr | Pro | Val | Leu | Thr | Ser | Leu |  |
|  |  |  | 345 |  |  |  |  | 350 |  |  |  | 355 |  |  |  |  |
| gat | gtg | ccc | cct | gag | atg | atg | ccc | acc | gtc | ata | gat | gaa | tac | cta | gga | 1340 |
| Asp | Val | Pro | Pro | Glu | Met | Met | Pro | Thr | Val | Ile | Asp | Glu | Tyr | Leu | Gly |  |
|  |  | 360 |  |  |  |  | 365 |  |  |  |  | 370 |  |  |  |  |
| agc | aac | tcg | gac | gca | caa | gcc | aaa | tgc | cag | gcg | ttc | cag | gaa | ttc | atg | 1388 |
| Ser | Asn | Ser | Asp | Ala | Gln | Ala | Lys | Cys | Gln | Ala | Phe | Gln | Glu | Phe | Met |  |
|  | 375 |  |  |  |  | 380 |  |  |  |  | 385 |  |  |  |  |  |
| ggt | gac | gta | ttc | atc | aat | gtt | ccc | acc | gtc | agt | ttt | tca | aga | tac | ctt | 1436 |
| Gly | Asp | Val | Phe | Ile | Asn | Val | Pro | Thr | Val | Ser | Phe | Ser | Arg | Tyr | Leu |
| 390 |  |  |  |  | 395 |  |  |  |  | 400 |  |  |  |  | 405 |  |
| cga | gat | tct | gga | agc | cct | gtc | ttt | ttc | tat | gag | ttc | cag | cat | cga | ccc | 1484 |

```
Arg Asp Ser Gly Ser Pro Val Phe Phe Tyr Glu Phe Gln His Arg Pro
                410                 415                 420 agt tct ttt gcg aag atc aaa cct gcc tgg gtg aag gct gat cat ggg    1532
Ser Ser Phe Ala Lys Ile Lys Pro Ala Trp Val Lys Ala Asp His Gly
            425                 430                 435 gcc gag ggt gct ttt gtg ttc gga ggt ccc ttc ctc atg gac gag agc    1580
Ala Glu Gly Ala Phe Val Phe Gly Gly Pro Phe Leu Met Asp Glu Ser
        440                 445                 450 tcc cgc ctg gcc ttt cca gag gcc aca gag gag gag aag cag cta agc    1628
Ser Arg Leu Ala Phe Pro Glu Ala Thr Glu Glu Glu Lys Gln Leu Ser
    455                 460                 465 ctc acc atg atg gcc cag tgg acc cac ttt gcc cgg aca ggg gac ccc    1676
Leu Thr Met Met Ala Gln Trp Thr His Phe Ala Arg Thr Gly Asp Pro
470                 475                 480                 485 aat agc aag gct ctg cct cct tgg ccc caa ttc aac cag gcg gaa caa    1724
Asn Ser Lys Ala Leu Pro Pro Trp Pro Gln Phe Asn Gln Ala Glu Gln
                490                 495                 500 tat ctg gag atc aac cca gtg cca cgg gcc gga cag aag ttc agg gag    1772
Tyr Leu Glu Ile Asn Pro Val Pro Arg Ala Gly Gln Lys Phe Arg Glu
            505                 510                 515 gcc tgg atg cag ttc tgg tca gag acg ctc ccc agc aag ata caa cag    1820
Ala Trp Met Gln Phe Trp Ser Glu Thr Leu Pro Ser Lys Ile Gln Gln
        520                 525                 530 tgg cac cag aag cag aag aac agg aag gcc cag gag gac ctc tga        1865
Trp His Gln Lys Gln Lys Asn Arg Lys Ala Gln Glu Asp Leu  *
    535                 540                 545 ggccaggcct gaaccttctt ggctggggca aaccactctt caagtggtgg cagagtccca  1925
gcacggcagc ccgcctctcc ccctgctgag actttaatct ccaccagccc ttaaagtgtc  1985
ggccgctctg tgactggagt tatgctcttt tgaaatgtca caaggccgcc tcccacctct  2045
ggggcattgt acaagttctt ccctctcaaa aaaaaaaaaa aa                     2087

<210> SEQ ID NO 2
<211> LENGTH: 547
<212> TYPE: PRT
<213> ORGANISM: Homo Sapiens

<400> SEQUENCE: 2

Met Leu Cys Gly Pro Glu Val Ala Gln Pro Glu Val Asp Thr Thr Leu
1               5                   10                  15

Gly Arg Val Arg Gly Arg Gln Val Gly Val Lys Gly Thr Asp Arg Leu
            20                  25                  30

Val Asn Val Phe Leu Gly Ile Pro Phe Ala Gln Pro Pro Leu Gly Pro
        35                  40                  45

Asp Arg Phe Ser Ala Pro His Pro Ala Gln Pro Trp Glu Gly Val Arg
    50                  55                  60

Asp Ala Ser Thr Ala Pro Pro Met Cys Leu Gln Asp Val Glu Ser Met
65                  70                  75                  80

Asn Ser Ser Arg Phe Val Leu Asn Gly Lys Gln Gln Ile Phe Ser Val
                85                  90                  95

Ser Glu Asp Cys Leu Val Leu Asn Val Tyr Ser Pro Ala Glu Val Pro
            100                 105                 110

Ala Gly Ser Gly Arg Pro Val Met Val Trp Val His Gly Gly Ala Leu
        115                 120                 125

Ile Thr Gly Ala Ala Thr Ser Tyr Asp Gly Ser Ala Leu Ala Ala Tyr
    130                 135                 140

Gly Asp Val Val Val Thr Val Gln Tyr Arg Leu Gly Val Leu Gly
```

```
              145                 150                 155                 160
        Phe Phe Ser Thr Gly Asp Glu His Ala Pro Gly Asn Gln Gly Phe Leu
                        165                 170                 175
        Asp Val Ala Ala Leu Arg Trp Val Gln Glu Asn Ile Ala Pro Phe
                        180                 185                 190
        Gly Gly Asp Leu Asn Cys Val Thr Val Phe Gly Gly Ser Ala Gly Gly
                        195                 200                 205
        Ser Ile Ile Ser Gly Leu Val Leu Ser Pro Val Ala Gly Leu Phe
                210                 215                 220
        His Arg Ala Ile Thr Gln Ser Gly Val Ile Thr Thr Pro Gly Ile Ile
        225                 230                 235                 240
        Asp Ser His Pro Trp Pro Leu Ala Gln Lys Ile Ala Asn Thr Leu Ala
                        245                 250                 255
        Cys Ser Ser Ser Pro Ala Glu Met Val Gln Cys Leu Gln Gln Lys
                        260                 265                 270
        Glu Gly Glu Glu Leu Val Leu Ser Lys Lys Leu Lys Asn Thr Ile Tyr
                        275                 280                 285
        Pro Leu Thr Val Asp Gly Thr Val Phe Pro Lys Ser Pro Lys Glu Leu
                290                 295                 300
        Leu Lys Glu Lys Pro Phe His Ser Val Pro Phe Leu Met Gly Val Asn
        305                 310                 315                 320
        Asn His Glu Phe Ser Trp Leu Ile Pro Arg Gly Trp Gly Leu Leu Asp
                        325                 330                 335
        Thr Met Glu Gln Met Ser Arg Glu Asp Met Leu Ala Ile Ser Thr Pro
                        340                 345                 350
        Val Leu Thr Ser Leu Asp Val Pro Pro Glu Met Met Pro Thr Val Ile
                        355                 360                 365
        Asp Glu Tyr Leu Gly Ser Asn Ser Asp Ala Gln Ala Lys Cys Gln Ala
                        370                 375                 380
        Phe Gln Glu Phe Met Gly Asp Val Phe Ile Asn Val Pro Thr Val Ser
        385                 390                 395                 400
        Phe Ser Arg Tyr Leu Arg Asp Ser Gly Ser Pro Val Phe Phe Tyr Glu
                        405                 410                 415
        Phe Gln His Arg Pro Ser Ser Phe Ala Lys Ile Lys Pro Ala Trp Val
                        420                 425                 430
        Lys Ala Asp His Gly Ala Glu Gly Ala Phe Val Phe Gly Gly Pro Phe
                        435                 440                 445
        Leu Met Asp Glu Ser Ser Arg Leu Ala Phe Pro Glu Ala Thr Glu Glu
                        450                 455                 460
        Glu Lys Gln Leu Ser Leu Thr Met Met Ala Gln Trp Thr His Phe Ala
        465                 470                 475                 480
        Arg Thr Gly Asp Pro Asn Ser Lys Ala Leu Pro Pro Trp Pro Gln Phe
                        485                 490                 495
        Asn Gln Ala Glu Gln Tyr Leu Glu Ile Asn Pro Val Pro Arg Ala Gly
                        500                 505                 510
        Gln Lys Phe Arg Glu Ala Trp Met Gln Phe Trp Ser Glu Thr Leu Pro
                        515                 520                 525
        Ser Lys Ile Gln Gln Trp His Gln Lys Gln Asn Arg Lys Ala Gln
                530                 535                 540
        Glu Asp Leu
        545

<210> SEQ ID NO 3
```

```
<211> LENGTH: 1644
<212> TYPE: DNA
<213> ORGANISM: Homo Sapiens
<220> FEATURE:
<221> NAME/KEY: CDS
<222> LOCATION: (1)...(1644)

<400> SEQUENCE: 3 atg ctg tgt ggg ccc gaa gtt gct cag cct gaa gta gac acc acc ctg        48
Met Leu Cys Gly Pro Glu Val Ala Gln Pro Glu Val Asp Thr Thr Leu
 1               5                  10                  15 ggt cgt gtg cga ggc cgg cag gtg ggc gtg aag ggc aca gac cgc ctt        96
Gly Arg Val Arg Gly Arg Gln Val Gly Val Lys Gly Thr Asp Arg Leu
            20                  25                  30 gtg aat gtc ttt ctg ggc att cca ttt gcc cag ccg cca ctg ggc cct       144
Val Asn Val Phe Leu Gly Ile Pro Phe Ala Gln Pro Pro Leu Gly Pro
        35                  40                  45 gac cgg ttc tca gcc cca cac cca gca cag ccc tgg gag ggt gtg cgg       192
Asp Arg Phe Ser Ala Pro His Pro Ala Gln Pro Trp Glu Gly Val Arg
    50                  55                  60 gat gcc agc act gcg ccc cca atg tgc cta caa gac gtg gag agc atg       240
Asp Ala Ser Thr Ala Pro Pro Met Cys Leu Gln Asp Val Glu Ser Met
65                  70                  75                  80 aac agc agc aga ttt gtc ctc aac gga aaa cag cag atc ttc tcc gtt       288
Asn Ser Ser Arg Phe Val Leu Asn Gly Lys Gln Gln Ile Phe Ser Val
                85                  90                  95 tca gag gac tgc ctg gtc ctc aac gtc tat agc cca gct gag gtc ccc       336
Ser Glu Asp Cys Leu Val Leu Asn Val Tyr Ser Pro Ala Glu Val Pro
            100                 105                 110 gca ggg tcc ggt agg ccg gtc atg gta tgg gtc cat gga ggc gct ctg       384
Ala Gly Ser Gly Arg Pro Val Met Val Trp Val His Gly Gly Ala Leu
        115                 120                 125 ata act ggc gct gcc acc tcc tac gat gga tca gct ctg gct gcc tat       432
Ile Thr Gly Ala Ala Thr Ser Tyr Asp Gly Ser Ala Leu Ala Ala Tyr
    130                 135                 140 ggg gat gtg gtc gtg gtt aca gtc cag tac cgc ctt ggg gtc ctt ggc       480
Gly Asp Val Val Val Val Thr Val Gln Tyr Arg Leu Gly Val Leu Gly
145                 150                 155                 160 ttc ttc agc act gga gat gag cat gca cct ggc aac cag ggc ttc cta       528
Phe Phe Ser Thr Gly Asp Glu His Ala Pro Gly Asn Gln Gly Phe Leu
                165                 170                 175 gat gtg gta gct gct ttg cgc tgg gtg caa gaa aac atc gcc ccc ttc       576
Asp Val Val Ala Ala Leu Arg Trp Val Gln Glu Asn Ile Ala Pro Phe
            180                 185                 190 ggg ggt gac ctc aac tgt gtc act gtc ttt ggt gga tct gcc ggt ggg       624
Gly Gly Asp Leu Asn Cys Val Thr Val Phe Gly Gly Ser Ala Gly Gly
        195                 200                 205 agc atc atc tct ggc ctg gtc ctg tcc cca gtg gct gca ggg ctg ttc       672
Ser Ile Ile Ser Gly Leu Val Leu Ser Pro Val Ala Ala Gly Leu Phe
    210                 215                 220 cac aga gcc atc aca cag agt ggg gtc atc acc acc cca ggg atc atc       720
His Arg Ala Ile Thr Gln Ser Gly Val Ile Thr Thr Pro Gly Ile Ile
225                 230                 235                 240 gac tct cac cct tgg ccc cta gct cag aaa atc gca aac acc ttg gcc       768
Asp Ser His Pro Trp Pro Leu Ala Gln Lys Ile Ala Asn Thr Leu Ala
                245                 250                 255 tgc agc tcc agc tcc ccg gct gag atg gtg cag tgc ctt cag cag aaa       816
Cys Ser Ser Ser Ser Pro Ala Glu Met Val Gln Cys Leu Gln Gln Lys
            260                 265                 270 gaa gga gaa gag ctg gtc ctt agc aag aag ctg aaa aat act atc tat       864
Glu Gly Glu Glu Leu Val Leu Ser Lys Lys Leu Lys Asn Thr Ile Tyr
```

-continued

```
                      275                 280                 285
cct ctc acc gtt gat ggc act gtc ttc ccc aaa agc ccc aag gaa ctc        912
Pro Leu Thr Val Asp Gly Thr Val Phe Pro Lys Ser Pro Lys Glu Leu
    290                 295                 300 ctg aag gag aag ccc ttc cac tct gtg ccc ttc ctc atg ggt gtc aac        960
Leu Lys Glu Lys Pro Phe His Ser Val Pro Phe Leu Met Gly Val Asn
305                 310                 315                 320 aac cat gag ttc agc tgg ctc atc ccc agg ggc tgg ggt ctc ctg gat       1008
Asn His Glu Phe Ser Trp Leu Ile Pro Arg Gly Trp Gly Leu Leu Asp
                325                 330                 335 aca atg gag cag atg agc cgg gag gac atg ctg gcc atc tca aca ccc       1056
Thr Met Glu Gln Met Ser Arg Glu Asp Met Leu Ala Ile Ser Thr Pro
            340                 345                 350 gtc ttg acc agt ctg gat gtg ccc cct gag atg atg ccc acc gtc ata       1104
Val Leu Thr Ser Leu Asp Val Pro Pro Glu Met Met Pro Thr Val Ile
        355                 360                 365 gat gaa tac cta gga agc aac tcg gac gca caa gcc aaa tgc cag gcg       1152
Asp Glu Tyr Leu Gly Ser Asn Ser Asp Ala Gln Ala Lys Cys Gln Ala
    370                 375                 380 ttc cag gaa ttc atg ggt gac gta ttc atc aat gtt ccc acc gtc agt       1200
Phe Gln Glu Phe Met Gly Asp Val Phe Ile Asn Val Pro Thr Val Ser
385                 390                 395                 400 ttt tca aga tac ctt cga gat tct gga agc cct gtc ttt ttc tat gag       1248
Phe Ser Arg Tyr Leu Arg Asp Ser Gly Ser Pro Val Phe Phe Tyr Glu
                405                 410                 415 ttc cag cat cga ccc agt tct ttt gcg aag atc aaa cct gcc tgg gtg       1296
Phe Gln His Arg Pro Ser Ser Phe Ala Lys Ile Lys Pro Ala Trp Val
            420                 425                 430 aag gct gat cat ggg gcc gag ggt gct ttt gtg ttc gga ggt ccc ttc       1344
Lys Ala Asp His Gly Ala Glu Gly Ala Phe Val Phe Gly Gly Pro Phe
        435                 440                 445 ctc atg gac gag agc tcc cgc ctg gcc ttt cca gag gcc aca gag gag       1392
Leu Met Asp Glu Ser Ser Arg Leu Ala Phe Pro Glu Ala Thr Glu Glu
    450                 455                 460 gag aag cag cta agc ctc acc atg atg gcc cag tgg acc cac ttt gcc       1440
Glu Lys Gln Leu Ser Leu Thr Met Met Ala Gln Trp Thr His Phe Ala
465                 470                 475                 480 cgg aca ggg gac ccc aat agc aag gct ctg cct cct tgg ccc caa ttc       1488
Arg Thr Gly Asp Pro Asn Ser Lys Ala Leu Pro Pro Trp Pro Gln Phe
                485                 490                 495 aac cag gcg gaa caa tat ctg gag atc aac cca gtg cca cgg gcc gga       1536
Asn Gln Ala Glu Gln Tyr Leu Glu Ile Asn Pro Val Pro Arg Ala Gly
            500                 505                 510 cag aag ttc agg gag gcc tgg atg cag ttc tgg tca gag acg ctc ccc       1584
Gln Lys Phe Arg Glu Ala Trp Met Gln Phe Trp Ser Glu Thr Leu Pro
        515                 520                 525 agc aag ata caa cag tgg cac cag aag cag aag aac agg aag gcc cag       1632
Ser Lys Ile Gln Gln Trp His Gln Lys Gln Lys Asn Arg Lys Ala Gln
    530                 535                 540 gag gac ctc tga                                                        1644
Glu Asp Leu *
545
```

<210> SEQ ID NO 4
<211> LENGTH: 554
<212> TYPE: PRT
<213> ORGANISM: Mus Musculus

<400> SEQUENCE: 4

Met Ala Cys Leu Leu Leu Ile Phe Pro Thr Thr Val Ile Gly Pro Lys

```
             1               5                  10                 15
           Val Thr Gln Pro Glu Val Asp Thr Pro Leu Gly Arg Val Arg Gly Arg
                        20                  25                 30
           Gln Val Gly Val Lys Asp Thr Asp Arg Met Val Asn Val Phe Leu Gly
                        35                  40                 45
           Ile Pro Phe Ala Gln Ala Pro Leu Gly Pro Leu Arg Phe Ser Ala Pro
                        50                  55                 60
           Leu Pro Pro Gln Pro Trp Glu Gly Val Arg Asp Ala Ser Ile Asn Pro
           65                       70                  75                 80
           Pro Met Cys Leu Gln Asp Val Glu Arg Met Ser Asn Ser Arg Phe Thr
                             85                  90                 95
           Leu Asn Glu Lys Met Lys Ile Phe Pro Ile Ser Glu Asp Cys Leu Thr
                            100                 105                110
           Leu Asn Ile Tyr Ser Pro Thr Glu Ile Thr Ala Gly Asp Lys Arg Pro
                            115                 120                125
           Val Met Val Trp Ile His Gly Gly Ser Leu Arg Val Gly Ser Ser Thr
                            130                 135                140
           Ser His Asp Gly Ser Ala Leu Ala Ala Tyr Gly Asp Val Val Val Val
           145                     150                 155                160
           Thr Val Gln Tyr Arg Leu Gly Ile Phe Gly Phe Leu Ser Thr Gly Asp
                            165                 170                175
           Lys His Met Pro Gly Asn Arg Gly Phe Leu Asp Val Val Ala Ala Leu
                            180                 185                190
           Arg Trp Val Gln Gly Asn Ile Ala Pro Phe Gly Asp Pro Asn Cys
                            195                 200                205
           Val Thr Ile Phe Gly Asn Ser Ala Gly Gly Ile Ile Val Ser Ser Leu
                            210                 215                220
           Leu Leu Ser Pro Met Ser Ala Gly Leu Phe His Arg Ala Ile Ser Gln
           225                     230                 235                240
           Ser Gly Val Val Ile Ser Lys Ile Leu Glu Asp Leu Asn Ala Trp Ser
                            245                 250                255
           Glu Ala Gln Asn Phe Ala Asn Ser Val Ala Cys Gly Ser Ala Ser Pro
                            260                 265                270
           Ala Glu Leu Val Gln Cys Leu Leu Gln Lys Glu Gly Lys Asp Leu Ile
                            275                 280                285
           Thr Lys Lys Asn Val Asn Ile Ser Tyr Thr Val Asn Asp Ser Phe Phe
                            290                 295                300
           Pro Gln Arg Pro Gln Lys Leu Leu Ala Asn Lys Gln Phe Pro Thr Val
           305                     310                 315                320
           Pro Tyr Leu Leu Gly Val Thr Asn His Glu Phe Gly Trp Leu Leu Leu
                            325                 330                335
           Lys Phe Trp Asn Ile Leu Asp Lys Met Glu His Leu Ser Gln Glu Asp
                            340                 345                350
           Leu Leu Glu Asn Ser Arg Pro Leu Leu Ala His Met Gln Leu Pro Pro
                            355                 360                365
           Glu Ile Met Pro Thr Val Ile Asp Glu Tyr Leu Asp Asn Gly Ser Asp
                            370                 375                380
           Glu Ser Ala Thr Arg Tyr Ala Leu Gln Glu Leu Leu Gly Asp Ile Thr
           385                     390                 395                400
           Leu Val Ile Pro Thr Leu Ile Phe Ser Lys Tyr Leu Gln Asp Ala Gly
                            405                 410                415
           Cys Pro Val Phe Leu Tyr Glu Phe Gln His Thr Pro Ser Ser Phe Ala
                            420                 425                430
```

```
Lys Phe Lys Pro Ala Trp Val Lys Ala Asp His Ser Ser Glu Asn Ala
        435                 440                 445

Phe Val Phe Gly Gly Pro Phe Leu Thr Asp Glu Ser Ser Leu Leu Ala
    450                 455                 460

Phe Pro Glu Ala Thr Glu Glu Lys Gln Leu Ser Leu Thr Met Met
465                 470                 475                 480

Ala Gln Trp Ser Gln Phe Ala Arg Thr Gly Asn Pro Asn Gly Lys Gly
                485                 490                 495

Leu Pro Pro Trp Pro Gln Leu Asn Gln Leu Glu Gln Tyr Leu Glu Ile
            500                 505                 510

Gly Leu Glu Pro Arg Thr Gly Val Lys Leu Lys Lys Gly Arg Leu Gln
        515                 520                 525

Phe Trp Thr Glu Thr Leu Pro Arg Lys Ile Gln Glu Trp His Arg Glu
    530                 535                 540

Gln Arg Ser Arg Lys Val Pro Glu Glu Leu
545                 550
```

<210> SEQ ID NO 5
<211> LENGTH: 565
<212> TYPE: PRT
<213> ORGANISM: Rattus Norvegicus

<400> SEQUENCE: 5

```
Met Arg Leu Tyr Pro Leu Val Trp Leu Phe Leu Ala Ala Cys Thr Ala
 1               5                  10                  15

Trp Gly Tyr Pro Ser Ser Pro Pro Val Val Asn Thr Val Lys Gly Lys
                20                  25                  30

Val Leu Gly Lys Tyr Val Asn Leu Glu Gly Phe Ala Gln Pro Val Ala
            35                  40                  45

Val Phe Leu Gly Ile Pro Phe Ala Lys Pro Pro Leu Gly Ser Leu Arg
        50                  55                  60

Phe Ala Pro Pro Gln Pro Ala Glu Pro Trp Asn Phe Val Lys Asn Thr
65                  70                  75                  80

Thr Ser Tyr Pro Pro Met Cys Ser Gln Asp Ala Val Gly Gly Gln Val
                85                  90                  95

Leu Ser Glu Leu Phe Thr Asn Arg Lys Glu Asn Ile Pro Leu Gln Phe
            100                 105                 110

Ser Glu Asp Cys Leu Tyr Leu Asn Val Tyr Thr Pro Ala Asp Leu Thr
        115                 120                 125

Lys Asn Ser Arg Leu Pro Val Met Val Trp Ile His Gly Gly Gly Leu
    130                 135                 140

Val Val Gly Gly Ala Ser Thr Tyr Asp Gly Gln Val Leu Ser Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu His Trp Val Gln Asp Asn Ile Ala Asn Phe
        195                 200                 205

Gly Gly Asn Pro Gly Ser Val Thr Ile Phe Gly Glu Ser Ala Gly Gly
    210                 215                 220

Phe Ser Val Ser Ala Leu Val Leu Ser Pro Leu Ala Lys Asn Leu Phe
225                 230                 235                 240

His Arg Ala Ile Ser Glu Ser Gly Val Val Leu Thr Ser Ala Leu Ile
```

```
                    245                 250                 255
Thr Thr Asp Ser Lys Pro Ile Ala Lys Leu Ile Ala Thr Leu Ser Gly
            260                 265                 270

Cys Lys Thr Thr Thr Ser Ala Val Met Val His Cys Leu Arg Gln Lys
            275                 280                 285

Thr Glu Asp Glu Leu Leu Glu Thr Ser Leu Lys Leu Asn Leu Phe Lys
            290                 295                 300

Leu Asp Leu Leu Gly Asn Pro Lys Glu Ser Tyr Pro Phe Leu Pro Thr
305                 310                 315                 320

Val Ile Asp Gly Val Val Leu Pro Lys Thr Pro Glu Glu Ile Leu Ala
                325                 330                 335

Glu Lys Ser Phe Asn Thr Val Pro Tyr Ile Val Gly Ile Asn Lys Gln
                340                 345                 350

Glu Phe Gly Trp Ile Ile Pro Thr Leu Met Gly Tyr Pro Leu Ser Glu
                355                 360                 365

Gly Lys Leu Asp Gln Lys Thr Ala Lys Ser Leu Leu Trp Lys Ser Tyr
            370                 375                 380

Pro Thr Leu Lys Ile Ser Glu Lys Met Ile Pro Val Val Ala Glu Lys
385                 390                 395                 400

Tyr Phe Gly Gly Thr Asp Asp Pro Ala Lys Arg Lys Asp Leu Phe Gln
                405                 410                 415

Asp Leu Val Ala Asp Val Ile Phe Gly Val Pro Ser Val Met Val Ser
                420                 425                 430

Arg Ser His Arg Asp Ala Gly Ala Pro Thr Phe Met Tyr Glu Phe Glu
            435                 440                 445

Tyr Arg Pro Ser Phe Val Ser Ala Met Arg Pro Lys Thr Val Ile Gly
    450                 455                 460

Asp His Gly Asp Glu Leu Phe Ser Val Phe Gly Ser Pro Phe Leu Lys
465                 470                 475                 480

Asp Gly Ala Ser Glu Glu Thr Asn Leu Ser Lys Met Val Met Lys
                485                 490                 495

Tyr Trp Ala Asn Phe Ala Arg Asn Gly Ser Pro Asn Gly Gly Gly Leu
            500                 505                 510

Pro His Trp Pro Glu Tyr Asp Gln Lys Glu Gly Tyr Leu Lys Ile Gly
            515                 520                 525

Ala Ser Thr Gln Ala Ala Gln Arg Leu Lys Asp Lys Glu Val Ala Phe
            530                 535                 540

Trp Ser Glu Leu Arg Ala Lys Glu Ala Ala Glu Glu Pro Ser His Trp
545                 550                 555                 560

Lys His Val Glu Leu
                565
```

<210> SEQ ID NO 6
<211> LENGTH: 5
<212> TYPE: PRT
<213> ORGANISM: Artificial Sequence
<220> FEATURE:
<223> OTHER INFORMATION: Catalytic Serine Motif
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(4)
<223> OTHER INFORMATION: Xaa = any amino acid

<400> SEQUENCE: 6

Gly Xaa Ser Xaa Gly
 1               5

<210> SEQ ID NO 7
<211> LENGTH: 1512
<212> TYPE: DNA
<213> ORGANISM: Homo Sapiens
<220> FEATURE:
<221> NAME/KEY: CDS
<222> LOCATION: (342)...(1334)

<400> SEQUENCE: 7

| | |
|---|---|
| ccacgcgtcc ggactagttc catttccaca gctcctcctc cccggccgcg cgcccctccc | 60 |
| gccccgcgcg cgcctcctct ttctcgcggc cgagttcagc ccgggcagcc atatggggga | 120 |
| tacgccagca acagacgccg ccgccaagaa tctgcatccc taggccacgc taagaccctg | 180 |
| gggaagagcg caggagcccg ggagaagggc tggaaggagg ggactggacg tgcggagaat | 240 |
| tccccctaa aaggcagaag cccccgcccc caccctcgag ctccgctcgg gcagagcgcc | 300 |
| tgcctgcctg ccgctgctgc gggcgcccac ctcgcccagc c atg cca ggc ccg gcc | 356 |
|                                                                         Met Pro Gly Pro Ala | |
|                                                                           1               5 | |
| acc gac gcg ggg aag atc cct ttc tgc gac gcc aag gaa gaa atc cgt | 404 |
| Thr Asp Ala Gly Lys Ile Pro Phe Cys Asp Ala Lys Glu Glu Ile Arg | |
|            10                        15                     20 | |
| gcc ggg ctc gaa agc tct gag ggc ggc ggc ccg gag agg cca ggc | 452 |
| Ala Gly Leu Glu Ser Ser Glu Gly Gly Gly Pro Glu Arg Pro Gly | |
|               25                          30                      35 | |
| gcg cgc ggg cag cgg cag aac atc gtc tgg agg aat gtc gtc ctg atg | 500 |
| Ala Arg Gly Gln Arg Gln Asn Ile Val Trp Arg Asn Val Val Leu Met | |
|            40                        45                     50 | |
| agc ttg ctc cac ttg ggg gcc gtg tac tcc ctg gtc ctc atc ccc aaa | 548 |
| Ser Leu Leu His Leu Gly Ala Val Tyr Ser Leu Val Leu Ile Pro Lys | |
|   55                        60                     65 | |
| gcc aag cca ctc act ctg ctc tgg gcc tac ttc tgc ttc ctc ctg gcc | 596 |
| Ala Lys Pro Leu Thr Leu Leu Trp Ala Tyr Phe Cys Phe Leu Leu Ala | |
| 70                     75                     80                     85 | |
| gct ctg ggt gtg aca gct ggt gcc cat cgc ttg tgg agc cac agg tcc | 644 |
| Ala Leu Gly Val Thr Ala Gly Ala His Arg Leu Trp Ser His Arg Ser | |
|            90                        95                     100 | |
| tac cgg gcc aag ctg cct ctg agg ata ttt ctg gct gtc gcc aac tcc | 692 |
| Tyr Arg Ala Lys Leu Pro Leu Arg Ile Phe Leu Ala Val Ala Asn Ser | |
|            105                      110                   115 | |
| atg gct ttc cag aat gac atc ttc gag tgg tcc agg gac cac cga gcc | 740 |
| Met Ala Phe Gln Asn Asp Ile Phe Glu Trp Ser Arg Asp His Arg Ala | |
|      120                      125                   130 | |
| cac cac aag tac tca gag acg gat gct gac ccc cac aat gcc cgc cgg | 788 |
| His His Lys Tyr Ser Glu Thr Asp Ala Asp Pro His Asn Ala Arg Arg | |
|  135                       140                     145 | |
| ggc ttc ttc ttc tcc cat att ggg tgg ctg ttt gtt cgc aag cat cga | 836 |
| Gly Phe Phe Phe Ser His Ile Gly Trp Leu Phe Val Arg Lys His Arg | |
| 150                  155                   160                   165 | |
| gat gtt att gag aag ggg aga aag ctt gac gtc act gac ctg ctt gct | 884 |
| Asp Val Ile Glu Lys Gly Arg Lys Leu Asp Val Thr Asp Leu Leu Ala | |
|            170                      175                   180 | |
| gat cct gtg gtc cgg atc cag aga aag tac tat aag atc tcc gtg gtg | 932 |
| Asp Pro Val Val Arg Ile Gln Arg Lys Tyr Tyr Lys Ile Ser Val Val | |
|                185                      190                   195 | |
| ctc atg tgc ttt gtg gtc ccc acg ctg gtg ccc tgg tac atc tgg gga | 980 |
| Leu Met Cys Phe Val Val Pro Thr Leu Val Pro Trp Tyr Ile Trp Gly | |

-continued

```
                  200                 205                 210
gag agt ctg tgg aat tcc tac ttc ttg gcc tct att ctc cgc tat acc    1028
Glu Ser Leu Trp Asn Ser Tyr Phe Leu Ala Ser Ile Leu Arg Tyr Thr
    215                 220                 225 atc tca ctc aac atc agc tgg ctg gtc aac agc gcc gcc cac atg tat    1076
Ile Ser Leu Asn Ile Ser Trp Leu Val Asn Ser Ala Ala His Met Tyr
230                 235                 240                 245 gga aac cgg ccc tat gac aag cac atc agc cct cgg cag aac cca ctc    1124
Gly Asn Arg Pro Tyr Asp Lys His Ile Ser Pro Arg Gln Asn Pro Leu
                250                 255                 260 gtc gct ctg ggt gcc att ggt gaa ggc ttc cat aat tac cat cac acc    1172
Val Ala Leu Gly Ala Ile Gly Glu Gly Phe His Asn Tyr His His Thr
            265                 270                 275 ttt ccc ttt gac tac tct gcg agt gaa ttt ggc tta aat ttt aac cca    1220
Phe Pro Phe Asp Tyr Ser Ala Ser Glu Phe Gly Leu Asn Phe Asn Pro
        280                 285                 290 acc acc tgg ttc att gat ttc atg tgc tgg ctg ggg ctg gcc act gac    1268
Thr Thr Trp Phe Ile Asp Phe Met Cys Trp Leu Gly Leu Ala Thr Asp
    295                 300                 305 cgc aaa cgg gca acc aag ccg atg atc gag gcc cgg aag gcc agg act    1316
Arg Lys Arg Ala Thr Lys Pro Met Ile Glu Ala Arg Lys Ala Arg Thr
310                 315                 320                 325 gga gac agc agt gct tga acttggaaca gccatcccac atgtctgccg           1364
Gly Asp Ser Ser Ala *
                330 ttgcaacctc ggttcatggc tttggttaca atagctctct tgtacattgg atcgtgggag  1424 ggggcagagg gtggggaagg aacgagtcaa tgtggtttgg gaatgttttt gtttatctca  1484 aaataatgtt gaaatacaat tatcaatg                                     1512

<210> SEQ ID NO 8
<211> LENGTH: 330
<212> TYPE: PRT
<213> ORGANISM: Homo Sapiens

<400> SEQUENCE: 8

Met Pro Gly Pro Ala Thr Asp Ala Gly Lys Ile Pro Phe Cys Asp Ala
1               5                   10                  15

Lys Glu Glu Ile Arg Ala Gly Leu Glu Ser Ser Glu Gly Gly Gly Gly
            20                  25                  30

Pro Glu Arg Pro Gly Ala Arg Gly Gln Arg Gln Asn Ile Val Trp Arg
        35                  40                  45

Asn Val Val Leu Met Ser Leu Leu His Leu Gly Ala Val Tyr Ser Leu
    50                  55                  60

Val Leu Ile Pro Lys Ala Lys Pro Leu Thr Leu Leu Trp Ala Tyr Phe
65                  70                  75                  80

Cys Phe Leu Leu Ala Ala Leu Gly Val Thr Ala Gly Ala His Arg Leu
                85                  90                  95

Trp Ser His Arg Ser Tyr Arg Ala Lys Leu Pro Leu Arg Ile Phe Leu
            100                 105                 110

Ala Val Ala Asn Ser Met Ala Phe Gln Asn Asp Ile Phe Glu Trp Ser
        115                 120                 125

Arg Asp His Arg Ala His His Lys Tyr Ser Glu Thr Asp Ala Asp Pro
    130                 135                 140

His Asn Ala Arg Arg Gly Phe Phe Ser His Ile Gly Trp Leu Phe
145                 150                 155                 160

Val Arg Lys His Arg Asp Val Ile Glu Lys Gly Arg Lys Leu Asp Val
```

-continued

```
                  165                 170                 175
Thr Asp Leu Leu Ala Asp Pro Val Val Arg Ile Gln Arg Lys Tyr Tyr
            180                 185                 190

Lys Ile Ser Val Val Leu Met Cys Phe Val Val Pro Thr Leu Val Pro
        195                 200                 205

Trp Tyr Ile Trp Gly Glu Ser Leu Trp Asn Ser Tyr Phe Leu Ala Ser
    210                 215                 220

Ile Leu Arg Tyr Thr Ile Ser Leu Asn Ile Ser Trp Leu Val Asn Ser
225                 230                 235                 240

Ala Ala His Met Tyr Gly Asn Arg Pro Tyr Asp Lys His Ile Ser Pro
                245                 250                 255

Arg Gln Asn Pro Leu Val Ala Leu Gly Ala Ile Gly Glu Gly Phe His
            260                 265                 270

Asn Tyr His His Thr Phe Pro Phe Asp Tyr Ser Ala Ser Glu Phe Gly
        275                 280                 285

Leu Asn Phe Asn Pro Thr Thr Trp Phe Ile Asp Phe Met Cys Trp Leu
    290                 295                 300

Gly Leu Ala Thr Asp Arg Lys Arg Ala Thr Lys Pro Met Ile Glu Ala
305                 310                 315                 320

Arg Lys Ala Arg Thr Gly Asp Ser Ser Ala
                325                 330

<210> SEQ ID NO 9
<211> LENGTH: 990
<212> TYPE: DNA
<213> ORGANISM: Homo Sapiens
<220> FEATURE:
<221> NAME/KEY: CDS
<222> LOCATION: (1)...(990)

<400> SEQUENCE: 9 atg cca ggc ccg gcc acc gac gcg ggg aag atc cct ttc tgc gac gcc      48
Met Pro Gly Pro Ala Thr Asp Ala Gly Lys Ile Pro Phe Cys Asp Ala
 1               5                  10                  15 aag gaa gaa atc cgt gcc ggg ctc gaa agc tct gag ggc ggc ggc ggc      96
Lys Glu Glu Ile Arg Ala Gly Leu Glu Ser Ser Glu Gly Gly Gly Gly
                20                  25                  30 ccg gag agg cca ggc gcg cgc ggg cag cgg cag aac atc gtc tgg agg     144
Pro Glu Arg Pro Gly Ala Arg Gly Gln Arg Gln Asn Ile Val Trp Arg
            35                  40                  45 aat gtc gtc ctg atg agc ttg ctc cac ttg ggg gcc gtg tac tcc ctg     192
Asn Val Val Leu Met Ser Leu Leu His Leu Gly Ala Val Tyr Ser Leu
        50                  55                  60 gtg ctc atc ccc aaa gcc aag cca ctc act ctg ctc tgg gcc tac ttc     240
Val Leu Ile Pro Lys Ala Lys Pro Leu Thr Leu Leu Trp Ala Tyr Phe
65                  70                  75                  80 tgc ttc ctc ctg gcc gct ctg ggt gtg aca gct ggt gcc cat cgc ttg     288
Cys Phe Leu Leu Ala Ala Leu Gly Val Thr Ala Gly Ala His Arg Leu
                85                  90                  95 tgg agc cac agg tcc tac cgg gcc aag ctg cct ctg agg ata ttt ctg     336
Trp Ser His Arg Ser Tyr Arg Ala Lys Leu Pro Leu Arg Ile Phe Leu
            100                 105                 110 gct gtc gcc aac tcc atg gct ttc cag aat gac atc ttc gag tgg tcc     384
Ala Val Ala Asn Ser Met Ala Phe Gln Asn Asp Ile Phe Glu Trp Ser
        115                 120                 125 agg gac cac cga gcc cac cac aag tac tca gag acg gat gct gac ccc     432
Arg Asp His Arg Ala His His Lys Tyr Ser Glu Thr Asp Ala Asp Pro
    130                 135                 140
```

```
cac aat gcc cgc cgg ggc ttc ttc ttc tcc cat att ggg tgg ctg ttt         480
His Asn Ala Arg Arg Gly Phe Phe Phe Ser His Ile Gly Trp Leu Phe
145                 150                 155                 160 gtt cgc aag cat cga gat gtt att gag aag ggg aga aag ctt gac gtc         528
Val Arg Lys His Arg Asp Val Ile Glu Lys Gly Arg Lys Leu Asp Val
                165                 170                 175 act gac ctg ctt gct gat cct gtg gtc cgg atc cag aga aag tac tat         576
Thr Asp Leu Leu Ala Asp Pro Val Val Arg Ile Gln Arg Lys Tyr Tyr
            180                 185                 190 aag atc tcc gtg gtg ctc atg tgc ttt gtg gtc ccc acg ctg gtg ccc         624
Lys Ile Ser Val Val Leu Met Cys Phe Val Val Pro Thr Leu Val Pro
        195                 200                 205 tgg tac atc tgg gga gag agt ctg tgg aat tcc tac ttc ttg gcc tct         672
Trp Tyr Ile Trp Gly Glu Ser Leu Trp Asn Ser Tyr Phe Leu Ala Ser
    210                 215                 220 att ctc cgc tat acc atc tca ctc aac atc agc tgg ctg gtc aac agc         720
Ile Leu Arg Tyr Thr Ile Ser Leu Asn Ile Ser Trp Leu Val Asn Ser
225                 230                 235                 240 gcc gcc cac atg tat gga aac cgg ccc tat gac aag cac atc agc cct         768
Ala Ala His Met Tyr Gly Asn Arg Pro Tyr Asp Lys His Ile Ser Pro
                245                 250                 255 cgg cag aac cca ctc gtc gct ctg ggt gcc att ggt gaa ggc ttc cat         816
Arg Gln Asn Pro Leu Val Ala Leu Gly Ala Ile Gly Glu Gly Phe His
            260                 265                 270 aat tac cat cac acc ttt ccc ttt gac tac tct gcg agt gaa ttt ggc         864
Asn Tyr His His Thr Phe Pro Phe Asp Tyr Ser Ala Ser Glu Phe Gly
        275                 280                 285 tta aat ttt aac cca acc acc tgg ttc att gat ttc atg tgc tgg ctg         912
Leu Asn Phe Asn Pro Thr Thr Trp Phe Ile Asp Phe Met Cys Trp Leu
    290                 295                 300 ggg ctg gcc act gac cgc aaa cgg gca acc aag ccg atg atc gag gcc         960
Gly Leu Ala Thr Asp Arg Lys Arg Ala Thr Lys Pro Met Ile Glu Ala
305                 310                 315                 320 cgg aag gcc agg act gga gac agc agt gct                                 990
Arg Lys Ala Arg Thr Gly Asp Ser Ser Ala
                325                 330
```

<210> SEQ ID NO 10
<211> LENGTH: 248
<212> TYPE: PRT
<213> ORGANISM: Artificial Sequence
<220> FEATURE:
<223> OTHER INFORMATION: Consensus Sequence

<400> SEQUENCE: 10

```
Ile Leu Leu Gly Ala Leu His Leu Gly Ala Leu Tyr Leu Leu Ala Leu
1               5                   10                  15

Leu Pro Thr Glu Leu Lys Trp Lys Thr Val Ile Val Ala Leu Leu Leu
                20                  25                  30

Tyr Val Ile Thr Gly Gly Leu Gly Ile Thr Ala Gly Tyr His Arg Leu
            35                  40                  45

Trp Ser His Arg Ser Tyr Lys Ala Lys Leu Pro Leu Arg Ile Phe Leu
        50                  55                  60

Ala Ile Phe Gly Thr Leu Ala Val Gln Gly Ser Ile Tyr Glu Trp Ala
65                  70                  75                  80

Arg Asp His Arg Ala His His Lys Tyr Ser Asp Thr Asp Ala Asp Pro
                85                  90                  95

His Asp Ala Asn Arg Gly Phe Phe Phe Ser His Val Gly Trp Leu Leu
            100                 105                 110
```

-continued

```
Val Lys Lys His Pro Ala Val Lys Glu Lys Gly Lys Lys Leu Asp Leu
        115                 120                 125

Ser Asp Leu Lys Ala Asp Pro Val Val Arg Phe Gln His Arg Tyr Tyr
    130                 135                 140

Ile Pro Leu Met Val Leu Met Gly Phe Ile Leu Pro Thr Leu Val Pro
145                 150                 155                 160

Gly Tyr Leu Trp Gly Glu Thr Phe Trp Gly Gly Phe Val Trp Ala Gly
                165                 170                 175

Phe Leu Arg Leu Val Phe Val Leu His Ala Thr Trp Cys Val Asn Ser
                180                 185                 190

Ala Ala His Lys Phe Gly Tyr Arg Pro Tyr Asp Ser Arg Ile Thr Pro
            195                 200                 205

Arg Asn Asn Trp Leu Val Ala Leu Val Thr Phe Gly Glu Gly Trp His
    210                 215                 220

Asn Phe His His Thr Phe Pro Tyr Asp Tyr Arg Asn Ala Glu Lys Trp
225                 230                 235                 240

Lys Trp Glu Tyr Asp Leu Thr Lys
                245

<210> SEQ ID NO 11
<211> LENGTH: 248
<212> TYPE: PRT
<213> ORGANISM: Artificial Sequence
<220> FEATURE:
<223> OTHER INFORMATION: Conserved Iron Binding Motif
<220> FEATURE:
<221> NAME/KEY: VARIANT
<222> LOCATION: (2)...(5)
<223> OTHER INFORMATION: Xaa = Any Amino Acid
<220> FEATURE:
<221> NAME/KEY: VARIANT
<222> LOCATION: (7)...(47)
<223> OTHER INFORMATION: Xaa = Any Amino Acid
<220> FEATURE:
<221> NAME/KEY: VARIANT
<222> LOCATION: (49)...(51)
<223> OTHER INFORMATION: Xaa = Any Amino Acid
<220> FEATURE:
<221> NAME/KEY: VARIANT
<222> LOCATION: (54)...(242)
<223> OTHER INFORMATION: Xaa = Any Amino Acid
<220> FEATURE:
<221> NAME/KEY: VARIANT
<222> LOCATION: (244)...(246)
<223> OTHER INFORMATION: Xaa = Any Amino Acid

<400> SEQUENCE: 11

His Xaa Xaa Xaa Xaa His Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa His
            35                  40                  45

Xaa Xaa Xaa His His Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
```

```
                115                 120                 125
Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa His Xaa Xaa Xaa His His
            245

<210> SEQ ID NO 12
<211> LENGTH: 15
<212> TYPE: PRT
<213> ORGANISM: Artificial Sequence
<220> FEATURE:
<223> OTHER INFORMATION: Fatty Acid Desaturase Family 1 Signature
      Sequence
<220> FEATURE:
<221> NAME/KEY: VARIANT
<222> LOCATION: (3)...(3)
<223> OTHER INFORMATION: Xaa = Any Amino Acid
<220> FEATURE:
<221> NAME/KEY: VARIANT
<222> LOCATION: (4)...(4)
<223> OTHER INFORMATION: Xaa = Phe or Tyr
<220> FEATURE:
<221> NAME/KEY: VARIANT
<222> LOCATION: (7)...(7)
<223> OTHER INFORMATION: Xaa = Phe or Tyr
<220> FEATURE:
<221> NAME/KEY: VARIANT
<222> LOCATION: (10)...(10)
<223> OTHER INFORMATION: Xaa = Any Amino Acid
<220> FEATURE:
<221> NAME/KEY: VARIANT
<222> LOCATION: (13)...(13)
<223> OTHER INFORMATION: Xaa = Any Amino Acid

<400> SEQUENCE: 12

Gly Glu Xaa Xaa His Asn Xaa His His Xaa Phe Pro Xaa Asp Tyr
1               5                   10                  15

<210> SEQ ID NO 13
<211> LENGTH: 359
<212> TYPE: PRT
<213> ORGANISM: Homo Sapiens

<400> SEQUENCE: 13

Met Pro Ala His Leu Leu Gln Asp Asp Ile Ser Ser Ser Tyr Thr Thr
1               5                   10                  15

Thr Thr Thr Ile Thr Ala Pro Pro Ser Arg Val Leu Gln Asn Gly Gly
            20                  25                  30

Asp Lys Leu Glu Thr Met Pro Leu Tyr Leu Glu Asp Ile Arg Pro
        35                  40                  45

Asp Ile Lys Asp Asp Ile Tyr Asp Pro Thr Tyr Lys Asp Lys Glu Gly
    50                  55                  60
```

-continued

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Phe Val Ser Ala
                100                 105                 110

Leu Gly Ile Thr Ala Gly Ala His Arg Leu Trp Ser His Arg Ser Tyr
                115                 120                 125

Lys Ala Arg Leu Pro Leu Arg Leu Phe Leu Ile Ile Ala Asn Thr Met
        130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
                180                 185                 190

Val Lys Glu Lys Gly Ser Thr Leu Asp Leu Ser Asp Leu Glu Ala Glu
        195                 200                 205

Lys Leu Val Met Phe Gln Arg Arg Tyr Tyr Lys Pro Gly Leu Leu Leu
        210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
                260                 265                 270

Tyr Arg Pro Tyr Asp Lys Asn Ile Ser Pro Arg Glu Asn Ile Leu Val
                275                 280                 285

Ser Leu Gly Ala Val Gly Glu Gly Phe His Asn Tyr His His Ser Phe
        290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
                325                 330                 335

Lys Lys Val Ser Lys Ala Ala Ile Leu Ala Arg Ile Lys Arg Thr Gly
                340                 345                 350

Asp Gly Asn Tyr Lys Ser Gly
        355

<210> SEQ ID NO 14
<211> LENGTH: 358
<212> TYPE: PRT
<213> ORGANISM: Rattus Norvegicus

<400> SEQUENCE: 14

Met Pro Ala His Met Leu Gln Glu Ile Ser Ser Tyr Thr Thr Thr
1               5                   10                  15

Thr Thr Ile Thr Glu Pro Pro Ser Gly Asn Leu Gln Asn Gly Arg Glu
                20                  25                  30

Lys Met Lys Lys Val Pro Leu Tyr Leu Glu Glu Asp Ile Arg Pro Glu
                35                  40                  45

Met Arg Glu Asp Ile His Asp Pro Ser Tyr Gln Asp Glu Glu Gly Pro
        50                  55                  60

Pro Pro Lys Leu Glu Tyr Val Trp Arg Asn Ile Ile Leu Met Ala Leu

```
                65                  70                  75                  80
Leu His Val Gly Ala Leu Tyr Gly Ile Thr Leu Ile Pro Ser Ser Lys
                    85                  90                  95
Val Tyr Thr Leu Leu Trp Gly Ile Phe Tyr Tyr Leu Ile Ser Ala Leu
                100                 105                 110
Gly Ile Thr Ala Gly Ala His Arg Leu Trp Ser His Arg Thr Tyr Lys
                115                 120                 125
Ala Arg Leu Pro Leu Arg Ile Phe Leu Ile Ile Ala Asn Thr Met Ala
            130                 135                 140
Phe Gln Asn Asp Val Tyr Glu Trp Ala Arg Asp His Arg Ala His His
145                 150                 155                 160
Lys Phe Ser Glu Thr His Ala Asp Pro His Asn Ser Arg Arg Gly Phe
                165                 170                 175
Phe Phe Ser His Val Gly Trp Leu Leu Val Arg Lys His Pro Ala Val
                180                 185                 190
Lys Glu Lys Gly Gly Lys Leu Asp Met Ser Asp Leu Lys Ala Glu Lys
                195                 200                 205
Leu Val Met Phe Gln Arg Arg Tyr Tyr Lys Pro Gly Leu Leu Leu Met
            210                 215                 220
Cys Phe Ile Leu Pro Thr Leu Val Pro Trp Tyr Cys Trp Gly Glu Thr
225                 230                 235                 240
Phe Leu His Ser Leu Phe Val Ser Thr Phe Leu Arg Tyr Thr Leu Val
                245                 250                 255
Leu Asn Ala Thr Trp Leu Val Asn Ser Ala Ala His Leu Tyr Gly Tyr
                260                 265                 270
Arg Pro Tyr Asp Lys Asn Ile Gln Ser Arg Glu Asn Ile Leu Val Ser
                275                 280                 285
Leu Gly Ser Val Gly Glu Gly Phe His Asn Tyr His His Ala Phe Pro
            290                 295                 300
Tyr Asp Tyr Ser Ala Ser Glu Tyr Arg Trp His Ile Asn Phe Thr Thr
305                 310                 315                 320
Phe Phe Ile Asp Cys Met Ala Ala Leu Gly Leu Ala Tyr Asp Arg Lys
                325                 330                 335
Lys Val Ser Lys Ala Ala Val Leu Ala Arg Ile Lys Arg Thr Gly Asp
                340                 345                 350
Gly Ser His Lys Ser Ser
            355

<210> SEQ ID NO 15
<211> LENGTH: 357
<212> TYPE: PRT
<213> ORGANISM: Gallus Gallus

<400> SEQUENCE: 15

Met Pro Ala His Leu Leu Gln Glu Glu Phe Ser Ser Ala Ser Ser
  1               5                  10                  15
Thr Thr Thr Val Thr Ser Arg Val Thr Lys Asn Gly Asn Val Ile Met
                 20                  25                  30
Glu Lys Asp Leu Leu Asn His Asp Val Ala Ala Glu Arg Gly Met
             35                  40                  45
Val Asp Asp Leu Phe Asp Glu Thr Tyr Arg Glu Lys Glu Gly Pro Lys
             50                  55                  60
Pro Pro Leu Arg Tyr Val Trp Arg Asn Ile Ile Leu Met Ser Leu Leu
65                  70                  75                  80
```

```
His Leu Gly Ala Ile Ile Gly Leu Thr Leu Ile Pro Ser Ala Lys Ile
                85                  90                  95

Gln Thr Leu Ala Trp Ala Ile Leu Cys Phe Val Leu Ser Ala Leu Gly
            100                 105                 110

Ile Thr Ala Gly Ser His Arg Leu Trp Ser His Arg Ser Tyr Lys Ala
        115                 120                 125

Thr Leu Pro Leu Arg Ile Phe Leu Thr Ile Ala Asn Ser Met Ala Phe
    130                 135                 140

Gln Asn Asp Ile Tyr Glu Trp Ala Arg Asp His Arg Val His His Lys
145                 150                 155                 160

Phe Ser Glu Thr His Ala Asp Pro His Asn Ala Met Arg Gly Tyr Phe
                165                 170                 175

Phe Ser His Met Ala Trp Leu Leu Val Arg Lys His Pro Asp Val Ile
            180                 185                 190

Glu Lys Gly Gln Lys Leu Asp Leu Ser Asp Leu Lys Ala Asp Lys Val
        195                 200                 205

Val Met Phe Gln Arg Arg Tyr Tyr Lys Pro Ser Val Val Leu Leu Cys
    210                 215                 220

Phe Thr Leu Pro Thr Leu Val Pro Trp Tyr Phe Trp Asp Glu Ser Ile
225                 230                 235                 240

Ile Ile Ser Phe Phe Ile Pro Ala Ile Leu Arg Tyr Thr Leu Gly Leu
                245                 250                 255

Asn Ala Thr Trp Leu Val Asn Ser Ala Ala His Met Phe Gly Asn Arg
            260                 265                 270

Pro Tyr Asp Gln Asn Ile Asn Pro Arg Glu Asn Pro Leu Val Ser Val
        275                 280                 285

Gly Ala Leu Gly Glu Gly Phe His Asn Tyr His His Thr Phe Pro Tyr
    290                 295                 300

Asp Tyr Ser Thr Ser Glu Phe Gly Trp Arg Phe Asn Leu Thr Thr Ala
305                 310                 315                 320

Phe Ile Asp Leu Met Cys Leu Leu Gly Leu Ala Ser Asp Arg Lys Lys
                325                 330                 335

Val Ser Lys Glu Val Ile Leu Ala Arg Lys Met Arg Thr Gly Asp Gly
            340                 345                 350

Ser His Lys Ser Gly
        355

<210> SEQ ID NO 16
<211> LENGTH: 1327
<212> TYPE: DNA
<213> ORGANISM: Homo Sapiens
<220> FEATURE:
<221> NAME/KEY: CDS
<222> LOCATION: (107)...(1096)

<400> SEQUENCE: 16
cacgcgtccg ggaaagagct ggttccctgg caggctggag ggcaggagct ggggccacgc      60
tggtctggga tagttgggca gggaggctgt ctacctggtc tccaga atg gac ggc       115
                                                    Met Asp Gly
                                                     1 cct gtg gca gag cat gcc aag cag gag ccc ttt cac gtg gtc aca cct     163
Pro Val Ala Glu His Ala Lys Gln Glu Pro Phe His Val Val Thr Pro
    5                  10                  15 ctg ttg gag agc tgg gcg ctg tcc cag gtg gcg ggc atg cct gtc ttc     211
Leu Leu Glu Ser Trp Ala Leu Ser Gln Val Ala Gly Met Pro Val Phe
 20                  25                  30                  35
```

-continued

```
ctc aag tgt gag aat gtg cag ccc agc ggc tcc ttc aag att cgg ggc      259
Leu Lys Cys Glu Asn Val Gln Pro Ser Gly Ser Phe Lys Ile Arg Gly
             40                  45                  50 att ggg cat ttc tgc cag gag atg gcc aag aag gga tgc aga cac ctg      307
Ile Gly His Phe Cys Gln Glu Met Ala Lys Lys Gly Cys Arg His Leu
         55                  60                  65 gtg tgc tcc tca ggg ggt aat gcg ggc atc gct gct gcc tat gct gct      355
Val Cys Ser Ser Gly Gly Asn Ala Gly Ile Ala Ala Ala Tyr Ala Ala
     70                  75                  80 agg aag ctg ggc att cct gcc acc atc gtg ctc ccc gag agc acc tcc      403
Arg Lys Leu Gly Ile Pro Ala Thr Ile Val Leu Pro Glu Ser Thr Ser
 85                  90                  95 ctg cag gtg gtg cag agg ctg cag gcg gag ggg gcc gag gtt cag ctg      451
Leu Gln Val Val Gln Arg Leu Gln Ala Glu Gly Ala Glu Val Gln Leu
100                 105                 110                 115 act gga aag gtc tgg gac gag gcc aat ctg agg gcg caa gag ttg gcc      499
Thr Gly Lys Val Trp Asp Glu Ala Asn Leu Arg Ala Gln Glu Leu Ala
                120                 125                 130 aag agg gac ggc tgg gag aat gtc ccc ccg ttt gac cac ccc cta ata      547
Lys Arg Asp Gly Trp Glu Asn Val Pro Pro Phe Asp His Pro Leu Ile
            135                 140                 145 tgg aaa ggc cac gcc agc ctg gtg cag gag ctg aaa gca gtg ctg agg      595
Trp Lys Gly His Ala Ser Leu Val Gln Glu Leu Lys Ala Val Leu Arg
        150                 155                 160 acc cca cca ggt gcc ctg gtg ctg gca gtt ggg ggt ggg ggt ctc ctg      643
Thr Pro Pro Gly Ala Leu Val Leu Ala Val Gly Gly Gly Gly Leu Leu
    165                 170                 175 gcc ggg gtg gtg gct ggc ctg ctg gag gtg ggc tgg cag cat gta ccc      691
Ala Gly Val Val Ala Gly Leu Leu Glu Val Gly Trp Gln His Val Pro
180                 185                 190                 195 atc att gcc atg gag acc cat ggg gca cac tgc ttc aat gcg gcc atc      739
Ile Ile Ala Met Glu Thr His Gly Ala His Cys Phe Asn Ala Ala Ile
                200                 205                 210 aca gcc ggc aag ctg gtc aca ctt cca gac atc acc agt gtg gcc aag      787
Thr Ala Gly Lys Leu Val Thr Leu Pro Asp Ile Thr Ser Val Ala Lys
            215                 220                 225 agc ctg ggt gcc aag acg gtg gct cgg gcc ctg gag tgc atg cag           835
Ser Leu Gly Ala Lys Thr Val Ala Ala Arg Ala Leu Glu Cys Met Gln
        230                 235                 240 gtg tgc aag att cac tct gaa gtg gtg gag gac acc gag gct gtg agc      883
Val Cys Lys Ile His Ser Glu Val Val Glu Asp Thr Glu Ala Val Ser
    245                 250                 255 gct gtg cag cag ctc ctg gat gat gag cgt atg ctg gtg gag cct gcc      931
Ala Val Gln Gln Leu Leu Asp Asp Glu Arg Met Leu Val Glu Pro Ala
260                 265                 270                 275 tgt ggg gca gcc tta gca gcc atc tac tca ggc ctc ctg cgg agg ctc      979
Cys Gly Ala Ala Leu Ala Ala Ile Tyr Ser Gly Leu Leu Arg Arg Leu
                280                 285                 290 cag gcc gag ggc tgc ctg ccc cct tcc ctg act tca gtt gtg gta atc     1027
Gln Ala Glu Gly Cys Leu Pro Pro Ser Leu Thr Ser Val Val Val Ile
            295                 300                 305 gtg tgt gga ggc aac aac atc aac agc cga gag ctg cag gcc ttg aaa     1075
Val Cys Gly Gly Asn Asn Ile Asn Ser Arg Glu Leu Gln Ala Leu Lys
        310                 315                 320 acc cac ctg ggc cag gtc tga ggggtcccat cctggcccca aagacccctg        1126
Thr His Leu Gly Gln Val *
    325 agaggcccat ggacagtcct gtgtctggat gaggaggact cagtgctggc agatggcagt   1186 ggaagctgcc ctgtgcaact gtgctggctg cctcctgaag gaagccctcc tggactgctt   1246
```

```
cttttggctc tccgacaact ccggccaata aacactttct gaattgagtt tgcgaataaa    1306
aaaaaaaaaa aaaaaaaaaa a                                              1327
```

<210> SEQ ID NO 17
<211> LENGTH: 329
<212> TYPE: PRT
<213> ORGANISM: Homo Sapiens

<400> SEQUENCE: 17

```
Met Asp Gly Pro Val Ala Glu His Ala Lys Gln Glu Pro Phe His Val
1               5                   10                  15

Val Thr Pro Leu Leu Glu Ser Trp Ala Leu Ser Gln Val Ala Gly Met
            20                  25                  30

Pro Val Phe Leu Lys Cys Glu Asn Val Gln Pro Ser Gly Ser Phe Lys
        35                  40                  45

Ile Arg Gly Ile Gly His Phe Cys Gln Glu Met Ala Lys Lys Gly Cys
    50                  55                  60

Arg His Leu Val Cys Ser Ser Gly Gly Asn Ala Gly Ile Ala Ala Ala
65                  70                  75                  80

Tyr Ala Ala Arg Lys Leu Gly Ile Pro Ala Thr Ile Val Leu Pro Glu
                85                  90                  95

Ser Thr Ser Leu Gln Val Val Gln Arg Leu Gln Ala Glu Gly Ala Glu
            100                 105                 110

Val Gln Leu Thr Gly Lys Val Trp Asp Glu Ala Asn Leu Arg Ala Gln
        115                 120                 125

Glu Leu Ala Lys Arg Asp Gly Trp Glu Asn Val Pro Pro Phe Asp His
    130                 135                 140

Pro Leu Ile Trp Lys Gly His Ala Ser Leu Val Gln Glu Leu Lys Ala
145                 150                 155                 160

Val Leu Arg Thr Pro Pro Gly Ala Leu Val Leu Ala Val Gly Gly Gly
                165                 170                 175

Gly Leu Leu Ala Gly Val Val Ala Gly Leu Leu Glu Val Gly Trp Gln
            180                 185                 190

His Val Pro Ile Ile Ala Met Glu Thr His Gly Ala His Cys Phe Asn
        195                 200                 205

Ala Ala Ile Thr Ala Gly Lys Leu Val Thr Leu Pro Asp Ile Thr Ser
    210                 215                 220

Val Ala Lys Ser Leu Gly Ala Lys Thr Val Ala Ala Arg Ala Leu Glu
225                 230                 235                 240

Cys Met Gln Val Cys Lys Ile His Ser Glu Val Val Glu Asp Thr Glu
                245                 250                 255

Ala Val Ser Ala Val Gln Gln Leu Leu Asp Asp Glu Arg Met Leu Val
            260                 265                 270

Glu Pro Ala Cys Gly Ala Ala Leu Ala Ala Ile Tyr Ser Gly Leu Leu
        275                 280                 285

Arg Arg Leu Gln Ala Glu Gly Cys Leu Pro Pro Ser Leu Thr Ser Val
    290                 295                 300

Val Val Ile Val Cys Gly Gly Asn Asn Ile Asn Ser Arg Glu Leu Gln
305                 310                 315                 320

Ala Leu Lys Thr His Leu Gly Gln Val
                325
```

<210> SEQ ID NO 18
<211> LENGTH: 990

```
<212> TYPE: DNA
<213> ORGANISM: Homo Sapiens
<220> FEATURE:
<221> NAME/KEY: CDS
<222> LOCATION: (1)...(990)

<400> SEQUENCE: 18 atg gac ggc cct gtg gca gag cat gcc aag cag gag ccc ttt cac gtg      48
Met Asp Gly Pro Val Ala Glu His Ala Lys Gln Glu Pro Phe His Val
 1               5                  10                  15 gtc aca cct ctg ttg gag agc tgg gcg ctg tcc cag gtg gcg ggc atg      96
Val Thr Pro Leu Leu Glu Ser Trp Ala Leu Ser Gln Val Ala Gly Met
             20                  25                  30 cct gtc ttc ctc aag tgt gag aat gtg cag ccc agc ggc tcc ttc aag     144
Pro Val Phe Leu Lys Cys Glu Asn Val Gln Pro Ser Gly Ser Phe Lys
         35                  40                  45 att cgg ggc att ggg cat ttc tgc cag gag atg gcc aag aag gga tgc     192
Ile Arg Gly Ile Gly His Phe Cys Gln Glu Met Ala Lys Lys Gly Cys
 50                  55                  60 aga cac ctg gtg tgc tcc tca ggg ggt aat gcg ggc atc gct gct gcc     240
Arg His Leu Val Cys Ser Ser Gly Gly Asn Ala Gly Ile Ala Ala Ala
 65                  70                  75                  80 tat gct gct agg aag ctg ggc att cct gcc acc atc gtg ctc ccc gag     288
Tyr Ala Ala Arg Lys Leu Gly Ile Pro Ala Thr Ile Val Leu Pro Glu
                 85                  90                  95 agc acc tcc ctg cag gtg gtg cag agg ctg cag gcg gag ggg gcc gag     336
Ser Thr Ser Leu Gln Val Val Gln Arg Leu Gln Ala Glu Gly Ala Glu
            100                 105                 110 gtt cag ctg act gga aag gtc tgg gac gag gcc aat ctg agg gcg caa     384
Val Gln Leu Thr Gly Lys Val Trp Asp Glu Ala Asn Leu Arg Ala Gln
        115                 120                 125 gag ttg gcc aag agg gac ggc tgg gag aat gtc ccc ccg ttt gac cac     432
Glu Leu Ala Lys Arg Asp Gly Trp Glu Asn Val Pro Pro Phe Asp His
    130                 135                 140 ccc cta ata tgg aaa ggc cac gcc agc ctg gtg cag gag ctg aaa gca     480
Pro Leu Ile Trp Lys Gly His Ala Ser Leu Val Gln Glu Leu Lys Ala
145                 150                 155                 160 gtg ctg agg acc cca cca ggt gcc ctg gtg ctg gca gtt ggg ggt ggg     528
Val Leu Arg Thr Pro Pro Gly Ala Leu Val Leu Ala Val Gly Gly Gly
                165                 170                 175 ggt ctc ctg gcc ggg gtg gtg gct ggc ctg ctg gag gtg ggc tgg cag     576
Gly Leu Leu Ala Gly Val Val Ala Gly Leu Leu Glu Val Gly Trp Gln
            180                 185                 190 cat gta ccc atc att gcc atg gag acc cat ggg gca cac tgc ttc aat     624
His Val Pro Ile Ile Ala Met Glu Thr His Gly Ala His Cys Phe Asn
        195                 200                 205 gcg gcc atc aca gcc ggc aag ctg gtc aca ctt cca gac atc acc agt     672
Ala Ala Ile Thr Ala Gly Lys Leu Val Thr Leu Pro Asp Ile Thr Ser
    210                 215                 220 gtg gcc aag agc ctg ggt gcc aag acg gtg gcc gct cgg gcc ctg gag     720
Val Ala Lys Ser Leu Gly Ala Lys Thr Val Ala Ala Arg Ala Leu Glu
225                 230                 235                 240 tgc atg cag gtg tgc aag att cac tct gaa gtg gtg gag gac acc gag     768
Cys Met Gln Val Cys Lys Ile His Ser Glu Val Val Glu Asp Thr Glu
                245                 250                 255 gct gtg agc gct gtg cag cag ctc ctg gat gat gag cgt atg ctg gtg     816
Ala Val Ser Ala Val Gln Gln Leu Leu Asp Asp Glu Arg Met Leu Val
            260                 265                 270 gag cct gcc tgt ggg gca gcc tta gca gcc atc tac tca ggc ctc ctg     864
Glu Pro Ala Cys Gly Ala Ala Leu Ala Ala Ile Tyr Ser Gly Leu Leu
        275                 280                 285
```

-continued

```
cgg agg ctc cag gcc gag ggc tgc ctg ccc cct tcc ctg act tca gtt    912
Arg Arg Leu Gln Ala Glu Gly Cys Leu Pro Pro Ser Leu Thr Ser Val
    290                 295                 300 gtg gta atc gtg tgt gga ggc aac aac atc aac agc cga gag ctg cag    960
Val Val Ile Val Cys Gly Gly Asn Asn Ile Asn Ser Arg Glu Leu Gln
305                 310                 315                 320 gcc ttg aaa acc cac ctg ggc cag gtc tga                            990
Ala Leu Lys Thr His Leu Gly Gln Val *
                325

<210> SEQ ID NO 19
<211> LENGTH: 15
<212> TYPE: PRT
<213> ORGANISM: Artificial Sequence
<220> FEATURE:
<223> OTHER INFORMATION: Serine/Threonine Dehydratase
      Pyridoxal-Phosphate Attachment Site Conserved Sequence
<220> FEATURE:
<221> NAME/KEY: VARIANT
<222> LOCATION: (1)...(1)
<223> OTHER INFORMATION: Xaa = Asp, Glu, Ser or His
<220> FEATURE:
<221> NAME/KEY: VARIANT
<222> LOCATION: (2)...(6)
<223> OTHER INFORMATION: Xaa = Any Amino Acid
<220> FEATURE:
<221> NAME/KEY: VARIANT
<222> LOCATION: (7)...(7)
<223> OTHER INFORMATION: Xaa = Ser, Thr, Val or Gly
<220> FEATURE:
<221> NAME/KEY: VARIANT
<222> LOCATION: (8)...(8)
<223> OTHER INFORMATION: Xaa = Any Amino Acid
<220> FEATURE:
<221> NAME/KEY: VARIANT
<222> LOCATION: (9)...(9)
<223> OTHER INFORMATION: Xaa = Ala or Ser
<220> FEATURE:
<221> NAME/KEY: VARIANT
<222> LOCATION: (10)...(10)
<223> OTHER INFORMATION: Xaa = Phe, Tyr or Ile
<220> FEATURE:
<221> NAME/KEY: VARIANT
<222> LOCATION: (12)...(12)
<223> OTHER INFORMATION: Xaa = Any Amino Acid
<220> FEATURE:
<221> NAME/KEY: VARIANT
<222> LOCATION: (13)...(13)
<223> OTHER INFORMATION: Xaa = Arg, Val, Met or Phe
<220> FEATURE:
<221> NAME/KEY: VARIANT
<222> LOCATION: (14)...(14)
<223> OTHER INFORMATION: Xaa = Gly or Ala
<220> FEATURE:
<221> NAME/KEY: VARIANT
<222> LOCATION: (15)...(15)
<223> OTHER INFORMATION: Xaa = Leu, Ile, Val, Met, Gly or Ala

<400> SEQUENCE: 19

Xaa Xaa Xaa Xaa Xaa Xaa Xaa Xaa Xaa Xaa Lys Xaa Xaa Xaa Xaa
1               5                   10                  15

<210> SEQ ID NO 20
<211> LENGTH: 3669
<212> TYPE: DNA
<213> ORGANISM: Homo Sapiens
<220> FEATURE:
<221> NAME/KEY: CDS
<222> LOCATION: (106)...(2859)

<400> SEQUENCE: 20
ccacgcgtcc ggcctggact ggaagcgtgc aacactccag agtcgtagga gtgaacactg    60
```

-continued

```
cacaggaatc tctgcccatc tcaggagaaa ccaaacttgg ggaaa atg ttt gcg gtc      117
                                              Met Phe Ala Val
                                                1 cac ttg atg gca ttt tac ttc agc aag ctg aag gag gac cag atc aag        165
His Leu Met Ala Phe Tyr Phe Ser Lys Leu Lys Glu Asp Gln Ile Lys
 5                  10                  15                  20 aag gtg gac agg ttc ctg tat cac atg cgg ctc tcc gat gac acc ctt        213
Lys Val Asp Arg Phe Leu Tyr His Met Arg Leu Ser Asp Asp Thr Leu
                25                  30                  35 ttg gac atc atg agg cgg ttc cgg gct gag atg gag aag ggc ctg gca        261
Leu Asp Ile Met Arg Arg Phe Arg Ala Glu Met Glu Lys Gly Leu Ala
            40                  45                  50 aag gac acc aac ccc acg gct gca gtg aag atg ttg ccc acc ttc gtc        309
Lys Asp Thr Asn Pro Thr Ala Ala Val Lys Met Leu Pro Thr Phe Val
                55                  60                  65 agg gcc att ccc gat ggt tcc gaa aat ggg gag ttc ctt tcc ctg gat        357
Arg Ala Ile Pro Asp Gly Ser Glu Asn Gly Glu Phe Leu Ser Leu Asp
        70                  75                  80 ctc gga ggg tcc aag ttc cga gtg ctg aag gtg caa gtc gct gaa gag        405
Leu Gly Gly Ser Lys Phe Arg Val Leu Lys Val Gln Val Ala Glu Glu
 85                  90                  95                 100 ggg aag cga cac gtg cag atg gag agt cag ttc tac cca acg ccc aat        453
Gly Lys Arg His Val Gln Met Glu Ser Gln Phe Tyr Pro Thr Pro Asn
                105                 110                 115 gaa atc atc cgc ggg aac ggc ata gag ctg ttt gaa tat gta gct gac        501
Glu Ile Ile Arg Gly Asn Gly Ile Glu Leu Phe Glu Tyr Val Ala Asp
            120                 125                 130 tgt ctg gca gat ttc atg aag acc aaa gat tta aag cat aag aaa ttg        549
Cys Leu Ala Asp Phe Met Lys Thr Lys Asp Leu Lys His Lys Lys Leu
                135                 140                 145 ccc ctt ggc cta act ttt tct ttc ccc tgt cga cag act aaa ctg gaa        597
Pro Leu Gly Leu Thr Phe Ser Phe Pro Cys Arg Gln Thr Lys Leu Glu
        150                 155                 160 gag ggt gtc cta ctt tcg tgg aca aaa aag ttt aag gca cga gga gtt        645
Glu Gly Val Leu Leu Ser Trp Thr Lys Lys Phe Lys Ala Arg Gly Val
165                 170                 175                 180 cag gac acg gat gtg gtg agc cgt ctg acc aaa gcc atg aga aga cac        693
Gln Asp Thr Asp Val Val Ser Arg Leu Thr Lys Ala Met Arg Arg His
                185                 190                 195 aag gac atg gac gtg gac atc ctg gcc ctg gtc aat gac acc gtg ggg        741
Lys Asp Met Asp Val Asp Ile Leu Ala Leu Val Asn Asp Thr Val Gly
            200                 205                 210 acc atg atg acc tgt gcc tat gac gac ccc tac tgc gaa gtt ggt gtc        789
Thr Met Met Thr Cys Ala Tyr Asp Asp Pro Tyr Cys Glu Val Gly Val
                215                 220                 225 atc atc gga act ggc acc aat gcg tgt tac atg gag gac atg agc aac        837
Ile Ile Gly Thr Gly Thr Asn Ala Cys Tyr Met Glu Asp Met Ser Asn
        230                 235                 240 att gac ctg gtg gag ggc gac gag ggc agg atg tgc atc aac aca gag        885
Ile Asp Leu Val Glu Gly Asp Glu Gly Arg Met Cys Ile Asn Thr Glu
245                 250                 255                 260 tgg ggg gcc ttc ggg gac gac ggg gcc ctg gag gac att cgc act gag        933
Trp Gly Ala Phe Gly Asp Asp Gly Ala Leu Glu Asp Ile Arg Thr Glu
                265                 270                 275 ttc gac agg gag ctg gac ctc ggc tct ctc aac cca gga aag caa ctg        981
Phe Asp Arg Glu Leu Asp Leu Gly Ser Leu Asn Pro Gly Lys Gln Leu
            280                 285                 290 ttc gag aag atg atc agt ggc ctg tac ctg ggg gag ctt gtc agg ctt       1029
Phe Glu Lys Met Ile Ser Gly Leu Tyr Leu Gly Glu Leu Val Arg Leu
```

-continued

```
                295                 300                 305
atc ttg ctg aag atg gcc aag gct ggc ctc ctg ttt ggt ggt gag aaa    1077
Ile Leu Leu Lys Met Ala Lys Ala Gly Leu Leu Phe Gly Gly Glu Lys
        310                 315                 320 tct tct gct ctc cac act aag ggc aag atc gaa aca cgg cac gtg gct    1125
Ser Ser Ala Leu His Thr Lys Gly Lys Ile Glu Thr Arg His Val Ala
325                 330                 335                 340 gcc atg gag aag tat aaa gaa ggc ctt gct aat aca aga gag atc ctg    1173
Ala Met Glu Lys Tyr Lys Glu Gly Leu Ala Asn Thr Arg Glu Ile Leu
                345                 350                 355 gtg gac ctg ggt ctg gaa ccg tct gag gct gac tgc att gcc gtc cag    1221
Val Asp Leu Gly Leu Glu Pro Ser Glu Ala Asp Cys Ile Ala Val Gln
        360                 365                 370 cat gtc tgt acc atc gtc tcc ttc cgc tcg gcc aat ctc tgt gca gca    1269
His Val Cys Thr Ile Val Ser Phe Arg Ser Ala Asn Leu Cys Ala Ala
375                 380                 385 gct ctg gcg gcc atc ctg aca cgc ctc cgg gag aac aag aag gtg gaa    1317
Ala Leu Ala Ala Ile Leu Thr Arg Leu Arg Glu Asn Lys Lys Val Glu
                390                 395                 400 cgg ctc cgg acc aca gtg ggc atg gac ggc acc ctc tac aag ata cac    1365
Arg Leu Arg Thr Thr Val Gly Met Asp Gly Thr Leu Tyr Lys Ile His
405                 410                 415                 420 cct cag tac cca aaa cgc ctg cac aag gtg gtg agg aaa ctg gtc cca    1413
Pro Gln Tyr Pro Lys Arg Leu His Lys Val Val Arg Lys Leu Val Pro
                425                 430                 435 agc tgt gat gtc cgc ttc ctc ctg tca gag agt ggc agc acc aag ggg    1461
Ser Cys Asp Val Arg Phe Leu Leu Ser Glu Ser Gly Ser Thr Lys Gly
        440                 445                 450 gcc gcc atg gtg acc gcg gtg gcc tcc cgc gtg cag gcc cag cgg aag    1509
Ala Ala Met Val Thr Ala Val Ala Ser Arg Val Gln Ala Gln Arg Lys
                455                 460                 465 cag atc gac agg gtg ctg gct ttg ttc cag ctg acc cga gag cag ctc    1557
Gln Ile Asp Arg Val Leu Ala Leu Phe Gln Leu Thr Arg Glu Gln Leu
        470                 475                 480 gtg gac gtg cag gcc aag atg cgg gct gag ctg gag tat ggg ctg aag    1605
Val Asp Val Gln Ala Lys Met Arg Ala Glu Leu Glu Tyr Gly Leu Lys
485                 490                 495                 500 aag aag agc cac ggg ctg gcc acg gtc agg atg ctg ccc acc tac gtc    1653
Lys Lys Ser His Gly Leu Ala Thr Val Arg Met Leu Pro Thr Tyr Val
                505                 510                 515 tgc ggg ctg ccg gac ggc aca gag aaa gga aag ttt ctc gcc ctg gat    1701
Cys Gly Leu Pro Asp Gly Thr Glu Lys Gly Lys Phe Leu Ala Leu Asp
        520                 525                 530 ctt ggg gga acc aac ttc cgg gtc ctc ctg gtg aag atc aga agt gga    1749
Leu Gly Gly Thr Asn Phe Arg Val Leu Leu Val Lys Ile Arg Ser Gly
        535                 540                 545 cgg agg tca gtg cga atg tac aac aag atc ttc gcc atc ccc ctg gag    1797
Arg Arg Ser Val Arg Met Tyr Asn Lys Ile Phe Ala Ile Pro Leu Glu
550                 555                 560 atc atg cag ggc act ggt gag gag ctc ttt gat cac att gtg cag tgc    1845
Ile Met Gln Gly Thr Gly Glu Glu Leu Phe Asp His Ile Val Gln Cys
565                 570                 575                 580 atc gcc gac ttc ctg gac tac atg ggc ctc aag gga gcc tcc cta cct    1893
Ile Ala Asp Phe Leu Asp Tyr Met Gly Leu Lys Gly Ala Ser Leu Pro
                585                 590                 595 ttg ggc ttc aca ttc tca ttt ccc tgc agg cag atg agc att gac aag    1941
Leu Gly Phe Thr Phe Ser Phe Pro Cys Arg Gln Met Ser Ile Asp Lys
                600                 605                 610 gga aca ctc ata ggg tgg acc aaa ggt ttc aag gcc act gac tgt gaa    1989
```

-continued

```
                Gly Thr Leu Ile Gly Trp Thr Lys Gly Phe Lys Ala Thr Asp Cys Glu
                            615                 620                 625 ggg gag gac gtg gtg gac atg ctc agg gaa gcc atc aag agg aga aac        2037
Gly Glu Asp Val Val Asp Met Leu Arg Glu Ala Ile Lys Arg Arg Asn
630                 635                 640 gag ttt gac ctg gac att gtt gca gtc gtg aat gat aca gtg ggg acc        2085
Glu Phe Asp Leu Asp Ile Val Ala Val Val Asn Asp Thr Val Gly Thr
645                 650                 655                 660 atg atg acc tgt ggc tat gaa gat cct aat tgt gag att ggc ctg att        2133
Met Met Thr Cys Gly Tyr Glu Asp Pro Asn Cys Glu Ile Gly Leu Ile
                665                 670                 675 gca gga aca ggc agc aac atg tgc tac atg gag gac atg agg aac atc        2181
Ala Gly Thr Gly Ser Asn Met Cys Tyr Met Glu Asp Met Arg Asn Ile
            680                 685                 690 gag atg gtg gag ggg ggt gaa ggg aag atg tgc atc aat aca gag tgg        2229
Glu Met Val Glu Gly Gly Glu Gly Lys Met Cys Ile Asn Thr Glu Trp
        695                 700                 705 gga gga ttt gga gac aat ggc tgc ata gat gac atc cgg acc cga tac        2277
Gly Gly Phe Gly Asp Asn Gly Cys Ile Asp Asp Ile Arg Thr Arg Tyr
    710                 715                 720 gac acg gag gtg gat gag ggg tcc ttg aat cct ggc aag cag aga tac        2325
Asp Thr Glu Val Asp Glu Gly Ser Leu Asn Pro Gly Lys Gln Arg Tyr
725                 730                 735                 740 gag aaa atg acc agt ggg atg tac ttg ggg gag att gtg cgg cag atc        2373
Glu Lys Met Thr Ser Gly Met Tyr Leu Gly Glu Ile Val Arg Gln Ile
                745                 750                 755 ctg atc gac ctg acc aag cag ggt ctc ctc ttc cga ggg cag att tca        2421
Leu Ile Asp Leu Thr Lys Gln Gly Leu Leu Phe Arg Gly Gln Ile Ser
            760                 765                 770 gag cgt ctc cgg acc agg ggc atc ttc gaa acc aag ttc ctg tcc cag        2469
Glu Arg Leu Arg Thr Arg Gly Ile Phe Glu Thr Lys Phe Leu Ser Gln
        775                 780                 785 atc gaa agc gat cgg ctg gcc ctt ctc cag gtc agg agg att ctg cag        2517
Ile Glu Ser Asp Arg Leu Ala Leu Leu Gln Val Arg Arg Ile Leu Gln
    790                 795                 800 cag ctg ggc ctg gac agc acg tgt gag gac agc atc gtg gtg aag gag        2565
Gln Leu Gly Leu Asp Ser Thr Cys Glu Asp Ser Ile Val Val Lys Glu
805                 810                 815                 820 gtg tgc gga gcc gtg tcc cgg cgg gcg gcc cag ctc tgc ggt gct ggc        2613
Val Cys Gly Ala Val Ser Arg Arg Ala Ala Gln Leu Cys Gly Ala Gly
                825                 830                 835 ctg gcc gct ata gtg gaa aaa agg aga gaa gac cag ggg cta gag cac        2661
Leu Ala Ala Ile Val Glu Lys Arg Arg Glu Asp Gln Gly Leu Glu His
            840                 845                 850 ctg agg atc act gtg ggt gtg gac ggc acc ctg tac aag ctg cac cct        2709
Leu Arg Ile Thr Val Gly Val Asp Gly Thr Leu Tyr Lys Leu His Pro
        855                 860                 865 cac ttt tct aga ata ttg cag gaa act gtg aag gaa cta gcc cct cga        2757
His Phe Ser Arg Ile Leu Gln Glu Thr Val Lys Glu Leu Ala Pro Arg
    870                 875                 880 tgt gat gtg aca ttc atg ctg tca gaa gat ggc agt gga aaa ggg gca        2805
Cys Asp Val Thr Phe Met Leu Ser Glu Asp Gly Ser Gly Lys Gly Ala
885                 890                 895                 900 gca ctg atc act gct gtg gcc aag agg tta cag cag gca cag aag gag        2853
Ala Leu Ile Thr Ala Val Ala Lys Arg Leu Gln Gln Ala Gln Lys Glu
                905                 910                 915 aac tag gaaccctgg gattggacct gatgcatctt ggatactgaa cagcttttcc          2909
Asn * tctggcagat cagttggtca gagaccaatg ggcaccctcc tggctgacct caccttctgg      2969
```

-continued

```
atggccgaaa gagaacccca ggttctcggg tactcttagt atcttgtact ggatttgcag    3029
tgacattaca tgacatctct atttggtata tttgggccaa aatgggccaa cttatgaaat    3089
caaagtgtct gtcctgagag atccccttc aacacattgt tcaggtgagg cttgagctgt     3149
caattctcta tggctttcag tcttgtggct gcgggacttg gaaatatata gaatctgccc    3209
atgtggctgg caggctgttt ccccattggg atgcttaagc catctcttat agggattgg     3269 accctgtact tgtggatgaa cattggagag caagaggaac tcacgttatg aactagggg     3329 atctcatcta acttgtcctt aacttgccat gttgacttca aacctgttaa gagaacaaag    3389
actttgaagt atccagcccc agggtgcaga gaggttgatt gccagggagc actgcaggaa    3449
tcattgcatg cttaaagcga gttatgtcag caccctgtag gattttgttc cttattaagt    3509
gtgtgccatg tggtggggtg ctgtctgggg catctgtttt tcattttgcc tgtggtttgt    3569
gttgcagstg ttgatagttg ttttaaggat tgttaggtat aggaaatcca gtaaattaat    3629 aaaaaattt tgattttcca ataaaaaaaa aaaaaaaaa                            3669
```

<210> SEQ ID NO 21
<211> LENGTH: 917
<212> TYPE: PRT
<213> ORGANISM: Homo Sapiens

<400> SEQUENCE: 21

```
Met Phe Ala Val His Leu Met Ala Phe Tyr Phe Ser Lys Leu Lys Glu
 1               5                  10                  15

Asp Gln Ile Lys Lys Val Asp Arg Phe Leu Tyr His Met Arg Leu Ser
            20                  25                  30

Asp Asp Thr Leu Leu Asp Ile Met Arg Arg Phe Arg Ala Glu Met Glu
        35                  40                  45

Lys Gly Leu Ala Lys Asp Thr Asn Pro Thr Ala Ala Val Lys Met Leu
    50                  55                  60

Pro Thr Phe Val Arg Ala Ile Pro Asp Gly Ser Glu Asn Gly Glu Phe
65                  70                  75                  80

Leu Ser Leu Asp Leu Gly Gly Ser Lys Phe Arg Val Leu Lys Val Gln
                85                  90                  95

Val Ala Glu Glu Gly Lys Arg His Val Gln Met Glu Ser Gln Phe Tyr
           100                 105                 110

Pro Thr Pro Asn Glu Ile Ile Arg Gly Asn Gly Ile Glu Leu Phe Glu
       115                 120                 125

Tyr Val Ala Asp Cys Leu Ala Asp Phe Met Lys Thr Lys Asp Leu Lys
   130                 135                 140

His Lys Lys Leu Pro Leu Gly Leu Thr Phe Ser Phe Pro Cys Arg Gln
145                 150                 155                 160

Thr Lys Leu Glu Glu Gly Val Leu Leu Ser Trp Thr Lys Phe Lys
                165                 170                 175

Ala Arg Gly Val Gln Asp Thr Asp Val Val Ser Arg Leu Thr Lys Ala
           180                 185                 190

Met Arg Arg His Lys Asp Met Asp Val Asp Ile Leu Ala Leu Val Asn
       195                 200                 205

Asp Thr Val Gly Thr Met Met Thr Cys Ala Tyr Asp Asp Pro Tyr Cys
   210                 215                 220

Glu Val Gly Val Ile Ile Gly Thr Gly Thr Asn Ala Cys Tyr Met Glu
225                 230                 235                 240

Asp Met Ser Asn Ile Asp Leu Val Glu Gly Asp Glu Gly Arg Met Cys
```

-continued

```
                245                 250                 255
Ile Asn Thr Glu Trp Gly Ala Phe Gly Asp Asp Gly Ala Leu Glu Asp
                260                 265                 270
Ile Arg Thr Glu Phe Asp Arg Glu Leu Asp Leu Gly Ser Leu Asn Pro
                275                 280                 285
Gly Lys Gln Leu Phe Glu Lys Met Ile Ser Gly Leu Tyr Leu Gly Glu
            290                 295                 300
Leu Val Arg Leu Ile Leu Leu Lys Met Ala Lys Ala Gly Leu Leu Phe
305                 310                 315                 320
Gly Gly Glu Lys Ser Ser Ala Leu His Thr Lys Gly Lys Ile Glu Thr
                325                 330                 335
Arg His Val Ala Ala Met Glu Lys Tyr Lys Glu Gly Leu Ala Asn Thr
                340                 345                 350
Arg Glu Ile Leu Val Asp Leu Gly Leu Glu Pro Ser Glu Ala Asp Cys
                355                 360                 365
Ile Ala Val Gln His Val Cys Thr Ile Val Ser Phe Arg Ser Ala Asn
                370                 375                 380
Leu Cys Ala Ala Ala Leu Ala Ala Ile Leu Thr Arg Leu Arg Glu Asn
385                 390                 395                 400
Lys Lys Val Glu Arg Leu Arg Thr Thr Val Gly Met Asp Gly Thr Leu
                405                 410                 415
Tyr Lys Ile His Pro Gln Tyr Pro Lys Arg Leu His Lys Val Val Arg
                420                 425                 430
Lys Leu Val Pro Ser Cys Asp Val Arg Phe Leu Leu Ser Glu Ser Gly
                435                 440                 445
Ser Thr Lys Gly Ala Ala Met Val Thr Ala Val Ala Ser Arg Val Gln
            450                 455                 460
Ala Gln Arg Lys Gln Ile Asp Arg Val Leu Ala Leu Phe Gln Leu Thr
465                 470                 475                 480
Arg Glu Gln Leu Val Asp Val Gln Ala Lys Met Arg Ala Glu Leu Glu
                485                 490                 495
Tyr Gly Leu Lys Lys Lys Ser His Gly Leu Ala Thr Val Arg Met Leu
            500                 505                 510
Pro Thr Tyr Val Cys Gly Leu Pro Asp Gly Thr Glu Lys Gly Lys Phe
            515                 520                 525
Leu Ala Leu Asp Leu Gly Gly Thr Asn Phe Arg Val Leu Leu Val Lys
530                 535                 540
Ile Arg Ser Gly Arg Arg Ser Val Arg Met Tyr Asn Lys Ile Phe Ala
545                 550                 555                 560
Ile Pro Leu Glu Ile Met Gln Gly Thr Gly Glu Glu Leu Phe Asp His
                565                 570                 575
Ile Val Gln Cys Ile Ala Asp Phe Leu Asp Tyr Met Gly Leu Lys Gly
                580                 585                 590
Ala Ser Leu Pro Leu Gly Phe Thr Phe Ser Phe Pro Cys Arg Gln Met
                595                 600                 605
Ser Ile Asp Lys Gly Thr Leu Ile Gly Trp Thr Lys Gly Phe Lys Ala
            610                 615                 620
Thr Asp Cys Glu Gly Glu Asp Val Val Asp Met Leu Arg Glu Ala Ile
625                 630                 635                 640
Lys Arg Arg Asn Glu Phe Asp Leu Asp Ile Val Ala Val Val Asn Asp
                645                 650                 655
Thr Val Gly Thr Met Met Thr Cys Gly Tyr Glu Asp Pro Asn Cys Glu
                660                 665                 670
```

```
Ile Gly Leu Ile Ala Gly Thr Gly Ser Asn Met Cys Tyr Met Glu Asp
            675                 680                 685

Met Arg Asn Ile Glu Met Val Glu Gly Gly Glu Gly Lys Met Cys Ile
        690                 695                 700

Asn Thr Glu Trp Gly Gly Phe Gly Asp Asn Gly Cys Ile Asp Asp Ile
705                 710                 715                 720

Arg Thr Arg Tyr Asp Thr Glu Val Asp Glu Gly Ser Leu Asn Pro Gly
                725                 730                 735

Lys Gln Arg Tyr Glu Lys Met Thr Ser Gly Met Tyr Leu Gly Glu Ile
            740                 745                 750

Val Arg Gln Ile Leu Ile Asp Leu Thr Lys Gln Gly Leu Leu Phe Arg
        755                 760                 765

Gly Gln Ile Ser Glu Arg Leu Arg Thr Arg Gly Ile Phe Glu Thr Lys
    770                 775                 780

Phe Leu Ser Gln Ile Glu Ser Asp Arg Leu Ala Leu Leu Gln Val Arg
785                 790                 795                 800

Arg Ile Leu Gln Gln Leu Gly Leu Asp Ser Thr Cys Glu Asp Ser Ile
                805                 810                 815

Val Val Lys Glu Val Cys Gly Ala Val Ser Arg Arg Ala Ala Gln Leu
            820                 825                 830

Cys Gly Ala Gly Leu Ala Ala Ile Val Glu Lys Arg Arg Glu Asp Gln
        835                 840                 845

Gly Leu Glu His Leu Arg Ile Thr Val Gly Val Asp Gly Thr Leu Tyr
    850                 855                 860

Lys Leu His Pro His Phe Ser Arg Ile Leu Gln Glu Thr Val Lys Glu
865                 870                 875                 880

Leu Ala Pro Arg Cys Asp Val Thr Phe Met Leu Ser Glu Asp Gly Ser
                885                 890                 895

Gly Lys Gly Ala Ala Leu Ile Thr Ala Val Ala Lys Arg Leu Gln Gln
            900                 905                 910

Ala Gln Lys Glu Asn
        915

<210> SEQ ID NO 22
<211> LENGTH: 2754
<212> TYPE: DNA
<213> ORGANISM: Homo Sapiens
<220> FEATURE:
<221> NAME/KEY: CDS
<222> LOCATION: (1)...(2754)

<400> SEQUENCE: 22 atg ttt gcg gtc cac ttg atg gca ttt tac ttc agc aag ctg aag gag      48
Met Phe Ala Val His Leu Met Ala Phe Tyr Phe Ser Lys Leu Lys Glu
  1               5                  10                  15 gac cag atc aag aag gtg gac agg ttc ctg tat cac atg cgg ctc tcc      96
Asp Gln Ile Lys Lys Val Asp Arg Phe Leu Tyr His Met Arg Leu Ser
              20                  25                  30 gat gac acc ctt ttg gac atc atg agg cgg ttc cgg gct gag atg gag     144
Asp Asp Thr Leu Leu Asp Ile Met Arg Arg Phe Arg Ala Glu Met Glu
          35                  40                  45 aag ggc ctg gca aag gac acc aac ccc acg gct gca gtg aag atg ttg     192
Lys Gly Leu Ala Lys Asp Thr Asn Pro Thr Ala Ala Val Lys Met Leu
      50                  55                  60 ccc acc ttc gtc agg gcc att ccc gat ggt tcc gaa aat ggg gag ttc     240
Pro Thr Phe Val Arg Ala Ile Pro Asp Gly Ser Glu Asn Gly Glu Phe
 65                  70                  75                  80
```

-continued

```
ctt tcc ctg gat ctc gga ggg tcc aag ttc cga gtg ctg aag gtg caa        288
Leu Ser Leu Asp Leu Gly Gly Ser Lys Phe Arg Val Leu Lys Val Gln
             85                  90                  95 gtc gct gaa gag ggg aag cga cac gtg cag atg gag agt cag ttc tac        336
Val Ala Glu Glu Gly Lys Arg His Val Gln Met Glu Ser Gln Phe Tyr
        100                 105                 110 cca acg ccc aat gaa atc atc cgc ggg aac ggc ata gag ctg ttt gaa        384
Pro Thr Pro Asn Glu Ile Ile Arg Gly Asn Gly Ile Glu Leu Phe Glu
    115                 120                 125 tat gta gct gac tgt ctg gca gat ttc atg aag acc aaa gat tta aag        432
Tyr Val Ala Asp Cys Leu Ala Asp Phe Met Lys Thr Lys Asp Leu Lys
130                 135                 140 cat aag aaa ttg ccc ctt ggc cta act ttt tct ttc ccc tgt cga cag        480
His Lys Lys Leu Pro Leu Gly Leu Thr Phe Ser Phe Pro Cys Arg Gln
145                 150                 155                 160 act aaa ctg gaa gag ggt gtc cta ctt tcg tgg aca aaa aag ttt aag        528
Thr Lys Leu Glu Glu Gly Val Leu Leu Ser Trp Thr Lys Lys Phe Lys
                165                 170                 175 gca cga gga gtt cag gac acg gat gtg gtg agc cgt ctg acc aaa gcc        576
Ala Arg Gly Val Gln Asp Thr Asp Val Val Ser Arg Leu Thr Lys Ala
            180                 185                 190 atg aga aga cac aag gac atg gac gtg gac atc ctg gcc ctg gtc aat        624
Met Arg Arg His Lys Asp Met Asp Val Asp Ile Leu Ala Leu Val Asn
        195                 200                 205 gac acc gtg ggg acc atg atg acc tgt gcc tat gac gac ccc tac tgc        672
Asp Thr Val Gly Thr Met Met Thr Cys Ala Tyr Asp Asp Pro Tyr Cys
    210                 215                 220 gaa gtt ggt gtc atc atc gga act ggc acc aat gcg tgt tac atg gag        720
Glu Val Gly Val Ile Ile Gly Thr Gly Thr Asn Ala Cys Tyr Met Glu
225                 230                 235                 240 gac atg agc aac att gac ctg gtg gag ggc gac gag ggc agg atg tgc        768
Asp Met Ser Asn Ile Asp Leu Val Glu Gly Asp Glu Gly Arg Met Cys
                245                 250                 255 atc aac aca gag tgg ggg gcc ttc ggg gac gac ggg gcc ctg gag gac        816
Ile Asn Thr Glu Trp Gly Ala Phe Gly Asp Asp Gly Ala Leu Glu Asp
            260                 265                 270 att cgc act gag ttc gac agg gag ctg gac ctc ggc tct ctc aac cca        864
Ile Arg Thr Glu Phe Asp Arg Glu Leu Asp Leu Gly Ser Leu Asn Pro
        275                 280                 285 gga aag caa ctg ttc gag aag atg atc agt ggc ctg tac ctg ggg gag        912
Gly Lys Gln Leu Phe Glu Lys Met Ile Ser Gly Leu Tyr Leu Gly Glu
    290                 295                 300 ctt gtc agg ctt atc ttg ctg aag atg gcc aag gct ggc ctc ctg ttt        960
Leu Val Arg Leu Ile Leu Leu Lys Met Ala Lys Ala Gly Leu Leu Phe
305                 310                 315                 320 ggt ggt gag aaa tct tct gct ctc cac act aag ggc aag atc gaa aca       1008
Gly Gly Glu Lys Ser Ser Ala Leu His Thr Lys Gly Lys Ile Glu Thr
                325                 330                 335 cgg cac gtg gct gcc atg gag aag tat aaa gaa ggc ctt gct aat aca       1056
Arg His Val Ala Ala Met Glu Lys Tyr Lys Glu Gly Leu Ala Asn Thr
            340                 345                 350 aga gag atc ctg gtg gac ctg ggt ctg gaa ccg tct gag gct gac tgc       1104
Arg Glu Ile Leu Val Asp Leu Gly Leu Glu Pro Ser Glu Ala Asp Cys
        355                 360                 365 att gcc gtc cag cat gtc tgt acc atc gtc tcc ttc cgc tcg gcc aat       1152
Ile Ala Val Gln His Val Cys Thr Ile Val Ser Phe Arg Ser Ala Asn
    370                 375                 380 ctc tgt gca gca gct ctg gcg gcc atc ctg aca cgc ctc cgg gag aac       1200
Leu Cys Ala Ala Ala Leu Ala Ala Ile Leu Thr Arg Leu Arg Glu Asn
```

-continued

```
           385                 390                 395                 400
aag aag gtg gaa cgg ctc cgg acc aca gtg ggc atg gac ggc acc ctc      1248
Lys Lys Val Glu Arg Leu Arg Thr Thr Val Gly Met Asp Gly Thr Leu
                    405                 410                 415 tac aag ata cac cct cag tac cca aaa cgc ctg cac aag gtg gtg agg      1296
Tyr Lys Ile His Pro Gln Tyr Pro Lys Arg Leu His Lys Val Val Arg
                420                 425                 430 aaa ctg gtc cca agc tgt gat gtc cgc ttc ctc ctg tca gag agt ggc      1344
Lys Leu Val Pro Ser Cys Asp Val Arg Phe Leu Leu Ser Glu Ser Gly
            435                 440                 445 agc acc aag ggg gcc gcc atg gtg acc gcg gtg gcc tcc cgc gtg cag      1392
Ser Thr Lys Gly Ala Ala Met Val Thr Ala Val Ala Ser Arg Val Gln
        450                 455                 460 gcc cag cgg aag cag atc gac agg gtg ctg gct ttg ttc cag ctg acc      1440
Ala Gln Arg Lys Gln Ile Asp Arg Val Leu Ala Leu Phe Gln Leu Thr
465                 470                 475                 480 cga gag cag ctc gtg gac gtg cag gcc aag atg cgg gct gag ctg gag      1488
Arg Glu Gln Leu Val Asp Val Gln Ala Lys Met Arg Ala Glu Leu Glu
                485                 490                 495 tat ggg ctg aag aag aag agc cac ggg ctg gcc acg gtc agg atg ctg      1536
Tyr Gly Leu Lys Lys Lys Ser His Gly Leu Ala Thr Val Arg Met Leu
                500                 505                 510 ccc acc tac gtc tgc ggg ctg ccg gac ggc aca gag aaa gga aag ttt      1584
Pro Thr Tyr Val Cys Gly Leu Pro Asp Gly Thr Glu Lys Gly Lys Phe
            515                 520                 525 ctc gcc ctg gat ctt ggg gga acc aac ttc cgg gtc ctc ctg gtg aag      1632
Leu Ala Leu Asp Leu Gly Gly Thr Asn Phe Arg Val Leu Leu Val Lys
        530                 535                 540 atc aga agt gga cgg agg tca gtg cga atg tac aac aag atc ttc gcc      1680
Ile Arg Ser Gly Arg Arg Ser Val Arg Met Tyr Asn Lys Ile Phe Ala
545                 550                 555                 560 atc ccc ctg gag atc atg cag ggc act ggt gag gag ctc ttt gat cac      1728
Ile Pro Leu Glu Ile Met Gln Gly Thr Gly Glu Glu Leu Phe Asp His
                565                 570                 575 att gtg cag tgc atc gcc gac ttc ctg gac tac atg ggc ctc aag gga      1776
Ile Val Gln Cys Ile Ala Asp Phe Leu Asp Tyr Met Gly Leu Lys Gly
                580                 585                 590 gcc tcc cta cct ttg ggc ttc aca ttc tca ttt ccc tgc agg cag atg      1824
Ala Ser Leu Pro Leu Gly Phe Thr Phe Ser Phe Pro Cys Arg Gln Met
            595                 600                 605 agc att gac aag gga aca ctc ata ggg tgg acc aaa ggt ttc aag gcc      1872
Ser Ile Asp Lys Gly Thr Leu Ile Gly Trp Thr Lys Gly Phe Lys Ala
        610                 615                 620 act gac tgt gaa ggg gag gac gtg gtg gac atg ctc agg gaa gcc atc      1920
Thr Asp Cys Glu Gly Glu Asp Val Val Asp Met Leu Arg Glu Ala Ile
625                 630                 635                 640 aag agg aga aac gag ttt gac ctg gac att gtt gca gtc gtg aat gat      1968
Lys Arg Arg Asn Glu Phe Asp Leu Asp Ile Val Ala Val Val Asn Asp
                645                 650                 655 aca gtg ggg acc atg atg acc tgt ggc tat gaa gat cct aat tgt gag      2016
Thr Val Gly Thr Met Met Thr Cys Gly Tyr Glu Asp Pro Asn Cys Glu
                660                 665                 670 att ggc ctg att gca gga aca ggc agc aac atg tgc tac atg gag gac      2064
Ile Gly Leu Ile Ala Gly Thr Gly Ser Asn Met Cys Tyr Met Glu Asp
            675                 680                 685 atg agg aac atc gag atg gtg gag ggg ggt gaa ggg aag atg tgc atc      2112
Met Arg Asn Ile Glu Met Val Glu Gly Gly Glu Gly Lys Met Cys Ile
        690                 695                 700 aat aca gag tgg gga gga ttt gga gac aat ggc tgc ata gat gac atc      2160
```

| | | | | | | | | | | | | | | | | |
|---|---|---|---|---|---|---|---|---|---|---|---|---|---|---|---|---|
|Asn|Thr|Glu|Trp|Gly|Gly|Phe|Gly|Asp|Asn|Gly|Cys|Ile|Asp|Asp|Ile| |
|705| | | |710| | | |715| | | |720| | | | |

```
cgg acc cga tac gac acg gag gtg gat gag ggg tcc ttg aat cct ggc      2208
Arg Thr Arg Tyr Asp Thr Glu Val Asp Glu Gly Ser Leu Asn Pro Gly
                725                 730                 735 aag cag aga tac gag aaa atg acc agt ggg atg tac ttg ggg gag att      2256
Lys Gln Arg Tyr Glu Lys Met Thr Ser Gly Met Tyr Leu Gly Glu Ile
            740                 745                 750 gtg cgg cag atc ctg atc gac ctg acc aag cag ggt ctc ctc ttc cga      2304
Val Arg Gln Ile Leu Ile Asp Leu Thr Lys Gln Gly Leu Leu Phe Arg
        755                 760                 765 ggg cag att tca gag cgt ctc cgg acc agg ggc atc ttc gaa acc aag      2352
Gly Gln Ile Ser Glu Arg Leu Arg Thr Arg Gly Ile Phe Glu Thr Lys
    770                 775                 780 ttc ctg tcc cag atc gaa agc gat cgg ctg gcc ctt ctc cag gtc agg      2400
Phe Leu Ser Gln Ile Glu Ser Asp Arg Leu Ala Leu Leu Gln Val Arg
785                 790                 795                 800 agg att ctg cag cag ctg ggc ctg gac agc acg tgt gag gac agc atc      2448
Arg Ile Leu Gln Gln Leu Gly Leu Asp Ser Thr Cys Glu Asp Ser Ile
                805                 810                 815 gtg gtg aag gag gtg tgc gga gcc gtg tcc cgg cgg gcg gcc cag ctc      2496
Val Val Lys Glu Val Cys Gly Ala Val Ser Arg Arg Ala Ala Gln Leu
            820                 825                 830 tgc ggt gct ggc ctg gcc gct ata gtg gaa aaa agg aga gaa gac cag      2544
Cys Gly Ala Gly Leu Ala Ala Ile Val Glu Lys Arg Arg Glu Asp Gln
        835                 840                 845 ggg cta gag cac ctg agg atc act gtg ggt gtg gac ggc acc ctg tac      2592
Gly Leu Glu His Leu Arg Ile Thr Val Gly Val Asp Gly Thr Leu Tyr
    850                 855                 860 aag ctg cac cct cac ttt tct aga ata ttg cag gaa act gtg aag gaa      2640
Lys Leu His Pro His Phe Ser Arg Ile Leu Gln Glu Thr Val Lys Glu
865                 870                 875                 880 cta gcc cct cga tgt gat gtg aca ttc atg ctg tca gaa gat ggc agt      2688
Leu Ala Pro Arg Cys Asp Val Thr Phe Met Leu Ser Glu Asp Gly Ser
                885                 890                 895 gga aaa ggg gca gca ctg atc act gct gtg gcc aag agg tta cag cag      2736
Gly Lys Gly Ala Ala Leu Ile Thr Ala Val Ala Lys Arg Leu Gln Gln
            900                 905                 910 gca cag aag gag aac tag                                              2754
Ala Gln Lys Glu Asn *
        915

<210> SEQ ID NO 23
<211> LENGTH: 482
<212> TYPE: PRT
<213> ORGANISM: Artificial Sequence
<220> FEATURE:
<223> OTHER INFORMATION: Consensus Sequence

<400> SEQUENCE: 23

Ala Asp Leu Leu Gln Ala Val Glu Glu Leu Asp Asp Phe Thr Val
1               5                   10                  15

Ser Thr Glu Thr Leu Arg Glu Val Thr Lys Arg Phe Ile Lys Glu Met
                20                  25                  30

Glu Lys Gly Leu Ser Pro Pro Lys Glu Gly Gly Asn Thr Ala Ser Val
            35                  40                  45

Val Lys Met Leu Pro Thr Phe Val Arg Ser Thr Pro Thr Gly Thr Glu
        50                  55                  60

Lys Gly Asp Phe Leu Ala Leu Asp Leu Gly Gly Thr Asn Phe Arg Val
65                  70                  75                  80
```

-continued

Leu Leu Val Lys Leu Gly Gly Asn Gly Lys Gly Val Glu Met Thr Gln
             85                  90                  95

Ser Lys Tyr Arg Ile Pro Glu Glu Leu Met Thr Gly Glu Asn Val Thr
            100                 105                 110

Gly Glu Gln Leu Phe Asp Phe Ile Ala Glu Cys Ile Lys Asp Phe Met
            115                 120                 125

Asp Glu Gln Phe Pro Lys Gly Lys Glu Pro Leu Pro Leu Gly Phe
        130                 135                 140

Thr Phe Ser Phe Pro Cys Ser Gln Thr Ser Ile Asn Glu Gly Ile Leu
145                 150                 155                 160

Ile Arg Trp Thr Lys Gly Phe Lys Ile Gly Arg Ala Thr Asn Ser Gly
                165                 170                 175

Val Glu Gly His Asp Val Val Gln Leu Leu Arg Glu Ala Ile Lys Arg
            180                 185                 190

Arg Gly Ala Phe Pro Ile Asp Val Val Ala Val Val Asn Asp Thr Val
        195                 200                 205

Gly Thr Leu Met Ser Cys Ala Tyr Thr Lys Gly Arg Gly Asp Pro Glu
    210                 215                 220

Cys Glu Thr Val Ile Gly Leu Ile Val Gly Thr Gly Thr Asn Ala Cys
225                 230                 235                 240

Tyr Met Glu Glu Met Arg Asn Ile Glu Lys Leu Glu Gly Lys Leu Lys
                245                 250                 255

Asp Asp Ile Pro Asp Glu Gly Arg Met Cys Ile Asn Met Glu Trp Gly
            260                 265                 270

Ala Phe Gly Asp Asn Gly His Leu Asp Leu Pro Arg Thr Lys Tyr Asp
        275                 280                 285

Val Val Ile Asp Glu Glu Ser Pro Asn Pro Gly Gln Gln Leu Phe Glu
    290                 295                 300

Lys Met Ile Ser Gly Met Tyr Leu Gly Glu Ile Val Arg Leu Ile Leu
305                 310                 315                 320

Leu Asp Leu Thr Lys Glu Gly Leu Leu Phe Lys Gly Gln Asp Ser Pro
                325                 330                 335

Lys Leu Lys Thr Arg Gly Ser Phe Glu Thr Ser Val Leu Ser Arg Ile
            340                 345                 350

Glu Ser Asp Pro Ser Glu Asn Leu Glu Asp Val Arg Ala Ile Leu Gln
        355                 360                 365

Thr Ala Leu Gly Leu Glu Thr Thr Asp Glu Glu Arg Lys Leu Val Arg
    370                 375                 380

Arg Val Cys Glu Ala Val Ser Thr Arg Ala Ala Arg Leu Cys Ala Ala
385                 390                 395                 400

Gly Leu Ala Ala Ile Leu Lys Lys Ile Arg Glu Asn Arg Gly Arg Glu
                405                 410                 415

Arg Leu Lys Val Thr Val Gly Val Asp Gly Ser Val Tyr Lys Leu Tyr
            420                 425                 430

Pro Gly Phe Lys Glu Arg Leu Ala Glu Ala Leu Arg Asp Leu Leu Pro
        435                 440                 445

Asp Cys Glu Gly Ser Glu Glu Asp Lys Lys Val Ser Ile Ile Pro Ala
    450                 455                 460

Glu Asp Gly Ser Gly Lys Gly Ala Ala Leu Val Ala Ala Val Ala Ala
465                 470                 475                 480

Lys Leu

```
<210> SEQ ID NO 24
<211> LENGTH: 26
<212> TYPE: PRT
<213> ORGANISM: Artificial Sequence
<220> FEATURE:
<223> OTHER INFORMATION: Hexokinase Signature Domain
<220> FEATURE:
<221> NAME/KEY: VARIANT
<222> LOCATION: (10)...(10)
<223> OTHER INFORMATION: Xaa = Any Amino Acid
<220> FEATURE:
<221> NAME/KEY: VARIANT
<222> LOCATION: (12)...(12)
<223> OTHER INFORMATION: Xaa = Any Amino Acid
<220> FEATURE:
<221> NAME/KEY: VARIANT
<222> LOCATION: (15)...(16)
<223> OTHER INFORMATION: Xaa = Any Amino Acid
<220> FEATURE:
<221> NAME/KEY: VARIANT
<222> LOCATION: (18)...(18)
<223> OTHER INFORMATION: Xaa = Any Amino Acid
<220> FEATURE:
<221> NAME/KEY: VARIANT
<222> LOCATION: (21)...(21)
<223> OTHER INFORMATION: Xaa = Any Amino Acid

<400> SEQUENCE: 24

Leu Gly Phe Thr Phe Ser Phe Pro Cys Xaa Gln Xaa Ser Ile Xaa Xaa
 1               5                  10                  15

Gly Xaa Leu Ile Xaa Trp Thr Lys Gly Phe
            20                  25

<210> SEQ ID NO 25
<211> LENGTH: 3544
<212> TYPE: DNA
<213> ORGANISM: Homo Sapiens
<220> FEATURE:
<221> NAME/KEY: CDS
<222> LOCATION: (589)...(2586)

<400> SEQUENCE: 25
tcctataggg agtcgccccg cgtccgaaaa gattataagt aaatactctg ctctttcaag      60
tgaaccaaac ctatcaaacc tgtttagaaa ataaaccagg cagaataaaa tgatgcgaaa     120
tgttcatttt aaaaaacttc aggatgggca caaacacaca gaagtgggaa atgaataaaa     180
gagtattgat aaattttga aaattgttga agctgagtaa tgggctttca gtccagtgta      240
aagctgttgg agcgcgggag caaaggtaaa gaatgatgta atgcgctggc tgctccaaag     300
catcttttgt tgtggaatgg ttattccagt catctcttta tgaatcaaat gtgagggggct    360 gctttgtgga cggagtcctt tgcaagagca catcaacggg aaagagaaag agacattcac    420
ttggagggct cttgctgaaa atgggtttaa ctctcctttt gccagtcacc accagcctga     480
cctcatacac ttttagtaca atggagtggc tgagcctttg agcacaccac cattacatca    540
tcgtggcaaa ttaagaagg aggtgggaaa agaggactta tgttgtc atg gcc cat        597
                                                  Met Ala His
                                                    1 gag atg att gga act caa att gtt act gag agg ttg gtg gct ctg ctg      645
Glu Met Ile Gly Thr Gln Ile Val Thr Glu Arg Leu Val Ala Leu Leu
      5                  10                  15 gaa agt gga acg gaa aaa gtg ctg cta att gat agc cgg cca ttt gtg      693
Glu Ser Gly Thr Glu Lys Val Leu Leu Ile Asp Ser Arg Pro Phe Val
 20                  25                  30                  35 gaa tac aat aca tcc cac att ttg gaa gcc att aat atc aac tgc tcc      741
Glu Tyr Asn Thr Ser His Ile Leu Glu Ala Ile Asn Ile Asn Cys Ser
              40                  45                  50
```

```
aag ctt atg aag cga agg ttg caa cag gac aaa gtg tta att aca gag    789
Lys Leu Met Lys Arg Arg Leu Gln Gln Asp Lys Val Leu Ile Thr Glu
            55                  60                  65 ctc atc cag cat tca gcg aaa cat aag gtt gac att gat tgc agt cag    837
Leu Ile Gln His Ser Ala Lys His Lys Val Asp Ile Asp Cys Ser Gln
        70                  75                  80 aag gtt gta gtt tac gat caa agc tcc caa gat gtt gcc tct ctc tct    885
Lys Val Val Val Tyr Asp Gln Ser Ser Gln Asp Val Ala Ser Leu Ser
85                  90                  95 tca gac tgt ttt ctc act gta ctt ctg ggt aaa ctg gag aag agc ttc    933
Ser Asp Cys Phe Leu Thr Val Leu Leu Gly Lys Leu Glu Lys Ser Phe
100                 105                 110                 115 aac tct gtt cac ctg ctt gca ggt ggg ttt gct gag ttc tct cgt tgt    981
Asn Ser Val His Leu Leu Ala Gly Gly Phe Ala Glu Phe Ser Arg Cys
                120                 125                 130 ttc cct ggc ctc tgt gaa gga aaa tcc act cta gtc cct acc tgc att   1029
Phe Pro Gly Leu Cys Glu Gly Lys Ser Thr Leu Val Pro Thr Cys Ile
            135                 140                 145 tct cag cct tgc tta cct gtt gcc aac att ggg cca acc cga att ctt   1077
Ser Gln Pro Cys Leu Pro Val Ala Asn Ile Gly Pro Thr Arg Ile Leu
        150                 155                 160 ccc aat ctt tat ctt ggc tgc cag cga gat gtc ctc aac aag gag ctg   1125
Pro Asn Leu Tyr Leu Gly Cys Gln Arg Asp Val Leu Asn Lys Glu Leu
165                 170                 175 atg cag cag aat ggg att ggt tat gtg tta aat gcc agc aat acc tgt   1173
Met Gln Gln Asn Gly Ile Gly Tyr Val Leu Asn Ala Ser Asn Thr Cys
180                 185                 190                 195 cca aag cct gac ttt atc ccc gag tct cat ttc ctg cgt gtg cct gtg   1221
Pro Lys Pro Asp Phe Ile Pro Glu Ser His Phe Leu Arg Val Pro Val
                200                 205                 210 aat gac agc ttt tgt gag aaa att ttg ccg tgg ttg gac aaa tca gta   1269
Asn Asp Ser Phe Cys Glu Lys Ile Leu Pro Trp Leu Asp Lys Ser Val
            215                 220                 225 gat ttc att gag aaa gca aaa gcc tcc aat gga tgt gtt cta gtg cac   1317
Asp Phe Ile Glu Lys Ala Lys Ala Ser Asn Gly Cys Val Leu Val His
        230                 235                 240 tgt tta gct ggg atc tcc cgc tcc gcc acc atc gct atc gcc tac atc   1365
Cys Leu Ala Gly Ile Ser Arg Ser Ala Thr Ile Ala Ile Ala Tyr Ile
245                 250                 255 atg aag agg atg gac atg tct tta gat gaa gct tac aga ttt gtg aaa   1413
Met Lys Arg Met Asp Met Ser Leu Asp Glu Ala Tyr Arg Phe Val Lys
260                 265                 270                 275 gaa aaa aga cct act ata tct cca aac ttc aat ttt ctg ggc caa ctc   1461
Glu Lys Arg Pro Thr Ile Ser Pro Asn Phe Asn Phe Leu Gly Gln Leu
                280                 285                 290 ctg gac tat gag aag aag att aag aac cag act gga gca tca ggg cca   1509
Leu Asp Tyr Glu Lys Lys Ile Lys Asn Gln Thr Gly Ala Ser Gly Pro
            295                 300                 305 aag agc aaa ctc aag ctg ctg cac ctg gag aag cca aat gaa cct gtc   1557
Lys Ser Lys Leu Lys Leu Leu His Leu Glu Lys Pro Asn Glu Pro Val
        310                 315                 320 cct gct gtc tca gag ggt gga cag aaa agc gag acg ccc ctc agt cca   1605
Pro Ala Val Ser Glu Gly Gly Gln Lys Ser Glu Thr Pro Leu Ser Pro
325                 330                 335 ccc tgt gcc gac tct gct acc tca gag gca gca gga caa agg ccc gtg   1653
Pro Cys Ala Asp Ser Ala Thr Ser Glu Ala Ala Gly Gln Arg Pro Val
340                 345                 350                 355 cat ccc gcc agc gtg ccc agc gtg ccc agc gtg cag ccg tcg ctg tta   1701
His Pro Ala Ser Val Pro Ser Val Pro Ser Val Gln Pro Ser Leu Leu
```

-continued

```
              360                 365                 370
gag gac agc ccg ctg gta cag gcg ctc agt ggg ctg cac ctg tcc gca    1749
Glu Asp Ser Pro Leu Val Gln Ala Leu Ser Gly Leu His Leu Ser Ala
            375                 380                 385 gac agg ctg gaa gac agc aat aag ctc aag cgt tcc ttc tct ctg gat    1797
Asp Arg Leu Glu Asp Ser Asn Lys Leu Lys Arg Ser Phe Ser Leu Asp
        390                 395                 400 atc aaa tca gtt tca tat tca gcc agc atg gca gca tcc tta cat ggc    1845
Ile Lys Ser Val Ser Tyr Ser Ala Ser Met Ala Ala Ser Leu His Gly
    405                 410                 415 ttc tcc tca tca gaa gat gct ttg gaa tac tac aaa cct tcc act act    1893
Phe Ser Ser Ser Glu Asp Ala Leu Glu Tyr Tyr Lys Pro Ser Thr Thr
420                 425                 430                 435 ctg gat ggg acc aac aag cta tgc cag ttc tcc cct gtt cag gaa cta    1941
Leu Asp Gly Thr Asn Lys Leu Cys Gln Phe Ser Pro Val Gln Glu Leu
            440                 445                 450 tcg gag cag act ccc gaa acc agt cct gat aag gag gaa gca agc atc    1989
Ser Glu Gln Thr Pro Glu Thr Ser Pro Asp Lys Glu Glu Ala Ser Ile
        455                 460                 465 ccc aag aag ctg cag acc gcc agg cct tca gac agc cag agc aag cga    2037
Pro Lys Lys Leu Gln Thr Ala Arg Pro Ser Asp Ser Gln Ser Lys Arg
    470                 475                 480 ttg cat tcg gtc aga acc agc agt ggc acc gcc cag agg tcc ctt        2085
Leu His Ser Val Arg Thr Ser Ser Gly Thr Ala Gln Arg Ser Leu
485                 490                 495 tta tct cca ctg cat cga agt ggg agc gtg gag gac aat tac cac acc    2133
Leu Ser Pro Leu His Arg Ser Gly Ser Val Glu Asp Asn Tyr His Thr
500                 505                 510                 515 agc ttc ctt ttc ggc ctt tcc acc agc cag cag cac ctc acg aag tct    2181
Ser Phe Leu Phe Gly Leu Ser Thr Ser Gln Gln His Leu Thr Lys Ser
            520                 525                 530 gct ggc ctg ggc ctt aag ggc tgg cac tcg gat atc ttg gcc ccc cag    2229
Ala Gly Leu Gly Leu Lys Gly Trp His Ser Asp Ile Leu Ala Pro Gln
        535                 540                 545 acc tct acc cct tcc ctg acc agc agc tgg tat ttt gcc aca gag tcc    2277
Thr Ser Thr Pro Ser Leu Thr Ser Ser Trp Tyr Phe Ala Thr Glu Ser
    550                 555                 560 tca cac ttc tac tct gcc tca gcc atc tac gga ggc agt gcc agt tac    2325
Ser His Phe Tyr Ser Ala Ser Ala Ile Tyr Gly Gly Ser Ala Ser Tyr
565                 570                 575 tct gcc tac agc tgc agc cag ctg ccc act tgc gga gac caa gtc tat    2373
Ser Ala Tyr Ser Cys Ser Gln Leu Pro Thr Cys Gly Asp Gln Val Tyr
            580                 585                 590                 595 tct gtg cgc agg cgg cag aag cca agt gac aga gct gac tcg cgg cgg    2421
Ser Val Arg Arg Arg Gln Lys Pro Ser Asp Arg Ala Asp Ser Arg Arg
        600                 605                 610 agc tgg cat gaa gag agc ccc ttt gaa aag cag ttt aaa cgc aga agc    2469
Ser Trp His Glu Glu Ser Pro Phe Glu Lys Gln Phe Lys Arg Arg Ser
    615                 620                 625 tgc caa atg gaa ttt gga gag agc atc atg tca gag aac agg tca cgg    2517
Cys Gln Met Glu Phe Gly Glu Ser Ile Met Ser Glu Asn Arg Ser Arg
630                 635                 640 gaa gag ctg ggg aaa gtg ggc agt cag tct agc ttt tcg ggc agc atg    2565
Glu Glu Leu Gly Lys Val Gly Ser Gln Ser Ser Phe Ser Gly Ser Met
            645                 650                 655 gaa atc att gag gtc tcc tga gaagaaagac acttgtgact tctatagaca       2616
Glu Ile Ile Glu Val Ser  *
660                 665 atttttttt cttgttcaca aaaaaattcc ctgtaaatct gaaatatata tatgtacata   2676
```

```
catatatatt tttggaaaat ggagctatgg tgtaaaagca acaggtggat caacccagtt    2736
gttactctct taacatctgc atttgagaga tcagctaata cttctctcaa caaaaatgga    2796
agggcagatg ctagaatccc ccctagacgg aggaaaacca ttttattcag tgaattacac    2856
atcctcttgt tcttaaaaaa gcaagtgtct ttggtgttgg aggacaaaat cccctaccat    2916
tttcacgttg tgctactaag agatctcaaa tattagtctt tgtccggacc cttccatagt    2976
acaccttagc gctgagactg agccagcttg ggggtcaggt aggtagaccc tgttagggac    3036
agagccagtg gtaaatccaa agagaaatga tcctatccaa agctgattca caaacccacg    3096
ctcacctgac agccgaggga cacgagcatc actctgctgg acggaccatt aggggccttg    3156
ccaaggtcta ccttagagca aacccagtac ctcagacagg aaagtcgggg ctttgaccac    3216
taccatatct ggtagcccat tttctaggca ttgtgaatag gtaggtagct agtcacactt    3276
ttcagaccaa ttcaaactgt ctatgcacaa aattcccgtg ggcctagatg agataatttt    3336 tttttttcttc tcagctttat gaagagaagg gaaactgtct aggattcagc tgaaccacca    3396
ggaacctggc aacatcacga tttaagctaa ggttgggagg ctaacgagtc tacctccctc    3456
tttgtaaatc aaagaattgt ttaaaatggg attgtcaatc ctttaaataa agatgaactt    3516
ggtttcaaaa aaaaaaaaaa aaaaaagg                                       3544
```

<210> SEQ ID NO 26
<211> LENGTH: 665
<212> TYPE: PRT
<213> ORGANISM: Homo Sapiens

<400> SEQUENCE: 26

```
Met Ala His Glu Met Ile Gly Thr Gln Ile Val Thr Glu Arg Leu Val
 1               5                  10                  15

Ala Leu Leu Glu Ser Gly Thr Glu Lys Val Leu Leu Ile Asp Ser Arg
            20                  25                  30

Pro Phe Val Glu Tyr Asn Thr Ser His Ile Leu Glu Ala Ile Asn Ile
        35                  40                  45

Asn Cys Ser Lys Leu Met Lys Arg Arg Leu Gln Gln Asp Lys Val Leu
    50                  55                  60

Ile Thr Glu Leu Ile Gln His Ser Ala Lys His Lys Val Asp Ile Asp
65                  70                  75                  80

Cys Ser Gln Lys Val Val Tyr Asp Gln Ser Ser Gln Asp Val Ala
                85                  90                  95

Ser Leu Ser Ser Asp Cys Phe Leu Thr Val Leu Leu Gly Lys Leu Glu
            100                 105                 110

Lys Ser Phe Asn Ser Val His Leu Leu Ala Gly Gly Phe Ala Glu Phe
        115                 120                 125

Ser Arg Cys Phe Pro Gly Leu Cys Glu Gly Lys Ser Thr Leu Val Pro
    130                 135                 140

Thr Cys Ile Ser Gln Pro Cys Leu Pro Val Ala Asn Ile Gly Pro Thr
145                 150                 155                 160

Arg Ile Leu Pro Asn Leu Tyr Leu Gly Cys Gln Arg Asp Val Leu Asn
                165                 170                 175

Lys Glu Leu Met Gln Gln Asn Gly Ile Gly Tyr Val Leu Asn Ala Ser
            180                 185                 190

Asn Thr Cys Pro Lys Pro Asp Phe Ile Pro Glu Ser His Phe Leu Arg
        195                 200                 205

Val Pro Val Asn Asp Ser Phe Cys Glu Lys Ile Leu Pro Trp Leu Asp
```

-continued

```
            210                 215                 220
Lys Ser Val Asp Phe Ile Glu Lys Ala Lys Ala Ser Asn Gly Cys Val
225                 230                 235                 240

Leu Val His Cys Leu Ala Gly Ile Ser Arg Ser Ala Thr Ile Ala Ile
                    245                 250                 255

Ala Tyr Ile Met Lys Arg Met Asp Met Ser Leu Asp Glu Ala Tyr Arg
                260                 265                 270

Phe Val Lys Glu Lys Arg Pro Thr Ile Ser Pro Asn Phe Asn Phe Leu
                275                 280                 285

Gly Gln Leu Leu Asp Tyr Glu Lys Lys Ile Lys Asn Gln Thr Gly Ala
            290                 295                 300

Ser Gly Pro Lys Ser Lys Leu Lys Leu Leu His Leu Glu Lys Pro Asn
305                 310                 315                 320

Glu Pro Val Pro Ala Val Ser Glu Gly Gly Gln Lys Ser Glu Thr Pro
                    325                 330                 335

Leu Ser Pro Pro Cys Ala Asp Ser Ala Thr Ser Glu Ala Ala Gly Gln
                340                 345                 350

Arg Pro Val His Pro Ala Ser Val Pro Ser Val Pro Ser Val Gln Pro
                355                 360                 365

Ser Leu Leu Glu Asp Ser Pro Leu Val Gln Ala Leu Ser Gly Leu His
            370                 375                 380

Leu Ser Ala Asp Arg Leu Glu Asp Ser Asn Lys Leu Lys Arg Ser Phe
385                 390                 395                 400

Ser Leu Asp Ile Lys Ser Val Ser Tyr Ser Ala Ser Met Ala Ala Ser
                    405                 410                 415

Leu His Gly Phe Ser Ser Glu Asp Ala Leu Glu Tyr Tyr Lys Pro
                420                 425                 430

Ser Thr Thr Leu Asp Gly Thr Asn Lys Leu Cys Gln Phe Ser Pro Val
                435                 440                 445

Gln Glu Leu Ser Glu Gln Thr Pro Glu Thr Ser Pro Asp Lys Glu Glu
            450                 455                 460

Ala Ser Ile Pro Lys Lys Leu Gln Thr Ala Arg Pro Ser Asp Ser Gln
465                 470                 475                 480

Ser Lys Arg Leu His Ser Val Arg Thr Ser Ser Ser Gly Thr Ala Gln
                    485                 490                 495

Arg Ser Leu Leu Ser Pro Leu His Arg Ser Gly Ser Val Glu Asp Asn
                500                 505                 510

Tyr His Thr Ser Phe Leu Phe Gly Leu Ser Thr Ser Gln Gln His Leu
                515                 520                 525

Thr Lys Ser Ala Gly Leu Gly Leu Lys Gly Trp His Ser Asp Ile Leu
            530                 535                 540

Ala Pro Gln Thr Ser Thr Pro Ser Leu Thr Ser Ser Trp Tyr Phe Ala
545                 550                 555                 560

Thr Glu Ser Ser His Phe Tyr Ser Ala Ser Ala Ile Tyr Gly Gly Ser
                    565                 570                 575

Ala Ser Tyr Ser Ala Tyr Ser Cys Ser Gln Leu Pro Thr Cys Gly Asp
                580                 585                 590

Gln Val Tyr Ser Val Arg Arg Gln Lys Pro Ser Asp Arg Ala Asp
                595                 600                 605

Ser Arg Arg Ser Trp His Glu Glu Ser Pro Phe Glu Lys Gln Phe Lys
            610                 615                 620

Arg Arg Ser Cys Gln Met Glu Phe Gly Glu Ser Ile Met Ser Glu Asn
625                 630                 635                 640
```

Arg Ser Arg Glu Glu Leu Gly Lys Val Gly Ser Gln Ser Ser Phe Ser
            645                 650                 655

Gly Ser Met Glu Ile Ile Glu Val Ser
            660                 665

<210> SEQ ID NO 27
<211> LENGTH: 1998
<212> TYPE: DNA
<213> ORGANISM: Homo Sapiens
<220> FEATURE:
<221> NAME/KEY: CDS
<222> LOCATION: (1)...(1998)

<400> SEQUENCE: 27

```
atg gcc cat gag atg att gga act caa att gtt act gag agg ttg gtg       48
Met Ala His Glu Met Ile Gly Thr Gln Ile Val Thr Glu Arg Leu Val
 1               5                  10                  15 gct ctg ctg gaa agt gga acg gaa aaa gtg ctg cta att gat agc cgg       96
Ala Leu Leu Glu Ser Gly Thr Glu Lys Val Leu Leu Ile Asp Ser Arg
             20                  25                  30 cca ttt gtg gaa tac aat aca tcc cac att ttg gaa gcc att aat atc      144
Pro Phe Val Glu Tyr Asn Thr Ser His Ile Leu Glu Ala Ile Asn Ile
         35                  40                  45 aac tgc tcc aag ctt atg aag cga agg ttg caa cag gac aaa gtg tta      192
Asn Cys Ser Lys Leu Met Lys Arg Arg Leu Gln Gln Asp Lys Val Leu
 50                  55                  60 att aca gag ctc atc cag cat tca gcg aaa cat aag gtt gac att gat      240
Ile Thr Glu Leu Ile Gln His Ser Ala Lys His Lys Val Asp Ile Asp
 65                  70                  75                  80 tgc agt cag aag gtt gta gtt tac gat caa agc tcc caa gat gtt gcc      288
Cys Ser Gln Lys Val Val Val Tyr Asp Gln Ser Ser Gln Asp Val Ala
                 85                  90                  95 tct ctc tct tca gac tgt ttt ctc act gta ctt ctg ggt aaa ctg gag      336
Ser Leu Ser Ser Asp Cys Phe Leu Thr Val Leu Leu Gly Lys Leu Glu
            100                 105                 110 aag agc ttc aac tct gtt cac ctg ctt gca ggt ggg ttt gct gag ttc      384
Lys Ser Phe Asn Ser Val His Leu Leu Ala Gly Gly Phe Ala Glu Phe
        115                 120                 125 tct cgt tgt ttc cct ggc ctc tgt gaa gga aaa tcc act cta gtc cct      432
Ser Arg Cys Phe Pro Gly Leu Cys Glu Gly Lys Ser Thr Leu Val Pro
    130                 135                 140 acc tgc att tct cag cct tgc tta cct gtt gcc aac att ggg cca acc      480
Thr Cys Ile Ser Gln Pro Cys Leu Pro Val Ala Asn Ile Gly Pro Thr
145                 150                 155                 160 cga att ctt ccc aat ctt tat ctt ggc tgc agc gga gat gtc ctc aac      528
Arg Ile Leu Pro Asn Leu Tyr Leu Gly Cys Gln Arg Asp Val Leu Asn
                165                 170                 175 aag gag ctg atg cag cag aat ggg att ggt tat gtg tta aat gcc agc      576
Lys Glu Leu Met Gln Gln Asn Gly Ile Gly Tyr Val Leu Asn Ala Ser
            180                 185                 190 aat acc tgt cca aag cct gac ttt atc ccc gag tct cat ttc ctg cgt      624
Asn Thr Cys Pro Lys Pro Asp Phe Ile Pro Glu Ser His Phe Leu Arg
        195                 200                 205 gtg cct gtg aat gac agc ttt tgt gag aaa att ttg ccg tgg ttg gac      672
Val Pro Val Asn Asp Ser Phe Cys Glu Lys Ile Leu Pro Trp Leu Asp
    210                 215                 220 aaa tca gta gat ttc att gag aaa gca aaa gcc tcc aat gga tgt gtt      720
Lys Ser Val Asp Phe Ile Glu Lys Ala Lys Ala Ser Asn Gly Cys Val
225                 230                 235                 240 cta gtg cac tgt tta gct ggg atc tcc cgc tcc gcc acc atc gct atc      768
```

```
                Leu Val His Cys Leu Ala Gly Ile Ser Arg Ser Ala Thr Ile Ala Ile
                                245                 250                 255 gcc tac atc atg aag agg atg gac atg tct tta gat gaa gct tac aga          816
Ala Tyr Ile Met Lys Arg Met Asp Met Ser Leu Asp Glu Ala Tyr Arg
                260                 265                 270 ttt gtg aaa gaa aaa aga cct act ata tct cca aac ttc aat ttt ctg          864
Phe Val Lys Glu Lys Arg Pro Thr Ile Ser Pro Asn Phe Asn Phe Leu
                275                 280                 285 ggc caa ctc ctg gac tat gag aag aag att aag aac cag act gga gca          912
Gly Gln Leu Leu Asp Tyr Glu Lys Lys Ile Lys Asn Gln Thr Gly Ala
                290                 295                 300 tca ggg cca aag agc aaa ctc aag ctg ctg cac ctg gag aag cca aat          960
Ser Gly Pro Lys Ser Lys Leu Lys Leu Leu His Leu Glu Lys Pro Asn
305                 310                 315                 320 gaa cct gtc cct gct gtc tca gag ggt gga cag aaa agc gag acg ccc         1008
Glu Pro Val Pro Ala Val Ser Glu Gly Gly Gln Lys Ser Glu Thr Pro
                325                 330                 335 ctc agt cca ccc tgt gcc gac tct gct acc tca gag gca gca gga caa         1056
Leu Ser Pro Pro Cys Ala Asp Ser Ala Thr Ser Glu Ala Ala Gly Gln
                340                 345                 350 agg ccc gtg cat ccc gcc agc gtg ccc agc gtg ccc agc gtg cag ccg         1104
Arg Pro Val His Pro Ala Ser Val Pro Ser Val Pro Ser Val Gln Pro
                355                 360                 365 tcg ctg tta gag gac agc ccg ctg gta cag gcg ctc agt ggg ctg cac         1152
Ser Leu Leu Glu Asp Ser Pro Leu Val Gln Ala Leu Ser Gly Leu His
                370                 375                 380 ctg tcc gca gac agg ctg gaa gac agc aat aag ctc aag cgt tcc ttc         1200
Leu Ser Ala Asp Arg Leu Glu Asp Ser Asn Lys Leu Lys Arg Ser Phe
385                 390                 395                 400 tct ctg gat atc aaa tca gtt tca tat tca gcc agc atg gca gca tcc         1248
Ser Leu Asp Ile Lys Ser Val Ser Tyr Ser Ala Ser Met Ala Ala Ser
                405                 410                 415 tta cat ggc ttc tcc tca tca gaa gat gct ttg gaa tac tac aaa cct         1296
Leu His Gly Phe Ser Ser Ser Glu Asp Ala Leu Glu Tyr Tyr Lys Pro
                420                 425                 430 tcc act act ctg gat ggg acc aac aag cta tgc cag ttc tcc cct gtt         1344
Ser Thr Thr Leu Asp Gly Thr Asn Lys Leu Cys Gln Phe Ser Pro Val
                435                 440                 445 cag gaa cta tcg gag cag act ccc gaa acc agt cct gat aag gag gaa         1392
Gln Glu Leu Ser Glu Gln Thr Pro Glu Thr Ser Pro Asp Lys Glu Glu
                450                 455                 460 gcc agc atc ccc aag aag ctg cag acc gcc agg cct tca gac agc cag         1440
Ala Ser Ile Pro Lys Lys Leu Gln Thr Ala Arg Pro Ser Asp Ser Gln
465                 470                 475                 480 agc aag cga ttg cat tcg gtc aga acc agc agc agt ggc acc gcc cag         1488
Ser Lys Arg Leu His Ser Val Arg Thr Ser Ser Ser Gly Thr Ala Gln
                485                 490                 495 agg tcc ctt tta tct cca ctg cat cga agt ggg agc gtg gag gac aat         1536
Arg Ser Leu Leu Ser Pro Leu His Arg Ser Gly Ser Val Glu Asp Asn
                500                 505                 510 tac cac acc agc ttc ctt ttc ggc ctt tcc acc agc cag cag cac ctc         1584
Tyr His Thr Ser Phe Leu Phe Gly Leu Ser Thr Ser Gln Gln His Leu
                515                 520                 525 acg aag tct gct ggc ctg ggc ctt aag ggc tgg cac tcg gat atc ttg         1632
Thr Lys Ser Ala Gly Leu Gly Leu Lys Gly Trp His Ser Asp Ile Leu
                530                 535                 540 gcc ccc cag acc tct acc cct tcc ctg acc agc agc tgg tat ttt gcc         1680
Ala Pro Gln Thr Ser Thr Pro Ser Leu Thr Ser Ser Trp Tyr Phe Ala
545                 550                 555                 560
```

```
aca gag tcc tca cac ttc tac tct gcc tca gcc atc tac gga ggc agt    1728
Thr Glu Ser Ser His Phe Tyr Ser Ala Ser Ala Ile Tyr Gly Gly Ser
                565                 570                 575 gcc agt tac tct gcc tac agc tgc agc cag ctg ccc act tgc gga gac    1776
Ala Ser Tyr Ser Ala Tyr Ser Cys Ser Gln Leu Pro Thr Cys Gly Asp
            580                 585                 590 caa gtc tat tct gtg cgc agg cgg cag aag cca agt gac aga gct gac    1824
Gln Val Tyr Ser Val Arg Arg Arg Gln Lys Pro Ser Asp Arg Ala Asp
        595                 600                 605 tcg cgg cgg agc tgg cat gaa gag agc ccc ttt gaa aag cag ttt aaa    1872
Ser Arg Arg Ser Trp His Glu Glu Ser Pro Phe Glu Lys Gln Phe Lys
    610                 615                 620 cgc aga agc tgc caa atg gaa ttt gga gag agc atc atg tca gag aac    1920
Arg Arg Ser Cys Gln Met Glu Phe Gly Glu Ser Ile Met Ser Glu Asn
625                 630                 635                 640 agg tca cgg gaa gag ctg ggg aaa gtg ggc agt cag tct agc ttt tcg    1968
Arg Ser Arg Glu Glu Leu Gly Lys Val Gly Ser Gln Ser Ser Phe Ser
                645                 650                 655 ggc agc atg gaa atc att gag gtc tcc tga                            1998
Gly Ser Met Glu Ile Ile Glu Val Ser  *
                660                 665

<210> SEQ ID NO 28
<211> LENGTH: 1114
<212> TYPE: DNA
<213> ORGANISM: Homo Sapiens
<220> FEATURE:
<221> NAME/KEY: CDS
<222> LOCATION: (89)...(760)

<400> SEQUENCE: 28
ctataggagg tcgcccacgc gtccggggcg gtggcgcgct gacacctggc ggcggcggag    60
ggcgggcaga agcccgcggg ccagcacc atg gag gac gtg aag ctg gag ttc     112
                                Met Glu Asp Val Lys Leu Glu Phe
                                  1               5 cct tcc ctt cca cag tgc aag gaa gac gcc gag gag tgg acc tac cct    160
Pro Ser Leu Pro Gln Cys Lys Glu Asp Ala Glu Glu Trp Thr Tyr Pro
         10                  15                  20 atg aga cga gag atg cag gaa att tta cct gga ttg ttc tta ggc cca    208
Met Arg Arg Glu Met Gln Glu Ile Leu Pro Gly Leu Phe Leu Gly Pro
 25                  30                  35                  40 tat tca tct gct atg aaa agc aag cta cct gta cta cag aaa cat gga    256
Tyr Ser Ser Ala Met Lys Ser Lys Leu Pro Val Leu Gln Lys His Gly
                 45                  50                  55 ata acc cat ata ata tgc ata cga caa aat att gaa gca aac ttt att    304
Ile Thr His Ile Ile Cys Ile Arg Gln Asn Ile Glu Ala Asn Phe Ile
             60                  65                  70 aaa cca aac ttt cag cag tta ttt aga tat tta gtc ctg gat att gca    352
Lys Pro Asn Phe Gln Gln Leu Phe Arg Tyr Leu Val Leu Asp Ile Ala
         75                  80                  85 gat aat cca gtt gaa aat ata ata cgt ttc ttc cct atg act aag gaa    400
Asp Asn Pro Val Glu Asn Ile Ile Arg Phe Phe Pro Met Thr Lys Glu
 90                  95                 100 ttt att gat ggg agc tta caa atg gga gga aaa gtt ctt gtg cat gga    448
Phe Ile Asp Gly Ser Leu Gln Met Gly Gly Lys Val Leu Val His Gly
105                 110                 115                 120 aat gca ggg atc tcc aga agt gca gcc ttt gtt att gca tac att atg    496
Asn Ala Gly Ile Ser Arg Ser Ala Ala Phe Val Ile Ala Tyr Ile Met
                125                 130                 135 gaa aca ttt gga atg aag tac aga gat gct ttt gct tat gtt caa gaa    544
Glu Thr Phe Gly Met Lys Tyr Arg Asp Ala Phe Ala Tyr Val Gln Glu
```

-continued

```
                140                 145                 150
aga aga ttt tgt att aat cct aat gct gga ttt gtc cat caa ctt cag      592
Arg Arg Phe Cys Ile Asn Pro Asn Ala Gly Phe Val His Gln Leu Gln
        155                 160                 165 gaa tat gaa gcc atc tac cta gca aaa tta aca ata cag atg atg tca      640
Glu Tyr Glu Ala Ile Tyr Leu Ala Lys Leu Thr Ile Gln Met Met Ser
    170                 175                 180 cca ctc cag ata gaa agg tca tta tct gtt cat tct ggt acc aca ggc      688
Pro Leu Gln Ile Glu Arg Ser Leu Ser Val His Ser Gly Thr Thr Gly
185                 190                 195                 200 agt ttg aag aga aca cat gaa gaa gag gat gat ttt gga acc atg caa      736
Ser Leu Lys Arg Thr His Glu Glu Glu Asp Asp Phe Gly Thr Met Gln
                205                 210                 215 gtg gcg act gca cag aat ggc tga cttgaagagc aacatcatag agtgtgaatt     790
Val Ala Thr Ala Gln Asn Gly  *
                220 tctatttggg aaggagaaaa tacaagagaa aattataatg taaaatggta aaaacataag    850 tagttttttt ttcaattaca tgttgcttcc agacatactt ctctgcaact tgttgagcaa    910 catttttaaga tgttggactt ctgcaataga tgacactgat ggttttactc cttttttaa    970 aaacacatgc gcgcgcacac acacatgctt tacaagtttt attataaacc aagaattttg   1030 gacttgcaaa gaggtattat tgcaataatg cacttttcat acttgaaatt tatttgtatg   1090 atataaagtt attactttaa acaa                                          1114

<210> SEQ ID NO 29
<211> LENGTH: 223
<212> TYPE: PRT
<213> ORGANISM: Homo Sapiens

<400> SEQUENCE: 29

Met Glu Asp Val Lys Leu Glu Phe Pro Ser Leu Pro Gln Cys Lys Glu
1               5                   10                  15

Asp Ala Glu Glu Trp Thr Tyr Pro Met Arg Arg Glu Met Gln Glu Ile
            20                  25                  30

Leu Pro Gly Leu Phe Leu Gly Pro Tyr Ser Ser Ala Met Lys Ser Lys
        35                  40                  45

Leu Pro Val Leu Gln Lys His Gly Ile Thr His Ile Ile Cys Ile Arg
    50                  55                  60

Gln Asn Ile Glu Ala Asn Phe Ile Lys Pro Asn Phe Gln Gln Leu Phe
65                  70                  75                  80

Arg Tyr Leu Val Leu Asp Ile Ala Asp Asn Pro Val Glu Asn Ile Ile
                85                  90                  95

Arg Phe Phe Pro Met Thr Lys Glu Phe Ile Asp Gly Ser Leu Gln Met
            100                 105                 110

Gly Gly Lys Val Leu Val His Gly Asn Ala Gly Ile Ser Arg Ser Ala
        115                 120                 125

Ala Phe Val Ile Ala Tyr Ile Met Glu Thr Phe Gly Met Lys Tyr Arg
    130                 135                 140

Asp Ala Phe Ala Tyr Val Gln Glu Arg Arg Phe Cys Ile Asn Pro Asn
145                 150                 155                 160

Ala Gly Phe Val His Gln Leu Gln Glu Tyr Glu Ala Ile Tyr Leu Ala
                165                 170                 175

Lys Leu Thr Ile Gln Met Met Ser Pro Leu Gln Ile Glu Arg Ser Leu
            180                 185                 190

Ser Val His Ser Gly Thr Thr Gly Ser Leu Lys Arg Thr His Glu Glu
```

<210> SEQ ID NO 30
<211> LENGTH: 672
<212> TYPE: DNA
<213> ORGANISM: Homo Sapiens
<220> FEATURE:
<221> NAME/KEY: CDS
<222> LOCATION: (1)...(672)

<400> SEQUENCE: 30

```
atg gag gac gtg aag ctg gag ttc cct tcc ctt cca cag tgc aag gaa    48
Met Glu Asp Val Lys Leu Glu Phe Pro Ser Leu Pro Gln Cys Lys Glu
 1               5                  10                  15 gac gcc gag gag tgg acc tac cct atg aga cga gag atg cag gaa att    96
Asp Ala Glu Glu Trp Thr Tyr Pro Met Arg Arg Glu Met Gln Glu Ile
             20                  25                  30 tta cct gga ttg ttc tta ggc cca tat tca tct gct atg aaa agc aag   144
Leu Pro Gly Leu Phe Leu Gly Pro Tyr Ser Ser Ala Met Lys Ser Lys
         35                  40                  45 cta cct gta cta cag aaa cat gga ata acc cat ata ata tgc ata cga   192
Leu Pro Val Leu Gln Lys His Gly Ile Thr His Ile Ile Cys Ile Arg
     50                  55                  60 caa aat att gaa gca aac ttt att aaa cca aac ttt cag cag tta ttt   240
Gln Asn Ile Glu Ala Asn Phe Ile Lys Pro Asn Phe Gln Gln Leu Phe
 65                  70                  75                  80 aga tat tta gtc ctg gat att gca gat aat cca gtt gaa aat ata ata   288
Arg Tyr Leu Val Leu Asp Ile Ala Asp Asn Pro Val Glu Asn Ile Ile
                 85                  90                  95 cgt ttt ttc cct atg act aag gaa ttt att gat ggg agc tta caa atg   336
Arg Phe Phe Pro Met Thr Lys Glu Phe Ile Asp Gly Ser Leu Gln Met
            100                 105                 110 gga gga aaa gtt ctt gtg cat gga aat gca ggg atc tcc aga agt gca   384
Gly Gly Lys Val Leu Val His Gly Asn Ala Gly Ile Ser Arg Ser Ala
        115                 120                 125 gcc ttt gtt att gca tac att atg gaa aca ttt gga atg aag tac aga   432
Ala Phe Val Ile Ala Tyr Ile Met Glu Thr Phe Gly Met Lys Tyr Arg
    130                 135                 140 gat gct ttt gct tat gtt caa gaa aga aga ttt tgt att aat cct aat   480
Asp Ala Phe Ala Tyr Val Gln Glu Arg Arg Phe Cys Ile Asn Pro Asn
145                 150                 155                 160 gct gga ttt gtc cat caa ctt cag gaa tat gaa gcc atc tac cta gca   528
Ala Gly Phe Val His Gln Leu Gln Glu Tyr Glu Ala Ile Tyr Leu Ala
                165                 170                 175 aaa tta aca ata cag atg atg tca cca ctc cag ata gaa agg tca tta   576
Lys Leu Thr Ile Gln Met Met Ser Pro Leu Gln Ile Glu Arg Ser Leu
            180                 185                 190 tct gtt cat tct ggt acc aca ggc agt ttg aag aga aca cat gaa gaa   624
Ser Val His Ser Gly Thr Thr Gly Ser Leu Lys Arg Thr His Glu Glu
        195                 200                 205 gag gat gat ttt gga acc atg caa gtg gcg act gca cag aat ggc tga   672
Glu Asp Asp Phe Gly Thr Met Gln Val Ala Thr Ala Gln Asn Gly *
    210                 215                 220
```

<210> SEQ ID NO 31
<211> LENGTH: 173
<212> TYPE: PRT
<213> ORGANISM: Artificial Sequence
<220> FEATURE:
<223> OTHER INFORMATION: Consensus Sequence

```
<400> SEQUENCE: 31

Gly Pro Ser Glu Ile Leu Pro His Leu Tyr Leu Gly Ser Tyr Ser Thr
1               5                   10                  15

Ala Ser Glu Ala Asn Leu Ala Leu Leu Lys Lys Leu Gly Ile Thr His
            20                  25                  30

Val Ile Asn Val Thr Glu Glu Val Pro Asn Pro Phe Glu Leu Asp Lys
        35                  40                  45

Lys Asn Asp Arg His Tyr Thr Asn Ala Tyr Ile Ser Lys Asn Ser Gly
    50                  55                  60

Phe Thr Tyr Leu Gln Ile Pro Asn Val Asp Asp His Ile Tyr Tyr His
65                  70                  75                  80

Ile Ala Trp Asn His Glu Thr Lys Ile Ser Lys Tyr Phe Asp Glu Ala
                85                  90                  95

Val Asp Phe Ile Asp Asp Ala Arg Gln Lys Gly Gly Lys Val Leu Val
            100                 105                 110

His Cys Gln Ala Gly Ile Ser Arg Ser Ala Thr Leu Ile Ile Ala Tyr
        115                 120                 125

Leu Met Lys Thr Arg Asn Leu Ser Leu Asn Glu Ala Tyr Asp Phe Val
    130                 135                 140

Tyr Val Tyr His Ile Lys Glu Arg Arg Cys Pro Ile Ile Ser Pro Asn
145                 150                 155                 160

Phe Gly Phe Leu Arg Gln Leu Ile Glu Tyr Glu Arg Lys
                165                 170

<210> SEQ ID NO 32
<211> LENGTH: 172
<212> TYPE: PRT
<213> ORGANISM: Artificial Sequence
<220> FEATURE:
<223> OTHER INFORMATION: Consensus Sequence

<400> SEQUENCE: 32

Gly Pro Ser Glu Ile Leu Pro His Leu Tyr Leu Gly Ser Tyr Ser Asp
1               5                   10                  15

Ala Ser Glu Ala Asn Leu Ala Leu Leu Lys Lys Leu Gly Ile Thr His
            20                  25                  30

Val Ile Asn Val Thr Glu Glu Val Pro Asn Asn Phe Glu Leu Lys Lys
        35                  40                  45

Lys Asn Asp Arg Tyr Tyr Thr Asn Glu Tyr Ile Ser Lys Gly Ser Gly
    50                  55                  60

Phe Thr Tyr Leu Gln Ile Pro Asn Val Asp Asp Ile Tyr Tyr His Ile
65                  70                  75                  80

Ala Trp Asn Thr Glu Thr Lys Ile Ser Lys Tyr Leu Glu Glu Ala Val
                85                  90                  95

Glu Phe Ile Glu Asp Ala Glu Lys Lys Gly Gly Lys Val Leu Val His
            100                 105                 110

Cys Gln Ala Gly Val Ser Arg Ser Ala Thr Leu Val Ile Ala Tyr Leu
        115                 120                 125

Met Lys Thr Arg Asn Leu Ser Leu Arg Asp Ala Tyr Asp Phe Val Tyr
    130                 135                 140

Val Tyr His Ile Lys Glu Arg Arg Cys Pro Ile Ile Ser Pro Asn Phe
145                 150                 155                 160

Gly Phe Leu Arg Gln Leu Ile Glu Tyr Glu Arg Lys
                165                 170
```

-continued

```
<210> SEQ ID NO 33
<211> LENGTH: 131
<212> TYPE: PRT
<213> ORGANISM: Artificial Sequence
<220> FEATURE:
<223> OTHER INFORMATION: Consensus Sequence

<400> SEQUENCE: 33
```

Thr Ala Gly Glu Leu Lys Ala Leu Leu Glu Ser Ala Pro Lys Leu Ile
 1               5                  10                  15

Leu Ile Asp Val Arg Ser Pro Glu Phe Gly Glu Glu Tyr Glu Tyr Glu
            20                  25                  30

Gly Gly His Ile Pro Gly Ala Val Asn Val Pro Glu Glu Ile Glu
        35                  40                  45

Ala Leu Leu Asp Arg Ser Gly Ile Leu Pro Asp Ile Glu Lys Leu His
    50                  55                  60

Leu Leu Lys Asp Pro Glu Glu Leu Ala Lys Leu Phe Gly Glu Leu Gly
65                  70                  75                  80

Ser Ser Lys Asp Lys Arg Val Ile Val Tyr Cys Arg Ser Gly Arg Gly
                85                  90                  95

Leu Leu Arg Asn Arg Arg Ser Ala Leu Ala Ala Leu Leu Lys Lys
            100                 105                 110

Leu Gly Tyr Pro Glu Val Tyr Ile Leu Lys Gly Gly Tyr Lys Glu Trp
        115                 120                 125

Leu Ala Lys
    130

```
<210> SEQ ID NO 34
<211> LENGTH: 94
<212> TYPE: PRT
<213> ORGANISM: Artificial Sequence
<220> FEATURE:
<223> OTHER INFORMATION: Consensus Sequence

<400> SEQUENCE: 34
```

Val Leu Glu Glu Leu Lys Leu Leu Leu Asn Glu Asp Val Val Leu Leu
 1               5                  10                  15

Asp Val Arg Ser Pro Glu Glu Tyr Glu Gly Gly His Ile Pro Gly Ala
            20                  25                  30

Val Asn Ile Pro Leu Ser Glu Leu Leu Asp Arg Leu Gly Leu Asp Lys
        35                  40                  45

Asp Lys Pro Val Ile Val Tyr Cys Arg Ser Gly Val Arg Ser Ala Ala
    50                  55                  60

Lys Ala Ala Trp Leu Leu Arg Glu Leu Gly Phe Lys Asn Val Tyr Leu
65                  70                  75                  80

Leu Asp Gly Gly Tyr Lys Glu Trp Ser Ala Ala Gly Pro Pro
                85                  90

```
<210> SEQ ID NO 35
<211> LENGTH: 1182
<212> TYPE: DNA
<213> ORGANISM: Homo Sapiens
<220> FEATURE:
<221> NAME/KEY: CDS
<222> LOCATION: (326)...(1009)

<400> SEQUENCE: 35
tggaggtaga aaactttat tagcksgtcc ggttgaggcc tacagcgggg aaaggacttg      60
ccagattttc gccgcaagtc agggccatag cgggggggcat aacaaggcct cccaaccgaa    120
```

```
ggtcaagcaa gagctccgag cgtcccacac aagtcccgaa gggacactgt gacgccgcgc    180
tactgaaggc gcctgggttc ccggactcgg ccaccgcctc gccgcttccg ccctcagaa     240 gcatggcggc cacgtagccc ggcccggatt ggacgttggc ggtggacgcc aaacagttgg    300
caacacgatt ggctgctgcg gggtg atg acg tca ggg ggc ggt gtc gga gtg     352
                              Met Thr Ser Gly Gly Gly Val Gly Val
                              1                5 aat ggg ggc agc atg agg ccg ggc ggc ttt ttg ggc gcc gga cag cgg     400
Asn Gly Gly Ser Met Arg Pro Gly Gly Phe Leu Gly Ala Gly Gln Arg
 10              15                  20                  25 ctg agt aga gcc atg agc cga tgt gtt ttg gag cct cgc ccc ccg ggg     448
Leu Ser Arg Ala Met Ser Arg Cys Val Leu Glu Pro Arg Pro Pro Gly
                 30                  35                  40 aag cgg tgg atg gtg gct ggc ctg ggg aat ccc gga ctg ccc ggc acg     496
Lys Arg Trp Met Val Ala Gly Leu Gly Asn Pro Gly Leu Pro Gly Thr
             45                  50                  55 cga cac agc gtg ggc atg gcg gtg ctg ggg cag ctg gcg cgg cgg ctg     544
Arg His Ser Val Gly Met Ala Val Leu Gly Gln Leu Ala Arg Arg Leu
         60                  65                  70 ggt gtg gcg gag agt tgg acg cgc gac cgg cac tgt gcc gcc gac ctc     592
Gly Val Ala Glu Ser Trp Thr Arg Asp Arg His Cys Ala Ala Asp Leu
     75                  80                  85 gcc ctg gcc ccg ctg ggg gat gcc caa ctg gtc ctg ctc cgg cca cgg     640
Ala Leu Ala Pro Leu Gly Asp Ala Gln Leu Val Leu Leu Arg Pro Arg
 90                  95                 100                 105 cgg ctt atg aac gcc aac ggg cgc agc gtg gcc cgg gct gcg gag ctg     688
Arg Leu Met Asn Ala Asn Gly Arg Ser Val Ala Arg Ala Ala Glu Leu
                110                 115                 120 ttt ggg ctg act gcc gag gaa gtc tac ctg gtg cat gat gag ctg gac     736
Phe Gly Leu Thr Ala Glu Glu Val Tyr Leu Val His Asp Glu Leu Asp
            125                 130                 135 aag ccc ctg ggg aga ctg gct ctg aag ctg ggg ggc agt gcc agg ggc     784
Lys Pro Leu Gly Arg Leu Ala Leu Lys Leu Gly Gly Ser Ala Arg Gly
        140                 145                 150 cac aat gga gtc cgt tcc tgc att agc tgc ctc aac tcc aat gca atg     832
His Asn Gly Val Arg Ser Cys Ile Ser Cys Leu Asn Ser Asn Ala Met
    155                 160                 165 cca agg ctg cgg gtg ggt atc ggg cgc ccg gcg cac cct gag gcg gtt     880
Pro Arg Leu Arg Val Gly Ile Gly Arg Pro Ala His Pro Glu Ala Val
170                 175                 180                 185 cag gcc cat gtg ctg ggc tgc ttc tcc cct gct gag cag gag ctg ctg     928
Gln Ala His Val Leu Gly Cys Phe Ser Pro Ala Glu Gln Glu Leu Leu
                190                 195                 200 cct ctg ttg ctg gat cga gcc acc gac ctg atc ttg gac cac atc cgt     976
Pro Leu Leu Leu Asp Arg Ala Thr Asp Leu Ile Leu Asp His Ile Arg
            205                 210                 215 gag cga agc cag ggg ccc tca ctg ggg ccg tga cactagtggc catggctgcc   1029
Glu Arg Ser Gln Gly Pro Ser Leu Gly Pro *
        220                 225 tgcctgactg tagtgccccac caacccagcc actgccacag agctgccacg ccagccttgg  1089
tatctacttt ttatacaaat ctcctctaga ctgttccagg ctgcctgcgg attaaagtgg   1149
gggtgactgt gaaaaaaaaa aaaaaaaaaa gga                                1182

<210> SEQ ID NO 36
<211> LENGTH: 227
<212> TYPE: PRT
<213> ORGANISM: Homo Sapiens
```

<400> SEQUENCE: 36

| | | | | | | | | | | | | | | | |
|---|---|---|---|---|---|---|---|---|---|---|---|---|---|---|---|
|Met|Thr|Ser|Gly|Gly|Gly|Val|Gly|Val|Asn|Gly|Gly|Ser|Met|Arg|Pro|
|1| | | |5| | | | |10| | | | |15| |

Gly Gly Phe Leu Gly Ala Gly Gln Arg Leu Ser Arg Ala Met Ser Arg
                20                  25                  30

Cys Val Leu Glu Pro Arg Pro Pro Gly Lys Arg Trp Met Val Ala Gly
         35                  40                  45

Leu Gly Asn Pro Gly Leu Pro Gly Thr Arg His Ser Val Gly Met Ala
 50                  55                  60

Val Leu Gly Gln Leu Ala Arg Arg Leu Gly Val Ala Glu Ser Trp Thr
65                  70                  75                  80

Arg Asp Arg His Cys Ala Ala Asp Leu Ala Leu Ala Pro Leu Gly Asp
                 85                  90                  95

Ala Gln Leu Val Leu Leu Arg Pro Arg Leu Met Asn Ala Asn Gly
             100                 105                 110

Arg Ser Val Ala Arg Ala Ala Glu Leu Phe Gly Leu Thr Ala Glu Glu
             115                 120                 125

Val Tyr Leu Val His Asp Glu Leu Asp Lys Pro Leu Gly Arg Leu Ala
         130                 135                 140

Leu Lys Leu Gly Gly Ser Ala Arg Gly His Asn Gly Val Arg Ser Cys
145                 150                 155                 160

Ile Ser Cys Leu Asn Ser Asn Ala Met Pro Arg Leu Arg Val Gly Ile
                 165                 170                 175

Gly Arg Pro Ala His Pro Glu Ala Val Gln Ala His Val Leu Gly Cys
             180                 185                 190

Phe Ser Pro Ala Glu Gln Glu Leu Leu Pro Leu Leu Leu Asp Arg Ala
             195                 200                 205

Thr Asp Leu Ile Leu Asp His Ile Arg Glu Arg Ser Gln Gly Pro Ser
         210                 215                 220

Leu Gly Pro
225

<210> SEQ ID NO 37
<211> LENGTH: 684
<212> TYPE: DNA
<213> ORGANISM: Homo Sapiens
<220> FEATURE:
<221> NAME/KEY: CDS
<222> LOCATION: (1)...(684)

<400> SEQUENCE: 37

| atg | acg | tca | ggg | ggc | ggt | gtc | gga | gtg | aat | ggg | ggc | agc | atg | agg | ccg | 48 |
|---|---|---|---|---|---|---|---|---|---|---|---|---|---|---|---|---|
| Met | Thr | Ser | Gly | Gly | Gly | Val | Gly | Val | Asn | Gly | Gly | Ser | Met | Arg | Pro | |
| 1 | | | | 5 | | | | | 10 | | | | | 15 | | |

| ggc | ggc | ttt | ttg | ggc | gcc | gga | cag | cgg | ctg | agt | aga | gcc | atg | agc | cga | 96 |
|---|---|---|---|---|---|---|---|---|---|---|---|---|---|---|---|---|
| Gly | Gly | Phe | Leu | Gly | Ala | Gly | Gln | Arg | Leu | Ser | Arg | Ala | Met | Ser | Arg | |
| | | | 20 | | | | | 25 | | | | | 30 | | | |

| tgt | gtt | ttg | gag | cct | cgc | ccc | ccg | ggg | aag | cgg | tgg | atg | gtg | gct | ggc | 144 |
|---|---|---|---|---|---|---|---|---|---|---|---|---|---|---|---|---|
| Cys | Val | Leu | Glu | Pro | Arg | Pro | Pro | Gly | Lys | Arg | Trp | Met | Val | Ala | Gly | |
| | | 35 | | | | | 40 | | | | | 45 | | | | |

| ctg | ggg | aat | ccc | gga | ctg | ccc | ggc | acg | cga | cac | agc | gtg | ggc | atg | gcg | 192 |
|---|---|---|---|---|---|---|---|---|---|---|---|---|---|---|---|---|
| Leu | Gly | Asn | Pro | Gly | Leu | Pro | Gly | Thr | Arg | His | Ser | Val | Gly | Met | Ala | |
| 50 | | | | | 55 | | | | | 60 | | | | | | |

| gtg | ctg | ggg | cag | ctg | gcg | cgg | cgg | ctg | ggt | gtg | gcg | gag | agt | tgg | acg | 240 |
|---|---|---|---|---|---|---|---|---|---|---|---|---|---|---|---|---|
| Val | Leu | Gly | Gln | Leu | Ala | Arg | Arg | Leu | Gly | Val | Ala | Glu | Ser | Trp | Thr | |
| 65 | | | | 70 | | | | | 75 | | | | | 80 | | |

| cgc | gac | cgg | cac | tgt | gcc | gcc | gac | ctc | gcc | ctg | gcc | ccg | ctg | ggg | gat | 288 |
|---|---|---|---|---|---|---|---|---|---|---|---|---|---|---|---|---|

-continued

```
                    Arg Asp Arg His Cys Ala Ala Asp Leu Ala Leu Ala Pro Leu Gly Asp
                                    85                  90                  95 gcc caa ctg gtc ctg ctc cgg cca cgg cgg ctt atg aac gcc aac ggg         336
Ala Gln Leu Val Leu Leu Arg Pro Arg Arg Leu Met Asn Ala Asn Gly
                100                 105                 110 cgc agc gtg gcc cgg gct gcg gag ctg ttt ggg ctg act gcc gag gaa         384
Arg Ser Val Ala Arg Ala Ala Glu Leu Phe Gly Leu Thr Ala Glu Glu
            115                 120                 125 gtc tac ctg gtg cat gat gag ctg gac aag ccc ctg ggg aga ctg gct         432
Val Tyr Leu Val His Asp Glu Leu Asp Lys Pro Leu Gly Arg Leu Ala
        130                 135                 140 ctg aag ctg ggg ggc agt gcc agg ggc cac aat gga gtc cgt tcc tgc         480
Leu Lys Leu Gly Gly Ser Ala Arg Gly His Asn Gly Val Arg Ser Cys
145                 150                 155                 160 att agc tgc ctc aac tcc aat gca atg cca agg ctg cgg gtg ggt atc         528
Ile Ser Cys Leu Asn Ser Asn Ala Met Pro Arg Leu Arg Val Gly Ile
                165                 170                 175 ggg cgc ccg gcg cac cct gag gcg gtt cag gcc cat gtg ctg ggc tgc         576
Gly Arg Pro Ala His Pro Glu Ala Val Gln Ala His Val Leu Gly Cys
            180                 185                 190 ttc tcc cct gct gag cag gag ctg ctg cct ctg ttg ctg gat cga gcc         624
Phe Ser Pro Ala Glu Gln Glu Leu Leu Pro Leu Leu Leu Asp Arg Ala
        195                 200                 205 acc gac ctg atc ttg gac cac atc cgt gag cga agc cag ggg ccc tca         672
Thr Asp Leu Ile Leu Asp His Ile Arg Glu Arg Ser Gln Gly Pro Ser
210                 215                 220 ctg ggg ccg tga                                                         684
Leu Gly Pro *
225
```

<210> SEQ ID NO 38
<211> LENGTH: 193
<212> TYPE: PRT
<213> ORGANISM: Artificial Sequence
<220> FEATURE:
<223> OTHER INFORMATION: Consensus Sequence

<400> SEQUENCE: 38

```
Thr Ile Lys Leu Ile Val Gly Leu Gly Asn Pro Gly Lys Gln Tyr Ala
  1               5                   10                  15

Glu Thr Arg His Asn Ala Gly Phe Met Val Leu Asp Leu Leu Ala Ser
                20                  25                  30

Arg Leu Gly Leu Ser Leu Arg Glu Lys Arg Phe Phe Gly Leu Gly
            35                  40                  45

Gly Lys Val Leu Val Ser Gly Lys Lys His Cys Val Ile Leu Leu Lys
        50                  55                  60

Pro Arg Thr Tyr Met Asn Leu Ser Gly Lys Ala Val Leu Ala Leu Ala
65                  70                  75                  80

Ser Phe Tyr Lys Ile Lys Pro Glu Glu Ile Leu Val Val His Asp Asp
                85                  90                  95

Leu Asp Leu Pro Leu Gly Lys Ile Arg Leu Lys Gln Gly Gly Ala
            100                 105                 110

Gly Arg Gly His Asn Gly Leu Lys Ser Ile Ile Ser His Leu Gly Asn
        115                 120                 125

Thr Asn Asn Phe Asn Arg Leu Arg Ile Gly Ile Gly Arg Pro Asn Pro
130                 135                 140

Gly Ser Asn Asp Val Ala Glu Phe Val Leu Ser Lys Phe Ser Pro Ala
145                 150                 155                 160
```

```
Glu Arg Pro Leu Leu Glu Lys Ala Leu Asp Lys Ala Ile Glu Ala Leu
            165                 170                 175
Glu Met Ile Ile Glu Gly His Gly Met Asn Lys Leu Met Asn Arg Phe
        180                 185                 190
Asn

<210> SEQ ID NO 39
<211> LENGTH: 2629
<212> TYPE: DNA
<213> ORGANISM: Homo Sapiens
<220> FEATURE:
<221> NAME/KEY: CDS
<222> LOCATION: (257)...(2545)

<400> SEQUENCE: 39
gcacgagaca cctctcccct tcttactgct tccctccggc tataacttgc cagtcacagc      60
agccagctgc tgtagaagag gggaggaaac aagccagtgc aaggggagca aaagagaaaa     120
ggagccaggc tgggcttcct gatcccacag catcgcagag ctcggaggc acagctcaca      180 gacacaggaa acacaggact gctattctgc tctcctgccc acggtgatct ggtgccagct     240
ggtggaacag tgggtg atg gcg tcc ctg ctg caa gac cag ctg acc act gat    292
                  Met Ala Ser Leu Leu Gln Asp Gln Leu Thr Thr Asp
                   1               5                  10
``` cag gac ttg ctg ctg atg cag gaa ggc atg ccg atg cgc aag gtg agg    340
Gln Asp Leu Leu Leu Met Gln Glu Gly Met Pro Met Arg Lys Val Arg
         15                  20                  25 tcc aaa agc tgg aag aag cta aga tac ttc aga ctt cag aat gac ggc    388
Ser Lys Ser Trp Lys Lys Leu Arg Tyr Phe Arg Leu Gln Asn Asp Gly
 30                  35                  40 atg aca gtc tgg cat gca cgg cag gcc agg ggc agt gcc aag ccc agc    436
Met Thr Val Trp His Ala Arg Gln Ala Arg Gly Ser Ala Lys Pro Ser
 45                  50                  55                  60 ttc tca atc tct gat gtg gag aca ata cgt aat ggc cat gat tcc gag    484
Phe Ser Ile Ser Asp Val Glu Thr Ile Arg Asn Gly His Asp Ser Glu
             65                  70                  75 ttg ctg cgt agc ctg gca gag gag ctc ccc ctg gag cag ggc ttc acc    532
Leu Leu Arg Ser Leu Ala Glu Glu Leu Pro Leu Glu Gln Gly Phe Thr
         80                  85                  90 att gtc ttc cat ggc cgc cgc tcc aac ctg gac ctg atg gcc aac agt    580
Ile Val Phe His Gly Arg Arg Ser Asn Leu Asp Leu Met Ala Asn Ser
     95                 100                 105 gtt gag gag gcc cag ata tgg atg cga ggg ctc cag ctg ttg gtg gat    628
Val Glu Glu Ala Gln Ile Trp Met Arg Gly Leu Gln Leu Leu Val Asp
110                 115                 120 ctt gtc acc agc atg gac cat cag gag cgc ctg gac caa tgg ctg agc    676
Leu Val Thr Ser Met Asp His Gln Glu Arg Leu Asp Gln Trp Leu Ser
125                 130                 135                 140 gat tgg ttt caa cgt gga gac aaa aat cag gat ggt aag atg agt ttc    724
Asp Trp Phe Gln Arg Gly Asp Lys Asn Gln Asp Gly Lys Met Ser Phe
                145                 150                 155 caa gaa gtt cag cgg tta ttg cac cta atg aat gtg gaa atg gac caa    772
Gln Glu Val Gln Arg Leu Leu His Leu Met Asn Val Glu Met Asp Gln
            160                 165                 170 gaa tat gcc ttc agt ctt ttt cag gca gca gac acg tcc cag tct gga    820
Glu Tyr Ala Phe Ser Leu Phe Gln Ala Ala Asp Thr Ser Gln Ser Gly
        175                 180                 185 acc ctg gaa gga gaa gaa ttc gta cag ttc tat aag gca ttg act aaa    868
Thr Leu Glu Gly Glu Glu Phe Val Gln Phe Tyr Lys Ala Leu Thr Lys
    190                 195                 200

-continued

| | |
|---|---|
| cgt gct gag gtg cag gaa ctg ttt gaa agt ttt tca gct gat ggg cag<br>Arg Ala Glu Val Gln Glu Leu Phe Glu Ser Phe Ser Ala Asp Gly Gln<br>205                       210                   215                  220 | 916 |
| aag ctg act ctg ctg gaa ttt ttg gat ttc ctc caa gag gag cag aag<br>Lys Leu Thr Leu Leu Glu Phe Leu Asp Phe Leu Gln Glu Glu Gln Lys<br>                    225                  230                  235 | 964 |
| gag aga gac tgc acc tct gag ctt gct ctg gaa ctc att gac cgc tat<br>Glu Arg Asp Cys Thr Ser Glu Leu Ala Leu Glu Leu Ile Asp Arg Tyr<br>               240                  245                  250 | 1012 |
| gaa cct tca gac agt ggc aaa ctg cgg cat gtg ctg agt atg gat ggc<br>Glu Pro Ser Asp Ser Gly Lys Leu Arg His Val Leu Ser Met Asp Gly<br>                   255                  260                  265 | 1060 |
| ttc ctc agc tac ctc tgc tct aag gat gga gac atc ttc aac cca gcc<br>Phe Leu Ser Tyr Leu Cys Ser Lys Asp Gly Asp Ile Phe Asn Pro Ala<br>270                       275                   280 | 1108 |
| tgc ctc ccc atc tat cag gat atg act caa ccc ctg aac cac tac ttc<br>Cys Leu Pro Ile Tyr Gln Asp Met Thr Gln Pro Leu Asn His Tyr Phe<br>285                       290                   295                  300 | 1156 |
| atc tgc tct tct cat aac acc tac cta gtg ggg gac cag ctt tgc ggc<br>Ile Cys Ser Ser His Asn Thr Tyr Leu Val Gly Asp Gln Leu Cys Gly<br>                     305                  310                  315 | 1204 |
| cag agc agc gtc gag gga tat ata cgg gcc ctg aag cgg ggg tgc cgc<br>Gln Ser Ser Val Glu Gly Tyr Ile Arg Ala Leu Lys Arg Gly Cys Arg<br>               320                  325                  330 | 1252 |
| tgc gtg gag gtg gat gta tgg gat gga cct agc ggg gaa cct gtc gtt<br>Cys Val Glu Val Asp Val Trp Asp Gly Pro Ser Gly Glu Pro Val Val<br>                   335                  340                  345 | 1300 |
| tac cac gga cac acc ctg acc tcc cgc atc ctg ttc aaa gat gtc gtg<br>Tyr His Gly His Thr Leu Thr Ser Arg Ile Leu Phe Lys Asp Val Val<br>350                       355                   360 | 1348 |
| gcc aca gta gca cag tat gcc ttc cag aca tca gac tac cca gtc atc<br>Ala Thr Val Ala Gln Tyr Ala Phe Gln Thr Ser Asp Tyr Pro Val Ile<br>365                       370                   375                  380 | 1396 |
| ttg tcc ctg gag acc cac tgc agc tgg gag cag cag cag acc atg gcc<br>Leu Ser Leu Glu Thr His Cys Ser Trp Glu Gln Gln Gln Thr Met Ala<br>                   385                  390                  395 | 1444 |
| cgt cat ctg act gag atc ctg ggg gag cag ctg ctg agc acc acc ttg<br>Arg His Leu Thr Glu Ile Leu Gly Glu Gln Leu Leu Ser Thr Thr Leu<br>               400                  405                  410 | 1492 |
| gat ggg gtg ctg ccc act cag ctg ccc tcg cct gag gag ctt cgg agg<br>Asp Gly Val Leu Pro Thr Gln Leu Pro Ser Pro Glu Glu Leu Arg Arg<br>                   415                  420                  425 | 1540 |
| aag atc ctg gtg aag ggg aag aag tta aca ctt gag gaa gac ctg gaa<br>Lys Ile Leu Val Lys Gly Lys Lys Leu Thr Leu Glu Glu Asp Leu Glu<br>430                       435                   440 | 1588 |
| tat gag gaa gag gaa gca gaa cct gag ttg gaa gag tca gaa ttg gcg<br>Tyr Glu Glu Glu Glu Ala Glu Pro Glu Leu Glu Glu Ser Glu Leu Ala<br>445                       450                   455                  460 | 1636 |
| ctg gag tcc cag ttt gag act gag cct gag ccc cag gag cag aac ctt<br>Leu Glu Ser Gln Phe Glu Thr Glu Pro Glu Pro Gln Glu Gln Asn Leu<br>                   465                  470                  475 | 1684 |
| cag aat aag gac aaa aag aag aaa tcc aag ccc atc ttg tgt cca gcc<br>Gln Asn Lys Asp Lys Lys Lys Lys Ser Lys Pro Ile Leu Cys Pro Ala<br>               480                  485                  490 | 1732 |
| ctc tct tcc ctg gtt atc tac ttg aag tct gtc tca ttc cgc agc ttc<br>Leu Ser Ser Leu Val Ile Tyr Leu Lys Ser Val Ser Phe Arg Ser Phe<br>               495                  500                  505 | 1780 |
| aca cat tca aag gag cac tac cac ttc tac gag ata tca tct ttc tct<br>Thr His Ser Lys Glu His Tyr His Phe Tyr Glu Ile Ser Ser Phe Ser<br>510                       515                   520 | 1828 |

```
gaa acc aag gcc aag cgc ctc atc aag gag gct ggc aat gag ttt gtg     1876
Glu Thr Lys Ala Lys Arg Leu Ile Lys Glu Ala Gly Asn Glu Phe Val
525                 530                 535                 540 cag cac aat act tgg cag tta agc cgt gtg tat ccc agc ggc ctg agg     1924
Gln His Asn Thr Trp Gln Leu Ser Arg Val Tyr Pro Ser Gly Leu Arg
            545                 550                 555 aca gac tct tcc aac tac aac ccc cag gaa ctc tgg aat gca ggc tgc     1972
Thr Asp Ser Ser Asn Tyr Asn Pro Gln Glu Leu Trp Asn Ala Gly Cys
        560                 565                 570 cag atg gtg gcc atg aat atg cag act gca ggg ctt gaa atg gac atc     2020
Gln Met Val Ala Met Asn Met Gln Thr Ala Gly Leu Glu Met Asp Ile
    575                 580                 585 tgt gat ggg cat ttc cgc cag aat ggc ggc tgt ggc tat gtg ctg aag     2068
Cys Asp Gly His Phe Arg Gln Asn Gly Gly Cys Gly Tyr Val Leu Lys
590                 595                 600 cca gac ttc ctg cgt gat atc cag agt tct ttc cac cct gag aag ccc     2116
Pro Asp Phe Leu Arg Asp Ile Gln Ser Ser Phe His Pro Glu Lys Pro
605                 610                 615                 620 atc agc cct ttc aaa gcc cag act ctc tta atc cag gtg atc agc ggt     2164
Ile Ser Pro Phe Lys Ala Gln Thr Leu Leu Ile Gln Val Ile Ser Gly
            625                 630                 635 cag caa ctc ccc aaa gtg gac aag acc aaa gag ggg tcc att gtg gat     2212
Gln Gln Leu Pro Lys Val Asp Lys Thr Lys Glu Gly Ser Ile Val Asp
        640                 645                 650 cca ctg gtg aaa gtg cag atc ttt ggc gtt cgt cta gac aca gca cgg     2260
Pro Leu Val Lys Val Gln Ile Phe Gly Val Arg Leu Asp Thr Ala Arg
    655                 660                 665 cag gag acc aac tat gtg gag aac aat ggt ttt aat cca tac tgg ggg     2308
Gln Glu Thr Asn Tyr Val Glu Asn Asn Gly Phe Asn Pro Tyr Trp Gly
670                 675                 680 cag aca cta tgt ttc cgg gtg ctg gtg cct gaa ctt gcc atg ctg cgt     2356
Gln Thr Leu Cys Phe Arg Val Leu Val Pro Glu Leu Ala Met Leu Arg
685                 690                 695                 700 ttt gtg gta atg gat tat gac tgg aaa tcc cga aat gac ttt att ggt     2404
Phe Val Val Met Asp Tyr Asp Trp Lys Ser Arg Asn Asp Phe Ile Gly
            705                 710                 715 cag tac acc ctg cct tgg acc tgc atg caa caa ggt tac cgc cac att     2452
Gln Tyr Thr Leu Pro Trp Thr Cys Met Gln Gln Gly Tyr Arg His Ile
        720                 725                 730 cac ctg ctg tcc aaa gat ggc atc agc ctc cgc cca gct tcc atc ttt     2500
His Leu Leu Ser Lys Asp Gly Ile Ser Leu Arg Pro Ala Ser Ile Phe
    735                 740                 745 gtg tat atc tgc atc cag gaa ggc ctg gag ggg gat gag tcc tga         2545
Val Tyr Ile Cys Ile Gln Glu Gly Leu Glu Gly Asp Glu Ser *
750                 755                 760 ggtgggcatt tcacgggaag ggttggtgtg ctggctttag acggggagaa acatctggaa   2605
ggatgctcga ggggggccc gggc                                           2629

<210> SEQ ID NO 40
<211> LENGTH: 762
<212> TYPE: PRT
<213> ORGANISM: Homo Sapiens

<400> SEQUENCE: 40

Met Ala Ser Leu Leu Gln Asp Gln Leu Thr Thr Asp Gln Asp Leu Leu
 1               5                  10                  15

Leu Met Gln Glu Gly Met Pro Met Arg Lys Val Arg Ser Lys Ser Trp
            20                  25                  30
```

-continued

```
Lys Lys Leu Arg Tyr Phe Arg Leu Gln Asn Asp Gly Met Thr Val Trp
        35                  40                  45

His Ala Arg Gln Ala Arg Gly Ser Ala Lys Pro Ser Phe Ser Ile Ser
    50                  55                  60

Asp Val Glu Thr Ile Arg Asn Gly His Asp Ser Glu Leu Leu Arg Ser
65                  70                  75                  80

Leu Ala Glu Glu Leu Pro Leu Glu Gln Gly Phe Thr Ile Val Phe His
                85                  90                  95

Gly Arg Arg Ser Asn Leu Asp Leu Met Ala Asn Ser Val Glu Glu Ala
            100                 105                 110

Gln Ile Trp Met Arg Gly Leu Gln Leu Leu Val Asp Leu Val Thr Ser
        115                 120                 125

Met Asp His Gln Glu Arg Leu Asp Gln Trp Leu Ser Asp Trp Phe Gln
130                 135                 140

Arg Gly Asp Lys Asn Gln Asp Gly Lys Met Ser Phe Gln Glu Val Gln
145                 150                 155                 160

Arg Leu Leu His Leu Met Asn Val Glu Met Asp Gln Glu Tyr Ala Phe
                165                 170                 175

Ser Leu Phe Gln Ala Ala Asp Thr Ser Gln Ser Gly Thr Leu Glu Gly
            180                 185                 190

Glu Glu Phe Val Gln Phe Tyr Lys Ala Leu Thr Lys Arg Ala Glu Val
        195                 200                 205

Gln Glu Leu Phe Glu Ser Phe Ser Ala Asp Gly Gln Lys Leu Thr Leu
    210                 215                 220

Leu Glu Phe Leu Asp Phe Leu Gln Glu Glu Gln Lys Glu Arg Asp Cys
225                 230                 235                 240

Thr Ser Glu Leu Ala Leu Glu Leu Ile Asp Arg Tyr Glu Pro Ser Asp
                245                 250                 255

Ser Gly Lys Leu Arg His Val Leu Ser Met Asp Gly Phe Leu Ser Tyr
            260                 265                 270

Leu Cys Ser Lys Asp Gly Asp Ile Phe Asn Pro Ala Cys Leu Pro Ile
        275                 280                 285

Tyr Gln Asp Met Thr Gln Pro Leu Asn His Tyr Phe Ile Cys Ser Ser
    290                 295                 300

His Asn Thr Tyr Leu Val Gly Asp Gln Leu Cys Gly Gln Ser Ser Val
305                 310                 315                 320

Glu Gly Tyr Ile Arg Ala Leu Lys Arg Gly Cys Arg Cys Val Glu Val
                325                 330                 335

Asp Val Trp Asp Gly Pro Ser Gly Glu Pro Val Val Tyr His Gly His
            340                 345                 350

Thr Leu Thr Ser Arg Ile Leu Phe Lys Asp Val Val Ala Thr Val Ala
        355                 360                 365

Gln Tyr Ala Phe Gln Thr Ser Asp Tyr Pro Val Ile Leu Ser Leu Glu
    370                 375                 380

Thr His Cys Ser Trp Glu Gln Gln Thr Met Ala Arg His Leu Thr
385                 390                 395                 400

Glu Ile Leu Gly Glu Gln Leu Leu Ser Thr Thr Leu Asp Gly Val Leu
                405                 410                 415

Pro Thr Gln Leu Pro Ser Pro Glu Glu Leu Arg Arg Lys Ile Leu Val
            420                 425                 430

Lys Gly Lys Lys Leu Thr Leu Glu Glu Asp Leu Glu Tyr Glu Glu Glu
        435                 440                 445

Glu Ala Glu Pro Glu Leu Glu Glu Ser Glu Leu Ala Leu Glu Ser Gln
```

-continued

```
                     450                 455                 460
Phe Glu Thr Glu Pro Pro Gln Glu Gln Asn Leu Gln Asn Lys Asp
465                 470                 475                 480

Lys Lys Lys Lys Ser Lys Pro Ile Leu Cys Pro Ala Leu Ser Leu
                485                 490                 495

Val Ile Tyr Leu Lys Ser Val Ser Phe Arg Ser Phe Thr His Ser Lys
            500                 505                 510

Glu His Tyr His Phe Tyr Glu Ile Ser Ser Phe Ser Glu Thr Lys Ala
                515                 520                 525

Lys Arg Leu Ile Lys Glu Ala Gly Asn Glu Phe Val Gln His Asn Thr
            530                 535                 540

Trp Gln Leu Ser Arg Val Tyr Pro Ser Gly Leu Arg Thr Asp Ser Ser
545                 550                 555                 560

Asn Tyr Asn Pro Gln Glu Leu Trp Asn Ala Gly Cys Gln Met Val Ala
                565                 570                 575

Met Asn Met Gln Thr Ala Gly Leu Glu Met Asp Ile Cys Asp Gly His
            580                 585                 590

Phe Arg Gln Asn Gly Gly Cys Gly Tyr Val Leu Lys Pro Asp Phe Leu
            595                 600                 605

Arg Asp Ile Gln Ser Ser Phe His Pro Glu Lys Pro Ile Ser Pro Phe
            610                 615                 620

Lys Ala Gln Thr Leu Leu Ile Gln Val Ile Ser Gly Gln Gln Leu Pro
625                 630                 635                 640

Lys Val Asp Lys Thr Lys Glu Gly Ser Ile Val Asp Pro Leu Val Lys
                645                 650                 655

Val Gln Ile Phe Gly Val Arg Leu Asp Thr Ala Arg Gln Glu Thr Asn
            660                 665                 670

Tyr Val Glu Asn Asn Gly Phe Asn Pro Tyr Trp Gly Gln Thr Leu Cys
            675                 680                 685

Phe Arg Val Leu Val Pro Glu Leu Ala Met Leu Arg Phe Val Val Met
            690                 695                 700

Asp Tyr Asp Trp Lys Ser Arg Asn Asp Phe Ile Gly Gln Tyr Thr Leu
705                 710                 715                 720

Pro Trp Thr Cys Met Gln Gln Gly Tyr Arg His Ile His Leu Leu Ser
                725                 730                 735

Lys Asp Gly Ile Ser Leu Arg Pro Ala Ser Ile Phe Val Tyr Ile Cys
            740                 745                 750

Ile Gln Glu Gly Leu Glu Gly Asp Glu Ser
            755                 760
```

```
<210> SEQ ID NO 41
<211> LENGTH: 2289
<212> TYPE: DNA
<213> ORGANISM: Homo Sapiens
<220> FEATURE:
<221> NAME/KEY: CDS
<222> LOCATION: (1)...(2289)

<400> SEQUENCE: 41 atg gcg tcc ctg ctg caa gac cag ctg acc act gat cag gac ttg ctg      48
Met Ala Ser Leu Leu Gln Asp Gln Leu Thr Thr Asp Gln Asp Leu Leu
 1               5                  10                  15 ctg atg cag gaa ggc atg ccg atg cgc aag gtg agg tcc aaa agc tgg      96
Leu Met Gln Glu Gly Met Pro Met Arg Lys Val Arg Ser Lys Ser Trp
            20                  25                  30 aag aag cta aga tac ttc aga ctt cag aat gac ggc atg aca gtc tgg     144
```

-continued

| | | |
|---|---|---|
| Lys Lys Leu Arg Tyr Phe Arg Leu Gln Asn Asp Gly Met Thr Val Trp<br>35 40 45 | | |
| cat gca cgg cag gcc agg ggc agt gcc aag ccc agc ttc tca atc tct<br>His Ala Arg Gln Ala Arg Gly Ser Ala Lys Pro Ser Phe Ser Ile Ser<br>50 55 60 | | 192 |
| gat gtg gag aca ata cgt aat ggc cat gat tcc gag ttg ctg cgt agc<br>Asp Val Glu Thr Ile Arg Asn Gly His Asp Ser Glu Leu Leu Arg Ser<br>65 70 75 80 | | 240 |
| ctg gca gag gag ctc ccc ctg gag cag ggc ttc acc att gtc ttc cat<br>Leu Ala Glu Glu Leu Pro Leu Glu Gln Gly Phe Thr Ile Val Phe His<br>85 90 95 | | 288 |
| ggc cgc cgc tcc aac ctg gac ctg atg gcc aac agt gtt gag gag gcc<br>Gly Arg Arg Ser Asn Leu Asp Leu Met Ala Asn Ser Val Glu Glu Ala<br>100 105 110 | | 336 |
| cag ata tgg atg cga ggg ctc cag ctg ttg gtg gat ctt gtc acc agc<br>Gln Ile Trp Met Arg Gly Leu Gln Leu Leu Val Asp Leu Val Thr Ser<br>115 120 125 | | 384 |
| atg gac cat cag gag cgc ctg gac caa tgg ctg agc gat tgg ttt caa<br>Met Asp His Gln Glu Arg Leu Asp Gln Trp Leu Ser Asp Trp Phe Gln<br>130 135 140 | | 432 |
| cgt gga gac aaa aat cag gat ggt aag atg agt ttc caa gaa gtt cag<br>Arg Gly Asp Lys Asn Gln Asp Gly Lys Met Ser Phe Gln Glu Val Gln<br>145 150 155 160 | | 480 |
| cgg tta ttg cac cta atg aat gtg gaa atg gac caa gaa tat gcc ttc<br>Arg Leu Leu His Leu Met Asn Val Glu Met Asp Gln Glu Tyr Ala Phe<br>165 170 175 | | 528 |
| agt ctt ttt cag gca gca gac acg tcc cag tct gga acc ctg gaa gga<br>Ser Leu Phe Gln Ala Ala Asp Thr Ser Gln Ser Gly Thr Leu Glu Gly<br>180 185 190 | | 576 |
| gaa gaa ttc gta cag ttc tat aag gca ttg act aaa cgt gct gag gtg<br>Glu Glu Phe Val Gln Phe Tyr Lys Ala Leu Thr Lys Arg Ala Glu Val<br>195 200 205 | | 624 |
| cag gaa ctg ttt gaa agt ttt tca gct gat ggg cag aag ctg act ctg<br>Gln Glu Leu Phe Glu Ser Phe Ser Ala Asp Gly Gln Lys Leu Thr Leu<br>210 215 220 | | 672 |
| ctg gaa ttt ttg gat ttc ctc caa gag gag cag aag gag aga gac tgc<br>Leu Glu Phe Leu Asp Phe Leu Gln Glu Glu Gln Lys Glu Arg Asp Cys<br>225 230 235 240 | | 720 |
| acc tct gag ctt gct ctg gaa ctc att gac cgc tat gaa cct tca gac<br>Thr Ser Glu Leu Ala Leu Glu Leu Ile Asp Arg Tyr Glu Pro Ser Asp<br>245 250 255 | | 768 |
| agt ggc aaa ctg cgg cat gtg ctg agt atg gat ggc ttc ctc agc tac<br>Ser Gly Lys Leu Arg His Val Leu Ser Met Asp Gly Phe Leu Ser Tyr<br>260 265 270 | | 816 |
| ctc tgc tct aag gat gga gac atc ttc aac cca gcc tgc ctc ccc atc<br>Leu Cys Ser Lys Asp Gly Asp Ile Phe Asn Pro Ala Cys Leu Pro Ile<br>275 280 285 | | 864 |
| tat cag gat atg act caa ccc ctg aac cac tac ttc atc tgc tct tct<br>Tyr Gln Asp Met Thr Gln Pro Leu Asn His Tyr Phe Ile Cys Ser Ser<br>290 295 300 | | 912 |
| cat aac acc tac cta gtg ggg gac cag ctt tgc ggc cag agc agc gtc<br>His Asn Thr Tyr Leu Val Gly Asp Gln Leu Cys Gly Gln Ser Ser Val<br>305 310 315 320 | | 960 |
| gag gga tat ata cgg gcc ctg aag cgg ggg tgc cgc tgc gtg gag gtg<br>Glu Gly Tyr Ile Arg Ala Leu Lys Arg Gly Cys Arg Cys Val Glu Val<br>325 330 335 | | 1008 |
| gat gta tgg gat gga cct agc ggg gaa cct gtc gtt tac cac gga cac<br>Asp Val Trp Asp Gly Pro Ser Gly Glu Pro Val Val Tyr His Gly His<br>340 345 350 | | 1056 |

```
acc ctg acc tcc cgc atc ctg ttc aaa gat gtc gtg gcc aca gta gca    1104
Thr Leu Thr Ser Arg Ile Leu Phe Lys Asp Val Val Ala Thr Val Ala
            355                 360                 365 cag tat gcc ttc cag aca tca gac tac cca gtc atc ttg tcc ctg gag    1152
Gln Tyr Ala Phe Gln Thr Ser Asp Tyr Pro Val Ile Leu Ser Leu Glu
    370                 375                 380 acc cac tgc agc tgg gag cag cag cag acc atg gcc cgt cat ctg act    1200
Thr His Cys Ser Trp Glu Gln Gln Gln Thr Met Ala Arg His Leu Thr
385                 390                 395                 400 gag atc ctg ggg gag cag ctg ctg agc acc acc ttg gat ggg gtg ctg    1248
Glu Ile Leu Gly Glu Gln Leu Leu Ser Thr Thr Leu Asp Gly Val Leu
                405                 410                 415 ccc act cag ctg ccc tcg cct gag gag ctt cgg agg aag atc ctg gtg    1296
Pro Thr Gln Leu Pro Ser Pro Glu Glu Leu Arg Arg Lys Ile Leu Val
            420                 425                 430 aag ggg aag aag tta aca ctt gag gaa gac ctg gaa tat gag gaa gag    1344
Lys Gly Lys Lys Leu Thr Leu Glu Glu Asp Leu Glu Tyr Glu Glu Glu
        435                 440                 445 gaa gca gaa cct gag ttg gaa gag tca gaa ttg gcg ctg gag tcc cag    1392
Glu Ala Glu Pro Glu Leu Glu Glu Ser Glu Leu Ala Leu Glu Ser Gln
450                 455                 460 ttt gag act gag cct gag ccc cag gag cag aac ctt cag aat aag gac    1440
Phe Glu Thr Glu Pro Glu Pro Gln Glu Gln Asn Leu Gln Asn Lys Asp
465                 470                 475                 480 aaa aag aag aaa tcc aag ccc atc ttg tgt cca gcc ctc tct tcc ctg    1488
Lys Lys Lys Lys Ser Lys Pro Ile Leu Cys Pro Ala Leu Ser Ser Leu
                485                 490                 495 gtt atc tac ttg aag tct gtc tca ttc cgc agc ttc aca cat tca aag    1536
Val Ile Tyr Leu Lys Ser Val Ser Phe Arg Ser Phe Thr His Ser Lys
            500                 505                 510 gag cac tac cac ttc tac gag ata tca tct ttc tct gaa acc aag gcc    1584
Glu His Tyr His Phe Tyr Glu Ile Ser Ser Phe Ser Glu Thr Lys Ala
        515                 520                 525 aag cgc ctc atc aag gag gct ggc aat gag ttt gtg cag cac aat act    1632
Lys Arg Leu Ile Lys Glu Ala Gly Asn Glu Phe Val Gln His Asn Thr
    530                 535                 540 tgg cag tta agc cgt gtg tat ccc agc ggc ctg agg aca gac tct tcc    1680
Trp Gln Leu Ser Arg Val Tyr Pro Ser Gly Leu Arg Thr Asp Ser Ser
545                 550                 555                 560 aac tac aac ccc cag gaa ctc tgg aat gca ggc tgc cag atg gtg gcc    1728
Asn Tyr Asn Pro Gln Glu Leu Trp Asn Ala Gly Cys Gln Met Val Ala
                565                 570                 575 atg aat atg cag act gca ggg ctt gaa atg gac atc tgt gat ggg cat    1776
Met Asn Met Gln Thr Ala Gly Leu Glu Met Asp Ile Cys Asp Gly His
            580                 585                 590 ttc cgc cag aat ggc ggc tgt ggc tat gtg ctg aag cca gac ttc ctg    1824
Phe Arg Gln Asn Gly Gly Cys Gly Tyr Val Leu Lys Pro Asp Phe Leu
        595                 600                 605 cgt gat atc cag agt tct ttc cac cct gag aag ccc atc agc cct ttc    1872
Arg Asp Ile Gln Ser Ser Phe His Pro Glu Lys Pro Ile Ser Pro Phe
    610                 615                 620 aaa gcc cag act ctc tta atc cag gtg atc agc ggt cag caa ctc ccc    1920
Lys Ala Gln Thr Leu Leu Ile Gln Val Ile Ser Gly Gln Gln Leu Pro
625                 630                 635                 640 aaa gtg gac aag acc aaa gag ggg tcc att gtg gat cca ctg gtg aaa    1968
Lys Val Asp Lys Thr Lys Glu Gly Ser Ile Val Asp Pro Leu Val Lys
                645                 650                 655 gtg cag atc ttt ggc gtt cgt cta gac aca gca cgg cag gag acc aac    2016
Val Gln Ile Phe Gly Val Arg Leu Asp Thr Ala Arg Gln Glu Thr Asn
            660                 665                 670
```

| | | |
|---|---|---|
| tat gtg gag aac aat ggt ttt aat cca tac tgg ggg cag aca cta tgt<br>Tyr Val Glu Asn Asn Gly Phe Asn Pro Tyr Trp Gly Gln Thr Leu Cys<br>                                675                          680                         685 | 2064 |
| ttc cgg gtg ctg gtg cct gaa ctt gcc atg ctg cgt ttt gtg gta atg<br>Phe Arg Val Leu Val Pro Glu Leu Ala Met Leu Arg Phe Val Val Met<br>   690                           695                          700 | 2112 |
| gat tat gac tgg aaa tcc cga aat gac ttt att ggt cag tac acc ctg<br>Asp Tyr Asp Trp Lys Ser Arg Asn Asp Phe Ile Gly Gln Tyr Thr Leu<br>705                          710                          715                          720 | 2160 |
| cct tgg acc tgc atg caa caa ggt tac cgc cac att cac ctg ctg tcc<br>Pro Trp Thr Cys Met Gln Gln Gly Tyr Arg His Ile His Leu Leu Ser<br>                                725                          730                          735 | 2208 |
| aaa gat ggc atc agc ctc cgc cca gct tcc atc ttt gtg tat atc tgc<br>Lys Asp Gly Ile Ser Leu Arg Pro Ala Ser Ile Phe Val Tyr Ile Cys<br>   740                           745                          750 | 2256 |
| atc cag gaa ggc ctg gag ggg gat gag tcc tga<br>Ile Gln Glu Gly Leu Glu Gly Asp Glu Ser *<br>                                755                          760 | 2289 |

<210> SEQ ID NO 42
<211> LENGTH: 2171
<212> TYPE: DNA
<213> ORGANISM: Homo Sapiens
<220> FEATURE:
<221> NAME/KEY: CDS
<222> LOCATION: (232)...(2058)

<400> SEQUENCE: 42

| | |
|---|---|
| ccacgcgtcc gcccacgcgt ccgcagccaa ccagctatac ctctttgaa gattttaaga | 60 |
| acttagcctc ctgaacagtc ttcttcgaaa gtgaaaagtg gtaacagctg atgagtatca | 120 |
| agaaattatt ttccgcaaag gggcagagtt aattgtattt ggaacccatg acagcaccta | 180 |
| ctggggaaag acttctaagt gaggagaaac ggctctacag gtcatgaaac t atg gaa<br>                                                                                            Met Glu<br>                                                                                                           1 | 237 |
| atg aga tgg ttt ttg tca aag att cag gat gac ttc aga ggt gga aaa<br>Met Arg Trp Phe Leu Ser Lys Ile Gln Asp Asp Phe Arg Gly Gly Lys<br>      5                          10                            15 | 285 |
| att aac cta gaa aaa act cag agg tta ctt gaa aaa tta gat att cgg<br>Ile Asn Leu Glu Lys Thr Gln Arg Leu Leu Glu Lys Leu Asp Ile Arg<br> 20                        25                          30 | 333 |
| tgc agt tat att cat gtg aaa cag att ttt aag gac aat gac agg ctg<br>Cys Ser Tyr Ile His Val Lys Gln Ile Phe Lys Asp Asn Asp Arg Leu<br> 35                        40                          45                          50 | 381 |
| aaa caa gga aga atc acc ata gaa gaa ttt aga gca att tat cga att<br>Lys Gln Gly Arg Ile Thr Ile Glu Glu Phe Arg Ala Ile Tyr Arg Ile<br>                  55                          60                          65 | 429 |
| atc acg cac aga gaa gaa att att gag att ttc aac aca tat tct gaa<br>Ile Thr His Arg Glu Glu Ile Ile Glu Ile Phe Asn Thr Tyr Ser Glu<br>               70                          75                          80 | 477 |
| aac cgg aaa att ctt tta gca agt aat ctg gct caa ttt ctg aca caa<br>Asn Arg Lys Ile Leu Leu Ala Ser Asn Leu Ala Gln Phe Leu Thr Gln<br>   85                          90                          95 | 525 |
| gaa caa tat gca gct gag atg agt aaa gct att gct ttt gag atc att<br>Glu Gln Tyr Ala Ala Glu Met Ser Lys Ala Ile Ala Phe Glu Ile Ile<br>        100                        105                          110 | 573 |
| cag aaa tac gag cct atc gaa gaa gtt agg aaa gca cac caa atg tca<br>Gln Lys Tyr Glu Pro Ile Glu Glu Val Arg Lys Ala His Gln Met Ser<br>115                          120                          125                          130 | 621 |
| tta gaa ggt ttt aca aga tac atg gat tca cgt gaa tgt cta ctg ttt | 669 |

```
                 Leu Glu Gly Phe Thr Arg Tyr Met Asp Ser Arg Glu Cys Leu Leu Phe
                                 135                 140                 145 aaa aat gaa tgt aga aaa gtt tat caa gat atg act cat cca tta aat           717
Lys Asn Glu Cys Arg Lys Val Tyr Gln Asp Met Thr His Pro Leu Asn
                150                 155                 160 gat tat ttt att tca tct tca cat aac aca tat ttg gta tct gat caa           765
Asp Tyr Phe Ile Ser Ser Ser His Asn Thr Tyr Leu Val Ser Asp Gln
            165                 170                 175 tta ttg gga cca agt gac ctt tgg gga tat gca agt gcc ctt gtg aaa           813
Leu Leu Gly Pro Ser Asp Leu Trp Gly Tyr Ala Ser Ala Leu Val Lys
        180                 185                 190 gga tgc cgt tgt ttg gag att gac tgc tgg gat gga gca caa aat gaa           861
Gly Cys Arg Cys Leu Glu Ile Asp Cys Trp Asp Gly Ala Gln Asn Glu
195                 200                 205                 210 cct gtt gta tat cat ggc tac aca ctc aca agc aaa ctt ctg ttt aaa           909
Pro Val Val Tyr His Gly Tyr Thr Leu Thr Ser Lys Leu Leu Phe Lys
                215                 220                 225 act gtt atc caa gct ata cac aag tat gca ttc atg aca tct gac tac           957
Thr Val Ile Gln Ala Ile His Lys Tyr Ala Phe Met Thr Ser Asp Tyr
            230                 235                 240 cca gtg gtg ctc tct tta gaa aat cac tgc tcc act gcc caa caa gaa          1005
Pro Val Val Leu Ser Leu Glu Asn His Cys Ser Thr Ala Gln Gln Glu
        245                 250                 255 gta atg gca gac aat ttg cag gct act ttt gga gag tcc ttg ctt tct          1053
Val Met Ala Asp Asn Leu Gln Ala Thr Phe Gly Glu Ser Leu Leu Ser
    260                 265                 270 gat atg ctt gat gat ttt cct gat act cta cca tca cca gag gca cta          1101
Asp Met Leu Asp Asp Phe Pro Asp Thr Leu Pro Ser Pro Glu Ala Leu
275                 280                 285                 290 aaa ttc aaa ata tta gtt aaa aat aag aaa ata gga acc tta aag gaa          1149
Lys Phe Lys Ile Leu Val Lys Asn Lys Lys Ile Gly Thr Leu Lys Glu
                295                 300                 305 acc cat gaa aga aaa ggt tct gat aag cat gga gac aat caa gac aag          1197
Thr His Glu Arg Lys Gly Ser Asp Lys His Gly Asp Asn Gln Asp Lys
            310                 315                 320 gaa aca ggg gta aaa aag tta cct gga gta atg ctt ttc aag aaa aag          1245
Glu Thr Gly Val Lys Lys Leu Pro Gly Val Met Leu Phe Lys Lys Lys
        325                 330                 335 aag acc agg aag cta aaa att gct ctg gcc tta tct gat ctt gtc att          1293
Lys Thr Arg Lys Leu Lys Ile Ala Leu Ala Leu Ser Asp Leu Val Ile
    340                 345                 350 tat acg aaa gct gag aaa ttc aaa agc ttt caa cat tca aga tta tat          1341
Tyr Thr Lys Ala Glu Lys Phe Lys Ser Phe Gln His Ser Arg Leu Tyr
355                 360                 365                 370 cag caa ttt aat gaa aat aat tct att ggg gag aca caa gcc cga aaa          1389
Gln Gln Phe Asn Glu Asn Asn Ser Ile Gly Glu Thr Gln Ala Arg Lys
                375                 380                 385 ctt tca aaa ttg cga gtc cat gag ttt att ttt cac acc agg aag ttc          1437
Leu Ser Lys Leu Arg Val His Glu Phe Ile Phe His Thr Arg Lys Phe
            390                 395                 400 att acc aga ata tat ccc aaa gca aca aga gca gac tct tct aat ttt          1485
Ile Thr Arg Ile Tyr Pro Lys Ala Thr Arg Ala Asp Ser Ser Asn Phe
        405                 410                 415 aat ccc caa gaa ttt tgg aat ata ggt tgt caa atg gtg gct tta aat          1533
Asn Pro Gln Glu Phe Trp Asn Ile Gly Cys Gln Met Val Ala Leu Asn
    420                 425                 430 ttc cag acc cct ggt ctg ccc atg gat ctg caa aat ggg aaa ttt ttg          1581
Phe Gln Thr Pro Gly Leu Pro Met Asp Leu Gln Asn Gly Lys Phe Leu
435                 440                 445                 450
```

-continued

```
gat aat ggt ggt tct gga tat att ttg aaa cca cat ttc tta aga gag   1629
Asp Asn Gly Gly Ser Gly Tyr Ile Leu Lys Pro His Phe Leu Arg Glu
            455                 460                 465 agt aaa tca tac ttt aac cca agt aac ata aaa gag ggt atg cca att   1677
Ser Lys Ser Tyr Phe Asn Pro Ser Asn Ile Lys Glu Gly Met Pro Ile
        470                 475                 480 aca ctt aca ata agg ctc atc agt ggt atc cag ttg cct ctt act cat   1725
Thr Leu Thr Ile Arg Leu Ile Ser Gly Ile Gln Leu Pro Leu Thr His
    485                 490                 495 tca tca tct aac aaa ggt gat tca tta gta att ata gaa gtt ttt ggt   1773
Ser Ser Ser Asn Lys Gly Asp Ser Leu Val Ile Ile Glu Val Phe Gly
500                 505                 510 gtt cca aat gat caa atg aag cag cag act cgt gta att aaa aaa aat   1821
Val Pro Asn Asp Gln Met Lys Gln Gln Thr Arg Val Ile Lys Lys Asn
515                 520                 525                 530 gct ttt agt cca aga tgg aat gaa aca ttc aca ttt att att cat gtc   1869
Ala Phe Ser Pro Arg Trp Asn Glu Thr Phe Thr Phe Ile Ile His Val
                535                 540                 545 cca gaa ttg gca ttg ata cgt ttt gtt gtt gaa ggt caa ggt tta ata   1917
Pro Glu Leu Ala Leu Ile Arg Phe Val Val Glu Gly Gln Gly Leu Ile
            550                 555                 560 gca gga aat gaa ttt ctt ggg caa tat act ttg cca ctt cta tgc atg   1965
Ala Gly Asn Glu Phe Leu Gly Gln Tyr Thr Leu Pro Leu Leu Cys Met
        565                 570                 575 aac aaa ggt tat cgt cgt att cct ctg ttt tcc aga atg ggt gag agc   2013
Asn Lys Gly Tyr Arg Arg Ile Pro Leu Phe Ser Arg Met Gly Glu Ser
    580                 585                 590 ctt gag cct gct tca ctg ttt gtt tat gtt tgg tac gtc aga taa       2058
Leu Glu Pro Ala Ser Leu Phe Val Tyr Val Trp Tyr Val Arg *
595                 600                 605 cagctaatga taaatgacat atcattagct atgcatcgca ataaacagc caaaatgaaa    2118 aaaaaaaaaa aaaaaaaaaa attggcggcc gcaagcttat tcccttagt aag          2171
```

<210> SEQ ID NO 43
<211> LENGTH: 608
<212> TYPE: PRT
<213> ORGANISM: Homo Sapiens

<400> SEQUENCE: 43

```
Met Glu Met Arg Trp Phe Leu Ser Lys Ile Gln Asp Asp Phe Arg Gly
 1               5                  10                  15

Gly Lys Ile Asn Leu Glu Lys Thr Gln Arg Leu Leu Glu Lys Leu Asp
            20                  25                  30

Ile Arg Cys Ser Tyr Ile His Val Lys Gln Ile Phe Lys Asp Asn Asp
        35                  40                  45

Arg Leu Lys Gln Gly Arg Ile Thr Ile Glu Glu Phe Arg Ala Ile Tyr
    50                  55                  60

Arg Ile Ile Thr His Arg Glu Glu Ile Glu Ile Phe Asn Thr Tyr
65                  70                  75                  80

Ser Glu Asn Arg Lys Ile Leu Leu Ala Ser Asn Leu Ala Gln Phe Leu
                85                  90                  95

Thr Gln Glu Gln Tyr Ala Ala Glu Met Ser Lys Ala Ile Ala Phe Glu
            100                 105                 110

Ile Ile Gln Lys Tyr Glu Pro Ile Glu Glu Val Arg Lys Ala His Gln
        115                 120                 125

Met Ser Leu Glu Gly Phe Thr Arg Tyr Met Asp Ser Arg Glu Cys Leu
    130                 135                 140
```

-continued

```
Leu Phe Lys Asn Glu Cys Arg Lys Val Tyr Gln Asp Met Thr His Pro
145                 150                 155                 160

Leu Asn Asp Tyr Phe Ile Ser Ser His Asn Thr Tyr Leu Val Ser
            165                 170                 175

Asp Gln Leu Leu Gly Pro Ser Asp Leu Trp Gly Tyr Ala Ser Ala Leu
            180                 185                 190

Val Lys Gly Cys Arg Cys Leu Glu Ile Asp Cys Trp Asp Gly Ala Gln
            195                 200                 205

Asn Glu Pro Val Val Tyr His Gly Tyr Thr Leu Thr Ser Lys Leu Leu
            210                 215                 220

Phe Lys Thr Val Ile Gln Ala Ile His Lys Tyr Ala Phe Met Thr Ser
225                 230                 235                 240

Asp Tyr Pro Val Val Leu Ser Leu Glu Asn His Cys Ser Thr Ala Gln
                245                 250                 255

Gln Glu Val Met Ala Asp Asn Leu Gln Ala Thr Phe Gly Glu Ser Leu
            260                 265                 270

Leu Ser Asp Met Leu Asp Asp Phe Pro Asp Thr Leu Pro Ser Pro Glu
        275                 280                 285

Ala Leu Lys Phe Lys Ile Leu Val Lys Asn Lys Lys Ile Gly Thr Leu
        290                 295                 300

Lys Glu Thr His Glu Arg Lys Gly Ser Asp Lys His Gly Asp Asn Gln
305                 310                 315                 320

Asp Lys Glu Thr Gly Val Lys Lys Leu Pro Gly Val Met Leu Phe Lys
                325                 330                 335

Lys Lys Lys Thr Arg Lys Leu Lys Ile Ala Leu Ala Leu Ser Asp Leu
            340                 345                 350

Val Ile Tyr Thr Lys Ala Glu Lys Phe Lys Ser Phe Gln His Ser Arg
        355                 360                 365

Leu Tyr Gln Gln Phe Asn Glu Asn Ser Ile Gly Glu Thr Gln Ala
    370                 375                 380

Arg Lys Leu Ser Lys Leu Arg Val His Glu Phe Ile Phe His Thr Arg
385                 390                 395                 400

Lys Phe Ile Thr Arg Ile Tyr Pro Lys Ala Thr Arg Ala Asp Ser Ser
                405                 410                 415

Asn Phe Asn Pro Gln Glu Phe Trp Asn Ile Gly Cys Gln Met Val Ala
            420                 425                 430

Leu Asn Phe Gln Thr Pro Gly Leu Pro Met Asp Leu Gln Asn Gly Lys
        435                 440                 445

Phe Leu Asp Asn Gly Gly Ser Gly Tyr Ile Leu Lys Pro His Phe Leu
    450                 455                 460

Arg Glu Ser Lys Ser Tyr Phe Asn Pro Ser Asn Ile Lys Glu Gly Met
465                 470                 475                 480

Pro Ile Thr Leu Thr Ile Arg Leu Ile Ser Gly Ile Gln Leu Pro Leu
                485                 490                 495

Thr His Ser Ser Ser Asn Lys Gly Asp Ser Leu Val Ile Ile Glu Val
            500                 505                 510

Phe Gly Val Pro Asn Asp Gln Met Lys Gln Gln Thr Arg Val Ile Lys
        515                 520                 525

Lys Asn Ala Phe Ser Pro Arg Trp Asn Glu Thr Phe Thr Phe Ile Ile
    530                 535                 540

His Val Pro Glu Leu Ala Leu Ile Arg Phe Val Val Glu Gly Gln Gly
545                 550                 555                 560

Leu Ile Ala Gly Asn Glu Phe Leu Gly Gln Tyr Thr Leu Pro Leu Leu
```

-continued

```
                565                 570                 575
Cys Met Asn Lys Gly Tyr Arg Arg Ile Pro Leu Phe Ser Arg Met Gly
            580                 585                 590

Glu Ser Leu Glu Pro Ala Ser Leu Phe Val Tyr Val Trp Tyr Val Arg
            595                 600                 605

<210> SEQ ID NO 44
<211> LENGTH: 1827
<212> TYPE: DNA
<213> ORGANISM: Homo Sapiens
<220> FEATURE:
<221> NAME/KEY: CDS
<222> LOCATION: (1)...(1827)

<400> SEQUENCE: 44 atg gaa atg aga tgg ttt ttg tca aag att cag gat gac ttc aga ggt      48
Met Glu Met Arg Trp Phe Leu Ser Lys Ile Gln Asp Asp Phe Arg Gly
  1               5                  10                  15 gga aaa att aac cta gaa aaa act cag agg tta ctt gaa aaa tta gat      96
Gly Lys Ile Asn Leu Glu Lys Thr Gln Arg Leu Leu Glu Lys Leu Asp
                 20                  25                  30 att cgg tgc agt tat att cat gtg aaa cag att ttt aag gac aat gac     144
Ile Arg Cys Ser Tyr Ile His Val Lys Gln Ile Phe Lys Asp Asn Asp
             35                  40                  45 agg ctg aaa caa gga aga atc acc ata gaa gaa ttt aga gca att tat     192
Arg Leu Lys Gln Gly Arg Ile Thr Ile Glu Glu Phe Arg Ala Ile Tyr
         50                  55                  60 cga att atc acg cac aga gaa gaa att att gag att ttc aac aca tat     240
Arg Ile Ile Thr His Arg Glu Glu Ile Ile Glu Ile Phe Asn Thr Tyr
 65                  70                  75                  80 tct gaa aac cgg aaa att ctt tta gca agt aat ctg gct caa ttt ctg     288
Ser Glu Asn Arg Lys Ile Leu Leu Ala Ser Asn Leu Ala Gln Phe Leu
                 85                  90                  95 aca caa gaa caa tat gca gct gag atg agt aaa gct att gct ttt gag     336
Thr Gln Glu Gln Tyr Ala Ala Glu Met Ser Lys Ala Ile Ala Phe Glu
            100                 105                 110 atc att cag aaa tac gag cct atc gaa gaa gtt agg aaa gca cac caa     384
Ile Ile Gln Lys Tyr Glu Pro Ile Glu Glu Val Arg Lys Ala His Gln
        115                 120                 125 atg tca tta gaa ggt ttt aca aga tac atg gat tca cgt gaa tgt cta     432
Met Ser Leu Glu Gly Phe Thr Arg Tyr Met Asp Ser Arg Glu Cys Leu
    130                 135                 140 ctg ttt aaa aat gaa tgt aga aaa gtt tat caa gat atg act cat cca     480
Leu Phe Lys Asn Glu Cys Arg Lys Val Tyr Gln Asp Met Thr His Pro
145                 150                 155                 160 tta aat gat tat ttt att tca tct tca cat aac aca tat ttg gta tct     528
Leu Asn Asp Tyr Phe Ile Ser Ser Ser His Asn Thr Tyr Leu Val Ser
                165                 170                 175 gat caa tta ttg gga cca agt gac ctt tgg gga tat gca agt gcc ctt     576
Asp Gln Leu Leu Gly Pro Ser Asp Leu Trp Gly Tyr Ala Ser Ala Leu
            180                 185                 190 gtg aaa gga tgc cgt tgt ttg gag att gac tgc tgg gat gga gca caa     624
Val Lys Gly Cys Arg Cys Leu Glu Ile Asp Cys Trp Asp Gly Ala Gln
        195                 200                 205 aat gaa cct gtt gta tat cat ggc tac aca ctc aca agc aaa ctt ctg     672
Asn Glu Pro Val Val Tyr His Gly Tyr Thr Leu Thr Ser Lys Leu Leu
    210                 215                 220 ttt aaa act gtt atc caa gct ata cac aag tat gca ttc atg aca tct     720
Phe Lys Thr Val Ile Gln Ala Ile His Lys Tyr Ala Phe Met Thr Ser
225                 230                 235                 240
```

-continued

| | |
|---|---|
| gac tac cca gtg gtg ctc tct tta gaa aat cac tgc tcc act gcc caa<br>Asp Tyr Pro Val Val Leu Ser Leu Glu Asn His Cys Ser Thr Ala Gln<br>     245      250      255 | 768 |
| caa gaa gta atg gca gac aat ttg cag gct act ttt gga gag tcc ttg<br>Gln Glu Val Met Ala Asp Asn Leu Gln Ala Thr Phe Gly Glu Ser Leu<br>    260      265      270 | 816 |
| ctt tct gat atg ctt gat gat ttt cct gat act cta cca tca cca gag<br>Leu Ser Asp Met Leu Asp Asp Phe Pro Asp Thr Leu Pro Ser Pro Glu<br>  275      280      285 | 864 |
| gca cta aaa ttc aaa ata tta gtt aaa aat aag aaa ata gga acc tta<br>Ala Leu Lys Phe Lys Ile Leu Val Lys Asn Lys Lys Ile Gly Thr Leu<br>290      295      300 | 912 |
| aag gaa acc cat gaa aga aaa ggt tct gat aag cat gga gac aat caa<br>Lys Glu Thr His Glu Arg Lys Gly Ser Asp Lys His Gly Asp Asn Gln<br>305      310      315      320 | 960 |
| gac aag gaa aca ggg gta aaa aag tta cct gga gta atg ctt ttc aag<br>Asp Lys Glu Thr Gly Val Lys Lys Leu Pro Gly Val Met Leu Phe Lys<br>    325      330      335 | 1008 |
| aaa aag aag acc agg aag cta aaa att gct ctg gcc tta tct gat ctt<br>Lys Lys Lys Thr Arg Lys Leu Lys Ile Ala Leu Ala Leu Ser Asp Leu<br>    340      345      350 | 1056 |
| gtc att tat acg aaa gct gag aaa ttc aaa agc ttt caa cat tca aga<br>Val Ile Tyr Thr Lys Ala Glu Lys Phe Lys Ser Phe Gln His Ser Arg<br>     355      360      365 | 1104 |
| tta tat cag caa ttt aat gaa aat aat tct att ggg gag aca caa gcc<br>Leu Tyr Gln Gln Phe Asn Glu Asn Asn Ser Ile Gly Glu Thr Gln Ala<br>370      375      380 | 1152 |
| cga aaa ctt tca aaa ttg cga gtc cat gag ttt att ttt cac acc agg<br>Arg Lys Leu Ser Lys Leu Arg Val His Glu Phe Ile Phe His Thr Arg<br>385      390      395      400 | 1200 |
| aag ttc att acc aga ata tat ccc aaa gca aca aga gca gac tct tct<br>Lys Phe Ile Thr Arg Ile Tyr Pro Lys Ala Thr Arg Ala Asp Ser Ser<br>    405      410      415 | 1248 |
| aat ttt aat ccc caa gaa ttt tgg aat ata ggt tgt caa atg gtg gct<br>Asn Phe Asn Pro Gln Glu Phe Trp Asn Ile Gly Cys Gln Met Val Ala<br>    420      425      430 | 1296 |
| tta aat ttc cag acc cct ggt ctg ccc atg gat ctg caa aat ggg aaa<br>Leu Asn Phe Gln Thr Pro Gly Leu Pro Met Asp Leu Gln Asn Gly Lys<br>    435      440      445 | 1344 |
| ttt ttg gat aat ggt ggt tct gga tat att ttg aaa cca cat ttc tta<br>Phe Leu Asp Asn Gly Gly Ser Gly Tyr Ile Leu Lys Pro His Phe Leu<br>450      455      460 | 1392 |
| aga gag agt aaa tca tac ttt aac cca agt aac ata aaa gag ggt atg<br>Arg Glu Ser Lys Ser Tyr Phe Asn Pro Ser Asn Ile Lys Glu Gly Met<br>465      470      475      480 | 1440 |
| cca att aca ctt aca ata agg ctc atc agt ggt atc cag ttg cct ctt<br>Pro Ile Thr Leu Thr Ile Arg Leu Ile Ser Gly Ile Gln Leu Pro Leu<br>     485      490      495 | 1488 |
| act cat tca tca tct aac aaa ggt gat tca tta gta att ata gaa gtt<br>Thr His Ser Ser Ser Asn Lys Gly Asp Ser Leu Val Ile Ile Glu Val<br>    500      505      510 | 1536 |
| ttt ggt gtt cca aat gat caa atg aag cag cag act cgt gta att aaa<br>Phe Gly Val Pro Asn Asp Gln Met Lys Gln Gln Thr Arg Val Ile Lys<br>    515      520      525 | 1584 |
| aaa aat gct ttt agt cca aga tgg aat gaa aca ttc aca ttt att att<br>Lys Asn Ala Phe Ser Pro Arg Trp Asn Glu Thr Phe Thr Phe Ile Ile<br>530      535      540 | 1632 |
| cat gtc cca gaa ttg gca ttg ata cgt ttt gtt gtt gaa ggt caa ggt<br>His Val Pro Glu Leu Ala Leu Ile Arg Phe Val Val Glu Gly Gln Gly<br>545      550      555      560 | 1680 |

```
tta ata gca gga aat gaa ttt ctt ggg caa tat act ttg cca ctt cta    1728
Leu Ile Ala Gly Asn Glu Phe Leu Gly Gln Tyr Thr Leu Pro Leu Leu
            565                 570                 575 tgc atg aac aaa ggt tat cgt cgt att cct ctg ttt tcc aga atg ggt    1776
Cys Met Asn Lys Gly Tyr Arg Arg Ile Pro Leu Phe Ser Arg Met Gly
        580                 585                 590 gag agc ctt gag cct gct tca ctg ttt gtt tat gtt tgg tac gtc aga    1824
Glu Ser Leu Glu Pro Ala Ser Leu Phe Val Tyr Val Trp Tyr Val Arg
            595                 600                 605 taa                                                                 1827
*

<210> SEQ ID NO 45
<211> LENGTH: 85
<212> TYPE: PRT
<213> ORGANISM: Artificial Sequence
<220> FEATURE:
<223> OTHER INFORMATION: Consensus Amino Acid Sequence

<400> SEQUENCE: 45

Val Ile Lys Glu Gly Trp Leu Leu Lys Lys Ser Lys Ser Trp Lys Lys
 1               5                  10                  15

Arg Tyr Phe Val Leu Phe Asn Asn Val Leu Leu Tyr Tyr Lys Asp Ser
                20                  25                  30

Lys Lys Lys Pro Lys Gly Ser Ile Pro Leu Ser Gly Cys Gln Val Glu
            35                  40                  45

Lys Pro Asp Lys Asn Cys Phe Glu Ile Arg Thr Asp Arg Thr Leu Leu
        50                  55                  60

Leu Gln Ala Glu Ser Glu Glu Arg Lys Glu Trp Val Lys Ala Ile
65                  70                  75                  80

Gln Ser Ala Ile Arg
                85

<210> SEQ ID NO 46
<211> LENGTH: 29
<212> TYPE: PRT
<213> ORGANISM: Artificial Sequence
<220> FEATURE:
<223> OTHER INFORMATION: Consensus Amino Acid Sequence

<400> SEQUENCE: 46

Glu Leu Lys Glu Ala Phe Lys Glu Phe Asp Lys Asp Gly Asp Gly Lys
 1               5                  10                  15

Ile Ser Phe Glu Glu Phe Lys Ala Ala Leu Lys Lys Leu
                20                  25

<210> SEQ ID NO 47
<211> LENGTH: 29
<212> TYPE: PRT
<213> ORGANISM: Artificial Sequence
<220> FEATURE:
<223> OTHER INFORMATION: Consensus Amino Acid Sequence

<400> SEQUENCE: 47

Glu Leu Lys Glu Ala Phe Lys Glu Phe Asp Lys Asp Gly Asp Gly Lys
 1               5                  10                  15

Ile Ser Phe Glu Glu Phe Lys Ala Ala Leu Lys Lys Leu
                20                  25

<210> SEQ ID NO 48
<211> LENGTH: 153
```

```
<212> TYPE: PRT
<213> ORGANISM: Artificial Sequence
<220> FEATURE:
<223> OTHER INFORMATION: Consensus Amino Acid Sequence

<400> SEQUENCE: 48

Asp Met Ser Ile Pro Leu Ser His Tyr Phe Ile Ser Ser His Asn
1               5                   10                  15

Thr Tyr Leu Thr Gly Lys Gln Leu Trp Gly Lys Ser Ser Val Glu Ser
            20                  25                  30

Tyr Arg Gln Gln Leu Asp Ala Gly Cys Arg Cys Val Glu Leu Asp Cys
            35                  40                  45

Trp Asp Gly Lys Pro Asp Asp Glu Pro Ile Ile Tyr His Gly His Thr
50                  55                  60

Leu Thr Leu Glu Ile Lys Leu Lys Asp Val Leu Glu Ala Ile Lys Asp
65                  70                  75                  80

Phe Ala Phe Lys Pro Thr Ser Pro Tyr Pro Val Ile Leu Ser Leu Glu
                85                  90                  95

Asn His Cys Asn Ser Asp Asp Gln Gln Arg Lys Met Ala Lys Tyr Phe
            100                 105                 110

Lys Glu Ile Phe Gly Asp Met Leu Leu Thr Lys Pro Thr Leu Asp Ser
            115                 120                 125

Leu Thr Thr Glu Pro Gly Leu Pro Leu Pro Ser Leu Lys Asp Leu Arg
    130                 135                 140

Gly Lys Ile Leu Leu Lys Asn Lys Lys
145                 150

<210> SEQ ID NO 49
<211> LENGTH: 128
<212> TYPE: PRT
<213> ORGANISM: Artificial Sequence
<220> FEATURE:
<223> OTHER INFORMATION: Consensus Amino Acid Sequence

<400> SEQUENCE: 49

Glu Leu Ser Asn Leu Val Asn Tyr Ile Gln Ser Ile Lys Phe Arg Ser
1               5                   10                  15

Phe Glu Leu Ser Gly Glu Glu Lys Asn Thr Ser Tyr Glu Ile Ser Ser
            20                  25                  30

Phe Ser Glu Arg Lys Val Lys Ala Lys Lys Leu Leu Lys Glu Ser Pro
            35                  40                  45

Val Glu Phe Val Lys Tyr Asn Lys Arg Gln Leu Ser Arg Val Tyr Pro
50                  55                  60

Lys Gly Thr Arg Val Asp Ser Ser Asn Phe Met Pro Gln Val Phe Trp
65                  70                  75                  80

Asn Ala Gly Cys Gln Met Val Ala Leu Asn Phe Gln Thr Ser Asp Leu
                85                  90                  95

Pro Met Gln Ile Asn Asp Gly Met Phe Glu Tyr Asn Gly Gly Gln Pro
            100                 105                 110

Asp Gly Ser Phe Lys Ser Gly Tyr Leu Leu Lys Pro Glu Phe Leu Arg
            115                 120                 125

<210> SEQ ID NO 50
<211> LENGTH: 95
<212> TYPE: PRT
<213> ORGANISM: Artificial Sequence
<220> FEATURE:
<223> OTHER INFORMATION: Consensus Amino Acid Sequence
```

```
<400> SEQUENCE: 50

Leu Thr Val Thr Val Ile Glu Ala Arg Asn Leu Pro Lys Met Asp Lys
  1               5                  10                  15

Val Asn Gly Arg Leu Ser Asp Pro Tyr Val Lys Val Ser Leu Leu Gly
             20                  25                  30

Asp Lys Lys Asp Leu Lys Lys Phe Lys Thr Lys Val Val Lys Lys Thr
         35                  40                  45

Asn Gly Leu Asn Pro Val Trp Asn Glu Glu Thr Phe Val Phe Glu Lys
     50                  55                  60

Val Pro Leu Pro Glu Leu Ala Ser Lys Thr Leu Arg Phe Ala Val Tyr
 65                  70                  75                  80

Asp Glu Asp Arg Phe Ser Arg Asp Asp Phe Ile Gly Gln Val Thr
                 85                  90                  95

<210> SEQ ID NO 51
<211> LENGTH: 170
<212> TYPE: PRT
<213> ORGANISM: Artificial Sequence
<220> FEATURE:
<223> OTHER INFORMATION: Consensus Amino Acid Sequence

<400> SEQUENCE: 51

Ser Pro Asp Cys Asn Val Phe Asp Pro Glu His Lys Gln Val His Gln
  1               5                  10                  15

Asp Met Asn Gln Pro Leu Ser His Tyr Phe Ile Asn Ser Ser His Asn
             20                  25                  30

Thr Tyr Leu Thr Gly Asn Gln Leu Ser Ser Gly Glu Ser Ser Val Glu
         35                  40                  45

Met Tyr Arg Gln Ala Leu Leu Lys Gly Cys Arg Cys Ile Glu Leu Asp
     50                  55                  60

Cys Trp Asp Gly Lys Asp Gly Asp Pro Glu Pro Ile Ile Thr His Gly
 65                  70                  75                  80

His Thr Met Thr Thr Glu Ile Ser Phe Lys Asp Cys Leu Glu Ala Ile
                 85                  90                  95

Lys Glu His Ala Phe Val Thr Ser Glu Tyr Pro Val Ile Leu Ser Leu
                100                 105                 110

Glu Asn His Cys Asp Ser Thr Pro Gln Gln Gln Ala Lys Met Ala Glu
            115                 120                 125

Tyr Cys Lys Glu Val Phe Gly Asp Met Leu Phe Thr Glu Pro Leu Glu
        130                 135                 140

Glu Ser Pro Leu Glu Pro Gly Lys Glu Leu Pro Ser Pro Glu Glu Leu
145                 150                 155                 160

Lys Arg Lys Ile Leu Ile Lys Asn Lys Lys
                165                 170

<210> SEQ ID NO 52
<211> LENGTH: 202
<212> TYPE: PRT
<213> ORGANISM: Artificial Sequence
<220> FEATURE:
<223> OTHER INFORMATION: Consensus Amino Acid Sequence

<400> SEQUENCE: 52

Met Ala Ser Gln Ile Lys Lys Ile Ser Ser Thr Asn Asp Cys Leu Gln
  1               5                  10                  15

Phe Met Gln Lys Gly Ser Glu Leu Lys Lys Val Arg Ser Asn Ser Trp
             20                  25                  30
```

```
Lys Tyr Asn Arg Tyr Phe Thr Leu Asp Asp Asp Met Gln Thr Leu Trp
            35                  40                  45

Trp Glu Pro His Trp Phe Ser Lys Lys Asp Ser Glu Lys Pro Lys Phe
 50                  55                  60

Asp Ile Ser Asp Ile Lys Glu Ile Arg Met Gly Lys Asn Thr Glu Thr
65                  70                  75                  80

Phe Arg Asn Asn Gly Lys Glu Phe Gln Ile Gln Glu Pro Glu Asp Cys
                85                  90                  95

Cys Phe Ser Ile Ile Phe Gly Glu Asn Tyr Phe His Glu Ser Leu Asp
            100                 105                 110

Leu Val Ala Asn Ser Ala Asp Val Ala Asn Ile Trp Val Ser Gly Leu
        115                 120                 125

Arg Tyr Leu Val Asp Tyr Ala Lys His Met Leu Asp Asn Tyr Gln Glu
    130                 135                 140

Gln Leu Asp Gln Trp Leu Arg Glu Trp Phe Gln Gln Ala Asp Arg Asn
145                 150                 155                 160

Lys Asp Ser Arg Met Ser Phe Arg Glu Ala Gln Asn Leu Leu Lys Leu
                165                 170                 175

Met Asn Val Gln Met Asp Glu Glu Tyr Ala Phe Ser Ile Phe Arg Glu
            180                 185                 190

Cys Asp Phe Ser Gln Ser Asn Thr Leu Asp
        195                 200

<210> SEQ ID NO 53
<211> LENGTH: 119
<212> TYPE: PRT
<213> ORGANISM: Artificial Sequence
<220> FEATURE:
<223> OTHER INFORMATION: Consensus Amino Acid Sequence

<400> SEQUENCE: 53

Pro Glu Leu Ser Asp Leu Val Asn Tyr Cys Gln Pro Val Lys Phe Lys
 1               5                  10                  15

Gly Phe Glu Met Ala Glu Glu Lys Asn Thr Tyr Tyr His Met Ser Ser
            20                  25                  30

Phe Ser Glu Asn Lys Ala Glu Lys Leu Val Asn Lys Glu His Pro Lys
        35                  40                  45

Glu Phe Val Arg Tyr Asn Gln Arg Asn Leu Leu Arg Val Tyr Pro Lys
    50                  55                  60

Gly Thr Arg Ile Asp Ser Ser Asn Tyr Asn Pro Met Val Phe Trp Asn
65                  70                  75                  80

His Gly Cys Gln Met Val Ala Leu Asn Phe Gln Thr His Gly Arg Ser
                85                  90                  95

Met Trp Leu Asn Gln Gly Met Phe Arg Ala Asn Gly Gly Cys Gly Tyr
            100                 105                 110

Val Leu Lys Pro Asp Phe Leu
        115

<210> SEQ ID NO 54
<211> LENGTH: 40
<212> TYPE: PRT
<213> ORGANISM: Artificial Sequence
<220> FEATURE:
<223> OTHER INFORMATION: Consensus Amino Acid Sequence

<400> SEQUENCE: 54

Trp Thr Cys Met Lys His Gly Tyr Arg His Val Ser Leu Leu Ser Lys
 1               5                  10                  15
```

```
Asp Gly Thr Ser Leu His Pro Ala Ser His Phe Val Tyr Thr Cys Met
            20                  25                  30

Gln Glu Asp Leu Asp Met Asp Glu
        35                  40

<210> SEQ ID NO 55
<211> LENGTH: 63
<212> TYPE: PRT
<213> ORGANISM: Artificial Sequence
<220> FEATURE:
<223> OTHER INFORMATION: Consensus Amino Acid Sequence

<400> SEQUENCE: 55

Tyr Lys Pro Gln Arg Ala Trp Met His Gly Ala Gln Met Ile Ala Leu
1               5                   10                  15

Ser Arg Gln Asp Asp Lys Glu Lys Leu Trp Leu Met Gln Gly Met Phe
            20                  25                  30

Arg Ala Asn Gly Gly Cys Gly Tyr Val Lys Lys Pro Asn Phe Leu Leu
        35                  40                  45

Asn Ala Gly Ser Ser Gly Val Phe Tyr Pro Thr Glu Asn Pro Val
    50                  55                  60

<210> SEQ ID NO 56
<211> LENGTH: 29
<212> TYPE: PRT
<213> ORGANISM: Artificial Sequence
<220> FEATURE:
<223> OTHER INFORMATION: Consensus Amino Acid Sequence

<400> SEQUENCE: 56

Glu Leu Lys Glu Ala Phe Lys Glu Phe Asp Lys Asp Gly Asp Gly Lys
1               5                   10                  15

Ile Ser Phe Glu Glu Phe Lys Ala Ala Leu Lys Lys Leu
            20                  25

<210> SEQ ID NO 57
<211> LENGTH: 153
<212> TYPE: PRT
<213> ORGANISM: Artificial Sequence
<220> FEATURE:
<223> OTHER INFORMATION: Consensus Amino Acid Sequence

<400> SEQUENCE: 57

Asp Met Ser Ile Pro Leu Ser His Tyr Phe Ile Ser Ser Ser His Asn
1               5                   10                  15

Thr Tyr Leu Thr Gly Lys Gln Leu Trp Gly Lys Ser Ser Val Glu Ser
            20                  25                  30

Tyr Arg Gln Gln Leu Asp Ala Gly Cys Arg Cys Val Glu Leu Asp Cys
        35                  40                  45

Trp Asp Gly Lys Pro Asp Asp Glu Pro Ile Ile Tyr His Gly His Thr
    50                  55                  60

Leu Thr Leu Glu Ile Lys Leu Lys Asp Val Leu Glu Ala Ile Lys Asp
65                  70                  75                  80

Phe Ala Phe Lys Pro Thr Ser Pro Tyr Pro Val Ile Leu Ser Leu Glu
                85                  90                  95

Asn His Cys Asn Ser Asp Asp Gln Gln Arg Lys Met Ala Lys Tyr Phe
            100                 105                 110

Lys Glu Ile Phe Gly Asp Met Leu Leu Thr Lys Pro Thr Leu Asp Ser
        115                 120                 125
```

```
Leu Thr Thr Glu Pro Gly Leu Pro Leu Pro Ser Leu Lys Asp Leu Arg
        130                 135                 140

Gly Lys Ile Leu Leu Lys Asn Lys Lys
145                 150
```

<210> SEQ ID NO 58
<211> LENGTH: 128
<212> TYPE: PRT
<213> ORGANISM: Artificial Sequence
<220> FEATURE:
<223> OTHER INFORMATION: Consensus Amino Acid Sequence

<400> SEQUENCE: 58

```
Glu Leu Ser Asn Leu Val Asn Tyr Ile Gln Ser Ile Lys Phe Arg Ser
 1               5                  10                  15

Phe Glu Leu Ser Gly Glu Lys Asn Thr Ser Tyr Glu Ile Ser Ser
            20                  25                  30

Phe Ser Glu Arg Lys Val Lys Ala Lys Lys Leu Leu Lys Glu Ser Pro
        35                  40                  45

Val Glu Phe Val Lys Tyr Asn Lys Arg Gln Leu Ser Arg Val Tyr Pro
 50                  55                  60

Lys Gly Thr Arg Val Asp Ser Ser Asn Phe Met Pro Gln Val Phe Trp
65                  70                  75                  80

Asn Ala Gly Cys Gln Met Val Ala Leu Asn Phe Gln Thr Ser Asp Leu
                85                  90                  95

Pro Met Gln Ile Asn Asp Gly Met Phe Glu Tyr Asn Gly Gln Pro
            100                 105                 110

Asp Gly Ser Phe Lys Ser Gly Tyr Leu Leu Lys Pro Glu Phe Leu Arg
        115                 120                 125
```

<210> SEQ ID NO 59
<211> LENGTH: 95
<212> TYPE: PRT
<213> ORGANISM: Artificial Sequence
<220> FEATURE:
<223> OTHER INFORMATION: Consensus Amino Acid Sequence

<400> SEQUENCE: 59

```
Leu Thr Val Thr Val Ile Glu Ala Arg Asn Leu Pro Lys Met Asp Lys
 1               5                  10                  15

Val Asn Gly Arg Leu Ser Asp Pro Tyr Val Lys Val Ser Leu Leu Gly
            20                  25                  30

Asp Lys Lys Asp Leu Lys Lys Phe Lys Thr Lys Val Val Lys Lys Thr
        35                  40                  45

Asn Gly Leu Asn Pro Val Trp Asn Glu Glu Thr Phe Val Phe Glu Lys
 50                  55                  60

Val Pro Leu Pro Glu Leu Ala Ser Lys Thr Leu Arg Phe Ala Val Tyr
65                  70                  75                  80

Asp Glu Asp Arg Phe Ser Arg Asp Phe Ile Gly Gln Val Thr
                85                  90                  95
```

<210> SEQ ID NO 60
<211> LENGTH: 191
<212> TYPE: PRT
<213> ORGANISM: Artificial Sequence
<220> FEATURE:
<223> OTHER INFORMATION: Consensus Amino Acid Sequence

<400> SEQUENCE: 60

```
Ser Pro Asp Cys Asn Val Phe Asp Pro Glu His Lys Gln Val His Gln
```

```
                1               5                   10                  15
Asp Met Asn Gln Pro Leu Ser His Tyr Phe Ile Asn Ser Ser His Asn
                        20                  25                  30

Thr Tyr Leu Thr Gly Asn Gln Leu Ser Ser Gly Glu Ser Ser Val Glu
                        35                  40                  45

Met Tyr Arg Gln Ala Leu Leu Lys Gly Cys Arg Cys Ile Glu Leu Asp
                        50                  55                  60

Cys Trp Asp Gly Lys Asp Gly Asp Pro Glu Pro Ile Ile Thr His Gly
 65                     70                  75                  80

His Thr Met Thr Thr Glu Ile Ser Phe Lys Asp Cys Leu Glu Ala Ile
                        85                  90                  95

Lys Glu His Ala Phe Val Thr Ser Glu Tyr Pro Val Ile Leu Ser Leu
                        100                 105                 110

Glu Asn His Cys Asp Ser Thr Pro Gln Gln Gln Ala Lys Met Ala Glu
                        115                 120                 125

Tyr Cys Lys Glu Val Phe Gly Asp Met Leu Phe Thr Glu Pro Leu Glu
                        130                 135                 140

Glu Ser Pro Leu Glu Pro Gly Lys Glu Leu Pro Ser Pro Glu Glu Leu
145                     150                 155                 160

Lys Arg Lys Ile Leu Ile Lys Asn Lys Lys Leu Lys Glu His Ser Glu
                        165                 170                 175

Glu Lys Glu Ser Glu Glu Lys Lys Thr Asp Glu Glu Thr Glu Ser
                        180                 185                 190

<210> SEQ ID NO 61
<211> LENGTH: 128
<212> TYPE: PRT
<213> ORGANISM: Artificial Sequence
<220> FEATURE:
<223> OTHER INFORMATION: Consensus Amino Acid Sequence

<400> SEQUENCE: 61

Ser Asp Leu Val Asn Tyr Cys Gln Pro Val Lys Phe Lys Gly Phe Glu
 1               5                   10                  15

Met Ala Glu Glu Lys Asn Thr Tyr Tyr His Met Ser Ser Phe Ser Glu
                        20                  25                  30

Asn Lys Ala Glu Lys Leu Val Asn Lys Glu His Pro Lys Glu Phe Val
                        35                  40                  45

Arg Tyr Asn Gln Arg Asn Leu Leu Arg Val Tyr Pro Lys Gly Thr Arg
                        50                  55                  60

Ile Asp Ser Ser Asn Tyr Asn Pro Met Val Phe Trp Asn His Gly Cys
 65                     70                  75                  80

Gln Met Val Ala Leu Asn Phe Gln Thr His Gly Arg Ser Met Trp Leu
                        85                  90                  95

Asn Gln Gly Met Phe Arg Ala Asn Gly Gly Cys Gly Tyr Val Leu Lys
                        100                 105                 110

Pro Asp Phe Leu Leu Lys Ala Arg Pro Asn Asp Glu Val Phe Asp Pro
                        115                 120                 125

<210> SEQ ID NO 62
<211> LENGTH: 51
<212> TYPE: PRT
<213> ORGANISM: Artificial Sequence
<220> FEATURE:
<223> OTHER INFORMATION: Consensus Amino Acid Sequence
<220> FEATURE:
<221> NAME/KEY: VARIANT
<222> LOCATION: (2)...(2)
```

```
<223> OTHER INFORMATION: Xaa = Any Amino Acid
<220> FEATURE:
<221> NAME/KEY: VARIANT
<222> LOCATION: (41)...(42)
<223> OTHER INFORMATION: Xaa = Any Amino Acid

<400> SEQUENCE: 62

Asp Xaa Asp Asn Ser Ile Leu Val Phe Tyr Trp Asp Glu Asn Ser Thr
 1               5                  10                  15

Gly Asp Asn Gln Gly His Arg Lys Gly Pro Leu Ile Val Met Cys Asp
             20                  25                  30

Glu Asn Gln Ser Thr Ala Gly Cys Xaa Xaa Asp Glu Leu Ile Val Met
         35                  40                  45

Phe Tyr Trp
     50

<210> SEQ ID NO 63
<211> LENGTH: 4055
<212> TYPE: DNA
<213> ORGANISM: Homo Sapiens
<220> FEATURE:
<221> NAME/KEY: CDS
<222> LOCATION: (210)...(3752)

<400> SEQUENCE: 63
tactataggg agtcgaccca cgcgtccggc cgcgccgagc ctggtggccc aggtgccccg      60
cccgcgtcag ccctgctcca gccccgcgct agcccagcgc ccctcgcccc gggccgtccg     120
gaccgcgccc ccgcccaggg ccttgcgcac gccggggccc aggccgaggg ccgcagcgcc     180
ggggccggcg atgagcgcga ggagccggc atg agc gca gac agc agc cct ctc       233
                                 Met Ser Ala Asp Ser Ser Pro Leu
                                  1               5 gtg ggc agc acg ccc acc ggt tat ggg acc ctg acg ata ggg aca tca       281
Val Gly Ser Thr Pro Thr Gly Tyr Gly Thr Leu Thr Ile Gly Thr Ser
         10                  15                  20 ata gat ccc ctc agc tcc tca gtt tca tcc gtg agg ctc agc ggc tac       329
Ile Asp Pro Leu Ser Ser Ser Val Ser Ser Val Arg Leu Ser Gly Tyr
 25                  30                  35                  40 tgt ggc agt cca tgg agg gtc atc ggc tat cac gtc gtg gtc tgg atg       377
Cys Gly Ser Pro Trp Arg Val Ile Gly Tyr His Val Val Val Trp Met
                 45                  50                  55 atg gct ggg atc cct ttg ctg ctc ttc cgt tgg aag ccc ctg tgg ggg       425
Met Ala Gly Ile Pro Leu Leu Leu Phe Arg Trp Lys Pro Leu Trp Gly
             60                  65                  70 gtg cgg ctg cgg ctc cgg ccc tgc aac ctg gcc cac gcc gaa aca ctc       473
Val Arg Leu Arg Leu Arg Pro Cys Asn Leu Ala His Ala Glu Thr Leu
         75                  80                  85 gtt atc gaa ata aga gac aaa gag gat agt tcc tgg cag ctc ttc act       521
Val Ile Glu Ile Arg Asp Lys Glu Asp Ser Ser Trp Gln Leu Phe Thr
     90                  95                 100 gtc cag gtg cag act gag gcc atc ggc gag ggc agc ctg gag ccg tcc       569
Val Gln Val Gln Thr Glu Ala Ile Gly Glu Gly Ser Leu Glu Pro Ser
105                 110                 115                 120 cca cag tcc cag gca gag gat ggc cgg agc cag gcg gca gtt ggg gcg       617
Pro Gln Ser Gln Ala Glu Asp Gly Arg Ser Gln Ala Ala Val Gly Ala
                125                 130                 135 gta cca gag ggt gcc tgg aag gat acg gcc cag ctc cac aag agc gag       665
Val Pro Glu Gly Ala Trp Lys Asp Thr Ala Gln Leu His Lys Ser Glu
            140                 145                 150 gag gcg gtg agt gtc gga cag aag cgg gtg ctg cgg tat tac ctc ttc       713
Glu Ala Val Ser Val Gly Gln Lys Arg Val Leu Arg Tyr Tyr Leu Phe
```

-continued

| | | | | | | | | | | | | |
|---|---|---|---|---|---|---|---|---|---|---|---|---|
| | 155 | | | | 160 | | | | 165 | | | |
| cag | ggc | cag | cgc | tat | atc | tgg | atc | gag | acc | cag | caa | gcc | ttc | tac | cag | 761 |
| Gln | Gly | Gln | Arg | Tyr | Ile | Trp | Ile | Glu | Thr | Gln | Gln | Ala | Phe | Tyr | Gln | |
| 170 | | | | | 175 | | | | | 180 | | | | | | |
| gtc | agc | ctc | ctg | gac | cat | ggc | cgc | tct | tgt | gac | gac | gtc | cac | cgc | tcc | 809 |
| Val | Ser | Leu | Leu | Asp | His | Gly | Arg | Ser | Cys | Asp | Asp | Val | His | Arg | Ser | |
| 185 | | | | | 190 | | | | | 195 | | | | | 200 | |
| cgc | cat | ggc | ctc | agc | ctc | cag | gac | caa | atg | gtg | agg | aag | gcc | att | tac | 857 |
| Arg | His | Gly | Leu | Ser | Leu | Gln | Asp | Gln | Met | Val | Arg | Lys | Ala | Ile | Tyr | |
| | | | | 205 | | | | | 210 | | | | | 215 | | |
| ggc | ccc | aac | gtg | atc | agc | ata | ccg | gtc | aag | tcc | tac | ccc | cag | ctg | ctg | 905 |
| Gly | Pro | Asn | Val | Ile | Ser | Ile | Pro | Val | Lys | Ser | Tyr | Pro | Gln | Leu | Leu | |
| | | | 220 | | | | | 225 | | | | | 230 | | | |
| gtg | gac | gag | gca | ctg | aac | ccc | tac | tat | ggg | ttc | cag | gcc | ttc | agc | atc | 953 |
| Val | Asp | Glu | Ala | Leu | Asn | Pro | Tyr | Tyr | Gly | Phe | Gln | Ala | Phe | Ser | Ile | |
| | | 235 | | | | | 240 | | | | | 245 | | | | |
| gcg | ctg | tgg | ctg | gct | gac | cac | tac | tac | tgg | tac | gcc | ctg | tgc | atc | ttc | 1001 |
| Ala | Leu | Trp | Leu | Ala | Asp | His | Tyr | Tyr | Trp | Tyr | Ala | Leu | Cys | Ile | Phe | |
| | 250 | | | | | 255 | | | | | 260 | | | | | |
| ctc | att | tcc | tcc | atc | tcc | atc | tgc | ctg | tcg | ctg | tac | aag | acc | aga | aag | 1049 |
| Leu | Ile | Ser | Ser | Ile | Ser | Ile | Cys | Leu | Ser | Leu | Tyr | Lys | Thr | Arg | Lys | |
| 265 | | | | | 270 | | | | | 275 | | | | | 280 | |
| caa | agc | cag | act | cta | agg | gac | atg | gtc | aag | ttg | tcc | atg | cgg | gtg | tgc | 1097 |
| Gln | Ser | Gln | Thr | Leu | Arg | Asp | Met | Val | Lys | Leu | Ser | Met | Arg | Val | Cys | |
| | | | | 285 | | | | | 290 | | | | | 295 | | |
| gtg | tgc | cgg | cca | ggg | gga | gag | gaa | gag | tgg | gtg | gac | tcc | agt | gag | cta | 1145 |
| Val | Cys | Arg | Pro | Gly | Gly | Glu | Glu | Glu | Trp | Val | Asp | Ser | Ser | Glu | Leu | |
| | | | 300 | | | | | 305 | | | | | 310 | | | |
| gtg | ccc | gga | gac | tgc | ctg | gtg | ctg | ccc | cag | gag | ggt | ggg | ctg | atg | ccc | 1193 |
| Val | Pro | Gly | Asp | Cys | Leu | Val | Leu | Pro | Gln | Glu | Gly | Gly | Leu | Met | Pro | |
| | | 315 | | | | | 320 | | | | | 325 | | | | |
| tgt | gat | gcc | gcc | ctg | gtg | gcc | ggc | gag | tgc | atg | gtg | aat | gag | agc | tct | 1241 |
| Cys | Asp | Ala | Ala | Leu | Val | Ala | Gly | Glu | Cys | Met | Val | Asn | Glu | Ser | Ser | |
| | 330 | | | | | 335 | | | | | 340 | | | | | |
| ctg | aca | gga | gag | agc | att | cca | gtg | ctg | aag | acg | gca | ctg | ccg | gag | ggg | 1289 |
| Leu | Thr | Gly | Glu | Ser | Ile | Pro | Val | Leu | Lys | Thr | Ala | Leu | Pro | Glu | Gly | |
| 345 | | | | | 350 | | | | | 355 | | | | | 360 | |
| ctg | ggg | ccc | tac | tgt | gca | gag | aca | cac | cgg | cgg | cac | aca | ctc | ttc | tgc | 1337 |
| Leu | Gly | Pro | Tyr | Cys | Ala | Glu | Thr | His | Arg | Arg | His | Thr | Leu | Phe | Cys | |
| | | | | 365 | | | | | 370 | | | | | 375 | | |
| ggg | acc | ctc | atc | ttg | cag | gcc | cgg | gcc | tat | gtg | gga | ccg | cac | gtc | ctg | 1385 |
| Gly | Thr | Leu | Ile | Leu | Gln | Ala | Arg | Ala | Tyr | Val | Gly | Pro | His | Val | Leu | |
| | | | 380 | | | | | 385 | | | | | 390 | | | |
| gca | gtg | gtg | acc | cgc | aca | ggg | ttc | tgc | acg | gca | aaa | ggg | ggc | ctg | gtg | 1433 |
| Ala | Val | Val | Thr | Arg | Thr | Gly | Phe | Cys | Thr | Ala | Lys | Gly | Gly | Leu | Val | |
| | | | 395 | | | | | 400 | | | | | 405 | | | |
| agc | tcc | atc | ttg | cac | ccc | cgg | ccc | atc | aac | ttc | aag | ttc | tat | aaa | cac | 1481 |
| Ser | Ser | Ile | Leu | His | Pro | Arg | Pro | Ile | Asn | Phe | Lys | Phe | Tyr | Lys | His | |
| | | 410 | | | | | 415 | | | | | 420 | | | | |
| agc | atg | aag | ttt | gtg | gct | gcc | ctc | tct | gtc | ctg | gct | ctc | ctc | ggc | acc | 1529 |
| Ser | Met | Lys | Phe | Val | Ala | Ala | Leu | Ser | Val | Leu | Ala | Leu | Leu | Gly | Thr | |
| 425 | | | | | 430 | | | | | 435 | | | | | 440 | |
| atc | tac | agc | atc | ttc | atc | ctc | tac | cga | aac | cgg | gtg | cct | ctg | aat | gag | 1577 |
| Ile | Tyr | Ser | Ile | Phe | Ile | Leu | Tyr | Arg | Asn | Arg | Val | Pro | Leu | Asn | Glu | |
| | | | | 445 | | | | | 450 | | | | | 455 | | |
| att | gta | atc | cgg | gct | ctc | gac | ctg | gtg | acc | gtg | gtg | gtg | cca | cct | gcc | 1625 |
| Ile | Val | Ile | Arg | Ala | Leu | Asp | Leu | Val | Thr | Val | Val | Val | Pro | Pro | Ala | |
| | | | 460 | | | | | 465 | | | | | 470 | | | |
| ctg | cct | gct | gcc | atg | act | gtg | tgc | acg | ctc | tac | gcc | cag | agc | cga | ctg | 1673 |

```
              Leu Pro Ala Ala Met Thr Val Cys Thr Leu Tyr Ala Gln Ser Arg Leu
                          475                 480                 485 cgg aga cag ggc att ttc tgc atc cac cca ctg cgc atc aac ctg ggg          1721
Arg Arg Gln Gly Ile Phe Cys Ile His Pro Leu Arg Ile Asn Leu Gly
            490                 495                 500 ggc aag ctg cag ctg gtg tgt ttc gac aag acg ggc acc ctc act gag          1769
Gly Lys Leu Gln Leu Val Cys Phe Asp Lys Thr Gly Thr Leu Thr Glu
505                 510                 515                 520 gac ggc tta gac gtg atg ggg gtg gtg ccc ctg aag ggg cag gca ttc          1817
Asp Gly Leu Asp Val Met Gly Val Val Pro Leu Lys Gly Gln Ala Phe
                        525                 530                 535 ctg ccc ctg gtc cca gag cct cgc cgc ctg cct gtg ggg ccc ctc ctc          1865
Leu Pro Leu Val Pro Glu Pro Arg Arg Leu Pro Val Gly Pro Leu Leu
                540                 545                 550 cga gca ctg gcc acc tgc cat gcc ctc agc cgg ctc cag gac acc ccc          1913
Arg Ala Leu Ala Thr Cys His Ala Leu Ser Arg Leu Gln Asp Thr Pro
            555                 560                 565 gtg ggc gac ccc atg gac ttg aag atg gtg gag tct act ggc tgg gtc          1961
Val Gly Asp Pro Met Asp Leu Lys Met Val Glu Ser Thr Gly Trp Val
        570                 575                 580 ctg gag gaa gag ccg gct gca gac tca gca ttt ggg acc cag gtc ttg          2009
Leu Glu Glu Glu Pro Ala Ala Asp Ser Ala Phe Gly Thr Gln Val Leu
585                 590                 595                 600 gca gtg atg aga cct cca ctt tgg gag ccc cag ctg cag gca atg gag          2057
Ala Val Met Arg Pro Pro Leu Trp Glu Pro Gln Leu Gln Ala Met Glu
                        605                 610                 615 gag ccc ccg gtg cca gtc agc gtc ctc cac cgc ttc ccc ttc tct tcg          2105
Glu Pro Pro Val Pro Val Ser Val Leu His Arg Phe Pro Phe Ser Ser
                620                 625                 630 gct ctg cag cgc atg agt gtg gtg gtg gcg tgg cca ggg gcc act cag          2153
Ala Leu Gln Arg Met Ser Val Val Val Ala Trp Pro Gly Ala Thr Gln
            635                 640                 645 ccc gag gcc tac gtc aaa ggc tcc ccg gag ctg gtg gca ggg ctc tgc          2201
Pro Glu Ala Tyr Val Lys Gly Ser Pro Glu Leu Val Ala Gly Leu Cys
        650                 655                 660 aac ccc gag aca gtg ccc acc gac ttc gcc cag atg ctg cag agc tat          2249
Asn Pro Glu Thr Val Pro Thr Asp Phe Ala Gln Met Leu Gln Ser Tyr
665                 670                 675                 680 aca gct gct ggc tac cgt gtc gtg gcc ctg gcc agc aag cca ctg ccc          2297
Thr Ala Ala Gly Tyr Arg Val Val Ala Leu Ala Ser Lys Pro Leu Pro
                        685                 690                 695 act gtg ccc agc ctg gag gca gcc cag caa ctg acg agg gac act gtg          2345
Thr Val Pro Ser Leu Glu Ala Ala Gln Gln Leu Thr Arg Asp Thr Val
                700                 705                 710 gaa gga gac ctg agc ctc ctg ggg ctg ctg gtc atg agg aac cta ctg          2393
Glu Gly Asp Leu Ser Leu Leu Gly Leu Leu Val Met Arg Asn Leu Leu
            715                 720                 725 aag ccg cag aca acg cca gtt atc cag gct ctg cga agg acc cgc atc          2441
Lys Pro Gln Thr Thr Pro Val Ile Gln Ala Leu Arg Arg Thr Arg Ile
        730                 735                 740 cgc gcc gtc atg gtg aca ggg gac aac ctg cag aca gcg gtg act gtg          2489
Arg Ala Val Met Val Thr Gly Asp Asn Leu Gln Thr Ala Val Thr Val
745                 750                 755                 760 gcc cgg ggc tgt ggc atg gtg gcc ccc cag gag cat ctg atc atc gtc          2537
Ala Arg Gly Cys Gly Met Val Ala Pro Gln Glu His Leu Ile Ile Val
                        765                 770                 775 cac gcc acc cac cct gag cgg ggt cag cct gcc tct ctc gag ttc ctg          2585
His Ala Thr His Pro Glu Arg Gly Gln Pro Ala Ser Leu Glu Phe Leu
                780                 785                 790
```

-continued

| | |
|---|---|
| ccg atg gag tcc ccc aca gcc gtg aat ggc gtt aag gat cct gac cag<br>Pro Met Glu Ser Pro Thr Ala Val Asn Gly Val Lys Asp Pro Asp Gln<br>795                        800                        805 | 2633 |
| gct gca agc tac acc gtg gag cca gac ccc cga tcc agg cac ctg gcc<br>Ala Ala Ser Tyr Thr Val Glu Pro Asp Pro Arg Ser Arg His Leu Ala<br>810                        815                        820 | 2681 |
| ctc agc ggg ccc acc ttt ggt atc att gtg aag cac ttc ccc aag ctg<br>Leu Ser Gly Pro Thr Phe Gly Ile Ile Val Lys His Phe Pro Lys Leu<br>825                        830                        835                        840 | 2729 |
| ctg ccc aag gtc ctg gtc cag ggc act gtc ttt gcc cgc atg gcc cct<br>Leu Pro Lys Val Leu Val Gln Gly Thr Val Phe Ala Arg Met Ala Pro<br>                        845                        850                        855 | 2777 |
| gag cag aag aca gag ctg gtg tgc gag cta cag aag ctt cag tac tgc<br>Glu Gln Lys Thr Glu Leu Val Cys Glu Leu Gln Lys Leu Gln Tyr Cys<br>                        860                        865                        870 | 2825 |
| gtg ggc atg tgc gga gac ggt gcc aat gac tgt ggg gcc ctg aag gcg<br>Val Gly Met Cys Gly Asp Gly Ala Asn Asp Cys Gly Ala Leu Lys Ala<br>                        875                        880                        885 | 2873 |
| gct gat gtc ggc atc tcg ctg tcc cag gca gaa gcc tca gtg gtc tca<br>Ala Asp Val Gly Ile Ser Leu Ser Gln Ala Glu Ala Ser Val Val Ser<br>890                        895                        900 | 2921 |
| ccc ttc acc tcg agc atg gcc agt att gag tgc gtg ccc atg gtc atc<br>Pro Phe Thr Ser Ser Met Ala Ser Ile Glu Cys Val Pro Met Val Ile<br>905                        910                        915                        920 | 2969 |
| agg gag ggg cgc tgt tcc ctt gac act tcg ttc agc gtc ttc aag tac<br>Arg Glu Gly Arg Cys Ser Leu Asp Thr Ser Phe Ser Val Phe Lys Tyr<br>                        925                        930                        935 | 3017 |
| atg gct ctg tac agc ctg acc cag ttc atc tcc gtc ctg atc ctc tac<br>Met Ala Leu Tyr Ser Leu Thr Gln Phe Ile Ser Val Leu Ile Leu Tyr<br>                        940                        945                        950 | 3065 |
| acg atc aac acc aac ctg ggt gac ctg cag ttc ctg gcc atc gac ctg<br>Thr Ile Asn Thr Asn Leu Gly Asp Leu Gln Phe Leu Ala Ile Asp Leu<br>                        955                        960                        965 | 3113 |
| gtc atc acc acc aca gtg gca gtg ctc atg agc cgc acg ggg cca gcg<br>Val Ile Thr Thr Thr Val Ala Val Leu Met Ser Arg Thr Gly Pro Ala<br>970                        975                        980 | 3161 |
| ctg gtc ctg gga cgg gta cgg cca ccg ggg gcg ctg ctc agc gtg ccc<br>Leu Val Leu Gly Arg Val Arg Pro Pro Gly Ala Leu Leu Ser Val Pro<br>985                        990                        995                        1000 | 3209 |
| gtg ctc agc agc ctg ctg ctg cag atg gtc ctg gtg acc ggc gtg cag<br>Val Leu Ser Ser Leu Leu Leu Gln Met Val Leu Val Thr Gly Val Gln<br>                        1005                     1010                     1015 | 3257 |
| cta ggg ggc tac ttc ctg acc ctg gcc cag cca tgg ttc gtg cct ctg<br>Leu Gly Gly Tyr Phe Leu Thr Leu Ala Gln Pro Trp Phe Val Pro Leu<br>                        1020                     1025                     1030 | 3305 |
| aac agg aca gtg gcc gca cca gac aac ctg ccc aac tac gag aac acc<br>Asn Arg Thr Val Ala Ala Pro Asp Asn Leu Pro Asn Tyr Glu Asn Thr<br>                        1035                     1040                     1045 | 3353 |
| gtg gtc ttc tct ctg tcc agc ttc cag tac ctc atc ctg gct gca gcc<br>Val Val Phe Ser Leu Ser Ser Phe Gln Tyr Leu Ile Leu Ala Ala Ala<br>                        1050                     1055                     1060 | 3401 |
| gtg tcc aag ggg gcg ccc ttc gcc cgg ccg ctc tac acc aat gtg ccc<br>Val Ser Lys Gly Ala Pro Phe Arg Arg Pro Leu Tyr Thr Asn Val Pro<br>1065                    1070                     1075                     1080 | 3449 |
| ttc ctg gtg gcc ctg gcg ctc ctg agc tcc gtc ctg gtg ggc ctt gtc<br>Phe Leu Val Ala Leu Ala Leu Leu Ser Ser Val Leu Val Gly Leu Val<br>                        1085                     1090                     1095 | 3497 |
| ctg gtc ccc ggc ctc ctg cag ggg ccg ctg gcg ctg agg aac atc act<br>Leu Val Pro Gly Leu Leu Gln Gly Pro Leu Ala Leu Arg Asn Ile Thr<br>                        1100                     1105                     1110 | 3545 |

-continued

```
gac acc ggc ttc aag ctg ctg ctg ctg ggt ctg gtc acc ctc aac ttc        3593
Asp Thr Gly Phe Lys Leu Leu Leu Leu Gly Leu Val Thr Leu Asn Phe
    1115                1120                1125 gtg ggg gcc ttc atg ctg gag agc gtg cta gac cag tgc ctc ccc gcc        3641
Val Gly Ala Phe Met Leu Glu Ser Val Leu Asp Gln Cys Leu Pro Ala
1130                1135                1140 tgc ctg cgc cgc ctc cgg ccc aag cgg gcc tcc aag aag cgc ttc aag        3689
Cys Leu Arg Arg Leu Arg Pro Lys Arg Ala Ser Lys Lys Arg Phe Lys
1145                1150                1155                1160 cag ctg gaa cga gag ctg gcc gag cag ccc tgg cca ccg ctg ccc gcc        3737
Gln Leu Glu Arg Glu Leu Ala Glu Gln Pro Trp Pro Pro Leu Pro Ala
            1165                1170                1175 ggc ccc ctg agg tag tgcaggccca cgggcacccc agacactgga actccctgcc        3792
Gly Pro Leu Arg *
            1180 tctgagccac caactggacc cctctccagc aacaccaccg ccaccactc ccacatccct      3852 gaggttggcg actgtctaca ctcctccccc gagaccaccc ccaccctggg aagcgttga       3912 ctactgtccc ctaccttgga ccatcccgcg tagggtggc agcccccagc tcccctcagt      3972 gctgctgtca gtgtagcaaa taaagtcatg atatttcct ggcaaaaaaa aaaaaaaaaa      4032 aaaaaaaaaa aaaaaaaaaa aaa                                              4055

<210> SEQ ID NO 64
<211> LENGTH: 1180
<212> TYPE: PRT
<213> ORGANISM: Homo Sapiens

<400> SEQUENCE: 64

Met Ser Ala Asp Ser Ser Pro Leu Val Gly Ser Thr Pro Thr Gly Tyr
1               5                   10                  15

Gly Thr Leu Thr Ile Gly Thr Ser Ile Asp Pro Leu Ser Ser Ser Val
            20                  25                  30

Ser Ser Val Arg Leu Ser Gly Tyr Cys Gly Ser Pro Trp Arg Val Ile
        35                  40                  45

Gly Tyr His Val Val Trp Met Met Ala Gly Ile Pro Leu Leu Leu
    50                  55                  60

Phe Arg Trp Lys Pro Leu Trp Gly Val Arg Leu Arg Leu Arg Pro Cys
65                  70                  75                  80

Asn Leu Ala His Ala Glu Thr Leu Val Ile Glu Ile Arg Asp Lys Glu
                85                  90                  95

Asp Ser Ser Trp Gln Leu Phe Thr Val Gln Val Gln Thr Glu Ala Ile
            100                 105                 110

Gly Glu Gly Ser Leu Glu Pro Ser Pro Gln Ser Gln Ala Glu Asp Gly
        115                 120                 125

Arg Ser Gln Ala Ala Val Gly Ala Val Pro Glu Gly Ala Trp Lys Asp
    130                 135                 140

Thr Ala Gln Leu His Lys Ser Glu Glu Ala Val Ser Val Gly Gln Lys
145                 150                 155                 160

Arg Val Leu Arg Tyr Tyr Leu Phe Gln Gly Gln Arg Tyr Ile Trp Ile
                165                 170                 175

Glu Thr Gln Gln Ala Phe Tyr Gln Val Ser Leu Leu Asp His Gly Arg
            180                 185                 190

Ser Cys Asp Asp Val His Arg Ser Arg His Gly Leu Ser Leu Gln Asp
        195                 200                 205

Gln Met Val Arg Lys Ala Ile Tyr Gly Pro Asn Val Ile Ser Ile Pro
```

-continued

```
         210                 215                 220
Val Lys Ser Tyr Pro Gln Leu Leu Val Asp Glu Ala Leu Asn Pro Tyr
225                 230                 235                 240

Tyr Gly Phe Gln Ala Phe Ser Ile Ala Leu Trp Leu Ala Asp His Tyr
                245                 250                 255

Tyr Trp Tyr Ala Leu Cys Ile Phe Leu Ile Ser Ser Ile Ser Ile Cys
                260                 265                 270

Leu Ser Leu Tyr Lys Thr Arg Lys Gln Ser Gln Thr Leu Arg Asp Met
            275                 280                 285

Val Lys Leu Ser Met Arg Val Cys Val Arg Pro Gly Gly Glu Glu
290                 295                 300

Glu Trp Val Asp Ser Ser Glu Leu Val Pro Gly Asp Cys Leu Val Leu
305                 310                 315                 320

Pro Gln Glu Gly Gly Leu Met Pro Cys Asp Ala Ala Leu Val Ala Gly
                325                 330                 335

Glu Cys Met Val Asn Glu Ser Ser Leu Thr Gly Glu Ser Ile Pro Val
                340                 345                 350

Leu Lys Thr Ala Leu Pro Glu Gly Leu Gly Pro Tyr Cys Ala Glu Thr
            355                 360                 365

His Arg Arg His Thr Leu Phe Cys Gly Thr Leu Ile Leu Gln Ala Arg
            370                 375                 380

Ala Tyr Val Gly Pro His Val Leu Ala Val Val Thr Arg Thr Gly Phe
385                 390                 395                 400

Cys Thr Ala Lys Gly Gly Leu Val Ser Ser Ile Leu His Pro Arg Pro
                405                 410                 415

Ile Asn Phe Lys Phe Tyr Lys His Ser Met Lys Phe Val Ala Ala Leu
                420                 425                 430

Ser Val Leu Ala Leu Leu Gly Thr Ile Tyr Ser Ile Phe Ile Leu Tyr
            435                 440                 445

Arg Asn Arg Val Pro Leu Asn Glu Ile Val Ile Arg Ala Leu Asp Leu
            450                 455                 460

Val Thr Val Val Pro Pro Ala Leu Pro Ala Ala Met Thr Val Cys
465                 470                 475                 480

Thr Leu Tyr Ala Gln Ser Arg Leu Arg Arg Gln Gly Ile Phe Cys Ile
                485                 490                 495

His Pro Leu Arg Ile Asn Leu Gly Gly Lys Leu Gln Leu Val Cys Phe
                500                 505                 510

Asp Lys Thr Gly Thr Leu Thr Glu Asp Gly Leu Asp Val Met Gly Val
            515                 520                 525

Val Pro Leu Lys Gly Gln Ala Phe Leu Pro Leu Val Pro Glu Pro Arg
530                 535                 540

Arg Leu Pro Val Gly Pro Leu Arg Ala Leu Ala Thr Cys His Ala
545                 550                 555                 560

Leu Ser Arg Leu Gln Asp Thr Pro Val Gly Asp Pro Met Asp Leu Lys
            565                 570                 575

Met Val Glu Ser Thr Gly Trp Val Leu Glu Glu Pro Ala Ala Asp
                580                 585                 590

Ser Ala Phe Gly Thr Gln Val Leu Ala Val Met Arg Pro Pro Leu Trp
            595                 600                 605

Glu Pro Gln Leu Gln Ala Met Glu Glu Pro Val Pro Val Ser Val
            610                 615                 620

Leu His Arg Phe Pro Phe Ser Ser Ala Leu Gln Arg Met Ser Val Val
625                 630                 635                 640
```

```
Val Ala Trp Pro Gly Ala Thr Gln Pro Glu Ala Tyr Val Lys Gly Ser
                645                 650                 655

Pro Glu Leu Val Ala Gly Leu Cys Asn Pro Glu Thr Val Pro Thr Asp
            660                 665                 670

Phe Ala Gln Met Leu Gln Ser Tyr Thr Ala Ala Gly Tyr Arg Val Val
        675                 680                 685

Ala Leu Ala Ser Lys Pro Leu Pro Thr Val Pro Ser Leu Glu Ala Ala
    690                 695                 700

Gln Gln Leu Thr Arg Asp Thr Val Glu Gly Asp Leu Ser Leu Leu Gly
705                 710                 715                 720

Leu Leu Val Met Arg Asn Leu Leu Lys Pro Gln Thr Thr Pro Val Ile
                725                 730                 735

Gln Ala Leu Arg Arg Thr Arg Ile Arg Ala Val Met Val Thr Gly Asp
            740                 745                 750

Asn Leu Gln Thr Ala Val Thr Val Ala Arg Gly Cys Gly Met Val Ala
        755                 760                 765

Pro Gln Glu His Leu Ile Ile Val His Ala Thr His Pro Glu Arg Gly
    770                 775                 780

Gln Pro Ala Ser Leu Glu Phe Leu Pro Met Glu Ser Pro Thr Ala Val
785                 790                 795                 800

Asn Gly Val Lys Asp Pro Asp Gln Ala Ala Ser Tyr Thr Val Glu Pro
                805                 810                 815

Asp Pro Arg Ser Arg His Leu Ala Leu Ser Gly Pro Thr Phe Gly Ile
            820                 825                 830

Ile Val Lys His Phe Pro Lys Leu Leu Pro Lys Val Leu Val Gln Gly
        835                 840                 845

Thr Val Phe Ala Arg Met Ala Pro Glu Gln Lys Thr Glu Leu Val Cys
    850                 855                 860

Glu Leu Gln Lys Leu Gln Tyr Cys Val Gly Met Cys Gly Asp Gly Ala
865                 870                 875                 880

Asn Asp Cys Gly Ala Leu Lys Ala Ala Asp Val Gly Ile Ser Leu Ser
                885                 890                 895

Gln Ala Glu Ala Ser Val Val Ser Pro Phe Thr Ser Ser Met Ala Ser
            900                 905                 910

Ile Glu Cys Val Pro Met Val Ile Arg Glu Gly Arg Cys Ser Leu Asp
        915                 920                 925

Thr Ser Phe Ser Val Phe Lys Tyr Met Ala Leu Tyr Ser Leu Thr Gln
    930                 935                 940

Phe Ile Ser Val Leu Ile Leu Tyr Thr Ile Asn Thr Asn Leu Gly Asp
945                 950                 955                 960

Leu Gln Phe Leu Ala Ile Asp Leu Val Ile Thr Thr Val Ala Val
                965                 970                 975

Leu Met Ser Arg Thr Gly Pro Ala Leu Val Leu Gly Arg Val Arg Pro
            980                 985                 990

Pro Gly Ala Leu Leu Ser Val Pro Val Leu Ser Ser Leu Leu Leu Gln
        995                 1000                1005

Met Val Leu Val Thr Gly Val Gln Leu Gly Gly Tyr Phe Leu Thr Leu
    1010                1015                1020

Ala Gln Pro Trp Phe Val Pro Leu Asn Arg Thr Val Ala Ala Pro Asp
1025                1030                1035                1040

Asn Leu Pro Asn Tyr Glu Asn Thr Val Val Phe Ser Leu Ser Ser Phe
                1045                1050                1055
```

```
Gln Tyr Leu Ile Leu Ala Ala Val Ser Lys Gly Ala Pro Phe Arg
            1060                1065                1070

Arg Pro Leu Tyr Thr Asn Val Pro Phe Leu Val Ala Leu Ala Leu Leu
        1075                1080                1085

Ser Ser Val Leu Val Gly Leu Val Leu Val Pro Gly Leu Leu Gln Gly
        1090                1095                1100

Pro Leu Ala Leu Arg Asn Ile Thr Asp Thr Gly Phe Lys Leu Leu
1105                1110                1115                1120

Leu Gly Leu Val Thr Leu Asn Phe Val Gly Ala Phe Met Leu Glu Ser
            1125                1130                1135

Val Leu Asp Gln Cys Leu Pro Ala Cys Leu Arg Arg Leu Arg Pro Lys
            1140                1145                1150

Arg Ala Ser Lys Lys Arg Phe Lys Gln Leu Glu Arg Glu Leu Ala Glu
            1155                1160                1165

Gln Pro Trp Pro Pro Leu Pro Ala Gly Pro Leu Arg
        1170                1175                1180

<210> SEQ ID NO 65
<211> LENGTH: 3540
<212> TYPE: DNA
<213> ORGANISM: Homo Sapiens
<220> FEATURE:
<221> NAME/KEY: CDS
<222> LOCATION: (1)...(3540)

<400> SEQUENCE: 65 atg agc gca gac agc agc cct ctc gtg ggc agc acg ccc acc ggt tat    48
Met Ser Ala Asp Ser Ser Pro Leu Val Gly Ser Thr Pro Thr Gly Tyr
 1               5                  10                  15 ggg acc ctg acg ata ggg aca tca ata gat ccc ctc agc tcc tca gtt    96
Gly Thr Leu Thr Ile Gly Thr Ser Ile Asp Pro Leu Ser Ser Ser Val
             20                  25                  30 tca tcc gtg agg ctc agc ggc tac tgt ggc agt cca tgg agg gtc atc   144
Ser Ser Val Arg Leu Ser Gly Tyr Cys Gly Ser Pro Trp Arg Val Ile
         35                  40                  45 ggc tat cac gtc gtg gtc tgg atg atg gct ggg atc cct ttg ctg ctc   192
Gly Tyr His Val Val Val Trp Met Met Ala Gly Ile Pro Leu Leu Leu
     50                  55                  60 ttc cgt tgg aag ccc ctg tgg ggg gtg cgg ctg cgg ctc cgg ccc tgc   240
Phe Arg Trp Lys Pro Leu Trp Gly Val Arg Leu Arg Leu Arg Pro Cys
 65                  70                  75                  80 aac ctg gcc cac gcc gaa aca ctc gtt atc gaa ata aga gac aaa gag   288
Asn Leu Ala His Ala Glu Thr Leu Val Ile Glu Ile Arg Asp Lys Glu
                 85                  90                  95 gat agt tcc tgg cag ctc ttc act gtc cag gtg cag act gag gcc atc   336
Asp Ser Ser Trp Gln Leu Phe Thr Val Gln Val Gln Thr Glu Ala Ile
            100                 105                 110 ggc gag ggc agc ctg gag ccg tcc cca cag tcc cag gca gag gat ggc   384
Gly Glu Gly Ser Leu Glu Pro Ser Pro Gln Ser Gln Ala Glu Asp Gly
        115                 120                 125 cgg agc cag gcg gca gtt ggg gcg gta cca gag ggt gcc tgg aag gat   432
Arg Ser Gln Ala Ala Val Gly Ala Val Pro Glu Gly Ala Trp Lys Asp
    130                 135                 140 acg gcc cag ctc cac aag agc gag gag gcg gtg agt gtc gga cag aag   480
Thr Ala Gln Leu His Lys Ser Glu Glu Ala Val Ser Val Gly Gln Lys
145                 150                 155                 160 cgg gtg ctg cgg tat tac ctc ttc cag ggc cag cgc tat atc tgg atc   528
Arg Val Leu Arg Tyr Tyr Leu Phe Gln Gly Gln Arg Tyr Ile Trp Ile
                165                 170                 175
```

```
gag acc cag caa gcc ttc tac cag gtc agc ctc ctg gac cat ggc cgc        576
Glu Thr Gln Gln Ala Phe Tyr Gln Val Ser Leu Leu Asp His Gly Arg
            180                 185                 190 tct tgt gac gac gtc cac cgc tcc cgc cat ggc ctc agc ctc cag gac        624
Ser Cys Asp Asp Val His Arg Ser Arg His Gly Leu Ser Leu Gln Asp
        195                 200                 205 caa atg gtg agg aag gcc att tac ggc ccc aac gtg atc agc ata ccg        672
Gln Met Val Arg Lys Ala Ile Tyr Gly Pro Asn Val Ile Ser Ile Pro
    210                 215                 220 gtc aag tcc tac ccc cag ctg ctg gtg gac gag gca ctg aac ccc tac        720
Val Lys Ser Tyr Pro Gln Leu Leu Val Asp Glu Ala Leu Asn Pro Tyr
225                 230                 235                 240 tat ggg ttc cag gcc ttc agc atc gcg ctg tgg ctg gct gac cac tac        768
Tyr Gly Phe Gln Ala Phe Ser Ile Ala Leu Trp Leu Ala Asp His Tyr
                245                 250                 255 tac tgg tac gcc ctg tgc atc ttc ctc att tcc tcc atc tcc atc tgc        816
Tyr Trp Tyr Ala Leu Cys Ile Phe Leu Ile Ser Ser Ile Ser Ile Cys
            260                 265                 270 ctg tcg ctg tac aag acc aga aag caa agc cag act cta agg gac atg        864
Leu Ser Leu Tyr Lys Thr Arg Lys Gln Ser Gln Thr Leu Arg Asp Met
        275                 280                 285 gtc aag ttg tcc atg cgg gtg tgc gtg tgc cgg cca ggg gga gag gaa        912
Val Lys Leu Ser Met Arg Val Cys Val Cys Arg Pro Gly Gly Glu Glu
    290                 295                 300 gag tgg gtg gac tcc agt gag cta gtg ccc gga gac tgc ctg gtg ctg        960
Glu Trp Val Asp Ser Ser Glu Leu Val Pro Gly Asp Cys Leu Val Leu
305                 310                 315                 320 ccc cag gag ggt ggg ctg atg ccc tgt gat gcc gcc ctg gtg gcc ggc       1008
Pro Gln Glu Gly Gly Leu Met Pro Cys Asp Ala Ala Leu Val Ala Gly
                325                 330                 335 gag tgc atg gtg aat gag agc tct ctg aca gga gag agc att cca gtg       1056
Glu Cys Met Val Asn Glu Ser Ser Leu Thr Gly Glu Ser Ile Pro Val
            340                 345                 350 ctg aag acg gca ctg ccg gag ggg ctg ggg ccc tac tgt gca gag aca       1104
Leu Lys Thr Ala Leu Pro Glu Gly Leu Gly Pro Tyr Cys Ala Glu Thr
        355                 360                 365 cac cgg cgg cac aca ctc ttc tgc ggg acc ctc atc ttg cag gcc cgg       1152
His Arg Arg His Thr Leu Phe Cys Gly Thr Leu Ile Leu Gln Ala Arg
    370                 375                 380 gcc tat gtg gga ccg cac gtc ctg gca gtg gtg acc cgc aca ggg ttc       1200
Ala Tyr Val Gly Pro His Val Leu Ala Val Val Thr Arg Thr Gly Phe
385                 390                 395                 400 tgc acg gca aaa ggg ggc ctg gtg agc tcc atc ttg cac ccc cgg ccc       1248
Cys Thr Ala Lys Gly Gly Leu Val Ser Ser Ile Leu His Pro Arg Pro
                405                 410                 415 atc aac ttc aag ttc tat aaa cac agc atg aag ttt gtg gct gcc ctc       1296
Ile Asn Phe Lys Phe Tyr Lys His Ser Met Lys Phe Val Ala Ala Leu
            420                 425                 430 tct gtc ctg gct ctc ctc ggc acc atc tac agc atc ttc atc ctc tac       1344
Ser Val Leu Ala Leu Leu Gly Thr Ile Tyr Ser Ile Phe Ile Leu Tyr
        435                 440                 445 cga aac cgg gtg cct ctg aat gag att gta atc cgg gct ctc gac ctg       1392
Arg Asn Arg Val Pro Leu Asn Glu Ile Val Ile Arg Ala Leu Asp Leu
    450                 455                 460 gtg acc gtg gtg gtg cca cct gcc ctg cct gct gcc atg act gtg tgc       1440
Val Thr Val Val Val Pro Pro Ala Leu Pro Ala Ala Met Thr Val Cys
465                 470                 475                 480 acg ctc tac gcc cag agc cga ctg cgg aga cag ggc att ttc tgc atc       1488
Thr Leu Tyr Ala Gln Ser Arg Leu Arg Arg Gln Gly Ile Phe Cys Ile
                485                 490                 495
```

```
cac cca ctg cgc atc aac ctg ggg ggc aag ctg cag ctg gtg tgt ttc      1536
His Pro Leu Arg Ile Asn Leu Gly Gly Lys Leu Gln Leu Val Cys Phe
            500                 505                 510 gac aag acg ggc acc ctc act gag gac ggc tta gac gtg atg ggg gtg      1584
Asp Lys Thr Gly Thr Leu Thr Glu Asp Gly Leu Asp Val Met Gly Val
        515                 520                 525 gtg ccc ctg aag ggg cag gca ttc ctg ccc ctg gtc cca gag cct cgc      1632
Val Pro Leu Lys Gly Gln Ala Phe Leu Pro Leu Val Pro Glu Pro Arg
    530                 535                 540 cgc ctg cct gtg ggg ccc ctg ctc cga gca ctg gcc acc tgc cat gcc      1680
Arg Leu Pro Val Gly Pro Leu Leu Arg Ala Leu Ala Thr Cys His Ala
545                 550                 555                 560 ctc agc cgg ctc cag gac acc ccc gtg ggc gac ccc atg gac ttg aag      1728
Leu Ser Arg Leu Gln Asp Thr Pro Val Gly Asp Pro Met Asp Leu Lys
                565                 570                 575 atg gtg gag tct act ggc tgg gtc ctg gag gaa gag ccg gct gca gac      1776
Met Val Glu Ser Thr Gly Trp Val Leu Glu Glu Glu Pro Ala Ala Asp
            580                 585                 590 tca gca ttt ggg acc cag gtc ttg gca gtg atg aga cct cca ctt tgg      1824
Ser Ala Phe Gly Thr Gln Val Leu Ala Val Met Arg Pro Pro Leu Trp
        595                 600                 605 gag ccc cag ctg cag gca atg gag gag ccc ccg gtg cca gtc agc gtc      1872
Glu Pro Gln Leu Gln Ala Met Glu Glu Pro Pro Val Pro Val Ser Val
    610                 615                 620 ctc cac cgc ttc ccc ttc tct tcg gct ctg cag cgc atg agt gtg gtg      1920
Leu His Arg Phe Pro Phe Ser Ser Ala Leu Gln Arg Met Ser Val Val
625                 630                 635                 640 gtg gcg tgg cca ggg gcc act cag ccc gag gcc tac gtc aaa ggc tcc      1968
Val Ala Trp Pro Gly Ala Thr Gln Pro Glu Ala Tyr Val Lys Gly Ser
                645                 650                 655 ccg gag ctg gtg gca ggg ctc tgc aac ccc gag aca gtg ccc acc gac      2016
Pro Glu Leu Val Ala Gly Leu Cys Asn Pro Glu Thr Val Pro Thr Asp
            660                 665                 670 ttc gcc cag atg ctg cag agc tat aca gct gct ggc tac cgt gtc gtg      2064
Phe Ala Gln Met Leu Gln Ser Tyr Thr Ala Ala Gly Tyr Arg Val Val
        675                 680                 685 gcc ctg gcc agc aag cca ctg ccc act gtg ccc agc ctg gag gca gcc      2112
Ala Leu Ala Ser Lys Pro Leu Pro Thr Val Pro Ser Leu Glu Ala Ala
    690                 695                 700 cag caa ctg acg agg gac act gtg gaa gga gac ctg agc ctc ctg ggg      2160
Gln Gln Leu Thr Arg Asp Thr Val Glu Gly Asp Leu Ser Leu Leu Gly
705                 710                 715                 720 ctg ctg gtc atg agg aac cta ctg aag ccg cag aca acg cca gtt atc      2208
Leu Leu Val Met Arg Asn Leu Leu Lys Pro Gln Thr Thr Pro Val Ile
                725                 730                 735 cag gct ctg cga agg acc cgc atc cgc gcc gtc atg gtg aca ggg gac      2256
Gln Ala Leu Arg Arg Thr Arg Ile Arg Ala Val Met Val Thr Gly Asp
            740                 745                 750 aac ctg cag aca gcg gtg act gtg gcc cgg ggc tgt ggc atg gtg gcc      2304
Asn Leu Gln Thr Ala Val Thr Val Ala Arg Gly Cys Gly Met Val Ala
        755                 760                 765 ccc cag gag cat ctg atc atc gtc cac gcc acc cac cct gag cgg ggt      2352
Pro Gln Glu His Leu Ile Ile Val His Ala Thr His Pro Glu Arg Gly
    770                 775                 780 cag cct gcc tct ctc gag ttc ctg ccg atg gag tcc ccc aca gcc gtg      2400
Gln Pro Ala Ser Leu Glu Phe Leu Pro Met Glu Ser Pro Thr Ala Val
785                 790                 795                 800 aat ggc gtt aag gat cct gac cag gct gca agc tac acc gtg gag cca      2448
Asn Gly Val Lys Asp Pro Asp Gln Ala Ala Ser Tyr Thr Val Glu Pro
```

-continued

| | | | |
|---|---|---|---|
| 805 | 810 | 815 | |
| gac ccc cga tcc agg cac ctg gcc ctc agc ggg ccc acc ttt ggt atc<br>Asp Pro Arg Ser Arg His Leu Ala Leu Ser Gly Pro Thr Phe Gly Ile<br>820 825 830 | | | 2496 |
| att gtg aag cac ttc ccc aag ctg ctg ccc aag gtc ctg gtc cag ggc<br>Ile Val Lys His Phe Pro Lys Leu Leu Pro Lys Val Leu Val Gln Gly<br>835 840 845 | | | 2544 |
| act gtc ttt gcc cgc atg gcc cct gag cag aag aca gag ctg gtg tgc<br>Thr Val Phe Ala Arg Met Ala Pro Glu Gln Lys Thr Glu Leu Val Cys<br>850 855 860 | | | 2592 |
| gag cta cag aag ctt cag tac tgc gtg ggc atg tgc gga gac ggt gcc<br>Glu Leu Gln Lys Leu Gln Tyr Cys Val Gly Met Cys Gly Asp Gly Ala<br>865 870 875 880 | | | 2640 |
| aat gac tgt ggg gcc ctg aag gcg gct gat gtc ggc atc tcg ctg tcc<br>Asn Asp Cys Gly Ala Leu Lys Ala Ala Asp Val Gly Ile Ser Leu Ser<br>885 890 895 | | | 2688 |
| cag gca gaa gcc tca gtg gtc tca ccc ttc acc tcg agc atg gcc agt<br>Gln Ala Glu Ala Ser Val Val Ser Pro Phe Thr Ser Ser Met Ala Ser<br>900 905 910 | | | 2736 |
| att gag tgc gtg ccc atg gtc atc agg gag ggg cgc tgt tcc ctt gac<br>Ile Glu Cys Val Pro Met Val Ile Arg Glu Gly Arg Cys Ser Leu Asp<br>915 920 925 | | | 2784 |
| act tcg ttc agc gtc ttc aag tac atg gct ctg tac agc ctg acc cag<br>Thr Ser Phe Ser Val Phe Lys Tyr Met Ala Leu Tyr Ser Leu Thr Gln<br>930 935 940 | | | 2832 |
| ttc atc tcc gtc ctg atc ctc tac acg atc aac acc aac ctg ggt gac<br>Phe Ile Ser Val Leu Ile Leu Tyr Thr Ile Asn Thr Asn Leu Gly Asp<br>945 950 955 960 | | | 2880 |
| ctg cag ttc ctg gcc atc gac ctg gtc atc acc acc aca gtg gca gtg<br>Leu Gln Phe Leu Ala Ile Asp Leu Val Ile Thr Thr Thr Val Ala Val<br>965 970 975 | | | 2928 |
| ctc atg agc cgc acg ggg cca gcg ctg gtc ctg gga cgg gta cgg cca<br>Leu Met Ser Arg Thr Gly Pro Ala Leu Val Leu Gly Arg Val Arg Pro<br>980 985 990 | | | 2976 |
| ccg ggg gcg ctg ctc agc gtg ccc gtg ctc agc agc ctg ctg ctg cag<br>Pro Gly Ala Leu Leu Ser Val Pro Val Leu Ser Ser Leu Leu Leu Gln<br>995 1000 1005 | | | 3024 |
| atg gtc ctg gtg acc ggc gtg cag cta ggg ggc tac ttc ctg acc ctg<br>Met Val Leu Val Thr Gly Val Gln Leu Gly Gly Tyr Phe Leu Thr Leu<br>1010 1015 1020 | | | 3072 |
| gcc cag cca tgg ttc gtg cct ctg aac agg aca gtg gcc gca cca gac<br>Ala Gln Pro Trp Phe Val Pro Leu Asn Arg Thr Val Ala Ala Pro Asp<br>1025 1030 1035 1040 | | | 3120 |
| aac ctg ccc aac tac gag aac acc gtg gtc ttc tct ctg tcc agc ttc<br>Asn Leu Pro Asn Tyr Glu Asn Thr Val Val Phe Ser Leu Ser Ser Phe<br>1045 1050 1055 | | | 3168 |
| cag tac ctc atc ctg gct gca gcc gtg tcc aag ggg gcg ccc ttc cgc<br>Gln Tyr Leu Ile Leu Ala Ala Ala Val Ser Lys Gly Ala Pro Phe Arg<br>1060 1065 1070 | | | 3216 |
| cgg ccg ctc tac acc aat gtg ccc ttc ctg gtg gcc ctg gcg ctc ctg<br>Arg Pro Leu Tyr Thr Asn Val Pro Phe Leu Val Ala Leu Ala Leu Leu<br>1075 1080 1085 | | | 3264 |
| agc tcc gtc ctg gtg ggc ctt gtc ctg gtc ccc ggc ctc ctg cag ggg<br>Ser Ser Val Leu Val Gly Leu Val Leu Val Pro Gly Leu Leu Gln Gly<br>1090 1095 1100 | | | 3312 |
| ccg ctg gcg ctg agg aac atc act gac acc ggc ttc aag ctg ctg ctg<br>Pro Leu Ala Leu Arg Asn Ile Thr Asp Thr Gly Phe Lys Leu Leu Leu<br>1105 1110 1115 1120 | | | 3360 |
| ctg ggt ctg gtc acc ctc aac ttc gtg ggg gcc ttc atg ctg ctg gag agc<br> | | | 3408 |

```
Leu Gly Leu Val Thr Leu Asn Phe Val Gly Ala Phe Met Leu Glu Ser
            1125                1130                1135 gtg cta gac cag tgc ctc ccc gcc tgc ctg cgc cgc ctc cgg ccc aag      3456
Val Leu Asp Gln Cys Leu Pro Ala Cys Leu Arg Arg Leu Arg Pro Lys
            1140                1145                1150 cgg gcc tcc aag aag cgc ttc aag cag ctg gaa cga gag ctg gcc gag      3504
Arg Ala Ser Lys Lys Arg Phe Lys Gln Leu Glu Arg Glu Leu Ala Glu
            1155                1160                1165 cag ccc tgg cca ccg ctg ccc gcc ggc ccc ctg agg                      3540
Gln Pro Trp Pro Pro Leu Pro Ala Gly Pro Leu Arg
            1170                1175                1180

<210> SEQ ID NO 66
<211> LENGTH: 1187
<212> TYPE: PRT
<213> ORGANISM: Caenorhabditis elegans

<400> SEQUENCE: 66

Met Thr Leu Glu Ser Gly Asp His Thr Leu Thr Leu Phe Ala Tyr Arg
 1               5                  10                  15

Thr Gly Pro Phe Arg Thr Ile Leu Phe Tyr Ala Leu Thr Val Leu Thr
            20                  25                  30

Leu Gly Ile Phe Arg Leu Ile Leu His Trp Lys Gln Lys Trp Asp Val
        35                  40                  45

Lys Met Arg Met Val Pro Cys Thr Phe Glu Ala Ala Glu Tyr Ile Tyr
    50                  55                  60

Ile Ile Asp Asn His Asn Val Ser Glu Leu Gln Pro Val Leu Arg Lys
65                  70                  75                  80

Ser Asn Ala Thr Ile Pro Thr Glu Asn Gly Glu Met Arg Lys Val Pro
                85                  90                  95

Glu Leu Arg Trp Phe Val Tyr Arg Lys Leu Glu Tyr Val Trp Ile Asp
            100                 105                 110

Asp Leu Asn Ser Asp Glu Ser Val Asp Glu Ile Ser Asp Asn Asp Asn
        115                 120                 125

Cys Trp Lys Thr Ser Phe Glu Ile Ala Asn Arg Ile Pro Cys Arg Ser
130                 135                 140

Leu Leu Ala Val Ser Glu Ser Asn Phe Gly Leu Thr Leu Ser Glu Ile
145                 150                 155                 160

Ser Arg Arg Leu Glu Phe Tyr Gly Arg Asn Glu Ile Val Val Gln Leu
                165                 170                 175

Arg Pro Ile Leu Tyr Leu Leu Val Met Glu Val Ile Thr Pro Phe Tyr
            180                 185                 190

Val Phe Gln Ile Phe Ser Val Thr Val Trp Tyr Asn Asp Glu Tyr Ala
        195                 200                 205

Tyr Tyr Ala Ser Leu Ile Val Ile Leu Ser Leu Gly Ser Ile Val Met
    210                 215                 220

Asp Val Tyr Gln Ile Arg Thr Gln Glu Ile Arg Leu Arg Ser Met Val
225                 230                 235                 240

His Ser Thr Glu Ser Val Glu Val Ile Arg Glu Gly Thr Glu Met Thr
                245                 250                 255

Ile Gly Ser Asp Gln Leu Val Pro Gly Asp Ile Leu Ile Pro Pro
            260                 265                 270

His Gly Cys Leu Met Gln Cys Asp Ser Val Leu Met Asn Gly Thr Val
        275                 280                 285

Ile Val Asn Glu Ser Val Leu Thr Gly Glu Ser Val Pro Ile Thr Lys
    290                 295                 300
```

-continued

```
Val Ala Leu Thr Asp Glu Thr Asn Asp Ser Val Phe Asn Ile Glu Lys
305                 310                 315                 320

Asn Ser Lys Asn Val Leu Phe Cys Gly Thr Gln Val Leu Gln Thr Arg
            325                 330                 335

Phe Tyr Arg Gly Lys Lys Val Lys Ala Ile Val Leu Arg Thr Ala Tyr
            340                 345                 350

Ser Thr Leu Lys Gly Gln Leu Val Arg Ser Ile Met Tyr Pro Lys Pro
        355                 360                 365

Val Asp Phe Arg Phe Thr Lys Asp Leu Phe Lys Phe Ile Leu Phe Leu
    370                 375                 380

Ala Cys Ile Ser Gly Cys Gly Phe Ile Tyr Thr Ile Ile Val Met Ile
385                 390                 395                 400

Met Arg Gly Asn Thr Leu Arg Arg Ile Ile Val Arg Ser Leu Asp Ile
            405                 410                 415

Ile Thr Ile Thr Val Pro Pro Ala Leu Pro Ala Ala Met Ser Val Gly
            420                 425                 430

Ile Ile Asn Ala Gln Leu Arg Leu Lys Lys Lys Glu Ile Phe Cys Ile
        435                 440                 445

Ser Pro Ser Thr Ile Asn Thr Cys Gly Ala Ile Asn Val Val Cys Phe
    450                 455                 460

Asp Lys Thr Gly Thr Leu Thr Glu Asp Gly Leu Asp Phe His Val Val
465                 470                 475                 480

Arg Pro Val Met Ser Ala Val Asn Gln Glu Ile Gln Lys Val Lys Leu
            485                 490                 495

Glu Lys Ser Asn Arg Thr Glu Phe Met Gly Glu Met Thr Glu Leu Thr
            500                 505                 510

Ser Arg Asn Gly Leu Pro Phe Asp Gly Asp Leu Val Lys Ala Ile Ala
        515                 520                 525

Thr Cys His Ser Leu Thr Arg Ile Asn Gly Val Leu His Gly Asp Pro
    530                 535                 540

Leu Asp Leu Ile Leu Phe Gln Lys Thr Gly Trp Thr Met Glu Glu Gly
545                 550                 555                 560

Ile Glu Gly Asp Ile Glu Glu Thr Gln Arg Phe Asp Asn Val Gln
            565                 570                 575

Pro Ser Ile Ile Lys Pro Thr Asp Asp Lys Ser Ala Glu Tyr Ser Val
            580                 585                 590

Ile Arg Gln Phe Thr Phe Ser Ser Leu Gln Arg Met Ser Val Ile
        595                 600                 605

Val Phe Asp Pro Arg Glu Asp Arg Pro Asp Asn Met Met Leu Tyr Ser
    610                 615                 620

Lys Gly Ser Pro Glu Met Ile Leu Ser Leu Cys Asp Pro Asn Thr Val
625                 630                 635                 640

Pro Glu Asp Tyr Leu Leu Gln Val Asn Ser Tyr Ala Gln His Gly Phe
            645                 650                 655

Arg Leu Ile Ala Val Ala Arg Arg Pro Leu Asp Leu Asn Phe Asn Lys
            660                 665                 670

Ala Ser Lys Val Lys Arg Asp Ala Val Glu Cys Asp Leu Glu Met Leu
        675                 680                 685

Gly Leu Ile Val Met Glu Asn Arg Val Lys Pro Val Thr Leu Gly Val
    690                 695                 700

Ile Asn Gln Leu Asn Arg Ala Asn Ile Arg Thr Val Met Val Thr Gly
705                 710                 715                 720
```

-continued

```
Asp Asn Leu Leu Thr Gly Leu Ser Val Ala Arg Glu Cys Gly Ile Ile
            725                 730                 735
Arg Pro Ser Lys Arg Ala Phe Leu Val Glu His Val Pro Gly Glu Leu
            740                 745                 750
Asp Glu Tyr Gly Arg Thr Lys Ile Phe Val Lys Gln Ser Val Ser Ser
            755                 760                 765
Ser Asp Glu Val Ile Glu Asp Ala Ser Val Ser Ile Ser Met Cys
    770                 775                 780
Ser Ser Thr Trp Lys Gly Ser Glu Gly Asp Gly Phe Ser Pro Thr
785                 790                 795                 800
Asn Thr Glu Val Glu Thr Pro Asn Pro Val Thr Ala Asp Ser Leu Gly
            805                 810                 815
His Leu Ile Ala Ser Ser Tyr His Leu Ala Ile Ser Gly Pro Thr Phe
            820                 825                 830
Ala Val Ile Val His Glu Tyr Pro Glu Leu Val Asp Gln Leu Cys Ser
            835                 840                 845
Val Cys Asp Val Phe Ala Arg Met Ala Pro Asp Gln Lys Gln Ser Leu
850                 855                 860
Val Glu Gln Leu Gln Gln Ile Asp Tyr Thr Val Ala Met Cys Gly Asp
865                 870                 875                 880
Gly Ala Asn Asp Cys Ala Ala Leu Lys Ala Ala His Ala Gly Ile Ser
            885                 890                 895
Leu Ser Asp Ala Glu Ala Ser Ile Ala Ala Pro Phe Thr Ser Lys Val
            900                 905                 910
Pro Asp Ile Arg Cys Val Pro Thr Val Ile Ser Glu Gly Arg Ala Ala
            915                 920                 925
Leu Val Thr Ser Phe Gly Ile Phe Lys Tyr Met Ala Gly Tyr Ser Leu
            930                 935                 940
Thr Gln Phe Val Thr Val Met His Leu Tyr Trp Ile Ser Asn Ile Leu
945                 950                 955                 960
Thr Asp Gly Gln Phe Met Tyr Ile Asp Met Phe Leu Ile Thr Met Phe
            965                 970                 975
Ala Leu Leu Phe Gly Asn Thr Pro Ala Phe Tyr Arg Leu Ala His Thr
            980                 985                 990
Pro Pro Thr Arg Leu Leu Ser Ile Ala Ser Met Thr Ser Val Val
            995                 1000                1005
Gly Gln Leu Ile Ile Ile Gly Val Val Gln Phe Ile Val Phe Phe Ser
    1010                1015                1020
Thr Ser Gln Gln Pro Trp Phe Thr Pro Tyr Gln Pro Val Asp Asp
1025                1030                1035                1040
Glu Val Glu Asp Lys Arg Ser Met Gln Gly Thr Ala Leu Phe Cys Val
            1045                1050                1055
Ser Met Phe Gln Tyr Ile Ile Leu Ala Leu Val Tyr Ser Lys Gly Pro
            1060                1065                1070
Pro Phe Arg Gly Asn Leu Trp Ser Asn Lys Pro Ile Tyr Lys Lys Lys
            1075                1080                1085
Arg Ser Ile Glu Ala Ile Ile Asp Tyr Val Pro Thr Thr Asn Ser Asp
            1090                1095                1100
His Ile Arg Arg Pro Ser Ile Asn Gly Val Thr Ser Ser Arg Thr Glu
1105                1110                1115                1120
Ser Thr Leu Leu Ser Ala Glu Gly Gln Gln Leu His Met Thr Thr Ser
            1125                1130                1135
Lys Asn Gly Lys Gly Gly Glu Asn Pro His Ser Ser Ala Leu Phe Glu
```

-continued

```
                    1140                1145                1150
Arg Leu Ile Ser Arg Ile Gly Gly Glu Pro Thr Trp Leu Thr Asn Pro
        1155                1160                1165

Ile Pro Pro His Ser Leu Ser Glu Pro Glu Pro Glu Lys Leu Glu
    1170                1175                1180

Arg Thr Tyr
1185

<210> SEQ ID NO 67
<211> LENGTH: 7249
<212> TYPE: DNA
<213> ORGANISM: Homo Sapiens
<220> FEATURE:
<221> NAME/KEY: CDS
<222> LOCATION: (225)...(3995)

<400> SEQUENCE: 67
```

| | |
|---|---:|
| cacgcgtccg ggctgggctg aggcgaggcg gcggcggcga cagcggcggc cgggtccccc | 60 |
| gcggcccctg ggctggtcc ggccgcgagg gaggccgcgg aggaggcggc gcggcggcgg | 120 |
| ccagtgagcg gccccgatct gacagacatc cctgaatctt ggtgtttgga cataggagtg | 180 |
| atcttccatt gtttgaagca ctggaccttt aatccactgt aggt atg gac agg gaa<br>                                                                                                     Met Asp Arg Glu<br>                                                                                                                                   1 | 236 |
| gaa agg aag acc atc aat cag ggt caa gaa gat gaa atg gag att tat<br>Glu Arg Lys Thr Ile Asn Gln Gly Gln Glu Asp Glu Met Glu Ile Tyr<br> 5                      10                  15                  20 | 284 |
| ggt tac aat tta agt cgc tgg aag ctt gcc ata gtt tct tta gga gtg<br>Gly Tyr Asn Leu Ser Arg Trp Lys Leu Ala Ile Val Ser Leu Gly Val<br>                  25                  30                  35 | 332 |
| att tgc tct gat ggg ttt ctc ctc ctc ctc ctc tat tgg atg cct gag<br>Ile Cys Ser Asp Gly Phe Leu Leu Leu Leu Leu Tyr Trp Met Pro Glu<br>              40                  45                  50 | 380 |
| tgg cgg gtg aaa gcg acc tgt gtc aga gct gca att aaa gac tgt gaa<br>Trp Arg Val Lys Ala Thr Cys Val Arg Ala Ala Ile Lys Asp Cys Glu<br>      55                60                  65 | 428 |
| gta gtg ctg ctg agg act act gat gaa ttc aaa atg tgg ttt tgt gca<br>Val Val Leu Leu Arg Thr Thr Asp Glu Phe Lys Met Trp Phe Cys Ala<br>70                  75                  80 | 476 |
| aaa att cgc gtt ctt tct ttg gaa act tac cca gtt tca agt cca aaa<br>Lys Ile Arg Val Leu Ser Leu Glu Thr Tyr Pro Val Ser Ser Pro Lys<br>85                  90                  95                100 | 524 |
| tct atg tct aat aag ctt tca aat ggc cat gca gtt tgt tta att gag<br>Ser Met Ser Asn Lys Leu Ser Asn Gly His Ala Val Cys Leu Ile Glu<br>                105                 110                 115 | 572 |
| aat ccc act gaa gaa aat agg cac agg atc agt aaa tat tca cag act<br>Asn Pro Thr Glu Glu Asn Arg His Arg Ile Ser Lys Tyr Ser Gln Thr<br>            120                 125                 130 | 620 |
| gaa tca caa cag att cgt tat ttc acc cac cat agt gta aaa tat ttc<br>Glu Ser Gln Gln Ile Arg Tyr Phe Thr His His Ser Val Lys Tyr Phe<br>135                 140                 145 | 668 |
| tgg aat gat acc att cac aat ttt gat ttc tta aag gga ctg gat gaa<br>Trp Asn Asp Thr Ile His Asn Phe Asp Phe Leu Lys Gly Leu Asp Glu<br>            150                 155                 160 | 716 |
| ggt gtt tct tgt acg tca att tat gaa aag cat agt gca gga ctg aca<br>Gly Val Ser Cys Thr Ser Ile Tyr Glu Lys His Ser Ala Gly Leu Thr<br>165                 170                 175                 180 | 764 |
| aag ggg atg cat gcc tac aga aaa ctg ctt tat gga gta aat gaa att<br>Lys Gly Met His Ala Tyr Arg Lys Leu Leu Tyr Gly Val Asn Glu Ile<br>            185                 190                 195 | 812 |

```
gct gta aaa gtg cct tct gtt ttt aag ctt cta att aaa gag gtt ctc    860
Ala Val Lys Val Pro Ser Val Phe Lys Leu Leu Ile Lys Glu Val Leu
        200                 205                 210 aac cca ttt tac att ttc cag ctg ttc agt gtt ata ctg tgg agc act    908
Asn Pro Phe Tyr Ile Phe Gln Leu Phe Ser Val Ile Leu Trp Ser Thr
        215                 220                 225 gat gaa tac tat tac tat gct cta gct att gtg gtt atg tcc ata gta    956
Asp Glu Tyr Tyr Tyr Tyr Ala Leu Ala Ile Val Val Met Ser Ile Val
    230                 235                 240 tca atc gta agc tca cta tat tcc att aga aag caa tat gtt atg ttg   1004
Ser Ile Val Ser Ser Leu Tyr Ser Ile Arg Lys Gln Tyr Val Met Leu
245                 250                 255                 260 cat gac atg gtg gca act cat agt acc gta aga gtt tca gtt tgt aga   1052
His Asp Met Val Ala Thr His Ser Thr Val Arg Val Ser Val Cys Arg
            265                 270                 275 gta aat gaa gaa ata gaa gaa atc ttt tct acc gac ctt gtg cca gga   1100
Val Asn Glu Glu Ile Glu Glu Ile Phe Ser Thr Asp Leu Val Pro Gly
                280                 285                 290 gat gtc atg gtc att cca tta aat ggg aca ata atg cct tgt gat gct   1148
Asp Val Met Val Ile Pro Leu Asn Gly Thr Ile Met Pro Cys Asp Ala
            295                 300                 305 gtg ctt att aat ggt acc tgc att gta aac gaa agc atg tta aca gga   1196
Val Leu Ile Asn Gly Thr Cys Ile Val Asn Glu Ser Met Leu Thr Gly
        310                 315                 320 gaa agt gtt cca gtg aca aag act aat ttg cca aat cct tca gtg gat   1244
Glu Ser Val Pro Val Thr Lys Thr Asn Leu Pro Asn Pro Ser Val Asp
325                 330                 335                 340 gtg aaa gga ata gga gat gaa tta tat aat cca gaa aca cat aaa cga   1292
Val Lys Gly Ile Gly Asp Glu Leu Tyr Asn Pro Glu Thr His Lys Arg
                345                 350                 355 cat act ttg ttt tgt ggg aca act gtt att cag act cgt ttc tac act   1340
His Thr Leu Phe Cys Gly Thr Thr Val Ile Gln Thr Arg Phe Tyr Thr
            360                 365                 370 gga gaa ctc gtc aaa gcc ata gtt gtt aga aca gga ttt agt act tcc   1388
Gly Glu Leu Val Lys Ala Ile Val Val Arg Thr Gly Phe Ser Thr Ser
        375                 380                 385 aaa gga cag ctt gtt cgt tcc ata ttg tat ccc aaa cca act gat ttt   1436
Lys Gly Gln Leu Val Arg Ser Ile Leu Tyr Pro Lys Pro Thr Asp Phe
390                 395                 400 aaa ctc tac aga gat gcc tac ttg ttt cta cta tgt ctt gtg gca gtt   1484
Lys Leu Tyr Arg Asp Ala Tyr Leu Phe Leu Leu Cys Leu Val Ala Val
405                 410                 415                 420 gct ggc att ggg ttt atc tac act att att aat agc att tta aat gag   1532
Ala Gly Ile Gly Phe Ile Tyr Thr Ile Ile Asn Ser Ile Leu Asn Glu
                425                 430                 435 gta caa gtt ggg gtc ata att atc gag tct ctt gat att atc aca att   1580
Val Gln Val Gly Val Ile Ile Glu Ser Leu Asp Ile Ile Thr Ile
            440                 445                 450 act gtg ccc cct gca ctt cct gct gca atg act gct ggt att gtg tat   1628
Thr Val Pro Pro Ala Leu Pro Ala Ala Met Thr Ala Gly Ile Val Tyr
        455                 460                 465 gct cag aga aga ctg aaa aaa atc ggt att ttc tgt atc agt cct caa   1676
Ala Gln Arg Arg Leu Lys Lys Ile Gly Ile Phe Cys Ile Ser Pro Gln
470                 475                 480 aga ata aat att tgt gga cag ctc aat ctt gtt tgc ttt gac aag act   1724
Arg Ile Asn Ile Cys Gly Gln Leu Asn Leu Val Cys Phe Asp Lys Thr
485                 490                 495                 500 gga act cta act gaa gat ggt tta gat ctt tgg ggg att caa cga gtg   1772
Gly Thr Leu Thr Glu Asp Gly Leu Asp Leu Trp Gly Ile Gln Arg Val
```

-continued

|  |  |  |
|---|---|---|
| 505 | 510 | 515 |

| | |
|---|---|
| gaa aat gca cga ttt ctt tca cca gaa gaa aat gtg tgc aat gag atg<br>Glu Asn Ala Arg Phe Leu Ser Pro Glu Glu Asn Val Cys Asn Glu Met<br>520                             525                        530 | 1820 |
| ttg gta aaa tcc cag ttt gtt gct tgt atg gct act tgt cat tca ctt<br>Leu Val Lys Ser Gln Phe Val Ala Cys Met Ala Thr Cys His Ser Leu<br>    535                        540                        545 | 1868 |
| aca aaa att gaa gga gtg ctc tct ggt gat cca ctt gat ctg aaa atg<br>Thr Lys Ile Glu Gly Val Leu Ser Gly Asp Pro Leu Asp Leu Lys Met<br>550                             555                        560 | 1916 |
| ttt gag gct att gga tgg att ctg gaa gaa gca act gaa gaa gaa aca<br>Phe Glu Ala Ile Gly Trp Ile Leu Glu Glu Ala Thr Glu Glu Glu Thr<br>565                           570                        575                    580 | 1964 |
| gca ctt cat aat cga att atg ccc aca gtg gtt cgt cct ccc aaa caa<br>Ala Leu His Asn Arg Ile Met Pro Thr Val Val Arg Pro Pro Lys Gln<br>                        585                        590                    595 | 2012 |
| ctg ctt cct gaa tct acc cct gca gga aac caa gaa atg gag ctg ttt<br>Leu Leu Pro Glu Ser Thr Pro Ala Gly Asn Gln Glu Met Glu Leu Phe<br>                    600                        605                    610 | 2060 |
| gaa ctt cca gct act tat gag ata gga att gtt cgc cag ttc cca ttt<br>Glu Leu Pro Ala Thr Tyr Glu Ile Gly Ile Val Arg Gln Phe Pro Phe<br>615                           620                        625 | 2108 |
| tct tct gct ttg caa cgt atg agt gtg gtt gcc agg gtg ctg ggg gat<br>Ser Ser Ala Leu Gln Arg Met Ser Val Val Ala Arg Val Leu Gly Asp<br>    630                        635                        640 | 2156 |
| agg aaa atg gac gcc tac atg aaa gga gcg ccc gag gcc att gcc ggt<br>Arg Lys Met Asp Ala Tyr Met Lys Gly Ala Pro Glu Ala Ile Ala Gly<br>645                           650                        655                    660 | 2204 |
| ctc tgt aaa cct gaa aca gtt cct gtc gat ttt caa aac gtt ttg gaa<br>Leu Cys Lys Pro Glu Thr Val Pro Val Asp Phe Gln Asn Val Leu Glu<br>                    665                        670                    675 | 2252 |
| gac ttc act aaa cag ggc ttc cgt gtg att gct ctt gca cac aga aaa<br>Asp Phe Thr Lys Gln Gly Phe Arg Val Ile Ala Leu Ala His Arg Lys<br>              680                        685                    690 | 2300 |
| ttg gag tca aaa ctg aca tgg cat aaa gta cag aat att agc aga gat<br>Leu Glu Ser Lys Leu Thr Trp His Lys Val Gln Asn Ile Ser Arg Asp<br>695                           700                        705 | 2348 |
| gca att gag aac aac atg gat ttt atg gga tta att ata atg cag aac<br>Ala Ile Glu Asn Asn Met Asp Phe Met Gly Leu Ile Ile Met Gln Asn<br>    710                        715                        720 | 2396 |
| aaa tta aag caa gaa acc cct gca gta ctt gaa gat ttg cat aaa gcc<br>Lys Leu Lys Gln Glu Thr Pro Ala Val Leu Glu Asp Leu His Lys Ala<br>725                           730                        735                    740 | 2444 |
| aac att cgc acc gtc atg gtc aca ggt gac agt atg ttg act gct gtc<br>Asn Ile Arg Thr Val Met Val Thr Gly Asp Ser Met Leu Thr Ala Val<br>                    745                        750                    755 | 2492 |
| tct gtg gcc aga gat tgt gga atg att cta cct cag gat aaa gtg att<br>Ser Val Ala Arg Asp Cys Gly Met Ile Leu Pro Gln Asp Lys Val Ile<br>              760                        765                    770 | 2540 |
| att gct gaa gca tta cct cca aag gat ggg aaa gtt gcc aaa ata aat<br>Ile Ala Glu Ala Leu Pro Pro Lys Asp Gly Lys Val Ala Lys Ile Asn<br>775                           780                        785 | 2588 |
| tgg cat tat gca gac tcc ctc acg cag tgc agt cat cca tca gca att<br>Trp His Tyr Ala Asp Ser Leu Thr Gln Cys Ser His Pro Ser Ala Ile<br>    790                        795                        800 | 2636 |
| gac cca gag gct att ccg gtt aaa ttg gtc cat gat agc tta gag gat<br>Asp Pro Glu Ala Ile Pro Val Lys Leu Val His Asp Ser Leu Glu Asp<br>805                           810                        815                    820 | 2684 |
| ctt caa atg act cgt tat cat ttt gca atg aat gga aaa tca ttc tca | 2732 |

-continued

```
                Leu Gln Met Thr Arg Tyr His Phe Ala Met Asn Gly Lys Ser Phe Ser
                                825                 830                 835 gtg ata ctg gag cat ttt caa gac ctt gtt cct aag ttg atg ttg cat           2780
Val Ile Leu Glu His Phe Gln Asp Leu Val Pro Lys Leu Met Leu His
                840                 845                 850 ggc acc gtg ttt gcc cgt atg gca cct gat cag aag aca cag ttg ata           2828
Gly Thr Val Phe Ala Arg Met Ala Pro Asp Gln Lys Thr Gln Leu Ile
                855                 860                 865 gaa gca ttg caa aat gtt gat tat ttt gtt ggg atg tgt ggt gat ggc           2876
Glu Ala Leu Gln Asn Val Asp Tyr Phe Val Gly Met Cys Gly Asp Gly
            870                 875                 880 gca aat gat tgt ggt gct ttg aag agg gca cac gga ggc att tcc tta           2924
Ala Asn Asp Cys Gly Ala Leu Lys Arg Ala His Gly Gly Ile Ser Leu
885                 890                 895                 900 tcg gag ctc gaa gct tca gtg gca tct ccc ttt acc tct aag act cct           2972
Ser Glu Leu Glu Ala Ser Val Ala Ser Pro Phe Thr Ser Lys Thr Pro
                905                 910                 915 agt att tcc tgt gtg cca aac ctt atc agg gaa ggc cgt gct gct tta           3020
Ser Ile Ser Cys Val Pro Asn Leu Ile Arg Glu Gly Arg Ala Ala Leu
                920                 925                 930 ata act tcc ttc tgt gtg ttt aaa ttc atg gca ttg tac agc att atc           3068
Ile Thr Ser Phe Cys Val Phe Lys Phe Met Ala Leu Tyr Ser Ile Ile
                935                 940                 945 cag tac ttc agt gtt act ctg ctg tat tct atc tta agt aac cta gga           3116
Gln Tyr Phe Ser Val Thr Leu Leu Tyr Ser Ile Leu Ser Asn Leu Gly
            950                 955                 960 gac ttc cag ttt ctc ttc att gat ctg gca atc att ttg gta gtg gta           3164
Asp Phe Gln Phe Leu Phe Ile Asp Leu Ala Ile Ile Leu Val Val Val
965                 970                 975                 980 ttt aca atg agt tta aat cct gcc tgg aaa gaa ctt gtg gca caa aga           3212
Phe Thr Met Ser Leu Asn Pro Ala Trp Lys Glu Leu Val Ala Gln Arg
                985                 990                 995 cca cct tcg ggt ctt ata tct ggg gcc ctt ctc ttc tcc gtt ttg tct           3260
Pro Pro Ser Gly Leu Ile Ser Gly Ala Leu Leu Phe Ser Val Leu Ser
                1000                1005                1010 cag att atc atc tgc att gga ttt caa tct ttg ggt ttt ttt tgg gtc           3308
Gln Ile Ile Ile Cys Ile Gly Phe Gln Ser Leu Gly Phe Phe Trp Val
            1015                1020                1025 aaa cag caa cct tgg tat gaa gtg tgg cat cca aaa tca gat gct tgt           3356
Lys Gln Gln Pro Trp Tyr Glu Val Trp His Pro Lys Ser Asp Ala Cys
                1030                1035                1040 aat aca aca gga agc ggg ttt tgg aat tct tca cac gta gac aat gaa           3404
Asn Thr Thr Gly Ser Gly Phe Trp Asn Ser Ser His Val Asp Asn Glu
1045                1050                1055                1060 acc gaa ctt gat gaa cat aat ata caa aat tat gaa aat acc aca gtg           3452
Thr Glu Leu Asp Glu His Asn Ile Gln Asn Tyr Glu Asn Thr Thr Val
                1065                1070                1075 ttt ttt att tcc agt ttt cag tac ctc ata gtg gca att gcc ttt tca           3500
Phe Phe Ile Ser Ser Phe Gln Tyr Leu Ile Val Ala Ile Ala Phe Ser
                1080                1085                1090 aaa gga aaa ccc ttc agg caa cct tgc tac aaa aat tat ttt ttt gtt           3548
Lys Gly Lys Pro Phe Arg Gln Pro Cys Tyr Lys Asn Tyr Phe Phe Val
                1095                1100                1105 ttt tct gtg att ttt tta tat att ttt ata tta ttc atc atg ttg tat           3596
Phe Ser Val Ile Phe Leu Tyr Ile Phe Ile Leu Phe Ile Met Leu Tyr
            1110                1115                1120 cca gtt gcc tct gtt gac cag gtt ctt cag ata gtg tgt gta cca tat           3644
Pro Val Ala Ser Val Asp Gln Val Leu Gln Ile Val Cys Val Pro Tyr
1125                1130                1135                1140
```

| | |
|---|---|
| cag tgg cgt gta act atg ctc atc att gtt ctt gtc aat gcc ttt gtg<br>Gln Trp Arg Val Thr Met Leu Ile Ile Val Leu Val Asn Ala Phe Val<br>              1145                        1150                        1155 | 3692 |
| tct atc aca gtg gag aac ttc ttc ctt gac atg gtc ctt tgg aaa gtt<br>Ser Ile Thr Val Glu Asn Phe Phe Leu Asp Met Val Leu Trp Lys Val<br>1160                        1165                        1170 | 3740 |
| gtg ttc aac cga gac aaa caa gga gag tat cgg ttc agc acc aca cag<br>Val Phe Asn Arg Asp Lys Gln Gly Glu Tyr Arg Phe Ser Thr Thr Gln<br>              1175                        1180                        1185 | 3788 |
| cca ccg cag gag tca gtg gat cgg tgg gga aaa tgc tgc tta ccc tgg<br>Pro Pro Gln Glu Ser Val Asp Arg Trp Gly Lys Cys Cys Leu Pro Trp<br>    1190                        1195                        1200 | 3836 |
| gcc ctg ggc tgt aga aag aag aca cca aag gca aag tac atg tat ctg<br>Ala Leu Gly Cys Arg Lys Lys Thr Pro Lys Ala Lys Tyr Met Tyr Leu<br>1205                      1210                        1215                        1220 | 3884 |
| gcg cag gag ctc ttg gtt gat cca gaa tgg cca cca aaa cct cag aca<br>Ala Gln Glu Leu Leu Val Asp Pro Glu Trp Pro Pro Lys Pro Gln Thr<br>              1225                        1230                        1235 | 3932 |
| acc aca gaa gct aaa gct tta gtt aag gag aat gga tca tgt caa atc<br>Thr Thr Glu Ala Lys Ala Leu Val Lys Glu Asn Gly Ser Cys Gln Ile<br>        1240                        1245                        1250 | 3980 |
| atc acc ata aca tag cagtgaatca gtctcagtgg tattgctgat agcagtattc<br>Ile Thr Ile Thr *<br>        1255 | 4035 |
| aggaatatgt gattttagga gtttctgatc ctgtgtgtca gaatggcact agttcagttt | 4095 |
| atgtcccttc tgatatagta gcttatttga cagctttgct cttccttaaa ataaaaacag | 4155 |
| aaaaatatat cgtcctaaca gttaaattaa caatcaatcc ataaagtcct atatcttcat | 4215 |
| tcagcaaccc aaatattaca tacatttcca gaattttctt gattgttact ttcagtgata | 4275 |
| ttctttatat tgggtacagg agaagtttgg tgtttggtag ttttttcaac attagttttt | 4335 |
| gagactagtt tacctcttca catttatgct cacaaccctc ttgttagaaa agtctgtgtt | 4395 |
| tatatacagg ctgtaagttt gtgattgata aaaagaagat gagtgttaat tagcctccag | 4455 |
| tgaaaatata ctgaaagcct gttttcattt gattccaatg tttcttccaa agaattctgt | 4515 |
| ataaacatat gccaattccc tatgatggtc tagagttagg aatgagtgtt tatggtgttg | 4575 |
| cttatagaac aactcaggta atctccattt ctggttttat attttctgta caaactgcct | 4635 |
| gggttttatt tttctaatca gcaaggtgct tcactgcctt cttgagacgc ctctcaaagc | 4695 |
| tcttaaatgg ctcctgtgct atgtgtggtg ttggcagtct aatttgcttc tgttaaatgt | 4755 |
| tgtagaacct ttttcactag gaaataagat tcatttcttt cggcagtaga tgtagattca | 4815 |
| tcttttaacg tttcttcaaa tttgtttctg tcaggctttg tgttatttta aatggttttt | 4875 |
| taaaattttc ttctatgttt tcaattacct aaagacatag gataatagtt ttttttaagt | 4935 |
| tagaatttta cctcataaaa ttttttgagg tttgatgtat gtctctgtct tatcaataat | 4995 |
| gaggcttaaa aaatactgga tttgaatggc tgccgttttt tcaaagcaat atgaatttga | 5055 |
| tgagtttgtt ttatgccatt aggtggcgcc agaggtcaga acatgtctat tttgaattgg | 5115 |
| atcgttacaa atgagcatat ttgatgcgga aatttctggg agaaaaaaaa ttgaggaaat | 5175 |
| aaagttaaaa aattgacatt cattgagcca aagagatgt ggagaaacat ttttcacctt | 5235 |
| tctgtttggc ctgattaaca tttaaattct tgccaaaatt aaggtaactt ttaaaaaaca | 5295 |
| cctttttatag gtggatccag cagtctggca acgcccacag ttaccacaac acagaaaact | 5355 |
| gatcgtgcta taaatggac gctaaactat gaaaacagtg tgacattgtt ctctgttctt | 5415 |
| ccagagccag taacatgctt gctcgtgctt tctacttcta gctgatcatt cttttcccaa | 5475 |

```
catatattta caaattacca aattttacct agaattttag gaccaaatgg ttctcactct    5535
ttatgctgca aagacctgga tgatgtttgg taactataga aaaatagaaa ttacactcag    5595
gatcactgtt actgctattg ccactgatga ttcctgcaaa aatataatcg aagttttcca    5655
tcaaatgtat aatatgctat aatacacat  tagatgataa cagttgttcc atgaatgatt    5715
ctatgaagct atgcatctta gacctcttga gctgtgaatt agcactattt tctatagtta    5775
cttattctct ggatcatttt ataatttcca tattaatttc aaatatgctc gtgttattct    5835
tcagtgattt ccacaattgt gcattttatt ctttggttta agtactgaag catataatga    5895
aagtaattgc taagtagcag cttaaaaatt caattatccg attgtattta acatctttaa    5955
gagcatgatc ataagagct  attttttgaca cccccccccc acttttttaa catttagagt    6015
tagtaagggt tttatatctc ttctgtccat attgttttca aaggaatgag gtgtttaggt    6075
ggctggaaaa gcattgtag  gaagttagat ttgaatatag acaaggtggg ttattcacgt    6135
tgagaatgtt atttgaagaa tgcctgtgaa gccaggtgtg ggttctactc agtgccatag    6195
atagactgag tcttctctcg taggttacca ttacatagta attttgattc tgaattacac    6255
attaaattat ttgagtttat acagacctaa attttaaaat ctgtacatat attattttga    6315
tgtattaaga tgaatattgc tgatttaaat tttatttatg cacatactta aaggacagaa    6375
atgtctggga aagtaattgt taaataatga tatgtaactt tttaactttt taaataaata    6435
acaagatttt taatgtgtgt ctccctcagg gttgtttaaa gttttttttc tccctcaagt    6495
ataaatagtg gtaactatat gttttgtatc ttctagcacc aactgctgta aagcaatgct    6555
gcaaataatg cttgaataca agtggctaag ccaacaacag aataaatact tttatagtag    6615
ttttataatc ctgaaattcg aaagctttcc caattgcact tgcatctaaa caaaactgtt    6675
gcagttttta ctctatttat tttgttcccc atgtttatga aagtcctgca cagtttcaaa    6735
ggcatggtaa ataatatatc aatgtttatg tagtctgtta cagaaacagc tatagataac    6795
attatccagt gaagagcaaa attcaagctt tagaaaatat tcatgcatgc aattttgaca    6855
tatctaaaaa taggttttg  tatatttatg gtgggaggtg gttgggaact tttaacaaaa    6915
tggggtgtta attttgtac  agtctgtggg catttacaca ttttaatgt  attaaaattt    6975 ggtaattatg tgtacattaa attaataaaa gttacttcta gttatgattt gtgaattccc    7035
taagaccttg gattttttta agtaacttta tatcagaaat gatactgcat ctttatattt    7095
ttaaaattgt attgctgctc aagaatggta ccctcttgtc aaaaaggcat acattcataa    7155
ttgtacattc agcattgtaa ataatcttat gaaacctttt ttgattgaag ctattcaaaa    7215
taaaaatttt aatgaatgaa aaaaaaaaaa aaaa                                7249
```

<210> SEQ ID NO 68
<211> LENGTH: 1256
<212> TYPE: PRT
<213> ORGANISM: Homo Sapiens

<400> SEQUENCE: 68

Met Asp Arg Glu Glu Arg Lys Thr Ile Asn Gln Gly Gln Glu Asp Glu
 1               5                  10                  15

Met Glu Ile Tyr Gly Tyr Asn Leu Ser Arg Trp Lys Leu Ala Ile Val
            20                  25                  30

Ser Leu Gly Val Ile Cys Ser Asp Gly Phe Leu Leu Leu Leu Leu Tyr
        35                  40                  45

Trp Met Pro Glu Trp Arg Val Lys Ala Thr Cys Val Arg Ala Ala Ile

```
            50                  55                  60
Lys Asp Cys Glu Val Val Leu Leu Arg Thr Thr Asp Glu Phe Lys Met
 65                  70                  75                  80

Trp Phe Cys Ala Lys Ile Arg Val Leu Ser Leu Glu Thr Tyr Pro Val
                 85                  90                  95

Ser Ser Pro Lys Ser Met Ser Asn Lys Leu Ser Asn Gly His Ala Val
                100                 105                 110

Cys Leu Ile Glu Asn Pro Thr Glu Glu Asn Arg His Arg Ile Ser Lys
                115                 120                 125

Tyr Ser Gln Thr Glu Ser Gln Gln Ile Arg Tyr Phe Thr His His Ser
                130                 135                 140

Val Lys Tyr Phe Trp Asn Asp Thr Ile His Asn Phe Asp Phe Leu Lys
145                 150                 155                 160

Gly Leu Asp Glu Gly Val Ser Cys Thr Ser Ile Tyr Glu Lys His Ser
                165                 170                 175

Ala Gly Leu Thr Lys Gly Met His Ala Tyr Arg Lys Leu Leu Tyr Gly
                180                 185                 190

Val Asn Glu Ile Ala Val Lys Val Pro Ser Val Phe Lys Leu Leu Ile
                195                 200                 205

Lys Glu Val Leu Asn Pro Phe Tyr Ile Phe Gln Leu Phe Ser Val Ile
                210                 215                 220

Leu Trp Ser Thr Asp Glu Tyr Tyr Tyr Tyr Ala Leu Ala Ile Val Val
225                 230                 235                 240

Met Ser Ile Val Ser Ile Val Ser Ser Leu Tyr Ser Ile Arg Lys Gln
                245                 250                 255

Tyr Val Met Leu His Asp Met Val Ala Thr His Ser Thr Val Arg Val
                260                 265                 270

Ser Val Cys Arg Val Asn Glu Glu Ile Glu Glu Ile Phe Ser Thr Asp
                275                 280                 285

Leu Val Pro Gly Asp Val Met Val Ile Pro Leu Asn Gly Thr Ile Met
                290                 295                 300

Pro Cys Asp Ala Val Leu Ile Asn Gly Thr Cys Ile Val Asn Glu Ser
305                 310                 315                 320

Met Leu Thr Gly Glu Ser Val Pro Val Thr Lys Thr Asn Leu Pro Asn
                325                 330                 335

Pro Ser Val Asp Val Lys Gly Ile Gly Asp Glu Leu Tyr Asn Pro Glu
                340                 345                 350

Thr His Lys Arg His Thr Leu Phe Cys Gly Thr Thr Val Ile Gln Thr
                355                 360                 365

Arg Phe Tyr Thr Gly Glu Leu Val Lys Ala Ile Val Val Arg Thr Gly
                370                 375                 380

Phe Ser Thr Ser Lys Gly Gln Leu Val Arg Ser Ile Leu Tyr Pro Lys
385                 390                 395                 400

Pro Thr Asp Phe Lys Leu Tyr Arg Asp Ala Tyr Leu Phe Leu Leu Cys
                405                 410                 415

Leu Val Ala Val Ala Gly Ile Gly Phe Ile Tyr Thr Ile Ile Asn Ser
                420                 425                 430

Ile Leu Asn Glu Val Gln Val Gly Val Ile Ile Glu Ser Leu Asp
                435                 440                 445

Ile Ile Thr Ile Thr Val Pro Pro Ala Leu Pro Ala Ala Met Thr Ala
                450                 455                 460

Gly Ile Val Tyr Ala Gln Arg Arg Leu Lys Lys Ile Gly Ile Phe Cys
465                 470                 475                 480
```

-continued

```
Ile Ser Pro Gln Arg Ile Asn Ile Cys Gly Gln Leu Asn Leu Val Cys
            485                 490                 495
Phe Asp Lys Thr Gly Thr Leu Thr Glu Asp Gly Leu Asp Leu Trp Gly
            500                 505                 510
Ile Gln Arg Val Glu Asn Ala Arg Phe Leu Ser Pro Glu Glu Asn Val
            515                 520                 525
Cys Asn Glu Met Leu Val Lys Ser Gln Phe Val Ala Cys Met Ala Thr
            530                 535                 540
Cys His Ser Leu Thr Lys Ile Glu Gly Val Leu Ser Gly Asp Pro Leu
545                 550                 555                 560
Asp Leu Lys Met Phe Glu Ala Ile Gly Trp Ile Leu Glu Glu Ala Thr
            565                 570                 575
Glu Glu Glu Thr Ala Leu His Asn Arg Ile Met Pro Thr Val Val Arg
            580                 585                 590
Pro Pro Lys Gln Leu Leu Pro Glu Ser Thr Pro Ala Gly Asn Gln Glu
            595                 600                 605
Met Glu Leu Phe Glu Leu Pro Ala Thr Tyr Glu Ile Gly Ile Val Arg
            610                 615                 620
Gln Phe Pro Phe Ser Ser Ala Leu Gln Arg Met Ser Val Val Ala Arg
625                 630                 635                 640
Val Leu Gly Asp Arg Lys Met Asp Ala Tyr Met Lys Gly Ala Pro Glu
            645                 650                 655
Ala Ile Ala Gly Leu Cys Lys Pro Glu Thr Val Pro Val Asp Phe Gln
            660                 665                 670
Asn Val Leu Glu Asp Phe Thr Lys Gln Gly Phe Arg Val Ile Ala Leu
            675                 680                 685
Ala His Arg Lys Leu Glu Ser Lys Leu Thr Trp His Lys Val Gln Asn
            690                 695                 700
Ile Ser Arg Asp Ala Ile Glu Asn Asn Met Asp Phe Met Gly Leu Ile
705                 710                 715                 720
Ile Met Gln Asn Lys Leu Lys Gln Glu Thr Pro Ala Val Leu Glu Asp
            725                 730                 735
Leu His Lys Ala Asn Ile Arg Thr Val Met Val Thr Gly Asp Ser Met
            740                 745                 750
Leu Thr Ala Val Ser Val Ala Arg Asp Cys Gly Met Ile Leu Pro Gln
            755                 760                 765
Asp Lys Val Ile Ile Ala Glu Ala Leu Pro Pro Lys Asp Gly Lys Val
            770                 775                 780
Ala Lys Ile Asn Trp His Tyr Ala Asp Ser Leu Thr Gln Cys Ser His
785                 790                 795                 800
Pro Ser Ala Ile Asp Pro Glu Ala Ile Pro Val Lys Leu Val His Asp
            805                 810                 815
Ser Leu Glu Asp Leu Gln Met Thr Arg Tyr His Phe Ala Met Asn Gly
            820                 825                 830
Lys Ser Phe Ser Val Ile Leu Glu His Phe Gln Asp Leu Val Pro Lys
            835                 840                 845
Leu Met Leu His Gly Thr Val Phe Ala Arg Met Ala Pro Asp Gln Lys
850                 855                 860
Thr Gln Leu Ile Glu Ala Leu Gln Asn Val Asp Tyr Phe Val Gly Met
865                 870                 875                 880
Cys Gly Asp Gly Ala Asn Asp Cys Gly Ala Leu Lys Arg Ala His Gly
            885                 890                 895
```

Gly Ile Ser Leu Ser Glu Leu Glu Ala Ser Val Ala Ser Pro Phe Thr
            900                 905                 910

Ser Lys Thr Pro Ser Ile Ser Cys Val Pro Asn Leu Ile Arg Glu Gly
        915                 920                 925

Arg Ala Ala Leu Ile Thr Ser Phe Cys Val Phe Lys Phe Met Ala Leu
    930                 935                 940

Tyr Ser Ile Ile Gln Tyr Phe Ser Val Thr Leu Leu Tyr Ser Ile Leu
945                 950                 955                 960

Ser Asn Leu Gly Asp Phe Gln Phe Leu Phe Ile Asp Leu Ala Ile Ile
                965                 970                 975

Leu Val Val Val Phe Thr Met Ser Leu Asn Pro Ala Trp Lys Glu Leu
            980                 985                 990

Val Ala Gln Arg Pro Pro Ser Gly Leu Ile Ser Gly Ala Leu Leu Phe
        995                 1000                1005

Ser Val Leu Ser Gln Ile Ile Ile Cys Ile Gly Phe Gln Ser Leu Gly
    1010                1015                1020

Phe Phe Trp Val Lys Gln Gln Pro Trp Tyr Glu Val Trp His Pro Lys
1025                1030                1035                1040

Ser Asp Ala Cys Asn Thr Thr Gly Ser Gly Phe Trp Asn Ser Ser His
                1045                1050                1055

Val Asp Asn Glu Thr Glu Leu Asp Glu His Asn Ile Gln Asn Tyr Glu
            1060                1065                1070

Asn Thr Thr Val Phe Phe Ile Ser Ser Phe Gln Tyr Leu Ile Val Ala
        1075                1080                1085

Ile Ala Phe Ser Lys Gly Lys Pro Phe Arg Gln Pro Cys Tyr Lys Asn
    1090                1095                1100

Tyr Phe Phe Val Phe Ser Val Ile Phe Leu Tyr Ile Phe Ile Leu Phe
1105                1110                1115                1120

Ile Met Leu Tyr Pro Val Ala Ser Val Asp Gln Val Leu Gln Ile Val
                1125                1130                1135

Cys Val Pro Tyr Gln Trp Arg Val Thr Met Leu Ile Ile Val Leu Val
            1140                1145                1150

Asn Ala Phe Val Ser Ile Thr Val Glu Asn Phe Phe Leu Asp Met Val
        1155                1160                1165

Leu Trp Lys Val Phe Asn Arg Asp Lys Gln Gly Glu Tyr Arg Phe
    1170                1175                1180

Ser Thr Thr Gln Pro Pro Gln Glu Ser Val Asp Arg Trp Gly Lys Cys
1185                1190                1195                1200

Cys Leu Pro Trp Ala Leu Gly Cys Arg Lys Lys Thr Pro Lys Ala Lys
                1205                1210                1215

Tyr Met Tyr Leu Ala Gln Glu Leu Leu Val Asp Pro Gly Trp Pro Pro
            1220                1225                1230

Lys Pro Gln Thr Thr Thr Glu Ala Lys Ala Leu Val Lys Glu Asn Gly
        1235                1240                1245

Ser Cys Gln Ile Ile Thr Ile Thr
    1250                1255

<210> SEQ ID NO 69
<211> LENGTH: 3768
<212> TYPE: DNA
<213> ORGANISM: Homo Sapiens
<220> FEATURE:
<221> NAME/KEY: CDS
<222> LOCATION: (1)...(3768)

<400> SEQUENCE: 69

```
atg gac agg gaa gaa agg aag acc atc aat cag ggt caa gaa gat gaa        48
Met Asp Arg Glu Glu Arg Lys Thr Ile Asn Gln Gly Gln Glu Asp Glu
 1               5                  10                  15 atg gag att tat ggt tac aat ttg agt cgc tgg aag ctt gcc ata gtt        96
Met Glu Ile Tyr Gly Tyr Asn Leu Ser Arg Trp Lys Leu Ala Ile Val
                20                  25                  30 tct tta gga gtg att tgc tct gat ggg ttt ctc ctc ctc ctc ctc tat       144
Ser Leu Gly Val Ile Cys Ser Asp Gly Phe Leu Leu Leu Leu Leu Tyr
            35                  40                  45 tgg atg cct gag tgg cgg gtg aaa gcg acc tgt gtc aga gct gca att       192
Trp Met Pro Glu Trp Arg Val Lys Ala Thr Cys Val Arg Ala Ala Ile
    50                  55                  60 aaa gac tgt gaa gta gtg ctg ctg agg act act gat gaa ttc aaa atg       240
Lys Asp Cys Glu Val Val Leu Leu Arg Thr Thr Asp Glu Phe Lys Met
65                  70                  75                  80 tgg ttt tgt gca aaa att cgc gtt ctt tct ttg gaa act tac cca gtt       288
Trp Phe Cys Ala Lys Ile Arg Val Leu Ser Leu Glu Thr Tyr Pro Val
                85                  90                  95 tca agt cca aaa tct atg tct aat aag ctt tca aat ggc cat gca gtt       336
Ser Ser Pro Lys Ser Met Ser Asn Lys Leu Ser Asn Gly His Ala Val
                100                 105                 110 tgt tta att gag aat ccc act gaa gaa aat agg cac agg atc agt aaa       384
Cys Leu Ile Glu Asn Pro Thr Glu Glu Asn Arg His Arg Ile Ser Lys
            115                 120                 125 tat tca cag act gaa tca caa cag att cgt tat ttc acc cac cat agt       432
Tyr Ser Gln Thr Glu Ser Gln Gln Ile Arg Tyr Phe Thr His His Ser
130                 135                 140 gta aaa tat ttc tgg aat gat acc att cac aat ttt gat ttc tta aag       480
Val Lys Tyr Phe Trp Asn Asp Thr Ile His Asn Phe Asp Phe Leu Lys
145                 150                 155                 160 gga ctg gat gaa ggt gtt tct tgt acg tca att tat gaa aag cat agt       528
Gly Leu Asp Glu Gly Val Ser Cys Thr Ser Ile Tyr Glu Lys His Ser
                165                 170                 175 gca gga ctg aca aag ggg atg cat gcc tac aga aaa ctg ctt tat gga       576
Ala Gly Leu Thr Lys Gly Met His Ala Tyr Arg Lys Leu Leu Tyr Gly
            180                 185                 190 gta aat gaa att gct gta aaa gtg cct tct gtt ttt aag ctt cta att       624
Val Asn Glu Ile Ala Val Lys Val Pro Ser Val Phe Lys Leu Leu Ile
        195                 200                 205 aaa gag gtt ctc aac cca ttt tac att ttc cag ctg ttc agt gtt ata       672
Lys Glu Val Leu Asn Pro Phe Tyr Ile Phe Gln Leu Phe Ser Val Ile
210                 215                 220 ctg tgg agc act gat gaa tac tat tac tat gct cta gct att gtg gtt       720
Leu Trp Ser Thr Asp Glu Tyr Tyr Tyr Tyr Ala Leu Ala Ile Val Val
225                 230                 235                 240 atg tcc ata gta tca atc gta agc tca cta tat tcc att aga aag caa       768
Met Ser Ile Val Ser Ile Val Ser Ser Leu Tyr Ser Ile Arg Lys Gln
                245                 250                 255 tat gtt atg ttg cat gac atg gtg gca act cat agt acc gta aga gtt       816
Tyr Val Met Leu His Asp Met Val Ala Thr His Ser Thr Val Arg Val
            260                 265                 270 tca gtt tgt aga gta aat gaa gaa ata gaa gaa atc ttt tct acc gac       864
Ser Val Cys Arg Val Asn Glu Glu Ile Glu Glu Ile Phe Ser Thr Asp
        275                 280                 285 ctt gtg cca gga gat gtc atg gtc att cca tta aat ggg aca ata atg       912
Leu Val Pro Gly Asp Val Met Val Ile Pro Leu Asn Gly Thr Ile Met
290                 295                 300 cct tgt gat gct gtg ctt att aat ggt acc tgc att gta aac gaa agc       960
Pro Cys Asp Ala Val Leu Ile Asn Gly Thr Cys Ile Val Asn Glu Ser
```

-continued

```
            305                 310                 315                 320
atg tta aca gga gaa agt gtt cca gtg aca aag act aat ttg cca aat     1008
Met Leu Thr Gly Glu Ser Val Pro Val Thr Lys Thr Asn Leu Pro Asn
                325                 330                 335 cct tca gtg gat gtg aaa gga ata gga gat gaa tta tat aat cca gaa     1056
Pro Ser Val Asp Val Lys Gly Ile Gly Asp Glu Leu Tyr Asn Pro Glu
            340                 345                 350 aca cat aaa cga cat act ttg ttt tgt ggg aca act gtt att cag act     1104
Thr His Lys Arg His Thr Leu Phe Cys Gly Thr Thr Val Ile Gln Thr
        355                 360                 365 cgt ttc tac act gga gaa ctc gtc aaa gcc ata gtt gtt aga aca gga     1152
Arg Phe Tyr Thr Gly Glu Leu Val Lys Ala Ile Val Val Arg Thr Gly
    370                 375                 380 ttt agt act tcc aaa gga cag ctt gtt cgt tcc ata ttg tat ccc aaa     1200
Phe Ser Thr Ser Lys Gly Gln Leu Val Arg Ser Ile Leu Tyr Pro Lys
385                 390                 395                 400 cca act gat ttt aaa ctc tac aga gat gcc tac ttg ttt cta cta tgt     1248
Pro Thr Asp Phe Lys Leu Tyr Arg Asp Ala Tyr Leu Phe Leu Leu Cys
                405                 410                 415 ctt gtg gca gtt gct ggc att ggg ttt atc tac act att att aat agc     1296
Leu Val Ala Val Ala Gly Ile Gly Phe Ile Tyr Thr Ile Ile Asn Ser
            420                 425                 430 att tta aat gag gta caa gtt ggg gtc ata att atc gag tct ctt gat     1344
Ile Leu Asn Glu Val Gln Val Gly Val Ile Ile Ile Glu Ser Leu Asp
        435                 440                 445 att atc aca att act gtg ccc cct gca ctt cct gct gca atg act gct     1392
Ile Ile Thr Ile Thr Val Pro Pro Ala Leu Pro Ala Ala Met Thr Ala
    450                 455                 460 ggt att gtg tat gct cag aga aga ctg aaa aaa atc ggt att ttc tgt     1440
Gly Ile Val Tyr Ala Gln Arg Arg Leu Lys Lys Ile Gly Ile Phe Cys
465                 470                 475                 480 atc agt cct caa aga ata aat att tgt gga cag ctc aat ctt gtt tgc     1488
Ile Ser Pro Gln Arg Ile Asn Ile Cys Gly Gln Leu Asn Leu Val Cys
                485                 490                 495 ttt gac aag act gga act cta act gaa gat ggt tta gat ctt tgg ggg     1536
Phe Asp Lys Thr Gly Thr Leu Thr Glu Asp Gly Leu Asp Leu Trp Gly
            500                 505                 510 att caa cga gtg gaa aat gca cga ttt ctt tca cca gaa gaa aat gtg     1584
Ile Gln Arg Val Glu Asn Ala Arg Phe Leu Ser Pro Glu Glu Asn Val
        515                 520                 525 tgc aat gag atg ttg gta aaa tcc cag ttt gtt gct tgt atg gct act     1632
Cys Asn Glu Met Leu Val Lys Ser Gln Phe Val Ala Cys Met Ala Thr
    530                 535                 540 tgt cat tca ctt aca aaa att gaa gga gtg ctc tct ggt gat cca ctt     1680
Cys His Ser Leu Thr Lys Ile Glu Gly Val Leu Ser Gly Asp Pro Leu
545                 550                 555                 560 gat ctg aaa atg ttt gag gct att gga tgg att ctg gaa gaa gca act     1728
Asp Leu Lys Met Phe Glu Ala Ile Gly Trp Ile Leu Glu Glu Ala Thr
                565                 570                 575 gaa gaa gaa aca gca ctt cat aat cga att atg ccc aca gtg gtt cgt     1776
Glu Glu Glu Thr Ala Leu His Asn Arg Ile Met Pro Thr Val Val Arg
            580                 585                 590 cct ccc aaa caa ctg ctt cct gaa tct acc cct gca gga aac caa gaa     1824
Pro Pro Lys Gln Leu Leu Pro Glu Ser Thr Pro Ala Gly Asn Gln Glu
        595                 600                 605 atg gag ctg ttt gaa ctt cca gct act tat gag ata gga att gtt cgc     1872
Met Glu Leu Phe Glu Leu Pro Ala Thr Tyr Glu Ile Gly Ile Val Arg
    610                 615                 620 cag ttc cca ttt tct tct gct ttg caa cgt atg agt gtg gtt gcc agg     1920
```

```
                    -continued

Gln Phe Pro Phe Ser Ser Ala Leu Gln Arg Met Ser Val Val Ala Arg
625                 630                 635                 640 gtg ctg ggg gat agg aaa atg gac gcc tac atg aaa gga gcg ccc gag      1968
Val Leu Gly Asp Arg Lys Met Asp Ala Tyr Met Lys Gly Ala Pro Glu
                645                 650                 655 gcc att gcc ggt ctc tgt aaa cct gaa aca gtt cct gtc gat ttt caa      2016
Ala Ile Ala Gly Leu Cys Lys Pro Glu Thr Val Pro Val Asp Phe Gln
            660                 665                 670 aac gtt ttg gaa gac ttc act aaa cag ggc ttc cgt gtg att gct ctt      2064
Asn Val Leu Glu Asp Phe Thr Lys Gln Gly Phe Arg Val Ile Ala Leu
        675                 680                 685 gca cac aga aaa ttg gag tca aaa ctg aca tgg cat aaa gta cag aat      2112
Ala His Arg Lys Leu Glu Ser Lys Leu Thr Trp His Lys Val Gln Asn
    690                 695                 700 att agc aga gat gca att gag aac aac atg gat ttt atg gga tta att      2160
Ile Ser Arg Asp Ala Ile Glu Asn Asn Met Asp Phe Met Gly Leu Ile
705                 710                 715                 720 ata atg cag aac aaa tta aag caa gaa acc cct gca gta ctt gaa gat      2208
Ile Met Gln Asn Lys Leu Lys Gln Glu Thr Pro Ala Val Leu Glu Asp
                725                 730                 735 ttg cat aaa gcc aac att cgc acc gtc atg gtc aca ggt gac agt atg      2256
Leu His Lys Ala Asn Ile Arg Thr Val Met Val Thr Gly Asp Ser Met
            740                 745                 750 ttg act gct gtc tct gtg gcc aga gat tgt gga atg att cta cct cag      2304
Leu Thr Ala Val Ser Val Ala Arg Asp Cys Gly Met Ile Leu Pro Gln
        755                 760                 765 gat aaa gtg att att gct gaa gca tta cct cca aag gat ggg aaa gtt      2352
Asp Lys Val Ile Ile Ala Glu Ala Leu Pro Pro Lys Asp Gly Lys Val
    770                 775                 780 gcc aaa ata aat tgg cat tat gca gac tcc ctc acg cag tgc agt cat      2400
Ala Lys Ile Asn Trp His Tyr Ala Asp Ser Leu Thr Gln Cys Ser His
785                 790                 795                 800 cca tca gca att gac cca gag gct att ccg gtt aaa ttg gtc cat gat      2448
Pro Ser Ala Ile Asp Pro Glu Ala Ile Pro Val Lys Leu Val His Asp
                805                 810                 815 agc tta gag gat ctt caa atg act cgt tat cat ttt gca atg aat gga      2496
Ser Leu Glu Asp Leu Gln Met Thr Arg Tyr His Phe Ala Met Asn Gly
            820                 825                 830 aaa tca ttc tca gtg ata ctg gag cat ttt caa gac ctt gtt cct aag      2544
Lys Ser Phe Ser Val Ile Leu Glu His Phe Gln Asp Leu Val Pro Lys
        835                 840                 845 ttg atg ttg cat ggc acc gtg ttt gcc cgt atg gca cct gat cag aag      2592
Leu Met Leu His Gly Thr Val Phe Ala Arg Met Ala Pro Asp Gln Lys
    850                 855                 860 aca cag ttg ata gaa gca ttg caa aat gtt gat tat ttt gtt ggg atg      2640
Thr Gln Leu Ile Glu Ala Leu Gln Asn Val Asp Tyr Phe Val Gly Met
865                 870                 875                 880 tgt ggt gat ggc gca aat gat tgt ggt gct ttg aag agg gca cac gga      2688
Cys Gly Asp Gly Ala Asn Asp Cys Gly Ala Leu Lys Arg Ala His Gly
                885                 890                 895 ggc att tcc tta tcg gag ctc gaa gct tca gtg gca tct ccc ttt acc      2736
Gly Ile Ser Leu Ser Glu Leu Glu Ala Ser Val Ala Ser Pro Phe Thr
            900                 905                 910 tct aag act cct agt att tcc tgt gtg cca aac ctt atc agg gaa ggc      2784
Ser Lys Thr Pro Ser Ile Ser Cys Val Pro Asn Leu Ile Arg Glu Gly
        915                 920                 925 cgt gct gct tta ata act tcc ttc tgt gtg ttt aaa ttc atg gca ttg      2832
Arg Ala Ala Leu Ile Thr Ser Phe Cys Val Phe Lys Phe Met Ala Leu
    930                 935                 940
```

```
tac agc att atc cag tac ttc agt gtt act ctg ctg tat tct atc tta    2880
Tyr Ser Ile Ile Gln Tyr Phe Ser Val Thr Leu Leu Tyr Ser Ile Leu
945                 950                 955                 960 agt aac cta gga gac ttc cag ttt ctc ttc att gat ctg gca atc att    2928
Ser Asn Leu Gly Asp Phe Gln Phe Leu Phe Ile Asp Leu Ala Ile Ile
            965                 970                 975 ttg gta gtg gta ttt aca atg agt tta aat cct gcc tgg aaa gaa ctt    2976
Leu Val Val Val Phe Thr Met Ser Leu Asn Pro Ala Trp Lys Glu Leu
                980                 985                 990 gtg gca caa aga cca cct tcg ggt ctt ata tct ggg gcc ctt ctc ttc    3024
Val Ala Gln Arg Pro Pro Ser Gly Leu Ile Ser Gly Ala Leu Leu Phe
            995                 1000                1005 tcc gtt ttg tct cag att atc atc tgc att gga ttt caa tct ttg ggt    3072
Ser Val Leu Ser Gln Ile Ile Ile Cys Ile Gly Phe Gln Ser Leu Gly
        1010                1015                1020 ttt ttt tgg gtc aaa cag caa cct tgg tat gaa gtg tgg cat cca aaa    3120
Phe Phe Trp Val Lys Gln Gln Pro Trp Tyr Glu Val Trp His Pro Lys
1025                1030                1035                1040 tca gat gct tgt aat aca aca gga agc ggg ttt tgg aat tct tca cac    3168
Ser Asp Ala Cys Asn Thr Thr Gly Ser Gly Phe Trp Asn Ser Ser His
            1045                1050                1055 gta gac aat gaa acc gaa ctt gat gaa cat aat ata caa aat tat gaa    3216
Val Asp Asn Glu Thr Glu Leu Asp Glu His Asn Ile Gln Asn Tyr Glu
        1060                1065                1070 aat acc aca gtg ttt ttt att tcc agt ttt cag tac ctc ata gtg gca    3264
Asn Thr Thr Val Phe Phe Ile Ser Ser Phe Gln Tyr Leu Ile Val Ala
    1075                1080                1085 att gcc ttt tca aaa gga aaa ccc ttc agg caa cct tgc tac aaa aat    3312
Ile Ala Phe Ser Lys Gly Lys Pro Phe Arg Gln Pro Cys Tyr Lys Asn
        1090                1095                1100 tat ttt ttt gtt ttt tct gtg att ttt tta tat att ttt ata tta ttc    3360
Tyr Phe Phe Val Phe Ser Val Ile Phe Leu Tyr Ile Phe Ile Leu Phe
1105                1110                1115                1120 atc atg ttg tat cca gtt gcc tct gtt gac cag gtt ctt cag ata gtg    3408
Ile Met Leu Tyr Pro Val Ala Ser Val Asp Gln Val Leu Gln Ile Val
            1125                1130                1135 tgt gta cca tat cag tgg cgt gta act atg ctc atc att gtt ctt gtc    3456
Cys Val Pro Tyr Gln Trp Arg Val Thr Met Leu Ile Ile Val Leu Val
        1140                1145                1150 aat gcc ttt gtg tct atc aca gtg gag aac ttc ttc ctt gac atg gtc    3504
Asn Ala Phe Val Ser Ile Thr Val Glu Asn Phe Phe Leu Asp Met Val
        1155                1160                1165 ctt tgg aaa gtt gtg ttc aac cga gac aaa caa gga gag tat cgg ttc    3552
Leu Trp Lys Val Val Phe Asn Arg Asp Lys Gln Gly Glu Tyr Arg Phe
1170                1175                1180 agc acc aca cag cca ccg cag gag tca gtg gat cgg tgg gga aaa tgc    3600
Ser Thr Thr Gln Pro Pro Gln Glu Ser Val Asp Arg Trp Gly Lys Cys
1185                1190                1195                1200 tgc tta ccc tgg gcc ctg ggc tgt aga aag aag aca cca aag gca aag    3648
Cys Leu Pro Trp Ala Leu Gly Cys Arg Lys Lys Thr Pro Lys Ala Lys
            1205                1210                1215 tac atg tat ctg gcg cag gag ctc ttg gtt gat cca gaa tgg cca cca    3696
Tyr Met Tyr Leu Ala Gln Glu Leu Leu Val Asp Pro Glu Trp Pro Pro
        1220                1225                1230 aaa cct cag aca acc aca gaa gct aaa gct tta gtt aag gag aat gga    3744
Lys Pro Gln Thr Thr Thr Glu Ala Lys Ala Leu Val Lys Glu Asn Gly
            1235                1240                1245 tca tgt caa atc atc acc ata aca                                    3768
Ser Cys Gln Ile Ile Thr Ile Thr
        1250                1255
```

<210> SEQ ID NO 70
<211> LENGTH: 3919
<212> TYPE: DNA
<213> ORGANISM: Homo Sapiens
<220> FEATURE:
<221> NAME/KEY: CDS
<222> LOCATION: (68)...(3682)

<400> SEQUENCE: 70

| | | | | |
|---|---|---|---|---|
| ttaccggaag taaaacttcg aagtgaggc gttcctctgc ccggaagtga gcgccgcgct | | | | 60 |

| aggaaag | atg Met 1 | gcg Ala | gca Ala | gcg Ala | gcg Ala | gcg Ala 5 | gtg Val | ggc Gly | aac Asn | gcg Ala | gtg Val | ccc Pro 10 | tgc Cys | ggg Gly | 109 |
|---|---|---|---|---|---|---|---|---|---|---|---|---|---|---|---|
| gcc Ala 15 | cgg Arg | cct Pro | tgc Cys | ggg Gly 20 | gtc Val | cgg Arg | cct Pro | gac Asp | ggg Gly 25 | cag Gln | ccc Pro | aag Lys | ccc Pro | ggg Gly 30 | ccg Pro | 157 |
| cag Gln | ccg Pro | cgc Arg | gcg Ala | ctc Leu 35 | ctt Leu | gcc Ala | gcc Ala | ggg Gly | ccg Pro 40 | gcg Ala | ctc Leu | ata Ile | gcg Ala | aac Asn 45 | ggt Gly | 205 |
| gac Asp | gag Glu | ctg Leu 50 | gtg Val | gct Ala | gcc Ala | gtg Val | tgg Trp 55 | ccg Pro | tac Tyr | cgg Arg | cgg Arg | ttg Leu 60 | gcg Ala | ctg Leu | ttg Leu | 253 |
| cgg Arg | cgc Arg 65 | ctc Leu | acg Thr | gtg Val | ctg Leu 70 | cca Pro | ttc Phe | gcc Ala | ggg Gly | ctg Leu 75 | ctt Leu | tac Tyr | ccg Pro | gcc Ala | tgg Trp | 301 |
| ttg Leu 80 | ggt Gly | gcc Ala | gca Ala | gcc Ala | gct Ala 85 | ggc Gly | tgc Cys | tgg Trp | ggc Gly | tgg Trp 90 | ggc Gly | agc Ser | agt Ser | tgg Trp | gtg Val | 349 |
| cag Gln 95 | atc Ile | ccc Pro | gaa Glu | gct Ala | gcg Ala 100 | ctg Leu | ctc Leu | gtg Val | ctt Leu | gcc Ala 105 | acc Thr | atc Ile | tgc Cys | ctc Leu | gcg Ala 110 | 397 |
| cac His | gcg Ala | ctc Leu | act Thr 115 | gtc Val | ctc Leu | tcg Ser | ggg Gly | cat His 120 | tgg Trp | tct Ser | gtg Val | cac His | gcg Ala 125 | cat His | tgc Cys | 445 |
| gcg Ala | ctc Leu | acc Thr 130 | tgc Cys | acc Thr | ccg Pro | gag Glu | tac Tyr 135 | gac Asp | ccc Pro | agc Ser | aaa Lys | gcg Ala 140 | acc Thr | ttt Phe | gtg Val | 493 |
| aag Lys | gtg Val 145 | gcg Ala | cca Pro | acc Thr | ccc Pro | aat Asn 150 | aat Asn | ggc Gly | tcc Ser | acg Thr | gag Glu 155 | ctc Leu | gtg Val | gcc Ala | ctg Leu | 541 |
| cac His 160 | cgc Arg | aat Asn | gag Glu | ggc Gly | gaa Glu 165 | gac Asp | ggg Gly | ctt Leu | gag Glu | gtg Val 170 | ctg Leu | tcc Ser | ttc Phe | gaa Glu | ttc Phe | 589 |
| cag Gln 175 | aag Lys | atc Ile | aag Lys | tat Tyr | tcc Ser 180 | tac Tyr | gat Asp | gcc Ala | ctg Leu | gag Glu 185 | aag Lys | aag Lys | cag Gln | ttt Phe | ctc Leu 190 | 637 |
| ccc Pro | gtg Val | gcc Ala | ttt Phe 195 | cct Pro | gtg Val | gga Gly | aac Asn | gcc Ala 200 | ttc Phe | tca Ser | tac Tyr | tat Tyr | cag Gln 205 | agc Ser | aac Asn | 685 |
| aga Arg | ggc Gly | ttc Phe 210 | cag Gln | gaa Glu | gac Asp | tca Ser | gag Glu 215 | atc Ile | cga Arg | gca Ala | gct Ala | gag Glu 220 | aag Lys | aaa Lys | ttt Phe | 733 |
| ggg Gly | agc Ser 225 | aac Asn | aag Lys | gcc Ala | gag Glu | atg Met 230 | gtg Val | gtg Val | cct Pro | gac Asp | ttc Phe 235 | tcg Ser | gag Glu | ctt Leu | ttc Phe | 781 |
| aag Lys 240 | gag Glu | aga Arg | gcc Ala | aca Thr | gcc Ala 245 | ccc Pro | ttt Phe | ttt Phe | gta Val | ttt Phe 250 | cag Gln | gtg Val | ttc Phe | tgt Cys | gtg Val | 829 |
| ggg Gly | ctc Leu | tgg Trp | tgc Cys | ctg Leu | gat Asp | gag Glu | tac Tyr | tgg Trp | tac Tyr | tac Tyr | agc Ser | gtc Val | ttt Phe | acg Thr | cta Leu | 877 |

```
Gly Leu Trp Cys Leu Asp Glu Tyr Trp Tyr Tyr Ser Val Phe Thr Leu
255                 260                 265                 270 tcc atg ctg gtg gcg ttc gag gcc tcg ctg gtg cag cag cag atg cgg          925
Ser Met Leu Val Ala Phe Glu Ala Ser Leu Val Gln Gln Gln Met Arg
                    275                 280                 285 aac atg tcg gag atc cgg aag atg ggc aac aag ccc cac atg atc cag          973
Asn Met Ser Glu Ile Arg Lys Met Gly Asn Lys Pro His Met Ile Gln
                290                 295                 300 gtc tac cga agc cgc aag tgg agg ccc att gcc agt gat gag atc gta         1021
Val Tyr Arg Ser Arg Lys Trp Arg Pro Ile Ala Ser Asp Glu Ile Val
            305                 310                 315 cca ggg gac atc gtc tcc atc ggc cgc tcc cca cag gag aac ctg gtg         1069
Pro Gly Asp Ile Val Ser Ile Gly Arg Ser Pro Gln Glu Asn Leu Val
        320                 325                 330 cca tgt gac gtg ctt ctg ctg cga ggc cgc tgc atc gta gac gag gcc         1117
Pro Cys Asp Val Leu Leu Leu Arg Gly Arg Cys Ile Val Asp Glu Ala
335                 340                 345                 350 atg ctc acg ggg gag tcc gtg cca cag atg aag gag ccc atc gaa gac         1165
Met Leu Thr Gly Glu Ser Val Pro Gln Met Lys Glu Pro Ile Glu Asp
                355                 360                 365 ctc agc cca gac cgg gtg ctg gac ctc cag gct gat tcc cgg ctg cac         1213
Leu Ser Pro Asp Arg Val Leu Asp Leu Gln Ala Asp Ser Arg Leu His
            370                 375                 380 gtc atc ttc ggg ggc acc aag gtg gtg cag cac atc ccc cca cag aaa         1261
Val Ile Phe Gly Gly Thr Lys Val Val Gln His Ile Pro Pro Gln Lys
        385                 390                 395 gcc acc acg ggc ctg aag ccg gtt gac agc ggg tgc gtg gcc tac gtc         1309
Ala Thr Thr Gly Leu Lys Pro Val Asp Ser Gly Cys Val Ala Tyr Val
400                 405                 410 ctg cgg acc gga ttc aac aca tct cag ggc aag ctg ctg cgc acc atc         1357
Leu Arg Thr Gly Phe Asn Thr Ser Gln Gly Lys Leu Leu Arg Thr Ile
415                 420                 425                 430 ctc ttc ggg gtc aag agg gtg act gcg aac aac ctg gag acc ttc atc         1405
Leu Phe Gly Val Lys Arg Val Thr Ala Asn Asn Leu Glu Thr Phe Ile
                435                 440                 445 ttc atc ctc ttc ctc ctg gtg ttt gcc atc gct gca gct gcc tat gta         1453
Phe Ile Leu Phe Leu Leu Val Phe Ala Ile Ala Ala Ala Ala Tyr Val
            450                 455                 460 tgg att gaa ggt acc aag gac ccc agc cgg aac cgc tac aag ctg ttt         1501
Trp Ile Glu Gly Thr Lys Asp Pro Ser Arg Asn Arg Tyr Lys Leu Phe
        465                 470                 475 ctg gag tgc acc ctg atc ctc acc tcg gtc gtg cct cct gag ctg ccc         1549
Leu Glu Cys Thr Leu Ile Leu Thr Ser Val Val Pro Pro Glu Leu Pro
480                 485                 490 atc gag ctg tcc ctg gcc gtc aac acc tcc ctc atc gcc ctg gcc aag         1597
Ile Glu Leu Ser Leu Ala Val Asn Thr Ser Leu Ile Ala Leu Ala Lys
495                 500                 505                 510 ctc tac atg tac tgc aca gag ccc ttc cgg atc ccc ttt gct ggc aag         1645
Leu Tyr Met Tyr Cys Thr Glu Pro Phe Arg Ile Pro Phe Ala Gly Lys
                515                 520                 525 gtc gag gtg tgc tgc ttt gac aag acg ggg acg ttg acc agt gac agc         1693
Val Glu Val Cys Cys Phe Asp Lys Thr Gly Thr Leu Thr Ser Asp Ser
            530                 535                 540 ctg gtg gtg cgc ggt gtg gcc ggg ctg aga gac ggg aag gag gtg acc         1741
Leu Val Val Arg Gly Val Ala Gly Leu Arg Asp Gly Lys Glu Val Thr
        545                 550                 555 cca gtg tcc agc atc cct gta gaa aca cac cgg gcc ctg gcc tcg tgc         1789
Pro Val Ser Ser Ile Pro Val Glu Thr His Arg Ala Leu Ala Ser Cys
560                 565                 570
```

```
cac tcg ctc atg cag ctg gac gac ggc acc ctc gtg ggt gac cct cta   1837
His Ser Leu Met Gln Leu Asp Asp Gly Thr Leu Val Gly Asp Pro Leu
575             580                 585                 590 gag aag gcc atg ctg acg gcc gtg gac tgg acg ctg acc aaa gat gag   1885
Glu Lys Ala Met Leu Thr Ala Val Asp Trp Thr Leu Thr Lys Asp Glu
            595                 600                 605 aaa gta ttc ccc cga agt att aaa act cag ggg ctg aaa att cac cag   1933
Lys Val Phe Pro Arg Ser Ile Lys Thr Gln Gly Leu Lys Ile His Gln
        610                 615                 620 cgc ttt cat ttt gcc agt gcc ctg aag cga atg tcc gtg ctt gcc tcg   1981
Arg Phe His Phe Ala Ser Ala Leu Lys Arg Met Ser Val Leu Ala Ser
    625                 630                 635 tat gag aag ctg ggc tcc acc gac ctc tgc tac atc gcg gcc gtg aag   2029
Tyr Glu Lys Leu Gly Ser Thr Asp Leu Cys Tyr Ile Ala Ala Val Lys
640                 645                 650 ggg gcc ccc gaa act ctg cac tcc atg ttc tcc cag tgc ccg ccc gac   2077
Gly Ala Pro Glu Thr Leu His Ser Met Phe Ser Gln Cys Pro Pro Asp
655             660                 665                 670 tac cac cac atc cac acc gag atc tcc cgg gaa gga gcc cgc gtc ctg   2125
Tyr His His Ile His Thr Glu Ile Ser Arg Glu Gly Ala Arg Val Leu
            675                 680                 685 gcg ctg ggg tac aag gag ctg gga cac ctc act cac cag cag gcc cgg   2173
Ala Leu Gly Tyr Lys Glu Leu Gly His Leu Thr His Gln Gln Ala Arg
        690                 695                 700 gag gtc aag cgg gag gcc ctg gag tgc agc ctc aag ttc gtc ggc ttc   2221
Glu Val Lys Arg Glu Ala Leu Glu Cys Ser Leu Lys Phe Val Gly Phe
    705                 710                 715 att gtg gtc tcc tgc ccg ctc aag gct gac tcc aag gcc gtg atc cgg   2269
Ile Val Val Ser Cys Pro Leu Lys Ala Asp Ser Lys Ala Val Ile Arg
720                 725                 730 gag atc cag aat gcg tcc cac cgg gtg gtc atg atc acg gga gac aac   2317
Glu Ile Gln Asn Ala Ser His Arg Val Val Met Ile Thr Gly Asp Asn
735             740                 745                 750 ccg ctc act gca tgc cac gtg gcc cag gag ctg cac ttc att gaa aag   2365
Pro Leu Thr Ala Cys His Val Ala Gln Glu Leu His Phe Ile Glu Lys
            755                 760                 765 gcc cac acg ctg atc ctg cag cct ccc tcc gag aaa ggc cgg cag tgc   2413
Ala His Thr Leu Ile Leu Gln Pro Pro Ser Glu Lys Gly Arg Gln Cys
        770                 775                 780 gag tgg cgc tcc att gac ggc agc atc gtg ctg ccc ctg gcc cgg ggc   2461
Glu Trp Arg Ser Ile Asp Gly Ser Ile Val Leu Pro Leu Ala Arg Gly
    785                 790                 795 tcc cca aag gca ctg gcc ctg gag tac gca ctg tgc ctc aca ggc gac   2509
Ser Pro Lys Ala Leu Ala Leu Glu Tyr Ala Leu Cys Leu Thr Gly Asp
800                 805                 810 ggc ttg gcc cac ctg cag gcc acc gac ccc cag cag ctg ctc cgc ctc   2557
Gly Leu Ala His Leu Gln Ala Thr Asp Pro Gln Gln Leu Leu Arg Leu
815             820                 825                 830 atc ccc cat gtg cag gtg ttc gcc cgt gtg gct ccc aag cag aag gag   2605
Ile Pro His Val Gln Val Phe Ala Arg Val Ala Pro Lys Gln Lys Glu
            835                 840                 845 ttt gtc atc acc agc ctg aag gag ctg ggc tac gtg acc ctc atg tgt   2653
Phe Val Ile Thr Ser Leu Lys Glu Leu Gly Tyr Val Thr Leu Met Cys
        850                 855                 860 ggg gat ggc acc aac gac gtg ggc gcc ctg aag cat gct gac gtg ggt   2701
Gly Asp Gly Thr Asn Asp Val Gly Ala Leu Lys His Ala Asp Val Gly
    865                 870                 875 gtg gcg ctc ttg gcc aat gcc cct gag cgg gtt gtc gag cgg cga cgg   2749
Val Ala Leu Leu Ala Asn Ala Pro Glu Arg Val Val Glu Arg Arg Arg
880                 885                 890
```

-continued

```
cgg ccc cgg gac agc cca acc ctg agc aac agt ggc atc aga gcc acc    2797
Arg Pro Arg Asp Ser Pro Thr Leu Ser Asn Ser Gly Ile Arg Ala Thr
895                 900                 905                 910 tcc agg aca gcc aag cag cgg tcg ggg ctc cct ccc tcc gag gag cag    2845
Ser Arg Thr Ala Lys Gln Arg Ser Gly Leu Pro Pro Ser Glu Glu Gln
            915                 920                 925 cca acc tcc cag agg gac cgc ctg agc cag gtg ctg cga gac ctc gag    2893
Pro Thr Ser Gln Arg Asp Arg Leu Ser Gln Val Leu Arg Asp Leu Glu
        930                 935                 940 gac gag agt acg ccc att gtg aaa ctg ggg gat gcc agc atc gca gca    2941
Asp Glu Ser Thr Pro Ile Val Lys Leu Gly Asp Ala Ser Ile Ala Ala
    945                 950                 955 ccc ttc acc tcc aag ctc tca tcc atc cag tgc atc tgc cac gtg atc    2989
Pro Phe Thr Ser Lys Leu Ser Ser Ile Gln Cys Ile Cys His Val Ile
960                 965                 970 aag cag ggc cgc tgc acg ctg gtg acc acg cta cag atg ttc aag atc    3037
Lys Gln Gly Arg Cys Thr Leu Val Thr Thr Leu Gln Met Phe Lys Ile
975                 980                 985                 990 ctg gcg ctc aat gcc ctc atc ctg gcc tac agc cag agc gtc ctc tac    3085
Leu Ala Leu Asn Ala Leu Ile Leu Ala Tyr Ser Gln Ser Val Leu Tyr
                995                 1000                1005 ctg gag gga gtc aag ttc agt gac ttc cag gcc acc cta cag ggg ctg    3133
Leu Glu Gly Val Lys Phe Ser Asp Phe Gln Ala Thr Leu Gln Gly Leu
            1010                1015                1020 ctg ctg gcc ggc tgc ttc ctc ttc atc tcc cgt tcc aag ccc ctc aag    3181
Leu Leu Ala Gly Cys Phe Leu Phe Ile Ser Arg Ser Lys Pro Leu Lys
        1025                1030                1035 acc ctc tcc cga gaa cgg ccc ctg ccc aac atc ttc aac ctg tac acc    3229
Thr Leu Ser Arg Glu Arg Pro Leu Pro Asn Ile Phe Asn Leu Tyr Thr
    1040                1045                1050 atc ctc acc gtc atg ctc cag ttc ttt gtg cac ttc ctg agc ctt gtc    3277
Ile Leu Thr Val Met Leu Gln Phe Phe Val His Phe Leu Ser Leu Val
1055                1060                1065                1070 tac ctg tac cgt gag gcc cag gcc cgg agc ccc gag aag cag gag cag    3325
Tyr Leu Tyr Arg Glu Ala Gln Ala Arg Ser Pro Glu Lys Gln Glu Gln
                1075                1080                1085 ttc gtg gac ttg tac aag gag ttt gag cca agc ctg gtc aac agc acc    3373
Phe Val Asp Leu Tyr Lys Glu Phe Glu Pro Ser Leu Val Asn Ser Thr
            1090                1095                1100 gtc tac atc atg gcc atg gcc atg cag atg gcc acc ttc gcc atc aat    3421
Val Tyr Ile Met Ala Met Ala Met Gln Met Ala Thr Phe Ala Ile Asn
        1105                1110                1115 tac aaa ggc ccg ccc ttc atg gag agc ctg ccc gag aac aag ccc ctg    3469
Tyr Lys Gly Pro Pro Phe Met Glu Ser Leu Pro Glu Asn Lys Pro Leu
    1120                1125                1130 gtg tgg agt ctg gca gtt tca ctc ctg gcc atc att ggc ctg ctc ctc    3517
Val Trp Ser Leu Ala Val Ser Leu Leu Ala Ile Ile Gly Leu Leu Leu
1135                1140                1145                1150 ggc tcc tcg ccc gac ttc aac agc cag ttt ggc ctc gtg gac atc cct    3565
Gly Ser Ser Pro Asp Phe Asn Ser Gln Phe Gly Leu Val Asp Ile Pro
                1155                1160                1165 gtg gag ttc aag ctg gtc att gcc cag gtc ctg ctc ctg gac ttc tgc    3613
Val Glu Phe Lys Leu Val Ile Ala Gln Val Leu Leu Leu Asp Phe Cys
            1170                1175                1180 ctg gcg ctc ctg gcc gac cgc gtc ctg cag ttc ttc ctg ggg acc ccg    3661
Leu Ala Leu Leu Ala Asp Arg Val Leu Gln Phe Phe Leu Gly Thr Pro
        1185                1190                1195 aag ctg aaa gtg cct tcc tga gatggcagtg ctggtaccca ctgcccaccc      3712
Lys Leu Lys Val Pro Ser  *
```

-continued

```
                                                          1200
tggctgccgc tgggcgggaa ccccaacagg gccccgggag ggaaccctgc ccccaacccc   3772
ccacagcaag gctgtacagt ctcgcccttg gaagactgag ctgggacccc cacagccatc   3832
cgctggcttg ccagcagaa ccagcccaa gccagcacct ttggtaaata aagcagcatc     3892
tgagatttta aaaaaaaaaa aaaaaaa                                       3919

<210> SEQ ID NO 71
<211> LENGTH: 1204
<212> TYPE: PRT
<213> ORGANISM: Homo Sapiens

<400> SEQUENCE: 71

Met Ala Ala Ala Ala Val Gly Asn Ala Val Pro Cys Gly Ala Arg
 1               5                  10                  15

Pro Cys Gly Val Arg Pro Asp Gly Gln Pro Lys Pro Gly Pro Gln Pro
                20                  25                  30

Arg Ala Leu Leu Ala Ala Gly Pro Ala Leu Ile Ala Asn Gly Asp Glu
        35                  40                  45

Leu Val Ala Ala Val Trp Pro Tyr Arg Arg Leu Ala Leu Leu Arg Arg
    50                  55                  60

Leu Thr Val Leu Pro Phe Ala Gly Leu Leu Tyr Pro Ala Trp Leu Gly
65                  70                  75                  80

Ala Ala Ala Gly Cys Trp Gly Trp Gly Ser Ser Trp Val Gln Ile
                85                  90                  95

Pro Glu Ala Ala Leu Leu Val Leu Ala Thr Ile Cys Leu Ala His Ala
                100                 105                 110

Leu Thr Val Leu Ser Gly His Trp Ser Val His Ala His Cys Ala Leu
        115                 120                 125

Thr Cys Thr Pro Glu Tyr Asp Pro Ser Lys Ala Thr Phe Val Lys Val
    130                 135                 140

Ala Pro Thr Pro Asn Asn Gly Ser Thr Glu Leu Val Ala Leu His Arg
145                 150                 155                 160

Asn Glu Gly Glu Asp Gly Leu Glu Val Leu Ser Phe Glu Phe Gln Lys
                165                 170                 175

Ile Lys Tyr Ser Tyr Asp Ala Leu Glu Lys Lys Gln Phe Leu Pro Val
            180                 185                 190

Ala Phe Pro Val Gly Asn Ala Phe Ser Tyr Tyr Gln Ser Asn Arg Gly
        195                 200                 205

Phe Gln Glu Asp Ser Glu Ile Arg Ala Ala Glu Lys Lys Phe Gly Ser
    210                 215                 220

Asn Lys Ala Glu Met Val Val Pro Asp Phe Ser Glu Leu Phe Lys Glu
225                 230                 235                 240

Arg Ala Thr Ala Pro Phe Phe Val Phe Gln Val Phe Cys Val Gly Leu
                245                 250                 255

Trp Cys Leu Asp Glu Tyr Trp Tyr Tyr Ser Val Phe Thr Leu Ser Met
            260                 265                 270

Leu Val Ala Phe Glu Ala Ser Leu Val Gln Gln Gln Met Arg Asn Met
        275                 280                 285

Ser Glu Ile Arg Lys Met Gly Asn Lys Pro His Met Ile Gln Val Tyr
    290                 295                 300

Arg Ser Arg Lys Trp Arg Pro Ile Ala Ser Asp Glu Ile Val Pro Gly
305                 310                 315                 320

Asp Ile Val Ser Ile Gly Arg Ser Pro Gln Glu Asn Leu Val Pro Cys
```

-continued

```
                325                 330                 335
Asp Val Leu Leu Leu Arg Gly Arg Cys Ile Val Asp Glu Ala Met Leu
                340                 345                 350

Thr Gly Glu Ser Val Pro Gln Met Lys Glu Pro Ile Glu Asp Leu Ser
            355                 360                 365

Pro Asp Arg Val Leu Asp Leu Gln Ala Asp Ser Arg Leu His Val Ile
        370                 375                 380

Phe Gly Gly Thr Lys Val Val Gln His Ile Pro Pro Gln Lys Ala Thr
385                 390                 395                 400

Thr Gly Leu Lys Pro Val Asp Ser Gly Cys Val Ala Tyr Val Leu Arg
                405                 410                 415

Thr Gly Phe Asn Thr Ser Gln Gly Lys Leu Leu Arg Thr Ile Leu Phe
            420                 425                 430

Gly Val Lys Arg Val Thr Ala Asn Asn Leu Glu Thr Phe Ile Phe Ile
        435                 440                 445

Leu Phe Leu Leu Val Phe Ala Ile Ala Ala Ala Tyr Val Trp Ile
    450                 455                 460

Glu Gly Thr Lys Asp Pro Ser Arg Asn Arg Tyr Lys Leu Phe Leu Glu
465                 470                 475                 480

Cys Thr Leu Ile Leu Thr Ser Val Val Pro Glu Leu Pro Ile Glu
                485                 490                 495

Leu Ser Leu Ala Val Asn Thr Ser Leu Ile Ala Leu Ala Lys Leu Tyr
            500                 505                 510

Met Tyr Cys Thr Glu Pro Phe Arg Ile Pro Phe Ala Gly Lys Val Glu
        515                 520                 525

Val Cys Cys Phe Asp Lys Thr Gly Thr Leu Thr Ser Asp Ser Leu Val
530                 535                 540

Val Arg Gly Val Ala Gly Leu Arg Asp Gly Lys Glu Val Thr Pro Val
545                 550                 555                 560

Ser Ser Ile Pro Val Glu Thr His Arg Ala Leu Ala Ser Cys His Ser
                565                 570                 575

Leu Met Gln Leu Asp Asp Gly Thr Leu Val Gly Asp Pro Leu Glu Lys
            580                 585                 590

Ala Met Leu Thr Ala Val Asp Trp Thr Leu Thr Lys Asp Glu Lys Val
        595                 600                 605

Phe Pro Arg Ser Ile Lys Thr Gln Gly Leu Lys Ile His Gln Arg Phe
610                 615                 620

His Phe Ala Ser Ala Leu Lys Arg Met Ser Val Leu Ala Ser Tyr Glu
625                 630                 635                 640

Lys Leu Gly Ser Thr Asp Leu Cys Tyr Ile Ala Ala Val Lys Gly Ala
                645                 650                 655

Pro Glu Thr Leu His Ser Met Phe Ser Gln Cys Pro Pro Asp Tyr His
            660                 665                 670

His Ile His Thr Glu Ile Ser Arg Glu Gly Ala Arg Val Leu Ala Leu
        675                 680                 685

Gly Tyr Lys Glu Leu Gly His Leu Thr His Gln Gln Ala Arg Glu Val
        690                 695                 700

Lys Arg Glu Ala Leu Glu Cys Ser Leu Lys Phe Val Gly Phe Ile Val
705                 710                 715                 720

Val Ser Cys Pro Leu Lys Ala Asp Ser Lys Ala Val Ile Arg Glu Ile
                725                 730                 735

Gln Asn Ala Ser His Arg Val Val Met Ile Thr Gly Asp Asn Pro Leu
            740                 745                 750
```

-continued

```
Thr Ala Cys His Val Ala Gln Glu Leu His Phe Ile Glu Lys Ala His
        755                 760                 765

Thr Leu Ile Leu Gln Pro Pro Ser Glu Lys Gly Arg Gln Cys Glu Trp
        770                 775                 780

Arg Ser Ile Asp Gly Ser Ile Val Leu Pro Leu Ala Arg Gly Ser Pro
785                 790                 795                 800

Lys Ala Leu Ala Leu Glu Tyr Ala Leu Cys Leu Thr Gly Asp Gly Leu
                805                 810                 815

Ala His Leu Gln Ala Thr Asp Pro Gln Gln Leu Leu Arg Leu Ile Pro
                820                 825                 830

His Val Gln Val Phe Ala Arg Val Ala Pro Lys Gln Lys Glu Phe Val
                835                 840                 845

Ile Thr Ser Leu Lys Glu Leu Gly Tyr Val Thr Leu Met Cys Gly Asp
                850                 855                 860

Gly Thr Asn Asp Val Gly Ala Leu Lys His Ala Asp Val Gly Val Ala
865                 870                 875                 880

Leu Leu Ala Asn Ala Pro Glu Arg Val Val Glu Arg Arg Arg Pro
                885                 890                 895

Arg Asp Ser Pro Thr Leu Ser Asn Ser Gly Ile Arg Ala Thr Ser Arg
                900                 905                 910

Thr Ala Lys Gln Arg Ser Gly Leu Pro Pro Ser Glu Glu Gln Pro Thr
                915                 920                 925

Ser Gln Arg Asp Arg Leu Ser Gln Val Leu Arg Asp Leu Glu Asp Glu
                930                 935                 940

Ser Thr Pro Ile Val Lys Leu Gly Asp Ala Ser Ile Ala Ala Pro Phe
945                 950                 955                 960

Thr Ser Lys Leu Ser Ser Ile Gln Cys Ile Cys His Val Ile Lys Gln
                965                 970                 975

Gly Arg Cys Thr Leu Val Thr Thr Leu Gln Met Phe Lys Ile Leu Ala
                980                 985                 990

Leu Asn Ala Leu Ile Leu Ala Tyr Ser Gln Ser Val Leu Tyr Leu Glu
                995                 1000                1005

Gly Val Lys Phe Ser Asp Phe Gln Ala Thr Leu Gln Gly Leu Leu Leu
                1010                1015                1020

Ala Gly Cys Phe Leu Phe Ile Ser Arg Ser Lys Pro Leu Lys Thr Leu
1025                1030                1035                1040

Ser Arg Glu Arg Pro Leu Pro Asn Ile Phe Asn Leu Tyr Thr Ile Leu
                1045                1050                1055

Thr Val Met Leu Gln Phe Phe Val His Phe Leu Ser Leu Val Tyr Leu
                1060                1065                1070

Tyr Arg Glu Ala Gln Ala Arg Ser Pro Glu Lys Gln Glu Gln Phe Val
                1075                1080                1085

Asp Leu Tyr Lys Glu Phe Glu Pro Ser Leu Val Asn Ser Thr Val Tyr
                1090                1095                1100

Ile Met Ala Met Ala Met Gln Met Ala Thr Phe Ala Ile Asn Tyr Lys
1105                1110                1115                1120

Gly Pro Pro Phe Met Glu Ser Leu Pro Glu Asn Lys Pro Leu Val Trp
                1125                1130                1135

Ser Leu Ala Val Ser Leu Leu Ala Ile Ile Gly Leu Leu Leu Gly Ser
                1140                1145                1150

Ser Pro Asp Phe Asn Ser Gln Phe Gly Leu Val Asp Ile Pro Val Glu
                1155                1160                1165
```

-continued

```
Phe Lys Leu Val Ile Ala Gln Val Leu Leu Leu Asp Phe Cys Leu Ala
    1170                1175                1180

Leu Leu Ala Asp Arg Val Leu Gln Phe Phe Leu Gly Thr Pro Lys Leu
1185                1190                1195                1200

Lys Val Pro Ser

<210> SEQ ID NO 72
<211> LENGTH: 3612
<212> TYPE: DNA
<213> ORGANISM: Homo Sapiens
<220> FEATURE:
<221> NAME/KEY: CDS
<222> LOCATION: (1)...(3612)

<400> SEQUENCE: 72 atg gcg gca gcg gcg gcg gtg ggc aac gcg gtg ccc tgc ggg gcc cgg        48
Met Ala Ala Ala Ala Ala Val Gly Asn Ala Val Pro Cys Gly Ala Arg
  1               5                  10                  15 cct tgc ggg gtc cgg cct gac ggg cag ccc aag ccc ggg ccg cag ccg        96
Pro Cys Gly Val Arg Pro Asp Gly Gln Pro Lys Pro Gly Pro Gln Pro
             20                  25                  30 cgc gcg ctc ctt gcc gcc ggg ccg gcg ctc ata gcg aac ggt gac gag       144
Arg Ala Leu Leu Ala Ala Gly Pro Ala Leu Ile Ala Asn Gly Asp Glu
         35                  40                  45 ctg gtg gct gcc gtg tgg ccg tac cgg cgg ttg gcg ctg ttg cgg cgc       192
Leu Val Ala Ala Val Trp Pro Tyr Arg Arg Leu Ala Leu Leu Arg Arg
     50                  55                  60 ctc acg gtg ctg cca ttc gcc ggg ctg ctt tac ccg gcc tgg ttg ggt       240
Leu Thr Val Leu Pro Phe Ala Gly Leu Leu Tyr Pro Ala Trp Leu Gly
 65                  70                  75                  80 gcc gca gcc gct ggc tgc tgg ggc tgg ggc agc agt tgg gtg cag atc       288
Ala Ala Ala Ala Gly Cys Trp Gly Trp Gly Ser Ser Trp Val Gln Ile
                 85                  90                  95 ccc gaa gct gcg ctg ctc gtg ctt gcc acc atc tgc ctc gcg cac gcg       336
Pro Glu Ala Ala Leu Leu Val Leu Ala Thr Ile Cys Leu Ala His Ala
            100                 105                 110 ctc act gtc ctc tcg ggg cat tgg tct gtg cac gcg cat tgc gcg ctc       384
Leu Thr Val Leu Ser Gly His Trp Ser Val His Ala His Cys Ala Leu
        115                 120                 125 acc tgc acc ccg gag tac gac ccc agc aaa gcg acc ttt gtg aag gtg       432
Thr Cys Thr Pro Glu Tyr Asp Pro Ser Lys Ala Thr Phe Val Lys Val
    130                 135                 140 gcg cca acc ccc aac aat ggc tcc acg gag ctc gtg gcc ctg cac cgc       480
Ala Pro Thr Pro Asn Asn Gly Ser Thr Glu Leu Val Ala Leu His Arg
145                 150                 155                 160 aat gag ggc gaa gac ggg ctt gag gtg ctg tcc ttc gaa ttc cag aag       528
Asn Glu Gly Glu Asp Gly Leu Glu Val Leu Ser Phe Glu Phe Gln Lys
                165                 170                 175 atc aag tat tcc tac gat gcc ctg gag aag aag cag ttt ctc ccc gtg       576
Ile Lys Tyr Ser Tyr Asp Ala Leu Glu Lys Lys Gln Phe Leu Pro Val
            180                 185                 190 gcc ttt cct gtg gga aac gcc ttc tca tac tat cag agc aac aga ggc       624
Ala Phe Pro Val Gly Asn Ala Phe Ser Tyr Tyr Gln Ser Asn Arg Gly
        195                 200                 205 ttc cag gaa gac tca gag atc cga gca gct gag aag aaa ttt ggg agc       672
Phe Gln Glu Asp Ser Glu Ile Arg Ala Ala Glu Lys Lys Phe Gly Ser
    210                 215                 220 aac aag gcc gag atg gtg gtg cct gac ttc tcg gag ctt ttc aag gag       720
Asn Lys Ala Glu Met Val Val Pro Asp Phe Ser Glu Leu Phe Lys Glu
225                 230                 235                 240
```

-continued

| | | |
|---|---|---|
| aga gcc aca gcc ccc ttc ttt gta ttt cag gtg ttc tgt gtg ggg ctc<br>Arg Ala Thr Ala Pro Phe Phe Val Phe Gln Val Phe Cys Val Gly Leu<br>                    245                            250                          255 | 768 | |
| tgg tgc ctg gat gag tac tgg tac tac agc gtc ttt acg cta tcc atg<br>Trp Cys Leu Asp Glu Tyr Trp Tyr Tyr Ser Val Phe Thr Leu Ser Met<br>                260                            265                          270 | 816 | |
| ctg gtg gcg ttc gag gcc tcg ctg gtg cag cag cag atg cgg aac atg<br>Leu Val Ala Phe Glu Ala Ser Leu Val Gln Gln Gln Met Arg Asn Met<br>            275                            280                          285 | 864 | |
| tcg gag atc cgg aag atg ggc aac aag ccc cac atg atc cag gtc tac<br>Ser Glu Ile Arg Lys Met Gly Asn Lys Pro His Met Ile Gln Val Tyr<br>        290                        295                          300 | 912 | |
| cga agc cgc aag tgg agg ccc att gcc agt gat gag atc gta cca ggg<br>Arg Ser Arg Lys Trp Arg Pro Ile Ala Ser Asp Glu Ile Val Pro Gly<br>305                        310                          315                          320 | 960 | |
| gac atc gtc tcc atc ggc cgc tcc cca cag gag aac ctg gtg cca tgt<br>Asp Ile Val Ser Ile Gly Arg Ser Pro Gln Glu Asn Leu Val Pro Cys<br>                325                            330                          335 | 1008 | |
| gac gtg ctt ctg ctg cga ggc cgc tgc atc gta gac gag gcc atg ctc<br>Asp Val Leu Leu Leu Arg Gly Arg Cys Ile Val Asp Glu Ala Met Leu<br>            340                            345                          350 | 1056 | |
| acg ggg gag tcc gtg cca cag atg aag gag ccc atc gaa gac ctc agc<br>Thr Gly Glu Ser Val Pro Gln Met Lys Glu Pro Ile Glu Asp Leu Ser<br>                355                            360                          365 | 1104 | |
| cca gac cgg gtg ctg gac ctc cag gct gat tcc cgg ctg cac gtc atc<br>Pro Asp Arg Val Leu Asp Leu Gln Ala Asp Ser Arg Leu His Val Ile<br>        370                        375                          380 | 1152 | |
| ttc ggg ggc acc aag gtg gtg cag cac atc ccc cca cag aaa gcc acc<br>Phe Gly Gly Thr Lys Val Val Gln His Ile Pro Pro Gln Lys Ala Thr<br>385                        390                          395                          400 | 1200 | |
| acg ggc ctg aag ccg gtt gac agc ggg tgc gtg gcc tac gtc ctg cgg<br>Thr Gly Leu Lys Pro Val Asp Ser Gly Cys Val Ala Tyr Val Leu Arg<br>                        405                          410                          415 | 1248 | |
| acc gga ttc aac aca tct cag ggc aag ctg ctg cgc acc atc ctc ttc<br>Thr Gly Phe Asn Thr Ser Gln Gly Lys Leu Leu Arg Thr Ile Leu Phe<br>                  420                          425                          430 | 1296 | |
| ggg gtc aag agg gtg act gcg aac aac ctg gag acc ttc atc ttc atc<br>Gly Val Lys Arg Val Thr Ala Asn Asn Leu Glu Thr Phe Ile Phe Ile<br>                  435                          440                          445 | 1344 | |
| ctc ttc ctc ctg gtg ttt gcc atc gct gca gct gcc tat gta tgg att<br>Leu Phe Leu Leu Val Phe Ala Ile Ala Ala Ala Ala Tyr Val Trp Ile<br>        450                        455                          460 | 1392 | |
| gaa ggt acc aag gac ccc agc cgg aac cgc tac aag ctg ttt ctg gag<br>Glu Gly Thr Lys Asp Pro Ser Arg Asn Arg Tyr Lys Leu Phe Leu Glu<br>465                        470                          475                          480 | 1440 | |
| tgc acc ctg atc ctc acc tcg gtc gtg cct cct gag ctg ccc atc gag<br>Cys Thr Leu Ile Leu Thr Ser Val Val Pro Pro Glu Leu Pro Ile Glu<br>                        485                          490                          495 | 1488 | |
| ctg tcc ctg gcc gtc aac acc tcc ctc atc gcc ctg gcc aag ctc tac<br>Leu Ser Leu Ala Val Asn Thr Ser Leu Ile Ala Leu Ala Lys Leu Tyr<br>                500                            505                          510 | 1536 | |
| atg tac tgc aca gag ccc ttc cgg atc ccc ttt gct ggc aag gtc gag<br>Met Tyr Cys Thr Glu Pro Phe Arg Ile Pro Phe Ala Gly Lys Val Glu<br>            515                            520                          525 | 1584 | |
| gtg tgc tgc ttt gac aag acg ggg acg ttg acc agt gac agc ctg gtg<br>Val Cys Cys Phe Asp Lys Thr Gly Thr Leu Thr Ser Asp Ser Leu Val<br>        530                        535                          540 | 1632 | |
| gtg cgc ggt gtg gcc ggg ctg aga gac ggg aag gag gtg acc cca gtg<br>Val Arg Gly Val Ala Gly Leu Arg Asp Gly Lys Glu Val Thr Pro Val<br>545                        550                          555                          560 | 1680 | |

```
tcc agc atc cct gta gaa aca cac cgg gcc ctg gcc tcg tgc cac tcg      1728
Ser Ser Ile Pro Val Glu Thr His Arg Ala Leu Ala Ser Cys His Ser
                565                 570                 575 ctc atg cag ctg gac gac ggc acc ctc gtg ggt gac cct cta gag aag      1776
Leu Met Gln Leu Asp Asp Gly Thr Leu Val Gly Asp Pro Leu Glu Lys
            580                 585                 590 gcc atg ctg acg gcc gtg gac tgg acg ctg acc aaa gat gag aaa gta      1824
Ala Met Leu Thr Ala Val Asp Trp Thr Leu Thr Lys Asp Glu Lys Val
        595                 600                 605 ttc ccc cga agt att aaa act cag ggg ctg aaa att cac cag cgc ttt      1872
Phe Pro Arg Ser Ile Lys Thr Gln Gly Leu Lys Ile His Gln Arg Phe
    610                 615                 620 cat ttt gcc agt gcc ctg aag cga atg tcc gtg ctt gcc tcg tat gag      1920
His Phe Ala Ser Ala Leu Lys Arg Met Ser Val Leu Ala Ser Tyr Glu
625                 630                 635                 640 aag ctg ggc tcc acc gac ctc tgc tac atc gcg gcc gtg aag ggg gcc      1968
Lys Leu Gly Ser Thr Asp Leu Cys Tyr Ile Ala Ala Val Lys Gly Ala
                645                 650                 655 ccc gaa act ctg cac tcc atg ttc tcc cag tgc ccg ccc gac tac cac      2016
Pro Glu Thr Leu His Ser Met Phe Ser Gln Cys Pro Pro Asp Tyr His
            660                 665                 670 cac atc cac acc gag atc tcc cgg gaa gga gcc cgt gtc ctg gcg ctg      2064
His Ile His Thr Glu Ile Ser Arg Glu Gly Ala Arg Val Leu Ala Leu
        675                 680                 685 ggg tac aag gag ctg gga cac ctc act cac cag cag gcc cgg gag gtc      2112
Gly Tyr Lys Glu Leu Gly His Leu Thr His Gln Gln Ala Arg Glu Val
    690                 695                 700 aag cgg gag gcc ctg gag tgc agc ctc aag ttc gtc ggc ttc att gtg      2160
Lys Arg Glu Ala Leu Glu Cys Ser Leu Lys Phe Val Gly Phe Ile Val
705                 710                 715                 720 gtc tcc tgc ccg ctc aag gct gac tcc aag gcc gtg atc cgg gag atc      2208
Val Ser Cys Pro Leu Lys Ala Asp Ser Lys Ala Val Ile Arg Glu Ile
                725                 730                 735 cag aat gcg tcc cac cgg gtg gtc atg atc acg gga gac aac ccg ctc      2256
Gln Asn Ala Ser His Arg Val Val Met Ile Thr Gly Asp Asn Pro Leu
            740                 745                 750 act gca tgc cac gtg gcc cag gag ctg cac ttc att gaa aag gcc cac      2304
Thr Ala Cys His Val Ala Gln Glu Leu His Phe Ile Glu Lys Ala His
        755                 760                 765 acg ctg atc ctg cag cct ccc tcc gag aaa ggc cgg cag tgc gag tgg      2352
Thr Leu Ile Leu Gln Pro Pro Ser Glu Lys Gly Arg Gln Cys Glu Trp
    770                 775                 780 cgc tcc att gac ggc agc atc gtg ctg ccc ctg gcc cgg ggc tcc cca      2400
Arg Ser Ile Asp Gly Ser Ile Val Leu Pro Leu Ala Arg Gly Ser Pro
785                 790                 795                 800 aag gca ctg gcc ctg gag tac gca ctg tgc ctc aca ggc gac ggc ttg      2448
Lys Ala Leu Ala Leu Glu Tyr Ala Leu Cys Leu Thr Gly Asp Gly Leu
                805                 810                 815 gcc cac ctg cag gcc acc gac ccc cag cag ctg ctc cgc ctc atc ccc      2496
Ala His Leu Gln Ala Thr Asp Pro Gln Gln Leu Leu Arg Leu Ile Pro
            820                 825                 830 cat gtg cag gtg ttc gcc cgt gtg gct ccc aag cag aag gag ttt gtc      2544
His Val Gln Val Phe Ala Arg Val Ala Pro Lys Gln Lys Glu Phe Val
        835                 840                 845 atc acc agc ctg aag gag ctg ggc tac gtg acc ctc atg tgt ggg gat      2592
Ile Thr Ser Leu Lys Glu Leu Gly Tyr Val Thr Leu Met Cys Gly Asp
    850                 855                 860 ggc acc aac gac gtg ggc gcc ctg aag cat gct gac gtg ggt gtg gcg      2640
Gly Thr Asn Asp Val Gly Ala Leu Lys His Ala Asp Val Gly Val Ala
```

-continued

```
             865                 870                 875                 880 ctc ttg gcc aat gcc cct gag cgg gtt gtc gag cgg cga cgg cgg ccc          2688
Leu Leu Ala Asn Ala Pro Glu Arg Val Val Glu Arg Arg Arg Arg Pro
                    885                 890                 895 cgg gac agc cca acc ctg agc aac agt ggc atc aga gcc acc tcc agg          2736
Arg Asp Ser Pro Thr Leu Ser Asn Ser Gly Ile Arg Ala Thr Ser Arg
                900                 905                 910 aca gcc aag cag cgg tcg ggg ctc cct ccc tcc gag gag cag cca acc          2784
Thr Ala Lys Gln Arg Ser Gly Leu Pro Pro Ser Glu Glu Gln Pro Thr
            915                 920                 925 tcc cag agg gac cgc ctg agc cag gtg ctg cga gac ctc gag gac gag          2832
Ser Gln Arg Asp Arg Leu Ser Gln Val Leu Arg Asp Leu Glu Asp Glu
        930                 935                 940 agt acg ccc att gtg aaa ctg ggg gat gcc agc atc gca gca ccc ttc          2880
Ser Thr Pro Ile Val Lys Leu Gly Asp Ala Ser Ile Ala Ala Pro Phe
945                 950                 955                 960 acc tcc aag ctc tca tcc atc cag tgc atc tgc cac gtg atc aag cag          2928
Thr Ser Lys Leu Ser Ser Ile Gln Cys Ile Cys His Val Ile Lys Gln
                    965                 970                 975 ggc cgc tgc acg ctg gtg acc acg cta cag atg ttc aag atc ctg gcg          2976
Gly Arg Cys Thr Leu Val Thr Thr Leu Gln Met Phe Lys Ile Leu Ala
                980                 985                 990 ctc aat gcc ctc atc ctg gcc tac agc cag agc gtc ctc tac ctg gag          3024
Leu Asn Ala Leu Ile Leu Ala Tyr Ser Gln Ser Val Leu Tyr Leu Glu
            995                 1000                1005 gga gtc aag ttc agt gac ttc cag gcc acc cta cag ggg ctg ctg ctg          3072
Gly Val Lys Phe Ser Asp Phe Gln Ala Thr Leu Gln Gly Leu Leu Leu
        1010                1015                1020 gcc ggc tgc ttc ctc ttc atc tcc cgt tcc aag ccc ctc aag acc ctc          3120
Ala Gly Cys Phe Leu Phe Ile Ser Arg Ser Lys Pro Leu Lys Thr Leu
1025                1030                1035                1040 tcc cga gaa cgg ccc ctg ccc aac atc ttc aac ctg tac acc atc ctc          3168
Ser Arg Glu Arg Pro Leu Pro Asn Ile Phe Asn Leu Tyr Thr Ile Leu
                    1045                1050                1055 acc gtc atg ctc cag ttc ttt gtg cac ttc ctg agc ctt gtc tac ctg          3216
Thr Val Met Leu Gln Phe Phe Val His Phe Leu Ser Leu Val Tyr Leu
                1060                1065                1070 tac cgt gag gcc cag gcc cgg agc ccc gag aag cag gag cag ttc gtg          3264
Tyr Arg Glu Ala Gln Ala Arg Ser Pro Glu Lys Gln Glu Gln Phe Val
            1075                1080                1085 gac ttg tac aag gag ttt gag cca agc ctg gtc aac agc acc gtc tac          3312
Asp Leu Tyr Lys Glu Phe Glu Pro Ser Leu Val Asn Ser Thr Val Tyr
        1090                1095                1100 atc atg gcc atg gcc atg cag atg gcc acc ttc gcc atc aat tac aaa          3360
Ile Met Ala Met Ala Met Gln Met Ala Thr Phe Ala Ile Asn Tyr Lys
1105                1110                1115                1120 ggc ccg ccc ttc atg gag agc ctg ccc gag aac aag ccc ctg gtg tgg          3408
Gly Pro Pro Phe Met Glu Ser Leu Pro Glu Asn Lys Pro Leu Val Trp
                    1125                1130                1135 agt ctg gca gtt tca ctc ctg gcc atc att ggc ctg ctc ctc ggc tcc          3456
Ser Leu Ala Val Ser Leu Leu Ala Ile Ile Gly Leu Leu Leu Gly Ser
                1140                1145                1150 tcg ccc gac ttc aac agc cag ttt ggc ctc gtg gac atc cct gtg gag          3504
Ser Pro Asp Phe Asn Ser Gln Phe Gly Leu Val Asp Ile Pro Val Glu
            1155                1160                1165 ttc aag ctg gtc att gcc cag gtc ctg ctg gac ttc tgc ctg gcg          3552
Phe Lys Leu Val Ile Ala Gln Val Leu Leu Asp Phe Cys Leu Ala
        1170                1175                1180 ctc ctg gcc gac cgc gtc ctg cag ttc ttc ctg ggg acc ccg aag ctg          3600
```

```
Leu Leu Ala Asp Arg Val Leu Gln Phe Phe Leu Gly Thr Pro Lys Leu
1185                1190                1195                1200 aaa gtg cct tcc                                                    3612
Lys Val Pro Ser
```

<210> SEQ ID NO 73
<211> LENGTH: 7
<212> TYPE: PRT
<213> ORGANISM: Artificial Sequence
<220> FEATURE:
<223> OTHER INFORMATION: Consensus Amino Acid Sequence
<220> FEATURE:
<221> NAME/KEY: VARIANT
<222> LOCATION: (6)...(6)
<223> OTHER INFORMATION: Xaa = Leu, Ile, Val, or Met
<220> FEATURE:
<221> NAME/KEY: VARIANT
<222> LOCATION: (7)...(7)
<223> OTHER INFORMATION: Xaa = Thr or Ile

<400> SEQUENCE: 73

```
Asp Lys Thr Gly Thr Xaa Xaa
 1               5
```

<210> SEQ ID NO 74
<211> LENGTH: 1157
<212> TYPE: PRT
<213> ORGANISM: Caenorhabditis elegans

<400> SEQUENCE: 74

```
Met Gly Val Asp Gln Leu Val Glu Thr Ile Ile Pro Tyr Asn Leu Arg
 1               5                  10                  15

Ser Ile Ala Thr His Leu Tyr Val Pro Pro Phe Thr Ile Ile Thr Ala
                20                  25                  30

Ile Trp Thr Tyr Val Trp Leu Asn Ile Phe Gly Tyr Glu Glu Tyr Tyr
             35                  40                  45

Glu Leu Gly Met Leu Gly Tyr Ala Ala Ile Phe Val Ile Leu Ala Leu
         50                  55                  60

Val Leu Leu Phe Cys His Trp Met Met Pro Val Arg Cys Phe Leu Met
65                  70                  75                  80

Cys Ser Lys Gln Glu Asp Val Arg Ile Ala Ser His Val Cys Val Ile
                85                  90                  95

Pro Thr Gln Asn Asn Gly Trp Pro Glu Leu Val Lys Leu Met Arg Thr
            100                 105                 110

Thr Arg Asp Lys Gln Thr Lys Leu Trp Phe Glu Phe Gln Arg Val His
        115                 120                 125

Tyr Thr Trp Asp Glu Glu Ser Arg Glu Phe Gln Thr Lys Thr Leu Asp
    130                 135                 140

Thr Ala Lys Pro Met Val Phe Phe Gln Lys Ser His Gly Phe Glu Val
145                 150                 155                 160

Glu Glu His Val Lys Asp Ala Lys Tyr Leu Leu Gly Asp Asn Lys Thr
                165                 170                 175

Glu Met Ile Val Pro Gln Phe Leu Glu Met Phe Ile Glu Arg Ala Thr
            180                 185                 190

Ala Pro Phe Phe Val Phe Gln Val Phe Cys Val Gly Leu Trp Cys Leu
        195                 200                 205

Glu Asp Met Trp Tyr Tyr Ser Leu Phe Thr Leu Phe Met Leu Met Thr
    210                 215                 220

Phe Glu Ala Thr Leu Val Lys Gln Gln Met Lys Asn Met Ser Glu Ile
225                 230                 235                 240
```

-continued

```
Arg Asn Met Gly Asn Lys Thr Tyr Met Ile Asn Val Leu Arg Gly Lys
                245                 250                 255
Lys Trp Gln Lys Ile Lys Ile Glu Glu Leu Val Ala Gly Asp Ile Val
        260                 265                 270
Ser Ile Gly Arg Gly Ala Glu Glu Cys Val Pro Cys Asp Leu Leu
    275                 280                 285
Leu Leu Arg Gly Pro Cys Ile Val Asp Glu Ser Met Leu Thr Gly Glu
290                 295                 300
Ser Val Pro Gln Met Lys Glu Pro Ile Glu Asp Val Glu Lys Asp Lys
305                 310                 315                 320
Ile Phe Asp Ile Glu Thr Asp Ser Arg Leu His Val Ile Phe Gly Gly
                325                 330                 335
Thr Lys Ile Val Gln His Thr Ala Pro Gly Lys Ala Ala Glu Gly Met
                340                 345                 350
Val Lys Ser Pro Asp Gly Asn Cys Ile Cys Tyr Val Ile Arg Thr Gly
            355                 360                 365
Phe Asn Thr Ser Gln Gly Lys Leu Leu Arg Thr Ile Met Phe Gly Val
    370                 375                 380
Lys Lys Ala Thr Ala Asn Asn Leu Glu Thr Phe Cys Phe Ile Leu Phe
385                 390                 395                 400
Leu Leu Ile Phe Ala Ile Ala Ala Ala Tyr Leu Trp Ile Lys Gly
                405                 410                 415
Ser Val Asp Glu Thr Arg Ser Lys Tyr Lys Leu Phe Leu Glu Cys Thr
                420                 425                 430
Leu Ile Leu Thr Ser Val Ile Pro Pro Glu Leu Pro Ile Glu Leu Ser
            435                 440                 445
Leu Ala Val Asn Ser Ser Leu Met Ala Leu Gln Lys Leu Gly Ile Phe
    450                 455                 460
Cys Thr Glu Pro Phe Arg Ile Pro Phe Ala Gly Lys Val Asp Ile Cys
465                 470                 475                 480
Cys Phe Asp Lys Thr Gly Thr Leu Thr Thr Asp Asn Leu Val Val Glu
                485                 490                 495
Gly Val Ala Leu Asn Asn Gln Lys Glu Gly Met Ile Arg Asn Ala Glu
            500                 505                 510
Asp Leu Pro His Glu Ser Leu Gln Val Leu Ala Ser Cys His Ser Leu
    515                 520                 525
Val Arg Phe Glu Glu Asp Leu Val Gly Asp Pro Leu Glu Lys Ala Cys
530                 535                 540
Leu Ser Trp Cys Gly Trp Asn Leu Thr Lys Gly Asp Ala Val Met Pro
545                 550                 555                 560
Pro Lys Thr Ala Ala Lys Gly Ile Ser Gly Ile Lys Ile Phe His Arg
                565                 570                 575
Tyr His Phe Ser Ser Ala Met Lys Arg Met Thr Val Val Ala Gly Tyr
            580                 585                 590
Gln Ser Pro Gly Thr Ser Asp Thr Thr Phe Ile Val Ala Val Lys Gly
    595                 600                 605
Ala Pro Glu Val Leu Arg Asn Met Tyr Ala Asp Leu Pro Ser Asp Tyr
610                 615                 620
Asp Glu Thr Tyr Thr Arg Leu Thr Arg Gln Gly Ser Arg Val Leu Ala
625                 630                 635                 640
Met Gly Ile Arg Lys Leu Gly Glu Thr Arg Val Gly Glu Leu Arg Asp
                645                 650                 655
```

-continued

```
Lys Lys Arg Glu Asn Phe Glu Asn Asp Leu Ala Phe Ala Gly Phe Val
            660                 665                 670

Val Ile Ser Cys Pro Leu Lys Ser Asp Thr Lys Thr Met Ile Arg Glu
            675                 680                 685

Ile Met Asp Ser Ser His Val Ala Met Ile Thr Gly Asp Asn Pro
            690                 695                 700

Leu Thr Ala Cys His Val Ser Lys Val Leu Lys Phe Thr Lys Lys Ser
705                 710                 715                 720

Leu Pro Thr Leu Val Leu Asp Glu Pro Ala Asp Gly Val Asp Trp Met
                725                 730                 735

Trp Lys Ser Val Asp Gly Thr Ile Glu Leu Pro Leu Lys Pro Glu Thr
                740                 745                 750

Lys Asn Lys Met Glu Arg Lys Ala Phe Phe Asn Ser His Glu Phe Cys
            755                 760                 765

Leu Thr Gly Ser Ala Phe His His Leu Val His Asn Glu His Thr Phe
            770                 775                 780

Leu Arg Glu Leu Ile Leu His Val Lys Val Phe Ala Arg Met Ala Pro
785                 790                 795                 800

Lys Gln Lys Glu Arg Ile Ile Asn Glu Leu Lys Ser Leu Gly Lys Val
            805                 810                 815

Thr Leu Met Cys Gly Asp Gly Thr Asn Asp Val Gly Ala Leu Lys His
            820                 825                 830

Ala Asn Val Gly Val Ala Leu Leu Thr Asn Pro Tyr Asp Ala Glu Lys
            835                 840                 845

Ala Ala Glu Lys Glu Lys Glu Lys Ala Lys Ile Glu Glu Ala Arg
            850                 855                 860

Ser Leu Val Arg Ser Gly Ala Gln Leu Pro Gln Arg Pro Gly Ala Pro
865                 870                 875                 880

Gly Ala Pro Pro Ala Ala Asn Ala Ala Arg Pro Arg Leu Asp Asn Leu
                885                 890                 895

Met Lys Glu Leu Glu Glu Glu Lys Ala Gln Val Ile Lys Leu Gly
                900                 905                 910

Asp Ala Ser Ile Ala Ala Pro Phe Thr Ser Lys Tyr Thr Ser Ile Ala
            915                 920                 925

Ser Ile Cys His Val Ile Lys Gln Gly Arg Cys Thr Leu Val Thr Thr
            930                 935                 940

Leu Gln Met Phe Lys Ile Leu Ala Leu Asn Ala Leu Val Ser Ala Tyr
945                 950                 955                 960

Ser Leu Ser Ala Leu Tyr Leu Asp Gly Val Lys Phe Ser Asp Thr Gln
                965                 970                 975

Ala Thr Ile Gln Gly Leu Leu Leu Ala Ala Cys Phe Leu Phe Ile Ser
                980                 985                 990

Lys Ser Lys Pro Leu Lys Thr Leu Ser Arg Gln Arg Pro Met Ala Asn
            995                 1000                1005

Ile Phe Asn Ala Tyr Thr Leu Leu Thr Val Thr Leu Gln Phe Ile Val
        1010                1015                1020

His Phe Ser Cys Leu Leu Tyr Ile Val Gly Leu Ala His Glu Ala Asn
    1025                1030                1035                1040

Thr Glu Lys Ala Pro Val Asp Leu Glu Ala Lys Phe Thr Pro Asn Ile
                1045                1050                1055

Leu Asn Thr Thr Val Tyr Ile Ile Ser Met Ala Leu Gln Val Cys Thr
            1060                1065                1070

Phe Ala Val Asn Tyr Arg Gly Arg Pro Phe Met Glu Ser Leu Phe Glu
```

-continued

```
                  1075                1080                1085

Asn Lys Ala Met Leu Tyr Ser Ile Met Phe Ser Gly Gly Ala Val Phe
    1090                1095                1100

Thr Leu Ala Ser Gly Gln Ala Thr Asp Leu Met Ile Gln Phe Glu Leu
1105                1110                1115                1120

Val Val Leu Pro Glu Ala Leu Arg Asn Ala Leu Leu Met Cys Val Thr
                1125                1130                1135

Ala Asp Leu Val Ile Cys Tyr Ile Ile Asp Arg Gly Leu Asn Phe Leu
        1140                1145                1150

Leu Gly Asp Met Phe
        1155

<210> SEQ ID NO 75
<211> LENGTH: 9
<212> TYPE: PRT
<213> ORGANISM: Artificial Sequence
<220> FEATURE:
<223> OTHER INFORMATION: Consensus Amino Acid Sequence
<220> FEATURE:
<221> NAME/KEY: VARIANT
<222> LOCATION: (1)...(1)
<223> OTHER INFORMATION: Xaa = Asp, Asn, or Ser
<220> FEATURE:
<221> NAME/KEY: VARIANT
<222> LOCATION: (2)...(2)
<223> OTHER INFORMATION: Xaa = Gln, Glu, Asn, or Arg
<220> FEATURE:
<221> NAME/KEY: VARIANT
<222> LOCATION: (3)...(3)
<223> OTHER INFORMATION: Xaa = Ser or Ala
<220> FEATURE:
<221> NAME/KEY: VARIANT
<222> LOCATION: (4)...(4)
<223> OTHER INFORMATION: Xaa = Leu, Ile, Val, Ser, Ala or Asn
<220> FEATURE:
<221> NAME/KEY: VARIANT
<222> LOCATION: (5)...(5)
<223> OTHER INFORMATION: Xaa = Leu, Ile, or Val
<220> FEATURE:
<221> NAME/KEY: VARIANT
<222> LOCATION: (6)...(6)
<223> OTHER INFORMATION: Xaa = Thr, Ser, or Asn
<220> FEATURE:
<221> NAME/KEY: VARIANT
<222> LOCATION: (9)...(9)
<223> OTHER INFORMATION: Xaa = Ser or Asn

<400> SEQUENCE: 75

Xaa Xaa Xaa Xaa Xaa Xaa Gly Glu Xaa
 1               5

<210> SEQ ID NO 76
<211> LENGTH: 10
<212> TYPE: PRT
<213> ORGANISM: Artificial Sequence
<220> FEATURE:
<223> OTHER INFORMATION: Consensus Amino Acid Sequence
<220> FEATURE:
<221> NAME/KEY: VARIANT
<222> LOCATION: (1)...(1)
<223> OTHER INFORMATION: Xaa = Leu, Ile or Val
<220> FEATURE:
<221> NAME/KEY: VARIANT
<222> LOCATION: (2)...(2)
<223> OTHER INFORMATION: Xaa = Cys, Ala, Met, or Leu
<220> FEATURE:
<221> NAME/KEY: VARIANT
<222> LOCATION: (3)...(3)
<223> OTHER INFORMATION: Xaa = Ser, Thr, Phe or Leu
<220> FEATURE:
<221> NAME/KEY: VARIANT
```

```
<222> LOCATION: (9)...(9)
<223> OTHER INFORMATION: Xaa = Leu or Ile

<400> SEQUENCE: 76

Xaa Xaa Xaa Asp Lys Thr Gly Thr Xaa Thr
 1               5                  10

<210> SEQ ID NO 77
<211> LENGTH: 11
<212> TYPE: PRT
<213> ORGANISM: Artificial Sequence
<220> FEATURE:
<223> OTHER INFORMATION: Consensus Amino Acid Sequence
<220> FEATURE:
<221> NAME/KEY: VARIANT
<222> LOCATION: (1)...(1)
<223> OTHER INFORMATION: Xaa = Thr, Ile, or Val
<220> FEATURE:
<221> NAME/KEY: VARIANT
<222> LOCATION: (5)...(5)
<223> OTHER INFORMATION: Xaa = Any Amino Acid
<220> FEATURE:
<221> NAME/KEY: VARIANT
<222> LOCATION: (8)...(8)
<223> OTHER INFORMATION: Xaa = Ala, Ser or Gly
<220> FEATURE:
<221> NAME/KEY: VARIANT
<222> LOCATION: (10)...(10)
<223> OTHER INFORMATION: Xaa =e Ala, Ser, or Val

<400> SEQUENCE: 77

Xaa Gly Asp Gly Xaa Asn Asp Xaa Pro Xaa Leu
 1               5                  10

<210> SEQ ID NO 78
<211> LENGTH: 7
<212> TYPE: PRT
<213> ORGANISM: Artificial Sequence
<220> FEATURE:
<223> OTHER INFORMATION: Amino Acid Residues Important for Calcium
      Transport

<400> SEQUENCE: 78

Ile Pro Glu Gly Leu Pro Ala
 1               5

<210> SEQ ID NO 79
<211> LENGTH: 28
<212> TYPE: PRT
<213> ORGANISM: Homo Sapiens

<400> SEQUENCE: 79

Asp Leu Val Thr Val Val Pro Pro Ala Leu Pro Ala Ala Met Thr
 1               5                  10                  15

Val Cys Thr Leu Tyr Ala Gln Ser Arg Leu Arg Arg
                20                  25

<210> SEQ ID NO 80
<211> LENGTH: 28
<212> TYPE: PRT
<213> ORGANISM: Homo Sapiens

<400> SEQUENCE: 80

Asp Ile Ile Thr Ile Thr Val Pro Pro Ala Leu Pro Ala Ala Met Thr
 1               5                  10                  15

Ala Gly Ile Val Tyr Ala Gln Arg Arg Leu Lys Lys
                20                  25
```

-continued

<210> SEQ ID NO 81
<211> LENGTH: 28
<212> TYPE: PRT
<213> ORGANISM: Homo Sapiens

<400> SEQUENCE: 81

Leu Ile Leu Thr Ser Val Val Pro Pro Glu Leu Pro Ile Glu Leu Ser
1               5                   10                  15

Leu Ala Val Asn Thr Ser Leu Ile Ala Leu Ala Lys
            20                  25

<210> SEQ ID NO 82
<211> LENGTH: 29
<212> TYPE: PRT
<213> ORGANISM: Saccharomyces cerevisiae

<400> SEQUENCE: 82

Asp Ile Ile Thr Ile Val Val Pro Pro Ala Leu Pro Ala Thr Leu Thr
1               5                   10                  15

Ile Gly Thr Asn Phe Ala Leu Ser Arg Leu Lys Glu Lys
            20                  25

<210> SEQ ID NO 83
<211> LENGTH: 28
<212> TYPE: PRT
<213> ORGANISM: Saccharomyces cerevisiae

<400> SEQUENCE: 83

Leu Ile Ile Thr Ser Val Val Pro Pro Glu Leu Pro Met Glu Leu Thr
1               5                   10                  15

Met Ala Val Asn Ser Ser Leu Ala Ala Leu Ala Lys
            20                  25

<210> SEQ ID NO 84
<211> LENGTH: 28
<212> TYPE: PRT
<213> ORGANISM: Schizosaccharomyces pombe

<400> SEQUENCE: 84

Val Leu Thr Ile Leu Val Pro Pro Ala Leu Pro Ala Thr Leu Ser Val
1               5                   10                  15

Gly Ile Ala Asn Ser Ile Ala Arg Leu Ser Arg Ala
            20                  25

<210> SEQ ID NO 85
<211> LENGTH: 29
<212> TYPE: PRT
<213> ORGANISM: Caenorhabditis elegans

<400> SEQUENCE: 85

Asp Leu Val Thr Ile Val Val Pro Pro Ala Leu Pro Ala Val Met Gly
1               5                   10                  15

Ile Gly Ile Phe Tyr Ala Gln Arg Arg Leu Arg Gln Lys
            20                  25

<210> SEQ ID NO 86
<211> LENGTH: 29
<212> TYPE: PRT
<213> ORGANISM: Caenorhabditis elegans

<400> SEQUENCE: 86

Asp Ile Ile Thr Ile Val Val Pro Pro Ala Leu Pro Ala Ala Met Ser

```
                1               5                  10                 15
Val Gly Ile Ile Asn Ala Asn Ser Arg Leu Lys Lys Lys
                20                 25

<210> SEQ ID NO 87
<211> LENGTH: 29
<212> TYPE: PRT
<213> ORGANISM: Caenorhabditis elegans

<400> SEQUENCE: 87

Asp Ile Ile Thr Ile Thr Val Pro Pro Ala Leu Pro Ala Ala Met Ser
 1               5                  10                 15

Val Gly Ile Ile Asn Ala Gln Leu Arg Leu Lys Lys Lys
                20                 25

<210> SEQ ID NO 88
<211> LENGTH: 29
<212> TYPE: PRT
<213> ORGANISM: Caenorhabditis elegans

<400> SEQUENCE: 88

Leu Ile Leu Thr Ser Val Ile Pro Pro Glu Leu Pro Ile Glu Leu Ser
 1               5                  10                 15

Leu Ala Val Asn Ser Ser Leu Met Ala Leu Gln Lys Leu
                20                 25

<210> SEQ ID NO 89
<211> LENGTH: 29
<212> TYPE: PRT
<213> ORGANISM: Homo Sapiens

<400> SEQUENCE: 89

Ala Leu Ala Val Ala Ala Ile Pro Glu Gly Leu Pro Ala Val Ile Thr
 1               5                  10                 15

Thr Cys Leu Ala Leu Gly Thr Arg Arg Met Ala Lys Lys
                20                 25

<210> SEQ ID NO 90
<211> LENGTH: 29
<212> TYPE: PRT
<213> ORGANISM: Oryctolagus cuniculus

<400> SEQUENCE: 90

Ala Leu Ala Val Ala Ala Ile Pro Glu Gly Leu Pro Ala Val Ile Thr
 1               5                  10                 15

Thr Cys Leu Ala Leu Gly Thr Arg Arg Met Ala Lys Lys
                20                 25

<210> SEQ ID NO 91
<211> LENGTH: 29
<212> TYPE: PRT
<213> ORGANISM: Gallus gallus

<400> SEQUENCE: 91

Ala Leu Ala Val Ala Ala Ile Pro Glu Gly Leu Pro Ala Val Ile Thr
 1               5                  10                 15

Thr Cys Leu Ala Leu Gly Thr Arg Arg Met Ala Lys Lys
                20                 25

<210> SEQ ID NO 92
<211> LENGTH: 29
<212> TYPE: PRT
```

-continued

<213> ORGANISM: Felis catus

<400> SEQUENCE: 92

Ala Leu Ala Val Ala Ala Ile Pro Glu Gly Leu Pro Ala Val Ile Thr
1               5                   10                  15

Thr Cys Leu Ala Leu Gly Thr Arg Arg Met Ala Lys Lys
            20                  25

<210> SEQ ID NO 93
<211> LENGTH: 29
<212> TYPE: PRT
<213> ORGANISM: Procambarus clarkii

<400> SEQUENCE: 93

Ala Leu Ala Val Ala Ala Ile Pro Glu Gly Leu Pro Ala Val Ile Thr
1               5                   10                  15

Thr Cys Leu Ala Leu Gly Thr Arg Arg Met Ala Lys Lys
            20                  25

<210> SEQ ID NO 94
<211> LENGTH: 29
<212> TYPE: PRT
<213> ORGANISM: Homo Sapiens

<400> SEQUENCE: 94

Ala Leu Ala Val Ala Ala Ile Pro Glu Gly Leu Pro Ala Val Ile Thr
1               5                   10                  15

Thr Cys Leu Ala Leu Gly Thr Arg Arg Met Ala Lys Lys
            20                  25

<210> SEQ ID NO 95
<211> LENGTH: 29
<212> TYPE: PRT
<213> ORGANISM: Homo Sapiens

<400> SEQUENCE: 95

Ala Leu Ala Val Ala Ala Ile Pro Glu Gly Leu Pro Ala Val Ile Thr
1               5                   10                  15

Thr Cys Leu Ala Leu Gly Thr Arg Arg Met Ala Arg Lys
            20                  25

<210> SEQ ID NO 96
<211> LENGTH: 29
<212> TYPE: PRT
<213> ORGANISM: Drosophila melanogaster

<400> SEQUENCE: 96

Ala Val Ala Val Ala Ala Ile Pro Glu Gly Leu Pro Ala Val Ile Thr
1               5                   10                  15

Thr Cys Leu Ala Leu Gly Thr Arg Arg Met Ala Lys Lys
            20                  25

<210> SEQ ID NO 97
<211> LENGTH: 29
<212> TYPE: PRT
<213> ORGANISM: Saccharomyces cerevisiae

<400> SEQUENCE: 97

Ser Leu Ala Val Ala Ala Ile Pro Glu Gly Leu Pro Ile Ile Val Thr
1               5                   10                  15

Val Thr Leu Ala Leu Gly Val Leu Arg Met Ala Lys Arg
            20                  25

<210> SEQ ID NO 98
<211> LENGTH: 29
<212> TYPE: PRT
<213> ORGANISM: Saccharomyces cerevisiae

<400> SEQUENCE: 98

Thr Val Ile Val Val Ala Val Pro Glu Gly Leu Pro Leu Ala Val Thr
1               5                   10                  15

Leu Ala Leu Ala Phe Ala Thr Thr Arg Met Thr Lys Asp
            20                  25

<210> SEQ ID NO 99
<211> LENGTH: 29
<212> TYPE: PRT
<213> ORGANISM: Homo Sapiens

<400> SEQUENCE: 99

Thr Val Leu Val Val Ala Val Pro Glu Gly Leu Pro Leu Ala Val Thr
1               5                   10                  15

Ile Ser Leu Ala Tyr Ser Val Lys Lys Met Met Lys Asp
            20                  25

<210> SEQ ID NO 100
<211> LENGTH: 29
<212> TYPE: PRT
<213> ORGANISM: Homo Sapiens

<400> SEQUENCE: 100

Thr Val Leu Val Val Ala Val Pro Glu Gly Leu Pro Leu Ala Val Thr
1               5                   10                  15

Ile Ser Leu Ala Tyr Ser Val Lys Lys Met Met Lys Asp
            20                  25

<210> SEQ ID NO 101
<211> LENGTH: 29
<212> TYPE: PRT
<213> ORGANISM: Rattus norvegicus

<400> SEQUENCE: 101

Thr Val Leu Val Val Ala Val Pro Glu Gly Leu Pro Leu Ala Val Thr
1               5                   10                  15

Ile Ser Leu Ala Tyr Ser Val Lys Lys Met Met Lys Asp
            20                  25

<210> SEQ ID NO 102
<211> LENGTH: 29
<212> TYPE: PRT
<213> ORGANISM: Homo Sapiens

<400> SEQUENCE: 102

Thr Val Leu Val Val Ala Val Pro Glu Gly Leu Pro Leu Ala Val Thr
1               5                   10                  15

Ile Ser Leu Ala Tyr Ser Val Lys Lys Met Met Lys Asp
            20                  25

<210> SEQ ID NO 103
<211> LENGTH: 29
<212> TYPE: PRT
<213> ORGANISM: Homo Sapiens

<400> SEQUENCE: 103

```
Thr Val Leu Val Val Ala Val Pro Glu Gly Leu Pro Leu Ala Val Thr
 1               5                  10                  15

Ile Ser Leu Ala Tyr Ser Val Lys Lys Met Met Lys Asp
            20                  25
```

<210> SEQ ID NO 104
<211> LENGTH: 29
<212> TYPE: PRT
<213> ORGANISM: Saccharomyces cerevisiae

<400> SEQUENCE: 104

```
Thr Val Leu Ile Val Ser Cys Pro Cys Val Ile Gly Leu Ala Val Pro
 1               5                  10                  15

Ile Val Phe Val Ile Ala Ser Gly Val Ala Ala Lys Arg
            20                  25
```

<210> SEQ ID NO 105
<211> LENGTH: 29
<212> TYPE: PRT
<213> ORGANISM: Homo Sapiens

<400> SEQUENCE: 105

```
Thr Val Leu Cys Ile Ala Cys Pro Cys Ser Leu Gly Leu Ala Thr Pro
 1               5                  10                  15

Thr Ala Val Met Val Gly Thr Gly Val Gly Ala Gln Asn
            20                  25
```

<210> SEQ ID NO 106
<211> LENGTH: 29
<212> TYPE: PRT
<213> ORGANISM: Homo Sapiens

<400> SEQUENCE: 106

```
Thr Val Leu Cys Ile Ala Cys Pro Cys Ser Leu Gly Leu Ala Thr Pro
 1               5                  10                  15

Thr Ala Val Met Val Gly Thr Gly Val Ala Ala Gln Asn
            20                  25
```

<210> SEQ ID NO 107
<211> LENGTH: 29
<212> TYPE: PRT
<213> ORGANISM: Drosophila melanogaster

<400> SEQUENCE: 107

```
Gly Ile Ile Val Ala Asn Val Pro Glu Gly Leu Leu Ala Thr Val Thr
 1               5                  10                  15

Val Cys Leu Thr Leu Thr Ala Lys Arg Met Ala Ser Lys
            20                  25
```

<210> SEQ ID NO 108
<211> LENGTH: 29
<212> TYPE: PRT
<213> ORGANISM: Hydra vulgaris

<400> SEQUENCE: 108

```
Gly Ile Ile Val Ala Asn Val Pro Glu Gly Leu Leu Ala Thr Val Thr
 1               5                  10                  15

Val Cys Leu Thr Leu Thr Ala Lys Lys Met Ala Lys Lys
            20                  25
```

<210> SEQ ID NO 109
<211> LENGTH: 29

```
<212> TYPE: PRT
<213> ORGANISM: Bufo marinus

<400> SEQUENCE: 109

Gly Ile Ile Val Ala Asn Val Pro Glu Gly Leu Leu Ala Thr Val Thr
1               5                   10                  15

Val Cys Leu Thr Leu Thr Ala Lys Arg Met Ala Arg Lys
            20                  25

<210> SEQ ID NO 110
<211> LENGTH: 29
<212> TYPE: PRT
<213> ORGANISM: Homo Sapiens

<400> SEQUENCE: 110

Gly Ile Ile Val Ala Asn Val Pro Glu Gly Leu Leu Ala Thr Val Thr
1               5                   10                  15

Val Cys Leu Thr Leu Thr Ala Lys Arg Met Ala Arg Lys
            20                  25

<210> SEQ ID NO 111
<211> LENGTH: 29
<212> TYPE: PRT
<213> ORGANISM: Homo Sapiens

<400> SEQUENCE: 111

Gly Ile Ile Val Ala Asn Val Pro Glu Gly Leu Leu Ala Thr Val Thr
1               5                   10                  15

Val Cys Leu Thr Leu Thr Ala Lys Arg Met Ala Arg Lys
            20                  25

<210> SEQ ID NO 112
<211> LENGTH: 29
<212> TYPE: PRT
<213> ORGANISM: Homo Sapiens

<400> SEQUENCE: 112

Gly Ile Ile Val Ala Asn Val Pro Glu Gly Leu Leu Ala Thr Val Thr
1               5                   10                  15

Val Cys Leu Thr Val Thr Ala Lys Arg Met Ala Arg Lys
            20                  25

<210> SEQ ID NO 113
<211> LENGTH: 29
<212> TYPE: PRT
<213> ORGANISM: Homo Sapiens

<400> SEQUENCE: 113

Ile Leu Phe Asn Asn Leu Ile Pro Ile Ser Leu Leu Val Thr Leu Glu
1               5                   10                  15

Val Val Lys Phe Thr Gln Ala Tyr Phe Ile Asn Trp Asp
            20                  25

<210> SEQ ID NO 114
<211> LENGTH: 29
<212> TYPE: PRT
<213> ORGANISM: Saccharomyces cerevisiae

<400> SEQUENCE: 114

Ile Leu Phe Ser Asn Leu Val Pro Ile Ser Leu Phe Val Thr Val Glu
1               5                   10                  15
```

-continued

```
Leu Ile Lys Tyr Tyr Gln Ala Phe Met Ile Gly Ser Asp
         20                  25
```